US008685991B2

(12) United States Patent
Wagner et al.

(10) Patent No.: US 8,685,991 B2
(45) Date of Patent: *Apr. 1, 2014

(54) ANTI-INFECTIVE AGENTS AND USES THEREOF

(75) Inventors: Rolf Wagner, Antioch, IL (US); Warren M. Kati, Gurnee, IL (US); Dachun Liu, Vernon Hills, IL (US); Yaya Liu, Buffalo Grove, IL (US); Kenton L. Longenecker, Grayslake, IL (US); Clarence J. Maring, Palatine, IL (US); John K. Pratt, Kenosha, WI (US); Todd W. Rockway, Grayslake, IL (US); Kent D. Stewart, Gurnee, IL (US); Michael D. Tufano, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,609

(22) Filed: Apr. 3, 2012

(65) Prior Publication Data

US 2012/0213733 A1 Aug. 23, 2012

Related U.S. Application Data

(63) Continuation of application No. 12/725,689, filed on Mar. 17, 2010, which is a continuation of application No. PCT/US2008/076576, filed on Sep. 17, 2008.

(60) Provisional application No. 60/972,877, filed on Sep. 17, 2007, provisional application No. 61/096,791, filed on Sep. 13, 2008.

(51) Int. Cl.
C07D 239/54 (2006.01)

(52) U.S. Cl.
USPC ............................ 514/274; 544/311; 544/312

(58) Field of Classification Search
USPC .................................. 544/311, 312; 514/274
See application file for complete search history.

(56) References Cited

U.S. PATENT DOCUMENTS

| 4,239,888 | A | 12/1980 | Miller |
| 4,588,729 | A | 5/1986 | Teranishi et al. |
| 5,084,084 | A | 1/1992 | Satow et al. |
| 5,127,935 | A | 7/1992 | Satow et al. |
| 5,154,755 | A | 10/1992 | Satow et al. |
| 5,162,326 | A | 11/1992 | Naka et al. |
| 5,164,396 | A | 11/1992 | Grosscurt et al. |
| 6,380,387 | B1 | 4/2002 | Sidduri et al. |
| 6,537,948 | B1 | 3/2003 | Tohyama et al. |
| 8,178,548 | B2 * | 5/2012 | Donner et al. ............... 514/274 |
| 8,188,104 | B2 * | 5/2012 | Flengte et al. ............... 514/274 |

FOREIGN PATENT DOCUMENTS

| JP | 5213755 | A | 8/1993 |
| WO | 9705117 | A1 | 2/1997 |
| WO | 0142225 | A2 | 6/2001 |
| WO | 0142225 | A3 | 6/2001 |
| WO | 0190121 | A2 | 11/2001 |
| WO | 2005021500 | A1 | 3/2005 |
| WO | 2009039127 | A1 | 3/2009 |
| WO | 2009039134 | A1 | 3/2009 |
| WO | 2009039135 | A1 | 3/2009 |
| WO | 2010010017 | A1 | 1/2010 |

OTHER PUBLICATIONS

Camma et al., PubMed Abstract (Curr Pharm Des. 2004; 10(17):2123-30), 2004.*
Jacobsen et al., Efficient N-Arylation and N-Alkenylation of the Five DNA/RNA Nucleobases, Journal of Organic Chemistry, 2006, vol. 71, Issue 24. pp. 9183-9190.*
Baltrusis et al., CAPLUS Abstract 97:216122 (1982).*
Ansel H.C., et al., Ansel's Pharmaceutical Dosage forms and Drug Delivery Systems, 8th Edition, Lippincott Williams & Wilkins, 2005, Table of Contents.
Aulton M.E., ed., The Design of Dosage Forms : in Pharmaceutics: The Science of Dosage Form Design, 2nd Edition, Churchill Livingstone, 2004, Table of Contents.
Austin W.B., et al., "Facile Synthesis of Ethynylated Benzoic Acid Derivatives and Aromatic Compounds via Ethynyltrimethylsilane," Journal of Organic Chemistry, 1981, vol. 46 (11), pp. 2280-2286.
Baltrushis R.S., et al., "Bromo Derivatives of 1-(4-hydroxyphenyl)dihydrouracil and -(4-hydroxyphenyl)-5- or -6-Methyldihydrouracils," Chemistry of Heterocyclic Compounds, 1982, vol. 18 (9), pp. 1251-1254.
Blight K.J., et al., "Efficient Initiation of HCV RNA Replication in Cell Culture," 2000, vol. 290 (5498), pp. 1972-1974.
Blight K.J., et al., "Efficient Replication of Hepatitis C Virus Genotype 1 a RNAs in Cell Culture," 2003, vol. 77 (5), pp. 3181-3190.
Camma C., et al., "The Impact of Antiviral Treatments on the Course of Chronic Hepatitis C: An Evidence-Based Approach," Current Pharmaceutical Design, 2004, vol. 10 (17), pp. 2123-2130.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Gravel M., et al., "Practical Procedure for the Preparation of Functionalized (E)-1-Alkenylboronic Acids Including the Unprecedented 1-Alkoxycarbonyl Derivatives," 2004, vol. 36 (6), pp. 573-579.
Hilfiker R., et al., "Relevance of Solid-state Properties for Pharmaceutical Products," Polymorphism, 2006, pp. 1-19.

(Continued)

Primary Examiner — Deepak Rao
(74) Attorney, Agent, or Firm — Bradley E. Davis

(57) ABSTRACT

This invention relates to: (a) compounds and salts thereof that, inter alia, inhibit HCV; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

35 Claims, 46 Drawing Sheets

(56) References Cited

OTHER PUBLICATIONS

International Preliminary Report on Patentability and Written Opinion for Application No. PCT/US2008/076576, mailed on Feb. 12, 2010, 38 pages.
International Preliminary Report on Patentability and Written Opinion for Application No. PCT/US2008/076592, mailed on Mar. 24, 2010, 7 pages.
International Preliminary Report on Patentability and Written Opinion for Application No. PCT/US2008/076594, mailed on Mar. 24, 2010, 7 pages.
International Search Report for Application No. PCT/US2008/076576, mailed on Dec. 22, 2008, 4 pages.
International Search Report for Application No. PCT/US2008/076592, mailed on Feb. 16, 2009, 2 pages.
International Search Report for Application No. PCT/US2008/076594, mailed on Dec. 30, 2008, 2 pages.
Jacobsen M.F., et al., "Efficient N-Arylation and N-Alkenylation of the Five DNA/RNA Nucleobases," Journal of Organic Chemistry, 2006, vol. 71 (24), pp. 9183-9190.
Koch Uwe et al., "2-(2-thienyl)-5,6-dihydroxy-4-carboxypyrimidines as inhibitors of the hepatitis C virus NS5B polymerase: Discovery, SAR, modeling, and mutagenesis," Journal of Medicinal Chemistry, vol. 49(5), pp. 1693-1705 , 2006.
Lal G.S. et al., "A Convenient Synthesis of 5-Fluoropyrimidines Using 1-(Chloromethyl)-4-fluoro- 1,4-diazabicyclo [2.2.2]octane Bis(tetrafluoroborate)-SELECTFLUOR Reagent," J. Org. Chem, vol. 60 (22), pp. 7340-7342, 1995.
Lohmann V., et al., "Replication of Subgenomic Hepatitis C Virus RNAs in a Hepatoma Cell Line," Science, 1999, vol. 285 (5424), pp. 110-113.
Mathe C., et al., "L-nucleoside Enantiomers as Antivirals Drugs: A Mini-review," Antiviral Research, 2006, vol. 71, pp. 276-281.
Miller M.W., et al., "Anticoccidial Activity of 1-Phenyluracils," Journal of Medicinal Chemistry, 1983, vol. 26 (7), pp. 1075-1076.
Morrison J.F., et al., "Approaches to the Study and Analysis of the Inhibition of Enzymes by Slow- and Tight-Binding Inhibitors," Comments Molecular Cellular Biophysics, 1985, vol. 2(6), pp. 347-368.
Ohira S., "Methanolysis of Dimethyl (1-Diazo-2-0xopropyl)Phosphonate: Generation of Dimethyl(DiazoMethyl) Phosphonate and Reaction with Carbonyl Compounds," Synthetic Communications, 1989, vol. 19 (3-4), pp. 561-564.
Onitsuka K., et al., "Living Polymerization of Bulky Aryl Isocyanide with Arylrhodium Complexes," Organometallics, 2006, vol. 25 (5), pp. 1270-1278.
Remington J.P., ed., Pharmaceutical Sciences, 15th Edition, Mack Publishing Company, 1975, pp. 411-415.
Santana L., et al., "A Slightly Shorter Route to Carbocyclic Nucleosides. Synthesis of (±)-trans- I [2-(Hydroxymethyl)cyclopentylmethyl]uracil," Journal of Heterocyclic Chemistry, 1999, vol. 36, pp. 293-295.
Supplementary International Search Report for Application No. PCT/US2008/076576, mailed on Jan. 14, 2010, 2 pages.
Taylor W.P., et al., "Quiescent Affinity Inactivators of Protein Tyrosine Phosphatases," Bioorganic & Medicinal Chemistry, 1996, vol. 4 (9), pp. 1515-1520.
Ueno Y., et al., "Synthesis and Properties of Nucleic Acid Analogues Consisting of a Benzene-Phosphate Backbone," Journal of Organic Chemistry, 2005, vol. 70 (20), pp. 7925-7935.
Zhou T., et al., "Hypervalent Iodine in Synthesis: Part 86. Selective Copper-catalyzed N-monoarylation and N1, N3 Diarylation of Uracil and its Derivatives with Diaryliodonium Salts," Helvetica Chimica Acta, 2005, vol. 88 (2), pp. 290-296.
European Search Report for Application No. EP12185550, mailed on Dec. 14, 2012, 1 page.

\* cited by examiner

SEQUENCE LISTING

<160> NUMBER OF SEQ ID NOS: 1

<210> SEQ ID NO 1
<211> LENGTH: 171
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
gggcgaauug ggcccucuag augcaugcuc gagcggccgc cagugugaug gauaucugca    60
gaauucgccc uugguggcuc caucuuagcc cuagucacgg cuagcuguga aagguccgug   120
agccgcuuga cugcagagag ugcugauacu ggccucucug cagaucaagu c            171

ANTI-INFECTIVE AGENTS AND USES THEREOF

CROSS-REFERENCE TO RELATED PATENT APPLICATIONS

This patent application is a continuation application of U.S. patent application Ser. No. 12/725,689 (filed Mar. 17, 2010) which is a continuation of International Patent Application No. PCT/US2008/076576 (filed Sep. 17, 2008), which, in turn, claims priority to U.S. Provisional Patent Application No. 60/972,877 (filed Sep. 17, 2007) and U.S. Provisional Patent Application No. 61/096,791 (filed Sep. 13, 2008). The entire text of those applications is incorporated by reference into this application.

FIELD OF THE INVENTION

This invention is directed to: (a) compounds and salts thereof that, inter alia, are useful as hepatitis C virus (HCV) inhibitors; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to alleviate the symptoms of hepatitis C, thereby providing partial or complete relief. This invention provides compounds (including salts thereof), compositions, and methods of treatment that generally address such a need.

SUMMARY OF THE INVENTION

This invention is directed to compounds that correspond in structure to formula I:

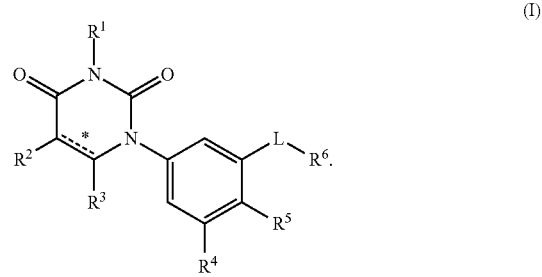

In formula I:

$\overset{*}{=\!=\!=}$ is selected from the group consisting of single carbon-carbon bond and double carbon-carbon bond;

$R^1$ is selected from the group consisting of hydrogen, methyl, and nitrogen-protecting group;

$R^2$ is selected from the group consisting of hydrogen, halo, hydroxy, methyl, cyclopropyl, and cyclobutyl;

$R^3$ is selected from the group consisting of hydrogen, halo, oxo, and methyl;

$R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
- (a) the amino, aminocarbonyl, and aminosulfonyl optionally are substituted with:
  - (1) one or two substituents independently selected from the group consisting of alkyl, alkenyl, alkynyl, and alkylsulfonyl, or
  - (2) two substituents that, together with the amino nitrogen, form a single-ring heterocyclyl, and
- (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
  - the amino optionally is substituted with:
    - (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
    - (2) two substituents that, together with the amino nitrogen, form a single-ring heterocyclyl, and
- (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
  - the amino optionally is substituted with:
    - (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
    - (2) two substituents that, together with the amino nitrogen, form a single-ring heterocyclyl;

$R^5$ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo;

L is selected from the group consisting of bond, $C(R^A)=C(R^B)$, CC, $C(O)N(R^C)$, $N(R^D)C(O)$, $C_1$-$C_2$-alkylene, $C(H)_2O$, $OC(H)_2$, cyclopropyl-1,2-ene, $C(H)_2N(R^L)$, $N(R^M)C(H)_2$, $C(O)CH_2$, and $CH_2C(O)$;

$R^A$, $R^B$, $R^L$, and $R^M$ are independently selected from the group consisting of hydrogen, $C_1$-$C_6$-alkyl, $C_1$-$C_6$-alkyloxy, $C_3$-$C_8$-cycloalkyl, and halo, wherein:
- the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl;

$R^C$ is selected from the group consisting of hydrogen and alkyl;

$R^D$ is selected from the group consisting of hydrogen and alkyl;

$R^6$ is selected from the group consisting of $C_5$-$C_6$-carbocyclyl, 5-6-membered heterocyclyl, fused 2-ring heterocyclyl, and fused 2-ring carbocyclyl, wherein each such substituent optionally is substituted with one or more substituents independently selected from the group consisting of $R^E$, $R^F$, $R^G$, $R^H$, $R^I$, $R^J$, and $R^K$;

each $R^E$ is independently selected from the group consisting of halo, nitro, hydroxy, oxo, carboxy, cyano, amino, imino, azido, and aldehydro, wherein:
- the amino optionally is substituted with one or two substituents independently selected from the group consisting of alkyl, alkenyl, and alkynyl;

each $R^F$ is independently selected from the group consisting of alkyl, alkenyl, and alkynyl, wherein:
- each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  - the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy,
- wherein:
  - amino portion of the alkylsulfonylamino optionally is substituted with a substituent selected from the group consisting of alkyl, alkenyl, and alkynyl;

each $R^G$ is independently selected from the group consisting of carbocyclyl and heterocyclyl, wherein:
- each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  - the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^H$ is independently selected from the group consisting of alkyloxy, alkenyloxy, alkynyloxy, alkylsulfonyloxy, alkenylsulfonyloxy, and alkynylsulfonyloxy, wherein:
- each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  - the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:

(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and (b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:

the carbocyclyl and heterocyclyl optionally are substituted with one or two substituents independently selected from the group consisting of halo, alkyl, and oxo;

each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and (2) the amino portion of the aminocarbonylalkyl optionally is substituted with one or two substituents independently selected from the group consisting of alkyl, alkenyl, and alkynyl, (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl, alkenyl, alkynyl, alkyloxy, alkenyloxy, and alkynyloxy, wherein:

the alkyl optionally is substituted with one or more hydroxy;

(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:

the amino optionally is substituted with one or two substituents independently selected from the group consisting of alkyl, alkenyl, and alkynyl; and each $R^K$ is independently selected from the group consisting of aminosulfonyl, alkylsulfonyl, alkenylsulfonyl, and alkynylsulfonyl, wherein:

(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:

the amino, aminosulfonyl, and aminocarbonyl optionally are substituted with one or two substituents independently selected from the group consisting of alkyl, alkenyl, and alkynyl; and (b) the aminosulfonyl optionally is substituted with one or two substituents independently selected from the group consisting of alkyl, alkenyl, and alkynyl.

This invention also is directed to the salts (including pharmaceutically acceptable salts) of the compounds of the invention.

This invention also is directed to compositions (including pharmaceutical compositions) that comprise one or more compounds and/or salts of the invention, and, optionally, one or more additional therapeutic agents.

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, inhibit replication of an RNA virus (including HCV), treat a disease treatable by inhibiting HCV ribonucleic acid (RNA) polymerase (including hepatitis C).

This invention also is directed to a use of one or more compounds and/or salts of the invention to prepare a medicament. The medicament optionally can comprise one or more additional therapeutic agents. In some embodiments, the medicament is useful for treating hepatitis C.

Further benefits of Applicants' invention will be apparent to one skilled in the art from reading this patent application.

DETAILED DESCRIPTION OF THE INVENTION

Figure 1:
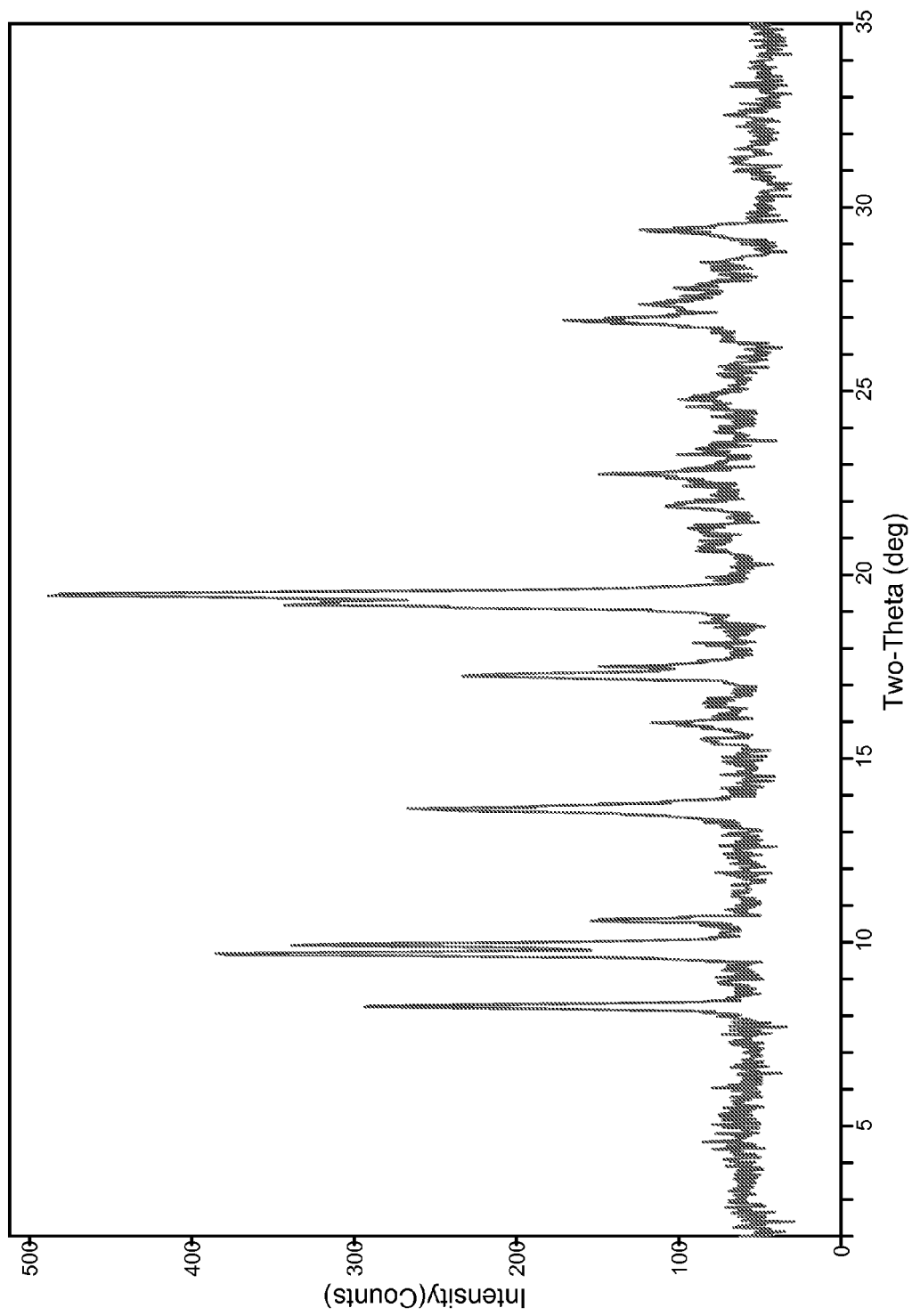
FIG. 1 shows an illustrative PXRD pattern for the ethanol solvate of compound IB-L0-2.3.
Figure 2:
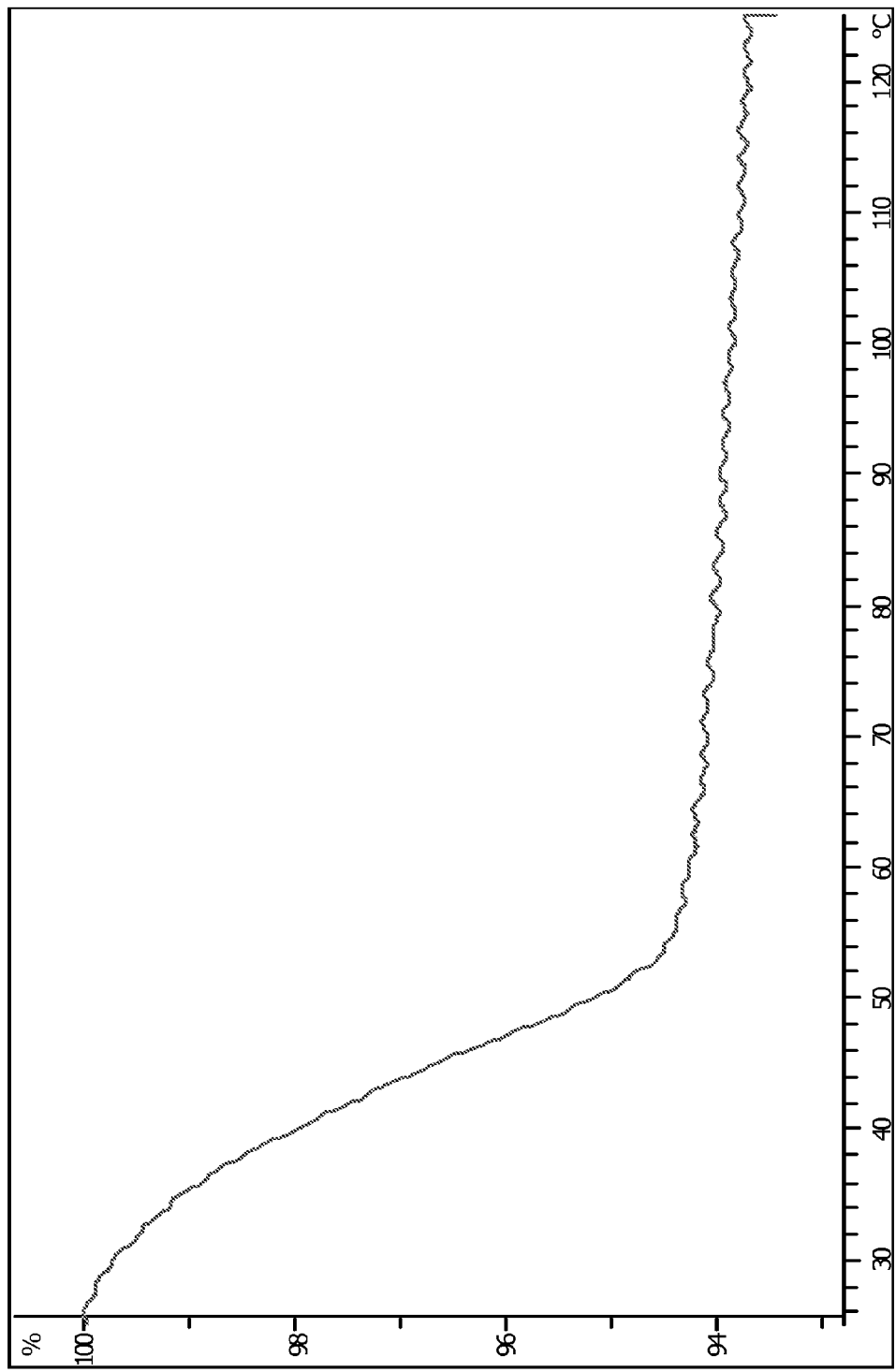
FIG. 2 shows an illustrative TGA profile of the ethanol solvate of compound IB-L0-2.3.

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

The term "alkyl" (alone or in combination with another term(s)) means a straight- or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl alternatively may be 2 or 3 rings fused together, such as naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl, cyclobutyl, cyclopentyl, and cyclohexyl. A cycloalkyl alternatively may be 2 or 3 carbon rings fused together, such as, decalinyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —NO$_2$.

The term "cyano" (alone or in combination with another term(s)) means —CN, which also may be depicted as —C≡N.

The term "keto" (alone or in combination with another term(s)) means an oxo radical, and may be depicted as =O.

The term "carboxy" (alone or in combination with another term(s)) means —C(O)—OH.

The term "amino" (alone or in combination with another term(s)) means —NH$_2$.

The term "imino" (alone or in combination with another term(s)) means =NH.

The term "aminoimino" (alone or in combination with another term(s)) means =NNH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkoxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkoxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "2-fused ring" heterocyclyl (alone or in combination with another term(s)) means a saturated, partially saturated, or aryl heterocyclyl containing 2 fused rings. Examples of 2-fused-ring heterocyclyls include indolizinyl, quinolizinyl, purinyl, naphthyridinyl, pteridinyl, indolyl, isoindolyl, indoleninyl, isoindazolyl, phthalazinyl, quinoxalinyl, quinazolinyl, benzodiazinyl, benzopyranyl, benzothiopyranyl, benzoxazolyl, anthranilyl, benzodioxolyl, benzodioxanyl, benzoxadiazolyl, benzofuranyl, isobenzofuranyl, benzothiazolyl, benzothiadiazolyl, benzimidazolyl, benzotriazolyl, benzoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

ChemDraw software has been used to generate the compound names in this patent application.

The term "amorphous" as applied to a compound refers to a solid-state in which the compound molecules are present in a disordered arrangement and do not form a distinguishable crystal lattice or unit cell. When subjected to X-ray powder diffraction, an amorphous compound does not produce any characteristic crystalline peaks.

The term "crystalline form" as applied to a compound refers to a solid-state in which the compound molecules are arranged to form a distinguishable crystal lattice (i) comprising distinguishable unit cells, and (ii) yielding diffraction pattern peaks when subjected to X-ray radiation.

The term "purity", unless otherwise qualified, means the chemical purity of a compound according to conventional HPLC assay.

The term "phase purity" means the solid-state purity of a compound with regard to a particular crystalline or amorphous form of the compound as determined by X-ray powder diffraction analytical methods.

The term "phase pure" refers to purity with respect to other solid-state forms of the compound, and does not necessarily imply a high degree of chemical purity with respect to other compounds.

The term "PXRD" means X-ray powder diffraction.
The term "TGA" means thermogravimetric analysis.
The term "DSC" means differential scanning calorimetry.

B. COMPOUNDS

This invention is directed, in part, to compounds that are phenyl-uracil derivatives that correspond in structure to formula I:

(I)

In these compounds, $\stackrel{*}{=\!=\!=}$ is selected from the group consisting of single carbon-carbon bond and double carbon-carbon bond.

In some embodiments, $\stackrel{*}{=\!=\!=}$ is a single carbon-carbon bond. In these embodiments, the compounds of formula I correspond in structure to the following formula (i.e., formula IA):

(IA)

In other embodiments, $\stackrel{*}{=\!=\!=}$ is a double carbon-carbon bond. In these embodiments, the compounds of formula I correspond in structure to the following formula (i.e., formula IB):

(IB)

B1. Substituent $R^1$ $R^1$ is selected from the group consisting of hydrogen, methyl, and nitrogen-protecting group.

In some embodiments, $R^1$ is hydrogen.
In some embodiments, $R^1$ is methyl.
In some embodiments, $R^1$ is selected from the group consisting of hydrogen and methyl.
In some embodiments, $R^1$ is a nitrogen-protecting group. In these embodiments, the compounds are useful as intermediates for the preparation of compounds of formula I. Nitrogen-protecting groups suitable for preparing compounds of formula I are known to those skilled in the art.

B2. Substituent $R^2$ $R^2$ is selected from the group consisting of hydrogen, halo, hydroxy, methyl, cyclopropyl, and cyclobutyl.

In some embodiments, $R^2$ is hydrogen.
In some embodiments, $R^2$ is halo. In some such embodiments, $R^2$ is selected from the group consisting of fluoro and chloro. In other such embodiments, $R^2$ is fluoro. In yet other such embodiments, $R^2$ is chloro. In yet other such embodiments, $R^2$ is bromo. In further such embodiments, $R^2$ is iodo.
In some embodiments, $R^2$ is hydroxy.
In some embodiments, $R^2$ is methyl.
In some embodiments, $R^2$ is cyclopropyl.
In some embodiments, $R^2$ is cyclobutyl.
In some embodiments, $R^2$ is selected from the group consisting of hydrogen, methyl, hydroxy, and halo. In some such embodiments, $R^2$ is selected from the group consisting of hydrogen, methyl, hydroxy, fluoro, and chloro. In other such embodiments, $R^2$ is selected from the group consisting of hydrogen, methyl, hydroxy, and fluoro. In yet other such embodiments, $R^2$ is selected from the group consisting of hydrogen, methyl, hydroxy, and chloro. In yet other such embodiments, $R^2$ is selected from the group consisting of hydrogen, methyl, hydroxy, and bromo. In further such embodiments, $R^2$ is selected from the group consisting of hydrogen, methyl, hydroxy, and iodo.

In some embodiments, $R^2$ is selected from the group consisting of hydrogen, methyl, and halo. In some such embodiments, $R^2$ is selected from the group consisting of hydrogen, methyl, fluoro, and chloro. In other such embodiments, $R^2$ is selected from the group consisting of hydrogen, methyl, and fluoro. In yet other such embodiments, $R^2$ is selected from the group consisting of hydrogen, methyl, and chloro. In yet other such embodiments, $R^2$ is selected from the group consisting of hydrogen, methyl, and bromo. In further such embodiments, $R^2$ is selected from the group consisting of hydrogen, methyl, and iodo.

In some embodiments, $R^2$ is selected from the group consisting of hydrogen and halo. In some such embodiments, $R^2$ is selected from the group consisting of hydrogen, fluoro, and chloro. In other such embodiments, $R^2$ is selected from the group consisting of hydrogen and fluoro. In yet other such embodiments, $R^2$ is selected from the group consisting of hydrogen and chloro. In yet other such embodiments, $R^2$ is selected from the group consisting of hydrogen and bromo. In further such embodiments, $R^2$ is selected from the group consisting of hydrogen and iodo.

B3. Substituent $R^3$ $R^3$ is selected from the group consisting of hydrogen, halo, oxo, and methyl. In some such embodiments, $R^3$ is selected from the group consisting of hydrogen, fluoro, oxo, and methyl. In other such embodiments, $R^3$ is selected from the group consisting of hydrogen, chloro, oxo, and methyl. In yet other such embodiments, $R^3$ is selected from the group consisting of hydrogen, bromo, oxo, and methyl. In yet other such embodiments, $R^3$ is selected from the group consisting of hydrogen, iodo, oxo, and methyl.

In some embodiments, $R^3$ is selected from the group consisting of hydrogen, halo, and oxo. In some such embodiments, $R^3$ is selected from the group consisting of hydrogen, fluoro, and oxo. In other such embodiments, $R^3$ is selected from the group consisting of hydrogen, chloro, and oxo. In yet other such embodiments, $R^3$ is selected from the group consisting of hydrogen, bromo, and oxo. In yet other such embodiments, $R^3$ is selected from the group consisting of hydrogen, iodo, and oxo.

In some embodiments, $R^3$ is selected from the group consisting of hydrogen and methyl.

In some embodiments, $R^3$ is hydrogen.

In some embodiments, $R^3$ is methyl.

In some embodiments, $R^3$ is oxo.

In some embodiments, $R^3$ is halo. In some such embodiments, $R^3$ is fluoro. In other such embodiments, $R^3$ is chloro. In yet other such embodiments, $R^3$ is bromo. In further such embodiments, $R^3$ is iodo.

B4. Substituent $R^4$ $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
(a) the amino, aminocarbonyl, and aminosulfonyl optionally are substituted with:
(1) one or two substituents independently selected from the group consisting of alkyl, alkenyl, alkynyl, and alkylsulfonyl, or
(2) two substituents that, together with the amino nitrogen, form a single-ring heterocyclyl,
(b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl, and
(c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the amino, aminocarbonyl, and aminosulfonyl optionally are substituted with:
(1) one or two substituents independently selected from the group consisting of alkyl, alkenyl, alkynyl, and alkylsulfonyl, or
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein: the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
(a) the amino, aminocarbonyl, and aminosulfonyl optionally are substituted with:
(1) one or two substituents independently selected from the group consisting of alkyl, alkenyl, and alkynyl, or,
(2) two substituents that, together with the amino nitrogen, form a single-ring heterocyclyl; and
(b) the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the amino, aminocarbonyl, and aminosulfonyl optionally are substituted with:
(1) one or two substituents independently selected from the group consisting of alkyl, alkenyl, and alkynyl, or,
(2) two substituents that, together with the amino nitrogen, form a single-ring heterocyclyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
(2) two substituents that, together with the amino nitrogen, form a single-ring heterocyclyl.

In some embodiments, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:
(a) the amino optionally is substituted with one or two substituents independently selected from the group consisting of alkyl, alkenyl, alkynyl, and alkylsulfonyl,
(b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and
(c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:
the amino optionally is substituted with one or two substituents independently selected from the group consisting of alkyl, alkenyl, alkynyl, and alkylsulfonyl.

In some embodiments, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:
(a) the amino optionally is substituted with one or two substituents independently selected from the group consisting of alkyl, alkenyl, alkynyl, and alkylsulfonyl,
(b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and
(c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:
the amino optionally is substituted with one or two substituents independently selected from the group consisting of alkyl, alkenyl, alkynyl, and alkylsulfonyl.

In some embodiments, $R^4$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^4$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with one or two substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with a substituent selected from the group consisting of alkyl, halo, and alkylsulfonylamino In some embodiments, $R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^4$ is selected from the group consisting of halo, tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^4$ is selected from the group consisting of tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^4$ is selected from the group consisting of halo, alkyl, haloalkyl, carboxyalkyl, hydroxyalkyl, alkyloxyalkyl, trimethylsilylalkynyl, alkylcarbocyclyl, carbocyclyl, alkylheterocyclyl, heterocyclyl, halocarbocyclyl, alkylsulfonylamino, and alkylsulfonyl.

In some embodiments, $R^4$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl.

In some embodiments, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^4$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^4$ is selected from the group consisting of halo, $C_1$-$C_4$-alkyl, $C_3$-$C_6$-carbocyclyl, and 5-6-membered heterocyclyl. In some such embodiments, $R^4$ is selected from the group consisting of halo, $C_1$-$C_4$-alkyl, $C_6$-carbocyclyl, and 5-6-membered heterocyclyl. In other such embodiments, $R^4$ is selected from the group consisting of halo, $C_1$-$C_4$-alkyl, phenyl, and 5-6-membered heteroaryl.

In some embodiments, $R^4$ is selected from the group consisting of $C_1$-$C_4$-alkyl, $C_3$-$C_6$-carbocyclyl, and 5-6-membered heterocyclyl. In some such embodiments, $R^4$ is selected from the group consisting of $C_1$-$C_4$-alkyl, $C_6$-carbocyclyl, and 5-6-membered heterocyclyl. In other such embodiments, $R^4$ is selected from the group consisting of $C_1$-$C_4$-alkyl, phenyl, and 5-6-membered heteroaryl.

In some embodiments, $R^4$ is selected from the group consisting of halo, tert-butyl, $C_3$-$C_6$-carbocyclyl, and 5-6-membered heterocyclyl. In some such embodiments, $R^4$ is selected from the group consisting of halo, tert-butyl, $C_6$-carbocyclyl, and 5-6-membered heterocyclyl. In other such embodiments, $R^4$ is selected from the group consisting of halo, tert-butyl, phenyl, and 5-6-membered heteroaryl.

In some embodiments, $R^4$ is selected from the group consisting of tert-butyl, $C_3$-$C_6$-carbocyclyl, and 5-6-membered heterocyclyl. In some such embodiments, $R^4$ is selected from the group consisting of tert-butyl, $C_6$-carbocyclyl, and 5-6-membered heterocyclyl. In other such embodiments, $R^4$ is selected from the group consisting of tert-butyl, phenyl, and 5-6-membered heteroaryl.

In some embodiments, $R^4$ is selected from the group consisting of $C_3$-$C_6$-carbocyclyl and 5-6-membered heterocyclyl. In some such embodiments, $R^4$ is selected from the group consisting of $C_6$-carbocyclyl, and 5-6-membered heterocyclyl. In other such embodiments, $R^4$ is selected from the group consisting of phenyl and 5-6-membered heteroaryl.

Suitable carbocyclyls for the above embodiments include, for example, cyclopropyl and phenyl.

Suitable heterocyclyls for the above embodiments include, for example, furanyl, thienyl, and pyridinyl.

In some embodiments, $R^4$ is selected from the group consisting of halo, alkyl, and alkyloxy.

In some embodiments, $R^4$ is alkyl.

In some embodiments, $R^4$ is tert-butyl.

B5. Substituent $R^5$ $R^5$ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo.

In some embodiments, $R^5$ is selected from the group consisting of hydrogen, hydroxy, alkyloxy, and halo. In some such embodiments, $R^5$ is selected from the group consisting of hydrogen, hydroxy, alkyloxy, and fluoro. In other such embodiments, $R^5$ is selected from the group consisting of hydrogen, hydroxy, alkyloxy, and fluoro. In yet other such embodiments, $R^5$ is selected from the group consisting of hydrogen, hydroxy, alkyloxy, and chloro. In yet other such embodiments, $R^5$ is selected from the group consisting of hydrogen, hydroxy, alkyloxy, and bromo. In further such embodiments, $R^5$ is selected from the group consisting of hydrogen, hydroxy, alkyloxy, and iodo.

In some embodiments, $R^5$ is selected from the group consisting of hydrogen, hydroxy, methoxy, and halo. In some such embodiments, $R^5$ is selected from the group consisting of hydrogen, hydroxy, methoxy, and fluoro. In other such embodiments, $R^5$ is selected from the group consisting of hydrogen, hydroxy, methoxy, and chloro. In yet other such embodiments, $R^5$ is selected from the group consisting of hydrogen, hydroxy, methoxy, and bromo. In further such embodiments, $R^5$ is selected from the group consisting of hydrogen, hydroxy, methoxy, and iodo.

In some embodiments, $R^5$ is selected from the group consisting of hydrogen, hydroxy, and alkyloxy. In some such embodiments, $R^5$ is selected from the group consisting of hydrogen, hydroxy, methoxy, and ethoxy.

In some embodiments, $R^5$ is s hydrogen.

In some embodiments, $R^5$ is hydroxy.

In some embodiments, $R^5$ is alkyloxy.

In some embodiments, $R^5$ is methoxy.

In some embodiments, $R^5$ is ethoxy.

B6. Substituent L

L is selected from the group consisting of bond, C(R$^A$)=C(R$^B$), C≡C, C(O)N(R$^C$), N(R$^D$)C(O), C$_1$-C$_2$-alkylene, C(H)$_2$O, OC(H)$_2$, cyclopropyl-1,2-ene, C(H)$_2$N(R$^L$), N(R$^M$)C(H)$_2$, C(O)CH$_2$, and CH$_2$C(O), wherein R$^A$, R$^B$, R$^C$, R$^D$, R$^L$, and R$^M$ are as discussed below.

In some embodiments, L is selected from the group consisting of bond, C(R$^A$)=C(R$^B$), C≡C, C(O)N(R$^C$), N(R$^D$)C(O), C$_1$-C$_2$-alkylene, C(H)$_2$O, OC(H)$_2$, cyclopropyl-1,2-ene, C(H)$_2$N(R$^L$), and N(R$^M$)C(H)$_2$.

In some embodiments, L is selected from the group consisting of C(R$^A$)=C(R$^B$), ethylene, and cyclopropyl-1,2-ene.

In some embodiments, L is selected from the group consisting of C(R$^A$)=C(R$^B$), C≡C, C(O)N(R$^C$), N(R$^D$)C(O), C$_1$-C$_2$-alkylene, C(H)$_2$O, OC(H)$_2$, cyclopropyl-1,2-ene, C(H)$_2$N(R$^L$), N(R$^M$)C(H)$_2$, C(O)CH$_2$, and CH$_2$C(O).

In some embodiments, L is selected from the group consisting of C(O)N(R$^C$), N(R$^D$)C(O), C(H)$_2$O, OC(H)$_2$, C(H)$_2$N(R$^L$), and N(R$^M$)C(H)$_2$.

In some embodiments, L is a bond. In these embodiments, the compounds of formula I correspond in structure to formula I-L0:

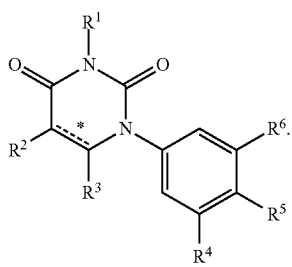

(I-L0)

In some such embodiments, the compounds correspond in structure to the following formula (i.e., formula IA-L0):

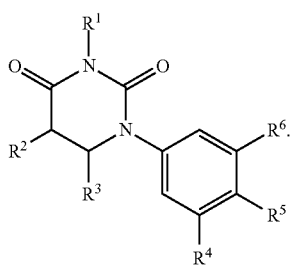

(IA-L0)

In other such embodiments, the compounds correspond in structure to the following formula (i.e., formula IB-L0):

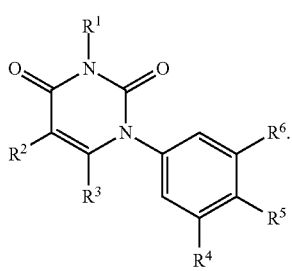

(IB-L0)

In some embodiments, L is C(R$^A$)=C(R$^B$), wherein R$^A$ and R$^B$ are as discussed below. In these embodiments, the compounds of formula I correspond in structure to formula I-L1:

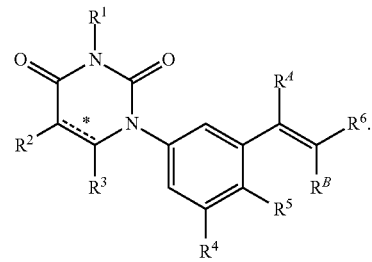

(I-L1)

In some such embodiments, the compounds correspond in structure to formula IA-L1:

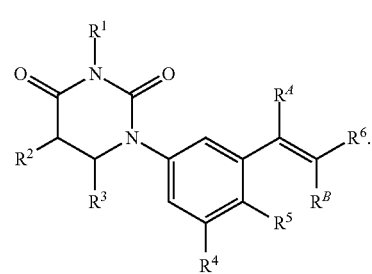

(IA-L1)

In other such embodiments, the compounds correspond in structure to formula IB-L1:

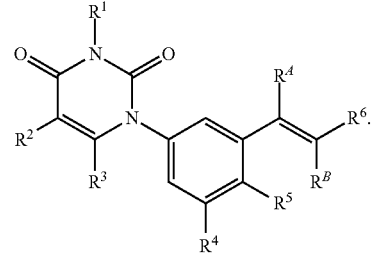

(IB-L1)

Typically, the compounds of formula I-L1 are more potent if R$^6$ and the phenyl-uracil are on opposite sides of the double bond (i.e., in trans configuration in relation to the double bond).

In some embodiments, L is C≡C. In these embodiments, the compounds of formula I correspond in structure to formula I-L2:

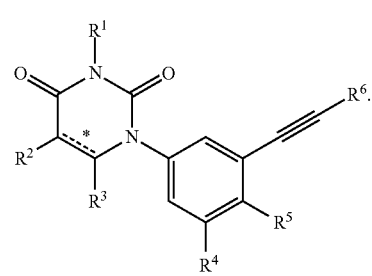

(I-L2)

In some such embodiments, the compounds correspond in structure to IA-L2:

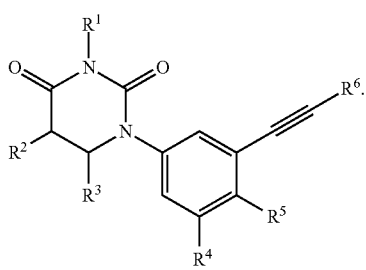
(IA-L2)

In other such embodiments, the compounds correspond in structure to formula IB-L2:

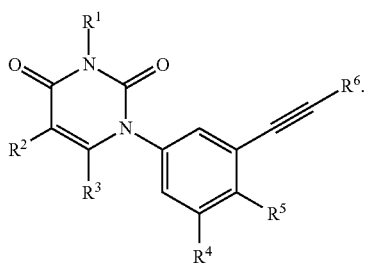
(IB-L2)

In some embodiments, L is C(O)N(R$^C$), wherein R$^C$ is as discussed below. In these embodiments, the compounds of formula I correspond in structure to formula I-L3:

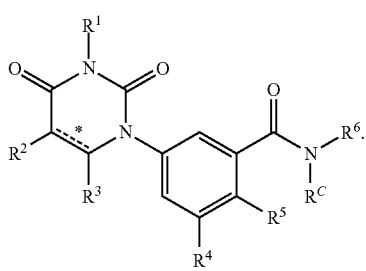
(I-L3)

In some such embodiments, the compounds correspond in structure to formula IA-L3:

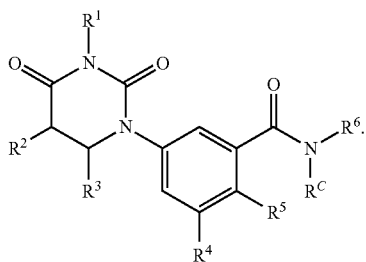
(IA-L3)

In other such embodiments, the compounds correspond in structure to formula IB-L3:

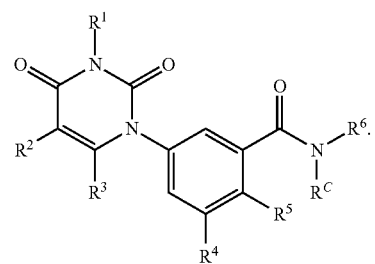
(IB-L3)

In some embodiments, L is N(R$^D$)C(O), wherein R$^D$ is as discussed below. In these embodiments, the compounds of formula I correspond in structure to formula I-L4:

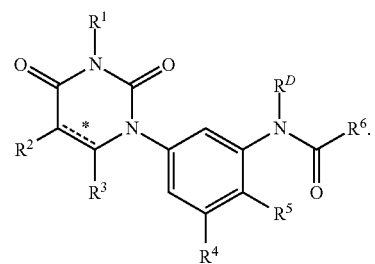
(I-L4)

In some such embodiments, the compounds correspond in structure to formula IA-L4:

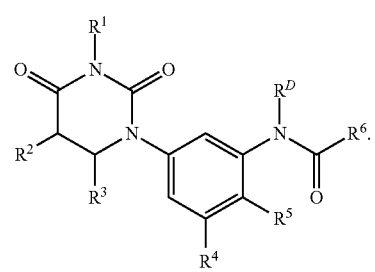
(IA-L4)

In other such embodiments, the compounds correspond in structure to formula IB-L4:

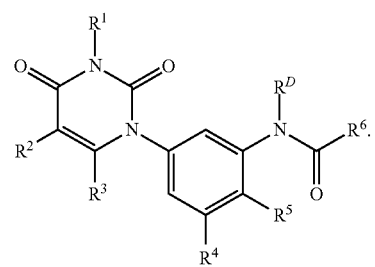
(IB-L4)

In some embodiments, L is $C_1$-$C_2$-alkylene. In these embodiments, the compounds of formula I correspond in structure to formula I-L5-1 (if L is methylene) or I-L5-2 (if L is ethylene):

(I-L5-1)

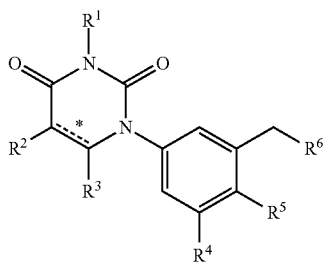

(I-L5-2)

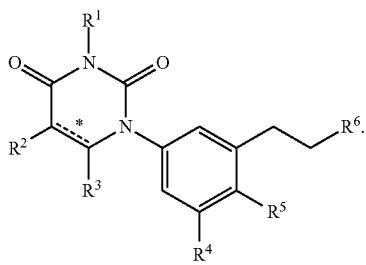

In some such embodiments, compounds correspond in structure to formula IA-L5-1 (if L is methylene) or IA-L5-2 (if L is ethylene):

(IA-L5-1)

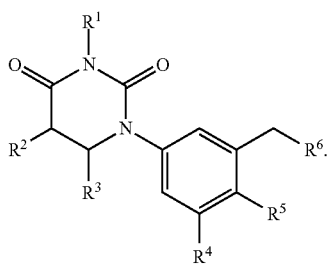

(IA-L5-2)

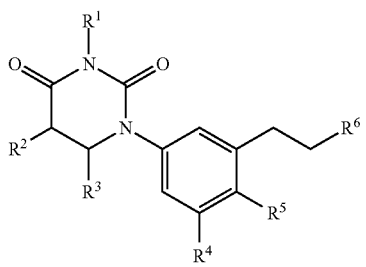

In other such embodiments, the compounds correspond in structure to formula IB-L5-1 (if L is methylene) or IB-L5-2 (if L is ethylene):

(IB-L5-1)

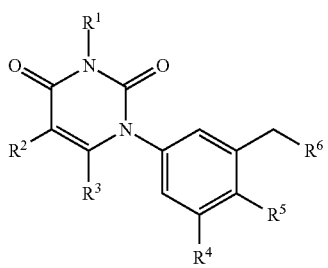

(IB-L5-2)

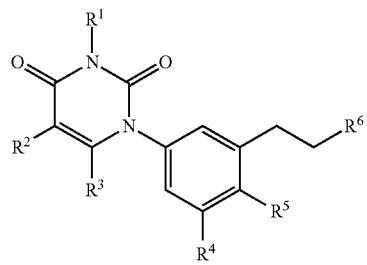

In some embodiments, L is $C(H)_2O$. In these embodiments, the compounds of formula I correspond in structure to formula I-L6:

(I-L6)

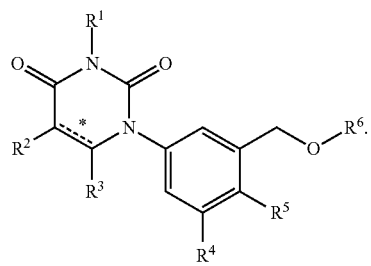

In some such embodiments, the compounds correspond in structure to formula IA-L6:

(IA-L6)

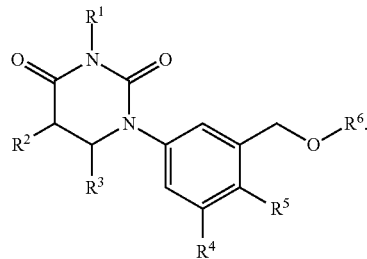

In other such embodiments, the compounds correspond in structure to formula IB-L6:

(IB-L6)

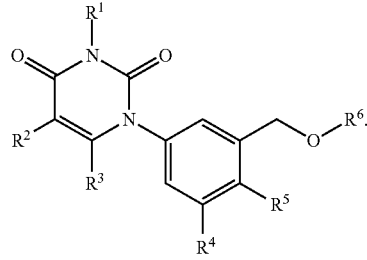

In some embodiments, L is $OC(H)_2$. In these embodiments, the compounds of formula I correspond in structure to formula I-L7:

(I-L7)

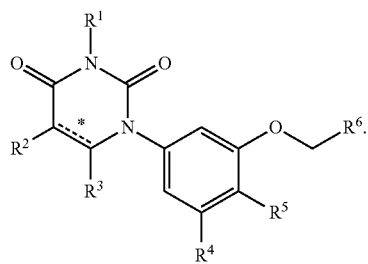

In some such embodiments, the compounds correspond in structure to formula IA-L7:

(IA-L7)

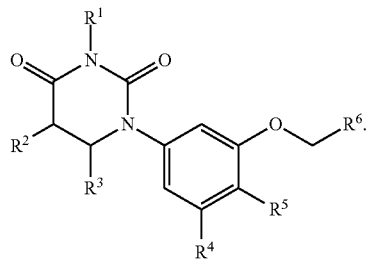

In other such embodiments, the compounds correspond in structure to formula IB-L7:

(IB-L7)

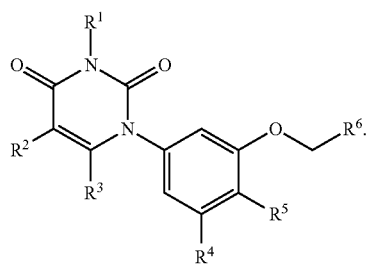

In some embodiments, L is cyclopropyl-1,2-ene. In these embodiments, the compounds of formula I correspond in structure to formula I-L8:

(I-L8)

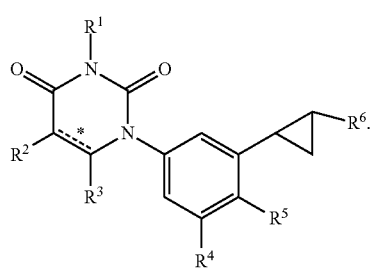

In some such embodiments, the compounds correspond in structure to formula IA-L8:

(IA-L8)

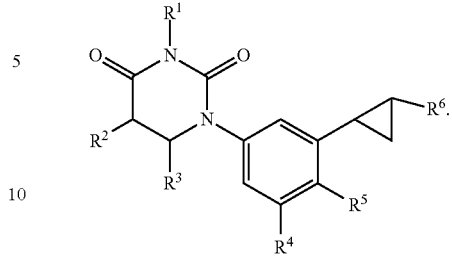

In other such embodiments, the compounds correspond in structure to formula IB-L8:

(IB-L8)

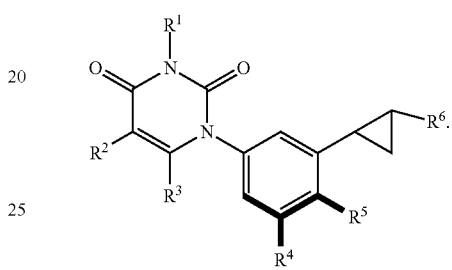

In some embodiments, L is selected from the group consisting of C≡C, ethylene, and cyclopropyl-1,2-ene.

In some embodiments, L is $C(H)_2N(R^L)$. In these embodiments, the compounds of formula I correspond in structure to formula I-L9:

(I-L9)

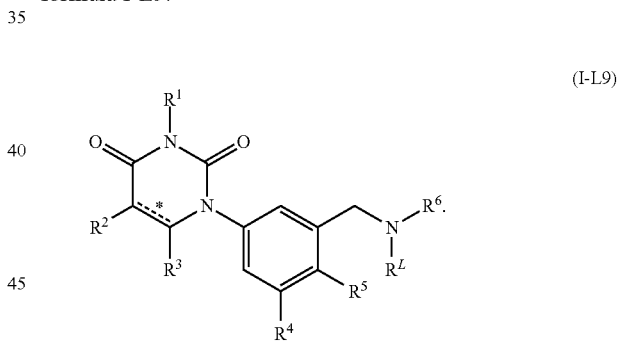

In some such embodiments, the compounds correspond in structure to formula IA-L9:

(IA-L9)

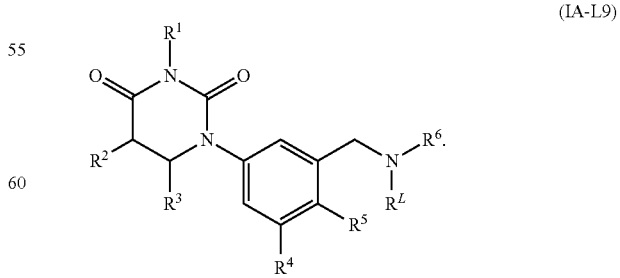

In other such embodiments, the compounds correspond in structure to formula IB-L9:

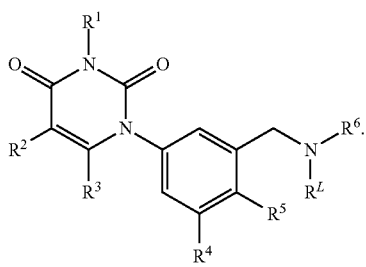
(IB-L9)

In some embodiments, L is N(R^M)C(H)_2. In these embodiments, the compounds of formula I correspond in structure to formula I-L10:

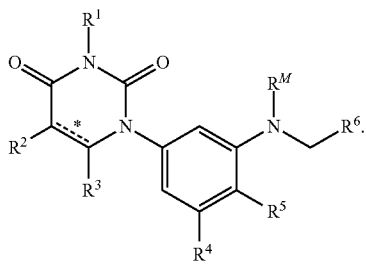
(I-L10)

In some such embodiments, the compounds correspond in structure to formula IA-L10:

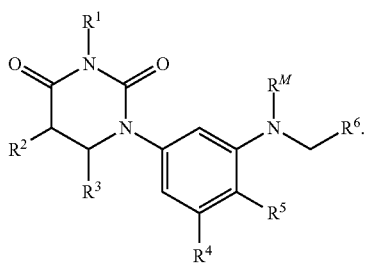
(IA-L10)

In other such embodiments, the compounds correspond in structure to formula IB-L10:

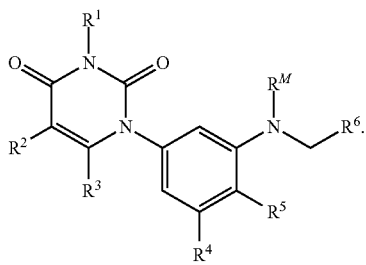
(IB-L10)

In some embodiments, L is C(O)C(H)_2. In these embodiments, the compounds of formula I correspond in structure to formula I-L11:

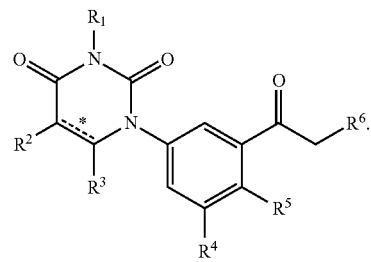
I-L11

In some such embodiments, the compounds correspond in structure to formula IA-L11:

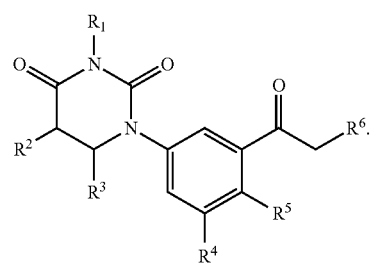
IA-L11

In other such embodiments, the compounds correspond in structure to formula IB-L11:

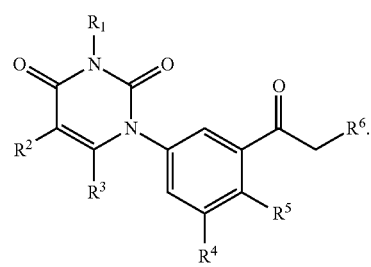
IB-L11

In some embodiments, L is C(H)_2C(O). In these embodiments, the compounds of formula I correspond in structure to formula I-L12:

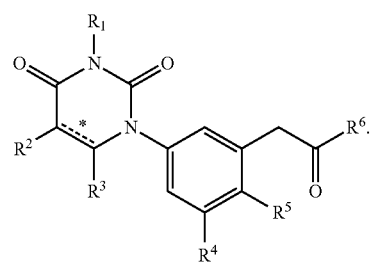
I-L12

In some such embodiments, the compounds correspond in structure to formula IA-L12:

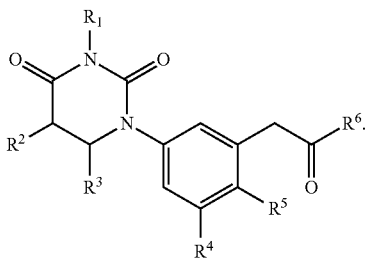

In other such embodiments, the compounds correspond in structure to formula IB-L12:

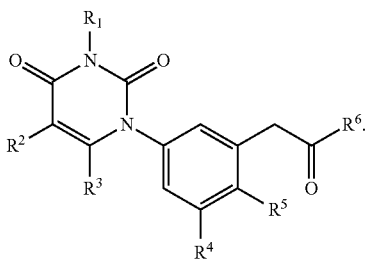

B7. Substituents $R^A$ and $R^B$ $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo, wherein:
- the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, one of $R^A$ and $R^B$ is hydrogen, and the other is selected from the group consisting of $C_1$-$C_6$-alkyl, $C_1$-$C_6$-alkyloxy, $C_3$-$C_8$-cycloalkyl, and halo, wherein:
- the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo.

In some of the above embodiments, $R^A$ is hydrogen. In other of the above embodiments, $R^B$ is hydrogen.

In some embodiment, one of $R^A$ and $R^B$ is hydrogen, and the other is selected from the group consisting of hydrogen, methyl, methoxy, and halo.

In some embodiments, $R^A$ is hydrogen, and $R^B$ is selected from the group consisting of methyl, methoxy, and halo. In some such embodiments, $R^B$ is selected from the group consisting of methyl, methoxy, and fluoro. In other such embodiments, $R^B$ is selected from the group consisting of methyl, methoxy, and chloro. In yet other such embodiments, $R^B$ is selected from the group consisting of methyl, methoxy, and bromo. In further such embodiments, $R^B$ is selected from the group consisting of methyl, methoxy, and iodo. In yet further such embodiments, $R^B$ is selected from the group consisting of methyl, methoxy, chloro, and fluoro.

In some embodiments, $R^B$ is hydrogen, and $R^A$ is selected from the group consisting of methyl, methoxy, and halo. In some such embodiments, $R^A$ is selected from the group consisting of methyl, methoxy, and fluoro. In other such embodiments, $R^A$ is selected from the group consisting of methyl, methoxy, and chloro. In yet other such embodiments, $R^A$ is selected from the group consisting of methyl, methoxy, and bromo. In further such embodiments, $R^A$ is selected from the group consisting of methyl, methoxy, and iodo. In yet further such embodiments, $R^A$ is selected from the group consisting of methyl, methoxy, chloro, and fluoro.

In some embodiments, $R^A$ is hydrogen, and $R^B$ is hydrogen.

B8. Substituent $R^C$ $R^C$ is selected from the group consisting of hydrogen and alkyl. In some such embodiments, $R^C$ is selected from the group consisting of hydrogen and methyl.

In some embodiments, $R^C$ is hydrogen.

In some embodiments, $R^C$ is alkyl. In some such embodiments, $R^C$ is methyl.

B9. Substituent $R^D$ $R^D$ is selected from the group consisting of hydrogen and alkyl. In some such embodiments, $R^D$ is selected from the group consisting of hydrogen and methyl.

In some embodiments, $R^D$ is hydrogen.

In some embodiments, $R^D$ is alkyl. In some such embodiments, $R^D$ is methyl.

B10. Substituent $R^L$ $R^L$ is selected from the group consisting of hydrogen, $C_1$-$C_6$-alkyl, $C_1$-$C_6$-alkyloxy, $C_3$-$C_8$-cycloalkyl, and halo, wherein:
- the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^L$ is selected from the group consisting of hydrogen, $C_1$-$C_6$-alkyl, $C_1$-$C_6$-alkyloxy, $C_3$-$C_8$-cycloalkyl, and halo.

In some embodiments, $R^L$ is selected from the group consisting of hydrogen, $C_1$-$C_6$-alkyl, $C_1$-$C_6$-alkyloxy, and halo, wherein:
- the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^L$ is selected from the group consisting of hydrogen, $C_1$-$C_6$-alkyl, $C_1$-$C_6$-alkyloxy, and halo.

In some of the above embodiments, $R^L$ is halo. In some such embodiments, the halo is fluoro. In other such embodiments, the halo is chloro. In yet other such embodiments, the halo is bromo. In further such embodiments, the halo is iodo.

In some of the above embodiments, $R^L$ is hydrogen.

In some of the above embodiments, $R^L$ is $C_1$-$C_6$-alkyl.

In some of the above embodiments, $R^L$ is $C_1$-$C_6$-alkyloxy.

B11. Substituent $R^M$ $R^M$ is selected from the group consisting of hydrogen, $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^M$ is selected from the group consisting of hydrogen, $C_1$-$C_6$-alkyl, $C_1$-$C_6$-alkyloxy, $C_3$-$C_8$-cycloalkyl, and halo.

In some embodiments, $R^M$ is selected from the group consisting of hydrogen, $C_1$-$C_6$-alkyl, $C_1$-$C_6$-alkyloxy, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^M$ is selected from the group consisting of hydrogen, $C_1$-$C_6$-alkyl, $C_1$-$C_6$-alkyloxy, and halo.

In some of the above embodiments, $R^M$ is halo. In some such embodiments, the halo is fluoro. In other such embodiments, the halo is chloro. In yet other such embodiments, the halo is bromo. In further such embodiments, the halo is iodo.

In some of the above embodiments, $R^M$ is hydrogen.

In some of the above embodiments, $R^M$ is $C_1$-$C_6$-alkyl.

In some of the above embodiments, $R^M$ is $C_1$-$C_6$-alkyloxy.

B12. Substituent $R^6$ $R^6$ is selected from the group consisting of $C_5$-$C_6$-carbocyclyl, 5-6-membered heterocyclyl, fused 2-ring carbocyclyl, and fused 2-ring heterocyclyl, wherein each such substituent optionally is substituted with one or more substituents independently selected from the group consisting of $R^E$, $R^F$, $R^G$, $R^I$, $R^J$, and $R^K$, wherein $R^E$, $R^F$, $R^G$, $R^H$, $R^I$, $R^J$, and $R^K$ are as described below. In some such embodiments, the $C_5$-$C_6$-carbocyclyl, 5-6-membered heterocyclyl, fused 2-ring carbocyclyl, and fused 2-ring heterocyclyl are not substituted. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^G$, $R^H$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, and $R^J$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^F$ and $R^J$. In other such embodiments, the $C_5$-$C_6$-carbocyclyl, 5-6-membered heterocyclyl, fused 2-ring carbocyclyl, and fused 2-ring heterocyclyl are substituted with R. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^G$, $R^H$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, and $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^F$ and $R^J$.

In some embodiments, $R^6$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl and 5-6-membered heterocyclyl are not substituted. In other such embodiments, the $C_5$-$C_6$-carbocyclyl and 5-6-membered heterocyclyl are substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl and 5-6-membered heterocyclyl are substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-membered heterocyclyl are substituted with one, two, or three substituents independently selected from the group consisting of $R^E$, $R^F$, $R^G$, $R^H$, $R^I$, $R^J$, and $R^K$.

In some embodiments, $R^6$ is $C_5$-$C_6$-carbocyclyl optionally substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl is not substituted. In other such embodiments, the $C_5$-$C_6$-carbocyclyl is substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl is substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with one, two, or three substituents independently selected from the group consisting of $R^E$, $R^F$, $R^G$, $R^H$, $R^I$, $R^J$, and $R^K$.

In some embodiments, $R^6$ is 5-6-membered heterocyclyl optionally substituted with one or more substituents independently selected from the group consisting of $R^E$, $R^F$, $R^G$, $R^H$, $R^I$, $R^J$, and $R^K$. In some such embodiments, the 5-6-membered heterocyclyl is not substituted. In other such embodiments, the 5-6-membered heterocyclyl is substituted with a substituent selected from the group consisting of $R^E$, $R^F$, $R^G$, $R^H$, $R^I$, $R^J$, and $R^K$. In yet other such embodiments, the 5-6-membered heterocyclyl is substituted with two substituents independently selected from the group consisting of $R^E$, $R^F$, $R^G$, $R^H$, $R^I$, $R^J$, and $R^K$. In further such embodiments, the 5-6-membered heterocyclyl is substituted with three substituents independently selected from the group consisting of $R^E$, $R^F$, $R^G$, $R^H$, $R^I$, $R^J$, and $R^K$. In further such embodiments, the 5-6-membered heterocyclyl is substituted with one, two, or three substituents independently selected from the group consisting of $R^E$, $R^F$, $R^G$, $R^H$, $R^I$, $R^J$, and $R^K$.

In some embodiments, $R^6$ is selected from the group consisting of fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the fused 2-ring carbocyclyl and fused 2-ring heterocyclyl are not substituted. In other such embodiments, the fused 2-ring carbocyclyl and fused 2-ring heterocyclyl are substituted with a substituent selected from the group consisting of $R^E$, $R^F$, $R^G$, $R^H$, $R^I$, $R^J$, and $R^K$. In yet other such embodiments, the fused 2-ring carbocyclyl and fused 2-ring heterocyclyl are substituted with two substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with three substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with one, two, or three substituents independently selected from the group consisting of $R^E$, $R^F$, $R^G$, $R^H$, $R^I$, $R^J$, and $R^K$.

In some embodiments, $R^6$ is fused 2-ring carbocyclyl optionally substituted with one or more substituents independently selected from the group consisting of $R^E$, $R^F$, $R^G$, $R^H$, $R^I$, $R^J$, and $R^K$. In some such embodiments, the fused 2-ring carbocyclyl is not substituted. In other such embodiments, the fused 2-ring carbocyclyl is substituted with a substituent selected from the group consisting of $R^E$, $R^F$, $R^G$, $R^H$, $R^I$, $R^J$, and $R^K$. In yet other such embodiments, the fused 2-ring carbocyclyl is substituted with two substituents independently selected from the group consisting of $R^E$, $R^F$, $R^G$, $R^H$, $R^I$, $R^J$, and $R^K$. In further such embodiments, the fused 2-ring carbocyclyl is substituted with three substituents independently selected from the group consisting of $R^E$, $R^F$, $R^G$, $R^H$, $R^I$, $R^J$, and $R^K$. In further such embodiments, the fused 2-ring carbocyclyl is substituted with one, two, or three substituents independently selected from the group consisting of $R^E$, $R^F$, $R^G$, $R^H$, $R^I$, $R^J$, and $R^K$.

In some embodiments, $R^6$ is fused 2-ring heterocyclyl optionally substituted with one or more substituents independently selected from the group consisting of $R^E$, $R^F$, $R^G$, $R^H$, $R^I$, $R^J$, and $R^K$. In some such embodiments, the fused 2-ring heterocyclyl is not substituted. In other such embodiments, the fused 2-ring heterocyclyl is substituted with a substituent selected from the group consisting of $R^E$, $R^F$, $R^G$, $R^H$, $R^I$, $R^J$, and $R^K$. In yet other such embodiments, the fused 2-ring heterocyclyl is substituted with two substituents independently selected from the group consisting of $R^E$, $R^F$, $R^G$, $R^H$, $R^I$, $R^J$, and $R^K$. In further such embodiments, the fused 2-ring heterocyclyl is substituted with three substituents independently selected from the group consisting of $R^E$, $R^F$, $R^G$, $R^H$, $R^I$, $R^J$, and $R^K$. In further such embodiments, the fused 2-ring heterocyclyl is substituted with one, two, or three substituents independently selected from the group consisting of $R^E$, $R^F$, $R^G$, $R^H$, $R^I$, $R^J$, and $R^K$.

In some of the above embodiments, the optionally substituted $C_5$-$C_6$-carbocyclyl is selected from the group consisting of cyclopentyl, cyclopentenyl, cyclopentadienyl, cyclohexyl, cyclohexenyl, cyclohexadienyl, and phenyl. In some such embodiments, the optionally substituted $C_5$-$C_6$-carbocyclyl is phenyl.

In some of the above embodiments, the optionally substituted $C_5$-$C_6$-carbocyclyl is $C_5$-carbocyclyl. Examples of $C_5$-carbocyclyls include cyclopentyl, cyclopentenyl, and cyclopentadienyl.

In other of the above embodiments, the optionally substituted $C_5$-$C_6$-carbocyclyl is $C_6$-carbocyclyl. Examples of $C_6$-carbocyclyls include cyclohexyl, cyclohexenyl, cyclohexadienyl, and phenyl.

In some of the above embodiments, the optionally substituted 5-6-membered-heterocyclyl is selected from the group consisting of furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted 5-6-membered-heterocyclyl is 5-membered heterocyclyl. Examples of such 5-membered heterocyclyl include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

In other of the above embodiments, the optionally substituted 5-6-membered-heterocyclyl is 6-membered heterocyclyl. Examples of 6-membered heterocyclyls include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted fused 2-ring carbocyclyl is selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl. In some such embodiments, the optionally substituted fused 2-ring carbocyclyl is selected from the group consisting of naphthalenyl and dihydroindenyl. In some such embodiments, the optionally substituted fused 2-ring carbocyclyl is naphthalenyl. In other such embodiments, the optionally substituted fused 2-ring carbocyclyl is dihydroindenyl. In further such embodiments, the optionally substituted fused 2-ring carbocyclyl is indenyl.

In some of the above embodiments, the optionally substituted fused 2-ring heterocyclyl is selected from the group consisting of

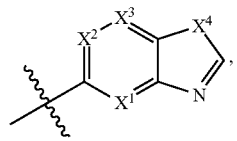 (H1)

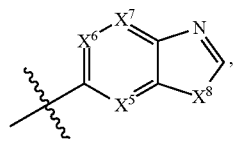 (H2)

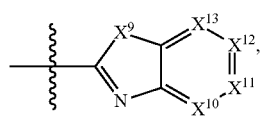 (H3)

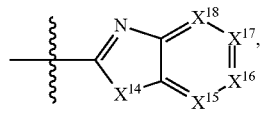 (H4)

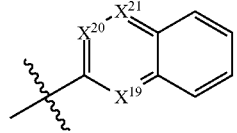 (H5)

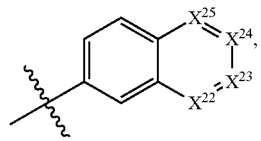 (H6)

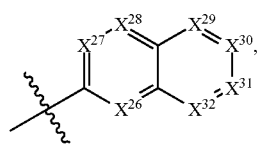 (H7)

-continued

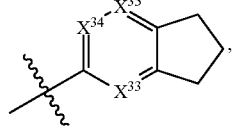 (H8)

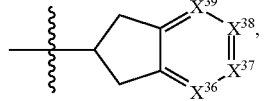 (H9)

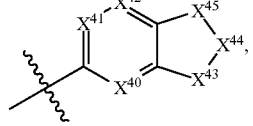 (H10)

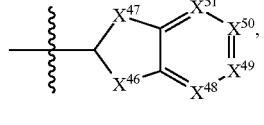 (H11)

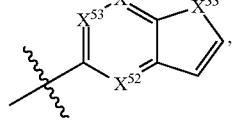 (H12)

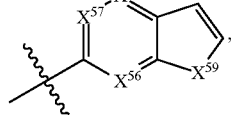 (H13)

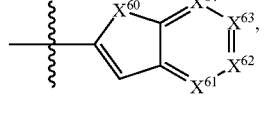 (H14)

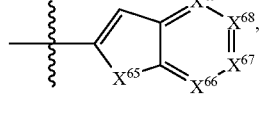 (H15)

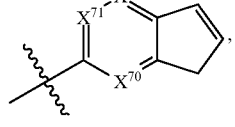 (H16)

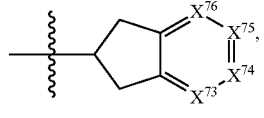 (H17)

(H18)

-continued (H19)

[chemical structure with $X^{77}$, $X^{78}$]

(H20)

[benzoxazole structure]

(H21)

[benzisoxazole structure], and (H22)

[isoindoline structure];

$X^1$, $X^2$, and $X^3$ are independently selected from the group consisting of N and C(H);
$X^4$ is selected from the group consisting of N(H), O, and S;
$X^5$, $X^6$, and $X^7$ are independently selected from the group consisting of N and C(H);
$X^8$ is selected from the group consisting of N(H), O, and S;
$X^9$ is selected from the group consisting of N(H), O, and S;
$X^{10}$, $X^{11}$, $X^{12}$, and $X^{13}$ are independently selected from the group consisting of N and C(H);
$X^{14}$ is selected from the group consisting of N(H), O, and S;
$X^{15}$, $X^{16}$, $X^{17}$, and $X^{18}$ are independently selected from the group consisting of N and C(H);
one or more of $X^{19}$, $X^{20}$, and $X^{21}$ is N, and the remaining one(s) is/are C(H);
one or more of $X^{22}$, $X^{23}$, $X^{24}$, and $X^{25}$ is N, and the remaining one(s) is/are C(H);
one or more of $X^{26}$, $X^{27}$, and $X^{28}$ is N, and the remaining one(s) is/are C(H);
one or more of $X^{29}$, $X^{30}$, $X^{31}$, and $X^{32}$ is N, and the remaining one(s) is/are C(H);
one or more of $X^{33}$, $X^{34}$, and $X^{35}$ is N, and the remaining one(s) is/are C(H);
one or more of $X^{36}$, $X^{37}$, $X^{38}$, and $X^{39}$ is N, and the remaining one(s) is/are C(H);
$X^{40}$, $X^{41}$, and $X^{42}$ are independently selected from the group consisting of N and C(H);
one of $X^{43}$, $X^{44}$, and $X^{45}$ is selected from the group consisting of N(H), O, and S, and the remaining two are C(H)$_2$;
one of $X^{46}$ and $X^{47}$ is selected from the group consisting of N(H), O, and S, and the other one is C(H)$_2$;
$X^{48}$, $X^{49}$, $X^{50}$, and $X^{51}$ are independently selected from the group consisting of N and C(H);
$X^{52}$, $X^{53}$, and $X^{54}$ are independently selected from the group consisting of N and C(H);
$X^{55}$ is selected from the group consisting of N(H), O, and S;
$X^{56}$, $X^{57}$, and $X^{58}$ are independently selected from the group consisting of N and C(H);
$X^{59}$ is selected from the group consisting of N(H), O, and S;
$X^{60}$ is selected from the group consisting of N(H), O, and S;
$X^{61}$, $X^{62}$, $X^{63}$, and $X^{64}$ are independently selected from the group consisting of N and C(H);
$X^{65}$ is selected from the group consisting of N(H), O, and S;
$X^{66}$, $X^{67}$, $X^{68}$, and $X^{69}$ are independently selected from the group consisting of N and C(H);
one or more of $X^{70}$, $X^{71}$, and $X^{72}$ is N, and the remaining one(s) is/are C(H);
one or more of $X^{73}$, $X^{74}$, $X^{75}$, and $X^{76}$ is N, and the remaining one(s) is/are C(H); and
one of $X^{77}$ and $X^{78}$ is N(H), and the remaining one is C(H)$_2$.

In some of the above embodiments, the optionally substituted fused 2-ring heterocyclyl is selected from the group consisting of (H1)

[structure with $X^1$, $X^2$, $X^3$, $X^4$]

(H2)

[structure with $X^5$, $X^6$, $X^7$, $X^8$]

(H3)

[structure with $X^9$, $X^{10}$, $X^{11}$, $X^{12}$, $X^{13}$]

(H4)

[structure with $X^{14}$, $X^{15}$, $X^{16}$, $X^{17}$, $X^{18}$]

(H5)

[structure with $X^{19}$, $X^{20}$, $X^{21}$]

(H6)

[structure with $X^{22}$, $X^{23}$, $X^{24}$, $X^{25}$]

(H7)

[structure with $X^{26}$, $X^{27}$, $X^{28}$, $X^{29}$, $X^{30}$, $X^{31}$, $X^{32}$]

(H8)

[structure with $X^{33}$, $X^{34}$, $X^{35}$]

(H9)

[structure with $X^{36}$, $X^{37}$, $X^{38}$, $X^{39}$]

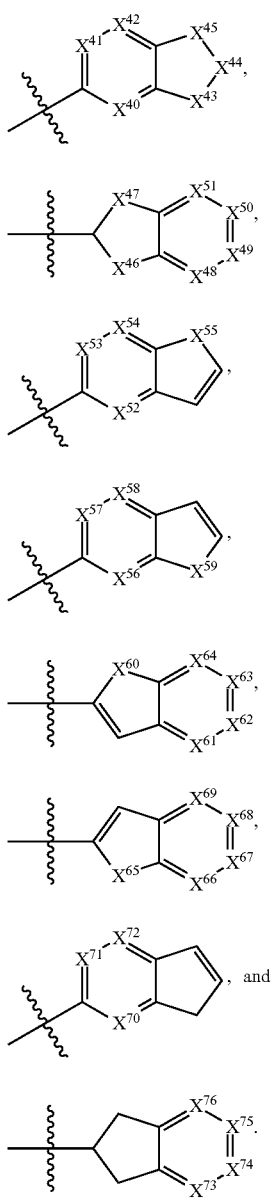

In some of the above embodiments, the optionally substituted fused 2-ring heterocyclyl is selected from the group consisting of:

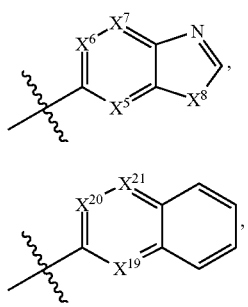

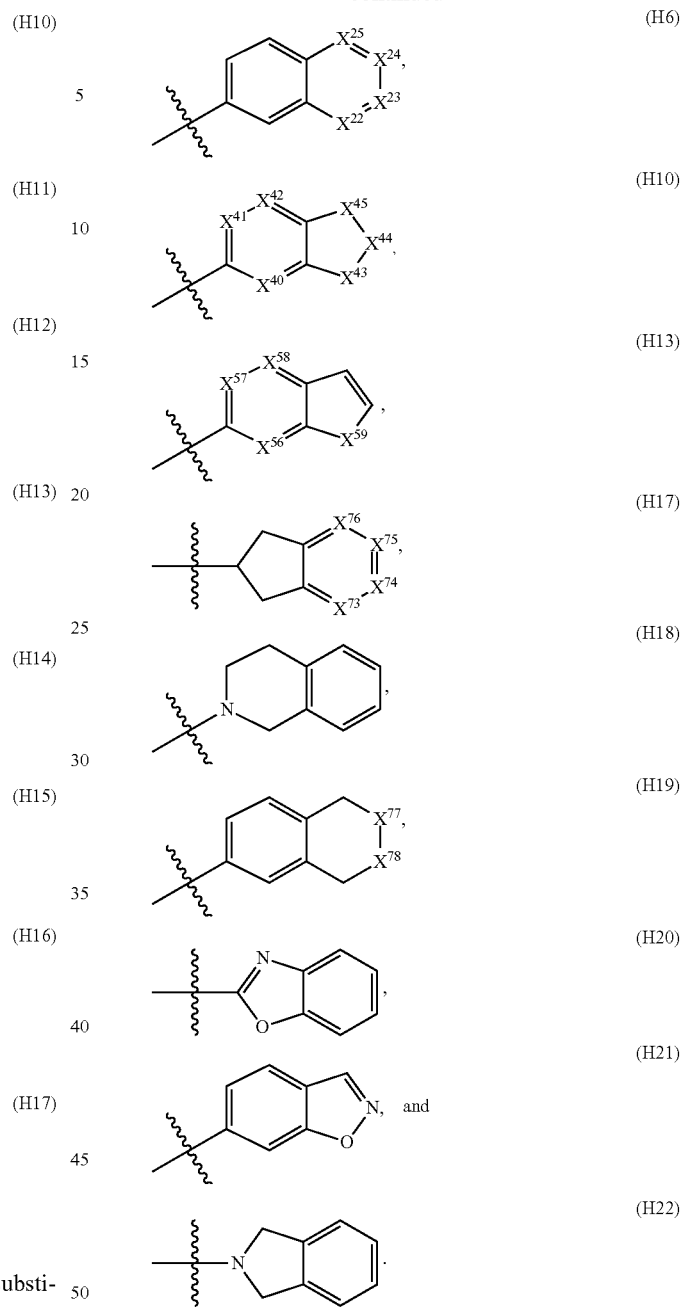

In some of the above embodiments, $X^1$, $X^2$, and $X^3$ are C(H).
In some of the above embodiments, $X^5$, $X^6$, and $X^7$ are C(H).
In some of the above embodiments, $X^{10}$, $X^{11}$, $X^{12}$, and $X^{13}$ are C(H).
In some of the above embodiments, $X^{15}$, $X^{16}$, $X^{17}$, and $X^{18}$ are C(H).
In some of the above embodiments, one of $X^{19}$, $X^{20}$, and $X^{21}$ is N.
In some of the above embodiments, one of $X^{22}$, $X^{23}$, $X^{24}$, and $X^{25}$ is N.
In some of the above embodiments, one of $X^{26}$, $X^{27}$, and $X^{28}$ is N, and one of $X^{29}$, $X^{30}$, $X^{31}$, and $X^{32}$ is N.
In some of the above embodiments, $X^{40}$, $X^{41}$, and $X^{42}$ are C(H).

In some of the above embodiments, $X^{48}$, $X^{49}$, $X^{50}$, and $X^{51}$ are C(H).

In some of the above embodiments, $X^{52}$, $X^{53}$, and $X^{54}$ are C(H).

In some of the above embodiments, $X^{56}$, $X^{57}$, and $X^{58}$ are C(H).

In some of the above embodiments, $X^{61}$, $X^{62}$, $X^{63}$, and $X^{64}$ are C(H).

In some of the above embodiments, $X^{66}$, $X^{67}$, $X^{68}$, and $X^{69}$ are C(H).

In some of the above embodiments, one or more of $X^{70}$, $X^{71}$, and $X^{72}$ is N, and the remaining one(s) is/are C(H).

In some of the above embodiments, one or more of $X^{73}$, $X^{74}$, $X^{75}$, and $X^{76}$ is N, and the remaining one(s) is/are C(H).

B13. Substituent $R^E$

Each $R^E$ is independently selected from the group consisting of halo, nitro, hydroxy, oxo, carboxy, cyano, amino, imino, azido, and aldehydro, wherein the amino optionally is substituted with one or two substituents independently selected from the group consisting of alkyl, alkenyl, and alkynyl.

In some embodiment, each $R^E$ is independently selected from the group consisting of halo, nitro, hydroxy, oxo, carboxy, amino, imino, and aldehydro, wherein the amino optionally is substituted with one or two independently selected alkyl.

In some embodiment, each $R^E$ is independently selected from the group consisting of halo, nitro, hydroxy, oxo, carboxy, amino, imino, aldehydro, and alkylamino.

In some embodiment, each $R^E$ is independently selected from the group consisting of chloro, fluoro, nitro, hydroxy, oxo, carboxy, amino, imino, aldehydro, and alkylamino.

In some embodiment, each $R^E$ is independently selected from the group consisting of halo, nitro, hydroxy, oxo, carboxy, cyano, amino, imino, and azido. In some such embodiments, each $R^E$ is halo. In other such embodiments, each $R^E$ is nitro. In yet other such embodiments, each $R^E$ is hydroxy. In yet other such embodiments, each $R^E$ is oxo. In yet other such embodiments, each $R^E$ is carboxy. In yet other such embodiments, each $R^E$ is cyano. In yet other such embodiments, each $R^E$ is amino. In further such embodiments, each $R^E$ is imino. In yet further such embodiments, each $R^E$ is and azido.

In some embodiments, each $R^E$ is independently selected from the group consisting of halo, nitro, hydroxy, oxo, carboxy, cyano, amino, and imino.

B14. Substituent $R^F$

Each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy,
    wherein:
      amino portion of the alkylsulfonylamino optionally is substituted with a substituent selected from the group consisting of alkyl, alkenyl, and alkynyl.

In some embodiment, each $R^F$ is independently selected from the group consisting of alkyl, alkenyl, and alkynyl, wherein:
  each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, imino, aminosulfonyl, and aminocarbonyl optionally are substituted with one or two substituents independently selected from the group consisting of alkyl, alkenyl, alkynyl, alkylsulfonyl, alkenylsulfonyl, alkynylsulfonyl, and alkylsulfonylamino, wherein:
      amino portion of the alkylsulfonylamino optionally is substituted with a substituent selected from the group consisting of alkyl, alkenyl, and alkynyl.

In some of the above embodiments, each $R^F$ is independently selected from the group consisting of the alkyl, alkynyl, and alkynyl, wherein such substituents are not substituted.

In some embodiments, each $R^F$ is independently selected from the group consisting of alkyl, alkenyl, and alkynyl, wherein:
  each such substituent optionally is substituted with one or two substituents independently selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
    the amino, imino, aminosulfonyl, and aminocarbonyl optionally are substituted with one or two substituents independently selected from the group consisting of alkyl, alkylsulfonyl, and alkylsulfonylamino,
    wherein:
      amino portion of the alkylsulfonylamino optionally is substituted with alkyl.

In some embodiments, each $R^F$ is an independently selected alkyl optionally substituted with a substituent selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
  the amino, imino, aminosulfonyl, and aminocarbonyl optionally are substituted with one or two substituents independently selected from the group consisting of alkyl, alkylsulfonyl, and alkylsulfonylamino, wherein:
    amino portion of the alkylsulfonylamino optionally is substituted with alkyl.

In some embodiments, each $R^F$ is an independently selected alkyl optionally substituted with a substituent selected from the group consisting of carboxy, halo, amino, imino, and aminosulfonyl, wherein:
  the amino, imino, and aminosulfonyl optionally are substituted with one or two substituents independently selected from the group consisting of alkyl, alkylsulfonyl, and alkylsulfonylamino.

In some embodiments, each $R^F$ is an independently selected alkyl optionally substituted with amino, wherein the amino optionally is substituted with alkylsulfonyl.

In some embodiments, each $R^F$ is an independently selected alkyl substituted with amino, wherein the amino is substituted with alkylsulfonyl. In some such embodiments, each $R^F$ is methylsulfonylaminomethyl.

In some embodiments, each $R^F$ is independently selected from the group consisting of alkyl, alkenyl, and alkynyl, wherein:
  each such substituent optionally is substituted with one, two, or three substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

In some embodiments, each $R^F$ is independently selected alkyl substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

B15. Substituent $R^G$

Each $R^G$ is independently selected from the group consisting of carbocyclyl and heterocyclyl, wherein:
  each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^G$ is independently selected from the group consisting of carbocyclyl and heterocyclyl, wherein such substituents are not substituted.

In some embodiments, each $R^G$ is independently selected from the group consisting of carbocyclyl and heterocyclyl, wherein:
  each such substituent optionally is substituted with one or two substituents independently selected from the group consisting of alkyl, carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl and alkylsulfonyl.

In some of the above embodiments, the carbocyclyl is $C_3$-$C_6$-carbocyclyl.

In some of the above embodiments, the heterocyclyl is 5-6-membered heterocyclyl.

B16. Substituent $R^H$

Each $R^H$ is independently selected from the group consisting of alkyloxy, alkenyloxy, alkynyloxy, alkylsulfonyloxy, alkenylsulfonyloxy, and alkynylsulfonyloxy, wherein:
  each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^H$ is independently selected from the group consisting of alkyloxy, alkenyloxy, alkynyloxy, alkylsulfonyloxy, alkenylsulfonyloxy, and alkynylsulfonyloxy, wherein such substituents are not substituted.

In some embodiments, each $R^H$ is independently selected from the group consisting of alkyloxy and alkylsulfonyloxy, wherein:
  each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
    the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
  each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, wherein:
    the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
  each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl.

In some embodiments, each $R^H$ is independently selected alkyloxy.

In some embodiments, each $R^H$ is independently selected alkylsulfonyloxy.

B17. Substituent $R^I$

Each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:

(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
(b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
the carbocyclyl and heterocyclyl optionally are substituted with one or two substituents independently selected from the group consisting of halo, alkyl, and oxo.

In some embodiments, each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein such substituents are not substituted.

In some embodiments, each $R^I$ is independently selected from the group consisting of alkylcarbonyl, aminocarbonyl, alkyloxycarbonyl, carbocyclylcarbonyl, and heterocyclylcarbonyl, wherein:
(a) the alkylcarbonyl optionally is substituted with a substituent selected from the group consisting of carboxy, hydroxy, halo, amino, nitro, oxo, aminosulfonyl, alkyloxycarbonyl, alkylcarbonyloxy, alkyloxy, and aminocarbonyl, and
(b) the aminocarbonyl optionally is substituted with a substituent selected from the group consisting of alkyl, alkyloxyalkyl, alkylsulfonyl, and alkylsulfonylamino.

In some embodiments, each $R^I$ is independently selected from the group consisting of alkylcarbonyl and aminocarbonyl, wherein:
the aminocarbonyl optionally is substituted with a substituent selected from the group consisting of alkyl, alkyloxyalkyl, alkylsulfonyl, and alkylsulfonylamino.

In some embodiment, each $R^I$ is independently selected from the group consisting of alkylcarbonyl, alkenylcarbonyl, alkynylcarbonyl, and aminocarbonyl, wherein:
(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
(b) the aminocarbonyl optionally is substituted with one or two substituents independently selected from the group consisting of alkyl, alkenyl, alkynyl, and alkylsulfonylamino.

In some of the above embodiments, each $R^I$ is independently selected from the group consisting of alkylcarbonyl, alkenylcarbonyl, alkynylcarbonyl, and aminocarbonyl, wherein such substituents are not substituted.

In some embodiments, each $R^I$ is independently selected from the group consisting of alkylcarbonyl and aminocarbonyl, wherein:
(a) the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl, and
(b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
(a) the alkylcarbonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, and
(b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl.

In some embodiments, each $R^I$ is independently selected alkylcarbonyl.

In some embodiments, each $R^I$ is independently selected aminocarbonyl.

B18. Substituent $R^J$

Each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;
(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl.

In some embodiment, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;
(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl; and In some of the above embodiments, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein such substituents are not substituted.

In some embodiments, each $R^J$ is independently selected from the group consisting of carbocyclylsulfonylamino, heterocyclylsulfonylamino, alkylcarbonylamino, alkyloxycarbonylamino, alkylsulfonylamino, aminocarbonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy;
(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:
the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl,
(b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy;
(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:
the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:
the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is independently selected from the group consisting of carbocyclylsulfonylamino, heterocyclylsulfonylamino, alkylsulfonylamino, and alkylsulfonylaminoimino, wherein:
the alkyl portion of the alkylsulfonylamino and alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is independently selected from the group consisting of carbocyclylsulfonylamino, heterocyclylsulfonylamino, alkylsulfonylamino, and alkylsulfonylaminoimino, wherein:
the carbocyclyl and heterocyclyl portions of such substituents optionally are substituted with one or two substituents independently selected from the group consisting of alkyl, carboxy, hydroxy, alkyloxy, halo, nitro, cyano, and amino In some embodiments, each $R^J$ is independently selected from the group consisting of carbocyclylsulfonylamino and heterocyclylsulfonylamino, wherein:
the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^J$ is independently selected from the group consisting of alkylsulfonylamino, alkenylsulfonylamino, alkynylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
(a) the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylamino. In some such embodiments, each $R^J$ is methylsulfonylamino.

In some embodiments, each $R^J$ is an independently selected alkylsulfonylaminoimino, wherein:
(a) the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylaminoimino. In some such embodiments, each $R^J$ is methylsulfonylaminoimino.

In some embodiments, each $R^J$ is independently selected from the group consisting of alkylcarbonylamino and alkyloxycarbonylamino, wherein:
the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

B19. Substituent $R^K$

Each $R^K$ is independently selected from the group consisting of aminosulfonyl, alkylsulfonyl, alkenylsulfonyl, and alkynylsulfonyl, wherein:
(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, and alkynyl; and
(b) the aminosulfonyl optionally is substituted with one or two substituents independently selected from the group consisting of alkyl, alkenyl, and alkynyl.

In some of the above embodiments, each $R^K$ is independently selected from the group consisting of aminosulfonyl, alkylsulfonyl, alkenylsulfonyl, and alkynylsulfonyl, wherein such substituents are not substituted.

In some embodiments, each $R^K$ is independently selected from the group consisting of aminosulfonyl and alkylsulfonyl, wherein:
(a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
(b) the aminosulfonyl optionally is substituted with one or two substituents independently selected alkyl.

In some embodiments, each $R^K$ is independently selected from the group consisting of aminosulfonyl and alkylsulfonyl.

C. EMBODIMENTS OF COMPOUNDS OF FORMULA I

Various embodiments of substituents $R^1, R^2, R^3, R^4, R^5, L, R^A, R^B, R^C, R^D, R^6, R^E, R^F, R^G, R^H, R^I, R^J$, and $R^K$ have been discussed above. These substituent embodiments can be combined to form various embodiments of compounds of formula I. All embodiments of compounds of formula I formed by combining the substituent embodiments discussed above are within the scope of Applicants' invention, and some illustrative embodiments of the compounds of formula I are provided below.

In some embodiments, the compounds of formula I correspond in structure to formula I-L0:

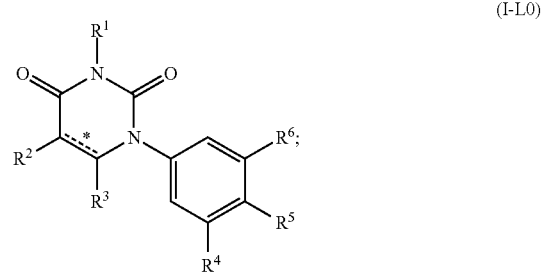

(I-L0)

$\stackrel{*}{=\!=\!=}$ is selected from the group consisting of single carbon-carbon bond and double carbon-carbon bond;
$R^1$ is selected from the group consisting of hydrogen and methyl;
$R^2$ is selected from the group consisting of hydrogen and halo
$R^3$ is selected from the group consisting of hydrogen and halo;
$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino;
$R^5$ is selected from the group consisting of hydrogen, hydroxy, alkyloxy, and halo;
$R^6$ is selected from the group consisting of $C_5$-$C_6$-carbocyclyl, 5-6-membered heterocyclyl, fused 2-ring heterocyclyl, and fused 2-ring carbocyclyl, wherein each such substituent is substituted with one, two, or three substituents independently selected from the group consisting of $R^E, R^F, R^I, R^J$, and $R^K$;
each $R^E$ is independently selected from the group consisting of chloro, fluoro, nitro, hydroxy, oxo, carboxy, amino, imino, aldehydro, and alkylamino;
each $R^F$ is an independently selected alkyl optionally substituted with a substituent selected from the group consisting of carboxy, halo, amino, imino, and aminosulfonyl, wherein:
the amino, imino, and aminosulfonyl optionally are substituted with one or two substituents independently selected from the group consisting of alkyl, alkylsulfonyl, and alkylsulfonylamino;
each $R^I$ is independently selected from the group consisting of alkylcarbonyl and aminocarbonyl, wherein:
the aminocarbonyl optionally is substituted with a substituent selected from the group consisting of alkyl, alkyloxyalkyl, alkylsulfonyl, and alkylsulfonylamino;
each $R^J$ is independently selected from the group consisting of alkylsulfonylamino, alkenylsulfonylamino, alkynylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy; and
each $R^K$ is independently selected from the group consisting of aminosulfonyl and alkylsulfonyl, wherein:
(a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
(b) the aminosulfonyl optionally is substituted with one or two substituents independently selected alkyl.

In some embodiments, in the compounds of formula I:

$\stackrel{*}{=\!=\!=}$ is selected from the group consisting of single carbon-carbon bond and double carbon-carbon bond;
$R^1$ is selected from the group consisting of hydrogen and methyl;
$R^2$ is selected from the group consisting of hydrogen and halo;
$R^3$ is selected from the group consisting of hydrogen and halo;
$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino;
$R^5$ is selected from the group consisting of hydrogen, hydroxy, alkyloxy, and halo;
L is selected from the group consisting of $C(R^A)=C(R^B)$, ethylene, and cyclopropyl-1,2-ene;
one of $R^A$ and $R^B$ is hydrogen, and the other is selected from the group consisting of hydrogen, methyl, methoxy, and halo;
$R^6$ is selected from the group consisting of $C_5$-$C_6$-carbocyclyl and 5-6-membered heterocyclyl, wherein each such substituent is substituted with one, two, or three substituents independently selected from the group consisting of $R^E$, $R^F$, and $R^J$;

each $R^E$ is independently selected from the group consisting of chloro, fluoro, nitro, hydroxy, oxo, carboxy, amino, imino, aldehydro, and alkylamino;
each $R^F$ is an independently selected alkyl optionally substituted with a substituent selected from the group consisting of carboxy, halo, amino, imino, and aminosulfonyl, wherein:
the amino, imino, and aminosulfonyl optionally are substituted with one or two substituents independently selected from the group consisting of alkyl, alkylsulfonyl, and alkylsulfonylamino;
each $R^I$ is independently selected from the group consisting of alkylcarbonyl and aminocarbonyl, wherein:
the aminocarbonyl optionally is substituted with a substituent selected from the group consisting of alkyl, alkyloxyalkyl, alkylsulfonyl, and alkylsulfonylamino; and
each $R^J$ is independently selected from the group consisting of alkylsulfonylamino, alkenylsulfonylamino, alkynylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein the alkyl optionally is substituted with one or more hydroxy.

In some embodiments, the compounds of formula I correspond in structure to formula I-L0:

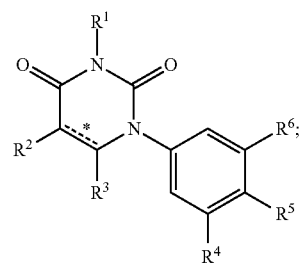

(I-L0)

$\stackrel{*}{=\!=\!=}$ is selected from the group consisting of single carbon-carbon bond and double carbon-carbon bond;
$R^1$ is hydrogen;
$R^2$ is selected from the group consisting of hydrogen and halo R³ is hydrogen;

R⁴ is tert-butyl;

R⁵ is selected from the group consisting of hydrogen, hydroxy, methoxy, and halo;

R⁶ is a fused 2-ring carbocyclyl selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl, wherein each such substituent is substituted with a substituent selected from the group consisting of $R^F$ and $R^J$;

$R^F$ is alkylsulfonylaminoalkyl; and $R^J$ is alkylsulfonylamino

Examples of compounds of formula I (and salts thereof) are shown in Tables 1 through 38 below. The synthesis examples below provide step-by-step preparation instructions for some of these compounds. The remaining compounds were prepared utilizing the general method-of-preparation discussion, specific synthesis examples below, and/or the discussion throughout this application.

TABLE 1

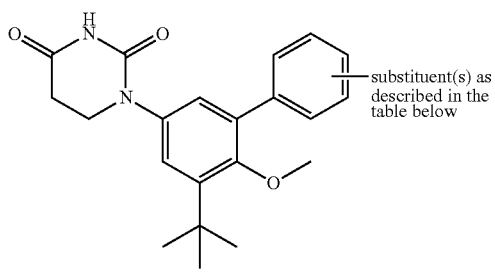

| compound | substituent(s) |
|---|---|
| IA-L0-1.1 | -4-C(H)=NN(H)S(O)₂CH₃ |
| IA-L0-1.2 | -4-C(CH₃)=NN(H)S(O)₂CH₃ |
| IA-L0-1.3 | -3-F and -4-C(H)=NN(H)S(O)₂CH₃ and -5-F |
| IA-L0-1.4 | -3-F and -4-C(H)=NN(H)S(O)₂CH₃ |
| IA-L0-1.5 | -3-C(H)=NN(H)S(O)₂CH₃ and -4-OCH₃ |
| IA-L0-1.6 | -2-F and -3-F and -4-C(H)=NN(H)S(O)₂CH₃ |
| IA-L0-1.7 | -3-C(H)=NN(H)S(O)₂CH₃ |
| IA-L0-1.8 | -3-C(CH₃)=NN(H)S(O)₂CH₃ |

TABLE 2

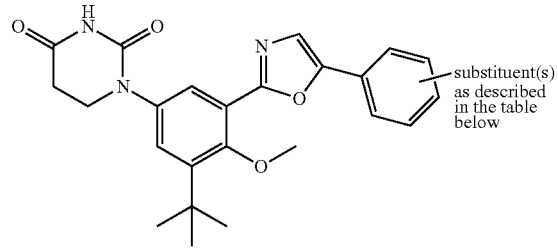

| compound | substituent(s) |
|---|---|
| IA-L0-1.9 | -3-N(H)S(O)₂CH₃ |
| IA-L0-1.10 | -3-NO₂ |
| IA-L0-1.11 | -4-NO₂ |

TABLE 3

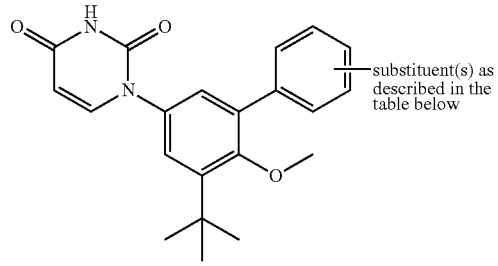

| compound | substituent(s) |
|---|---|
| IB-L0-1.1 | -4-C(H)=NN(H)S(O)₂CH₃ |
| IB-L0-1.2 | -4-N(H)S(O)₂CH₃ |
| IB-L0-1.3 | -3-F and -4-C(H)=NN(H)S(O)₂CH₃ |
| IB-L0-1.4 | -4-C(H)₂C(H)₂N(H)S(O)₂CH₃ |
| IB-L0-1.5 | -4-C(CH₃)=NN(H)S(O)₂CH₃ |
| IB-L0-1.6 | -3-C(H)=NN(H)S(O)₂CH₃ and -4-OCH₃ |
| IB-L0-1.7 | -4-N(H)C(O)N(H)S(O)₂CH₃ |
| IB-L0-1.8 | -4-C(O)N(H)N(H)S(O)₂CH₃ |
| IB-L0-1.9 | -3-C(CH₃)=NN(H)S(O)₂CH₃ |
| IB-L0-1.10 | -3-C(H)=NN(H)S(O)₂CH₃ |

TABLE 4

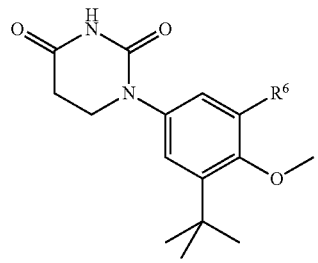

| compound | ring/ring structure | substituent(s) |
|---|---|---|
| IA-L0-2.1 | benzimidazol-2-yl | -5-N(H)S(O)₂CH₃ |
| IA-L0-2.2 | benzthiazol-2-yl | -6-N(H)S(O)₂CH₃ |
| IA-L0-2.3 | benzthiazol-2yl | — |
| IA-L0-2.4 | benzthiazol-2-yl | -5-N(H)S(O)₂CH₃ |
| IA-L0-2.5 | benzoxazol-2-yl | -6-N(H)S(O)₂CH₃ |
| IA-L0-2.6 | benzoxazol-2-yl | -6-NO₂ |
| IA-L0-2.7 | benzoxazol-2-yl | -5-NO₂ |
| IA-L0-2.8 | benzoxazol-2-yl | -5-N(H)S(O)₂CH₃ |
| IA-L0-2.9 | naphthalen-2-yl | -6-N(H)S(O)₂CH₃ |
| IA-L0-2.10 | benzimidazol-2-yl | -5-N[S(O)₂CH₃]₂ |

TABLE 5

[Structure: uracil-N-phenyl-naphthalene scaffold with R4, R5, and additional substituent(s)]

| compound | R⁴ | R⁵ | substituent(s) |
|---|---|---|---|
| IB-L0-2.1 | —C(CH₃)₃ | —OCH₃ | —H |
| IB-L0-2.2 | —C(CH₃)₃ | —OCH₃ | —OCH₃ |
| IB-L0-2.3 | —C(CH₃)₃ | —OCH₃ | —N(H)S(O)₂CH₃ |
| IB-L0-2.8 | —C(CH₃)₃ | —H | —N(H)S(O)₂CH₃ |
| IB-L0-2.14 | —C(CH₃)₃ | —Cl | —N(H)S(O)₂CH₃ |
| IB-L0-2.23 | —C(CH₃)₃ | —OC(H)₂CH₃ | —N(H)S(O)₂CH₃ |
| IB-L0-2.52 | —C(CH₃)₂C(H)₂C(H)₃ | —OCH₃ | —N(H)S(O)₂CH₃ |
| IB-L0-2.53 | thiophen-3-yl | —OCH₃ | —N(H)S(O)₂CH₃ |
| IB-L0-2.54 | —C(CH₃)₂C(H)₂OH | —OCH₃ | —N(H)S(O)₂CH₃ |
| IB-L0-2.56 | —CF₃ | —OCH₃ | —N(H)S(O)₂CH₃ |
| IB-L0-2.57 | —I | —OCH₃ | —N(H)S(O)₂CH₃ |
| IB-L0-2.58 | 5-methylfuran-2-yl | —OCH₃ | —N(H)S(O)₂CH₃ |
| IB-L0-2.59 | furan-2-yl | —OCH₃ | —N(H)S(O)₂CH₃ |
| IB-L0-2.60 | —C(F)₂CF₃ | —OCH₃ | —N(H)S(O)₂CH₃ |
| IB-L0-2.61 | thiophen-2-yl | —OCH₃ | —N(H)S(O)₂CH₃ |
| IB-L0-2.64 | furan-3-yl | —OCH₃ | —N(H)S(O)₂CH₃ |
| IB-L0-2.66 | —C(CH₃)₂C(H)₂OCH₃ | —OCH₃ | —N(H)S(O)₂CH₃ |
| IB-L0-2.68 | —S(O)₂CH₃ | —OCH₃ | —N(H)S(O)₂CH₃ |
| IB-L0-2.69 | —Br | —OCH₃ | —N(H)S(O)₂CH₃ |
| IB-L0-2.70 | —C(CH₃)₂C(O)OCH₃ | —OCH₃ | —N(H)S(O)₂CH₃ |
| IB-L0-2.71 | phenyl | —OCH₃ | —N(H)S(O)₂CH₃ |
| IB-L0-2.72 | —C(O)OCH₃ | —OCH₃ | —N(H)S(O)₂CH₃ |
| IB-L0-2.73 | 5-methylthiophen-2-yl | —OCH₃ | —N(H)S(O)₂CH₃ |
| IB-L0-2.74 | 3-chlorophenyl | —OCH₃ | —N(H)S(O)₂CH₃ |
| IB-L0-2.75 | —N(H)S(O)₂CH₃ | —OCH₃ | —N(H)S(O)₂CH₃ |

TABLE 5-continued

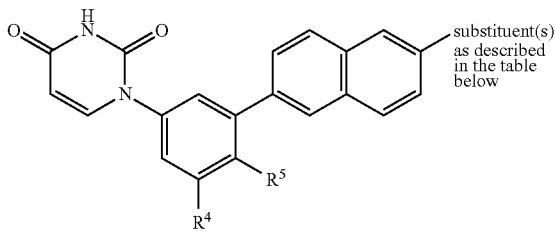

| compound | R⁴ | R⁵ | substituent(s) |
|---|---|---|---|
| IB-L0-2.76 |  | —OCH₃ | —N(H)S(O)₂CH₃ |
| IB-L0-2.77 | —C(CH₃)₂C(O)OH | —OCH₃ | —N(H)S(O)₂CH₃ |
| IB-L0-2.78 | —C≡CSi(CH₃)₃ | —OCH₃ | —N(H)S(O)₂CH₃ |

TABLE 6

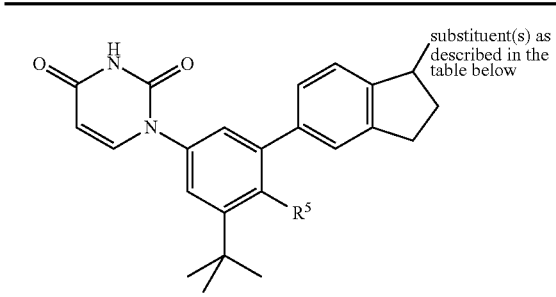

| compound | R⁵ | substituent(s) |
|---|---|---|
| IB-L0-2.4 | —OCH₃ | =NN(H)S(O)₂CH₃ |
| IB-L0-2.7 | —H | =NN(H)S(O)₂CH₃ |
| IB-L0-2.9 | —OCH₃ | (S) —C(H)₂N(H)S(O)₂CH₃ |
| IB-L0-2.10 | —OCH₃ | (R) —F and —C(H)₂N(H)S(O)₂CH₃ |
| IB-L0-2.12 | —OCH₃ | —F and —C(H)₂N(H)S(O)₂CH₃ |
| IB-L0-2.15 | —OCH₃ | (R) —C(H)₂N(H)S(O)₂CH₃ |
| IB-L0-2.17 | —OCH₃ | —C(H)₂N(H)S(O)₂CH₃ |
| IB-L0-2.20 | —OCH₃ | (S) —F and —C(H)₂N(H)S(O)₂CH₃ |
| IB-L0-2.22 | —OCH₃ | (S) —C(CH₃)₂N(H)S(O)₂CH₃ |
| IB-L0-2.24 | —OCH₃ | =NN(H)C(O)OCH₃ |
| IB-L0-2.25 | —OCH₃ | —CH₃ and —C(H)₂N(H)S(O)₂CH₃ |
| IB-L0-2.29 | —OCH₃ | —C(CH₃)₂N(H)S(O)₂CH₃ |
| IB-L0-2.31 | —OCH₃ | —N(H)N(H)S(O)₂CH₃ |
| IB-L0-2.34 | —OCH₃ | —C(O)N(H)S(O)₂CH₃ |
| IB-L0-2.36 | —OCH₃ | —OH |
| IB-L0-2.37 | —OCH₃ | (R) —C(CH₃)₂N(H)S(O)₂CH₃ |
| IB-L0-2.44 | —OCH₃ | —N(H)S(O)₂CH₃ |
| IB-L0-2.50 | —OCH₃ | =O |

TABLE 7

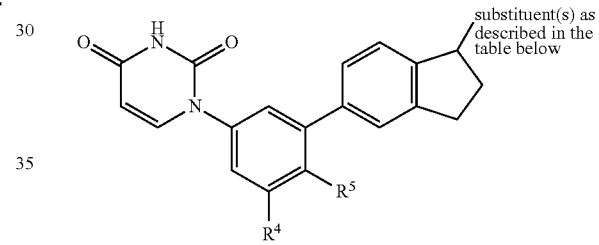

| compound | R⁴ | R⁵ | substituent(s) |
|---|---|---|---|
| IB-L0-2.51 |  | —OCH₃ | =NN(H)S(O)₂CH₃ |
| IB-L0-2.55 | furan-2-yl | —OCH₃ | =NN(H)S(O)₂CH₃ |

TABLE 8

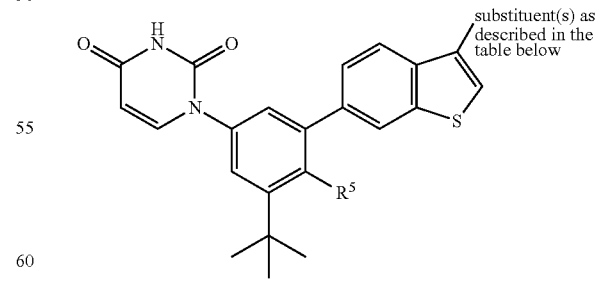

| compound | R⁵ | substituent(s) |
|---|---|---|
| IB-L0-2.11 | —OCH₃ | C(H)₂N(H)S(O)₂CH₃ |
| IB-L0-2.21 | —OCH₃ | —C(H)₂N(CH₃)S(O)₂CH₃ |
| IB-L0-2.35 | —Cl | —C(H)₂N(H)S(O)₂CH₃ |

TABLE 9

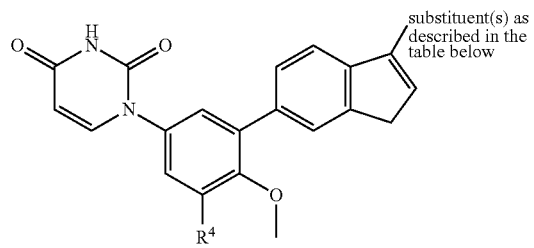

| compound | R⁴ | substituent(s) |
|---|---|---|
| IB-L0-2.13 | —C(CH₃)₃ | —C(H)₂N(H)S(O)₂CH₃ |
| IB-L0-2.16 | —C(CH₃)₃ | —C(H)₂N(CH₃)S(O)₂CH₃ |
| IB-L0-2.41 | —C(CH₃)₃ | —C(CH₃)₂N(H)S(O)₂CH₃ |
| IB-L0-2.62 | thiophen-3-yl | —C(H)₂N(H)S(O)₂CH₃ |
| IB-L0-2.63 | thiophen-2-yl | —C(H)₂N(H)S(O)₂CH₃ |
| IB-L0-2.65 | furan-2-yl | —C(H)₂N(H)S(O)₂CH₃ |
| IB-L0-2.67 | furan-3-yl | —C(H)₂N(H)S(O)₂CH₃ |

TABLE 10

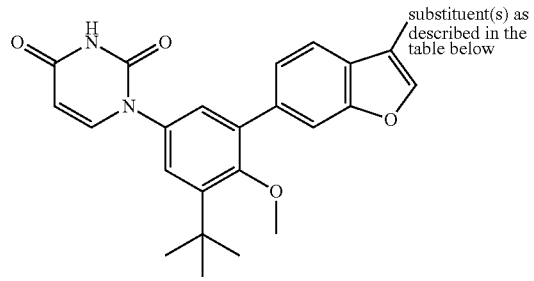

| compound | substituent(s) |
|---|---|
| IB-L0-2.18 | —C(H)₂N(H)S(O)₂CH₃ |
| IB-L0-2.42 | —CH₃ |

TABLE 11

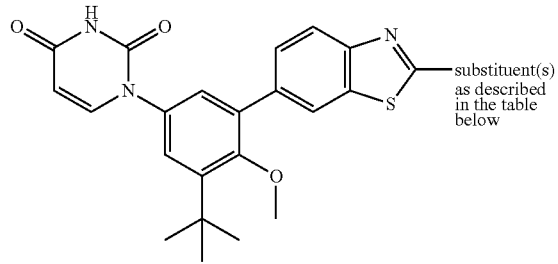

| compound | substituent(s) |
|---|---|
| IB-L0-2.27 | —NH₂ |
| IB-L0-2.28 | —N(H)S(O)₂CH₃ |

TABLE 11-continued

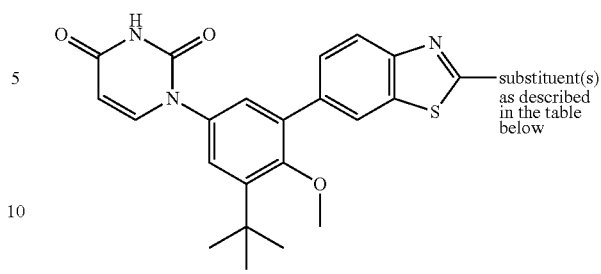

| compound | substituent(s) |
|---|---|
| IB-L0-2.33 | —H |
| IB-L0-2.38 | —Cl |
| IB-L0-2.39 | —NH₂ |
| IB-L0-2.46 | —N(H)C(H)₂C(H)₂CH₃ |
| IB-L0-2.47 | 2,5-dimethylpyrrol-1-yl |
| IB-L0-2.49 | —N(H)C(O)CH₃ |

TABLE 12

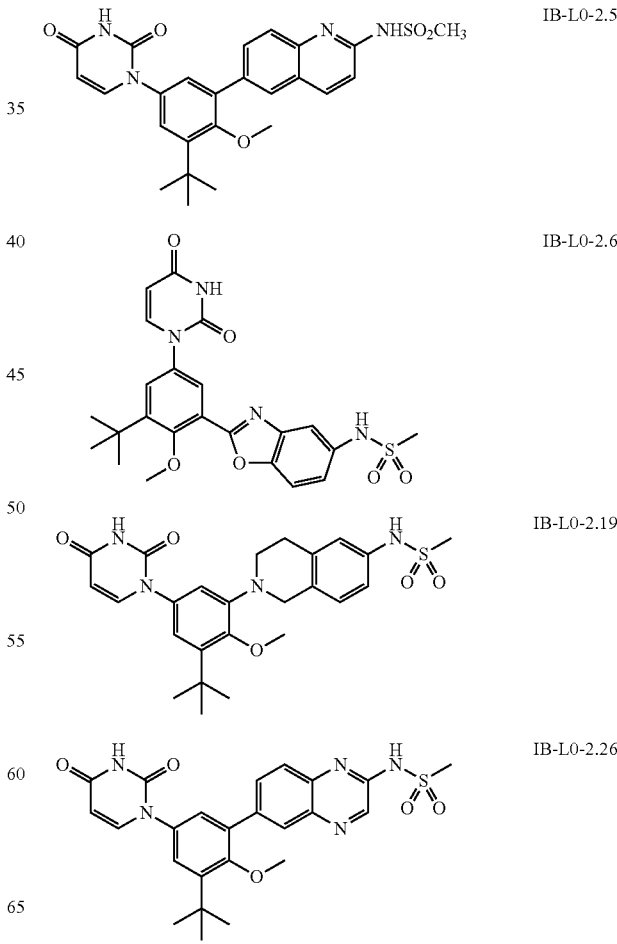

IB-L0-2.5

IB-L0-2.6

IB-L0-2.19

IB-L0-2.26

TABLE 12-continued

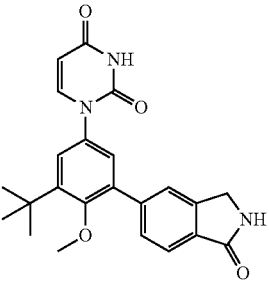 [SMILES: COc1c(-c2ccc3c(c2)CNC3=O)cc(-n2ccc(=O)[nH]c2=O)cc1C(C)(C)C] IB-L0-2.30

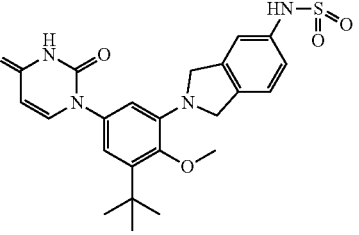 IB-L0-2.32

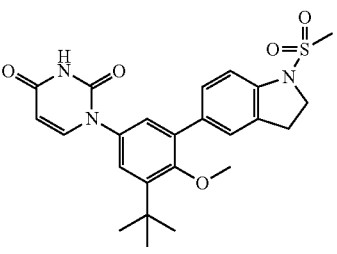 [SMILES: COc1c(-c2ccc3c(c2)CCN3S(C)(=O)=O)cc(-n2ccc(=O)[nH]c2=O)cc1C(C)(C)C] IB-L0-2.40

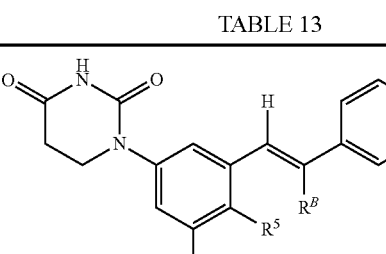 IB-L0-2.43

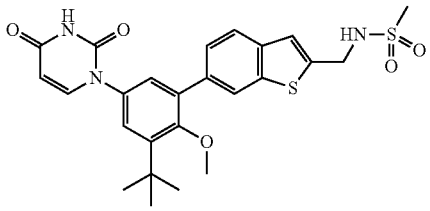 [SMILES: COc1c(-c2ccc3cc(CNS(C)(=O)=O)sc3c2)cc(-n2ccc(=O)[nH]c2=O)cc1C(C)(C)C] IB-L0-2.45

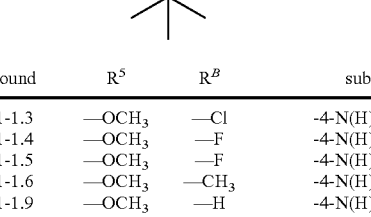 IB-L0-2.48

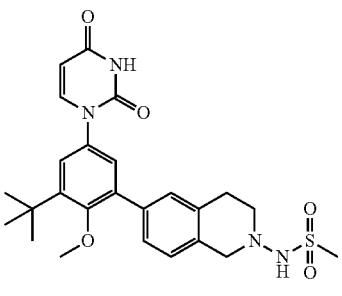 [SMILES: COc1c(-c2ccc3c(c2)CCN(NS(C)(=O)=O)C3)cc(-n2ccc(=O)[nH]c2=O)cc1C(C)(C)C] IB-L0-2.79

TABLE 13

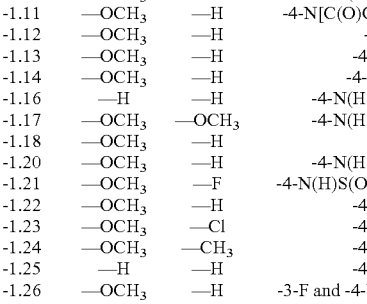

substituent(s) as described in the table below

| compound | $R^5$ | $R^B$ | substituent(s) |
|---|---|---|---|
| IA-L1-1.3 | —OCH$_3$ | —Cl | -4-N(H)S(O)$_2$CH$_3$ [Z] |
| IA-L1-1.4 | —OCH$_3$ | —F | -4-N(H)S(O)$_2$CH$_3$ [Z] |
| IA-L1-1.5 | —OCH$_3$ | —F | -4-N(H)S(O)$_2$CH$_3$ [E] |
| IA-L1-1.6 | —OCH$_3$ | —CH$_3$ | -4-N(H)S(O)$_2$CH$_3$ [E] |
| IA-L1-1.9 | —OCH$_3$ | —H | -4-N(H)S(O)$_2$CH$_3$ [E] |
| IA-L1-1.10 | —OCH$_3$ | —H | -4-N(H)S(O)$_2$CH$_3$ [Z] |
| IA-L1-1.11 | —OCH$_3$ | —H | -4-N[C(O)CH$_3$]S(O)$_2$CH$_3$ [E] |
| IA-L1-1.12 | —OCH$_3$ | —H | -4-F [E] |
| IA-L1-1.13 | —OCH$_3$ | —H | -4-NH$_2$ [E] |
| IA-L1-1.14 | —OCH$_3$ | —H | -4-OCH$_3$ [E] |
| IA-L1-1.16 | —H | —H | -4-N(H)S(O)$_2$CH$_3$ [E] |
| IA-L1-1.17 | —OCH$_3$ | —OCH$_3$ | -4-N(H)S(O)$_2$CH$_3$ [Z] |
| IA-L1-1.18 | —OCH$_3$ | —H | — [E] |
| IA-L1-1.20 | —OCH$_3$ | —H | -4-N(H)S(O)$_2$CH$_3$ [Z] |
| IA-L1-1.21 | —OCH$_3$ | —F | -4-N(H)S(O)$_2$CH$_3$ [Z]:[E] (1:1) |
| IA-L1-1.22 | —OCH$_3$ | —H | -4-NO$_2$ [E] |
| IA-L1-1.23 | —OCH$_3$ | —Cl | -4-NO$_2$ [Z] |
| IA-L1-1.24 | —OCH$_3$ | —CH$_3$ | -4-NO$_2$ [E] |
| IA-L1-1.25 | —H | —H | -4-NO$_2$ [E] |
| IA-L1-1.26 | —OCH$_3$ | —H | -3-F and -4-N(H)S(O)$_2$CH$_3$ [E] |
| IA-L1-1.27 | —OCH$_3$ | —H | -2-OCH$_3$ and -4-N(H)S(O)$_2$CH$_3$ [E] |

TABLE 14

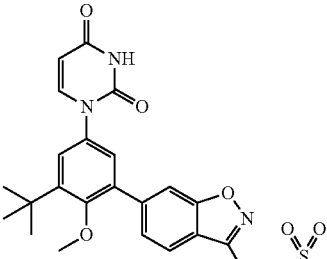

substituent(s) as described in the table below

| compound | substituent(s) |
|---|---|
| IB-L1-1.1 | -4-N(H)S(O)$_2$CH$_3$ [E] |
| IB-L1-1.4 | -2-C(O)OH and -4-N(H)S(O)$_2$CH$_3$ [E] |
| IB-L1-1.5 | -3-F and -4-N(H)S(O)$_2$CH$_3$ [E] |
| IB-L1-1.6 | -2-C(O)H and -4-N(H)S(O)$_2$CH$_3$ [E] |
| IB-L1-1.7 | -2-C(O)OCH$_3$ and -4-N(H)S(O)$_2$CH$_3$ [E] |

TABLE 14-continued

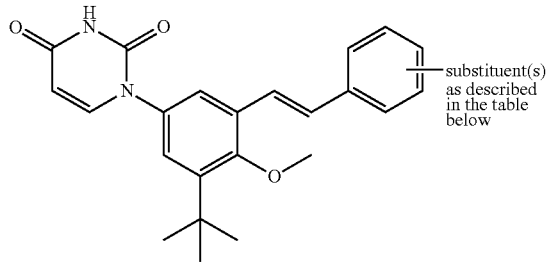

substituent(s) as described in the table below

| compound | substituent(s) |
|---|---|
| IB-L1-1.8 | -2-C(H)=N(OH) and -4-N(H)S(O)$_2$CH$_3$ [E] |
| IB-L1-1.9 | -2-C(O)N(H)CH$_2$CH$_2$OCH$_3$ and -4-N(H)S(O)$_2$CH$_3$ [E] |
| IB-L1-1.10 | -2-CH2OH and -4-N(H)S(O)$_2$CH$_3$ [E] |
| IB-L1-1.11 | -2-C(O)OC(H)$_2$CH$_3$ and -4-N(H)S(O)$_2$CH$_3$ [E] |
| IB-L1-1.13 | -2-C(H)$_2$OCH$_3$ and -4-N(H)S(O)$_2$CH$_3$ [E] |
| IB-L1-1.14 | -2-C(O)N(CH$_3$)$_2$ and -4-N(H)S(O)$_2$CH$_3$ [E] |
| IB-L1-1.15 | -2-CH$_3$ and -4-N(H)S(O)$_2$CH$_3$ and -5-F [E] |
| IB-L1-1.16 | imidazol-2-yl and -4-N(H)S(O)$_2$CH$_3$ [E] |
| IB-L1-1.17 | -2-C(O)N(H)CH$_3$ and -4-N(H)S(O)$_2$CH$_3$ [E] |
| IB-L1-1.18 | -2- [sulfolane with N-methyl-N-acetyl substituent] and -4-N(H)S(O)$_2$CH$_2$ [E] |
| IB-L1-1.19 | -2-C(H)=NOCH$_3$ and -4-N(H)S(O)$_2$CH$_3$ [E] |
| IB-L1-1.21 | -2-C(O)NH$_2$ and -4-N(H)S(O)$_2$CH$_3$ [E] |
| IB-L1-1.22 | -2- [N-acetyl azetidine] and -4-N(H)S(O)$_2$CH$_3$ [E] |
| IB-L1-1.23 | -2- [N-acetyl morpholine] and -4-N(H)S(O)$_2$CH$_3$ [E] |
| IB-L1-1.24 | -2-C(O)N(CH$_3$)C(H)$_2$C(H)$_2$OCH$_3$ and -4-N(H)S(O)$_2$CH$_3$ [E] |
| IB-L1-1.25 | -2-C(H)$_2$OC(H)(CH$_3$)$_2$ and -4-N(H)S(O)$_2$CH$_3$ [E] |
| IB-L1-1.26 | -2- [2-methyl oxazole] and -4-N(H)S(O)$_2$CH$_3$ [E] |
| IB-L1-1.27 | -2- [N-acetyl pyrrolidine] and -4-N(H)S(O)$_2$CH$_3$ [E] |
| IB-L1-1.28 | -2-NH$_2$ and -4-N(H)S(O)$_2$CH$_3$ [E] |
| IB-L1-1.29 | -2- [N-ethyl-3-hydroxyazetidine] and -4-N(H)S(O)$_2$CH$_3$ [E] |
| IB-L1-1.31 | -2-C(H)$_2$N(H)C(H)$_2$C(H)$_2$C(H)(CH$_3$)$_2$ and -4-N(H)S(O)$_2$CH$_3$ [E] |

TABLE 14-continued

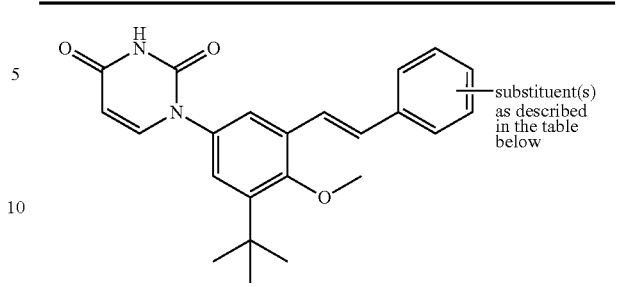

substituent(s) as described in the table below

| compound | substituent(s) |
|---|---|
| IB-L1-1.32 | -2-N(H)C(O)OC(CH$_3$)$_3$ and -4-N(H)S(O)$_2$CH$_3$ [E] |
| IB-L1-1.33 | -2- [N-ethyl pyrrolidine] and -4-N(H)S(O)$_2$CH$_3$ [E] |
| IB-L1-1.34 | -4-N(H)S(O)$_2$CH$_3$ [Z] |

TABLE 15

| compound | R$^4$ |
|---|---|
| IB-L1-1.45 | —C(CH$_3$)$_2$C(H)$_2$OH [E] |
| IB-L1-1.46 | furan-2-yl [E] |
| IB-L1-1.47 | thiophen-3-yl [E] |
| IB-L1-1.48 | thiophen-2-yl [E] |
| IB-L1-1.49 | —S(O)$_2$CH$_3$ [E] |
| IB-L1-1.50 | furan-3-yl [E] |
| IB-L1-1.51 | —I [E] |
| IB-L1-1.52 | —Br [E] |
| IB-L1-1.53 | pyridin-3-yl [E] |
| IB-L1-1.55 | pyridin-4-yl [E] |

TABLE 16

| compound | R² | R⁵ |
|---|---|---|
| IB-L1-1.2 | —F | —OCH₃ [E] |
| IB-L1-1.12 | —H | —Cl [E] |
| IB-L1-1.20 | —Cl | —OCH₃ [E] |
| IB-L1-1.30 | —H | —OCH₂CH₃ [E] |

TABLE 17

| compound | R⁵ | R⁶ ring/ring structure | R⁶ substituent(s) |
|---|---|---|---|
| IA-L2-1.1 | —H | phenyl | -4-N(H)S(O)₂CH₃ |
| IA-L2-1.2 | —H | phenyl | -2-CH₃ and -4-N(H)S(O)₂CH₃ |
| IA-L2-1.3 | —H | phenyl | -2-Cl and -4-N(H)S(O)₂CH₃ |
| IA-L2-1.4 | —OCH₃ | phenyl | — |
| IA-L2-1.26 | —OCH₃ | pyridin-3-yl | -6-N(H)S(O)₂CH₃ |
| IA-L2-1.7 | —OCH₃ | phenyl | -3-N(H)S(O)₂CH₃ |
| IA-L2-1.8 | —OCH₃ | phenyl | -4-N(H)S(O)₂CH₃ |
| IA-L2-1.9 | —OCH₃ | phenyl | -2-CH₃ and -4-N(H)S(O)₂CH₃ |
| IA-L2-1.10 | —OCH₃ | phenyl | -3-CH₃ and -4-N(H)S(O)₂CH₃ |
| IA-L2-1.11 | —OCH₃ | phenyl | 2-C(H)₂C(H)₃ and -4-N(H)S(O)₂CH₃ |
| IA-L2-1.12 | —OCH₃ | phenyl | -2-F and -4-N(H)S(O)₂CH₃ |
| IA-L2-1.13 | —OCH₃ | phenyl | -3-F and -4-N(H)S(O)₂CH₃ |
| IA-L2-1.14 | —OCH₃ | phenyl | -2-Cl and -4-N(H)S(O)₂CH₃ |
| IA-L2-1.15 | —OCH₃ | phenyl | -3-Cl and -4-N(H)S(O)₂CH₃ |
| IA-L2-1.16 | —OCH₃ | phenyl | -2-OCH₃ and -4-N(H)S(O)₂CH₃ |
| IA-L2-1.17 | —OCH₃ | phenyl | -3-OCF₃ and -4-N(H)S(O)₂CH₃ |
| IA-L2-1.18 | —OCH₃ | phenyl | -2-CF₃ and -4-N(H)S(O)₂CH₃ |
| IA-L2-1.19 | —OCH₃ | phenyl | -3-CF₃ and -4-N(H)S(O)₂CH₃ |
| IA-L2-1.20 | —OCH₃ | phenyl | -2-CH₃ and -4-N(H)S(O)₂CH₃ and -5-F |
| IA-L2-1.21 | —OCH₃ | phenyl | -2-Cl and -3-F and -4-N(H)S(O)₂CH₃ |
| IA-L2-1.22 | —OCH₃ | phenyl | -2-CF₃ and -4-N(H)S(O)₂CH₃ and -5-F |

TABLE 17-continued

| compound | R⁵ | R⁶ ring/ring structure | R⁶ substituent(s) |
|---|---|---|---|
| IA-L2-1.24 | —OCH₃ | pyridin-2-yl | -3-CH₃ and -5-N(H)S(O)₂CH₃ |
| IA-L2-1.25 | —OCH₃ | pyridin-2-yl | -5-N(H)S(O)₂CH₃ |
| IA-L2-1.26 | —OCH₃ | pyridin-3-yl | -6-N(H)S(O)₂CH₃ [C(F)₃C(O)OH salt] |

TABLE 18

IA-L2-1.23

IA-L2-2.1

TABLE 19

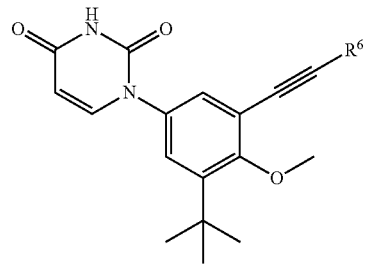

| compound | R⁶ ring/ring structure | substituent(s) |
|---|---|---|
| IB-L2-1.1 | phenyl | -2-CH₃ and -4-N(H)S(O)₂CH₃ |
| IB-L2-1.2 | phenyl | -2-Cl and -4-N(H)S(O)₂CH₃ |
| IB-L2-1.3 | phenyl | -2-CH₃ and -4-N(H)S(O)₂CH₃ and -5-F |
| IB-L2-1.4 | phenyl | -3-F and -4-N(H)S(O)₂CH₃ and -5-F |
| IB-L2-1.5 | phenyl | -2-CF₃ and -4-N(H)S(O)₂CH₃ and -5-F |
| IB-L2-1.6 | phenyl | -2-OH and -4-N(H)S(O)₂CH₃ |
| IB-L2-1.7 | phenyl | -2-C(O)OCH₃ and -4-N(H)S(O)₂CH₃ |
| IB-L2-1.8 | pyridin-2-yl | -5-N(H)S(O)₂CH₃ |
| IB-L2-1.9 | pyrazin-2-yl | -5-N(H)S(O)₂CH₃ |
| IB-L2-1.10 | phenyl | -2-C(CH₃)₃ and -4-N(H)S(O)₂CH₃ |
| IB-L2-1.11 | phenyl | -2-(acetyl morpholine) and -4-N(H)S(O)₂CH₃ |
| IB-L2-1.12 | phenyl | -2-N(H)C(O)CH₃ and -4-N(H)S(O)₂CH₃ |

TABLE 20

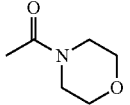

IB-L2-1.15

IB-L2-2.1

TABLE 21

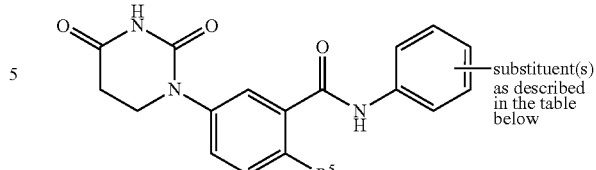

substituent(s) as described in the table below

| compound | R⁵ | substituent(s) |
|---|---|---|
| IA-L3-1.3 | —OH | — |
| IA-L3-1.4 | —OH | -4-N(CH₃)S(O)₂CH₃ |
| IA-L3-1.5 | —OH | -3-N(H)S(O)₂CH₃ |
| IA-L3-1.6 | —OH | -4-N(H)S(O)₂CH₃ |
| IA-L3-1.7 | —OH | -4-N(H)S(O)₂CH₂CH(CH₃)₂ |
| IA-L3-1.8 | —OH | -4-N(H)S(O)₂CH₂CH₂OCH₃ |
| IA-L3-1.9 | —OH | -4-N(H)S(O)₂CH₂CF₃ |
| IA-L3-1.10 | —OH | -4-N(H)S(O)₂phenyl |
| IA-L3-1.11 | —OH | -3-C(H)₂N(H)S(O)₂CH₃ |
| IA-L3-1.12 | —OH | -4-N(H)S(O)₂CH₂phenyl |
| IA-L3-1.13 | —OH | -4-(3,5-dimethylisoxazol-4-ylsulfonylamino) |
| IA-L3-1.14 | —OH | -4-(2-morpholinoethylsulfonylamino) |
| IA-L3-1.15 | —OH | -4-C(H)₂C(O)OH |
| IA-L3-1.16 | —OH | -4-C(H)₂S(O)₂N(H)CH₃ |
| IA-L3-1.17 | —OH | -4-OC(H)₂C≡N |
| IA-L3-1.18 | —OH | -4-OC(H)₂C(O)NH₂ |
| IA-L3-1.19 | —OH | -4-OS(O)₂CH₃ |
| IA-L3-1.20 | —OH | -2-S(O)₂CH₃ |
| IA-L3-1.21 | —OH | -4-S(O)₂CH₃ |
| IA-L3-1.22 | —OH | -2-S(O)₂NH₂ |
| IA-L3-1.24 | —OCH₃ | — |
| IA-L3-1.28 | —OCH₃ | -2-C(H)₂CH₃ |
| IA-L3-1.30 | —OCH₃ | -4-C(H)₂C(O)OH |
| IA-L3-1.31 | —OCH₃ | -4-C(H)₂S(O)₂N(H)CH₃ |
| IA-L3-1.32 | —OCH₃ | -4-CF₃ |
| IA-L3-1.33 | —OCH₃ | -4-OH |
| IA-L3-1.34 | —OCH₃ | -2-OCH₃ |
| IA-L3-1.35 | —OCH₃ | -3-OCH₃ |
| IA-L3-1.36 | —OCH₃ | -4-OCH₃ |
| IA-L3-1.37 | —OCH₃ | -2-OC(H)₂CH₃ |
| IA-L3-1.38 | —OCH₃ | -4-OC(H)₂C≡N |
| IA-L3-1.39 | —OCH₃ | -4-OC(H)₂C(O)NH₂ |
| IA-L3-1.40 | —OCH₃ | -4-OCF₃ |
| IA-L3-1.41 | —OCH₃ | -4-OS(O)₂CH₃ |
| IA-L3-1.42 | —OCH₃ | -4-C(O)CH₃ |
| IA-L3-1.43 | —OCH₃ | -4-C(O)C(H)₂C(O)OC(H)₂CH₃ |
| IA-L3-1.44 | —OCH₃ | -3-C(O)NH₂ |
| IA-L3-1.45 | —OCH₃ | -4-F |
| IA-L3-1.46 | —OCH₃ | -4-Cl |
| IA-L3-1.47 | —OCH₃ | -4-N(H)C(O)CH₃ |
| IA-L3-1.48 | —OCH₃ | -4-N(H)C(O)C(H)₂OC(O)CH₃ |
| IA-L3-1.49 | —OCH₃ | -4-N(H)C(O)OCH₃ |
| IA-L3-1.50 | —OCH₃ | -4-N(H)C(O)OC(CH₃)₃ |
| IA-L3-1.51 | —OCH₃ | -4-N(H)S(O)₂CH₃ |
| IA-L3-1.52 | —OCH₃ | -4-N(H)S(O)₂C(H)₂CH(CH₃)₂ |
| IA-L3-1.53 | —OCH₃ | -4-N(H)S(O)₂C(H)₂OH |
| IA-L3-1.54 | —OCH₃ | -4-N(H)S(O)₂C(H)₂C(H)₂OCH₃ |
| IA-L3-1.55 | —OCH₃ | -4-N(H)S(O)₂C(H)₂CF₃ |
| IA-L3-1.56 | —OCH₃ | -4-N(H)S(O)₂C(H)₂C(H)₂N[C(H)₂C(H)₂OH]₂ |
| IA-L3-1.57 | —OCH₃ | -4-N(H)S(O)₂C(H)₂phenyl |

TABLE 21-continued

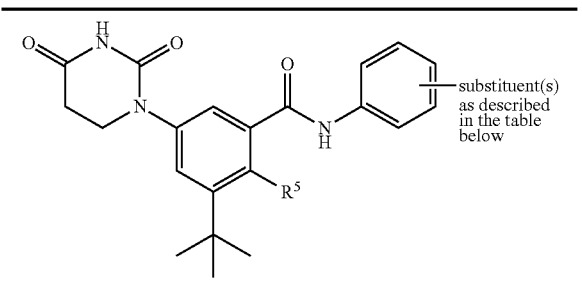

substituent(s) as described in the table below

| compound | R⁵ | substituent(s) |
|---|---|---|
| IA-L3-1.58 | —OCH₃ | -4-N(H)S(O)₂CH₂CH₂-morpholine |
| IA-L3-1.59 | —OCH₃ | -4-N(H)S(O)₂-(3,5-dimethylisoxazol-4-yl) |
| IA-L3-1.60 | —OCH₃ | -4-N(H)S(O)₂phenyl |
| IA-L3-1.62 | —OCH₃ | -4-N(CH₃)S(O)₂CH₃ |
| IA-L3-1.63 | —OCH₃ | -4-N[C(H)₂CH₃]S(O)₂CH₃ |
| IA-L3-1.64 | —OCH₃ | -4-N[C(H)₂OC(O)CH₃]S(O)₂CH₃ |
| IA-L3-1.65 | —OCH₃ | -4-N[C(H)₂OC(O)C(CH₃)₃]S(O)₂CH₃ |
| IA-L3-1.66 | —OCH₃ | -4-N(CH₂-cyclopropyl)S(O)₂CH₃ |
| IA-L3-1.67 | —OCH₃ | -4-N(CH₂-(4-methoxyphenyl))S(O)₂CH₃ |

TABLE 21-continued

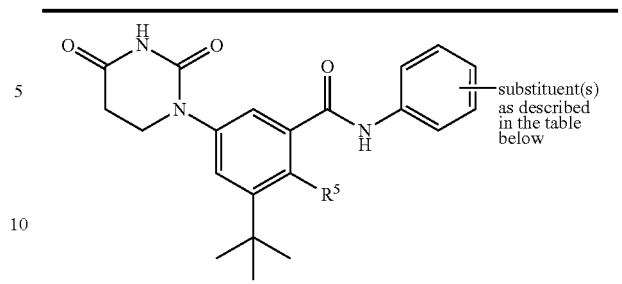

substituent(s) as described in the table below

| compound | R⁵ | substituent(s) |
|---|---|---|
| IA-L3-1.69 | —OCH₃ | -4-N[C(O)CH₃]S(O)₂CH₃ |
| IA-L3-1.70 | —OCH₃ | -4-N[C(O)C(H)₂CH₃]S(O)₂CH₃ |
| IA-L3-1.71 | —OCH₃ | -4-N[C(O)C(H)₂C(H)₂CH₃]S(O)₂CH₃ |
| IA-L3-1.72 | —OCH₃ | -4-N[C(O)C(H)(CH₃)₂]S(O)₂CH₃ |
| IA-L3-1.73 | —OCH₃ | -4-N[C(O)OCH₃]S(O)₂CH₃ |
| IA-L3-1.74 | —OCH₃ | -4-N[C(O)OC(H)₂CH₃]S(O)₂CH₃ |
| IA-L3-1.76 | —OCH₃ | -4-N[C(O)OC(H)₂C(H)(CH₃)₂]S(O)₂CH₃ |
| IA-L3-1.77 | —OCH₃ | -4-N[C(O)OC(H)₂C(H)₂OCH₃]S(O)₂CH₃ |
| IA-L3-1.78 | —OCH₃ | -4-S(O)₂CH₃ |
| IA-L3-1.79 | —OCH₃ | -2-S(O)₂CH₃ |
| IA-L3-1.80 | —OCH₃ | -2-S(O)₂NH₂ |
| IA-L3-1.81 | —OCH₃ | -2-CH₃ and 3-OH |
| IA-L3-1.82 | —OCH₃ | -2-CH₃ and -4-F |
| IA-L3-1.83 | —OCH₃ | -2-CH₃ and -4-N(H)S(O)₂CH₃ |
| IA-L3-1.84 | —OCH₃ | -2-CF₃ and -4-N(H)S(O)₂CH₃ |
| IA-L3-1.85 | —OCH₃ | -2-OCH₃ and -4-N(H)S(O)₂CH₃ |
| IA-L3-1.86 | —OCH₃ | -2-OCH₃ and -5-N(H)C(O)CH₃ |
| IA-L3-1.87 | —OCH₃ | -3-NO₂ and -4-N(H)S(O)₂CH₃ |
| IA-L3-1.105 | —H | -4-N(H)S(O)₂CH₃ |
| IA-L3-1.107 | —OCH₃ | -4-N(H)₂ [Cl—] |
| IA-L3-1.108 | —OCH₃ | -4-N[C(H)₂C(H)═C(H)₂]S(O)₂CH₃ |
| IA-L3-1.119 | —OH | -2-OCH₃ and -4-N(H)S(O)₂CH₃ |
| IA-L3-1.120 | —OCH₃ | -3-C(H)₂N(H)S(O)₂CH₃ |
| IA-L3-1.121 | —OCH₃ | -4-N(H)S(O)₂-(2,5-dimethoxyphenyl) |
| IA-L3-1.122 | —OCH₃ | -4-N(H)S(O)₂C(H)₂C(H)₂OH |
| IA-L3-1.123 | —OCH₃ | -4-N[C(H)₂OC(O)C(H)₂C(H)₂CH₃]S(O)₂CH₃ |

TABLE 22

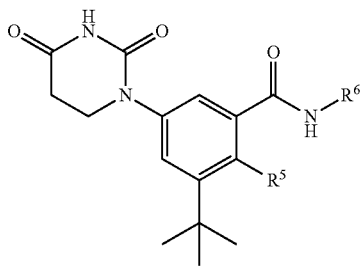

| compound | R⁵ | ring/ring structure | substituent(s) |
|---|---|---|---|
| IA-L3-1.89 | —OH | thiophen-2-yl | -3-S(O)₂NH₂ and -4-C(H)₂N(H)S(O)₂CH₃ |
| IA-L3-1.90 | —OCH₃ | thiophen-2-yl | -3-S(O)₂NH₂ and -4-C(H)₂N(H)S(O)₂CH₃ |
| IA-L3-1.91 | —OH | thiophen-2-yl | -4-C(H)₂N(H)S(O)₂CH₃ |
| IA-L3-1.94 | —OCH₃ | thiophen-2-yl | -4-C(H)₂N(H)S(O)₂CH₃ |

TABLE 22-continued

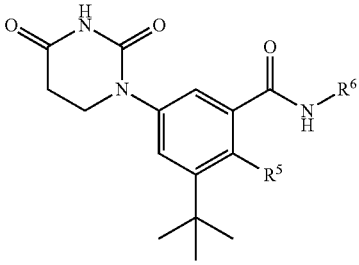

| compound | R⁵ | R⁶ ring/ring structure | R⁶ substituent(s) |
|---|---|---|---|
| IA-L3-1.95 | —OH | thiophen-2-yl | -4-C(H)$_2$N(CH$_3$)S(O)$_2$CH$_3$ |
| IA-L3-1.96 | —OCH$_3$ | thiophen-2-yl | -4-C(H)$_2$N[C(O)OC(CH$_3$)$_3$]S(O)$_2$CH$_3$ |
| IA-L3-1.97 | —OCH$_3$ | thiophen-2-yl | 4-C(H)$_2$N(CH$_3$)S(O)$_2$CH$_3$ |
| IA-L3-1.98 | —OH | thiophen-2-yl | -4-C(H)$_2$N[C(O)OC(CH$_3$)$_3$] S(O)$_2$CH$_3$ |
| IA-L3-1.99 | —OCH$_3$ | pyridin-3-yl | -6-N(H)S(O)$_2$CH$_3$ |
| IA-L3-1.100 | —OCH$_3$ | pyridin-3-yl | -6-N(H)$_2$ [Cl⁻] |
| IA-L3-1.101 | —OCH$_3$ | pyridin-2-yl | -5-N[S(O)$_2$CH$_3$]$_2$ |
| IA-L3-1.102 | —OCH$_3$ | pyridin-2-yl | -5-N(H)S(O)$_2$CH$_3$ |
| IA-L3-1.103 | —OCH$_3$ | cyclohexyl | -4-N(H)S(O)$_2$CH$_3$ |
| IA-L3-1.104 | —OH | thiazol-2-yl | |

TABLE 23

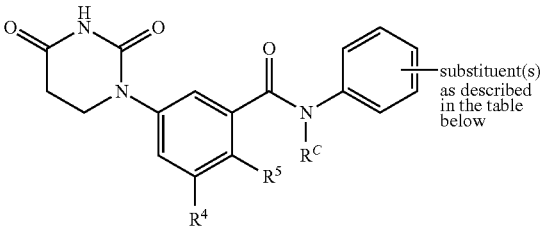

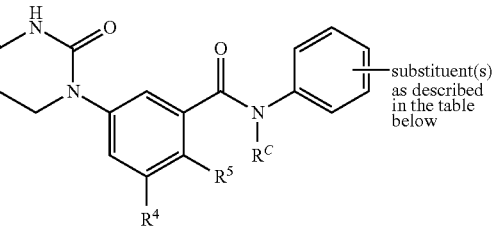

| compound | R⁴ | R⁵ | R$^C$ | substituent(s) |
|---|---|---|---|---|
| IA-L3-1.1 | —C(CH$_3$)$_3$ | —OH | —CH$_3$ | — |
| IA-L3-1.2 | —C(CH$_3$)$_3$ | —OH | —CH$_3$ | -4-N(H)S(O)$_2$CH$_3$ |
| IA-L3-1.27 | —C(CH$_3$)$_3$ | —OCH$_3$ | —CH$_3$ | -4-N(H)S(O)$_2$CH$_3$ |
| IA-L3-1.111 | —C(H)(CH$_3$)$_2$ | —OCH$_3$ | —H | -4-N(H)S(O)$_2$CH$_3$ |
| IA-L3-1.112 | —CH$_2$CH$_3$ | —OCH$_3$ | —H | -4-N(H)S(O)$_2$CH$_3$ |
| IA-L3-1.113 | —CH$_2$CH$_3$ | —OH | —H | -4-N(H)S(O)$_2$CH$_3$ |
| IA-L3-1.114 | —H | —OH | —H | -4-N(H)S(O)$_2$CH$_3$ |

TABLE 24

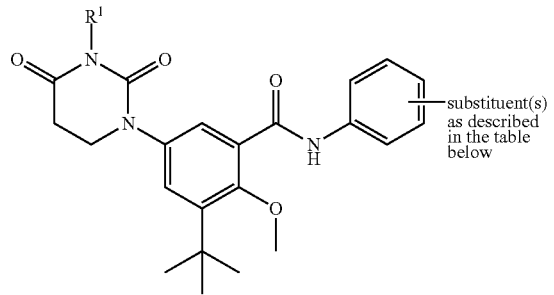

| compound | R¹ | substituent(s) |
|---|---|---|
| IA-L3-1.88 | —C(H)$_2$OC(O)C(H)$_2$C(H)$_2$CH$_3$ | -4-N[C(H)$_2$OC(O)CH$_2$CH$_2$CH$_3$]S(O)$_2$CH$_3$ |
| IA-L3-1.25 | —CH$_3$ | -4-N(H)S(O)$_2$CH$_3$ |
| IA-L3-1.26 | —CH$_3$ | -4-N(CH$_3$)S(O)$_2$CH$_3$ |
| IA-L3-1.115 | —C(H)$_2$C(O)N(H)CH$_2$CH$_3$ | -4-N[C(H)$_2$C(O)N(H)CH$_2$CH$_3$]S(O)$_2$CH$_3$ |
| IA-L3-1.116 | —C(H)$_2$OC(O)C(CH$_3$)$_3$ | -4-N[C(H)$_2$OC(O)C(CH$_3$)$_3$]S(O)$_2$CH$_3$ |

TABLE 24-continued

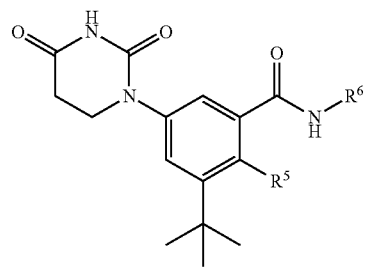

| compound | R¹ | substituent(s) |
|---|---|---|
| IA-L3-1.117 | (1,3-dioxolan-2-ylmethyl) | -4-N(H)S(O)$_2$CH$_3$ |
| IA-L3-1.118 | —CH$_2$C═CH$_2$ | -4-N[C(H)$_2$C═CH$_2$]S(O)$_2$CH$_3$ |

TABLE 25

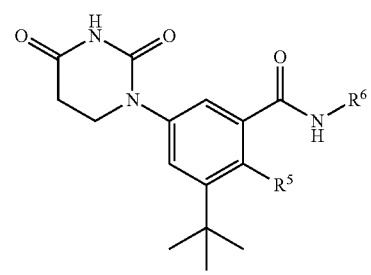

| compound | R⁵ | R⁶ |
|---|---|---|
| IA-L3-2.1 | —OH | quinolin-6-yl |
| IA-L3-2.2 | —OCH$_3$ | 2-oxoindolin-5-yl |
| IA-L3-2.3 | —OCH$_3$ | 2,2-dioxo-1,3-dihydrobenzo[c]thiophen-5-yl |
| IA-L3-2.4 | —OCH$_3$ | 2-oxo-1,2,3,4-tetrahydroquinolin-6-yl |
| IA-L3-2.5 | —OH | 2,2-dioxo-1,3-dihydrobenzo[c]thiophen-5-yl |

TABLE 26

| compound | R³ | R⁵ |
|---|---|---|
| IB-L3-1.1 | —H | —OCH$_3$ |
| IB-L3-1.2 | —H | —OH |
| IB-L3-1.3 | —CH$_3$ | —OCH$_3$ |
| IB-L3-1.4 | —CH$_3$ | —OH |

TABLE 27

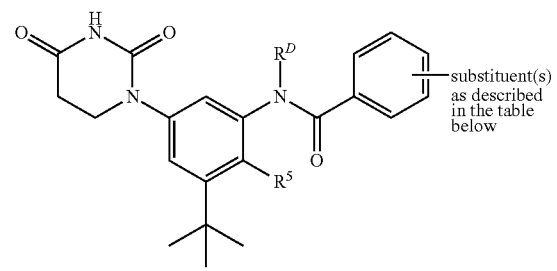

| compound | $R^5$ | $R^D$ | substituent(s) |
|---|---|---|---|
| IA-L4-1.1 | —H | —H | -4-N(H)S(O)$_2$CH$_3$ |
| IA-L4-1.2 | —OH | —H | — |
| IA-L4-1.3 | —OH | —H | -4-N(H)S(O)$_2$CH$_3$ |
| IA-L4-1.4 | —OH | —H | -4-CH$_2$S(O)$_2$CH$_3$ |
| IA-L4-1.5 | —OH | —H | -4-NO$_2$ |
| IA-L4-1.6 | —OH | —H | -4-NH$_2$ |
| IA-L4-1.7 | —OCH$_3$ | —CH$_3$ | -4-N(H)S(O)$_2$CH$_3$ |
| IA-L4-1.8 | —OCH$_3$ | —H | — |
| IA-L4-1.9 | —OCH$_3$ | —H | -4-N(H)S(O)$_2$CH$_3$ |
| IA-L4-1.10 | —OCH$_3$ | —H | -4-CH$_2$S(O)$_2$CH$_3$ |
| IA-L4-1.11 | —OCH$_3$ | —H | -2-OCH$_3$ and -4-N(H)S(O)$_2$CH$_3$ |
| IA-L4-1.12 | —OCH$_3$ | —H | -2-Cl and -4-N(H)S(O)$_2$CH$_3$ |

TABLE 28

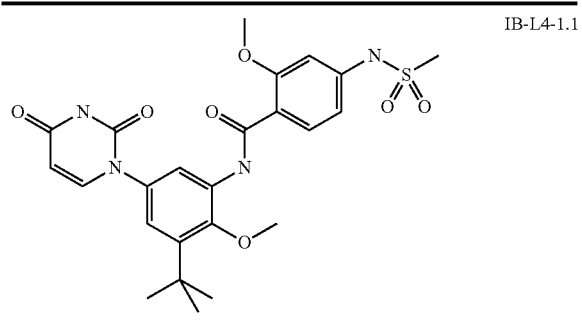

IB-L4-1.1

TABLE 29

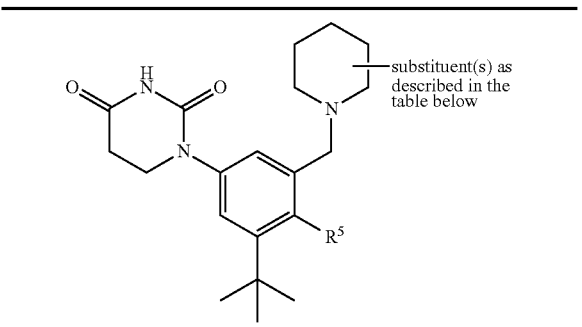

| compound | $R^5$ | substituent(s) |
|---|---|---|
| IA-L5-1.1 | —OH | -4-N(H)C(O)OC(CH$_3$)$_3$ |
| IA-L5-1-1.2 | —OH | -3-C(H)$_2$N(H)S(O)$_2$CH$_3$ |
| IA-L5-1-1.3 | —OH | -3-C(O)OC(H)$_2$CH$_3$ |
| IA-L5-1-1.4 | —OH | -3-CH$_3$ [C(F)3C(O)O$^-$] |
| IA-L5-1-1.5 | —OH | -4-C(O)OCH$_3$ |
| IA-L5-1-1.6 | —OH | -3-OH [C(F)3C(O)O$^-$] |
| IA-L5-1-1.7 | —OH | -3-C(O)N[C(H)$_2$CH$_3$]$_2$ [C(F)$_3$C(O)O$^-$] |
| IA-L5-1-1.8 | —OH | -3-C(O)NH$_2$ [C(F)$_3$C(O)O$^-$] |

TABLE 30

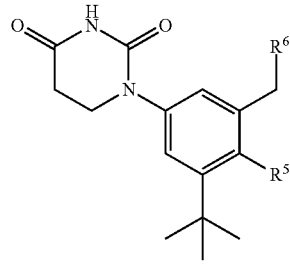

| compound | $R^5$ | $R^6$ ring/ring structure | substituent(s) |
|---|---|---|---|
| IA-L5-1-1.10 | —OH | piperazin-1-yl | -4-C(O)OC(CH$_3$)$_3$ |
| IA-L5-1-1.11 | —OH | pyrrolidin-1-yl | -3-N(H)S(O)$_2$CH$_3$ |
| IA-L5-1-1.12 | —OH | pyrrolidin-1-yl | -3-N(H)C(O)OC(CH$_3$)$_3$ |
| IA-L5-1-1.13 | —OH | morpholin-4-yl | -2-C(H)$_3$ and -6-C(H)$_3$ [C(F)$_3$C(O)O$^-$] |
| IA-L5-1-1.14 | —OH | morpholin-4-yl | — [C(F)$_3$C(O)O$^-$] |

TABLE 31

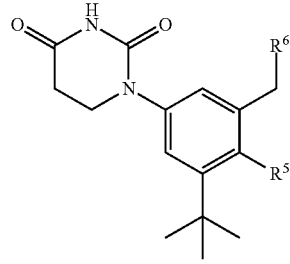

| compound | $R^5$ | $R^6$ |
|---|---|---|
| IA-L5-1-2.1 | —OCH$_3$ | (1-methylindol-3-yl) |
| IA-L5-1-2.2 | —OH | (6-methanesulfonamido-1,2,3,4-tetrahydroquinolin-1-yl) |

TABLE 32

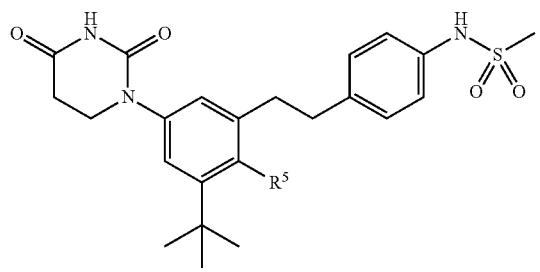

| compound | R⁵ |
|---|---|
| IA-L5-2-1.1 | —OCH₃ |
| IA-L5-2-1.2 | —H |

TABLE 33

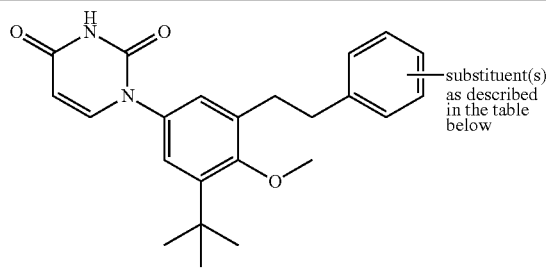

| compound | substituent(s) |
|---|---|
| IB-L5-2-1.1 | -2-C(O)OCH₃ and -4-N(H)S(O)₂CH₃ |
| IB-L5-2-1.2 | -4-N(H)S(O)₂CH₃ |

TABLE 34

IA-L6-1.1

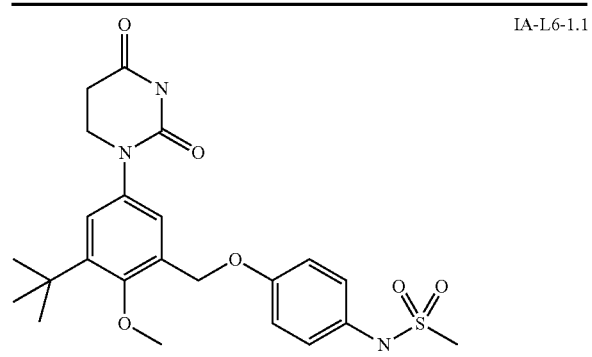

TABLE 35

IA-L8-1.1

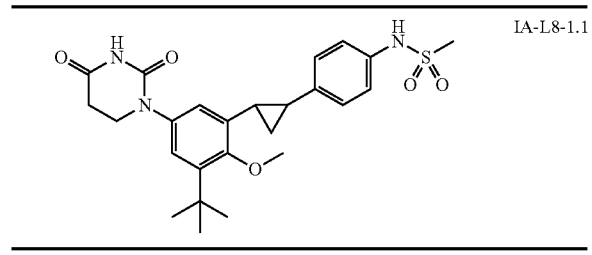

TABLE 36

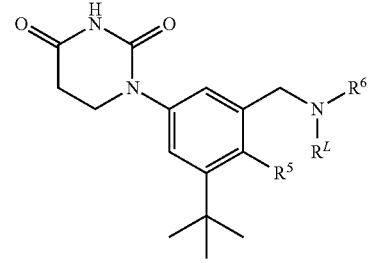

| compound | $R^L$ | $R^5$ | $R^6$ ring/ring structure | $R^6$ substituent(s) |
|---|---|---|---|---|
| IA-L9-1.1 | —CH₂CH₃ | —OH | cyclohexyl [C(F)₃C(O)O⁻] | — |
| IA-L9-1.2 | —CH₃ | —OH | cyclohexyl [C(F)₃C(O)O⁻] | — |
| IA-L9-1.3 | —H | —OH | phenyl | -4-N(H)S(O)₂CH₃ |
| IA-L9-1.4 | —H | —OCH₃ | phenyl | -4-N(H)S(O)₂CH₃ |

TABLE 37

IA-L11-1.1

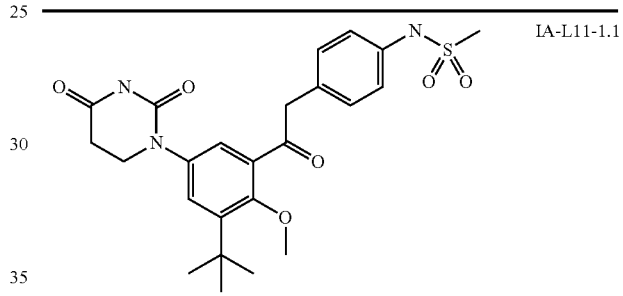

TABLE 38

IA-L12-1.1

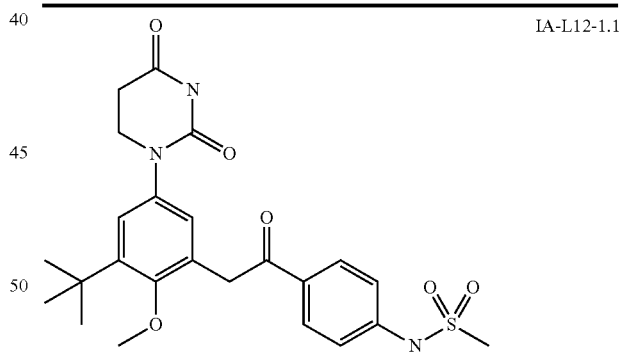

D. ISOMERS

This invention also is directed, in part, to all isomers of the compounds of formula I (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

E. SALTS

This invention also is directed, in part, to all salts of the compounds of formula I. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula I can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula I include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In some embodiments, the salt is sodium salt of N-(6-(3-tert-butyl-5-(2,4-dioxo-3,4-dihydro-pyrimidin-1(2H)-yl)-2-methoxyphenyl)naphthalen-2-yl)methanesulfonamide.

In some embodiments, the salt is monosodium salt of N-(6-(3-tert-butyl-5-(2,4-dioxo-3,4-dihydropyrimidin-1(2H)-yl)-2-methoxyphenyl)naphthalen-2-yl)methanesulfonamide.

In some embodiments, the salt is disodium salt of N-(6-(3-tert-butyl-5-(2,4-dioxo-3,4-dihydro-pyrimidin-1(2H)-yl)-2-methoxyphenyl)naphthalen-2-yl)methanesulfonamide.

In some embodiments, the salt is potassium salt of N-(6-(3-tert-butyl-5-(2,4-dioxo-3,4-dihydro-pyrimidin-1(2H)-yl)-2-methoxyphenyl)naphthalen-2-yl)methanesulfonamide.

In some embodiments, the salt is monopotassium salt of N-(6-(3-tert-butyl-5-(2,4-dioxo-3,4-dihydropyrimidin-1(2H)-yl)-2-methoxyphenyl)naphthalen-2-yl)methanesulfonamide.

In some embodiments, the salt is choline salt of N-(6-(3-tert-butyl-5-(2,4-dioxo-3,4-dihydro-pyrimidin-1(2H)-yl)-2-methoxyphenyl)naphthalen-2-yl)methanesulfonamide.

In some embodiments, the salt is monocholine salt of N-(6-(3-tert-butyl-5-(2,4-dioxo-3,4-dihydropyrimidin-1(2H)-yl)-2-methoxyphenyl)naphthalen-2-yl)methanesulfonamide.

In some embodiments, the salt is sodium salt of (E)-N-(4-(3-tert-butyl-5-(2,4-dioxo-3,4-dihydro-pyrimidin-1(2H)-yl)-2-methoxystyryl)phenyl)methanesulfonamide.

In some embodiments, the salt is disodium salt of (E)-N-(4-(3-tert-butyl-5-(2,4-dioxo-3,4-dihydropyrimidin-1(2H)-yl)-2-methoxystyryl)phenyl)methanesulfonamide.

In some embodiments, the salt is potassium salt of (E)-N-(4-(3-tert-butyl-5-(2,4-dioxo-3,4-dihydropyrimidin-1(2H)-yl)-2-methoxystyryl)phenyl)methanesulfonamide.

In some embodiments, the salt is monopotassium salt of (E)-N-(4-(3-tert-butyl-5-(2,4-dioxo-3,4-dihydropyrimidin-1(2H)-yl)-2-methoxystyryl)phenyl)methanesulfonamide.

F. PURITY

Compounds of formula I (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

G. CRYSTALLINE FORMS OF SOME SPECIFIC COMPOUNDS AND SALTS OF THE INVENTION

G1. Crystalline Forms of N-(6-(3-Tert-butyl-5-(2,4-dioxo-3,4-dihydropyrimidin-1(2H)-yl)-2-methoxyphenyl)naphthalen-2-yl)methanesulfonamide (compound IB-L0-2.3)

This invention also relates, in part, to crystalline forms of N-(6-(3-tert-butyl-5-(2,4-dioxo-3,4-dihydropyrimidin-1(2H)-yl)-2-methoxyphenyl)naphthalen-2-yl)methanesulfonamide (compound IB-L0-2.3), namely the solvate, hydrate, and solvent-free crystalline forms discussed below.

G1A. IB-L0-2.3 Solvates

This invention also relates, in part, to an ethanol solvate of compound IB-L0-2.3.

In some embodiments, the ethanol solvate has an X-ray powder diffraction pattern comprising one or more peaks selected from the group consisting of 8.3±0.2, 9.7±0.2, 10.6±0.2, 13.6±0.2, 17.2±0.2, 19.2±0.2, 22.7±0.2, 26.9±0.2, and 29.4±0.2 degrees two theta (2θ). In some such embodiments, the ethanol solvate has an X-ray powder diffraction pattern comprising three or more peaks selected from the group consisting of 8.3±0.2, 9.7±0.2, 10.6±0.2, 13.6±0.2, 17.2±0.2, 19.2±0.2, 22.7±0.2, 26.9±0.2, and 29.4±0.2 degrees 2θ. In other such embodiments, the ethanol solvate has an X-ray powder diffraction pattern comprising five or more peaks selected from the group consisting of 8.3±0.2, 9.7±0.2, 10.6±0.2, 13.6±0.2, 17.2±0.2, 19.2±0.2, 22.7±0.2, 26.9±0.2, and 29.4±0.2 degrees 2θ.

In some embodiments, the ethanol solvate has an X-ray powder diffraction pattern comprising one or more peaks selected from the group consisting of 8.3±0.2, 9.7±0.2, 10.0±0.2, 10.6±0.2, 13.6±0.2, 17.2±0.2, 17.5±0.2, 19.2±0.2, 19.4±0.2, 22.7±0.2, 26.9±0.2, and 29.4±0.2 degrees 2θ. In some such embodiments, the ethanol solvate has an X-ray powder diffraction pattern comprising three or more peaks selected from the group consisting of 8.3±0.2, 9.7±0.2, 10.0±0.2, 10.6±0.2, 13.6±0.2, 17.2±0.2, 17.5±0.2, 19.2±0.2, 19.4±0.2, 22.7±0.2, 26.9±0.2, and 29.4±0.2 degrees 2θ. In other embodiments, the ethanol solvate has an X-ray powder diffraction pattern comprising five or more peaks selected from the group consisting of 8.3±0.2, 9.7±0.2, 10.0±0.2, 10.6±0.2, 13.6±0.2, 17.2±0.2, 17.5±0.2, 19.2±0.2, 19.4±0.2, 22.7±0.2, 26.9±0.2, and 29.4±0.2 degrees 2θ.

In some embodiments, the ethanol solvate has an X-ray powder diffraction pattern substantially as shown in FIG. 1. The 2θ values for the peaks in FIG. 1 (and their intensities) are as follows: 8.25 (54), 9.67 (74), 9.92 (63), 10.59 (21), 13.64 (49), 17.25 (40), 17.51 (20), 19.19 (66), 19.43 (100), 22.75 (19), 26.92 (25), and 29.39 (18).

This invention also relates, in part, to an acetonitrile solvate of compound IB-L0-2.3.

In some embodiments, the acetonitrile solvate has an X-ray powder diffraction pattern comprising one or more peaks selected from the group consisting of 5.3±0.2, 8.3±0.2, 9.7±0.2, 10.5±0.2, 13.8±0.2, 17.2±0.2, 19.1±0.2, and 19.5±0.2 degrees 2θ. In some such embodiments, the acetonitrile solvate has an X-ray powder diffraction pattern comprising three or more peaks selected from the group consisting of 5.3±0.2, 8.3±0.2, 9.7±0.2, 10.5±0.2, 13.8±0.2, 17.2±0.2, 19.1±0.2, and 19.5±0.2 degrees 2θ. In other such embodiments, the acetonitrile solvate has an X-ray powder diffraction pattern comprising five or more peaks selected from the group consisting of 5.3±0.2, 8.3±0.2, 9.7±0.2, 10.5±0.2, 13.8±0.2, 17.2±0.2, 19.1±0.2, and 19.5±0.2 degrees 2θ.

In some embodiments, the acetonitrile solvate has an X-ray powder diffraction pattern comprising one or more peaks selected from the group consisting of 5.3±0.2, 8.3±0.2, 9.7±0.2, 10.5±0.2, 13.8±0.2, 17.2±0.2, 17.7±0.2, 19.1±0.2, 19.5±0.2, 22.0±0.2, 22.8±0.2, and 27.2±0.2 degrees 2θ. In some such embodiments, the acetonitrile solvate has an X-ray powder diffraction pattern comprising three or more peaks selected from the group consisting of 5.3±0.2, 8.3±0.2, 9.7±0.2, 10.5±0.2, 13.8±0.2, 17.2±0.2, 17.7±0.2, 19.1±0.2, 19.5±0.2, 22.0±0.2, 22.8±0.2, and 27.2±0.2 degrees 2θ. In other such embodiments, the acetonitrile solvate has an X-ray powder diffraction pattern comprising five or more peaks selected from the group consisting of 5.3±0.2, 8.3±0.2, 9.7±0.2, 10.5±0.2, 13.8±0.2, 17.2±0.2, 17.7±0.2, 19.1±0.2, 19.5±0.2, 22.0±0.2, 22.8±0.2, and 27.2±0.2 degrees 2θ.

Figure 3:
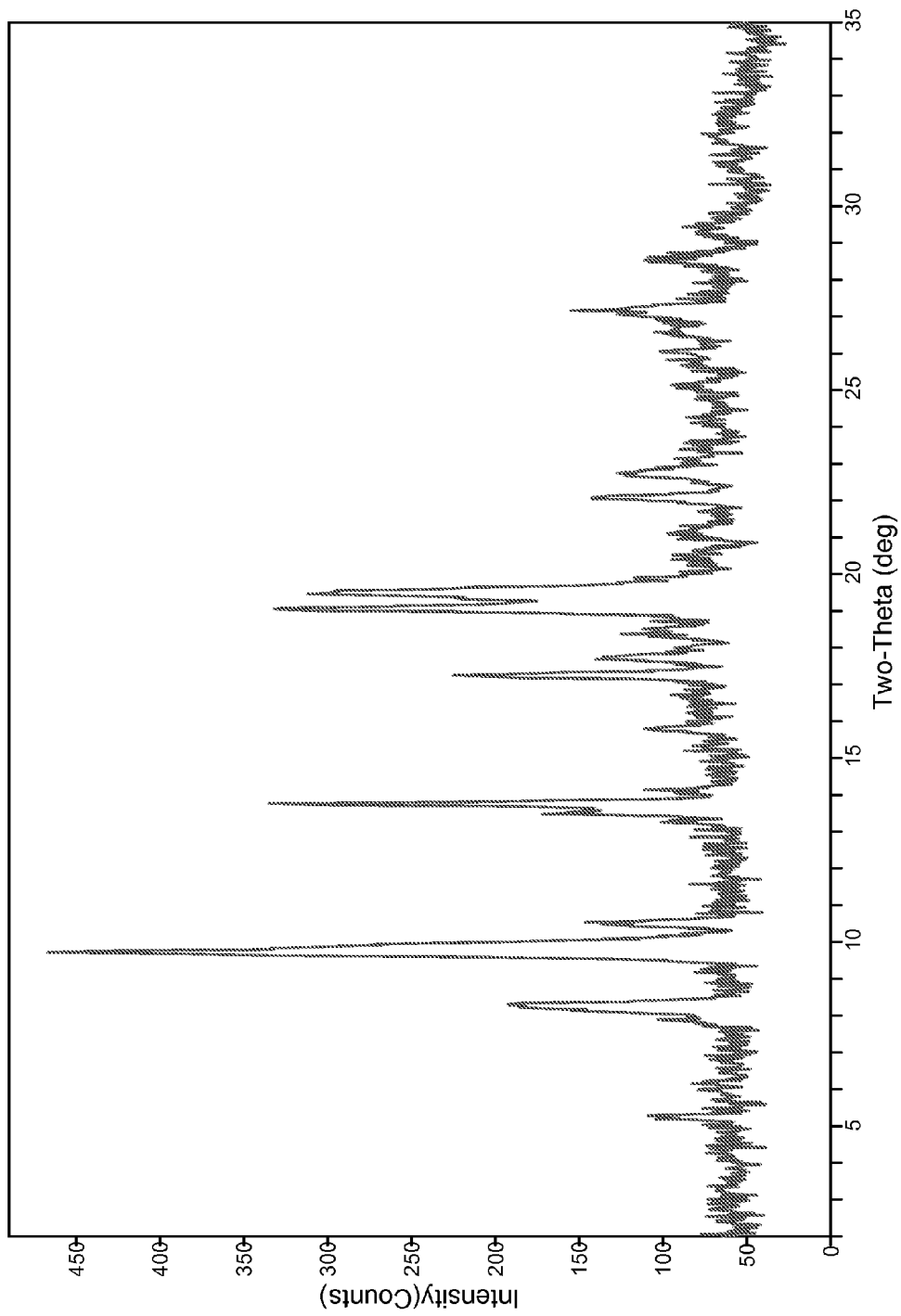
FIG. 3 shows an illustrative PXRD pattern for the acetonitrile solvate of compound IB-L0-2.3.

In some embodiments, the acetonitrile solvate has an X-ray powder diffraction pattern substantially as shown in FIG. 3. The 2θ values for the peaks in FIG. 3 (and their intensities) are as follows: 5.27 (14), 8.29 (33), 9.72 (100), 10.53 (20), 13.77 (67), 17.25 (38), 17.69 (17), 19.05 (63), 19.47 (58), 22.05 (19), 22.75 (16), and 27.17 (21).

This invention also relates, in part, to an ethyl acetate solvate of compound IB-L0-2.3.

In some embodiments, the ethyl acetate solvate has an X-ray powder diffraction pattern comprising one or more peaks selected from the group consisting of 7.9±0.2, 9.3±0.2, 9.7±0.2, 10.6±0.2, 18.7±0.2, 38.5±0.2, and 44.7±0.2 degrees 2θ. In some such embodiments, the ethyl acetate solvate has an X-ray powder diffraction pattern comprising three or more peaks selected from the group consisting of 7.9±0.2, 9.3±0.2, 9.7±0.2, 10.6±0.2, 18.7±0.2, 38.5±0.2, and 44.7±0.2 degrees 2θ. In other such embodiments, the ethyl acetate solvate has an X-ray powder diffraction pattern comprising five or more peaks selected from the group consisting of 7.9±0.2, 9.3±0.2, 9.7±0.2, 10.6±0.2, 18.7±0.2, 38.5±0.2, and 44.7±0.2 degrees 2θ.

In some embodiments, the ethyl acetate solvate has an X-ray powder diffraction pattern comprising one or more peaks selected from the group consisting of 7.9±0.2, 9.3±0.2, 9.7±0.2, 10.6±0.2, 13.7±0.2, 17.4±0.2, 18.7±0.2, 21.7±0.2, 22.0±0.2, 28.2±0.2, 38.5±0.2, and 44.7±0.2 degrees 2θ. In some such embodiments, the ethyl acetate solvate has an X-ray powder diffraction pattern comprising three or more peaks selected from the group consisting of 7.9±0.2, 9.3±0.2, 9.7±0.2, 10.6±0.2, 13.7±0.2, 17.4±0.2, 18.7±0.2, 21.7±0.2, 22.0±0.2, 28.2±0.2, 38.5±0.2, and 44.7±0.2 degrees 2θ. In other such embodiments, the ethyl acetate solvate has an X-ray powder diffraction pattern comprising five or more peaks selected from the group consisting of 7.9±0.2, 9.3±0.2, 9.7±0.2, 10.6±0.2, 13.7±0.2, 17.4±0.2, 18.7±0.2, 21.7±0.2, 22.0±0.2, 28.2±0.2, 38.5±0.2, and 44.7±0.2 degrees 2θ.

Figure 4:
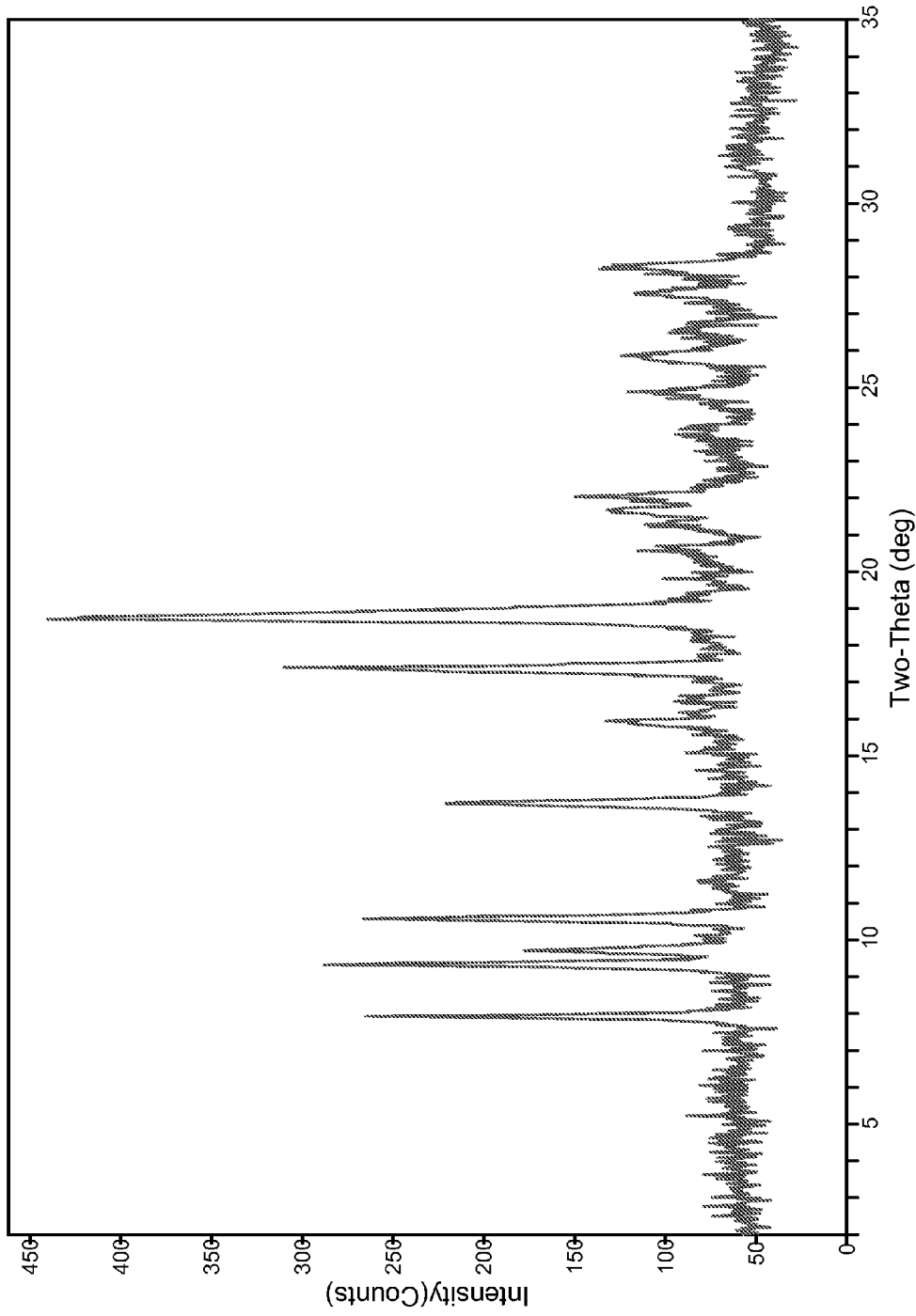
FIG. 4 shows an illustrative PXRD pattern for the ethyl acetate solvate of compound IB-L0-2.3.

In some embodiments, the ethyl acetate has an X-ray powder diffraction pattern substantially as shown in FIG. 4. The 2θ values for the peaks in FIG. 4 (and their intensities) are as follows: 7.94 (24), 9.33 (26), 9.72 (13), 10.58 (23), 13.71 (19), 17.40 (28), 18.72 (44), 21.69 (8), 22.04 (10), 28.23 (8), 38.45 (100), and 44.66 (95).

This invention also relates, in part, to a 2-propanol solvate of compound IB-L0-2.3.

In some embodiments, the 2-propanol solvate has an X-ray powder diffraction pattern comprising one or more peaks selected from the group consisting of 8.2±0.2, 9.3±0.2, 10.1±0.2, 16.3±0.2, 18.1±0.2, 18.6±0.2, 19.4±0.2, 21.6±0.2, and 22.5±0.2 degrees 2θ. In some such embodiments, the 2-propanol solvate has an X-ray powder diffraction pattern comprising three or more peaks selected from the group consisting of 8.2±0.2, 9.3±0.2, 10.1±0.2, 16.3±0.2, 18.1±0.2, 18.6±0.2, 19.4±0.2, 21.6±0.2, and 22.5±0.2 degrees 2θ. In other such embodiments, the 2-propanol solvate has an X-ray powder diffraction pattern comprising five or more peaks selected from the group consisting of 8.2±0.2, 9.3±0.2, 10.1±0.2, 16.3±0.2, 18.1±0.2, 18.6±0.2, 19.4±0.2, 21.6±0.2, and 22.5±0.2 degrees 2θ.

In some embodiments, the 2-propanol solvate has an X-ray powder diffraction pattern comprising one or more peaks selected from the group consisting of 8.2±0.2, 9.3±0.2, 10.1±0.2, 16.3±0.2, 18.1±0.2, 18.6±0.2, 19.4±0.2, 21.6±0.2, 22.5±0.2, 23.8±0.2, 26.0±0.2, and 28.0±0.2 degrees 2θ. In some such embodiments, the 2-propanol solvate has an X-ray powder diffraction pattern comprising three or more peaks selected from the group consisting of 8.2±0.2, 9.3±0.2, 10.1±0.2, 16.3±0.2, 18.1±0.2, 18.6±0.2, 19.4±0.2, 21.6±0.2, 22.5±0.2, 23.8±0.2, 26.0±0.2, and 28.0±0.2 degrees 2θ. In other such embodiments, the 2-propanol solvate has an X-ray powder diffraction pattern comprising five or more peaks selected from the group consisting of 8.2±0.2, 9.3±0.2, 10.1±0.2, 16.3±0.2, 18.1±0.2, 18.6±0.2, 19.4±0.2, 21.6±0.2, 22.5±0.2, 23.8±0.2, 26.0±0.2, and 28.0±0.2 degrees 2θ.

Figure 5:
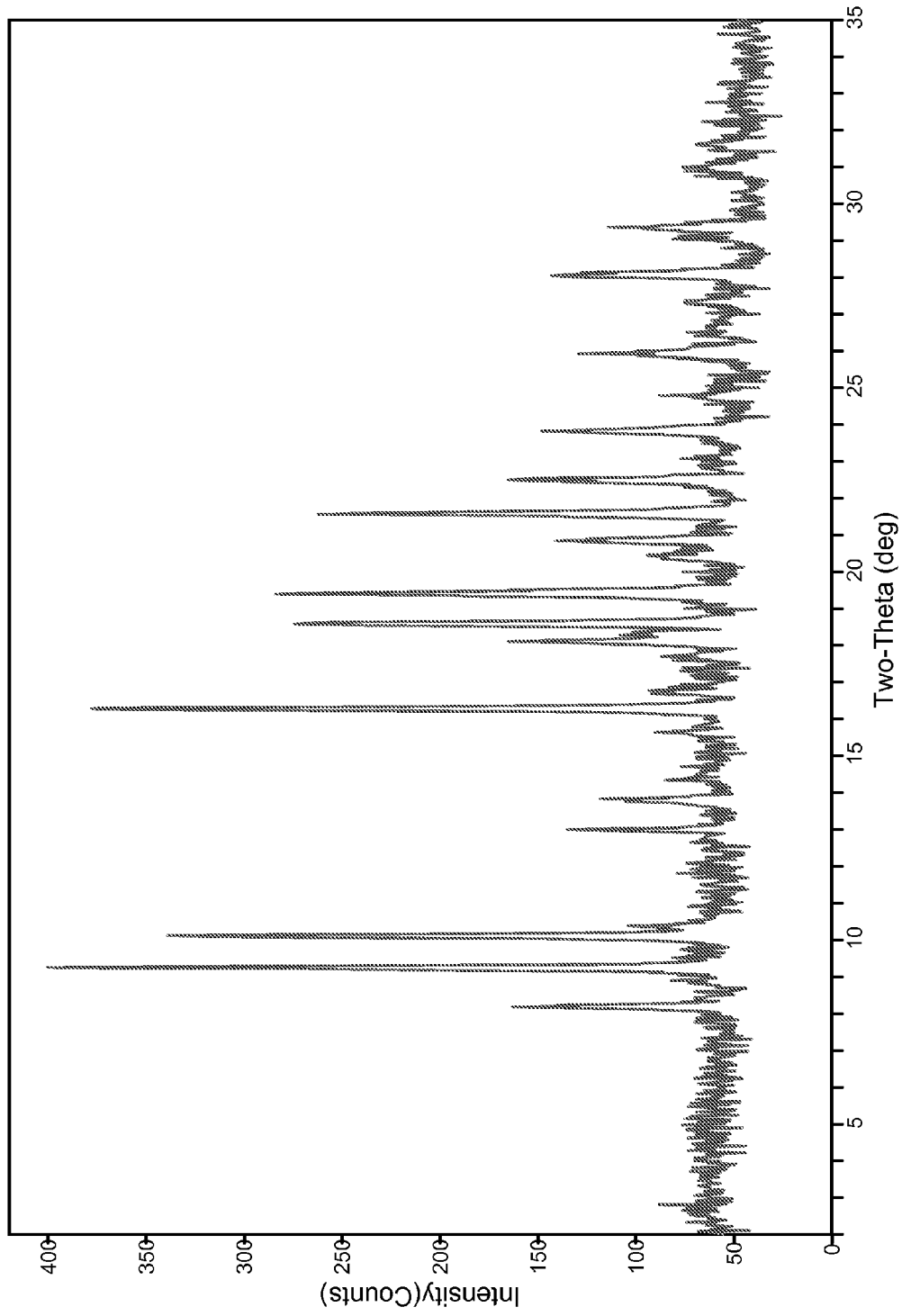
FIG. 5 shows an illustrative PXRD pattern for the 2-propanol solvate of compound IB-L0-2.3.

In some embodiments, the 2-propanol solvate has an X-ray powder diffraction pattern substantially as shown in FIG. 5. The 2θ values for the peaks in FIG. 5 (and their intensities) are as follows: 8.18 (32), 9.26 (100), 10.12 (81), 16.28 (93), 18.11 (30), 18.59 (63), 19.40 (67), 21.57 (60), 22.51 (31), 23.82 (29), 25.94 (24), and 28.05 (29).

This invention also relates, in part, to a methanol solvate of compound IB-L0-2.3.

In some embodiments, the methanol solvate has an X-ray powder diffraction pattern comprising one or more peaks selected from the group consisting of 8.4±0.2, 9.7±0.2, 10.1±0.2, 13.8±0.2, 17.4±0.2, 19.3±0.2, and 19.6±0.2 degrees 2θ. In some such embodiments, the methanol solvate has an X-ray powder diffraction pattern comprising three or more peaks selected from the group consisting of 8.4±0.2, 9.7±0.2, 10.1±0.2, 13.8±0.2, 17.4±0.2, 19.3±0.2, and 19.6±0.2 degrees 2θ. In other such embodiments, the methanol solvate has an X-ray powder diffraction pattern comprising five or more peaks selected from the group consisting of 8.4±0.2, 9.7±0.2, 10.1±0.2, 13.8±0.2, 17.4±0.2, 19.3±0.2, and 19.6±0.2 degrees 2θ.

In some embodiments, the methanol solvate has an X-ray powder diffraction pattern comprising one or more peaks selected from the group consisting of 8.4±0.2, 9.7±0.2, 10.1±0.2, 13.5±0.2, 13.8±0.2, 17.4±0.2, 19.3±0.2, 19.6±0.2, and 27.1±0.2 degrees 2θ. In some such embodiments, the methanol solvate has an X-ray powder diffraction pattern comprising three or more peaks selected from the group consisting of 8.4±0.2, 9.7±0.2, 10.1±0.2, 13.5±0.2, 13.8±0.2, 17.4±0.2, 19.3±0.2, 19.6±0.2, and 27.1±0.2 degrees 2θ. In other such embodiments, the methanol solvate has an X-ray powder diffraction pattern comprising five or more peaks selected from the group consisting of 8.4±0.2, 9.7±0.2, 10.1±0.2, 13.5±0.2, 13.8±0.2, 17.4±0.2, 19.3±0.2, 19.6±0.2, and 27.1±0.2 degrees 2θ.

Figure 6:
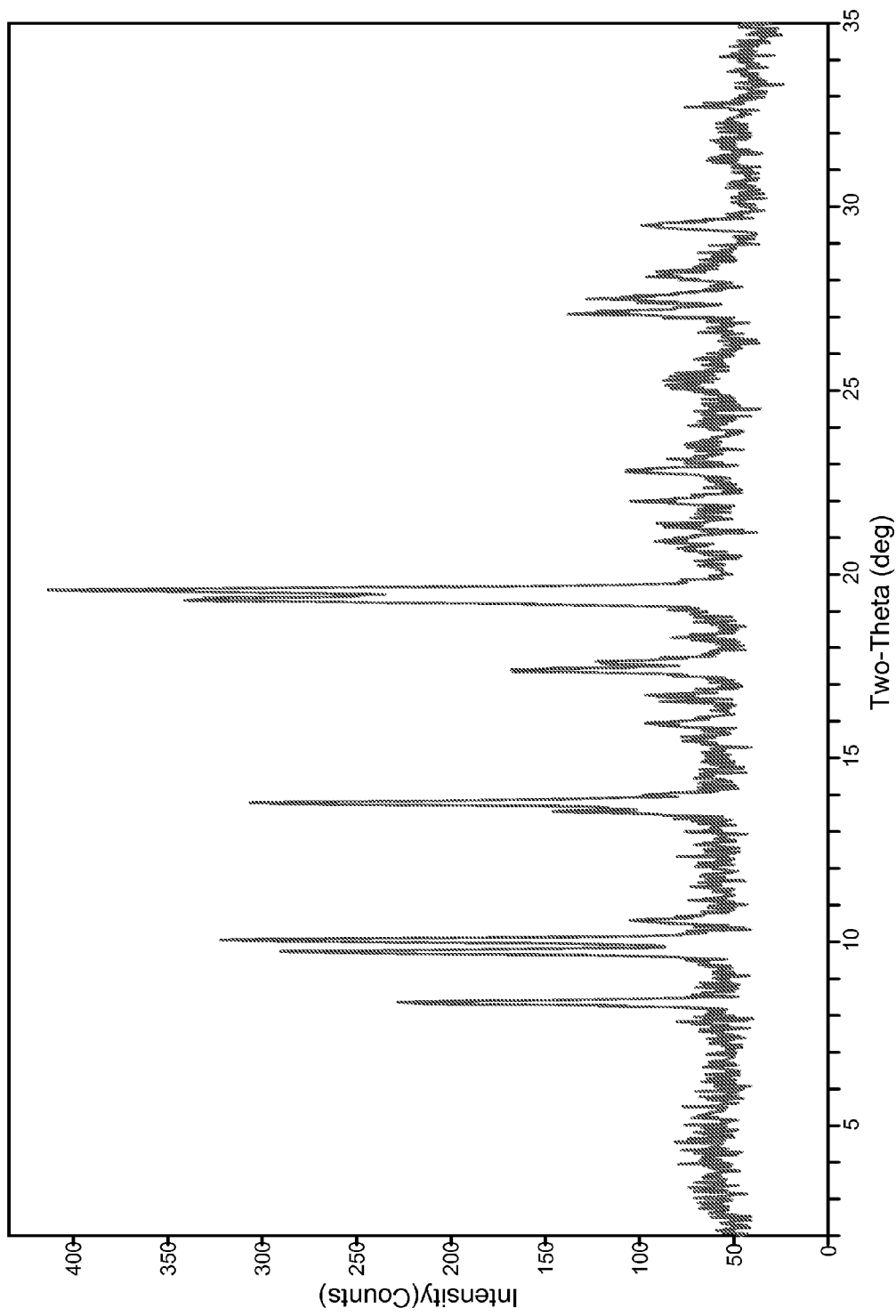
FIG. 6 shows an illustrative PXRD pattern for the methanol solvate of compound IB-L0-2.3.

In some embodiments, the methanol solvate has an X-ray powder diffraction pattern substantially as shown in FIG. 6. The 2θ values for the peaks in FIG. 6 (and their intensities) are as follows: 8.36 (48), 9.74 (65), 10.05 (74), 13.55 (24), 13.79 (69), 17.40 (32), 19.30 (80), 19.58 (100), and 27.08 (24).

This invention also relates, in part, to a 1-propanol solvate of compound IB-L0-2.3.

In some embodiments, the 1-propanol solvate has an X-ray powder diffraction pattern comprising one or more peaks selected from the group consisting of 8.2±0.2, 9.3±0.2, 10.1±0.2, 15.7±0.2, 16.2±0.2, 18.4±0.2, 19.3±0.2, 21.6±0.2, and 22.8±0.2 degrees 2θ. In some such embodiments, the 1-propanol solvate has an X-ray powder diffraction pattern comprising three or more peaks selected from the group consisting of 8.2±0.2, 9.3±0.2, 10.1±0.2, 15.7±0.2, 16.2±0.2, 18.4±0.2, 19.3±0.2, 21.6±0.2, and 22.8±0.2 degrees 2θ. In other such embodiments, the 1-propanol solvate has an X-ray powder diffraction pattern comprising five or more peaks selected from the group consisting of 8.2±0.2, 9.3±0.2, 10.1±0.2, 15.7±0.2, 16.2±0.2, 18.4±0.2, 19.3±0.2, 21.6±0.2, and 22.8±0.2 degrees 2θ.

In some embodiments, the 1-propanol solvate has an X-ray powder diffraction pattern comprising one or more peaks selected from the group consisting of 8.2±0.2, 9.3±0.2, 10.1±0.2, 10.5±0.2, 15.7±0.2, 16.2±0.2, 18.4±0.2, 18.6±0.2, 19.3±0.2, 21.0±0.2, 21.6±0.2, and 22.8±0.2 degrees 2θ. In some such embodiments, the 1-propanol solvate has an X-ray powder diffraction pattern comprising three or more peaks selected from the group consisting of 8.2±0.2, 9.3±0.2, 10.1±0.2, 10.5±0.2, 15.7±0.2, 16.2±0.2, 18.4±0.2, 18.6±0.2, 19.3±0.2, 21.0±0.2, 21.6±0.2, and 22.8±0.2 degrees 2θ. In other such embodiments, the 1-propanol solvate has an X-ray powder diffraction pattern comprising five or more peaks selected from the group consisting of 8.2±0.2, 9.3±0.2, 10.1±0.2, 10.5±0.2, 15.7±0.2, 16.2±0.2, 18.4±0.2, 18.6±0.2, 19.3±0.2, 21.0±0.2, 21.6±0.2, and 22.8±0.2 degrees 2θ.

Figure 7:
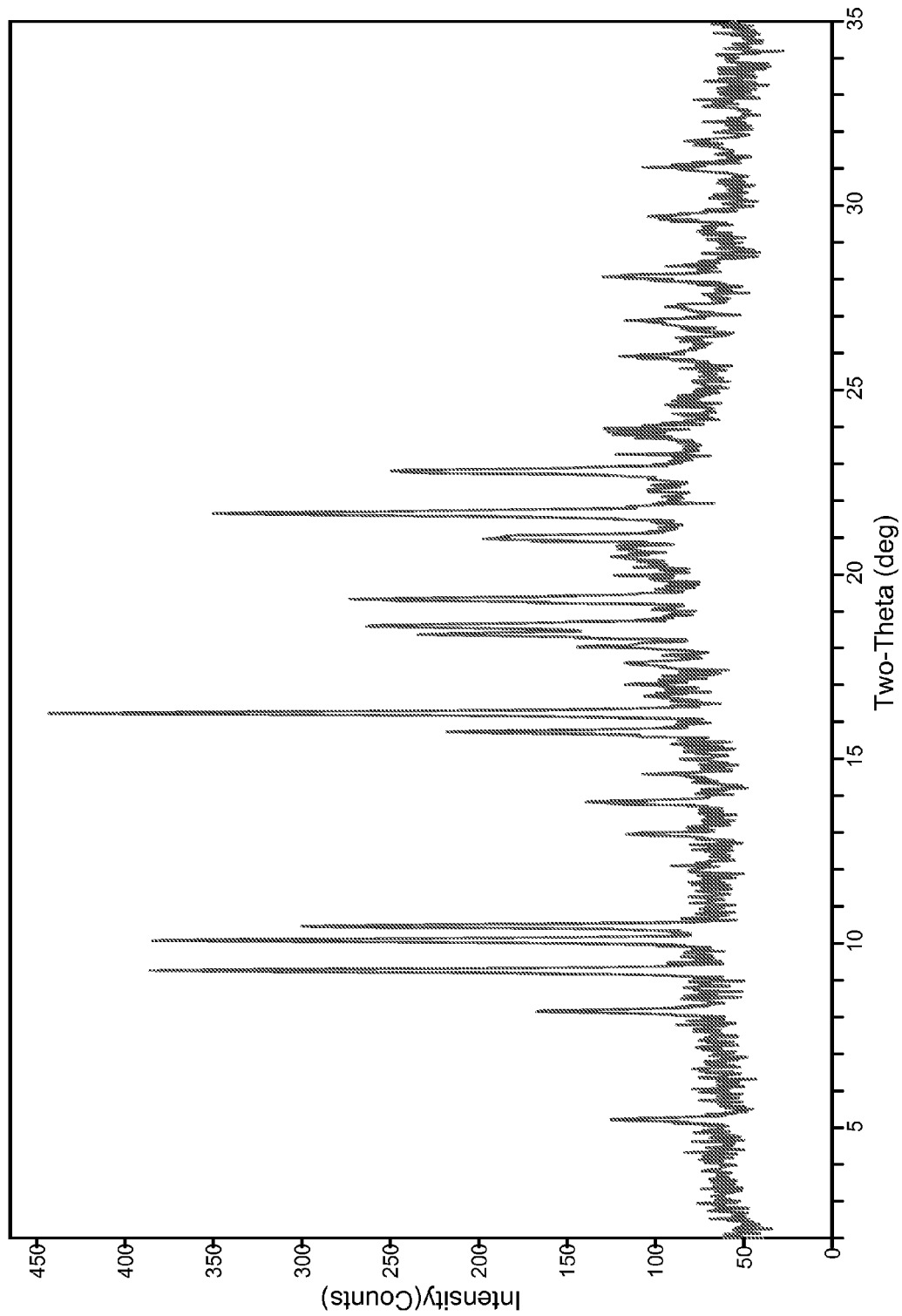
FIG. 7 shows an illustrative PXRD pattern for the 1-propanol solvate of compound IB-L0-2.3.

In some embodiments, the 1-propanol solvate has an X-ray powder diffraction pattern substantially as shown in FIG. 7. The 2θ values for the peaks in FIG. 7 (and their intensities) are as follows: 8.15 (27), 9.26 (87), 10.08 (84), 10.47 (62), 15.73 (40), 16.24 (100), 18.37 (41), 18.59 (49), 19.33 (50), 20.97 (28), 21.65 (71), and 22.81 (44).

This invention also relates, in part, to a process for preparing the above solvates by suspending compound IB-L0-2.3 in the corresponding solvent.

G1B. Solvent Free IB-L0-2.3

This invention also relates, in part, to a solvent free crystalline form of compound IB-L0-2.3.

In some embodiments, the solvent free compound IB-L0-2.3 has an X-ray powder diffraction pattern comprising one or more peaks selected from the group consisting of 6.2±0.2, 7.9±0.2, 9.9±0.2, 16.2±0.2, and 18.3±0.2 degrees two theta (2θ). In some such embodiments, the solvent free compound IB-L0-2.3 has an X-ray powder diffraction pattern comprising three or more peaks selected from the group consisting of 6.2±0.2, 7.9±0.2, 9.9±0.2, 16.2±0.2, and 18.3±0.2 degrees 2θ. In other such embodiments, the solvent free compound IB-L0-2.3 has an X-ray powder diffraction pattern comprising five or more peaks selected from the group consisting of 6.2±0.2, 7.9±0.2, 9.9±0.2, 16.2±0.2, and 18.3±0.2 degrees 2θ.

In some embodiments, the solvent free compound IB-L0-2.3 has an X-ray powder diffraction pattern comprising one or more peaks selected from the group consisting of 6.2±0.2, 7.9±0.2, 9.9±0.2, 10.1±0.2, 14.9±0.2, 16.2±0.2, 18.3±0.2, 19.8±0.2, and 26.5±0.2 degrees 2θ. In some such embodiments, the solvent free compound IB-L0-2.3 has an X-ray powder diffraction pattern comprising three or more peaks selected from the group consisting of 6.2±0.2, 7.9±0.2, 9.9±0.2, 10.1±0.2, 14.9±0.2, 16.2±0.2, 18.3±0.2, 19.8±0.2, and 26.5±0.2 degrees 2θ. In other such embodiments, the solvent free compound IB-L0-2.3 has an X-ray powder diffraction pattern comprising five or more peaks selected from the group consisting of 6.2±0.2, 7.9±0.2, 9.9±0.2, 10.1±0.2, 14.9±0.2, 16.2±0.2, 18.3±0.2, 19.8±0.2, and 26.5±0.2 degrees 2θ. In yet other such embodiments, the solvent free compound IB-L0-2.3 has an X-ray powder diffraction pattern comprising eight or more peaks selected from the group consisting of 6.2±0.2, 7.9±0.2, 9.9±0.2, 10.1±0.2, 14.9±0.2, 16.2±0.2, 18.3±0.2, 19.8±0.2, and 26.5±0.2 degrees 2θ.

Figure 8:
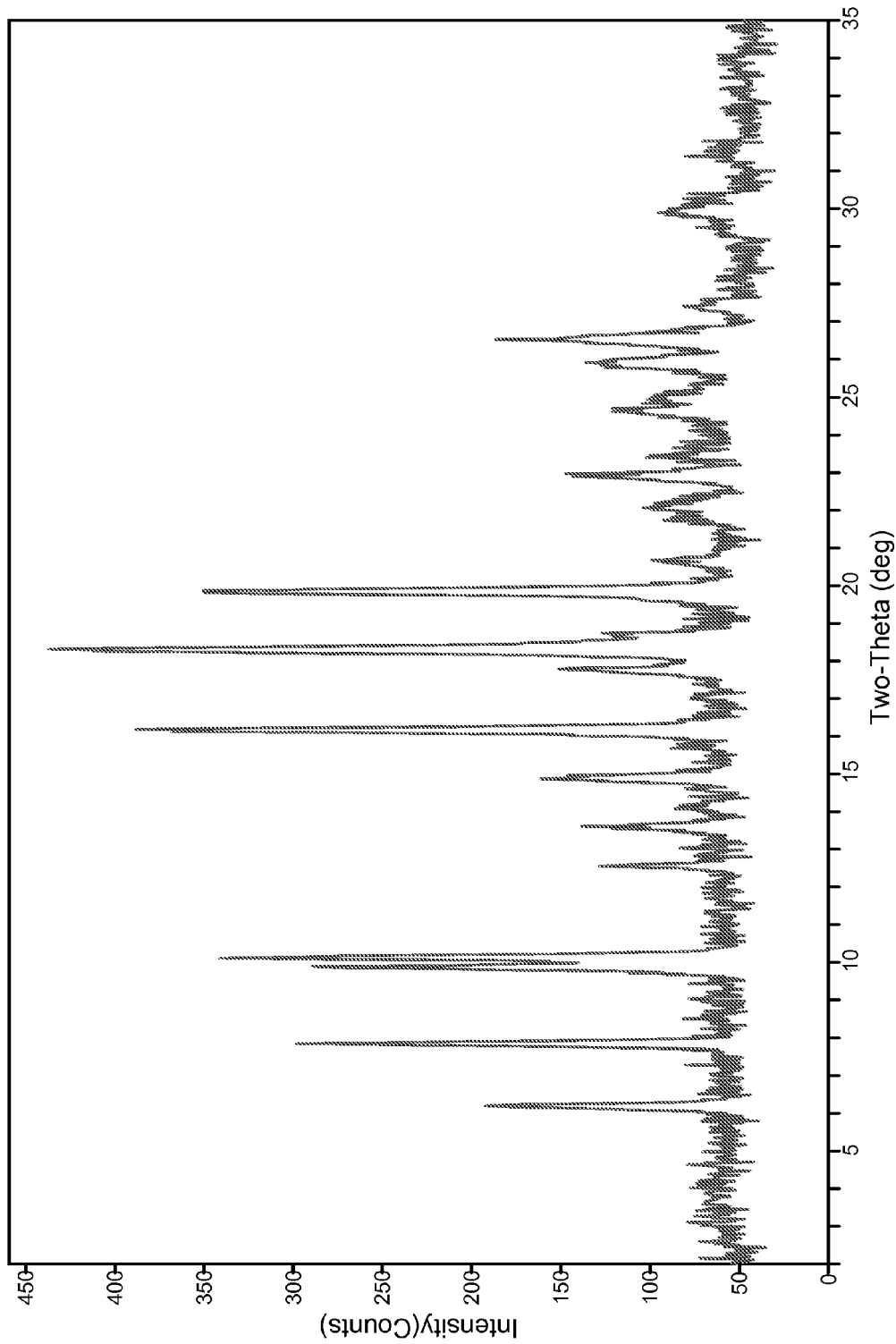
FIG. 8 shows an illustrative PXRD pattern for the solvent free crystalline compound IB-L0-2.3.

In some embodiments, the solvent free compound IB-L0-2.3 has an X-ray powder diffraction pattern substantially as shown in FIG. 8. The 2θ values for the peaks in FIG. 8 (and their intensities) are as follows: 6.20 (36), 7.85 (66), 9.89 (61), 10.12 (75), 14.87 (27), 16.19 (89), 18.32 (100), 19.82 (77), and 26.53 (34).

This invention also relates, in part, to a process for preparing the solvent free crystalline form of compound IB-L0-2.3 by desolvating one of IB-L0-2.3 solvates discussed above. A solvate can be desolvated by heating the solvate solid for about 10 min at ~125° C.

G1C. IB-L0-2.3 Hydrate

This invention also relates, in part, to a hydrate of compound IB-L0-2.3.

In some embodiments, the hydrate has an X-ray powder diffraction pattern comprising one or more peaks selected from the group consisting of 6.4±0.2, 12.9±0.2, 17.9±0.2, and 18.9±0.2 degrees 2θ. In some such embodiments, the hydrate has an X-ray powder diffraction pattern comprising three or more peaks selected from the group consisting of 6.4±0.2, 12.9±0.2, 17.9±0.2, and 18.9±0.2 degrees 2θ.

In some embodiments, the hydrate has an X-ray powder diffraction pattern comprising one or more peaks selected from the group consisting of 6.4±0.2, 12.9±0.2, 17.5±0.2, 17.9±0.2, 18.9±0.2, and 24.4±0.2 degrees 2θ. In some such embodiments, the hydrate has an X-ray powder diffraction pattern comprising three or more peaks selected from the group consisting of 6.4±0.2, 12.9±0.2, 17.5±0.2, 17.9±0.2, 18.9±0.2, and 24.4±0.2 degrees 2θ. In other such embodiments, the hydrate has an X-ray powder diffraction pattern comprising five or more peaks selected from the group consisting of 6.4±0.2, 12.9±0.2, 17.5±0.2, 17.9±0.2, 18.9±0.2, and 24.4±0.2 degrees 2θ.

In some embodiments, the hydrate has an X-ray powder diffraction pattern comprising one or more peaks selected from the group consisting of 6.4±0.2, 12.7±0.2, 12.9±0.2, 14.1±0.2, 15.7±0.2, 17.2±0.2, 17.5±0.2, 17.9±0.2, 18.9±0.2, 21.2±0.2, 24.4±0.2, and 25.0±0.2 degrees 2θ. In some such embodiments, the hydrate has an X-ray powder diffraction pattern comprising three or more peaks selected from the group consisting of 6.4±0.2, 12.7±0.2, 12.9±0.2, 14.1±0.2, 15.7±0.2, 17.2±0.2, 17.5±0.2, 17.9±0.2, 18.9±0.2, 21.2±0.2, 24.4±0.2, and 25.0±0.2 degrees 2θ. In other such embodiments, the hydrate has an X-ray powder diffraction pattern comprising five or more peaks selected from the group consisting of 6.4±0.2, 12.7±0.2, 12.9±0.2, 14.1±0.2, 15.7±0.2, 17.2±0.2, 17.5±0.2, 17.9±0.2, 18.9±0.2, 21.2±0.2, 24.4±0.2, and 25.0±0.2 degrees 2θ.

Figure 9:
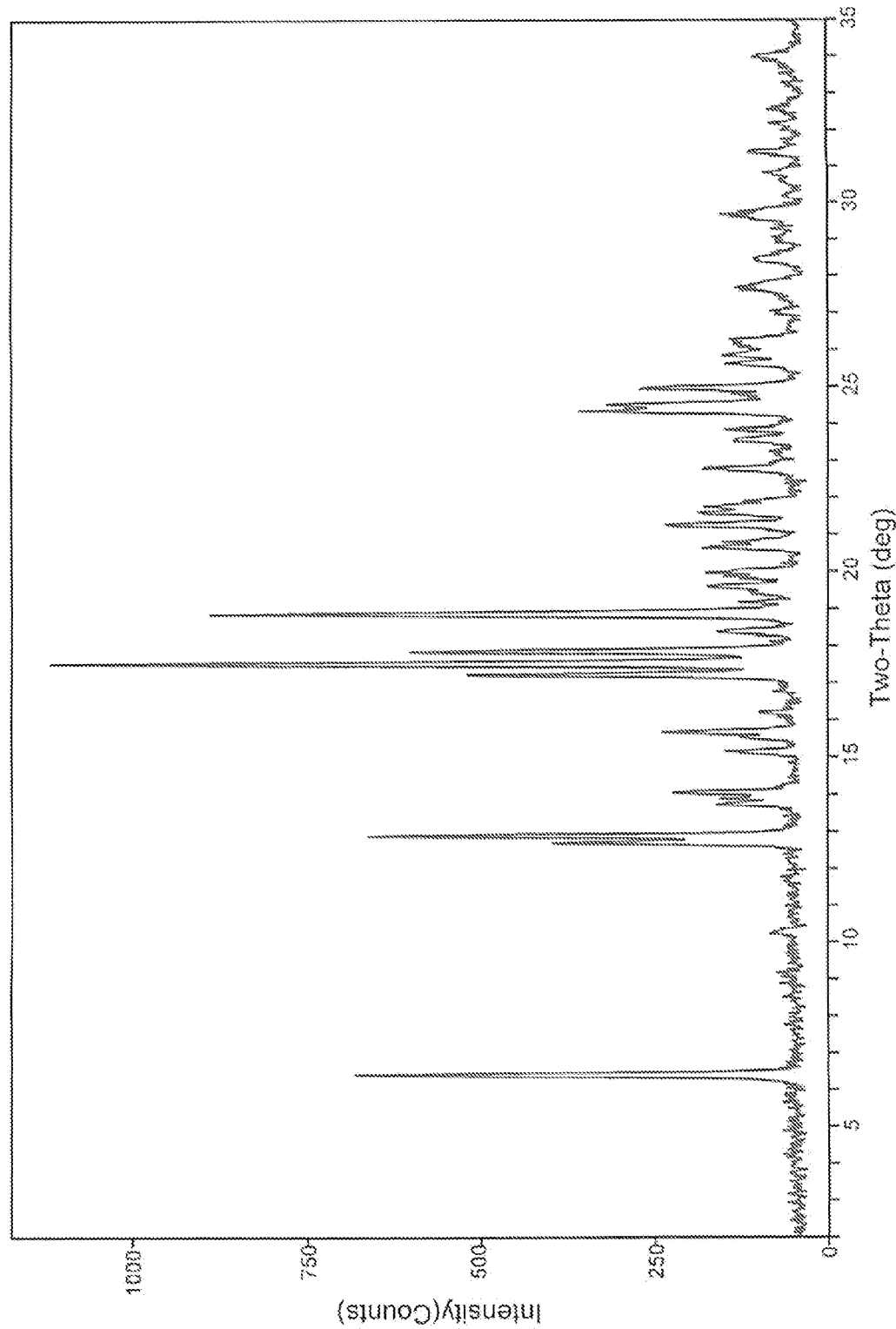
FIG. 9 shows an illustrative PXRD pattern for the hydrate of compound IB-L0-2.3.

In some embodiments, the hydrate has an X-ray powder diffraction pattern substantially as shown in FIG. 9. The 2θ values for the peaks in FIG. 9 (and their intensities) are as follows: 6.42 (60), 12.71 (33), 12.89 (58), 14.05 (17), 15.68 (18), 17.22 (44), 17.53 (100), 17.86 (51), 18.87 (77), 21.25 (17), 24.35 (28), and 24.95 (20).

This invention also relates, in part, to a process for preparing the hydrate by suspending the above-described solvent free crystalline compound in water. The hydrate was prepared by suspending 300 mg of the solvent free crystalline compound in 2 ml of water at 45° C. for four days.

G2. Crystalline Forms of N-(6-(3-Tert-butyl-5-(2,4-dioxo-3,4-dihydropyrimidin-1(2H)-yl)-2-methoxyphenyl)naphthalen-2-yl)methanesulfonamide, Monosodium Salt This invention also relates, in part, to crystalline forms of N-(6-(3-tert-butyl-5-(2,4-dioxo-3,4-dihydropyrimidin-1 (2H)-yl)-2-methoxyphenyl)naphthalen-2-yl)methanesulfonamide, monosodium salt, namely the pattern A, pattern B, and pattern C crystalline forms discussed below.

This invention relates, in part, to a pattern A crystalline monosodium salt.

In some embodiments, the pattern A monosodium salt has an X-ray powder diffraction pattern comprising one or more peaks selected from the group consisting of 4.6±0.2, 10.4±0.2, 12.0±0.2, 15.6±0.2, 18.6±0.2, 22.8±0.2, and 23.9±0.2 degrees 2θ. In some such embodiments, the pattern A monosodium salt has an X-ray powder diffraction pattern comprising three or more peaks selected from the group consisting of 4.6±0.2, 10.4±0.2, 12.0±0.2, 15.6±0.2, 18.6±0.2, 22.8±0.2, and 23.9±0.2 degrees 2θ. In other such embodiments, the pattern A monosodium salt has an X-ray powder diffraction pattern comprising five or more peaks selected from the group consisting of 4.6±0.2, 10.4±0.2, 12.0±0.2, 15.6±0.2, 18.6±0.2, 22.8±0.2, and 23.9±0.2 degrees 2θ.

In some embodiments, the pattern A monosodium salt has an X-ray powder diffraction pattern comprising one or more peaks selected from the group consisting of 4.6±0.2, 10.4±0.2, 12.0±0.2, 15.6±0.2, 18.6±0.2, 22.8±0.2, 23.3±0.2, and 23.9±0.2 degrees 2θ. In some such embodiments, the pattern A monosodium salt has an X-ray powder diffraction pattern comprising three or more peaks selected from the group consisting of 4.6±0.2, 10.4±0.2, 12.0±0.2, 15.6±0.2, 18.6±0.2, 22.8±0.2, 23.3±0.2, and 23.9±0.2 degrees 2θ. In other such embodiments, the pattern A monosodium salt has an X-ray powder diffraction pattern comprising five or more peaks selected from the group consisting of 4.6±0.2, 10.4±0.2, 12.0±0.2, 15.6±0.2, 18.6±0.2, 22.8±0.2, 23.3±0.2, and 23.9±0.2 degrees 2θ.

In some embodiments, the pattern A monosodium salt has an X-ray powder diffraction pattern comprising one or more peaks selected from the group consisting of 4.6±0.2, 10.4±0.2, 12.0±0.2, 15.6±0.2, 16.0±0.2, 18.6±0.2, 22.8±0.2, 23.3±0.2, 23.9±0.2, and 28.3±0.2 degrees 2θ. In some such embodiments, the pattern A monosodium salt has an X-ray powder diffraction pattern comprising three or more peaks selected from the group consisting of 4.6±0.2, 10.4±0.2, 12.0±0.2, 15.6±0.2, 16.0±0.2, 18.6±0.2, 22.8±0.2, 23.3±0.2, 23.9±0.2, and 28.3±0.2 degrees 2θ. In other such embodiments, the pattern A monosodium salt has an X-ray powder diffraction pattern comprising five or more peaks selected from the group consisting of 4.6±0.2, 10.4±0.2, 12.0±0.2, 15.6±0.2, 16.0±0.2, 18.6±0.2, 22.8±0.2, 23.3±0.2, 23.9±0.2, and 28.3±0.2 degrees 2θ. In other such embodiments, the pattern A monosodium salt has an X-ray powder diffraction pattern comprising eight or more peaks selected from the group consisting of 4.6±0.2, 10.4±0.2, 12.0±0.2, 15.6±0.2, 16.0±0.2, 18.6±0.2, 22.8±0.2, 23.3±0.2, 23.9±0.2, and 28.3±0.2 degrees 2θ.

Figure 10:
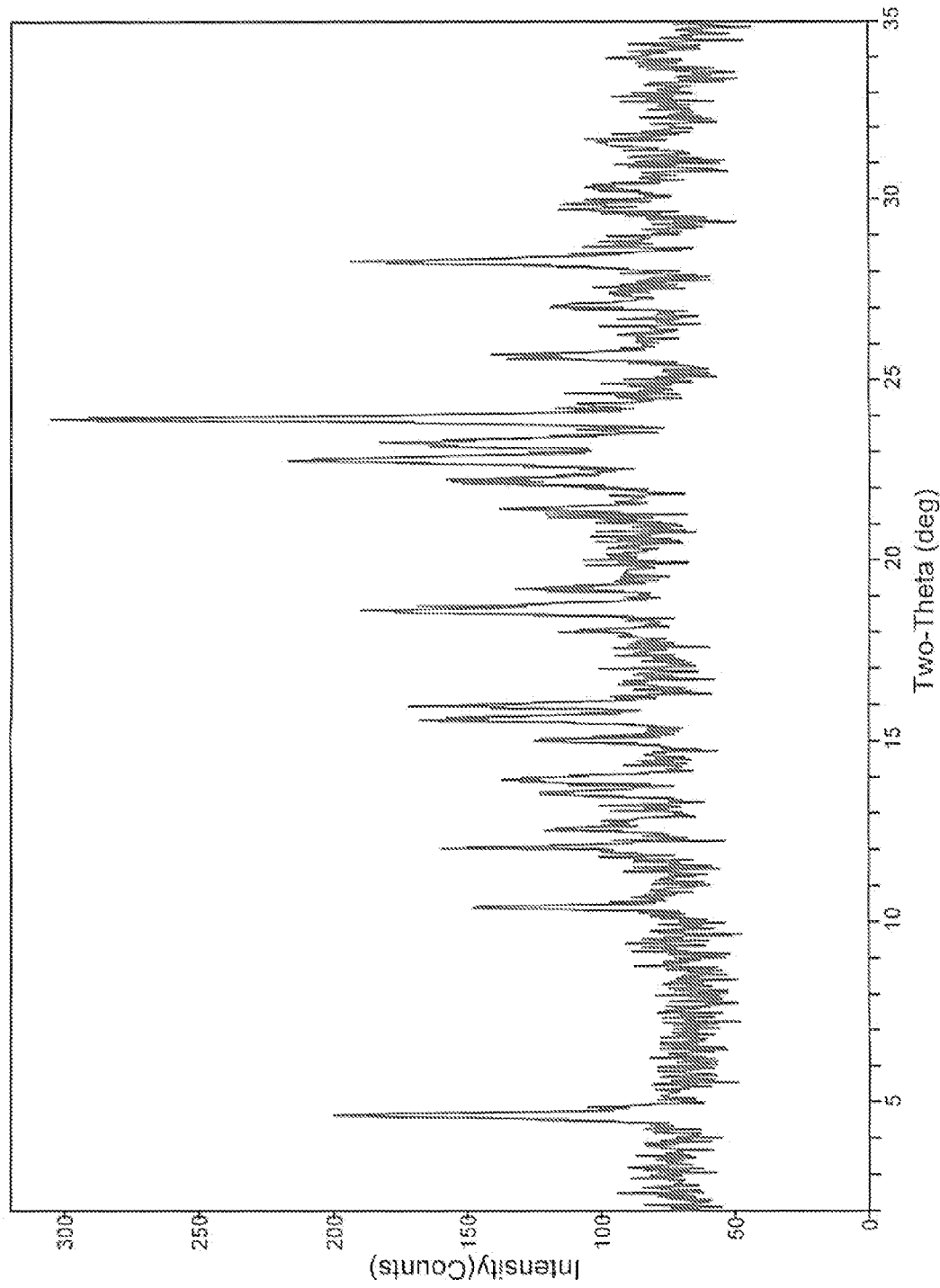
FIG. 10 shows an illustrative PXRD pattern for the pattern A monosodium salt of compound IB-L0-2.3.
Figure 11:
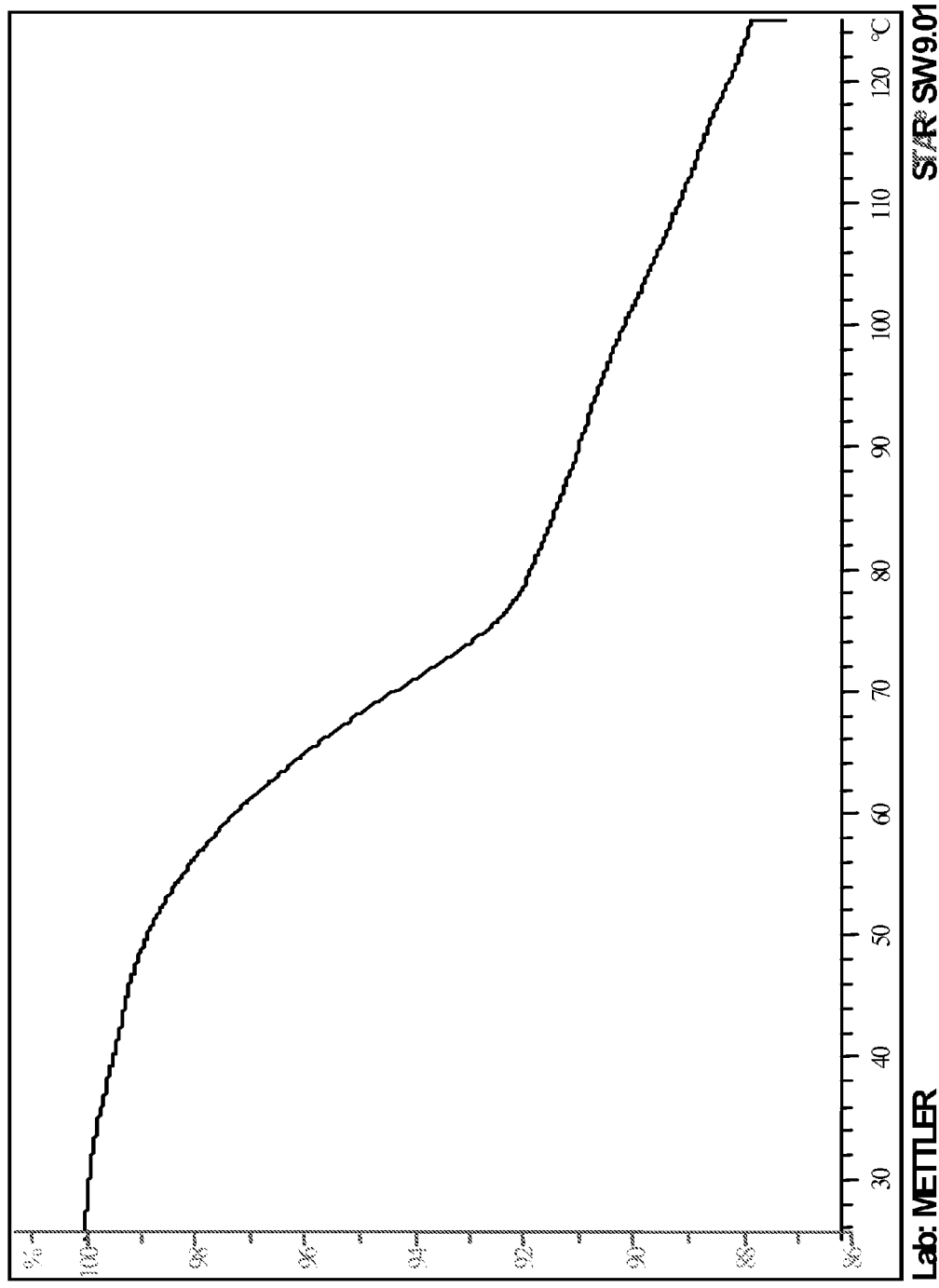
FIG. 11 shows an illustrative TGA profile of the pattern A monosodium salt of compound IB-L0-2.3.

In some embodiments, the pattern A monosodium salt has an X-ray powder diffraction pattern substantially as shown in FIG. 10. The 2θ values for the peaks in FIG. 10 (and their intensities) are as follows: 4.64 (62), 10.41 (38), 12.04 (38), 15.62 (44), 15.99 (44), 18.63 (49), 22.77 (60), 23.29 (40), 23.93 (100), and 28.31 (56).

This invention also relates, in part, to a process for preparing the pattern A monosodium salt. The pattern A monosodium salt was prepared by adding 1M aqueous NaOH (0.548 ml) to compound IB-L0-2.3 (225.72 mg), seeding the resulting suspension with crystalline N-(6-(3-tert-butyl-5-(2,4-dioxo-3,4-dihydropyrimidin-1(2H)-yl)-2-methoxyphenyl) naphthalen-2-yl)methanesulfonamide, disodium salt (prepared as discussed below), and equilibrating the resulting suspension at ambient conditions. The pattern A monosodium salt was formed on the following day through a solution-mediated process. The stoichiometry of the salt was presumed to be 1:1 based on the crystallization procedure. This invention also relates, in part, to a pattern B crystalline monosodium salt.

In some embodiments, the pattern B monosodium salt has an X-ray powder diffraction pattern comprising one or more peaks selected from the group consisting of 5.4±0.2, 10.8±0.2, 14.4±0.2, 16.3±0.2, 17.0±0.2, 21.6±0.2, 22.1±0.2, and 23.7±0.2 degrees 2θ. In some such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 21.6±0.2, 22.1±0.2, and 23.7±0.2 degrees 2θ. In other such embodiments, the pattern B monosodium salt has an X-ray powder diffraction pattern comprising five or more peaks selected from the group consisting of 5.4±0.2, 10.8±0.2, 14.4±0.2, 16.3±0.2, 17.0±0.2, 21.6±0.2, 22.1±0.2, and 23.7±0.2 degrees 2θ.

In some embodiments, the pattern B monosodium salt has an X-ray powder diffraction pattern comprising one or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ. In some such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ. In other such embodiments, the pattern B monosodium salt has an X-ray powder diffraction pattern comprising five or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ. In other such embodiments, the pattern B monosodium salt has an X-ray powder diffraction pattern comprising eight or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ.

In some embodiments, the pattern B monosodium salt has an X-ray powder diffraction pattern comprising one or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ. In some such embodiments, the pattern B monosodium salt has an X-ray powder diffraction pattern comprising two or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 29.1±0.2, and 31.8±0.2 degrees 2θ. In other such embodiments, the pattern B monosodium salt has an X-ray powder diffraction pattern comprising two or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, and 31.8±0.2 degrees 2θ. In yet other such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, and 31.8±0.2 degrees 2θ. In yet other such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 18.8±0.2, 19.2±0.2, 21.6±0.2, 22.1±0.2, and 23.7±0.2 degrees 2θ. In yet other such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 19.2±0.2, 21.6±0.2, 22.1±0.2, and 23.7±0.2 degrees 2θ. In yet other such embodiments, the pattern B monosodium salt has an X-ray powder diffraction pattern comprising three or more peaks selected from the group consisting of 5.4±0.2, 10.8±0.2, 16.3±0.2, 17.0±0.2, 18.8±0.2, 21.6±0.2, 22.1±0.2, and 23.7±0.2 degrees 2θ. In yet other such embodiments, the pattern B monosodium salt has an X-ray powder diffraction pattern comprising three or more peaks selected from the group consisting of 5.4±0.2, 10.8±0.2, 14.4±0.2, 16.3±0.2, 17.0±0.2, 21.6±0.2, 22.1±0.2, and 23.7±0.2 degrees 2θ. In yet other such embodiments, the pattern B monosodium salt has an X-ray powder diffraction pattern comprising three or more peaks selected from the group consisting of 5.4±0.2, 10.8±0.2, 16.3±0.2, 22.1±0.2, and 23.7±0.2 degrees 2θ.

In some embodiments, the pattern B monosodium salt has an X-ray powder diffraction pattern comprising peaks at 5.4±0.2, 10.8±0.2, and 16.3±0.2 degrees 2θ. In some such embodiments, the pattern B monosodium salt has an X-ray powder diffraction pattern comprising peaks at 5.4±0.2, 10.8±0.2, 16.3±0.2, and 22.1±0.2 degrees 2θ. In other such embodiments, the pattern B monosodium salt has an X-ray powder diffraction pattern comprising peaks at 5.4±0.2, 10.8±0.2, 16.3±0.2, 22.1±0.2, and 23.7±0.2 degrees 2θ. In yet other such embodiments, the pattern B monosodium salt has an X-ray powder diffraction pattern comprising peaks at 5.4±0.2, 10.8±0.2, 14.4±0.2, 16.3±0.2, 17.0±0.2, 21.6±0.2, 22.1±0.2, and 23.7±0.2 degrees 2θ. In yet other such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 21.6±0.2, 22.1±0.2, and 23.7±0.2 degrees 2θ. In yet other such embodiments, the pattern B monosodium salt has an X-ray powder diffraction pattern comprising peaks at 5.4±0.2, 10.8±0.2, 14.4±0.2, 16.3±0.2, 17.0±0.2, 19.2±0.2, 21.6±0.2, 22.1±0.2, and 23.7±0.2 degrees 2θ. In yet other such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 19.2±0.2, 21.6±0.2, 22.1±0.2, and 23.7±0.2 degrees 2θ. In further such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, and 31.8±0.2 degrees 2θ. In yet further such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, and 31.8±0.2 degrees 2θ. In yet further such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 29.1±0.2, and 31.8±0.2 degrees 2θ. In yet further such embodiments, the pattern B monosodium salt has an X-ray powder diffraction pattern comprising peaks at 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees 2θ.

Figure 12:
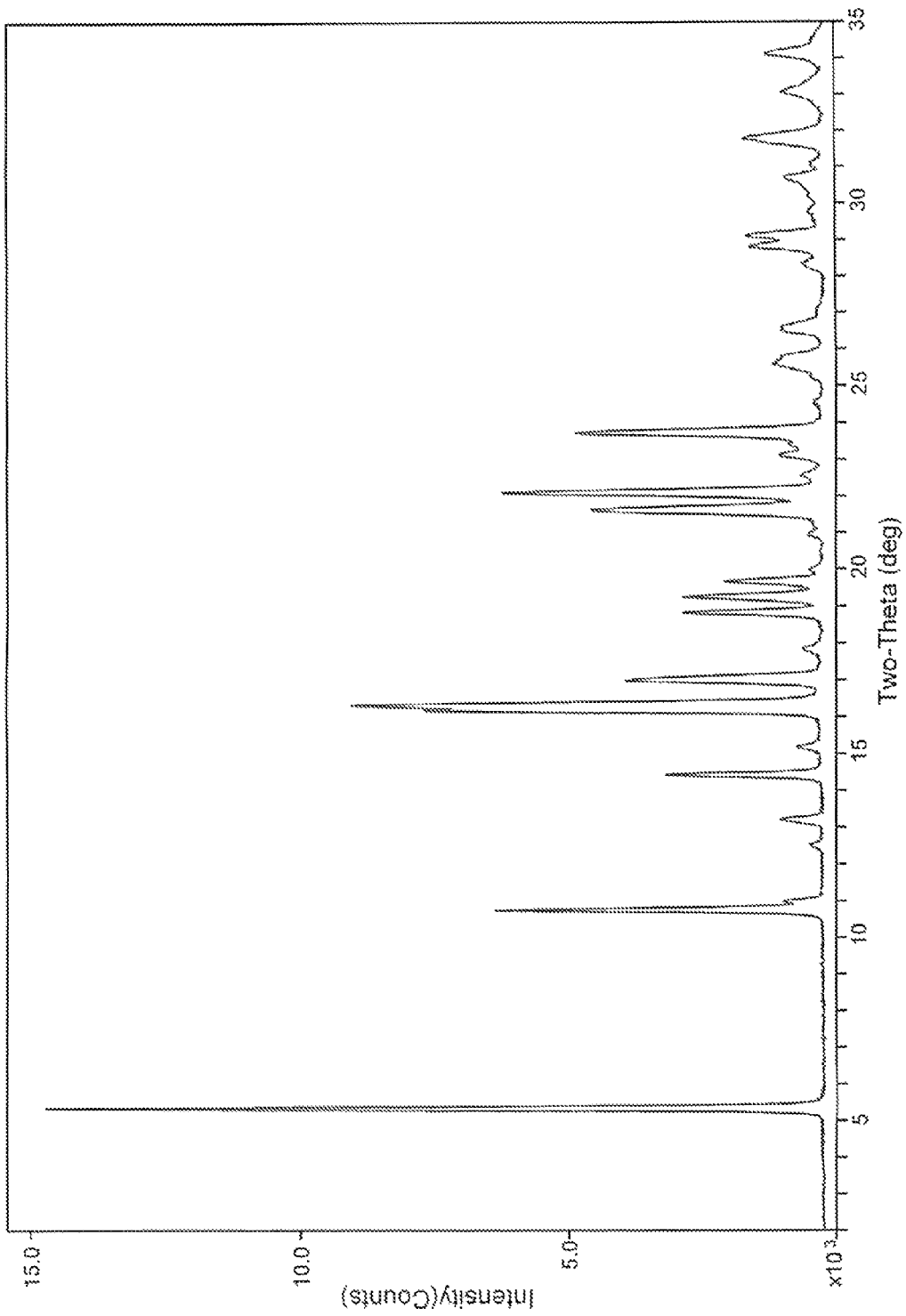
FIG. 12 shows an illustrative PXRD pattern for the pattern B monosodium salt of compound IB-L0-2.3.
Figure 13:
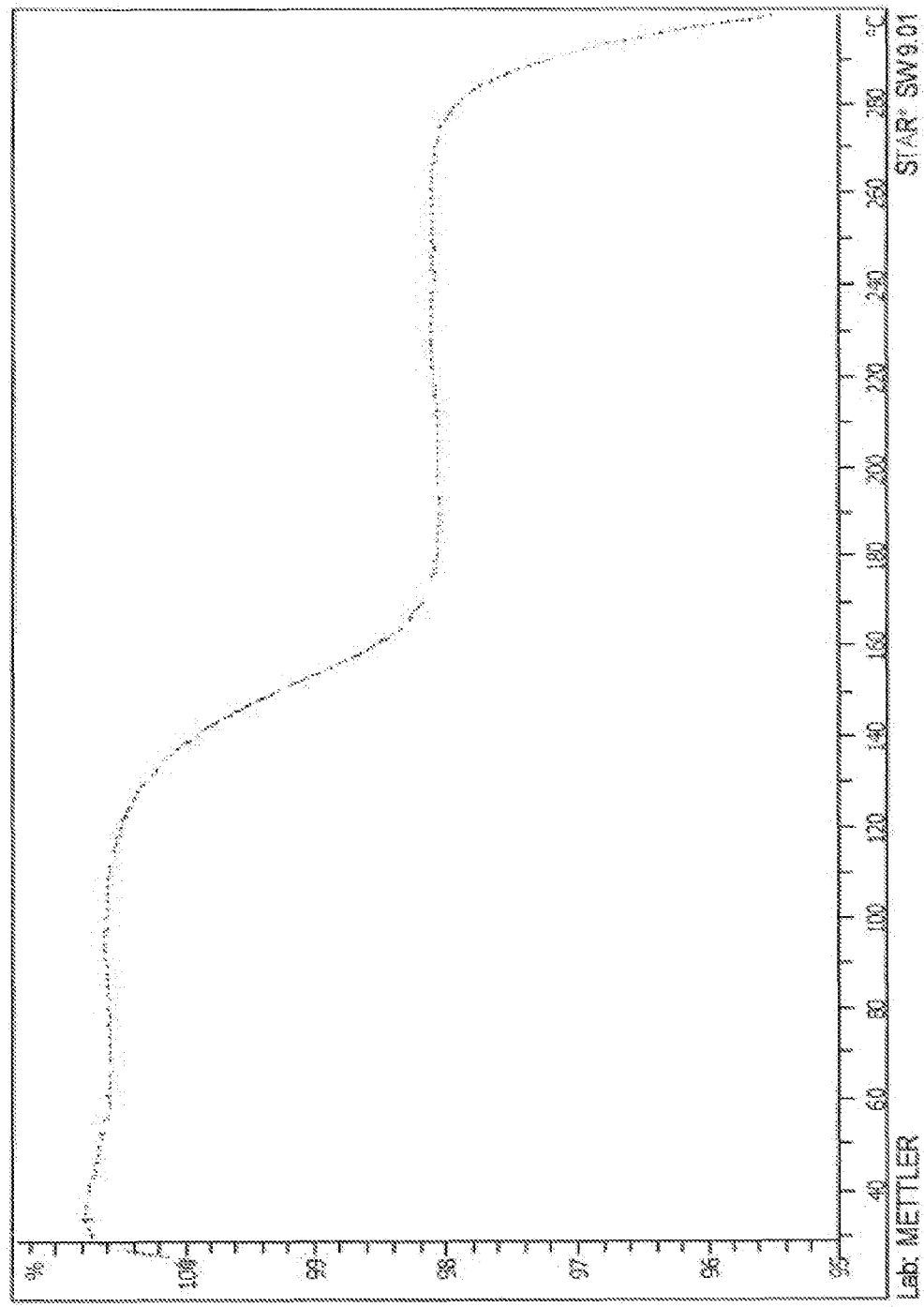
FIG. 13 shows an illustrative TGA profile of the pattern B monosodium salt of compound IB-L0-2.3.

In some embodiments, the pattern B monosodium salt has an X-ray powder diffraction pattern substantially as shown in FIG. 12. The 2θ values for the peaks in FIG. 12 (and their intensities) are as follows: 5.36 (100), 10.75 (42), 14.43 (20), 16.34 (60), 17.00 (25), 18.83 (18), 19.24 (18), 19.66 (12), 21.64 (29), 22.12 (41), 23.73 (32), 28.83 (9), 29.10 (9), and 31.78 (10).

This invention also relates, in part, to a process for preparing the pattern B monosodium salt. The pattern B monosodium salt can prepared by suspending the pattern A monosodium salt (for example, ~30 mg) in various organic solvents (e.g., ~125 ul acetonitrile, ethanol, 1-propanol, or 2-propanol) at room temperature. The pattern B monosodium salt was also prepared by seeding a solution with pattern B monosodium salt. Compound IB-L0-2.3 (12.5 g) was dissolved in DMSO (37.5 ml) at ~68° C. 1.04 g NaOH dissolved in 6.3 ml of water, 6.3 ml 2-propanol, and 12.5 ml 35.2:1 v/v 2-propanol/water was added. The solution was seeded with 125 mg of pattern B seeds slurried in 12.5 ml of 35.2:1 v/v 2-propanol/water, and the crystallization slurry was incubated at ~68° C. for ~1.5 h. 175 ml 35.2:1 v/v 2-propanol/water at ~68° C. was added over ~7 h, and the crystallization slurry was cooled to ~0° C. over no less than 7 h. The crystals were isolated by filtration and analyzed by PXRD. The crystals were then dried at ~50° C. under vacuum (approximately 3 inches of mercury). The dried crystals were analyzed by PXRD, which showed no change in comparison to the pre-drying sample. The stoichiometry of the pattern B monosodium salt was confirmed by ion chromatography.

This invention also relates, in part, to a pattern C crystalline monosodium salt.

In some embodiments, the pattern C monosodium salt has an X-ray powder diffraction pattern comprising one or more peaks selected from the group consisting of 5.0±0.2, 12.0±0.2, 17.5±0.2, 18.8±0.2, and 22.7±0.2 degrees 2θ. In some such embodiments, the pattern C monosodium salt has an X-ray powder diffraction pattern comprising three or more peaks selected from the group consisting of 5.0±0.2, 12.0±0.2, 17.5±0.2, 18.8±0.2, and 22.7±0.2 degrees 2θ.

In some embodiments, the pattern C monosodium salt has an X-ray powder diffraction pattern comprising one or more peaks selected from the group consisting of 5.0±0.2, 12.0±0.2, 17.5±0.2, 17.8±0.2, 18.8±0.2, and 22.7±0.2 degrees 2θ. In some such embodiments, the pattern A monosodium salt has an X-ray powder diffraction pattern comprising three or more peaks selected from the group consisting of 5.0±0.2, 12.0±0.2, 17.5±0.2, 17.8±0.2, 18.8±0.2, and 22.7±0.2 degrees 2θ. In other such embodiments, the pattern A monosodium salt has an X-ray powder diffraction pattern comprising five or more peaks selected from the group consisting of 5.0±0.2, 12.0±0.2, 17.5±0.2, 17.8±0.2, 18.8±0.2, and 22.7±0.2 degrees 2θ.

Figure 14:
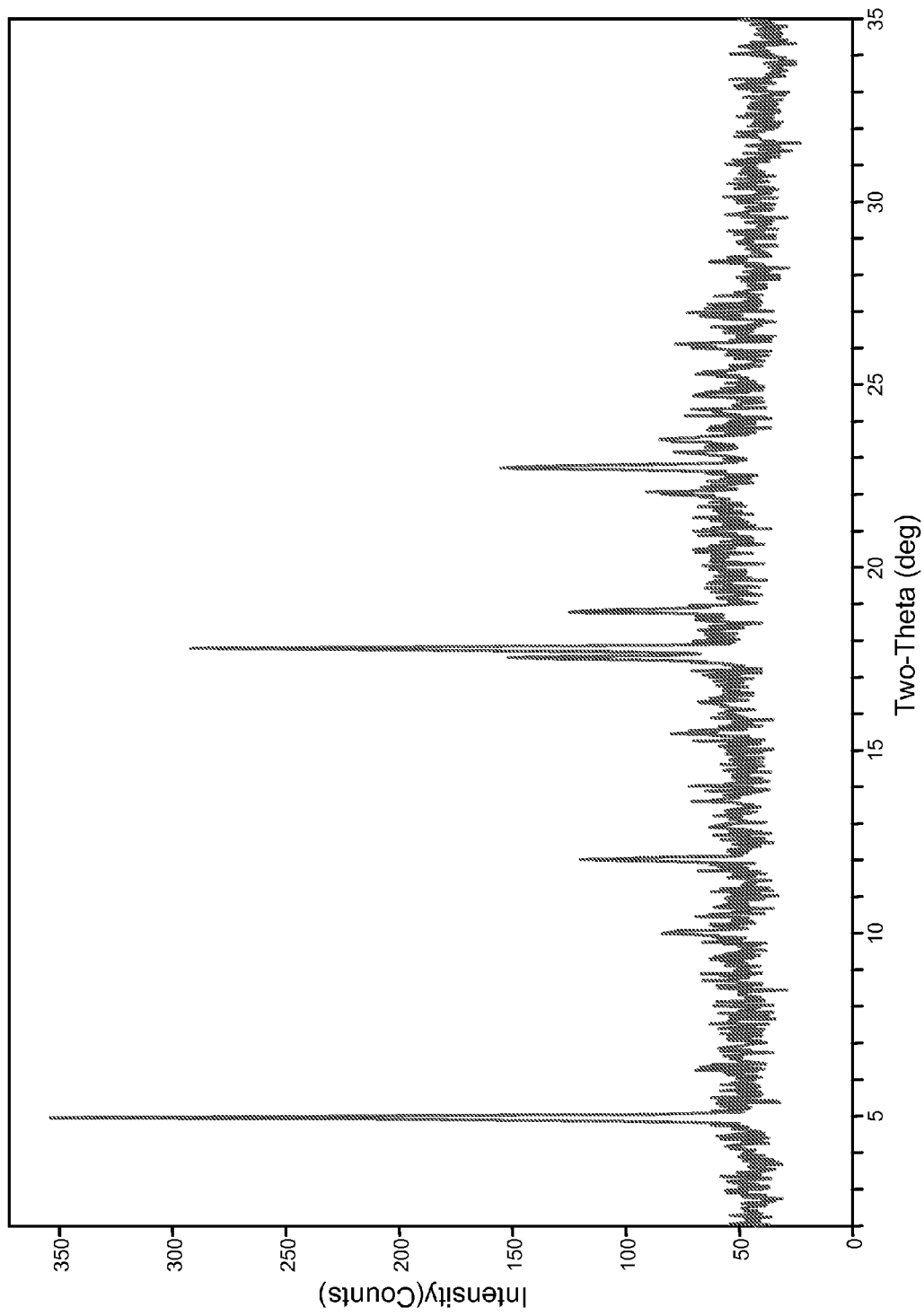
FIG. 14 shows an illustrative PXRD pattern for the pattern C monosodium salt of compound IB-L0-2.3.

In some embodiments, the pattern C monosodium salt has an X-ray powder diffraction pattern substantially as shown in FIG. 14. The 2θ values for the peaks in FIG. 14 (and their intensities) are as follows: 4.97 (100), 12.03 (24), 17.55 (32), 17.80 (77), 18.79 (23), and 22.74 (33).

This invention also relates, in part, to a process for preparing the pattern C monosodium salt. The pattern C monosodium salt was prepared as follows. Pattern B monosodium salt (100 mg) was dissolved in 400 ul DMSO and 2 ml 12:1 v/v 2-propanol/H₂O at 70° C. Pattern B monosodium salt seed crystals were added to the solution, and the solution was then cooled to ambient temperature over 20 min. Filtration yielded crystals of the pattern C monosodium salt.

G3. Crystalline Form of N-(6-(3-Tert-butyl-5-(2,4-dioxo-3,4-dihydropyrimidin-1(2H)-yl)-2-methoxyphenyl)naphthalen-2-yl)methanesulfonamide, Disodium Salt This invention also relates, in part, to a crystalline form of N-(6-(3-tert-butyl-5-(2,4-dioxo-3,4-dihydropyrimidin-1 (2H)-yl)-2-methoxyphenyl)naphthalen-2-yl)methanesulfonamide, disodium salt.

In some embodiments, the disodium salt has an X-ray powder diffraction pattern comprising one or more peaks selected from the group consisting of 4.8±0.2, 9.6±0.2, 10.5±0.2, 13.0±0.2, 14.6±0.2, 15.4±0.2, 16.8±0.2, and 23.0±0.2 degrees 2θ. In some such embodiments, the disodium salt has an X-ray powder diffraction pattern comprising three or more peaks selected from the group consisting of 4.8±0.2, 9.6±0.2, 10.5±0.2, 13.0±0.2, 14.6±0.2, 15.4±0.2, 16.8±0.2, and 23.0±0.2 degrees 2θ. In other such embodiments, the disodium salt has an X-ray powder diffraction pattern comprising five or more peaks selected from the group consisting of 4.8±0.2, 9.6±0.2, 10.5±0.2, 13.0±0.2, 14.6±0.2, 15.4±0.2, 16.8±0.2, and 23.0±0.2 degrees 2θ.

In some embodiments, the disodium salt has an X-ray powder diffraction pattern comprising one or more peaks selected from the group consisting of 4.8±0.2, 9.6±0.2, 10.5±0.2, 13.0±0.2, 14.6±0.2, 15.4±0.2, 16.8±0.2, 22.7±0.2, 23.0±0.2, and 23.3±0.2 degrees 2θ. In some such embodiments, the disodium salt has an X-ray powder diffraction pattern comprising three or more peaks selected from the group consisting of 4.8±0.2, 9.6±0.2, 10.5±0.2, 13.0±0.2, 14.6±0.2, 15.4±0.2, 16.8±0.2, 22.7±0.2, 23.0±0.2, and 23.3±0.2 degrees 2θ. In other such embodiments, the disodium salt has an X-ray powder diffraction pattern comprising five or more peaks selected from the group consisting of 4.8±0.2, 9.6±0.2, 10.5±0.2, 13.0±0.2, 14.6±0.2, 15.4±0.2, 16.8±0.2, 22.7±0.2, 23.0±0.2, and 23.3±0.2 degrees 2θ.

Figure 15:
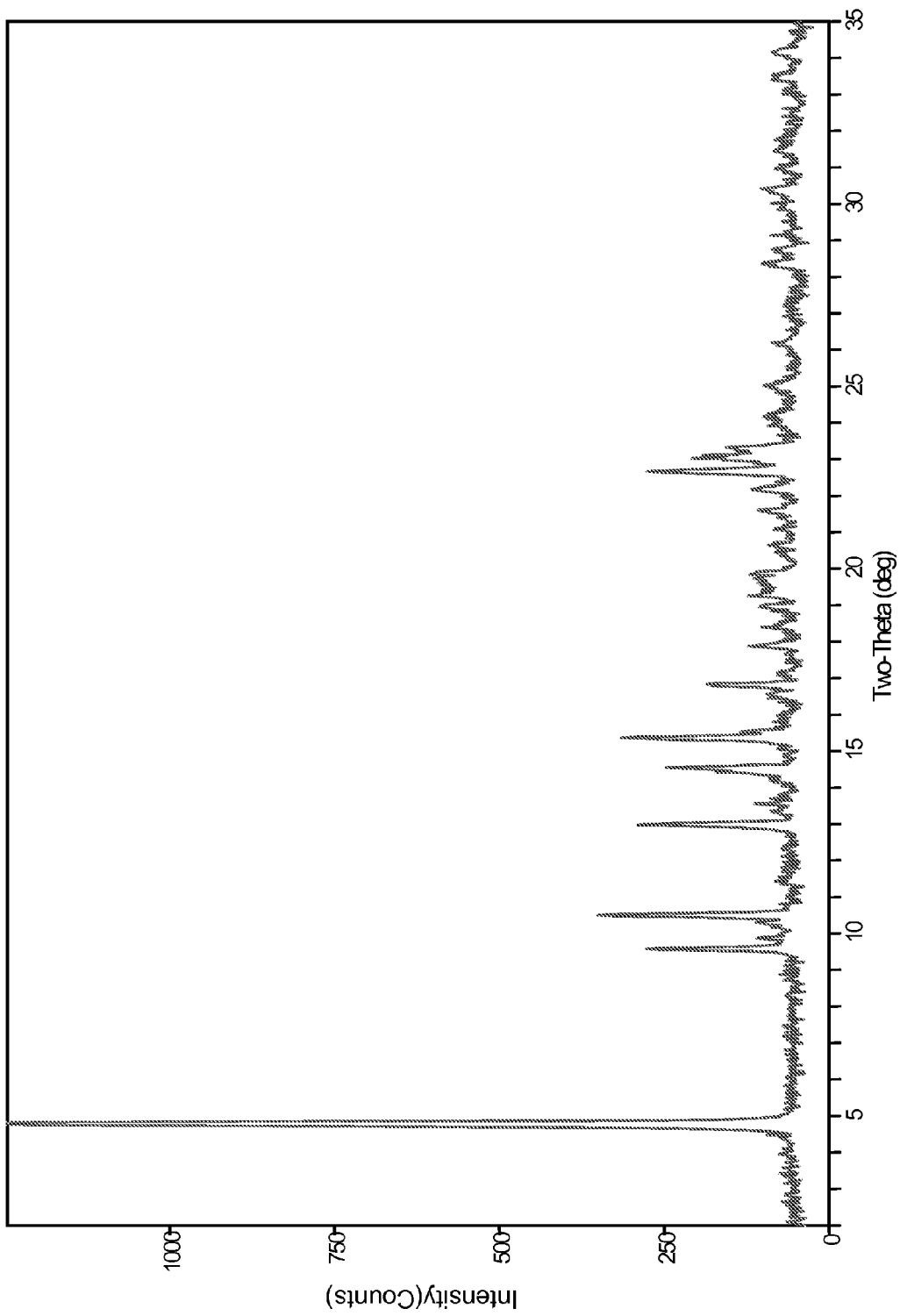
FIG. 15 shows an illustrative PXRD pattern for the disodium salt of compound IB-L0-2.3.
Figure 16:
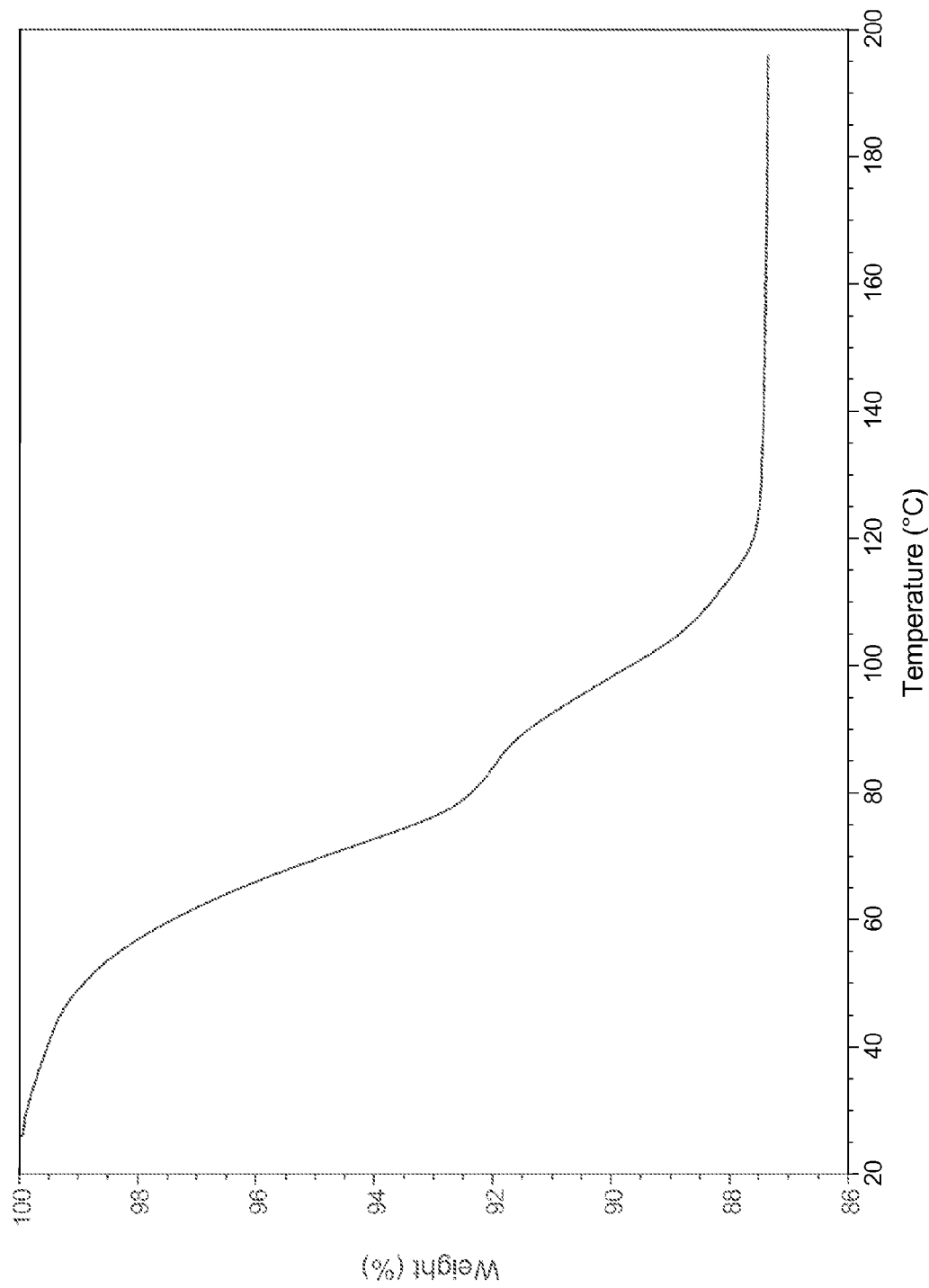
FIG. 16 shows an illustrative TGA profile of the disodium salt of compound IB-L0-2.3.

In some embodiments, the disodium salt has an X-ray powder diffraction pattern substantially as shown in FIG. 15. The 2θ values for the peaks in FIG. 15 (and their intensities) are as follows: 4.80 (100), 9.59 (10), 10.51 (13), 12.98 (11), 14.56 (8), 15.38 (12), 16.84 (6), 22.68 (10), 23.04 (6), and 23.33 (4).

This invention also relates, in part, to a process for preparing the disodium salt. The disodium salt was prepared by suspending compound IB-L0-2.3 (52.83 mg) in 1M aqueous NaOH (1.1 ml) (the molar ratio compound:NaOH was 1:10). The solution was heated to 36° C., and the solid dissolved completely to yield a clear solution. The solution was naturally cooled to ambient temperature, and the salt crystallized in 24 h. Alternatively, the disodium salt was prepared by suspending compound IB-L0-2.3 (51 mg) in EtOH (1 ml). NaOH in 1.2 ml of 5:1 v/v EtOH/H₂O (2.1 molar equivalent) was added. The reaction mixture was concentrated and 2 ml acetonitrile was added to induce crystallization. The stoichiometry of this solid was determined by ion chromatography.

G4. Crystalline Form of N-(6-(3-Tert-butyl-5-(2,4-dioxo-3,4-dihydropyrimidin-1(2H)-yl)-2-methoxyphenyl)naphthalen-2-yl)methanesulfonamide, Monopotassium Salt This invention also relates, in part, to a crystalline form of N-(6-(3-tert-butyl-5-(2,4-dioxo-3,4-dihydropyrimidin-1 (2H)-yl)-2-methoxyphenyl)naphthalen-2-yl)methanesulfonamide, monopotassium salt.

In some embodiments, the monopotassium salt has an X-ray powder diffraction pattern comprising one or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 23.5±0.2, 24.8±0.2, and 25.7±0.2 degrees 2θ. In some such embodiments, the monopotassium salt has an X-ray powder diffraction pattern comprising three or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 23.5±0.2, 24.8±0.2, and 25.7±0.2 degrees 2θ. In other such embodiments, the monopotassium salt has an X-ray powder diffraction pattern comprising five or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 23.5±0.2, 24.8±0.2, and 25.7±0.2 degrees 2θ.

In some embodiments, the monopotassium salt has an X-ray powder diffraction pattern comprising one or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 21.5±0.2, 23.5±0.2, 24.8±0.2, and 25.7±0.2 degrees 2θ. In some such embodiments, the monopotassium salt has an X-ray powder diffraction pattern comprising three or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 21.5±0.2, 23.5±0.2, 24.8±0.2, and 25.7±0.2 degrees 2θ. In other such embodiments, the monopotassium salt has an X-ray powder diffraction pattern comprising five or more peaks selected from the group consisting of 5.0±0.2, 9.9±0.2, 11.3±0.2, 13.3±0.2, 16.9±0.2, 18.1±0.2, 19.1±0.2, 20.0±0.2, 21.1±0.2, 21.5±0.2, 23.5±0.2, 24.8±0.2, and 25.7±0.2 degrees 2θ.

Figure 17:
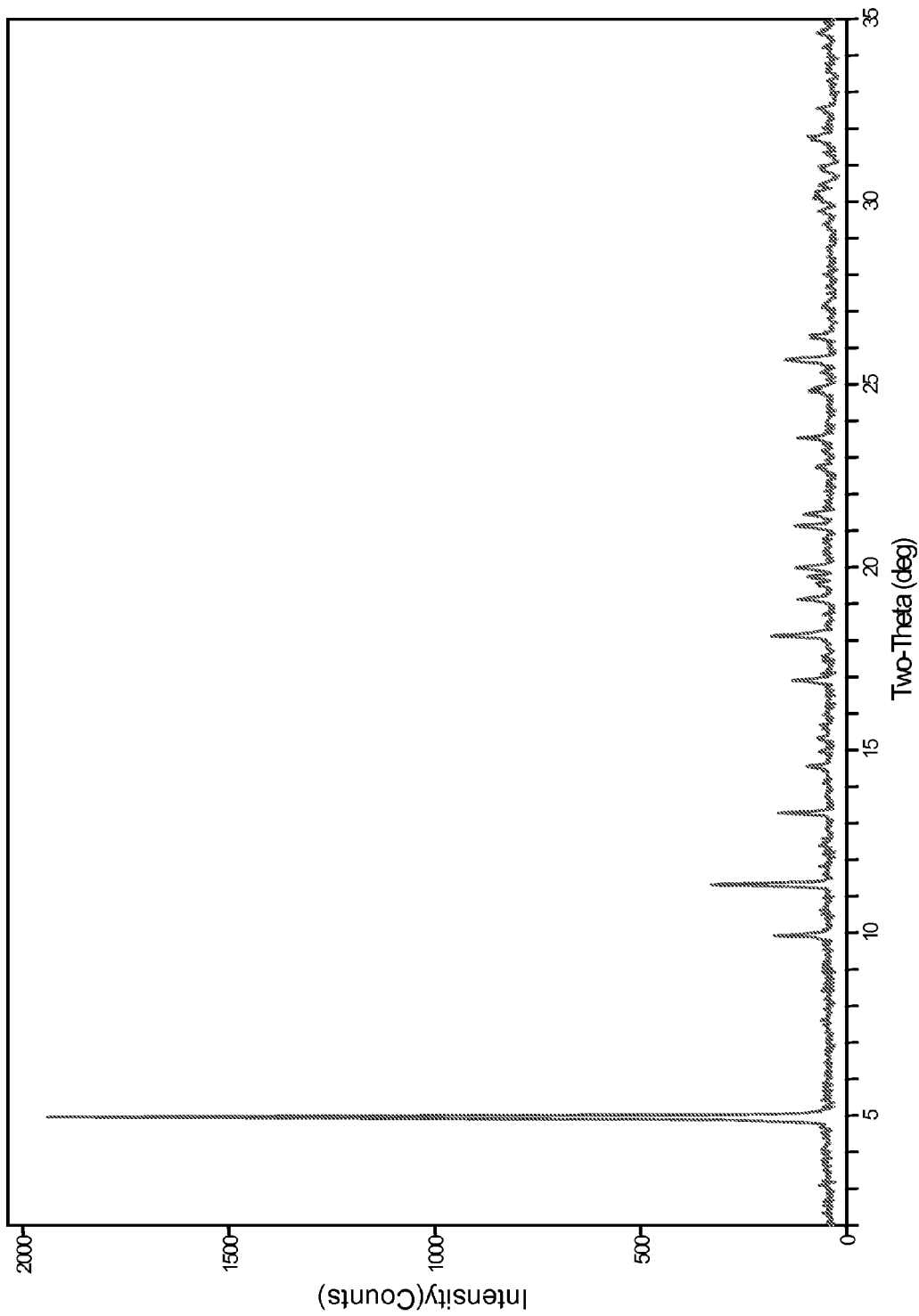
FIG. 17 shows an illustrative PXRD pattern for the monopotassium salt of compound IB-L0-2.3.
Figure 18:
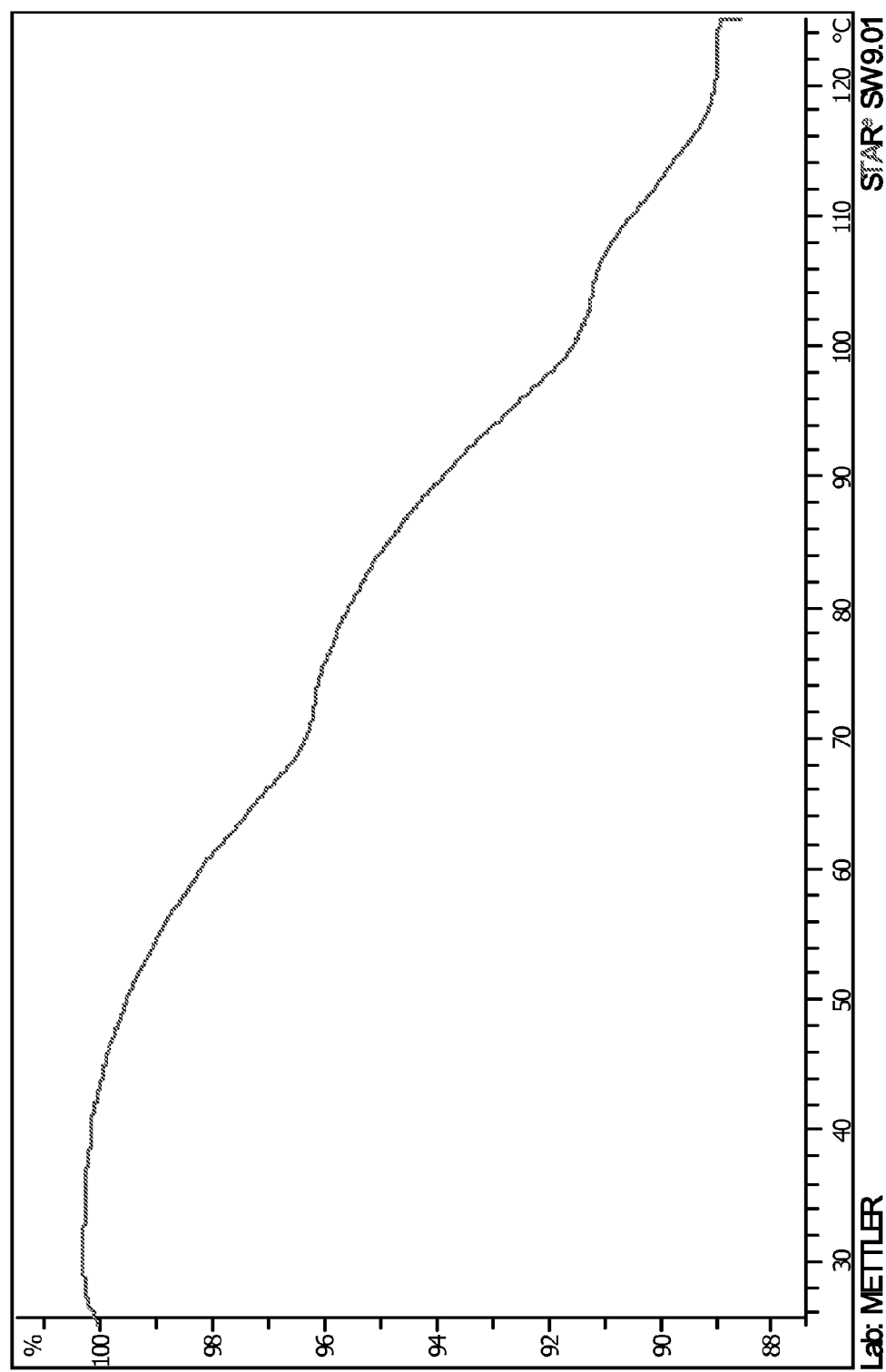
FIG. 18 shows an illustrative TGA profile of the monopotassium salt of compound IB-L0-2.3.

In some embodiments, the monopotassium salt has an X-ray powder diffraction pattern substantially as shown in FIG. 17. The 2θ values for the peaks in FIG. 17 (and their intensities) are as follows: 4.97 (100), 9.94 (7), 11.33 (15), 13.28 (7), 16.91 (5), 18.13 (7), 19.14 (4), 20.00 (4), 21.13 (4), 21.45 (4), 23.54 (4), 24.84 (3), and 25.67 (6).

This invention also relates, in part, to a process for preparing the monopotassium salt. The monopotassium salt was prepared in aqueous medium. 0.366 ml of 1M aqueous KOH was added to 150.56 mg of compound IB-L0-2.3 (molar ratio 1:1.2). The resulting suspension was equilibrated at ambient conditions. The monopotassium salt was formed on the following day through a solution-mediated process. Alternatively, the monopotassium salt was prepared by suspending compound IB-L0-2.3 (300 mg) in 3 ml acetonitrile. KOH in 1.3 mL of $H_2O$ (2.1 molar equivalent) was added. Additional 1 ml $H_2O$ was added to dissolve all solids. Afterwards, 12 ml acetonitrile was added to induce crystallization. The stoichiometry of the salt was confirmed by ion chromatograph.

G5. Crystalline Forms of N-(6-(3-Tert-butyl-5-(2,4-dioxo-3,4-dihydropyrimidin-1(2H)-yl)-2-methoxyphenyl)naphthalen-2-yl)methanesulfonamide, Monocholine Salt This invention also relates, in part, to crystalline forms of N-(6-(3-tert-butyl-5-(2,4-dioxo-3,4-dihydropyrimidin-1 (2H)-yl)-2-methoxyphenyl)naphthalen-2-yl)methanesulfonamide, monocholine salt, namely the pattern A and pattern B crystalline forms discussed below.

This invention relates, in part, to a pattern A crystalline monocholine salt.

In some embodiments, the pattern A monocholine salt has an X-ray powder diffraction pattern comprising one or more peaks selected from the group consisting of 10.9±0.2, 12.1±0.2, 13.4±0.2, 15.5±0.2, 17.0±0.2, 17.8±0.2, 18.3±0.2, 19.5±0.2, and 21.9±0.2 degrees 2θ. In some such embodiments, the pattern A monocholine salt has an X-ray powder diffraction pattern comprising three or more peaks selected from the group consisting of 10.9±0.2, 12.1±0.2, 13.4±0.2, 15.5±0.2, 17.0±0.2, 17.8±0.2, 18.3±0.2, 19.5±0.2, and 21.9±0.2 degrees 2θ. In other such embodiments, the pattern A monocholine salt has an X-ray powder diffraction pattern comprising five or more peaks selected from the group consisting of 10.9±0.2, 12.1±0.2, 13.4±0.2, 15.5±0.2, 17.0±0.2, 17.8±0.2, 18.3±0.2, 19.5±0.2, and 21.9±0.2 degrees 2θ.

In some embodiments, the pattern A monocholine salt has an X-ray powder diffraction pattern comprising one or more peaks selected from the group consisting of 10.9±0.2, 12.1±0.2, 13.0±0.2, 13.4±0.2, 13.6±0.2, 15.5±0.2, 17.0±0.2, 17.8±0.2, 18.3±0.2, 19.5±0.2, 19.7±0.2, and 21.9±0.2 degrees 2θ. In some such embodiments, the pattern A monocholine salt has an X-ray powder diffraction pattern comprising three or more peaks selected from the group consisting of degrees 2θ. In other such embodiments, the pattern A monocholine salt has an X-ray powder diffraction pattern comprising five or more peaks selected from the group consisting of degrees 2θ.

Figure 19:
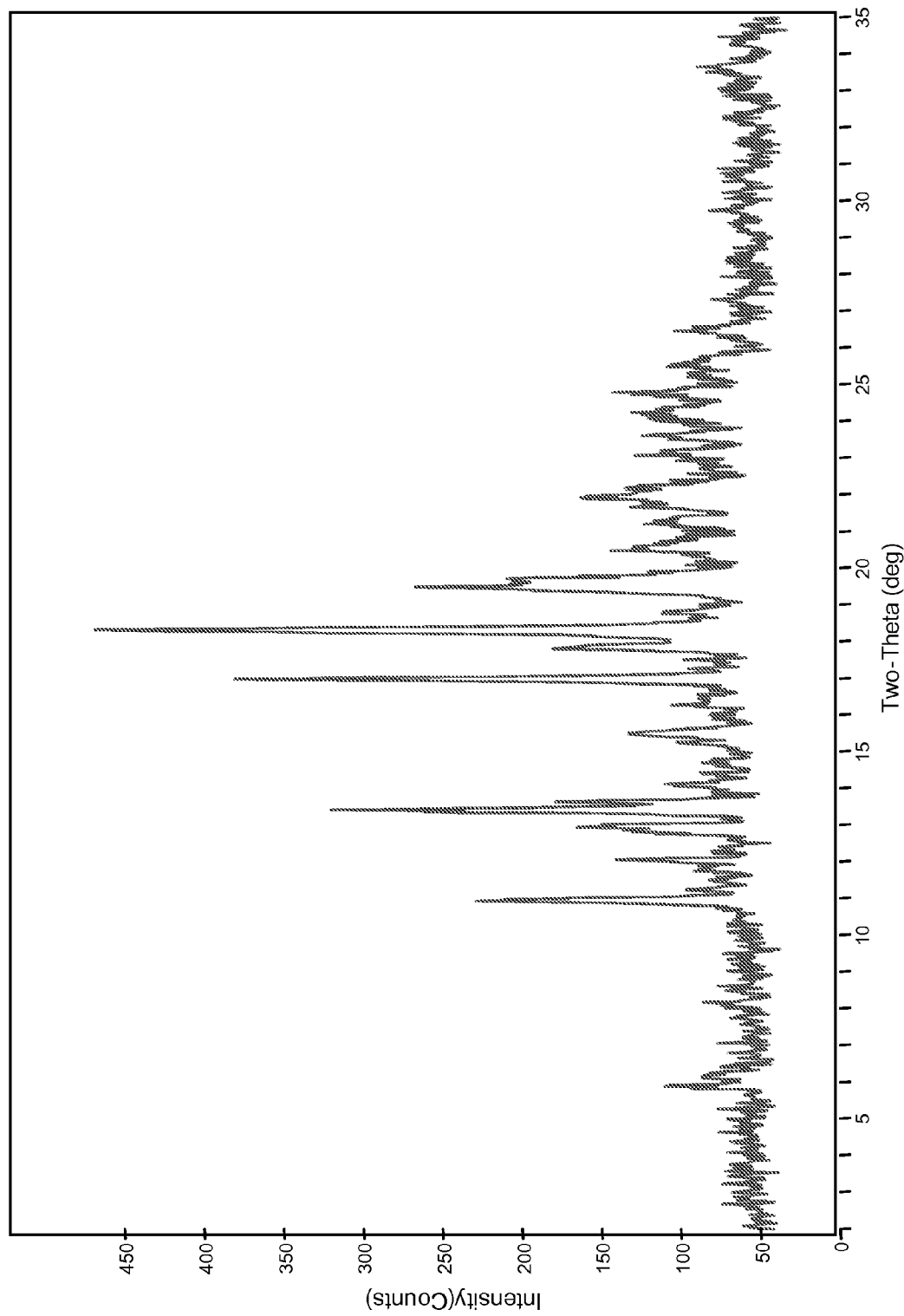
FIG. 19 shows an illustrative PXRD pattern for the pattern A monocholine salt of compound IB-L0-2.3.
Figure 20:
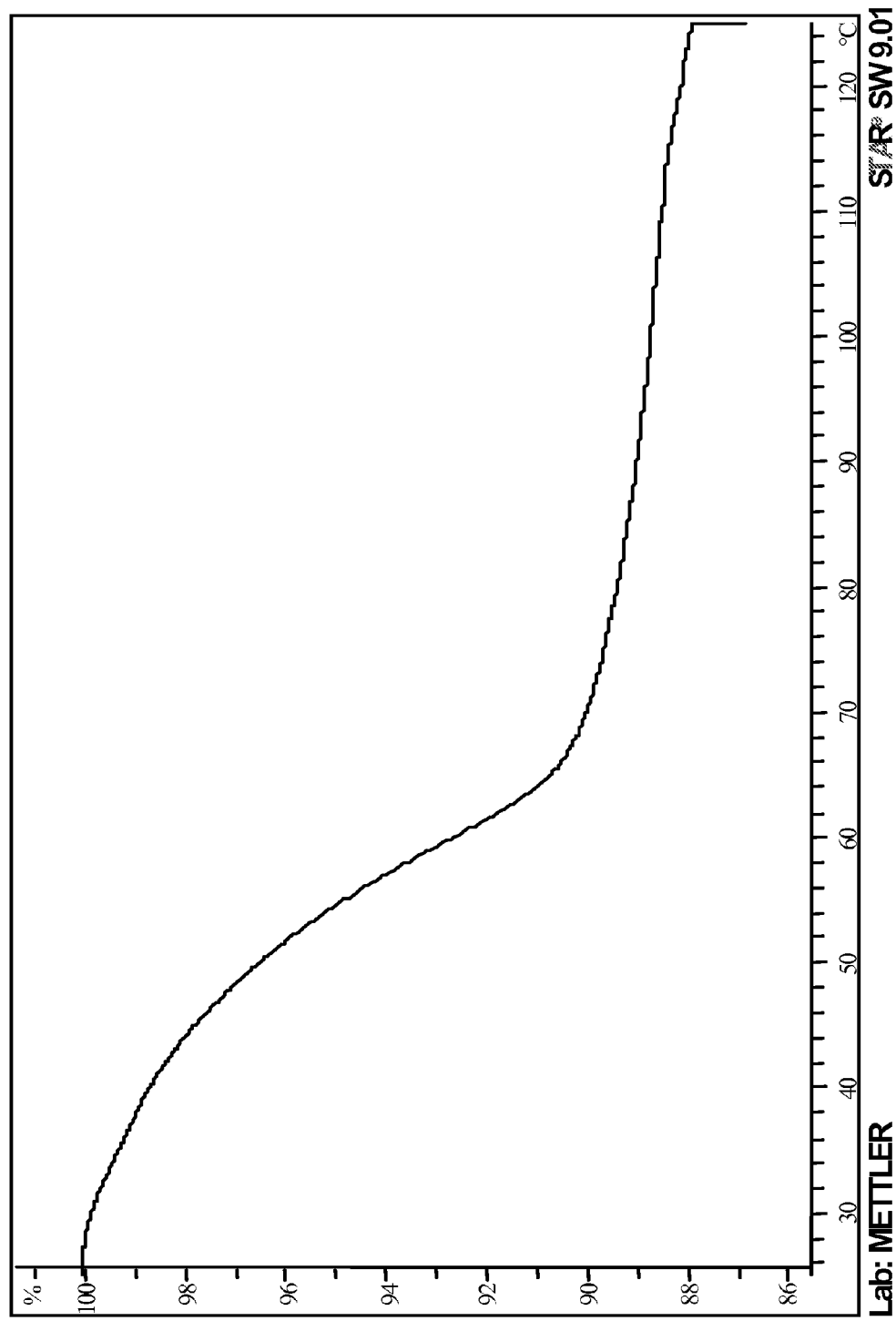
FIG. 20 shows an illustrative TGA profile of the pattern A monocholine salt of compound IB-L0-2.3.

In some embodiments, the pattern A monocholine salt has an X-ray powder diffraction pattern substantially as shown in FIG. 19. The 2θ values for the peaks in FIG. 19 (and their intensities) are as follows: 10.94 (42), 12.06 (20), 12.96 (26), 13.42 (64), 13.64 (27), 15.51 (18), 16.98 (78), 17.81 (26), 18.32 (100), 19.49 (48), 19.70 (33), and 21.91 (22).

This invention also relates, in part, to a process for preparing the pattern A monocholine salt. It was prepared in a solvent mixture of tetrahydrofuran (THF) and methanol. Compound IB-L0-2.3 (56.79 mg) was dissolved in THF at 60° C., 40.01 mg of choline hydroxide solution (45 wt % in methanol) was added resulting in a molar ratio of 1:1.2. The crystals formed upon natural cooling to ambient temperature.

This invention also relates, in part, to a pattern B crystalline monocholine salt.

In some embodiments, the pattern B monocholine salt has an X-ray powder diffraction pattern comprising one or more peaks selected from the group consisting of 8.0±0.2, 9.4±0.2, 11.0±0.2, 13.0±0.2, 13.7±0.2, 15.9±0.2, 17.0±0.2, 18.3±0.2, 18.9±0.2, 19.8±0.2, and 22.1±0.2 degrees 2θ. In some such embodiments, the pattern B monocholine salt has an X-ray powder diffraction pattern comprising three or more peaks selected from the group consisting of 8.0±0.2, 9.4±0.2, 11.0±0.2, 13.0±0.2, 13.7±0.2, 15.9±0.2, 17.0±0.2, 18.3±0.2, 18.9±0.2, 19.8±0.2, and 22.1±0.2 degrees 2θ. In other such embodiments, the pattern B monocholine salt has an X-ray powder diffraction pattern comprising five or more peaks selected from the group consisting of 8.0±0.2, 9.4±0.2, 11.0±0.2, 13.0±0.2, 13.7±0.2, 15.9±0.2, 17.0±0.2, 18.3±0.2, 18.9±0.2, 19.8±0.2, and 22.1±0.2 degrees 2θ.

In some embodiments, the pattern B monocholine salt has an X-ray powder diffraction pattern comprising one or more peaks selected from the group consisting of 8.0±0.2, 9.4±0.2, 11.0±0.2, 13.0±0.2, 13.3±0.2, 13.7±0.2, 15.9±0.2, 17.0±0.2, 17.4±0.2, 18.3±0.2, 18.9±0.2, 19.8±0.2, 21.8±0.2, and 22.1±0.2 degrees 2θ. In some such embodiments, the pattern B monocholine salt has an X-ray powder diffraction pattern comprising three or more peaks selected from the group consisting of 8.0±0.2, 9.4±0.2, 11.0±0.2, 13.0±0.2, 13.3±0.2, 13.7±0.2, 15.9±0.2, 17.0±0.2, 17.4±0.2, 18.3±0.2, 18.9±0.2, 19.8±0.2, 21.8±0.2, and 22.1±0.2 degrees 2θ. In other such embodiments, the pattern B monocholine salt has an X-ray powder diffraction pattern comprising five or more peaks selected from the group consisting of 8.0±0.2, 9.4±0.2, 11.0±0.2, 13.0±0.2, 13.3±0.2, 13.7±0.2, 15.9±0.2, 17.0±0.2, 17.4±0.2, 18.3±0.2, 18.9±0.2, 19.8±0.2, 21.8±0.2, and 22.1±0.2 degrees 2θ.

Figure 21:
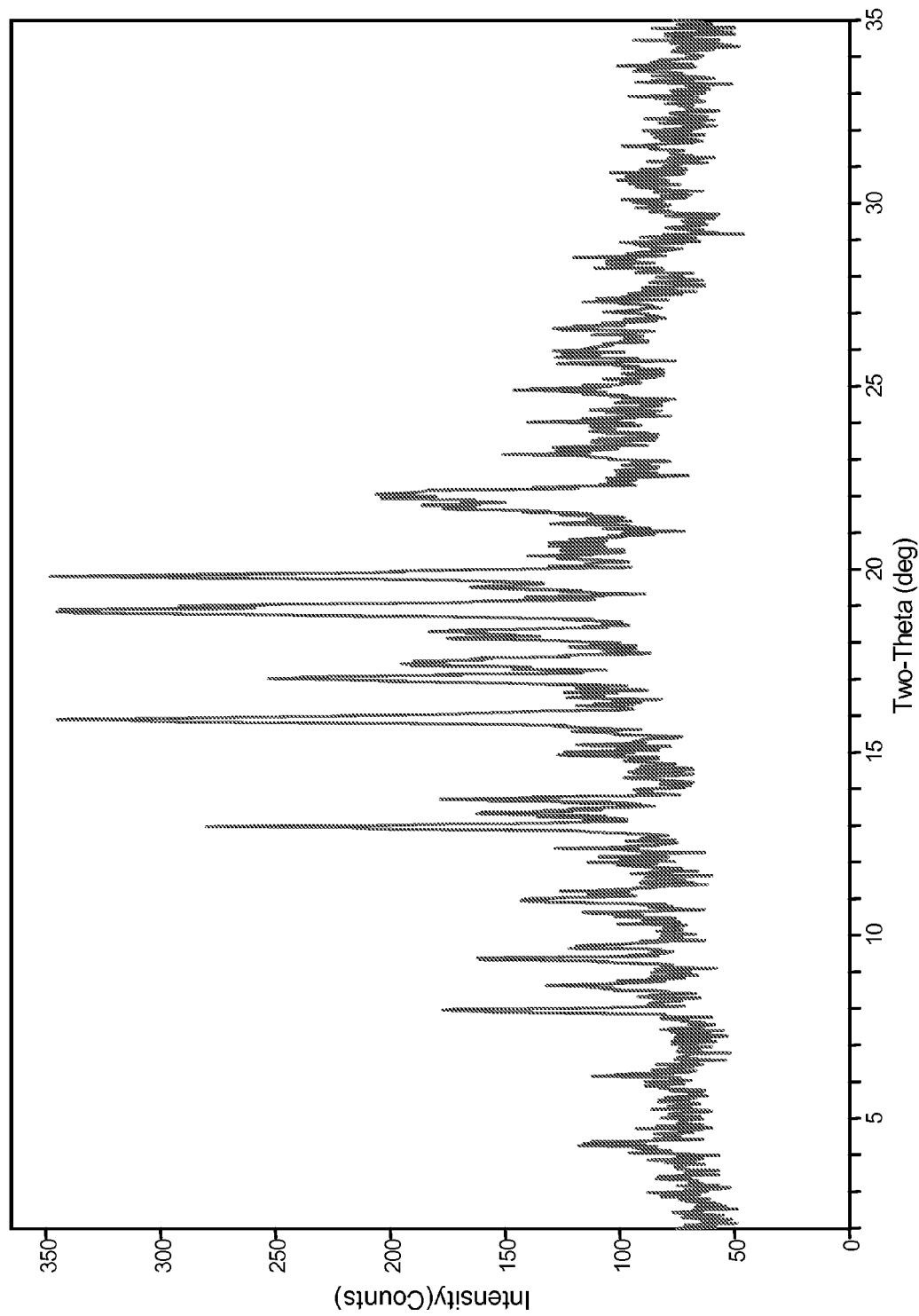
FIG. 21 shows an illustrative PXRD pattern for the pattern B monocholine salt of compound IB-L0-2.3.
Figure 22:
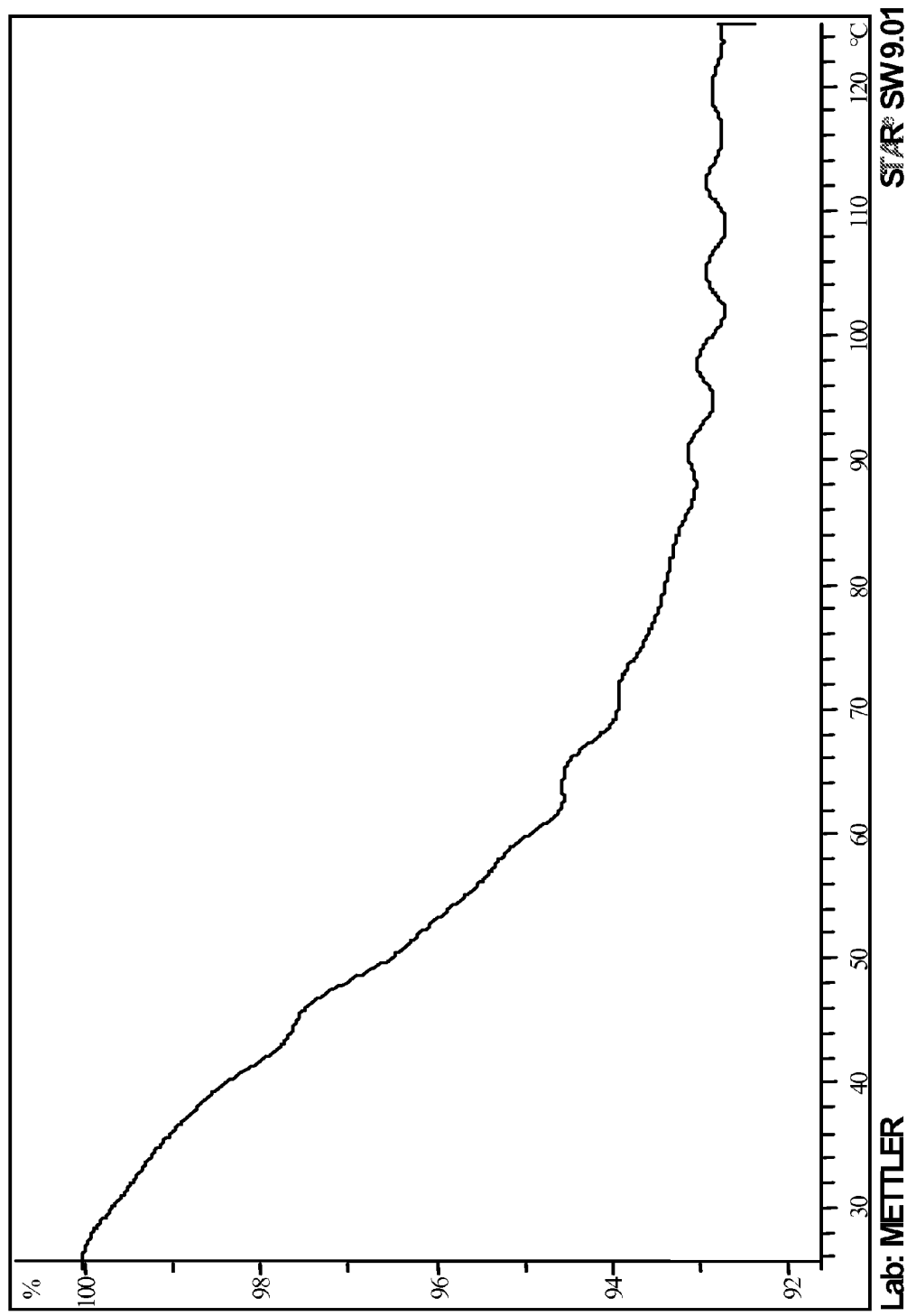
FIG. 22 shows an illustrative TGA profile of the pattern B monocholine salt of compound IB-L0-2.3.

In some embodiments, the pattern B monocholine salt has an X-ray powder diffraction pattern substantially as shown in FIG. 21. The 2θ values for the peaks in FIG. 21 (and their intensities) are as follows: 7.96 (41), 9.38 (34), 10.96 (24), 12.98 (76), 13.34 (33), 13.72 (37), 15.90 (100), 17.03 (60), 17.42 (37), 18.30 (31), 18.85 (93), 19.82 (90), 21.76 (38), and 22.06 (46).

This invention also relates, in part, to a process for preparing the pattern B monocholine salt. It was prepared by suspending amorphous choline salt in ethyl acetate for seven days.

G6. Crystalline Form of N-(6-(3-Tert-butyl-5-(2,4-dioxo-3,4-dihydropyrimidin-1(2H)-yl)-2-methoxyphenyl)naphthalen-2-yl)methanesulfonamide, Dicholine Salt This invention also relates, in part, to a crystalline form of N-(6-(3-tert-butyl-5-(2,4-dioxo-3,4-dihydropyrimidin-1 (2H)-yl)-2-methoxyphenyl)naphthalen-2-yl)methanesulfonamide, dicholine salt.

In some embodiments, the dicholine salt has an X-ray powder diffraction pattern comprising one or more peaks selected from the group consisting of 8.6±0.2, 11.0±0.2, 12.9±0.2, 17.0±0.2, 17.5±0.2, 18.9±0.2, 19.8±0.2, and 21.9±0.2 degrees 2θ. In some such embodiments, the dicholine salt has an X-ray powder diffraction pattern comprising three or more peaks selected from the group consisting of 8.6±0.2, 11.0±0.2, 12.9±0.2, 17.0±0.2, 17.5±0.2, 18.9±0.2, 19.8±0.2, and 21.9±0.2 degrees 2θ. In other such embodiments, the dicholine salt has an X-ray powder diffraction pattern comprising five or more peaks selected from the group consisting of 8.6±0.2, 11.0±0.2, 12.9±0.2, 17.0±0.2, 17.5±0.2, 18.9±0.2, 19.8±0.2, and 21.9±0.2 degrees 2θ.

In some embodiments, the dicholine salt has an X-ray powder diffraction pattern comprising one or more peaks selected from the group consisting of 8.6±0.2, 11.0±0.2, 12.9±0.2, 17.0±0.2, 17.5±0.2, 18.9±0.2, 19.8±0.2, 21.9±0.2, and 22.1±0.2 degrees 2θ. In some such embodiments, the dicholine salt has an X-ray powder diffraction pattern comprising three or more peaks selected from the group consisting of 8.6±0.2, 11.0±0.2, 12.9±0.2, 17.0±0.2, 17.5±0.2, 18.9±0.2, 19.8±0.2, 21.9±0.2, and 22.1±0.2 degrees 2θ. In other such embodiments, the dicholine salt has an X-ray powder diffraction pattern comprising five or more peaks selected from the group consisting of 8.6±0.2, 11.0±0.2, 12.9±0.2, 17.0±0.2, 17.5±0.2, 18.9±0.2, 19.8±0.2, 21.9±0.2, and 22.1±0.2 degrees 2θ.

Figure 23:
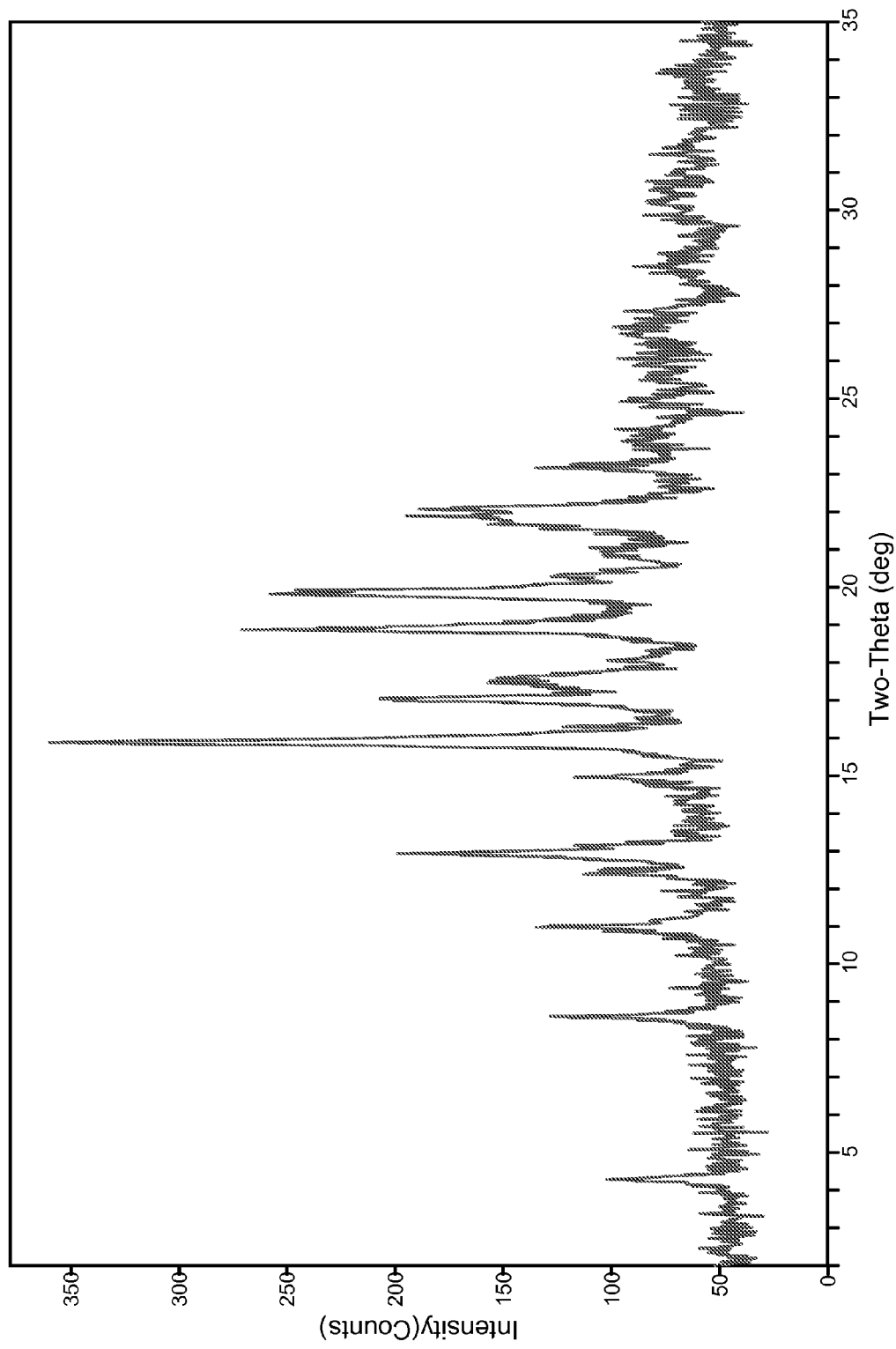
FIG. 23 shows an illustrative PXRD pattern for the dicholine salt of compound IB-L0-2.3.

In some embodiments, the dicholine salt has an X-ray powder diffraction pattern substantially as shown in FIG. 23. The 2θ values for the peaks in FIG. 23 (and their intensities) are as follows: 8.62 (28), 10.98 (29), 12.93 (50), 15.88 (100), 17.03 (42), 17.47 (29), 18.88 (66), 19.82 (57), 21.89 (42), 2.07 (41).

This invention also relates, in part, to a process for preparing the dicholine salt. It was prepared by suspending compound IB-L0-2.3 (200 mg) in 0.75 ml MeOH. Choline hydroxide in MeOH (210 ml, 45 wt %, 2.10 molar equivalent) was added. The reaction mixture was concentrated, and 4 ml acetonitrile and 6 ml isopropyl acetate were added. The reaction mixture was then seeded with trace amount of the compound IB-L0-2.3 monopotassium salt seed crystals (discussed above). The reaction mixture started to crystallize shortly after. The stoichiometry of the salt was determined by solution $^1$H NMR.

G7. Crystalline Forms of (E)-N-(4-(3-tert-butyl-5-(2,4-dioxo-3,4-dihydropyrimidin-1(2H)-yl)-2-methoxystyryl)phenyl)methanesulfonamide Disodium Salt This invention also relates, in part, to crystalline forms of (E)-N-(4-(3-tert-butyl-5-(2,4-dioxo-3,4-dihydropyrimidin-1 (2H)-yl)-2-methoxystyryl)phenyl)methanesulfonamide disodium salt, namely the nonahydrate and tetrahydrate crystalline forms discussed below.

This invention relates, in part, to a nonahydrate crystalline disodium salt. The crystallographic unit cell parameters of the nonahydrate crystalline disodium salt have been determined to be as follows: a is 8.9 Å, b is 9.4 Å, and c is 20.7 Å (more precisely, a is 8.926(2)Å, b is 9.415(2)Å, and c is 20.674(5) Å); the cell angles are: α—94.8°, β—93.3°, and γ—107.0° (more precisely, α is 94.796(4)°, β is 93.345(4)°, and γ is 107.013(4)°; and the cell volume is 1649 Å$^3$ (more precisely, 1649.3(7)Å$^3$). The salt crystallizes in the P-1 space group.

In some embodiments, the disodium salt nonahydrate has an X-ray powder diffraction pattern comprising one or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ. In some such embodiments, the disodium salt nonahydrate has an X-ray powder diffraction pattern comprising three or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ. In other such embodiments, the disodium salt nonahydrate has an X-ray powder diffraction pattern comprising five or more peaks selected from the group consisting of 4.3±0.2, 10.4±0.2, 10.9±0.2, 11.6±0.2, 12.9±0.2, 14.7±0.2, 16.4±0.2, 17.8±0.2, 19.4±0.2, 19.8±0.2, 20.8±0.2, 21.9±0.2, and 23.5±0.2 degrees 2θ.

In some embodiments, the disodium salt nonahydrate has an X-ray powder diffraction pattern comprising one or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ. In some such embodiments, the disodium salt nonahydrate has an X-ray powder diffraction pattern comprising three or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ. In other such embodiments, the disodium salt nonahydrate has an X-ray powder diffraction pattern comprising five or more peaks selected from the group consisting of 4.3±0.2, 10.4±0.2, 10.9±0.2, 11.6±0.2, 12.9±0.2, 14.7±0.2, 14.9±0.2, 16.4±0.2, 17.8±0.2, 19.4±0.2, 19.7±0.2, 19.8±0.2, 20.8±0.2, 20.9±0.2, 21.9±0.2, 22.1±0.2, and 23.5±0.2 degrees 2θ.

Figure 24:
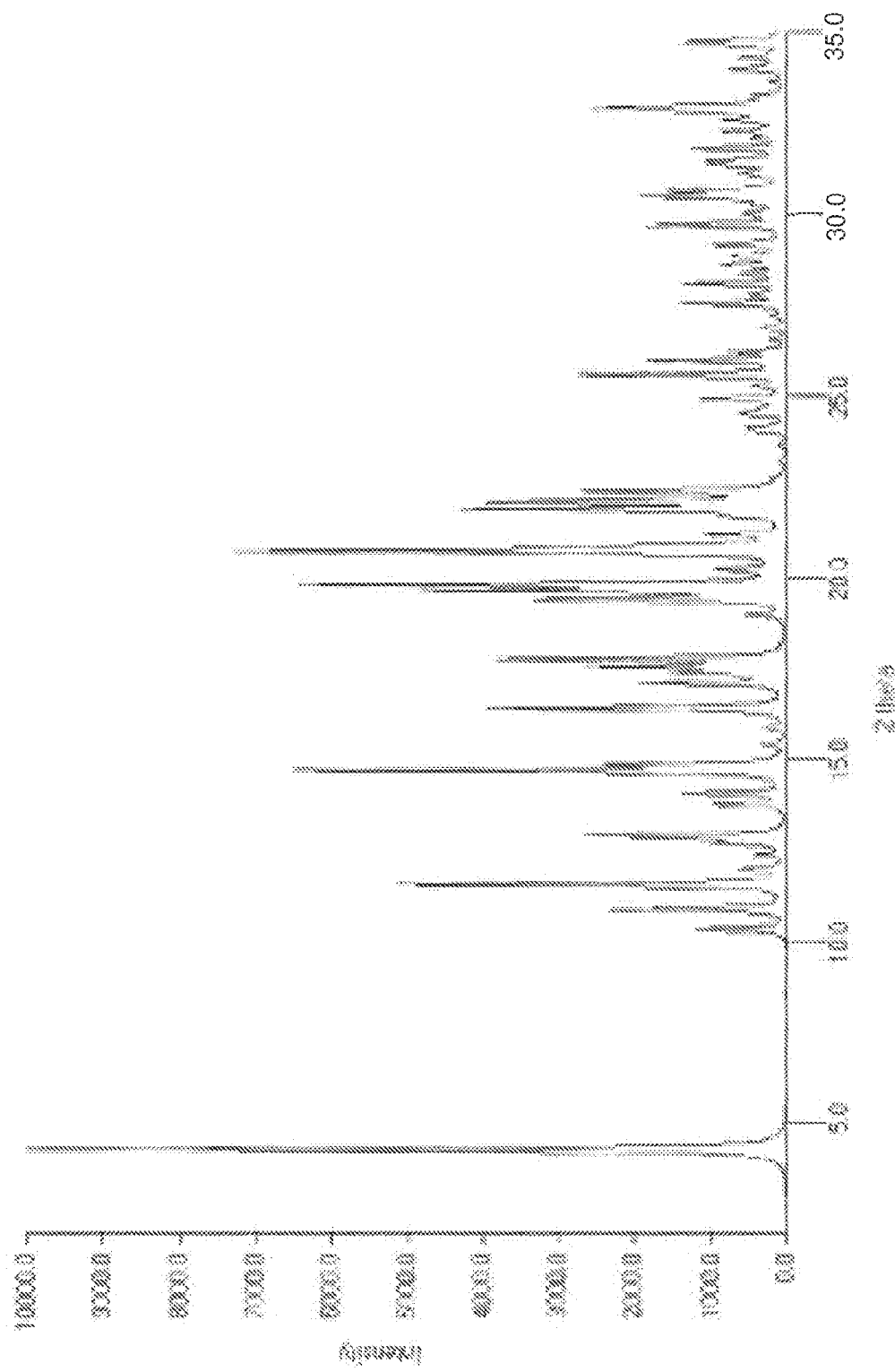
FIG. 24 shows an illustrative PXRD pattern for the disodium salt nonahydrate of compound IB-L1-1.1.

In some embodiments, the disodium salt nonahydrate has an X-ray powder diffraction pattern substantially as shown in FIG. 24. The 2θ values for the peaks in FIG. 24 (and their intensities) are as follows: 4.31 (100), 10.36 (12), 10.91 (23), 11.61 (52), 12.93 (24), 14.73 (65), 14.89 (20), 16.44 (41), 17.80 (38), 19.44 (26), 19.67 (37), 19.83 (59), 20.75 (69), 20.89 (21), 21.92 (43), 22.13 (40), and 22.42 (24).

This invention also relates, in part, to a process for preparing the disodium salt nonahydrate. It was prepared in aqueous medium. Aqueous NaOH (1M, 1.18 ml) was added to (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1) (27.82 mg) (molar ratio 1:20 acid:base). The resulting suspension was equilibrated at ambient conditions. The disodium salt nonahydrate formed seven days later through a solution-mediated process. Alternatively, the disodium salt nonahydrate was prepared by suspending 278.8 mg of compound IB-L1-1.1 in 1.25 ml THF while heated to about 50° C. Aqueous NaOH (1N, 1.5 ml, 2.2 molar equivalents) was added. The solid dissolved completely to yield a clear solution, which was naturally cooled to ambient temperatures. The salt crystallized spontaneously. The molecular structure was determined by single crystal diffractometry.

This invention relates, in part, to a tetrahydrate crystalline disodium salt.

In some embodiments, the disodium salt tetrahydrate has an X-ray powder diffraction pattern comprising one or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ. In some such embodiments, the disodium salt tetrahydrate has an X-ray powder diffraction pattern comprising three or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ. In other such embodiments, the disodium salt tetrahydrate has an X-ray powder diffraction pattern comprising five or more peaks selected from the group consisting of 4.8±0.2, 12.1±0.2, 14.0±0.2, 17.0±0.2, 17.5±0.2, 20.9±0.2, 21.6±0.2, 25.0±0.2, and 29.5±0.2 degrees 2θ.

In some embodiments, the disodium salt tetrahydrate has an X-ray powder diffraction pattern comprising one or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ. In some such embodiments, the disodium salt tetrahydrate has an X-ray powder diffraction pattern comprising three or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ. In other such embodiments, the disodium salt tetrahydrate has an X-ray powder diffraction pattern comprising five or more peaks selected from the group consisting of 4.8±0.2, 12.1±0.2, 14.0±0.2, 14.4±0.2, 17.0±0.2, 17.5±0.2, 20.9±0.2, 21.6±0.2, 25.0±0.2, 29.5±0.2, and 34.2±0.2 degrees 2θ.

Figure 25:
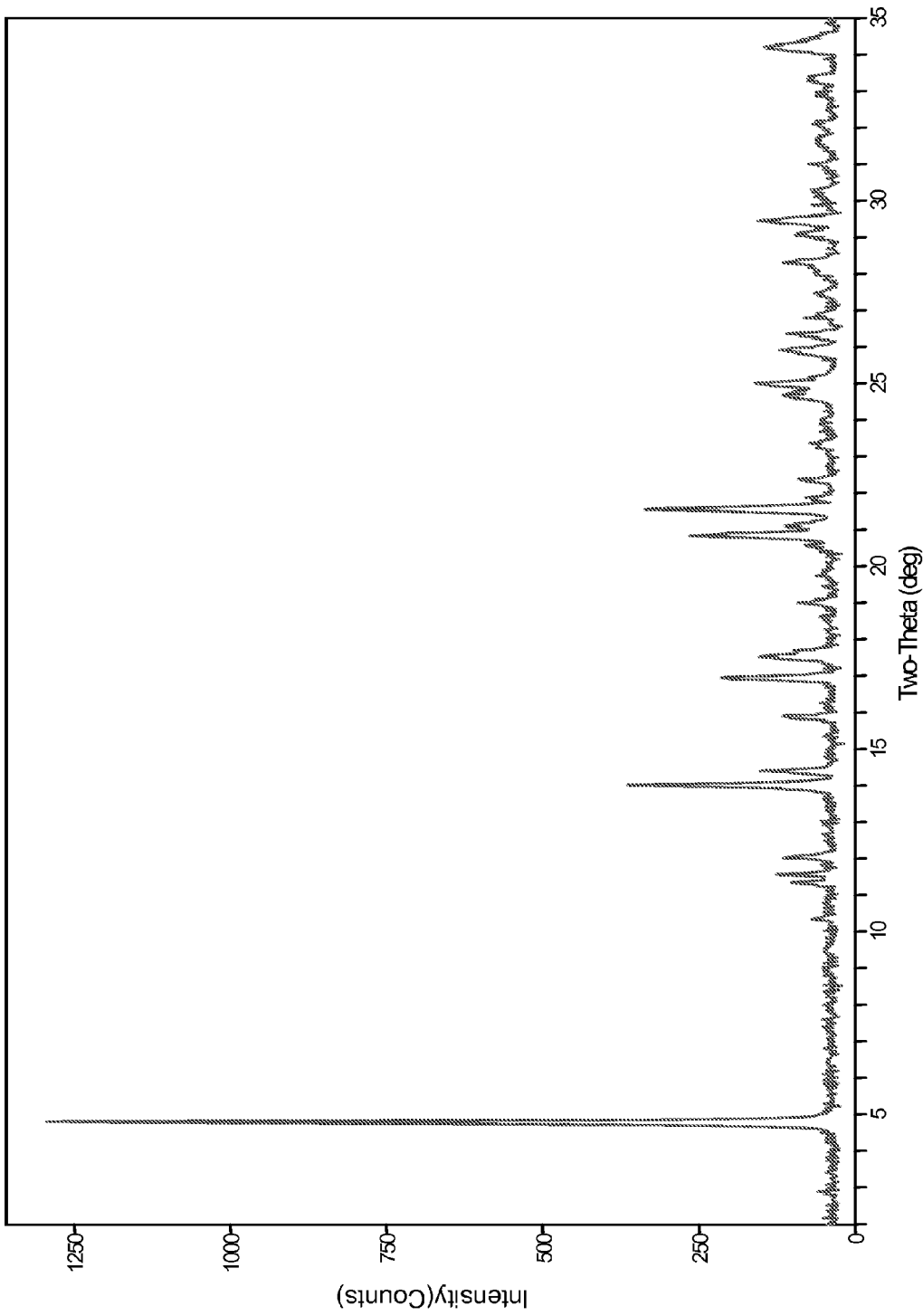
FIG. 25 shows an illustrative PXRD pattern for the disodium salt tetrahydrate of compound IB-L1-1.1.
Figure 26:
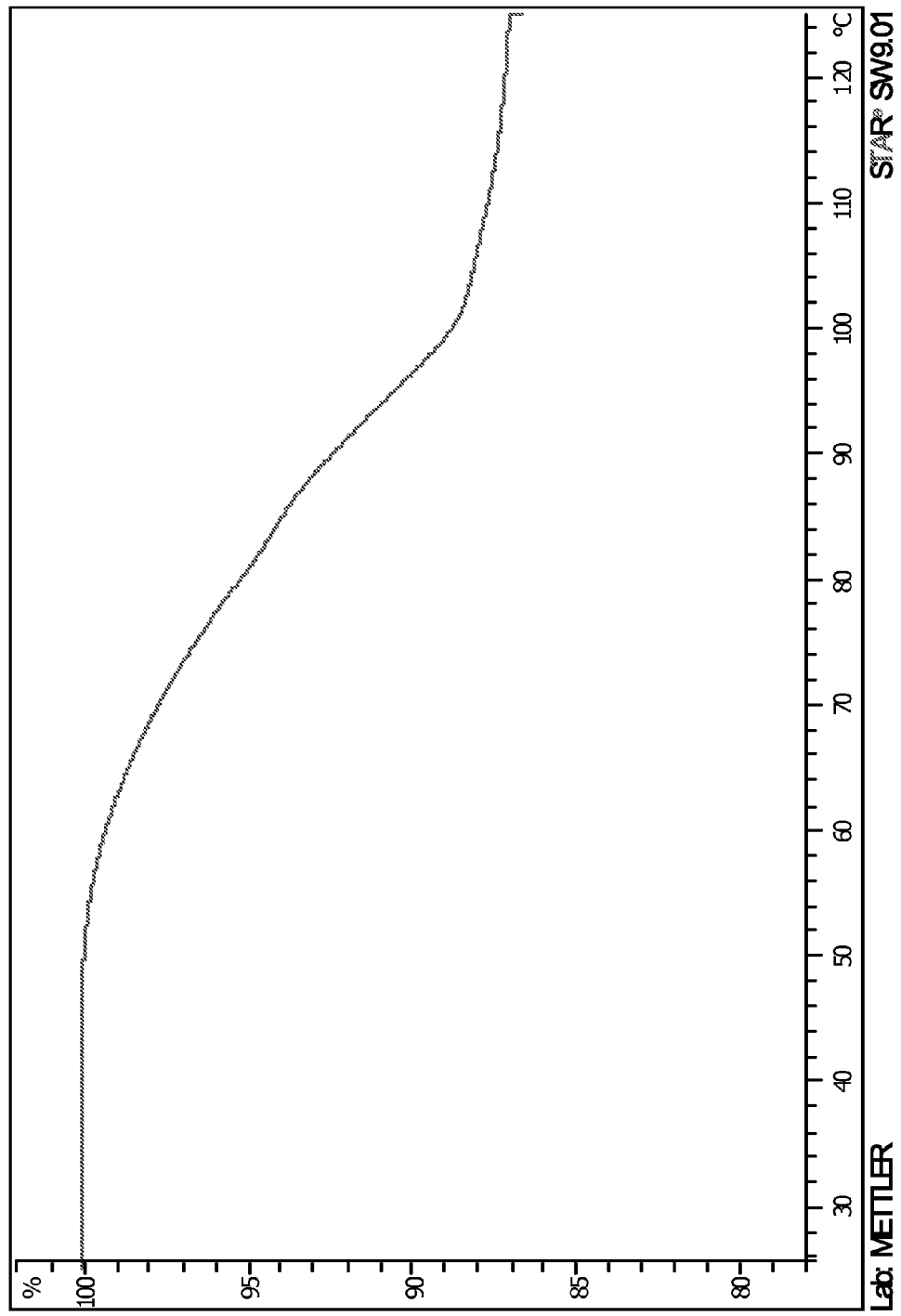
FIG. 26 shows an illustrative TGA profile of the disodium salt tetrahydrate of compound IB-L1-1.1.

In some embodiments, the disodium salt tetrahydrate has an X-ray powder diffraction pattern substantially as shown in FIG. 25. The 2θ values for the peaks in FIG. 25 (and their intensities) are as follows: 4.81 (100), 12.07 (7), 14.01 (27), 14.41 (8), 16.96 (18), 17.53 (11), 20.87 (18), 21.58 (22), 24.99 (11), 29.47 (9), and 34.20 (9).

This invention also relates, in part, to a process for preparing the disodium salt tetrahydrate by suspending the nonahydrate disodium salt in an organic solvent (e.g., ethanol, 1-propanol, or 2-propanol).

G8. Crystalline Form of (E)-N-(4-(3-tert-butyl-5-(2,4-dioxo-3,4-dihydropyrimidin-1(2H)-yl)-2-methoxy-styryl)phenyl)methanesulfonamide Dipotassium Salt This invention also relates, in part, to a crystalline (E)-N-(4-(3-tert-butyl-5-(2,4-dioxo-3,4-dihydropyrimidin-1(2H)-yl)-2-methoxystyryl)phenyl)methanesulfonamide dipotassium salt tetrahydrate.

The crystallographic unit cell parameters of the dipotassium salt tetrahydrate have been determined to be as follows: a is 14.5 Å, b is 10.8 Å, and c is 35.8 Å (more precisely, a is 14.454(14)Å, b is 10.763(14)Å, and c is 35.75(4)Å); the cell angle is: β—98.8° (more precisely, β is 98.82(3)°); and the cell volume is 5499 Å$^3$ (more precisely, 5499(11)Å$^3$). The salt crystallizes in the C2/c space group.

In some embodiments, the dipotassium salt tetrahydrate has an X-ray powder diffraction pattern comprising one or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ. In some such embodiments, the dipotassium salt tetrahydrate has an X-ray powder diffraction pattern comprising three or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ. In other such embodiments, the dipotassium salt tetrahydrate has an X-ray powder diffraction pattern comprising five or more peaks selected from the group consisting of 5.0±0.2, 11.9±0.2, 12.4±0.2, 13.7±0.2, 15.0±0.2, 16.5±0.2, 17.1±0.2, 20.8±0.2, 21.3±0.2, 22.2±0.2, 24.0±0.2, 26.4±0.2, and 29.3±0.2 degrees 2θ.

In some embodiments, the dipotassium salt tetrahydrate has an X-ray powder diffraction pattern comprising one or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ. In some such embodiments, the dipotassium salt tetrahydrate has an X-ray powder diffraction pattern comprising three or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ. In other such embodiments, the dipotassium salt tetrahydrate has an X-ray powder diffraction pattern comprising five or more peaks selected from the group consisting of 5.0±0.2, 11.9±0.2, 12.4±0.2, 12.6±0.2, 13.7±0.2, 15.0±0.2, 16.5±0.2, 16.7±0.2, 17.1±0.2, 20.7±0.2, 20.8±0.2, 21.3±0.2, 22.2±0.2, 22.4±0.2, 24.0±0.2, 26.4±0.2, and 29.3±0.2 degrees 2θ.

Figure 27:
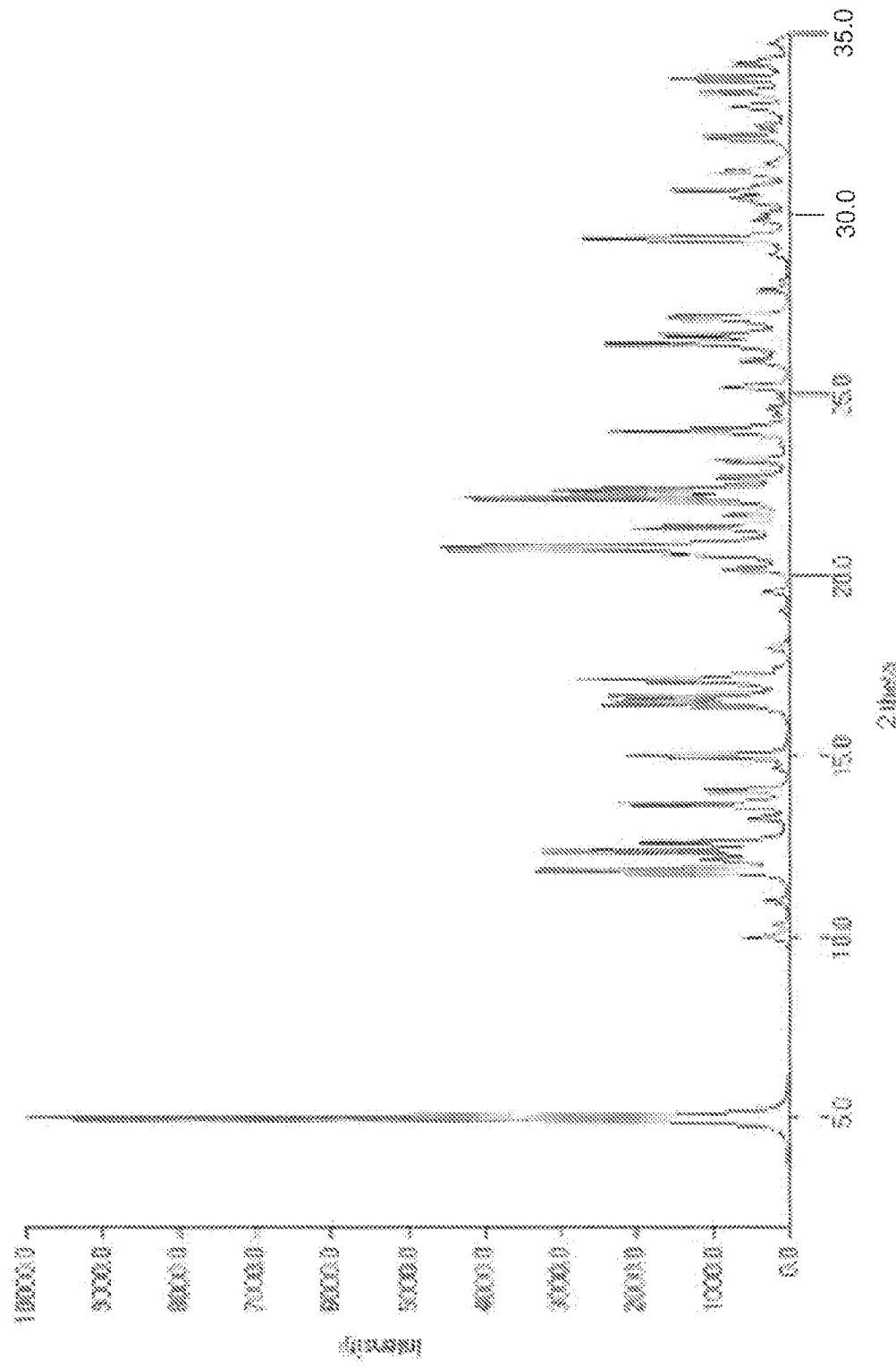
FIG. 27 shows an illustrative PXRD pattern for the dipotassium salt tetrahydrate of compound IB-L1-1.1.

In some embodiments, the dipotassium salt tetrahydrate has an X-ray powder diffraction pattern substantially as shown in FIG. 27. The 2θ values for the peaks in FIG. 27 (and their intensities) are as follows: 5.00 (100), 11.86 (34), 12.39 (32), 12.64 (19), 13.70 (23), 15.03 (21), 16.47 (24), 16.66 (24), 17.12 (28), 20.75 (29), 20.81 (33), 21.34 (22), 22.15 (46), 22.38 (31), 24.02 (24), 26.44 (24), and 29.32 (21).

This invention also relates, in part, to a process for preparing the dipotassium salt tetrahydrate by suspending compound IB-L1-1.1 (261.13 mg) in 1.25 ml THF while heated to about 50° C. Aqueous KOH (1N, 1.3 ml, 2.2 molar equivalent) was added. The solid dissolved completely to yield a clear solution, which was naturally cooled to ambient temperatures. Crystallization occurred during the slow evaporation process.

G9. Crystalline Forms of (E)-N-(4-(3-tert-butyl-5-(2,4-dioxo-3,4-dihydropyrimidin-1(2H)-yl)-2-methoxy-styryl)phenyl)methanesulfonamide Monopotassium Salt This invention also relates, in part, to crystalline forms of (E)-N-(4-(3-tert-butyl-5-(2,4-dioxo-3,4-dihydropyrimidin-1(2H)-yl)-2-methoxystyryl)phenyl)methanesulfonamide monopotassium salt, namely the trihydrate and dihydrate crystalline forms discussed below.

This invention relates, in part, to a monopotassium salt trihydrate. The crystallographic unit cell parameters of the trihydrate crystalline monopotassium salt have been determined to be as follows: a is 9.0 Å, b is 8.3 Å, and c is 18.6 Å (more precisely, a is 9.0393(16)Å, b is 8.3332(15)Å, and c is 18.582(3)Å); the cell angles are: α—80.5°, β—85.1°, and γ—80.5° (more precisely, α is 80.511(2)°, β is 85.134(3)°, and γ is 80.531(2°); and the cell volume is 1359 Å$^3$ (more precisely, 1359.3(4)Å$^3$). The salt crystallizes in the P-1 space group.

In some embodiments, the monopotassium salt trihydrate has an X-ray powder diffraction pattern comprising one or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ.

In some embodiments, the monopotassium salt trihydrate has an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ.

In some embodiments, the monopotassium salt trihydrate has an X-ray powder diffraction pattern comprising one or more peaks selected from the group consisting of 4.8±0.2, 10.8±0.2, 11.3±0.2, 13.4±0.2, 13.6±0.2, 15.3±0.2, 16.9±0.2, 21.2±0.2, 21.7±0.2, 21.7±0.2, 22.1±0.2, 22.5±0.2, 22.6±0.2, and 23.0±0.2 degrees 2θ. In some such embodiments, the monopotassium salt trihydrate has an X-ray powder diffraction pattern comprising three or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ. In other such embodiments, the monopotassium salt trihydrate has an X-ray powder diffraction pattern comprising five or more peaks selected from the group consisting of 4.8±0.2, 10.8±0.2, 11.3±0.2, 13.4±0.2, 15.3±0.2, 16.9±0.2, 21.2±0.2, 21.7±0.2, 22.1±0.2, 22.5±0.2, and 23.0±0.2 degrees 2θ.

Figure 28:
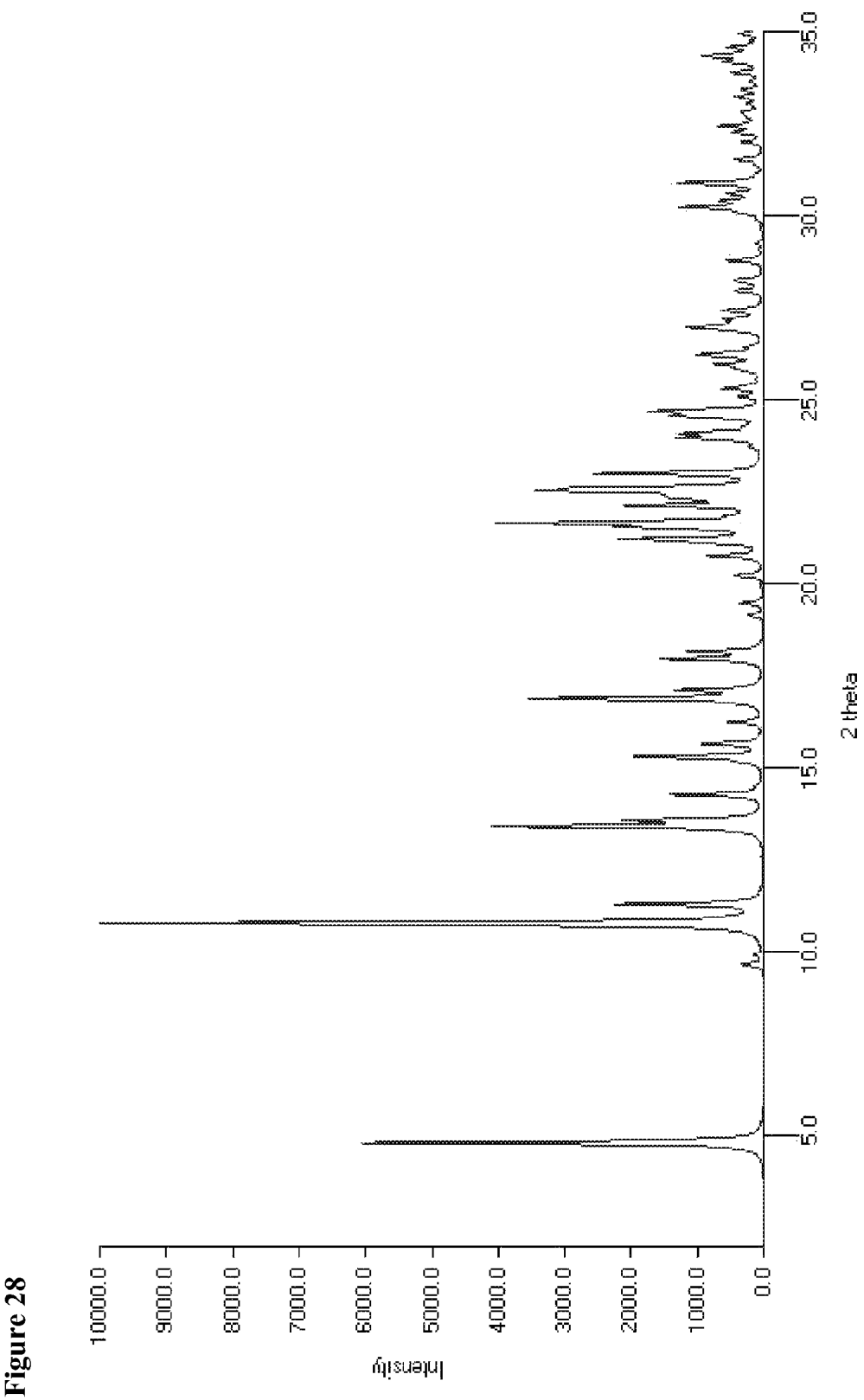
FIG. 28 shows an illustrative PXRD pattern for the monopotassium salt trihydrate of compound IB-L1-1.1.

In some embodiments, the monopotassium salt trihydrate has an X-ray powder diffraction pattern substantially as shown in FIG. 28. The 2θ values for the peaks in FIG. 28 (and their intensities) are as follows: 4.83 (60), 10.79 (100), 11.31 (22), 13.42 (41), 13.59 (18), 15.32 (21), 16.90 (38), 21.24 (22), 21.68 (20), 21.68 (21), 22.15 (22), 22.55 (29), 22.63 (23), and 23.02 (27).

This invention also relates, in part, to a process for preparing the monopotassium salt trihydrate. It was prepared by suspending compound IB-L1-1.1 (108.81 mg) in 0.4 ml THF while heated to about 50° C. Aqueous KOH solution (1N, 0.278 ml, 1.2 molar equivalent) was added. The solid dissolved completely to yield a clear solution. Additional 1.6 ml THF was added to the solution, which was then naturally cooled to ambient temperatures and crystallization was observed. Alternatively, the monopotassium salt trihydrate was prepared by suspending compound IB-L1-1.1 (343.89 mg) in 1.0 ml THF while heated to 50° C. Aqueous KOH (1 N, 0.878 ml, 1.2 molar equivalent) was added. The solid dissolved completely to yield a clear solution. Ethanol was added to the solution dropwise to a total volume of 4.0 ml. The solution was then naturally cooled to ambient temperature and crystallization was observed.

This invention relates, in part, to a monopotassium salt dihydrate.

In some embodiments, the monopotassium salt dihydrate has an X-ray powder diffraction pattern comprising one or more peaks selected from the group consisting of 7.7±0.2, 8.8±0.2, 16.1±0.2, and 19.7±0.2 degrees 2θ. In some such embodiments, the monopotassium salt dihydrate has an X-ray powder diffraction pattern comprising three or more peaks selected from the group consisting of degrees 2θ.

In some embodiments, the monopotassium salt dihydrate has an X-ray powder diffraction pattern comprising one or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ. In some such embodiments, the monopotassium salt dihydrate has an X-ray powder diffraction pattern comprising three or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ. In other such embodiments, the monopotassium salt dihydrate has an X-ray powder diffraction pattern comprising five or more peaks selected from the group consisting of 7.7±0.2, 8.8±0.2, 12.4±0.2, 14.0±0.2, 16.1±0.2, 17.7±0.2, 19.2±0.2, 19.7±0.2, 23.1±0.2, and 29.2±0.2 degrees 2θ.

Figure 29:
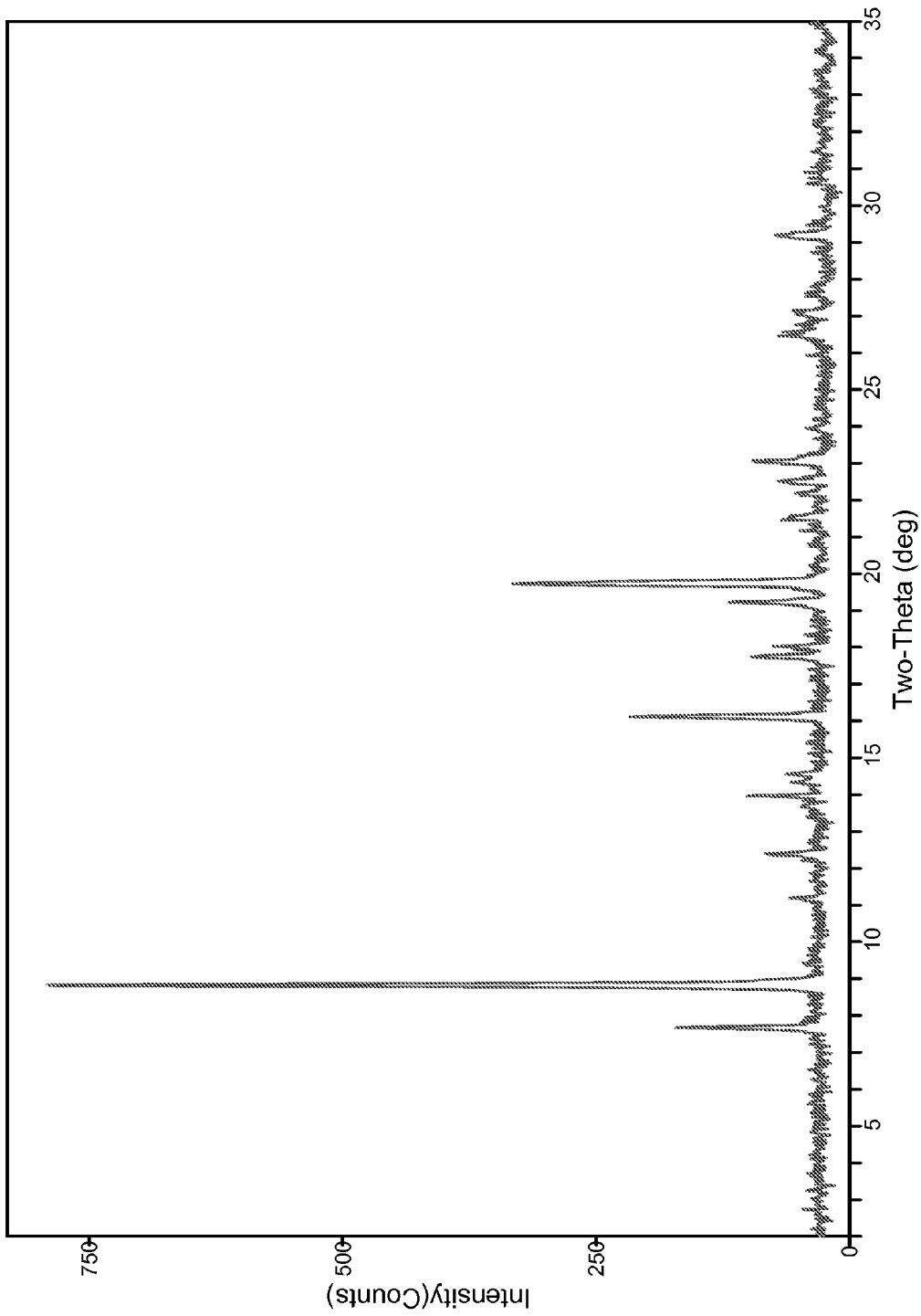
FIG. 29 shows an illustrative PXRD pattern for the monopotassium salt dihydrate of compound IB-L1-1.1.
Figure 30:
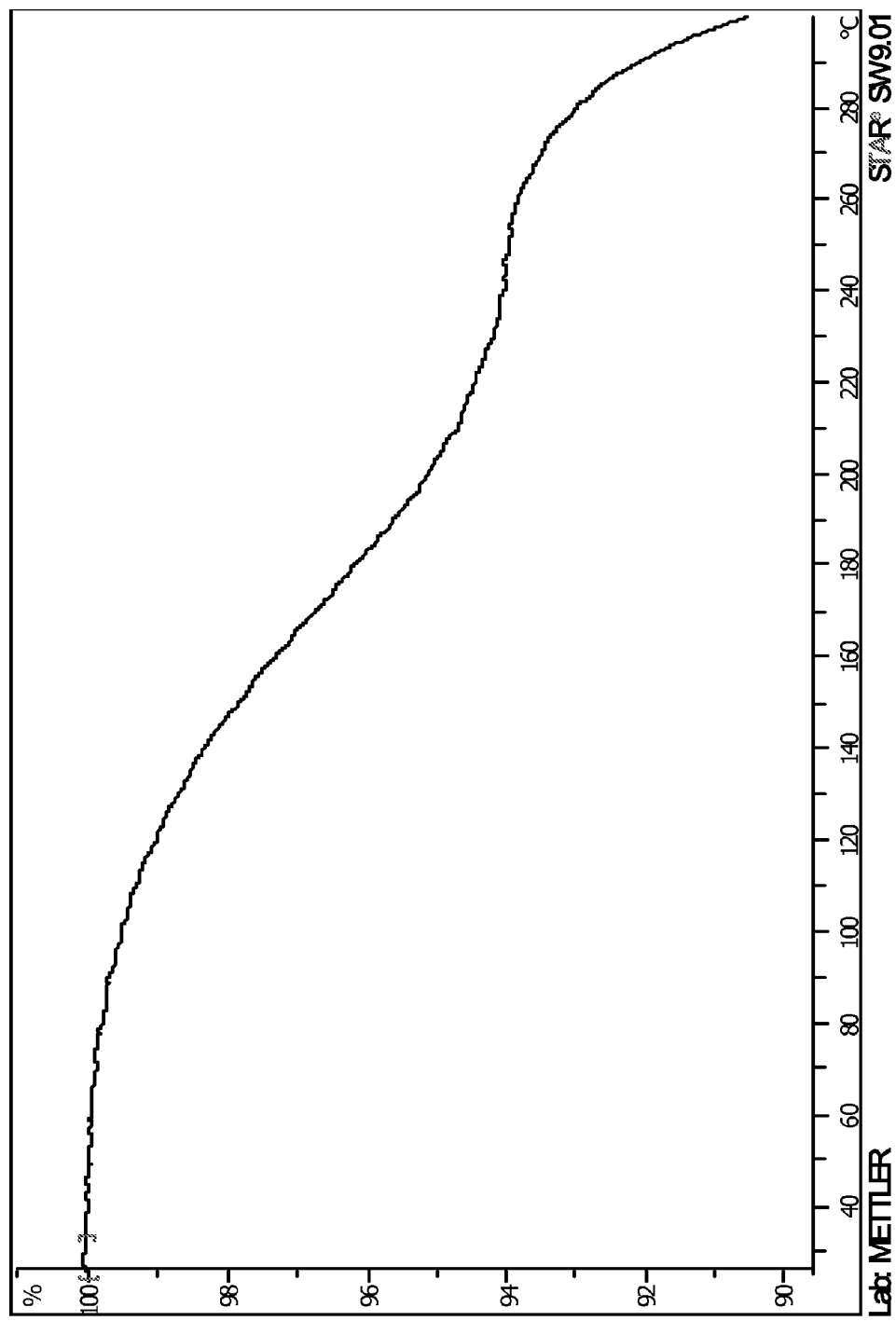
FIG. 30 shows an illustrative TGA profile of the monopotassium salt dihydrate of compound IB-L1-1.1.

In some embodiments, the monopotassium salt dihydrate has an X-ray powder diffraction pattern substantially as shown in FIG. 29. The 2θ values for the peaks in FIG. 29 (and their intensities) are as follows: 7.68 (19), 8.83 (100), 12.40 (7), 13.97 (10), 16.12 (25), 17.75 (9), 19.22 (12), 19.73 (40), 23.05 (9), and 29.21 (7).

This invention also relates, in part, to a process for preparing the monopotassium salt dihydrate. It was prepared by suspending the monopotassium salt trihydrate in media of low water activity, such as an ethanol/H$_2$O mixture (50/1 v/v). Alternatively, the monopotassium salt dihydrate was prepared by dissolving potassium trihydrate solid (1.8 g) in 36 mL of IPA and 4 ml water at 80° C. The resulting solution was cooled to 55° C. over 1 h. The solution was then seeded with 7.5 mg of dihydrate crystals at 55° C. and maintained at 55° C. for 1 h. Heptane (36 ml) was then added over 3 h. The reaction mixture was cooled to 0° C., and filtration yielded a material containing both di- and trihydrate crystals. The solid was then reslurried in 20 mL of 10:1 v/v EtOH/H$_2$O at 50° C. for 3 h and cooled to 25° C. over 5 h. The slurry was then mixed at 25° C. for additional 3 days and cooled to 0° C. over 3 h and held at this temperature for 2 h. The resulting crystals were filtered and air-dried on filter funnel for 1 h to give dihydrate. The dihydrate monopotassium salt was also prepared by slurrying a mixture of dihydrate and trihydrate crystals in 10:1 v/v EtOH/H$_2$O at 80° C. for 2 days. The potassium content was confirmed by ion chromatography.

G10. Crystalline Form of (E)-N-(4-(3-tert-butyl-5-(2,4-dioxo-3,4-dihydropyrimidin-1(2H)-yl)-2-methoxystyryl)phenyl)methanesulfonamide 1/7 Potassium Salt This invention also relates, in part, to a crystalline form of (E)-N-(4-(3-tert-butyl-5-(2,4-dioxo-3,4-dihydropyrimidin-1(2H)-yl)-2-methoxystyryl)phenyl)methanesulfonamide 1/7 potassium salt.

In some embodiments, the 1/7 potassium salt has an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ. In some such embodiments, the 1/7 potassium salt has an X-ray powder diffraction pattern comprising three or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ. In other such embodiments, the 1/7 potassium salt has an X-ray powder diffraction pattern comprising five or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 21.2±0.2, 22.1±0.2, and 22.9±0.2 degrees 2θ.

In some embodiments, the 1/7 potassium salt has an X-ray powder diffraction pattern comprising one or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ. In some such embodiments, the 1/7 potassium salt has an X-ray powder diffraction pattern comprising three or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ. In other such embodiments, the 1/7 potassium salt has an X-ray powder diffraction pattern comprising five or more peaks selected from the group consisting of 7.7±0.2, 8.3±0.2, 10.1±0.2, 10.6±0.2, 11.4±0.2, 12.0±0.2, 13.4±0.2, 15.6±0.2, 16.3±0.2, 16.7±0.2, 17.2±0.2, 18.3±0.2, 18.8±0.2, 19.4±0.2, 19.9±0.2, 20.2±0.2, 20.5±0.2, 20.8±0.2, 21.2±0.2, 22.1±0.2, 22.9±0.2, 24.3±0.2, 24.9±0.2, and 25.1±0.2 degrees 2θ.

Figure 31:
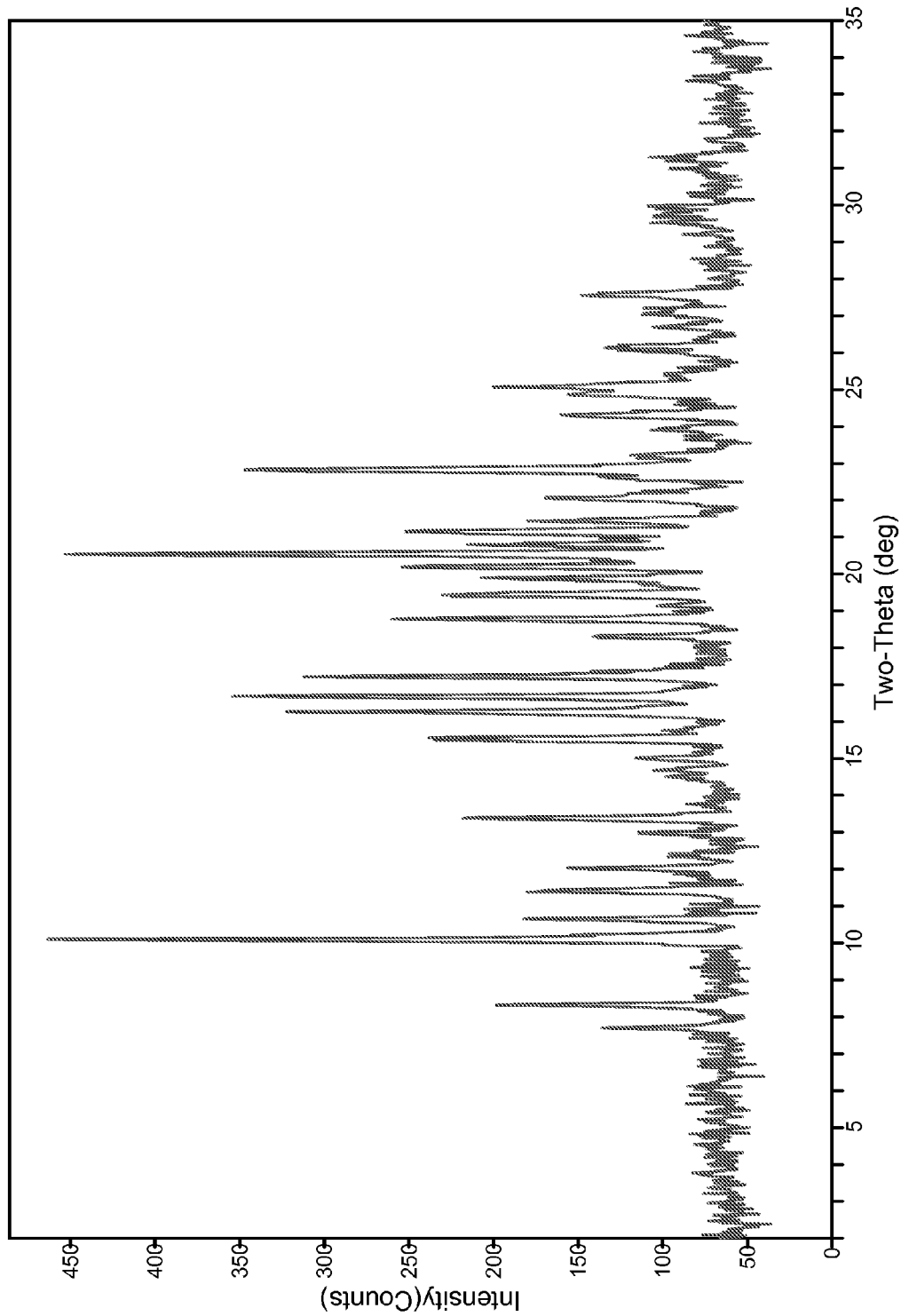
FIG. 31 shows an illustrative PXRD pattern for the 1/7 potassium salt of compound IB-L1-1.1.

In some embodiments, the 1/7 potassium salt has an X-ray powder diffraction pattern substantially as shown in FIG. 31. The 2θ values for the peaks in FIG. 31 (and their intensities) are as follows: 7.71 (19), 8.33 (34), 10.10 (100), 10.66 (29), 11.39 (27), 12.04 (22), 13.39 (39), 15.56 (41), 16.27 (62), 16.69 (70), 17.22 (59), 18.31 (18), 18.78 (47), 19.44 (36), 19.89 (28), 20.19 (33), 20.54 (87), 20.80 (33), 21.15 (47), 22.05 (24), 22.82 (67), 24.32 (22), 24.87 (22), and 25.07 (33).

This invention also relates, in part, to a process for preparing the 1/7 potassium salt. It was prepared by suspending compound IB-L1-1.1 (2 g) 6 ml THF at 50° C. One molar equivalent of KOH dissolved in 4.3 ml water was added, and the reaction mixture was heated to 65° C. to dissolve all solids. The solution was then cooled to ambient temperatures over 2 h and spontaneous crystallization took place. The slurry was then cooled to 5° C. and held at that temperature for 2 h. The pale yellow crystals were filtered and air-dried for 24 h at ambient conditions. The potassium content was determined by ion chromatography.

G11. Crystalline Form of (E)-N-(4-(3-tert-butyl-5-(2,4-dioxo-3,4-dihydropyrimidin-1(2H)-yl)-2-methoxystyryl)phenyl)methanesulfonamide Monodiethylamine Salt Tetrahydrate This invention also relates, in part, to crystalline (E)-N-(4-(3-tert-butyl-5-(2,4-dioxo-3,4-dihydropyrimidin-1(2H)-yl)-2-methoxystyryl)phenyl)methanesulfonamide monodiethylamine salt tetrahydrate.

In some embodiments, the monodiethylamine salt tetrahydrate has an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ. In some such embodiments, the monodiethylamine salt tetrahydrate has an X-ray powder diffraction pattern comprising three or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ. In other such embodiments, the monodiethylamine salt tetrahydrate has an X-ray powder diffraction pattern comprising five or more peaks selected from the group consisting of 9.5±0.2, 10.0±0.2, 11.8±0.2, 12.1±0.2, 14.4±0.2, 16.8±0.2, 17.6±0.2, 19.8±0.2, 20.8±0.2, 21.4±0.2, 21.8±0.2, and 29.8±0.2 degrees 2θ.

In some embodiments, the monodiethylamine salt tetrahydrate has an X-ray powder diffraction pattern comprising one or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ. In some such embodiments, the monodiethylamine salt tetrahydrate has an X-ray powder diffraction pattern comprising three or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ. In other such embodiments, the monodiethylamine salt tetrahydrate has an X-ray powder diffraction pattern comprising five or more peaks selected from the group consisting of 9.5±0.2, 10.0±0.2, 11.8±0.2, 12.1±0.2, 14.4±0.2, 16.8±0.2, 17.6±0.2, 19.4±0.2, 19.8±0.2, 20.8±0.2, 21.4±0.2, 21.8±0.2, 21.9±0.2, and 29.8±0.2 degrees 2θ.

Figure 32:
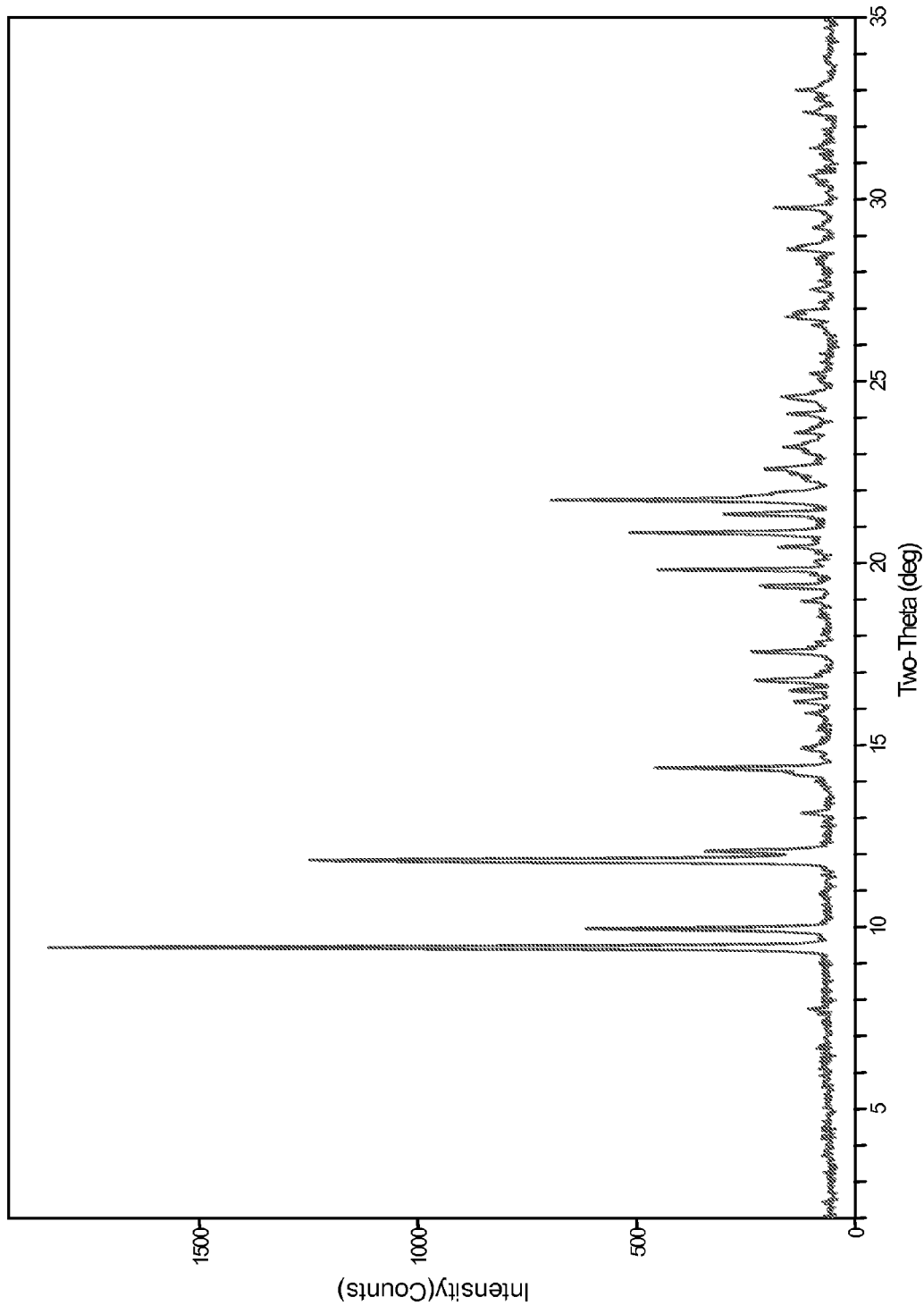
FIG. 32 shows an illustrative PXRD pattern for the monodiethylamine salt tetrahydrate of compound IB-L1-1.1.
Figure 33:
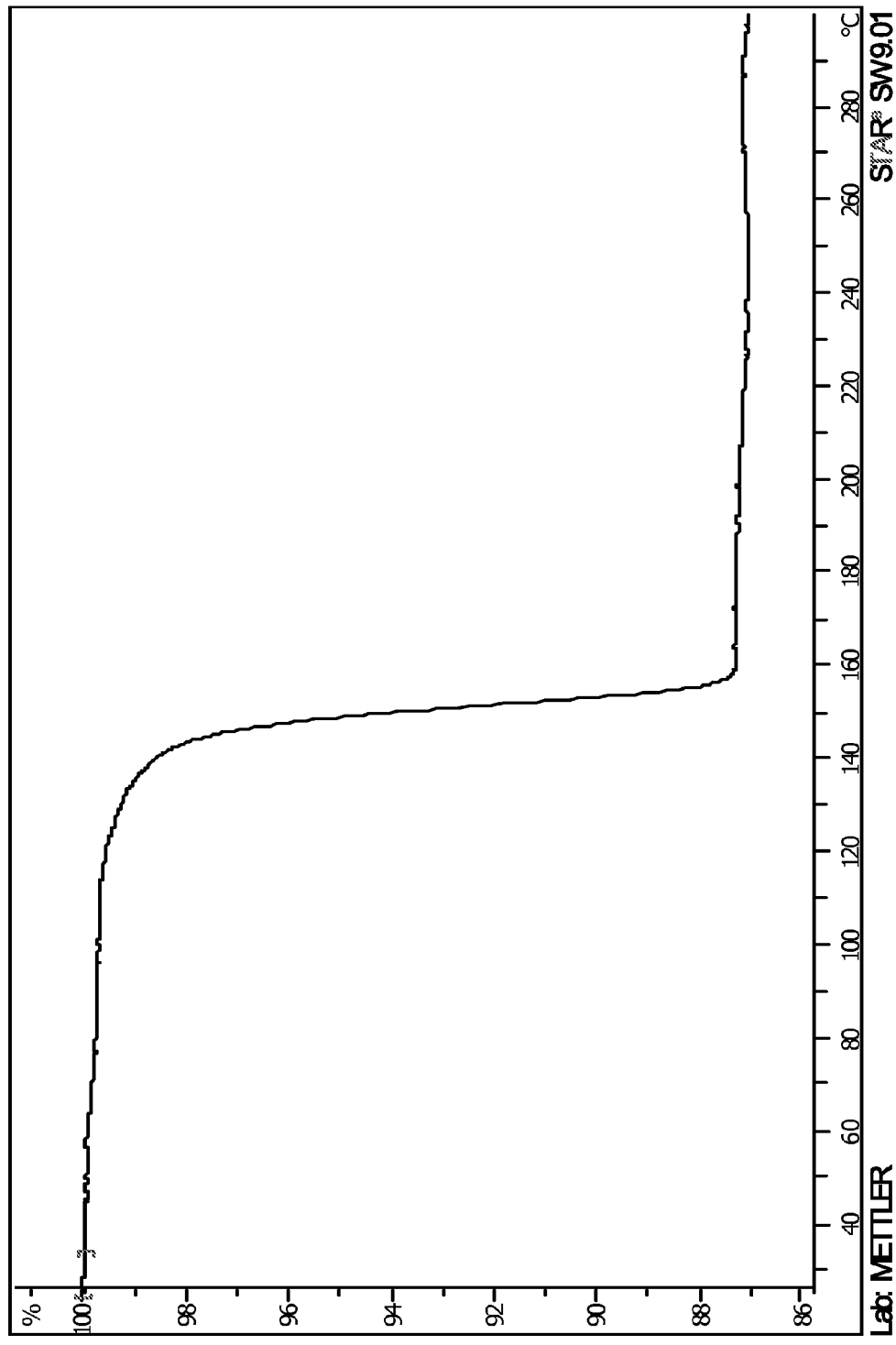
FIG. 33 shows an illustrative TGA profile of the monodiethylamine salt tetrahydrate of compound IB-L1-1.1.

In some embodiments, the monodiethylamine salt tetrahydrate has an X-ray powder diffraction pattern substantially as shown in FIG. 32. The 2θ values for the peaks in FIG. 32 (and their intensities) are as follows: 9.45 (100), 9.97 (31), 11.85 (67), 12.09 (16), 14.38 (22), 16.80 (9), 17.59 (10), 19.39 (8), 19.83 (21), 20.85 (25), 21.37 (12), 21.75 (34), 21.87 (8), and 29.78 (7).

This invention also relates, in part, to a process for preparing the monodiethylamine salt tetrahydrate. It was prepared in aqueous medium. Compound IB-L1-1.1 was slowly added to 500 ul of 1M diethylamine until no more solid can be dissolved into the solution. The solution was then evaporated slowly at ambient temperatures and the salt crystallized 2 days later. Alternatively, the monodiethylamine salt tetrahydrate was prepared by suspending 64.15 mg of compound IB-L1-1.1 in 400 ul 1M diethylamine while heated to 50° C. About 5 drops of THF (~20 ul) was added. The solid dissolved completely upon addition to yield a clear solution. The solution was then evaporated at ambient temperature, and the salt crystallized 4 days later. The stoichiometry of the salt was confirmed by solution $^1$H NMR.

G12. Crystalline Forms of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1)

This invention also relates, in part, to crystalline forms of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1), namely the true polymorphs (pattern A, pattern B, pattern C, and pattern D) and hydrate (pattern AH, pattern BH, pattern CH, and pattern DH) crystalline forms discussed below.

G12A. IB-L1-1.1 True Polymorphs

This invention relates, in part, to pattern A crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern A polymorph has an X-ray powder diffraction pattern comprising one or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ. In some such embodiments, the pattern A polymorph has an X-ray powder diffraction pattern comprising three or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ. In other such embodiments, the pattern A polymorph has an X-ray powder diffraction pattern comprising five or more peaks selected from the group consisting of 5.8±0.2, 9.9±0.2, 11.8±0.2, 12.4±0.2, 14.5±0.2, 18.8±0.2, 22.7±0.2, and 29.2±0.2 degrees 2θ.

In some embodiments, the pattern A polymorph has an X-ray powder diffraction pattern comprising one or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ. In some such embodiments, the pattern A polymorph has an X-ray powder diffraction pattern comprising three or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ. In other such embodiments, the pattern A polymorph has an X-ray powder diffraction pattern comprising five or more peaks selected from the group consisting of 5.8±0.2, 9.9±0.2, 11.8±0.2, 12.4±0.2, 14.0±0.2, 14.5±0.2, 15.3±0.2, 18.5±0.2, 18.8±0.2, 22.2±0.2, 22.7±0.2, 23.8±0.2, 26.0±0.2, and 29.2±0.2 degrees 2θ.

Figure 34:
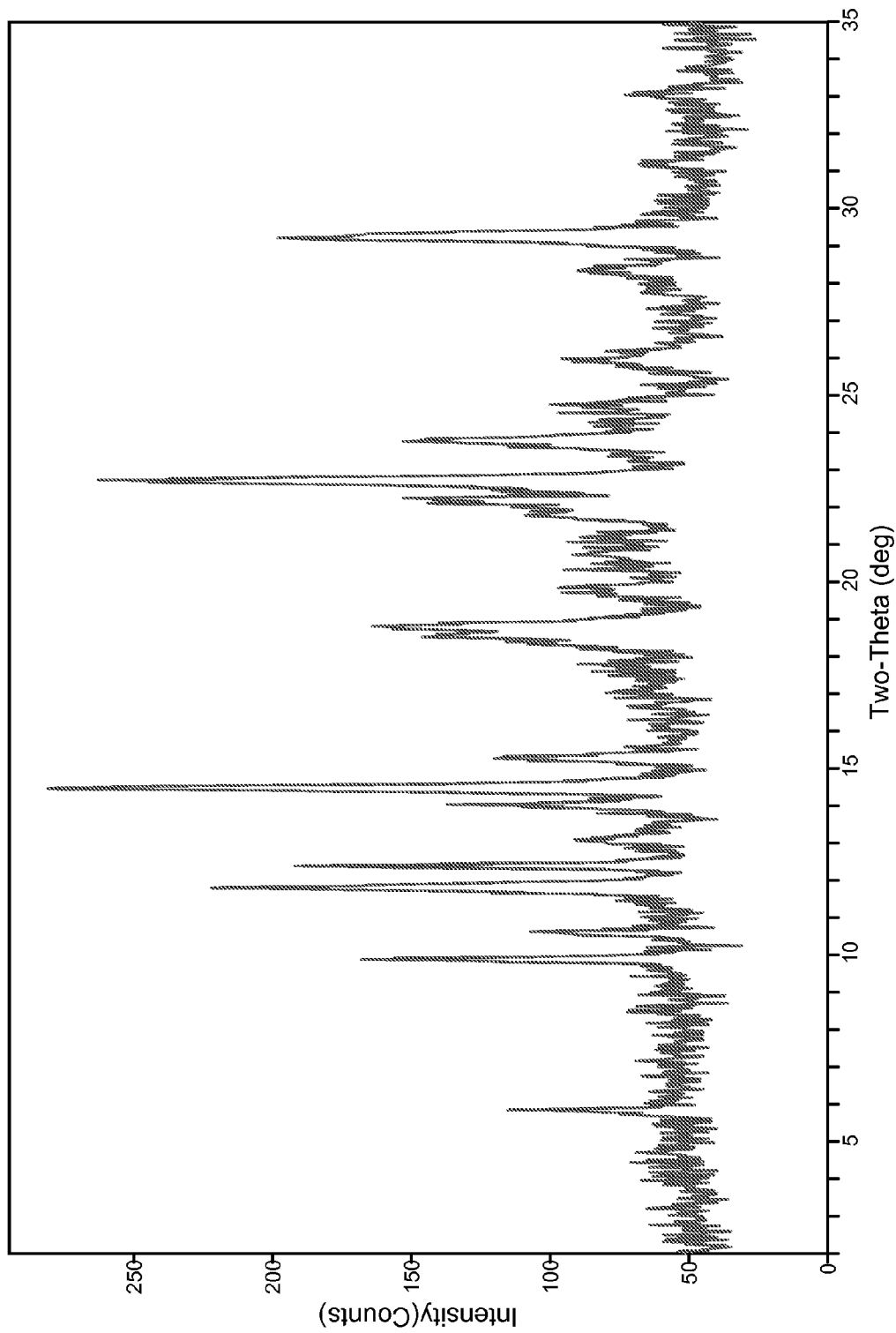
FIG. 34 shows an illustrative PXRD pattern for the pattern A polymorph of compound IB-L1-1.1.
Figure 35:
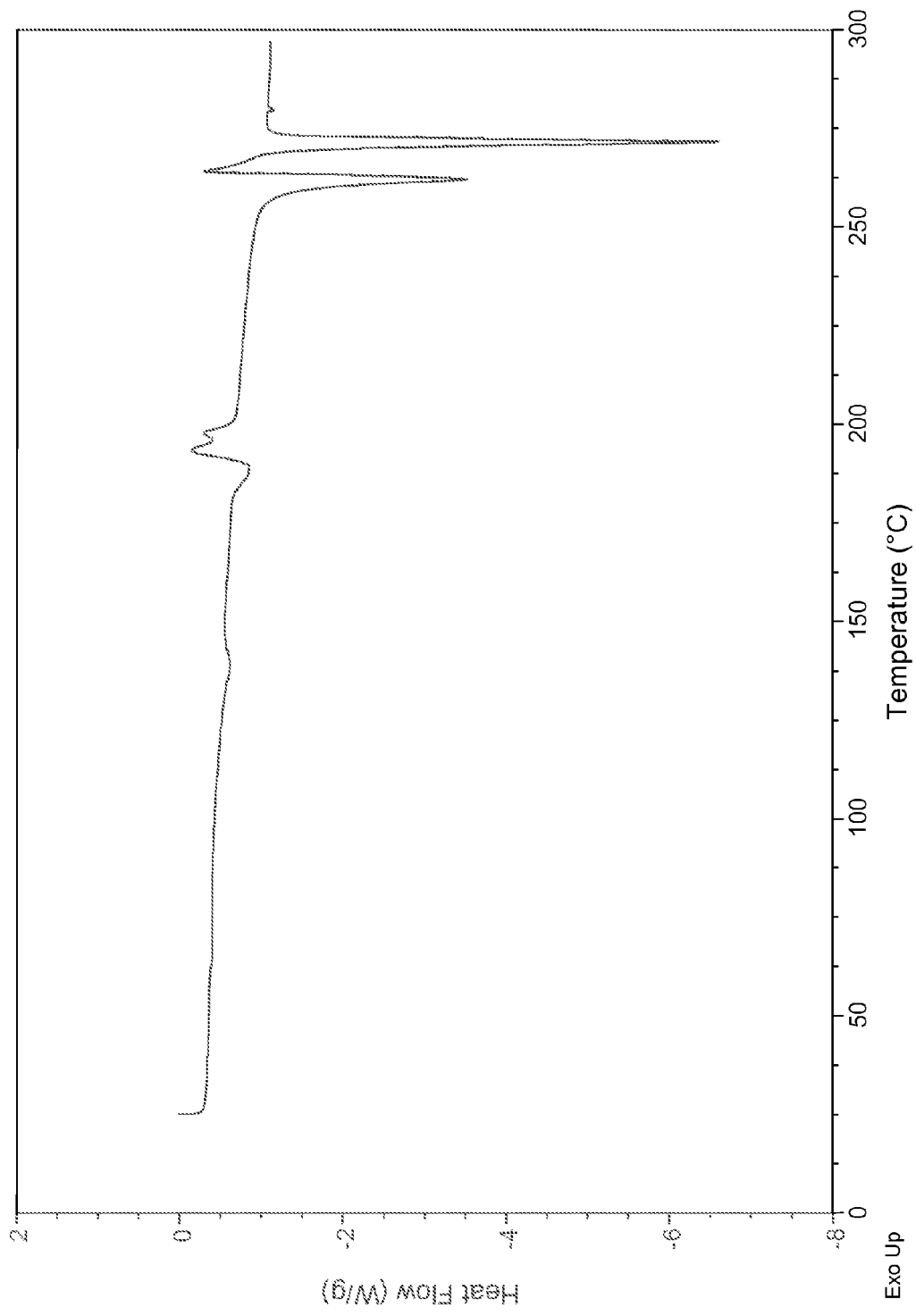
FIG. 35 shows an illustrative DSC profile of the pattern A polymorph of compound IB-L1-1.1.

In some embodiments, the pattern A polymorph has an X-ray powder diffraction pattern substantially as shown in FIG. 34. The 2θ values for the peaks in FIG. 34 (and their intensities) are as follows: 5.85 (28), 9.88 (51), 11.79 (73), 12.38 (56), 14.03 (38), 14.45 (100), 15.27 (29), 18.52 (39), 18.80 (47), 22.24 (40), 22.72 (77), 23.76 (39), 25.98 (22), and 29.21 (64).

This invention also relates, in part, to a process for preparing pattern A polymorph. Pattern A polymorph was prepared as discussed in Example F below.

This invention relates, in part, to pattern B crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern B polymorph has an X-ray powder diffraction pattern comprising one or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ. In some such embodiments, the pattern B polymorph has an X-ray powder diffraction pattern comprising three or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ. In other such embodiments, the pattern B polymorph has an X-ray powder diffraction pattern comprising five or more peaks selected from the group consisting of 11.5±0.2, 13.3±0.2, 15.4±0.2, 16.4±0.2, 17.1±0.2, 18.6±0.2, 19.4±0.2, 20.4±0.2, 21.6±0.2, 22.4±0.2, 24.0±0.2, 26.8±0.2, and 29.0±0.2 degrees 2θ.

Figure 36:
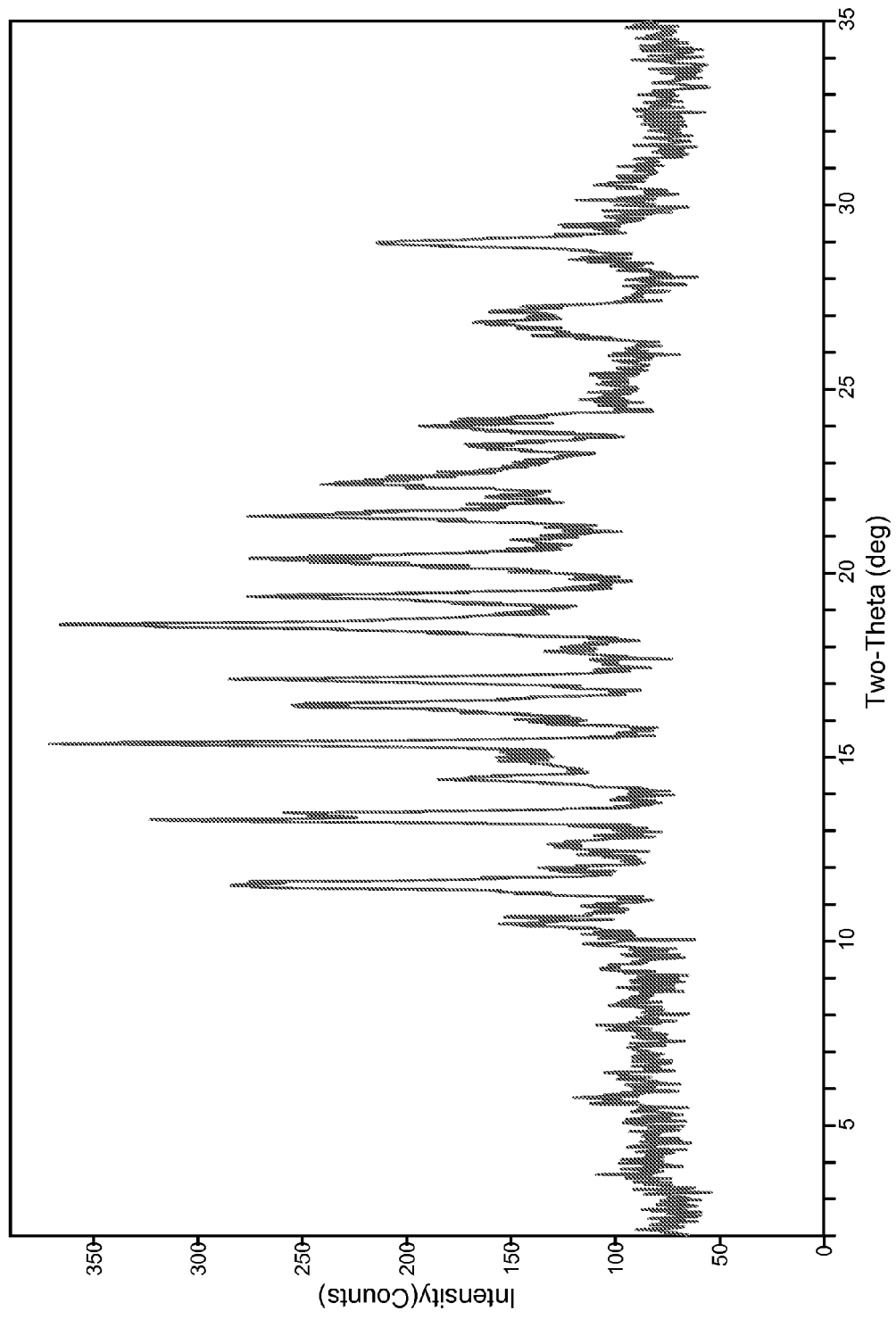
FIG. 36 shows an illustrative PXRD pattern for the pattern B polymorph of compound IB-L1-1.1.

In some embodiments, the pattern B polymorph has an X-ray powder diffraction pattern substantially as shown in FIG. 36. The 2θ values for the peaks in FIG. 36 (and their intensities) are as follows: 11.52 (71), 13.30 (87), 15.37 (100), 16.42 (60), 17.13 (69), 18.60 (97), 19.37 (56), 20.40 (62), 21.55 (55), 22.41 (39), 23.99 (33), 26.81 (31), and 28.98 (50).

This invention relates, in part, to pattern C crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern C polymorph has an X-ray powder diffraction pattern comprising one or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ. In some such embodiments, the pattern C polymorph has an X-ray powder diffraction pattern comprising three or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ. In other such embodiments, the pattern C polymorph has an X-ray powder diffraction pattern comprising five or more peaks selected from the group consisting of 7.7±0.2, 10.1±0.2, 10.6±0.2, 12.0±0.2, 13.4±0.2, 16.2±0.2, 19.4±0.2, 20.5±0.2, 21.4±0.2, 22.0±0.2, 22.6±0.2, 24.3±0.2, and 27.6±0.2 degrees 2θ.

Figure 37:
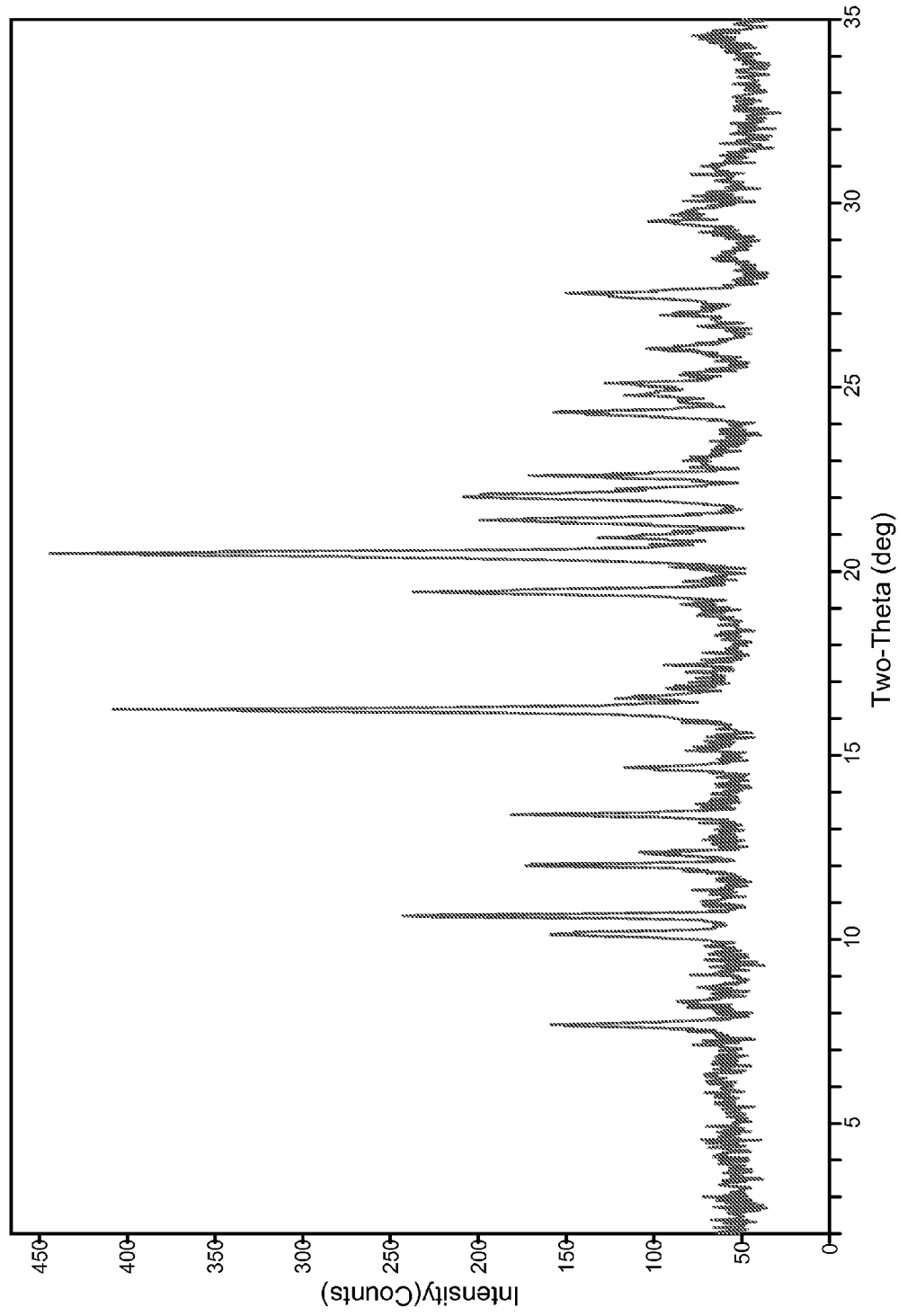
FIG. 37 shows an illustrative PXRD pattern for the pattern C polymorph of compound IB-L1-1.1.

In some embodiments, the pattern C polymorph has an X-ray powder diffraction pattern substantially as shown in FIG. 37. The 2θ values for the peaks in FIG. 37 (and their intensities) are as follows: 7.69 (27), 10.13 (27), 10.64 (49), 12.01 (31), 13.39 (33), 16.25 (91), 19.44 (46), 20.49 (100), 21.40 (35), 22.03 (37), 22.60 (30), 24.32 (23), and 27.55 (27).

This invention relates, in part, to pattern D crystalline (E)-N-(4-(3-tert-butyl-5-(2,4-dioxo-3,4-dihydropyrimidin-1(2H)-yl)-2-methoxystyryl)phenyl)methanesulfonamide.

In some embodiments, the pattern D polymorph has an X-ray powder diffraction pattern comprising one or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ. In some such embodiments, the pattern D polymorph has an X-ray powder diffraction pattern comprising three or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ. In other such embodiments, the pattern D polymorph has an X-ray powder diffraction pattern comprising five or more peaks selected from the group consisting of 5.8±0.2, 10.7±0.2, 11.2±0.2, 15.2±0.2, 16.1±0.2, 16.9±0.2, 19.9±0.2, 22.1±0.2, 24.7±0.2, and 26.0±0.2 degrees 2θ.

In some embodiments, the pattern D polymorph has an X-ray powder diffraction pattern comprising one or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ. In some such embodiments, the pattern D polymorph has an X-ray powder diffraction pattern comprising three or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ. In other such embodiments, the pattern D polymorph has an X-ray powder diffraction pattern comprising five or more peaks selected from the group consisting of 5.8±0.2, 10.7±0.2, 11.2±0.2, 15.2±0.2, 16.1±0.2, 16.9±0.2, 17.1±0.2, 19.9±0.2, 20.1±0.2, 22.1±0.2, 24.7±0.2, and 26.0±0.2 degrees 2θ.

Figure 38:
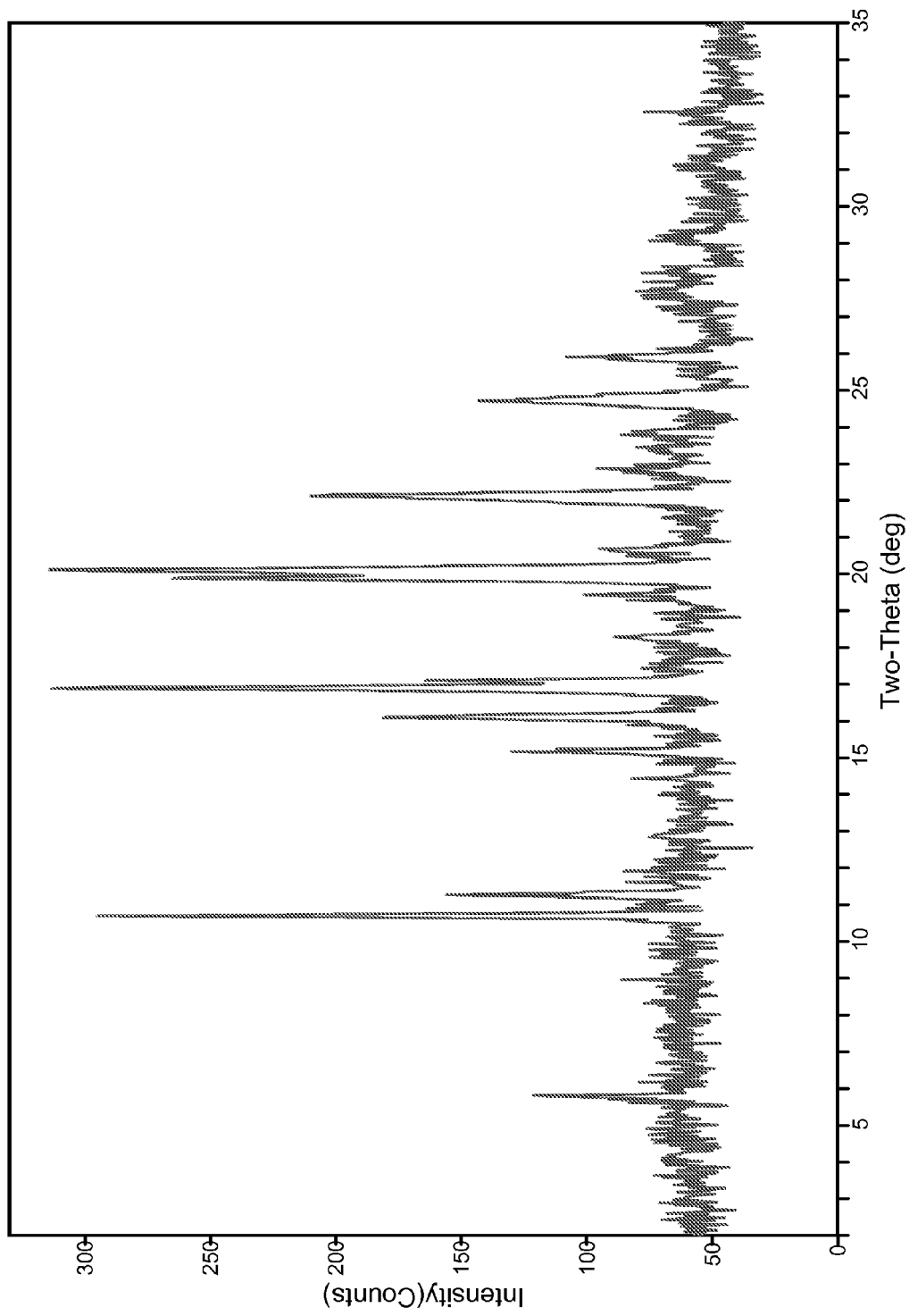
FIG. 38 shows an illustrative PXRD pattern for the pattern D polymorph of compound IB-L1-1.1.

In some embodiments, the pattern D polymorph has an X-ray powder diffraction pattern substantially as shown in FIG. 38. The 2θ values for the peaks in FIG. 38 (and their intensities) are as follows: 5.81 (24), 10.70 (91), 11.23 (60), 15.17 (28), 16.10 (48), 16.89 (100), 17.10 (42), 19.88 (81), 20.12 (100), 22.12 (59), 24.72 (37), and 25.91 (24).

This invention also relates, in part, to a process for preparing pattern B, C, and D polymorphs by heating pattern A polymorph to about 160, about 225, and about 268° C., respectively using DSC.

G12B. IB-L1-1.1 Hydrates

This invention also relates, in part, to hydrates of compound IB-L1-1.1, namely to hydrates A, B, C, D, and E discussed below.

This invention relates, in part, to a pattern A (E)-N-(4-(3-tert-butyl-5-(2,4-dioxo-3,4-dihydro-pyrimidin-1(2H)-yl)-2-methoxystyryl)phenyl)methanesulfonamide hydrate.

In some embodiments, the pattern A hydrate has an X-ray powder diffraction pattern comprising one or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ. In some such embodiments, the pattern A hydrate has an X-ray powder diffraction pattern comprising three or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ. In other such embodiments, the pattern A hydrate has an X-ray powder diffraction pattern comprising five or more peaks selected from the group consisting of 5.1±0.2, 7.9±0.2, 9.5±0.2, 10.3±0.2, 13.7±0.2, 16.5±0.2, 17.1±0.2, 17.5±0.2, 18.8±0.2, 19.2±0.2, 20.7±0.2, 21.3±0.2, 21.6±0.2, 25.8±0.2, 26.8±0.2, and 28.4±0.2 degrees 2θ.

Figure 39:
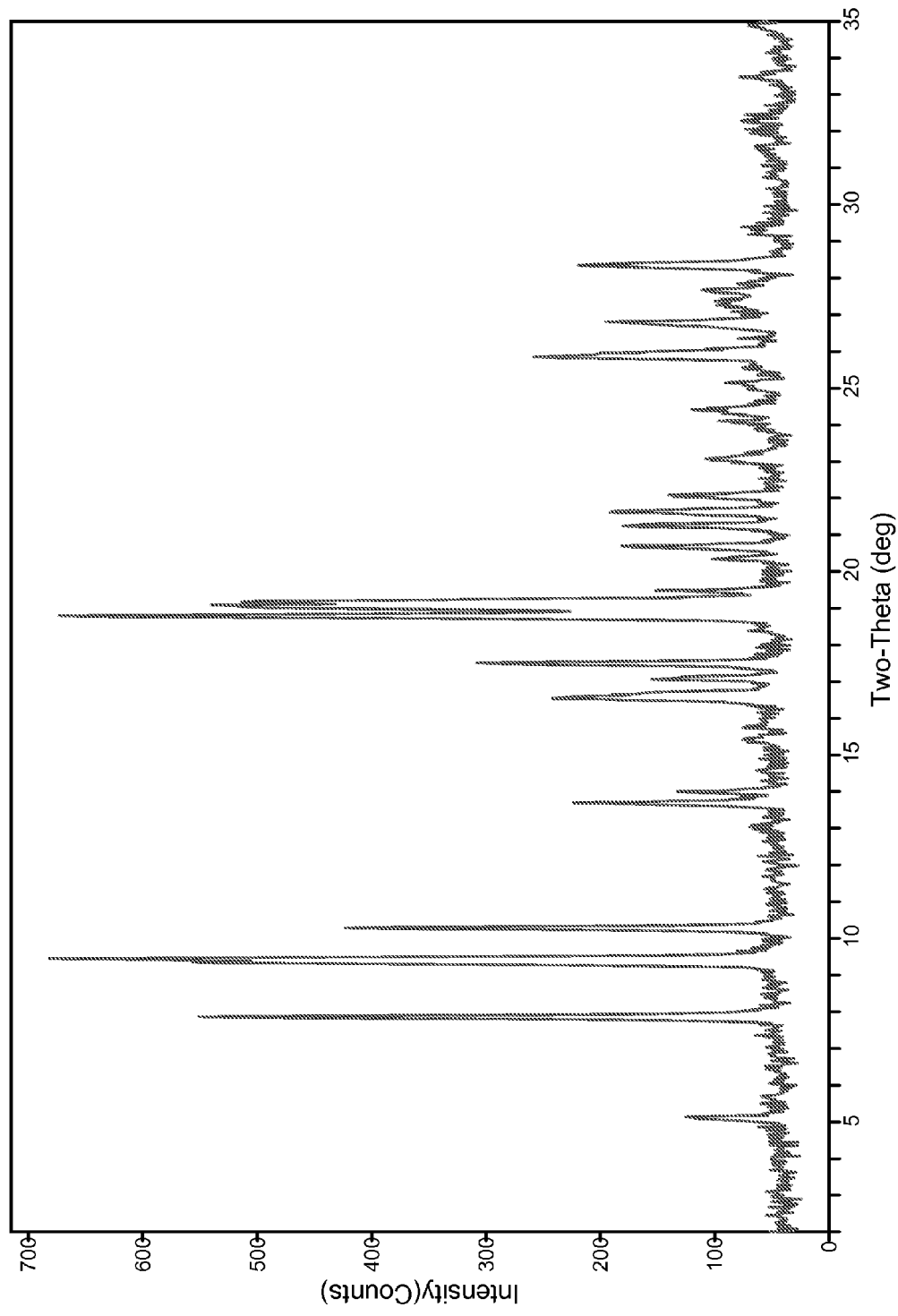
FIG. 39 shows an illustrative PXRD pattern for the pattern A hydrate of compound IB-L1-1.1.
Figure 40:
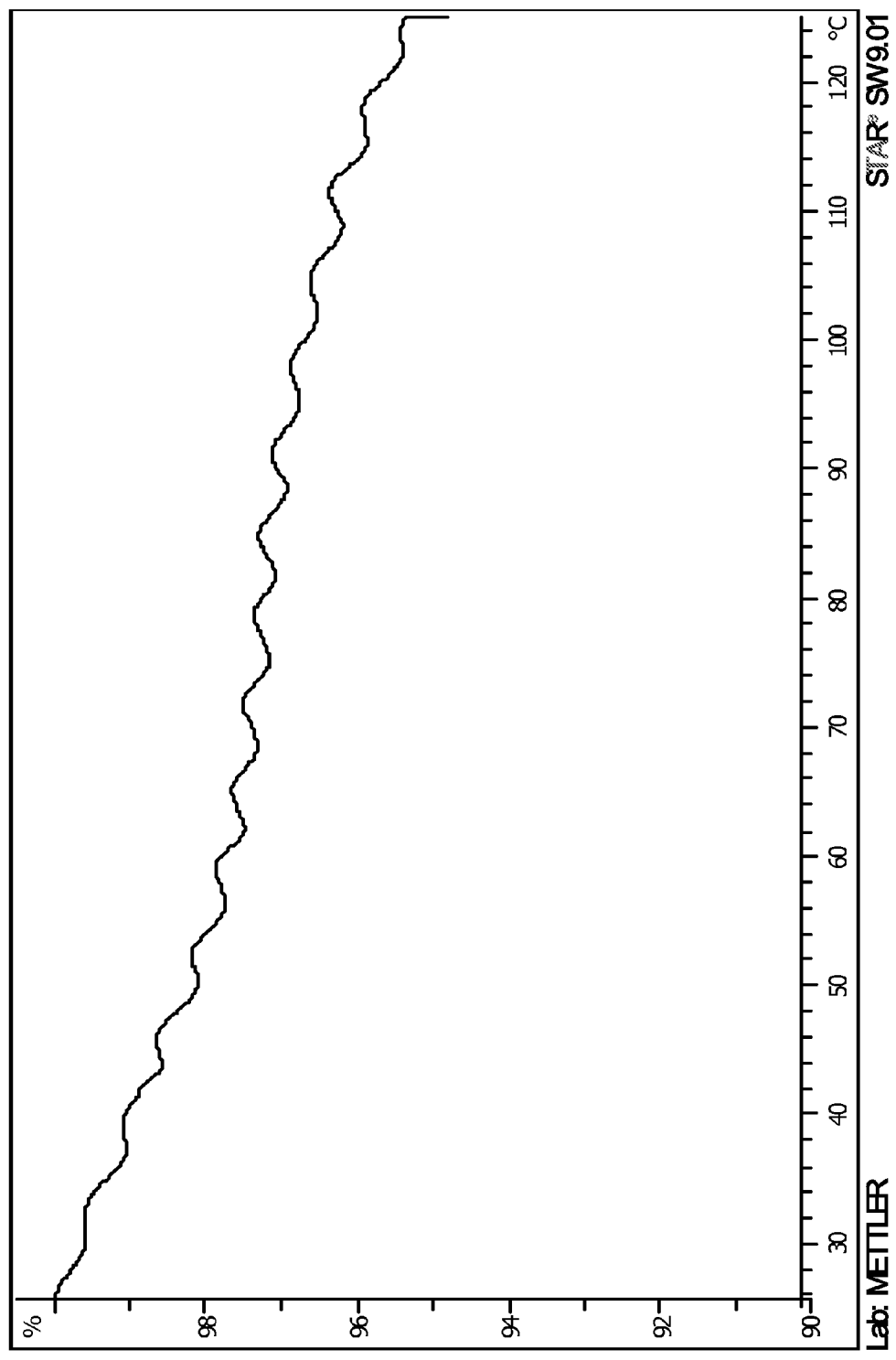
FIG. 40 shows an illustrative TGA profile of the pattern A hydrate of compound IB-L1-1.1.

In some embodiments, the pattern A hydrate has an X-ray powder diffraction pattern substantially as shown in FIG. 39. The 2θ values for the peaks in FIG. 39 (and their intensities) are as follows: 5.13 (13), 7.87 (80), 9.45 (100), 10.29 (60), 13.7 (28), 16.54 (30), 17.07 (17), 17.51 (40), 18.80 (99), 19.18 (74), 20.69 (21), 21.25 (21), 21.63 (23), 25.85 (32), 26.81 (20), and 28.35 (27).

This invention also relates, in part, to a process for preparing the pattern A hydrate by suspending pattern A polymorph (discussed above) in ethyl acetate. The recovered pattern A hydrate contains ~1 water molecules per molecule of compound IB-L1-1.1.

This invention also relates, in part, to a pattern B (E)-N-(4-(3-tert-butyl-5-(2,4-dioxo-3,4-dihydro-pyrimidin-1(2H)-yl)-2-methoxystyryl)phenyl)methanesulfonamide hydrate.

In some embodiments, the pattern B hydrate has an X-ray powder diffraction pattern comprising one or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ. In some such embodiments, the pattern B hydrate has an X-ray powder diffraction pattern comprising three or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ. In other such embodiments, the pattern B hydrate has an X-ray powder diffraction pattern comprising five or more peaks selected from the group consisting of 6.3±0.2, 7.7±0.2, 10.4±0.2, 12.7±0.2, 13.3±0.2, 14.9±0.2, 15.4±0.2, 16.4±0.2, 18.6±0.2, 18.9±0.2, 19.4±0.2, 22.5±0.2, 23.5±0.2, 24.0±0.2, 26.8±0.2, and 29.0±0.2 degrees 2θ.

In some embodiments, the pattern B hydrate has an X-ray powder diffraction pattern comprising one or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ. In some such embodiments, the pattern B hydrate has an X-ray powder diffraction pattern comprising three or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ. In other such embodiments, the pattern B hydrate has an X-ray powder diffraction pattern comprising five or more peaks selected from the group consisting of 6.3±0.2, 7.7±0.2, 10.4±0.2, 12.7±0.2, 13.3±0.2, 13.5±0.2, 14.9±0.2, 15.4±0.2, 16.4±0.2, 18.5±0.2, 18.6±0.2, 18.9±0.2, 19.4±0.2, 22.5±0.2, 23.5±0.2, 24.0±0.2, 26.8±0.2, and 29.0±0.2 degrees 2θ.

Figure 41:
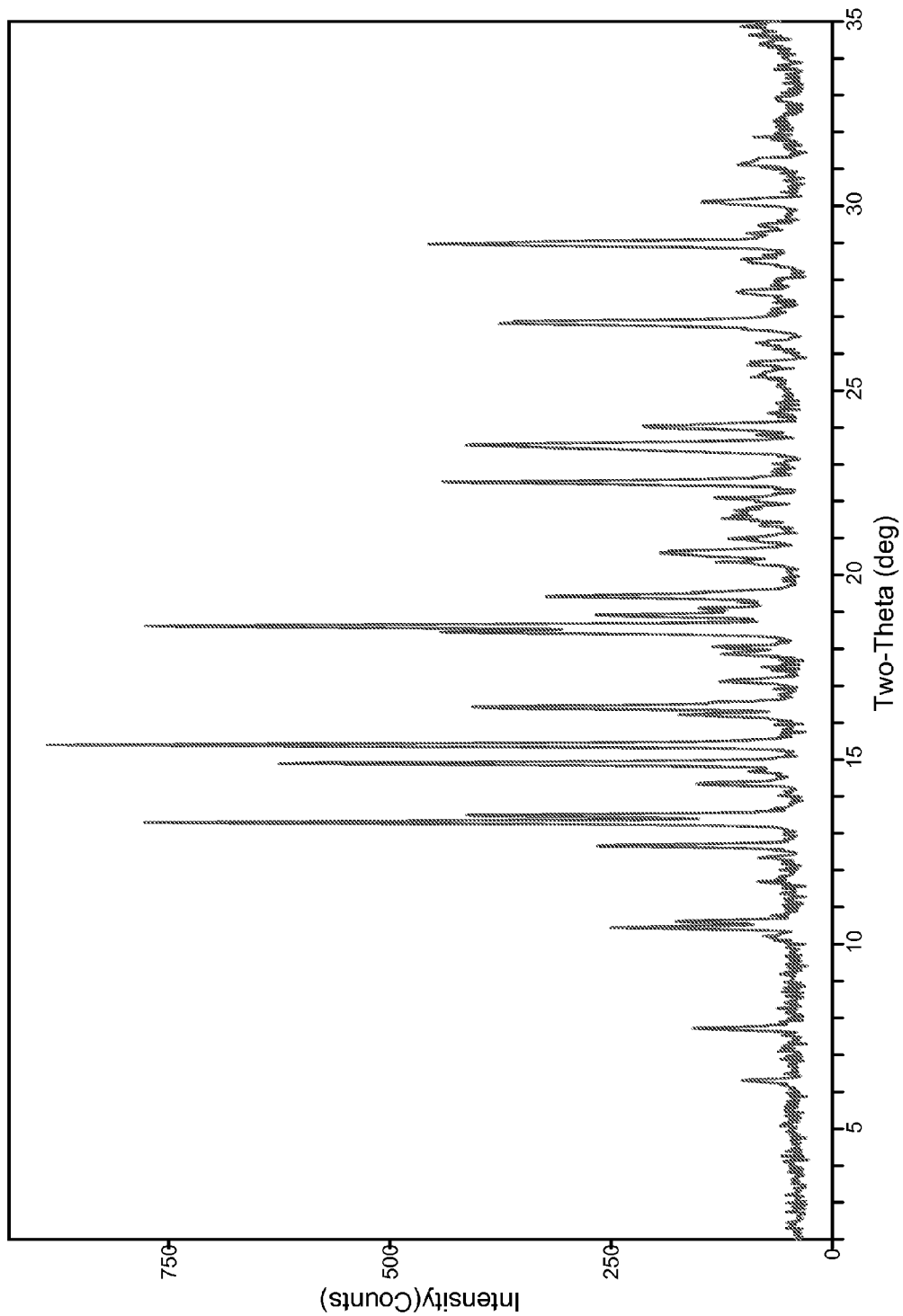
FIG. 41 shows an illustrative PXRD pattern for the pattern B hydrate of compound IB-L1-1.1.
Figure 42:
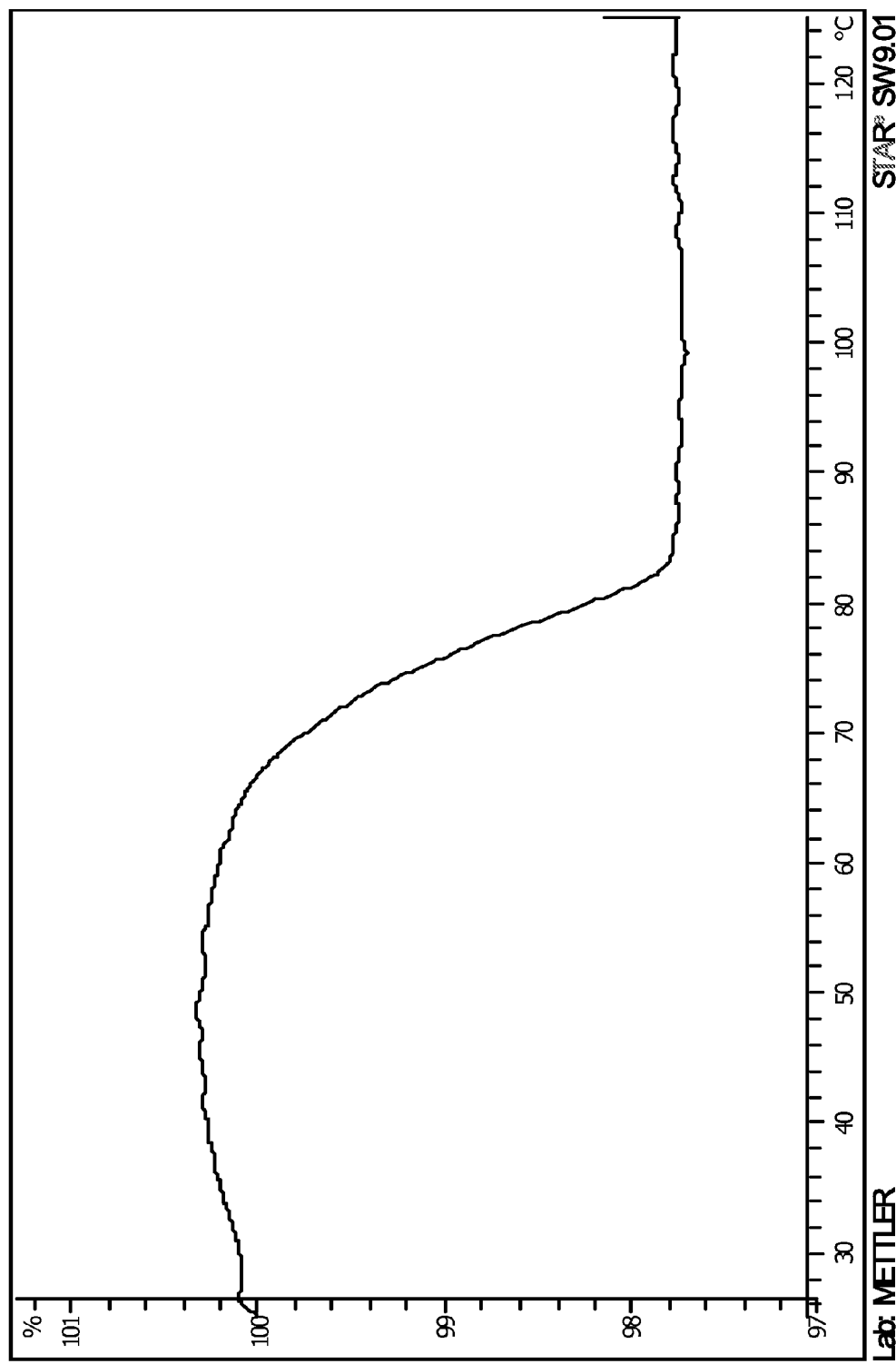
FIG. 42 shows an illustrative TGA profile of the pattern B hydrate of compound IB-L1-1.1.

In some embodiments, the pattern B hydrate has an X-ray powder diffraction pattern substantially as shown in FIG. 41. The 2θ values for the peaks in FIG. 41 (*and* their intensities) are as follows: 6.31 (7), 7.72 (14), 10.45 (24), 12.67 (26), 13.30 (88), 13.50 (44), 14.89 (70), 15.40 (100), 16.43 (43), 18.46 (47), 18.63 (86), 18.91 (26), 19.42 (33), 22.52 (47), 23.52 (44), 24.02 (20), 26.82 (40), and 28.97 (49).

This invention also relates, in part, to a process for preparing the pattern B hydrate by suspending pattern A polymorph (discussed above) in acetonitrile/water (9/1 v/v). The recovered pattern B hydrate contains ~0.7 water molecules per molecule of compound IB-L1-1.1.

This invention also relates, in part, to a pattern C (E)-N-(4-(3-tert-butyl-5-(2,4-dioxo-3,4-dihydropyrimidin-1(2H)-yl)-2-methoxystyryl)phenyl)methanesulfonamide hydrate.

In some embodiments, the pattern C hydrate has an X-ray powder diffraction pattern comprising one or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In some such embodiments, the pattern C hydrate has an X-ray powder diffraction pattern comprising three or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In other such embodiments, the pattern C hydrate has an X-ray powder diffraction pattern comprising five or more peaks selected from the group consisting of 10.5±0.2, 13.3±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ.

In some embodiments, the pattern C hydrate has an X-ray powder diffraction pattern comprising one or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In some such embodiments, the pattern C hydrate has an X-ray powder diffraction pattern comprising three or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ. In other such embodiments, the pattern C hydrate has an X-ray powder diffraction pattern comprising five or more peaks selected from the group consisting of 10.5±0.2, 13.3±0.2, 13.5±0.2, 14.9±0.2, 15.4±0.2, 16.4±0.2, 18.6±0.2, 19.0±0.2, 19.4±0.2, 22.5±0.2, 23.5±0.2, 26.9±0.2, and 29.0±0.2 degrees 2θ.

Figure 43:
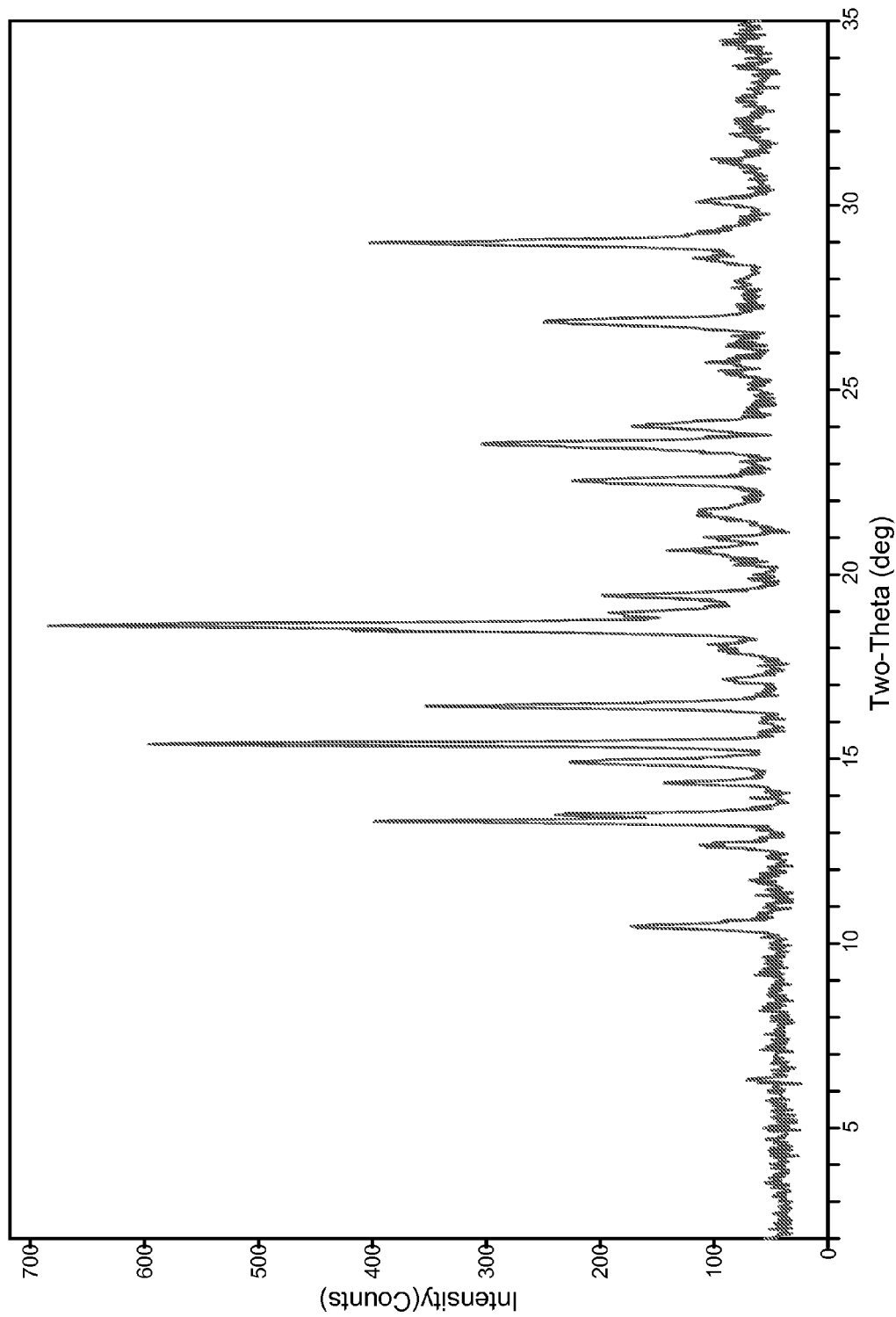
FIG. 43 shows an illustrative PXRD pattern for the pattern C hydrate of compound IB-L1-1.1.
Figure 44:
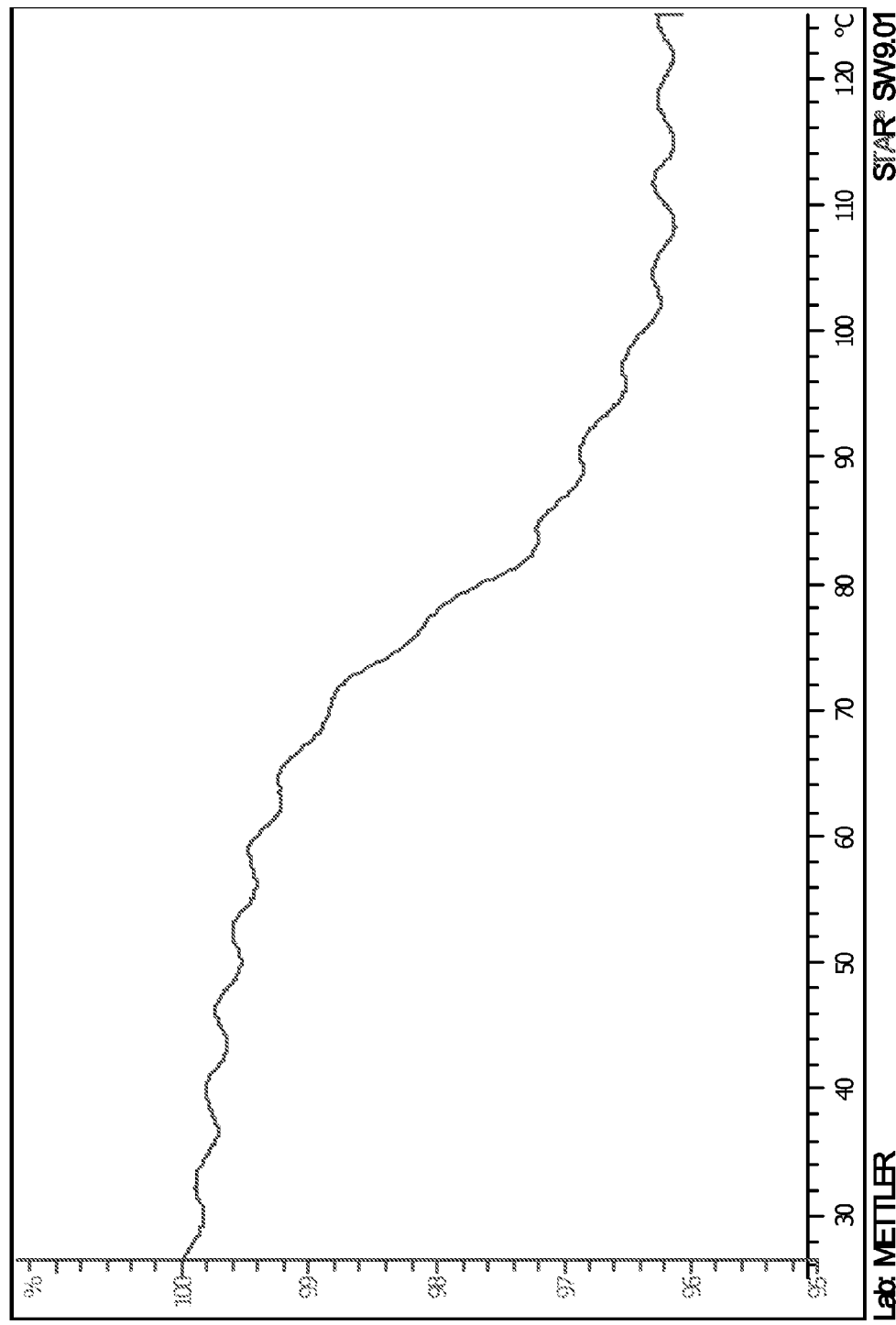
FIG. 44 shows an illustrative TGA profile of the pattern C hydrate of compound IB-L1-1.1.

In some embodiments, the pattern C hydrate has an X-ray powder diffraction pattern substantially as shown in FIG. 43. The 2θ values for the peaks in FIG. 43 (and their intensities) are as follows: 10.47 (21), 13.31 (56), 13.49 (31), 14.91 (28), 15.40 (86), 16.43 (48), 18.61 (100), 18.96 (20), 19.44 (19), 22.55 (26), 23.54 (39), 26.84 (29), and 28.99 (54).

This invention also relates, in part, to a process for preparing the pattern C hydrate by suspending pattern A polymorph (discussed above) in water. The recovered pattern C hydrate contains ~1 water molecules per molecule of compound IB-L1-1.1.

This invention also relates, in part, to a pattern D (E)-N-(4-(3-tert-butyl-5-(2,4-dioxo-3,4-dihydropyrimidin-1(2H)-yl)-2-methoxystyryl)phenyl)methanesulfonamide hydrate.

The crystallographic unit cell parameters of the pattern D hydrate salt have been determined to be as follows: a is 17.8 Å, b is 9.6 Å, and c is 27.0 Å (more precisely, a is 17.783(2)Å, b is 9.5651(12)Å, and c is 27.014(4)Å); the cell angle is:

β—93.3° (more precisely, β is 93.256(2)°; and the cell volume is 4588 Å$^3$ (more precisely, 4587.5(10)Å$^3$). The salt crystallizes in the C2/c space group.

In some embodiments, the pattern D hydrate has an X-ray powder diffraction pattern comprising one or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ. In some such embodiments, the pattern D hydrate has an X-ray powder diffraction pattern comprising three or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ. In other such embodiments, the pattern D hydrate has an X-ray powder diffraction pattern comprising five or more peaks selected from the group consisting of 6.6±0.2, 10.0±0.2, 10.5±0.2, 11.1±0.2, 11.6±0.2, 12.2±0.2, 14.2±0.2, 16.6±0.2, 17.1±0.2, 17.7±0.2, 18.5±0.2, 18.8±0.2, 19.3±0.2, 21.4±0.2, 22.7±0.2, 23.1±0.2, 23.6±0.2, 24.6±0.2, 25.2±0.2, 27.2±0.2, 29.1±0.2, and 31.0±0.2 degrees 2θ.

In some embodiments, the pattern D hydrate has an X-ray powder diffraction pattern comprising one or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ. In some such embodiments, the pattern D hydrate has an X-ray powder diffraction pattern comprising three or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ. In other such embodiments, the pattern D hydrate has an X-ray powder diffraction pattern comprising five or more peaks selected from the group consisting of 6.6±0.2, 10.0±0.2, 10.5±0.2, 11.1±0.2, 11.6±0.2, 12.2±0.2, 12.5±0.2, 14.2±0.2, 16.6±0.2, 17.1±0.2, 17.7±0.2, 18.5±0.2, 18.8±0.2, 19.3±0.2, 21.4±0.2, 22.7±0.2, 22.8±0.2, 23.1±0.2, 23.6±0.2, 24.6±0.2, 24.9±0.2, 25.2±0.2, 27.2±0.2, 29.1±0.2, and 31.0±0.2 degrees 2θ.

Figure 45:
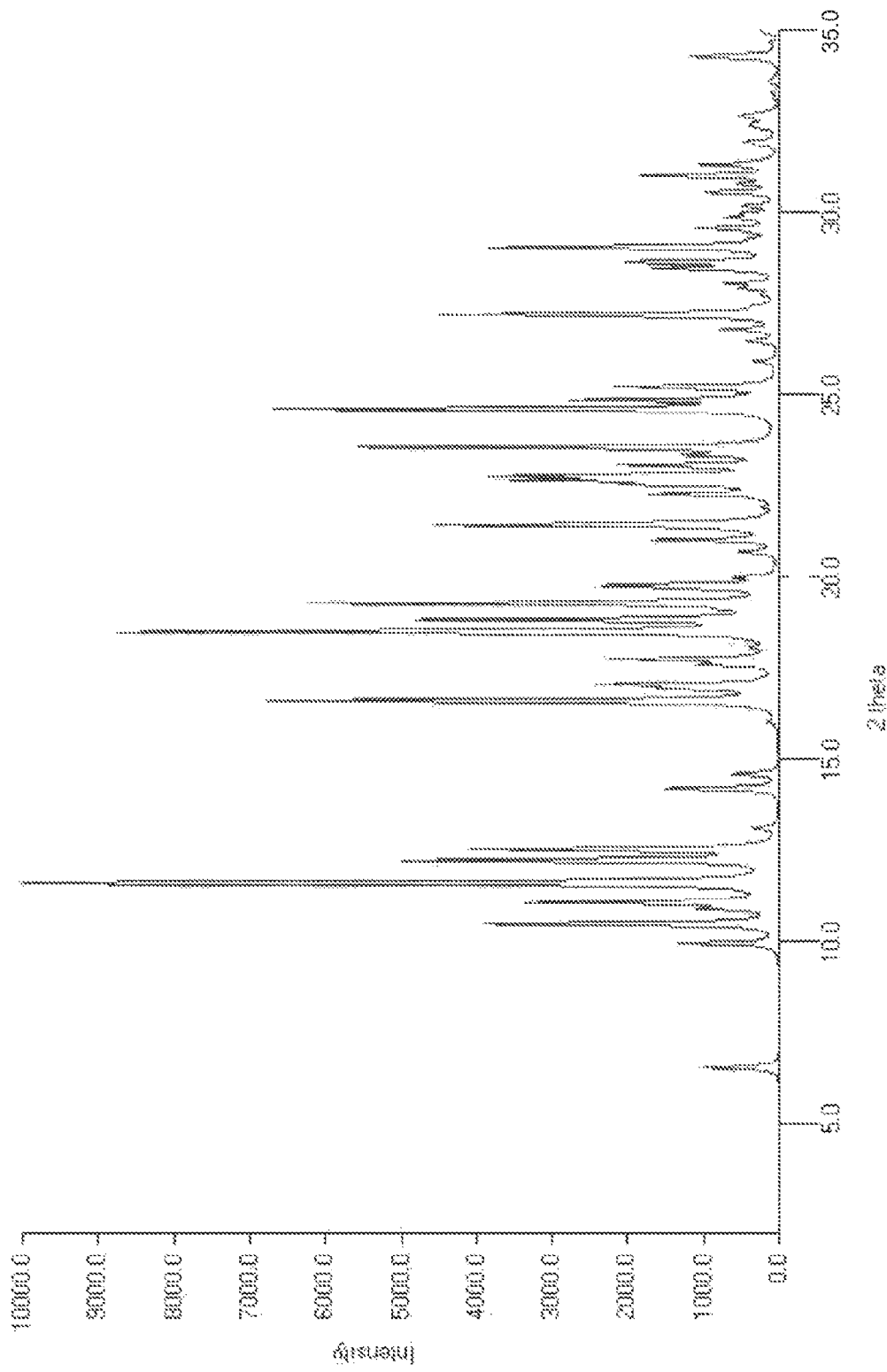
FIG. 45 shows an illustrative PXRD pattern for the pattern D hydrate of compound IB-L1-1.1.

In some embodiments, the pattern D hydrate has an X-ray powder diffraction pattern substantially as shown in FIG. 45. The 2θ values for the peaks in FIG. 45 (and their intensities) are as follows: 6.55 (10), 9.96 (12), 10.51 (37), 11.09 (31), 11.62 (100), 12.24 (44), 12.54 (40), 14.22 (15), 16.62 (68), 17.07 (22), 17.77 (21), 18.52 (82), 18.84 (47), 19.30 (63), 21.45 (34), 22.67 (30), 22.80 (34), 23.08 (20), 23.57 (58), 24.63 (73), 24.88 (26), 25.24 (21), 27.23 (36), 29.06 (41), and 31.04 (21).

This invention also relates, in part, to a process for preparing the pattern D hydrate. It was prepared by suspending pattern A polymorph (discussed above) in ethanol. Alternatively, it was prepared by suspending compound IB-L1-1.1 (103.03 mg) in 400 ul THF while heated to about 55° C. Aqueous NaOH (1M, 264 ul, 1.2 molar equivalent) was added. The solid dissolved completely to yield a clear solution. Ethanol (1.6 ml) was added to the solution. The solution was allowed to cool naturally to ambient temperatures. Crystals were formed during the slow evaporation process. Although it appears that the lattice can accommodate as much as 0.5 water molecules per molecule of compound IB-L1-1.1, the recovered pattern D hydrate contained ~0.2 water molecules per molecule of compound IB-L1-1.1.

This invention also relates, in part, to a pattern E (E)-N-(4-(3-tert-butyl-5-(2,4-dioxo-3,4-dihydropyrimidin-1(2H)-yl)-2-methoxystyryl)phenyl)methanesulfonamide hydrate.

The crystallographic unit cell parameters of the pattern E hydrate crystalline disodium salt have been determined to be as follows: a is 9.5 Å, b is 14.5 Å, and c is 17.3 Å (more precisely, a is 9.462(2)Å, b is 14.462(3)Å, and c is 17.281(4) Å); the cell angles are: α—84.9°, β—80.8°, and γ—81.8° (more precisely, α is 84.863(4)°, β is 80.760(4)°, and γ is 81.751(4)°; and the cell volume is 2304 Å$^3$ (more precisely, 2304.4(9)Å$^3$). The salt crystallizes in the P-1 space group.

In some embodiments, the pattern E hydrate has an X-ray powder diffraction pattern comprising one or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ. In some such embodiments, the pattern E hydrate has an X-ray powder diffraction pattern comprising three or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ. In other such embodiments, the pattern E hydrate has an X-ray powder diffraction pattern comprising five or more peaks selected from the group consisting of 6.2±0.2, 7.8±0.2, 10.2±0.2, 10.7±0.2, 12.1±0.2, 16.3±0.2, 19.7±0.2, 20.9±0.2, 21.8±0.2, 24.5±0.2, and 28.0±0.2 degrees 2θ.

In some embodiments, the pattern E hydrate has an X-ray powder diffraction pattern comprising one or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ. In some such embodiments, the pattern E hydrate has an X-ray powder diffraction pattern comprising three or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ. In other such embodiments, the pattern E hydrate has an X-ray powder diffraction pattern comprising five or more peaks selected from the group consisting of 6.2±0.2, 7.8±0.2, 10.2±0.2, 10.4±0.2, 10.7±0.2, 12.1±0.2, 16.3±0.2, 19.7±0.2, 20.9±0.2, 21.8±0.2, 24.5±0.2, and 28.0±0.2 degrees 2θ.

Figure 46:
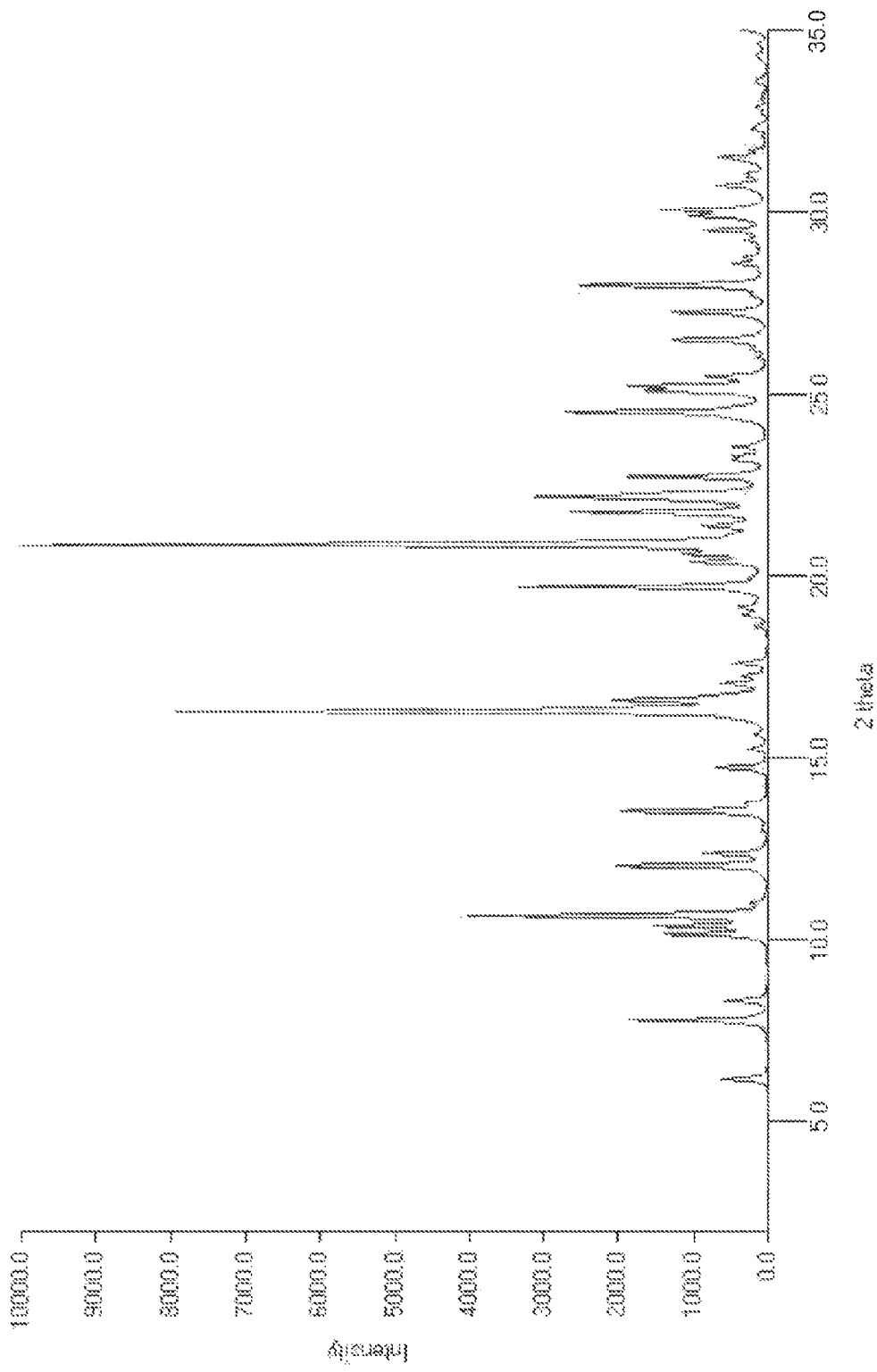
FIG. 46 shows an illustrative PXRD pattern for the pattern E hydrate of compound IB-L1-1.1.

In some embodiments, the pattern E hydrate has an X-ray powder diffraction pattern substantially as shown in FIG. 46. The 2θ values for the peaks in FIG. 46 (and their intensities) are as follows: 6.19 (6), 7.81 (18), 10.17 (13), 10.40 (14), 10.68 (39), 12.06 (20), 16.29 (78), 19.72 (32), 20.88 (100), 21.77 (27), 24.52 (25), and 28.01 (27).

This invention also relates, in part, to a process for preparing the pattern E hydrate. It was prepared by suspending compound IB-L1-1.1 (56.76 mg) in 200 ul THF while heated. Aqueous NaOH (1M, 146 uL, 1.2 molar equivalent) was added, which yielded a clear solution. Ethanol (800 ul) was added to the solution. The solution was allowed to cool naturally to ambient temperatures. Crystals were formed during the slow evaporation process. Although it appears that the lattice can accommodate as much as one water molecule per molecule of compound IB-L1-1.1, the recovered pattern D hydrate contained ~0.25 water molecules per molecule of compound IB-L1-1.1.

H. COMPOSITIONS

This invention also is directed, in part, to compositions comprising one or more compounds and/or salts of the invention (including the crystalline compounds and salts discussed in section G above). In some embodiments, the compositions comprise one or more substantially phase pure crystalline forms (compounds/salts/solvates/hydrates) discussed in section G above. The compositions can be pharmaceutical compositions.

In some embodiments, the compositions further comprise one or more additional therapeutic agents. Such therapeutic agents can, but need not be, additional HCV inhibitors.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

Applicants have discovered that some I-L1 compounds in which $R^6$ and the phenyluracil are in trans-position relative to the double bond, when in solution, tend to convert into the corresponding cis-isomer upon exposure to light; thus, it may be desirable to store such solutions under conditions that reduce exposure to light (e.g., in an amber bottle or in a dark place).

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

I. KITS

This invention also is directed, in part, to a kit comprising one or more compounds and/or salts of the in invention. The kit can optionally contain one or more additional therapeutic agents and/or instructions for, for example, using the kit.

J. METHODS OF USE

This invention also is directed, in part, to a method for inhibiting replication of an RNA virus. The method comprises exposing the virus to one or more compounds and/or salts of this invention. In some embodiments, replication of the RNA virus is inhibited in vitro. In other embodiments, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV.

This invention also is directed, in part, to a method for inhibiting HCV RNA polymerase. The method comprises exposing the polymerase with one or more compounds and/or salts of this invention. In some embodiments, HCV RNA polymerase activity is inhibited in vitro. In other embodiments, HCV RNA polymerase activity is inhibited in vivo.

The term "inhibiting" means reducing the level of RNA virus replication/HCV polymerase activity either in vitro or in vivo. For example, if a compound/salt of the invention reduces the level of RNA virus replication by at least about 10% compared to the level of RNA virus replication before the virus was exposed to the compound/salt, then the compound/salt inhibits RNA virus replication. In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV RNA polymerase. Thus, this invention also is directed, in part, to a method for treating hepatitis C in an animal in need of such treatment. These methods comprise administering to the animal one or more compounds and/or salts of the invention, and, optionally, one or more additional therapeutic agents. In some embodiments, a therapeutically effective amount of the compound(s) and/or salt(s) is administered to the animal. "Treating" means ameliorating, suppressing, eradicating, preventing, reducing the risk of, and/or delaying the onset of the disease being treated. Applicants specifically intend that the term "treating" encompass administration of the compounds and/or salts of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the compound(s) and/or salt(s) of the invention is/are co-administered with a second (or even a third, fourth, etc.) compound, such as, for example, another therapeutic agent used to treat hepatitis C (e.g., interferon or interferon/ribavirin combination, or an HCV inhibitor such as, for example, an HCV polymerase inhibitr or an HCV protease inhibitor). The compound(s) and/or salt(s) of this invention can also be co-administered with therapeutic agents other than therapeutic agents used to treat hepatitis C (e.g., anti-HIV agents). In these co-administration embodiments, the compound(s) and/or salt(s) of the invention and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

This invention also is directed, in part, to a use of one or more compounds and/or salts of the invention, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This invention also is directed, in part, to one or more compounds and/or salts of the invention, and, optionally one or more additional therapeutic agents, for use as a medicament. In some embodiments, the medicament is for inhibiting replication of an RNA virus. In other embodiments, the medicament is for treating hepatitis C.

K. INTERMEDIATE COMPOUNDS

This invention also is directed, in part, to intermediates that correspond in structure to formula II that can be used to prepare the compounds of formula I (and their salts) (although some intermediates can also be used, just like the compounds of formula I, as HCV inhibitors, and one skilled in the art can determine such ability of the compounds of formula II by utilizing, for example, the methods discussed below):

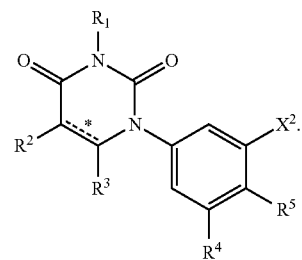

(II)

In formula II:

$\stackrel{*}{=\!=\!=}$, $R^1$, $R^2$, $R^3$, $R^4$, and $R^5$ are as discussed above for the compounds of formula I; and $X^2$ is halo.

The various embodiments for $\stackrel{*}{=\!=\!=}$, $R^1$, $R^2$, $R^3$, $R^4$, and $R^5$ (as well as their combinations) discussed above apply to the compounds of formula II. As to $X^2$, in some embodiments, $X^2$ is selected from the group consisting of chloro, bromo, and iodo. In other embodiments, $X^2$ is selected from the group consisting of chloro and bromo. In yet other embodiments, $X^2$ is selected from the group consisting of chloro and iodo. In yet other embodiments, $X^2$ is selected from the group consisting of iodo and bromo. In further embodiments, $X^2$ is fluoro. In yet further embodiments, $X^2$ is chloro. In yet further embodiments, $X^2$ is bromo. And in yet further embodiments, $X^2$ is iodo.

The various embodiments for $\stackrel{*}{=\!=\!=}$, $R^1$, $R^2$, $R^3$, $R^4$, $R^5$, and $X^2$ discussed above can be combined to form various embodiments of compounds of formula II, and all embodiments of compounds of formula II so formed are within the scope of Applicants' invention. Some exemplary embodiments of the compounds (and salts thereof) of formula II are discussed below.

In some embodiments, the compounds of formula II correspond in structure to formula IIA:

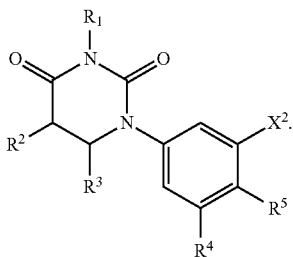

(IIA)

In other embodiments, the compounds of formula II correspond in structure to formula IIB:

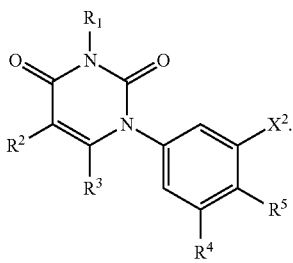

(IIB)

In some embodiments of the compounds of formula II:

$R^1$ is selected from the group consisting of hydrogen, methyl, and nitrogen-protecting group;

$R^2$ is selected from the group consisting of hydrogen and halo;

$R^3$ is selected from the group consisting of hydrogen and halo;

$R^4$ is selected from the group consisting of $C_1$-$C_4$-alkyl, $C_3$-$C_6$-carbocyclyl, and 5-6-membered heterocyclyl, wherein:

(a) the $C_1$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino;

$R^5$ is selected from the group consisting of hydrogen, hydroxy, alkyloxy, and halo; and $X^2$ is selected from the group consisting of chloro, bromo, and iodo.

In some embodiments of the compounds of formula II:

⸺*⸺ is a double carbon-carbon bond;

$R^1$ is hydrogen;

$R^2$ is selected from the group consisting of hydrogen and halo;

$R^3$ is hydrogen;

$R^4$ is tert-butyl;

$R^5$ is selected from the group consisting of hydrogen, hydroxy, and methoxy; and $X^2$ is selected from the group consisting of bromo and iodo.

In some embodiments of the compounds of formula II:

$R^1$ is selected from the group consisting of hydrogen and methyl;

$R^2$ is selected from the group consisting of hydrogen and methyl;

$R^3$ is selected from the group consisting of hydrogen and methyl;

$R^4$ is tert-butyl;

$R^5$ is selected from the group consisting of hydroxy and methoxy; and $X^2$ is selected from the group consisting of chloro, bromo, and iodo.

In some embodiments of the compounds of formula II:

⸺*⸺ is a double carbon-carbon bond;

$R^2$ is hydrogen;

$R^2$ is hydrogen;

$R^3$ is hydrogen;

$R^4$ is tert-butyl;

$R^5$ is selected from the group consisting of hydroxy and methoxy; and $X^2$ is selected from the group consisting of chloro, bromo, and iodo.

In some embodiments, the compound of formula II is selected from the group consisting of

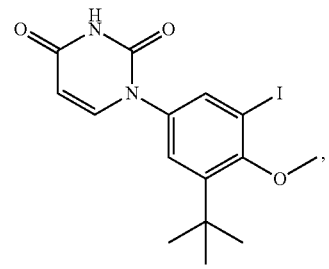

(II-I)

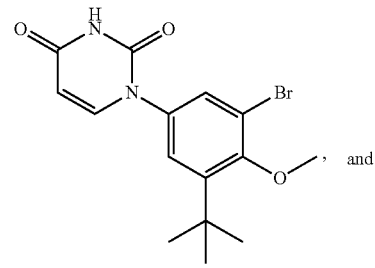

(II-Br)

, and

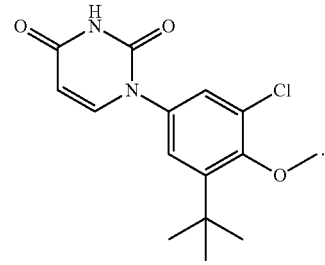

(II-Cl)

.

The discussion below provides instructions for the preparation of intermediate compounds of formula II (and salts thereof).

L. STARTING COMPOUNDS

This invention also is directed, in part, to starting compounds that correspond in structure to formula III that can be used to prepare the compounds of formulas II and I (and their salts):

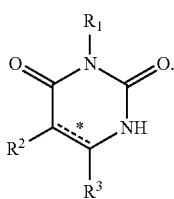

(III)

In formula III, $=\!\!\overset{*}{=}\!\!=$, $R^1$, $R^2$, and $R^3$ are as discussed above for the compounds of formula I and II. The various embodiments for $=\!\!\overset{*}{=}\!\!=$, $R^1$, $R^2$, and $R^3$ (as well as their combinations) discussed above apply to the compounds of formula III. The various embodiments for $=\!\!\overset{*}{=}\!\!=$, $R^1$, $R^2$, and $R^3$ discussed above can be combined to form various embodiments of compounds of formula III, and all embodiments of compounds of formula III so formed are within the scope of Applicants' invention. Some exemplary embodiments of the compounds (and salts thereof) of formula III are discussed below.

In some embodiments of the compounds of formula III:

$R^1$ is selected from the group consisting of hydrogen, methyl, and nitrogen-protecting group;

$R^2$ is selected from the group consisting of hydrogen and halo; and $R^3$ is selected from the group consisting of hydrogen and halo.

In some embodiments of the compounds of formula III:

$=\!\!\overset{*}{=}\!\!=$ is a double carbon-carbon bond;

$R^1$ is selected from the group consisting of hydrogen;

$R^2$ is selected from the group consisting of hydrogen and halo; and $R^3$ is selected from the group consisting of hydrogen.

In some embodiments of the compounds of formula III:

$R^1$ is selected from the group consisting of hydrogen and methyl;

$R^2$ is selected from the group consisting of hydrogen and methyl; and $R^3$ is selected from the group consisting of hydrogen and methyl.

In some embodiments, the compound of formula III is uracil.

This invention also is directed, in part, to starting compounds that correspond in structure to formula IV that can be used to prepare the compounds of formulas II and I (and their salts):

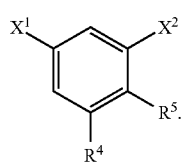

(IV)

In formula IV:

$R^4$, $R^5$, and $X^2$ are as discussed above for the compounds of formula I and II; and $X^1$ is halo.

The various embodiments for $R^4$, $R^5$, and $X^2$ (as well as their combinations) discussed above apply to the compounds of formula IV. As to $X^1$, in some embodiments, $X^1$ is selected from the group consisting of chloro, bromo, and iodo. In other embodiments, $X^1$ is selected from the group consisting of chloro and bromo. In yet other embodiments, $X^1$ is selected from the group consisting of chloro and iodo. In yet other embodiments, $X^1$ is selected from the group consisting of iodo and bromo. In further embodiments, $X^1$ is fluoro. In yet further embodiments, $X^1$ is chloro. In yet further embodiments, $X^1$ is bromo. And in yet further embodiments, $X^1$ is iodo. As to $X^1$ and $X^2$, in some embodiments, $X^1$ and $X^2$ are identical.

The various embodiments for $R^4$, $R^5$, $X^1$, and $X^2$ discussed above can be combined to form various embodiments of compounds of formula IV, and all embodiments of compounds of formula III so formed are within the scope of Applicants' invention. Some exemplary embodiments of the compounds (and salts thereof) of formula IV are discussed below.

In some embodiments of the compounds of formula IV:

$R^4$ is selected from the group consisting of $C_1$-$C_4$-alkyl, $C_3$-$C_6$-carbocyclyl, and 5-6-membered heterocyclyl, wherein:

(a) the $C_1$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino;

$R^5$ is selected from the group consisting of hydrogen, hydroxy, and alkyloxy;

$X^1$ is selected from the group consisting of chloro, bromo, and iodo; and $X^2$ is selected from the group consisting of chloro, bromo, and iodo.

In some embodiments of the compounds of formula IV:

$R^4$ is selected from the group consisting of tert-butyl;

$R^5$ is selected from the group consisting of hydrogen, hydroxy, and methoxy;

$X^1$ is selected from the group consisting of bromo and iodo; and $X^2$ is selected from the group consisting of bromo and iodo.

In some embodiments of the compounds of formula IV:

$R^4$ is selected from the group consisting of tert-butyl;

$R^5$ is selected from the group consisting of hydroxy and methoxy;

$X^1$ is selected from the group consisting of chloro, bromo, and iodo; and $X^2$ is selected from the group consisting of chloro, bromo, and iodo.

In some embodiments of the compounds of formula IV:

$R^4$ is tert-butyl;

$R^5$ is selected from the group consisting of hydroxy and methoxy;

$X^1$ is selected from the group consisting of chloro, bromo, and iodo; and $X^2$ is selected from the group consisting of chloro, bromo, and iodo.

In some embodiments, the compound of formula IV is selected from the group consisting of

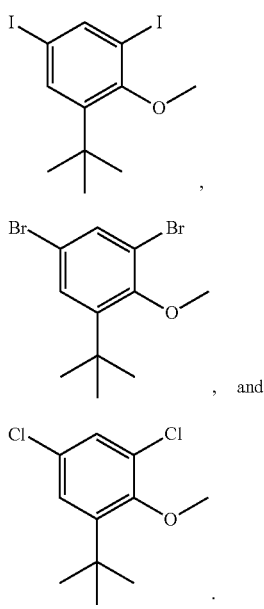

(IV-1)

(IV-Br)

, and (IV-Cl)

The discussion below provides instructions for the preparation of starting compounds of formula IV (and salts thereof).

L. METHODS FOR PREPARATION

This invention also is directed, in part, to a process for preparing compounds of formula II. The process comprises reacting a compound of formula III with a compound of formula IV in the presence of (i) copper (I) salt catalyst and (ii) nitrogenous heteroaryl ligand:

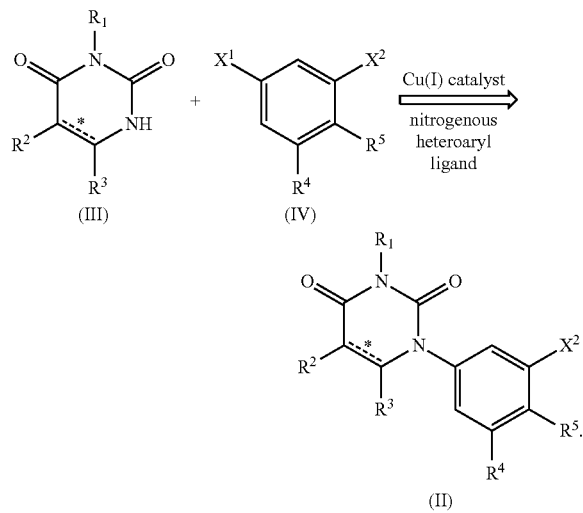

In the above process, $R^1$, $R^2$, $R^3$, $R^4$, $R^5$, $X^1$, and $X^2$ are as discussed above.

Applicants have discovered that the process generally results in the substitution of the N1 hydrogen of uracil derivative compound III thus resulting in intermediate compound II. When $X^2$ in intermediate compound II is chloro, bromo, or iodo, then compound II is suitable for subsequent reaction (e.g., Suzuki coupling with an appropriate boronic acid or boronate ester) to provide compound of formula I. In other words, when $X^2$ in intermediate compound II is chloro, bromo, or iodo, the above process is suitable for preparing compounds of formula I as well.

In some embodiments, compound III is uracil, and compound IV corresponds in structure to a compound selected from the group consisting of compound IV-I, IV-Br, and IV-Cl, with compounds IV-I and IV-Br typically resulting in better yield than compound IV-Cl.

Suitable Cu(I) catalysts include, for example, CuI, CuBr, CuCl, $Cu_2O$, and $CH_3C(O)OCu$. In some embodiments, the catalyst is selected from the group consisting of CuI and CuBr. In some such embodiments, the catalyst is CuI. In other such embodiments, the catalyst is CuBr.

In some embodiments, the process is conducted in the presence of a base. In some such embodiments, the base is an inorganic base. Suitable inorganic bases include, for example, potassium, sodium, and cesium salts (e.g., $K_2CO_3$, $K_3PO_4$, $Cs_2CO_3$, $Na_2CO_3$). In some embodiments, the base is selected from the group consisting of potassium salt and cesium salt. In some such embodiments, the salt is selected from the group consisting of $K_3PO_4$ and $Cs_2CO_3$. In some embodiments, the base comprises a potassium salt. In some such embodiments, the potassium salt is $K_2CO_3$. In other such embodiments, the potassium salt is $K_3PO_4$. In some embodiments, the base comprises a cesium salt. In some such embodiments, the potassium salt is $Cs_2CO_3$.

Typically, the process is conducted in the presence of a solvent. Suitable solvents include, for example, dimethylsulfoxide (DMSO), dimethylformamide (DMF), and acetonitrile (MeCN). In some embodiments, the solvent is DMSO.

Typically, the process is conducted at a temperature of from about 40 to about 130° C.

In some embodiments, the nitrogenous heteroaryl ligand comprises 8-hydroxyquinoline. In other embodiments, the ligand comprises 2-(2-pyridyl)-benzimidazole. In yet other embodiments, the ligand comprises a picolinamide compound corresponding in structure to formula V:

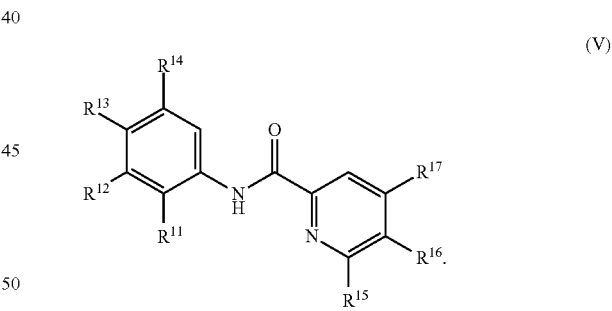

In formula V, $R^{11}$, $R^{12}$, $R^{13}$, $R^{14}$, $R^{15}$, $R^{16}$, and $R^{17}$ are independently selected from the group consisting of hydrogen, $C_{1-4}$-perfluoroalkyl, $C_{1-4}$-alkyloxy, $C_{1-4}$-haloalkyl, chloro, or cyano. In some embodiments, $R^{11}$, $R^{12}$, $R^{13}$, $R^{14}$, $R^{15}$, $R^{16}$, and $R^{17}$ are independently selected from the group consisting of hydrogen, methyl, methoxy, trifluoromethyl, chloro, and cyano. In some embodiments, the ligand of formula V comprises N-(4-cyanophenyl)picolinamide. In other embodiments, the ligand of formula V comprises N-(2-cyanophenyl)picolinamide.

In some embodiments, the process comprises (a) preparing a compound of formula IV; and (b) reacting a compound of formula III with a compound of formula IV in the presence of (i) copper (I) salt catalyst and (ii) nitrogenous heteroaryl ligand, optionally in the presence of inorganic base.

Compound of formula IV-I can be prepared by, for example, converting 2-tert-butylphenol into 2-tert-butyl-4,6-diiodophenol (by, for example, reacting it with NaI and NaOCl), and then converting the 2-tert-butyl-4,6-diiodophenol into 1-tert-butyl-3,5-diiodo-2-methoxybenzene (by, for example, treating it with CH$_3$I in the presence of a base, such as, for example, NaOH).
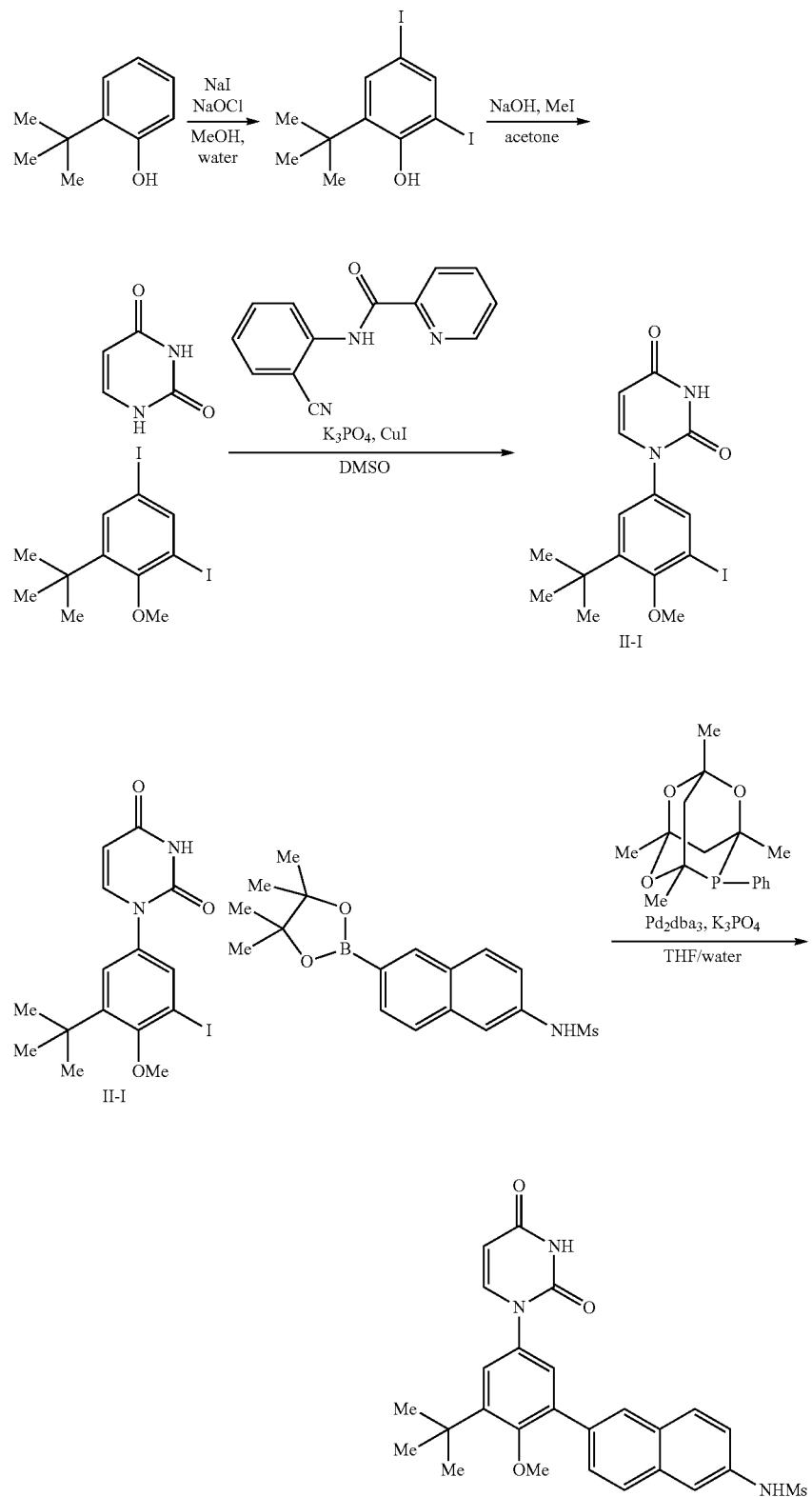

Compound of formula IV-Br can be prepared by, for example, converting 2-tert-butylphenol into 2,4-dibromo-6-tert-butylphenol (by, for example, reacting it with 1,3-dibromo-5,5-dimethylimidazolidine-2,4-dione), and then converting the 2,4-dibromo-6-tert-butylphenol into 1,5-dibromo-3-tert-butyl-2-methoxybenzene (by, for example, treating it with $CH_3I$ in the presence of KOtBu).

Additional information about the preparation of compounds of formulas I and II (and their salts) is provided in the general discussion and/or specific synthesis examples below. In the discussion below, $R^1$, $R^2$, $R^3$, $R^4$, $R^5$, L, $R^A$, $R^B$, $R^C$, $R^D$, $R^6$, $R^E$, $R^F$, $R^G$, $R^H$, $R^I$, $R^J$, $R^K$, $X^1$, and $X^2$ have the meaning discussed above unless otherwise stated.

35° C. over about 1 to about 5 h to provide compound (1-2). Compound (1-2) may then be reduced using conditions known to those skilled in the art to furnish the corresponding aniline (1-3). Typical conditions for this reduction include using hydrogen at a pressure of about 1 to about 5 atmospheres in the presence of a catalyst such as, for example, palladium or platinum on charcoal in a solvent such as, for example, tetrahydrofuran, ethyl acetate, ethanol, or hexane at or near ambient temperature over a period of about 1 to about 12 h. Dependent on the functional groups present, an alternative reduction procedure may be more appropriate such as, for example, using iron powder in the presence of a mild acid such as, for example, ammonium chloride or dilute hydro-

SCHEME 1

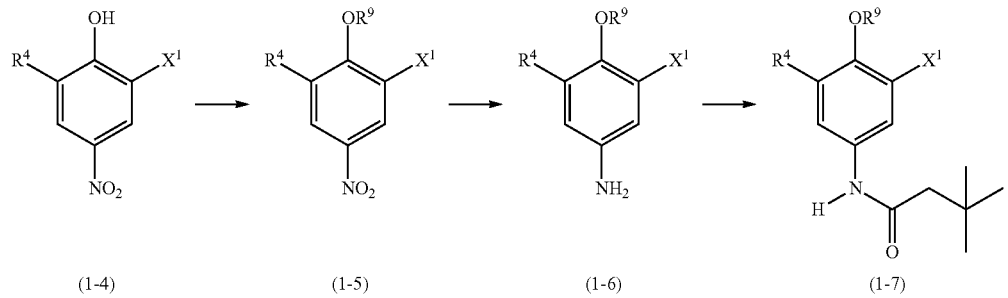

(1-4)　　(1-5)　　(1-6)　　(1-7)

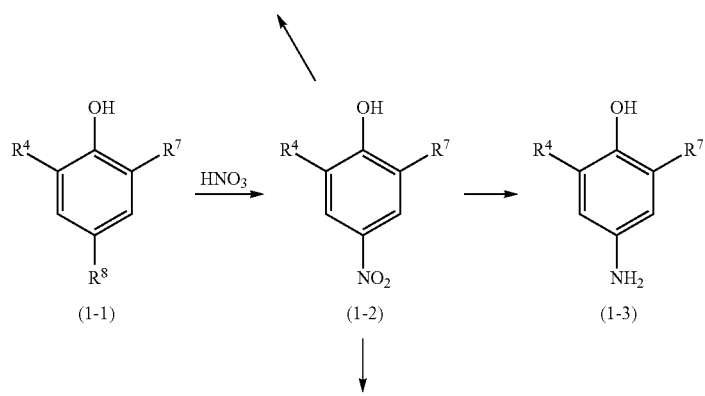

(1-1)　　(1-2)　　(1-3)

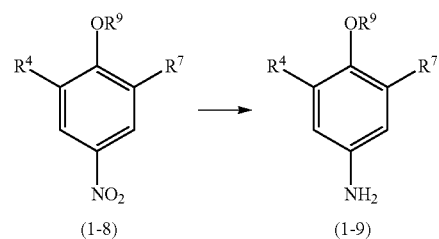

(1-8)　　(1-9)

Compound (1-1), wherein $R^7$ is, for example, hydrogen or —$CO_2Me$, and $R^8$ is, for example, hydrogen or t-butyl, may be treated with nitric acid in solvents such as, for example, acetic acid or water in a temperature range of about 0 to about chloric acid at reflux temperatures in a mixture of solvents containing, for example, methanol, water, and/or tetrahydrofuran over about 1 to about 12 h. Another set of reduction conditions includes the use of sodium borohydride in a solvent mixture such as, for example, water and tetrahydrofuran. Yet another set of reduction conditions includes the use of tin(II) chloride in the presence of hydrochloric acid in such solvents as, for example, water and methanol or mixtures thereof.

Compound (1-2) may be modified prior to reduction. For example, treatment of compound (1-2), wherein $R^7$ is hydrogen, with iodine monochloride in a mixture of methanol and water at or near ambient temperature over a period of about 8 to about 24 h supplies compound (1-4), wherein $X^1$ is iodine. Alternatively, compound (1-2) can be treated with pyridinium hydrobromide perbromide in a solvent such as, for example, acetic acid at or near ambient temperature over a period of about 2 to about 16 h to provide compound (1-4), wherein $X^1$ is bromine Modifications may be introduced at the phenol moiety in compound (1-4). For example, the phenol may be alkylated with alkyl halides (e.g., methyl iodide), alkyl sulfates (e.g., methyl sulfate), alkenyl halides (e.g., allyl bromide), alkynyl halides (e.g., propargyl bromide) in the presence of a base such as, for example, potassium carbonate in acetone, sodium hydride in dimethylformamide, or potassium t-butoxide in tetrahydrofuran, at temperatures from about 0 to about 35° C. over a period of about 1 to about 24 h to provide compound (1-5), wherein $R^9$ is, for example, alkyl, alkenyl, or alkynyl. Alternatively, alkylation may be achieved by using a reagent such as (trimethylsilyl) diazomethane in solvents such as, for example, methanol or t-butyl methyl ether, or mixtures thereof in a sealed tube at or near room temperature over about 8 to about 24 h. Compound (1-5) may subsequently be reduced to compound (1-6) using the iron powder or tin(II) chloride conditions described above. An alternative reduction procedure employs hydrogenation at approximately 1 atmosphere pressure with a catalyst such as 5% platinum on sulfided carbon in a solvent such as methanol. Protection of the resultant aniline of compound (1-6) with, for example, a t-butyl carbamate can be achieved by treatment with di-tert-butyl dicarbonate in a solvent such as, for example, tetrahydrofuran or dioxane at a temperature of about 50 to about 65° C. for about 1 to about 8 h provides compound (1-7).

Modifications may also occur at the phenol moiety in compound (1-2). One skilled in the art may alkylate the phenol of compound (1-2) using, for example, the conditions described above to obtain compound (1-8). Compound (1-8) is transformed into compound (1-9) using, for example, one or more of the appropriate reduction conditions described above.

Another modification of the phenol group in compound (1-2) is sulfonylation to furnish compound (1-8), wherein $R^9$ is alkylsulfonyl, carbocyclylsulfonyl, or haloalkylsulfonyl. Such a compound may be prepared by exposing compound (1-2) to sulfonyl chlorides such as, for example, methanesulfonyl chloride, cyclohexanesulfonyl chloride, benzenesulfonyl chloride, or 3-chloropropane sulfonyl chloride in the presence of a base such as, for example, triethylamine, diisopropylethylamine, or pyridine in a solvent such as, for example, dichloromethane at or near ambient temperature for a period of about 1 to about 24 h. One skilled in the art can then transform compound (1-8) into compound (1-9) with an appropriate set of reduction conditions.

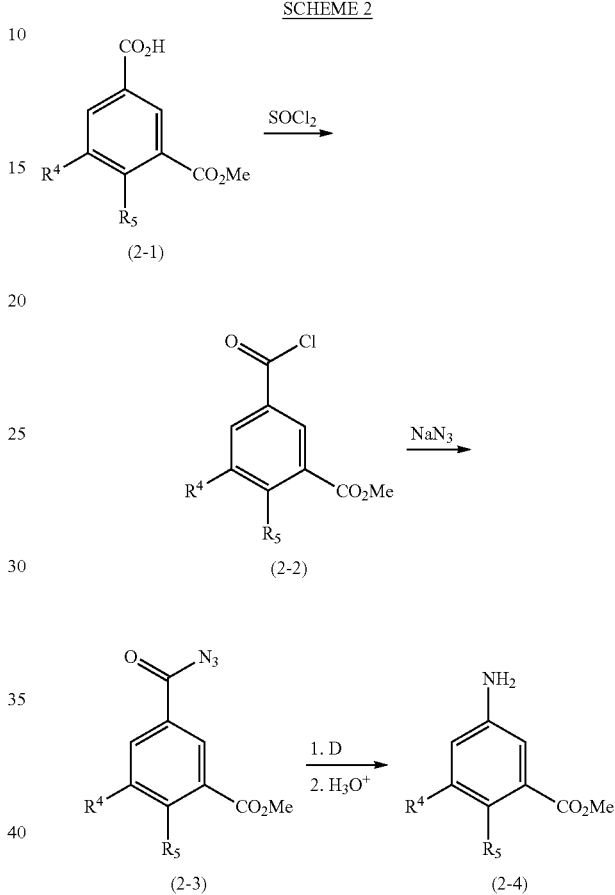

Aniline (2-4) can be prepared through use of the Curtius rearrangement. To this end, compound (2-1), wherein $R^4$ is not amino, can be treated in refluxing thionyl chloride with a catalytic amount of dimethylformamide for about 1 to about 4 h to obtain acid chloride (2-2). Treatment with thionyl chloride at the reflux temperature in solvents such as, for example, chloroform or toluene also furnishes compound (2-2). Compound (2-2) can be reacted with an aqueous solution of sodium azide in a solvent such as, for example, acetone over about 1 to about 8 h to provide acyl azide (2-3). Compound (2-3) can then undergo a Curtius rearrangement in refluxing solvents such as dioxane or toluene. The intermediate isocyanate is hydrolyzed with an aqueous acid such as dilute hydrochloric acid in a solvent such as dimethoxyethane to provide compound (2-4).

SCHEME 3

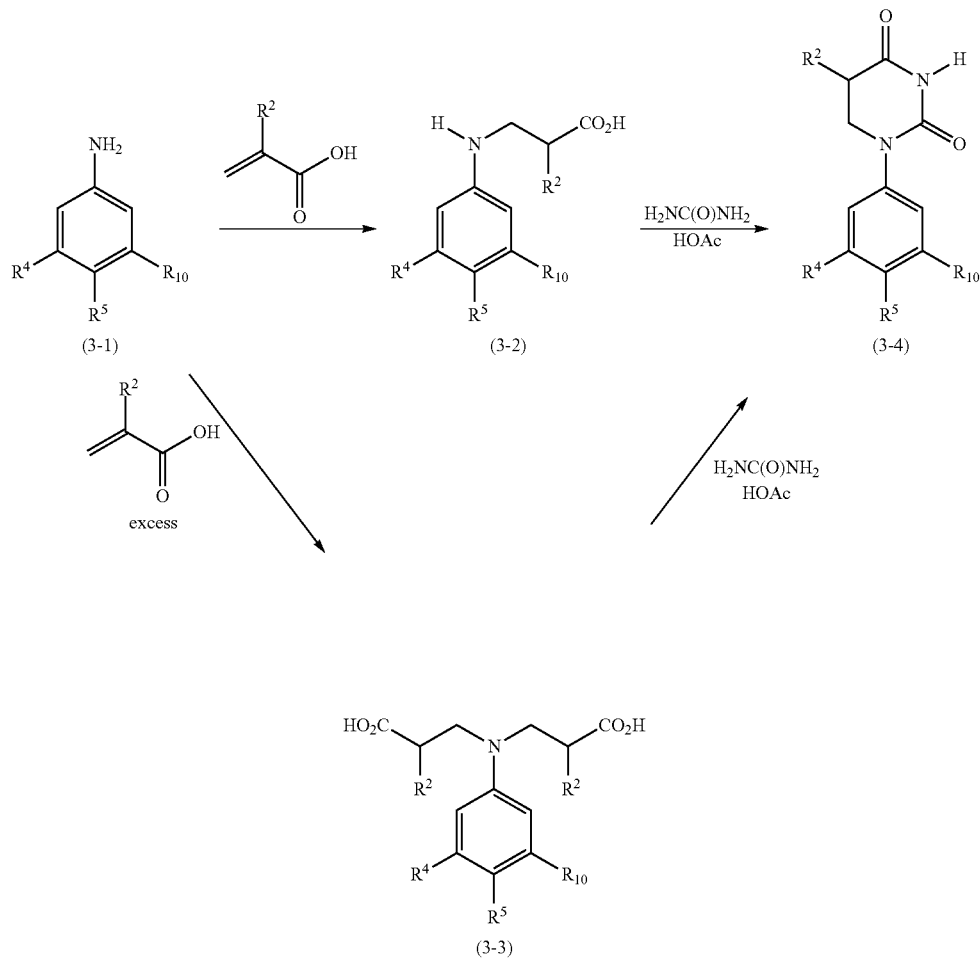

Compound (3-1), wherein $R^{10}$ is, for example, hydrogen, bromine, iodine, or —$CO_2Me$, can be treated with an acrylic acid either neat at or near ambient temperature in a solvent such as, for example, toluene and heated to reflux over a period of about 15 to about 48 h to supply compound (3-2). When excess of an acrylic acid is used, compound (3-3) is produced. Compound (3-2) or (3-3) can be treated with urea in a solvent such as, for example, acetic acid at about 100 to about 120° C. over about 2 to about 48 h to supply compound (3-4).

SCHEME 4

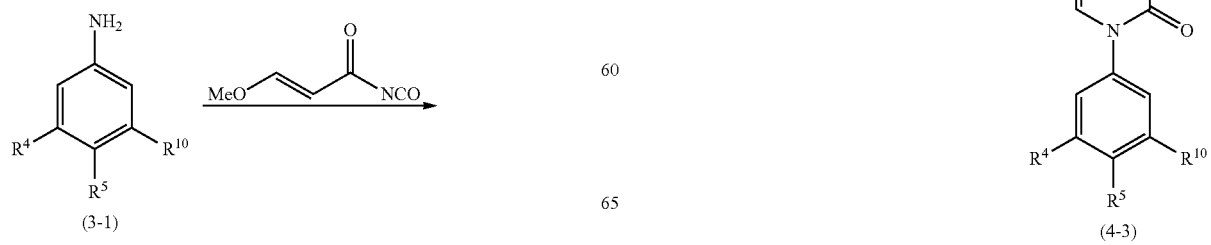

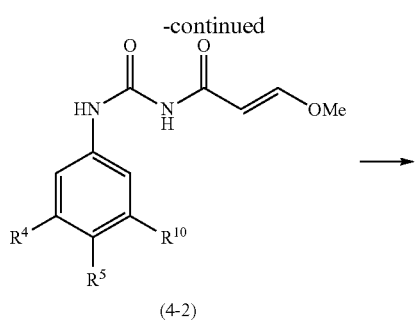

Compound (4-2) can be prepared from compound (3-1) dissolved in solvents such as, for example, dimethylformamide or dimethylacetamide by the addition of a benzene solution of (E)-3-methoxyacryloyl isocyanate (prepared as described by Santana, L.; et al. J. Heterocyclic Chem. 1999, 36, 293-295.) at a temperature of about −40 to about −15° C. under an inert atmosphere and then warming to ambient temperature for from about 30 min to about 4 h. Compound (4-2) can be treated with an acid such as, for example, sulfuric acid in mixtures of water and ethanol in a temperature range of from about 90 to about 110° C. for about 1 to about 8 h to supply compound (4-3). Alternatively, compound (4-2) can be cyclized to uracil (4-3) under the basic conditions described by Ueno, Y.; et al. J. Org. Chem. 70:7925-7935 (2005).

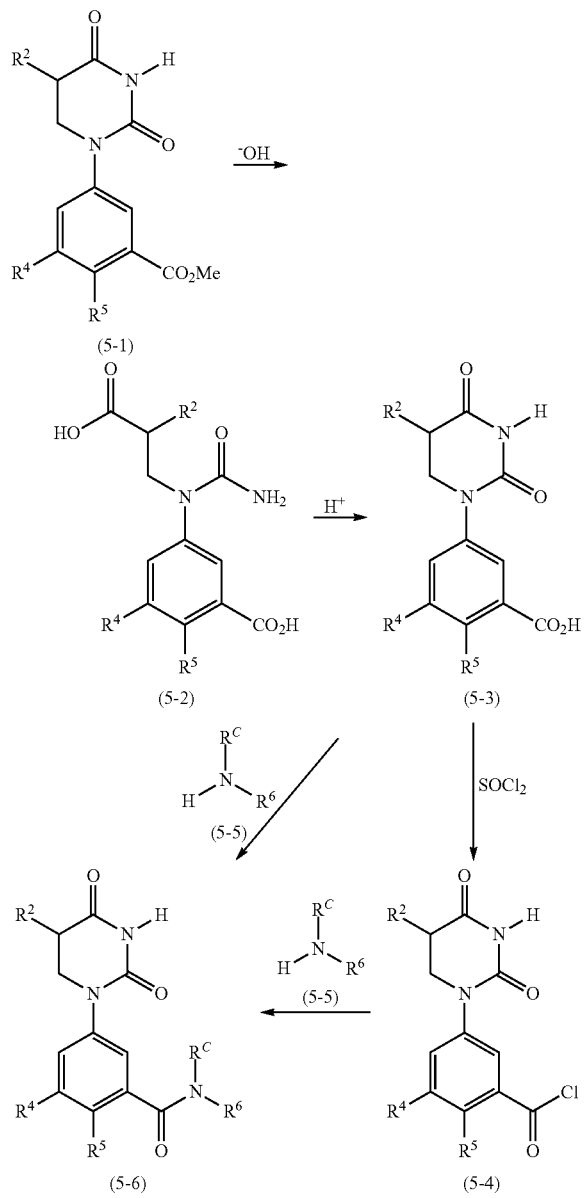

SCHEME 5

Compound (5-1) can be hydrolyzed with a base such as, for example, sodium hydroxide, lithium hydroxide, or potassium hydroxide in a solvent such as, for example, methanol, ethanol, or tetrahydrofuran, or mixtures thereof. The resultant reaction mixture can be stirred for a period of about 6 to about 48 h at ambient temperature. Acidification with a dilute aqueous acid supplies compound (5-2) where the ester has been hydrolyzed and the tetrahyrdopyrimidine ring opened.

Cyclization of compound (5-2) to compound (5-3) can be accomplished by treatment with a strong acid such as, for example, concentrated hydrochloric acid in a temperature range of about 90 to about 120° C. over a period of about 1 to about 3 h. Compound (5-3) can be treated in refluxing thionyl chloride, with or without a catalytic amount of dimethylformamide, for about 1 to about 4 h to deliver acid chloride (5-4). Treatment with thionyl chloride at the reflux temperature in solvents such as, for example, chloroform or toluene also furnishes compound (5-4).

Compound (5-4) can be treated with an amine or the corresponding salt (5-5) in solvents such as, for example, dioxane, dimethylformamide, dimethylacetamide, or dichloromethane optionally in the presence of a base such as, for example, pyridine, triethylamine, or diisopropylethylamine at temperatures ranging from at or near ambient to about 100° C. for between about 1 and about 24 h to provide compound (5-6).

Alternatively, compound (5-3) can be converted directly to compound (5-6) by reacting with an equimolar amount of amine (5-5) with a coupling reagent such as, for example, bis(2-oxo-3-oxazolidinyl)phosphinic chloride (BOPCl), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU) along with a coupling auxiliary such as, for example, 1-Hydroxy-7-azabenzotriazole (HOAT) or 1-hydroxybenzotriazole hydrate (HOBT) in the presence or absence of a base such as, for example, N-methyl morpholine, diisopropylethylamine in solvents such as, for example, tetrahydrofuran, N,N-dimethylacetamide, N,N-dimethylformamide, pyridine, and chloroform. Typical reactions can be carried out at between about 0 to about 65° C. or may be carried out in a microwave reactor to facilitate coupling.

SCHEME 6

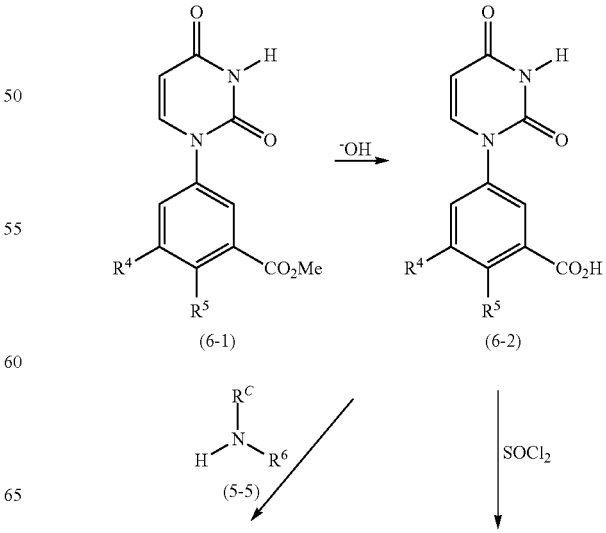

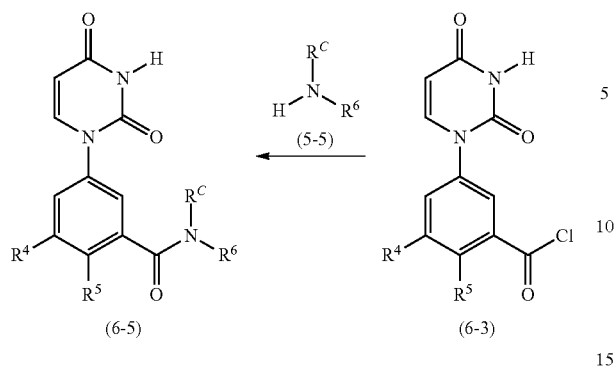

Compound (6-1) can be converted to compound (6-5) using the transformations described in Scheme 5 above.

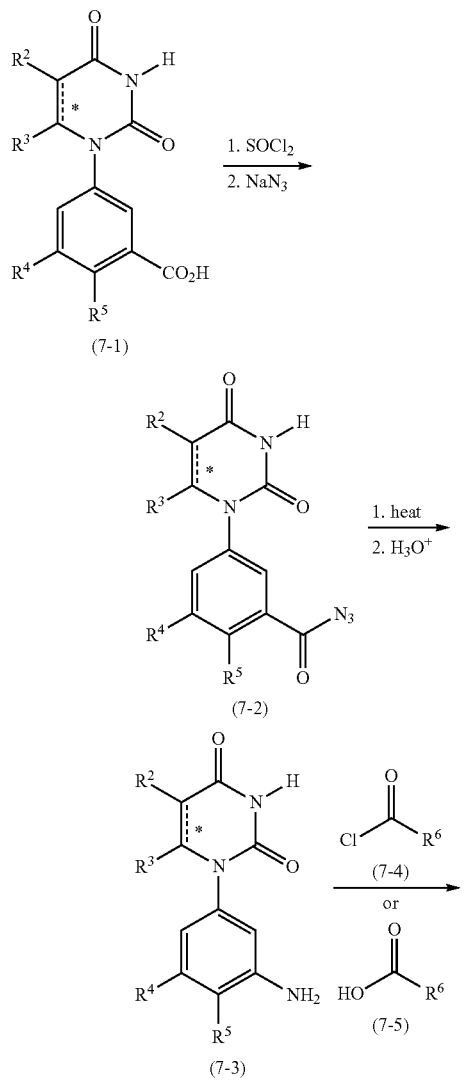

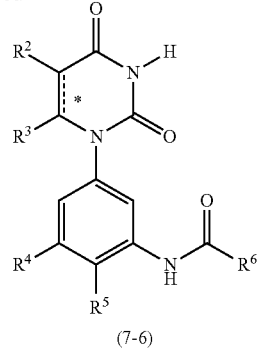

Compound (7-1) may be converted to acyl azide (7-2) in a two-step process. First, compound (7-1) can be treated in refluxing thionyl chloride with or without a catalytic amount of dimethyl-formamide for about 1 to about 4 h to deliver the corresponding acid chloride. Treatment with thionyl chloride at the reflux temperature in solvents such as, for example, chloroform or toluene also furnishes the desired acid chloride. The acid chloride can be reacted with an aqueous solution of sodium azide in a solvent such as, for example, acetone over about 1 to about 8 h to provide acyl azide (7-2). Compound (7-2) can then undergo a Curtius rearrangement in refluxing solvents such as, for example, dioxane or toluene. The intermediate isocyanate is hydrolyzed with an aqueous acid such as, for example, dilute hydrochloric acid in a solvent such as, for example, dimethoxyethane to provide compound (7-3). Compound (7-3) may be converted to compound (7-6) using either acid chloride (7-4) or carboxylic acid (7-5) and the amide bond forming conditions described in Schemes 5 and 6.

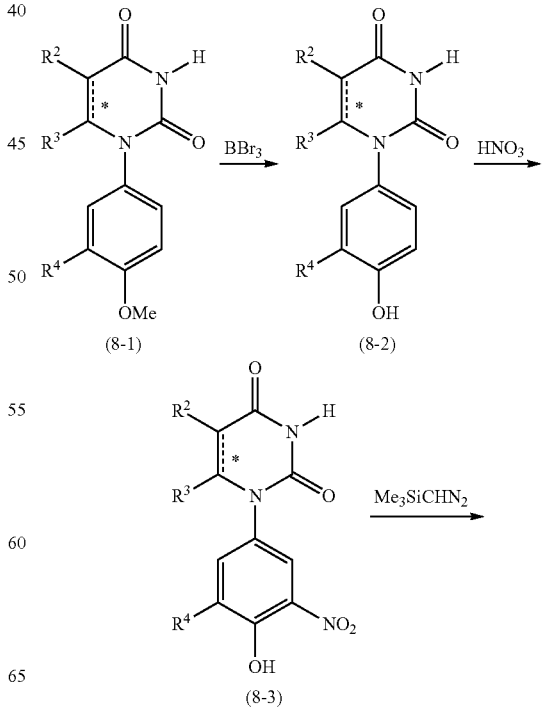

SCHEME 9

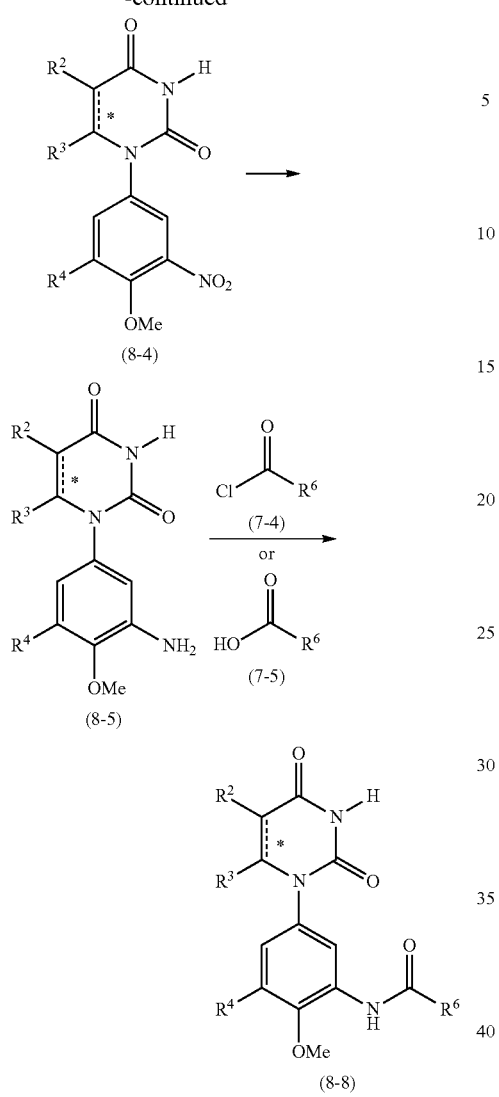

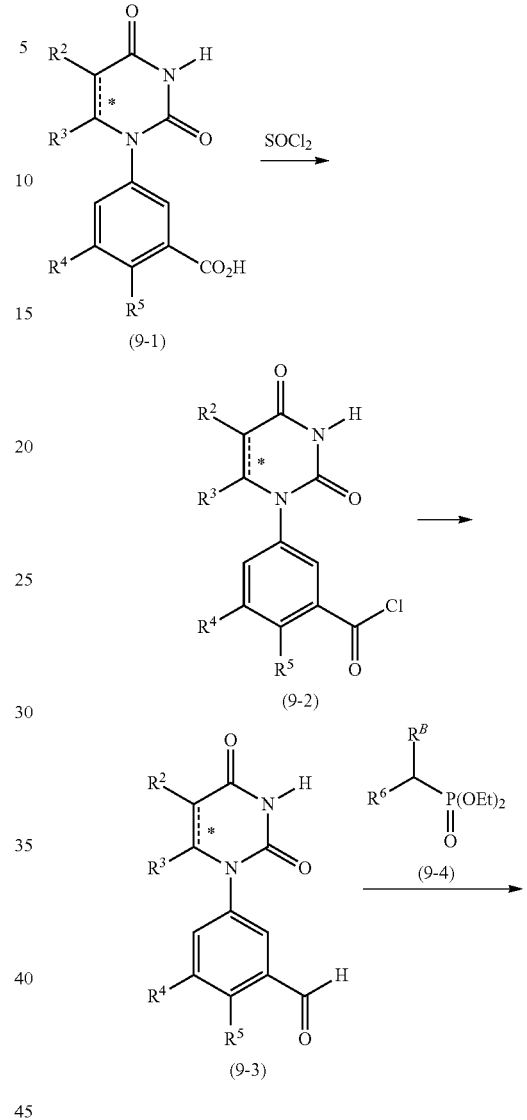

Compound (8-1) can be activated for nitration by removal of the methyl group with $BBr_3$ initially added at about 0° C. and then refluxed for about 10 to about 24 h in a solvent such as, for example, dichloromethane to provide compound (8-2). The phenol (8-2) can be treated with nitric acid in acetic acid over a period of about 1 to about 10 h at or near ambient temperature to supply compound (8-3). Compound (8-3) is then converted to the corresponding methyl ether (8-4) by treatment with a solution of (trimethylsilyl)diazomethane in tetrahydrofuran in a solvent such as, for example, methanol or a mixture of methanol and tetrahydrofuran at or near ambient temperature over about 8 to about 24 h. Compound (8-4) may be reduced to compound (8-5) using a set of reduction conditions described in Scheme 1 and suitable for the functional groups present. Compound (8-5) can be converted into compound (8-8) by coupling with acid chloride (7-4) or carboxylic acid (7-5) using conditions for amide bond formation described in Schemes 5 and 6.

Compound (9-1) can be treated in refluxing thionyl chloride for about 1 to about 4 h to obtain acid chloride (9-2). Treatment with thionyl chloride at the reflux temperature in solvents such as, for example, chloroform or toluene also furnishes compound (9-2). Compound (2) is converted to the corresponding aldehyde (9-3) by reduction with lithium tri-t-butoxyaluminum hydride in a solvent such as, for example, tetrahydrofuran at about −78° C. over from about 1 to about 8 h. The reduction can also be achieved by treatment with indium chloride and tributyltin hydride in the presence of triphenylphosphine in a solvent such as tetrahydrofuran or toluene at temperatures from about −40 to about 0° C. Compound (9-3) can be treated with compound (9-4) in the presence of a base such as potassium t-butoxide in a solvent such as dichloromethane at or near room temperature over a period of about 1 to about 8 h to provide compound (9-5).

ladium acetate, bis(triphenyl phosphine)palladium (II) chloride, tetrakis(triphenylphosphine)palladium, dichloro[1,1'-bis(di-tert-butylphosphino)ferrocene]palladium (II), or dichloro[1,1'-bis(diphenylphosphino)ferrocene]palladium (II) dichloromethane adduct. The reaction may be conducted in a solvent such as, for example, water, dioxane, dimethoxyethane, dimethylformamide, toluene, ethanol, tetrahydrofuran and the like or mixtures thereof. The reaction may be conducted at ambient or elevated temperatures.

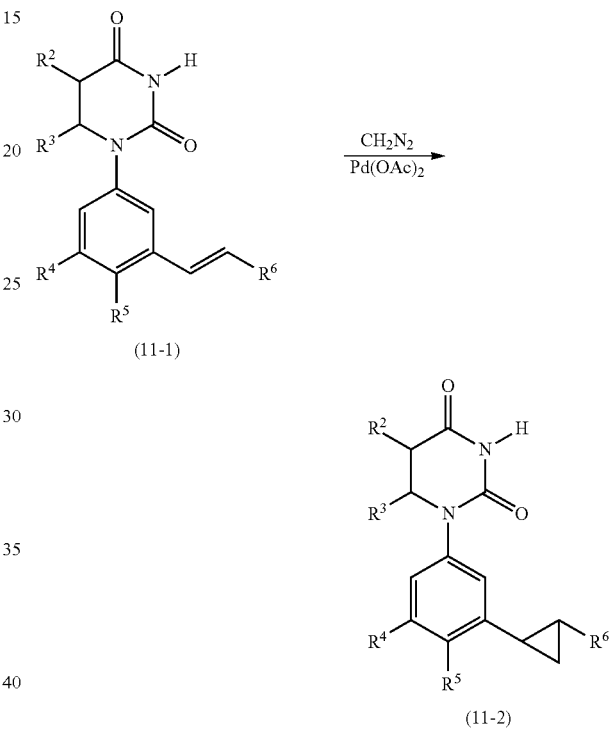

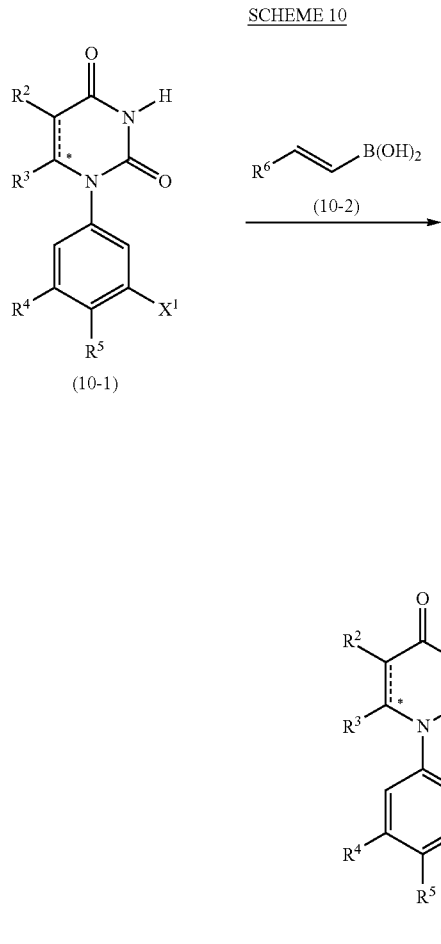

Compound (10-1), wherein $X^1$ is halo (e.g., bromine, iodine) can undergo a Suzuki reaction with vinyl boronic acid (10-2) to provide compound (10-3). The reaction typically requires the use of a base and a catalyst. Examples of bases include, for example, potassium carbonate, potassium phosphate, potassium t-butoxide, sodium carbonate, cesium carbonate, and cesium fluoride. Examples of catalysts include, for example, tris(dibenzylidineacetone)dipalladium (0), pal- Compound (11-1) can be converted to compound (11-2) by treatment with diazomethane in a solvent such as, for example, tetrahydrofuran in the presence of palladium acetate at or near room temperature over a period of about 30 min to about 4 h.

SCHEME 12

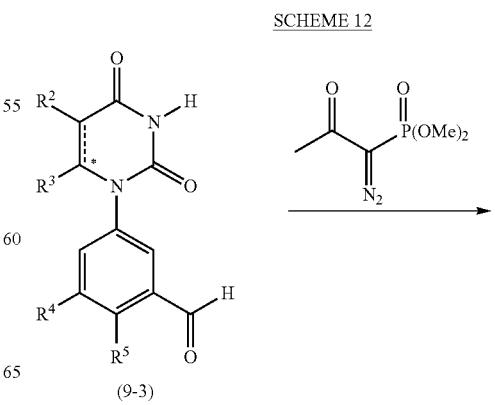

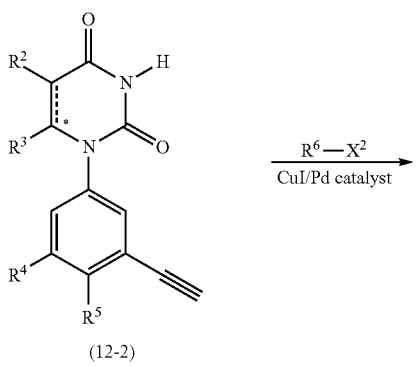

(12-2)

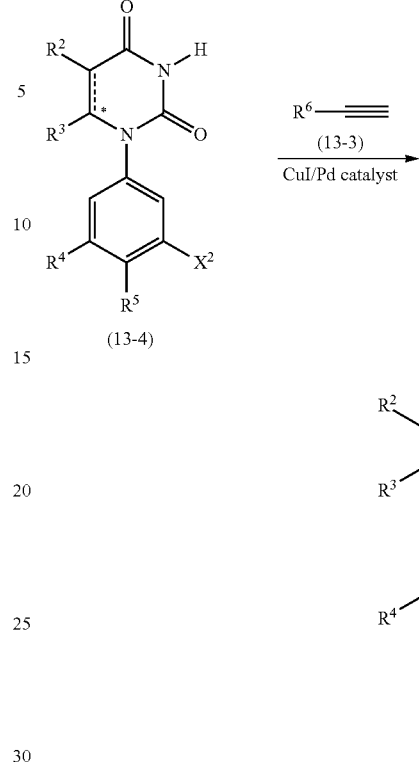

(13-4)

(13-5)

Compound (9-3) can be treated with dimethyl 1-diazo-2-oxopropylphosphonate (prepared as described by Ohira, S., Syn. Comm. 19:561-564 (1989)) in the presence of a base like potassium carbonate in a solvent such as, for example, methanol for about 8 to about 24 h at or near room temperature to supply alkyne (12-2). Compound (12-2) is then treated with $R^6$—$X^2$, wherein $X^2$ is iodine, bromine, or —O-triflate, in the presence of copper (I) iodide, palladium catalyst, base, and optionally additional triphenylphosphine in an inert atmosphere to provide compound (12-3). Suitable palladium catalysts include, for example, tris(dibenzylidineacetone)palladium (0), palladium acetate, bis(triphenylphosphine)palladium (II) chloride, or tetrakis(triphenylphosphine)palladium. Bases, which can be used, include, for example, triethylamine, diethylamine, diisopropylethylamine, potassium carbonate optionally in the presence of tetrabutylammonium bromide, and sodium bicarbonate. Solvents that may be used include, for example, acetonitrile, dimethylformamide, water, dioxane, and tetrahydrofuran, or mixtures thereof. The reaction can be conducted from room temperature to the reflux temperature of the solvents for about 1 to about 48 h. Heating at about 50 to about 120° C. in a microwave reactor from between about 5 and about 15 min also provides compound (12-3).

SCHEME 13

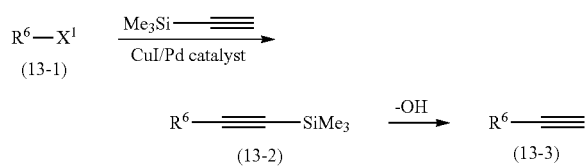

Compound (13-1), wherein $X^1$ is bromine or iodine, can be reacted in an inert atmosphere with (trimethylsilyl)acetylene in the presence of a catalyst such as, for example, palladium acetate/triphenylphosphine or copper iodide/bis(triphenylphosphine)palladium (II) chloride and a base such as, for example, triethylamine in a solvent such as, for example, toluene or acetonitrile to furnish compound (13-2). The reaction can be heated to about 70° C. to about 100° C. optionally in a sealed tube over a period of about 30 min to about 48 h. Compound (13-2) are converted to compound (13-3) by treatment with a base such as, for example, potassium carbonate or sodium hydroxide in a solvent such as, for example, methanol at ambient temperature. Compound (13-3) are reacted with compound (13-4), wherein X2 is bromine or iodine, in the presence of copper (I) iodide, palladium catalyst, base, and optionally additional triphenylphosphine in an inert atmosphere to provide compound (13-5). Suitable palladium catalysts include, for example, tris(dibenzylidineacetone)dipalladium (0), palladium acetate, bis(triphenylphosphine)palladium (II) chloride, or tetrakis(triphenylphosphine)palladium. Bases, which can be used, include, for example triethylamine, diethylamine, diisopropylethylamine, potassium carbonate optionally in the presence of tetrabutylammonium bromide, and sodium bicarbonate. Solvents that may be used include, for example, acetonitrile, dimethylformamide, water, dioxane, and tetrahydro-furan, or mixtures thereof. The reaction can be conducted from about 40° C. to the reflux temperature of the solvents for about 15 min to about 48 h. Microwave heating at about 50° C. to about 120° C. from between about 5 and about 15 min is an alternative heating process to provide compound (13-5).

SCHEME 14

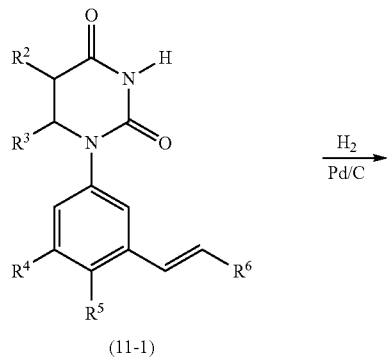

(11-1)

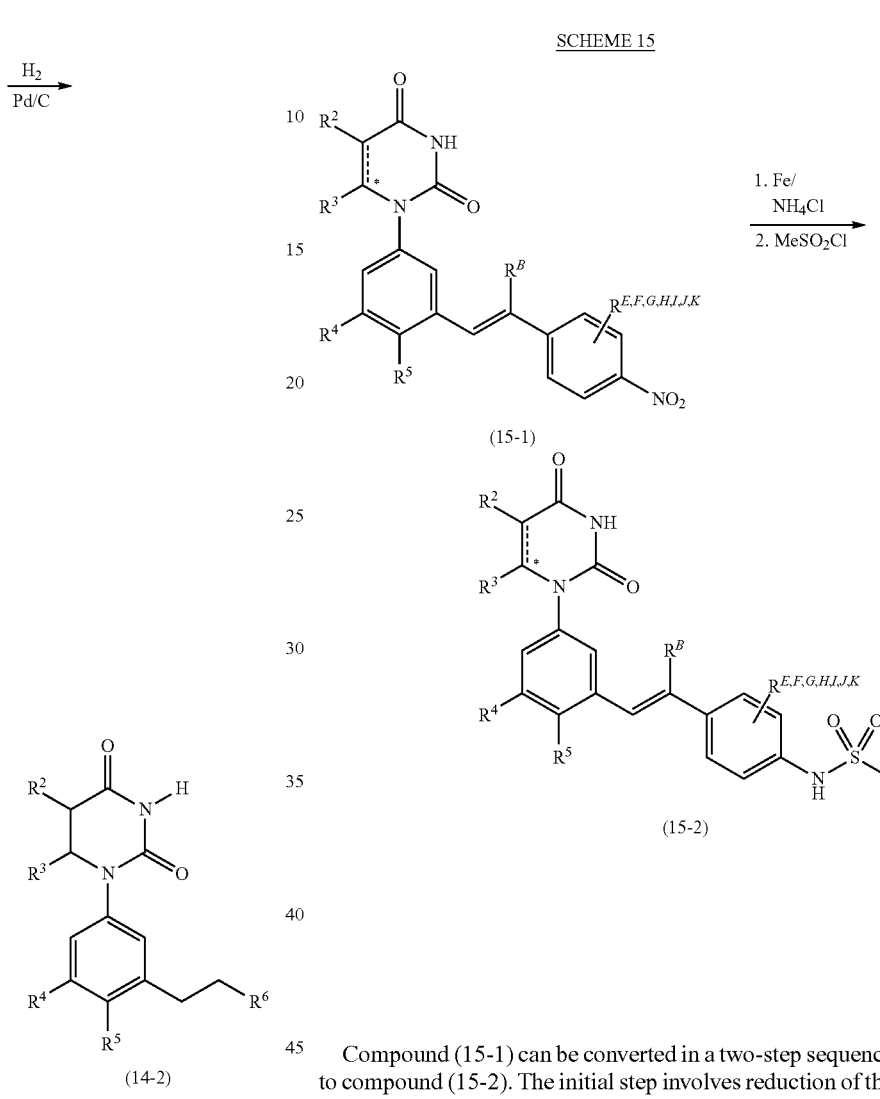

of a catalyst such as, for example, palladium or platinum on charcoal in a solvent such as, for example, tetrahydrofuran, ethyl acetate, ethanol, or hexane at or near ambient temperature over a period of about 1 to about 12 h.

SCHEME 15

Compound (15-1) can be converted in a two-step sequence to compound (15-2). The initial step involves reduction of the aromatic nitro moiety with iron powder in the presence of a mild acid such as, for example, ammonium chloride or dilute hydrochloric acid at temperatures from about 60 to about 80° C. in a mixture of solvents containing, for example, methanol, water, and tetrahydrofuran over about 1 to about 12 h. The second step consists of exposure of the aniline, prepared in the first step, to methanesulfonyl chloride in the presence of a base such as pyridine in a solvent such as dichloromethane at or near ambient temperature.

Compound (11-1) is reduced to supply compound (14-2). Typical conditions for this reduction include using hydrogen at a pressure of about 1 to about 5 atmospheres in the presence

SCHEME 16

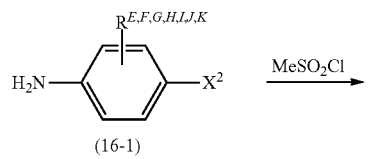

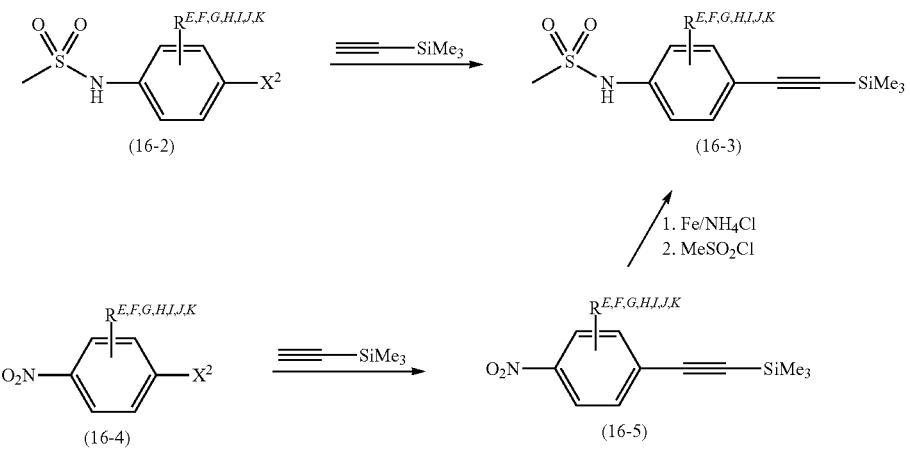

Aniline (16-1) and aromatic nitro compound (16-4), wherein $X^2$ is, for example, bromine, iodine, or triflate, can be converted to compound (16-3). Compound (16-1) can be transformed to compound (16-2) by treatment with methanesulfonyl chloride in the presence of a base such as pyridine in a solvent such as dichloromethane. Then compound (16-2) is converted to compound (16-3) by treatment in an inert atmosphere with (trimethylsilyl)acetylene in the presence of a catalyst such as, for example, palladium acetate, bis(triphenylphosphine)palladium (II) chloride, bis(triphenylphosphine)palladium (II) chloride in combination with copper(I) iodide and, when $X^2$ is bromine, triphenylphosphine, and a base such as, for example, triethylamine in a solvent such as toluene or acetonitrile at approximately 80° C.

Compound of formula (16-4) can be reacted in an inert atmosphere with (trimethylsilyl)acetylene in the presence of a catalyst such as, for example, bis(triphenylphosphine)palladium (II) chloride/copper(I) iodide and a base such as, for example, triethylamine in a solvent such as, for example, acetonitrile at approximately 80° C. to give compound (16-5). Compound (16-5) can be converted to compound (16-3) in a two-step sequence. The initial step involves reduction of the aromatic nitro moiety with iron powder in the presence of a mild acid such as, for example, ammonium chloride or dilute hydrochloric acid at temperatures from about 60 to about 80° C. in a mixture of solvents containing, for example, methanol, water, and tetrahydrofuran over about 1 to about 12 h. The second step consists of exposure of the aniline, prepared in the first step, to methanesulfonyl chloride in the presence of a base such as pyridine in a solvent such as dichloromethane at or near ambient temperature.

Removal of the trimethylsilyl group of compound (16-3) is accomplished as described for the production of compound (13-3) in Scheme 13 above.

SCHEME 17

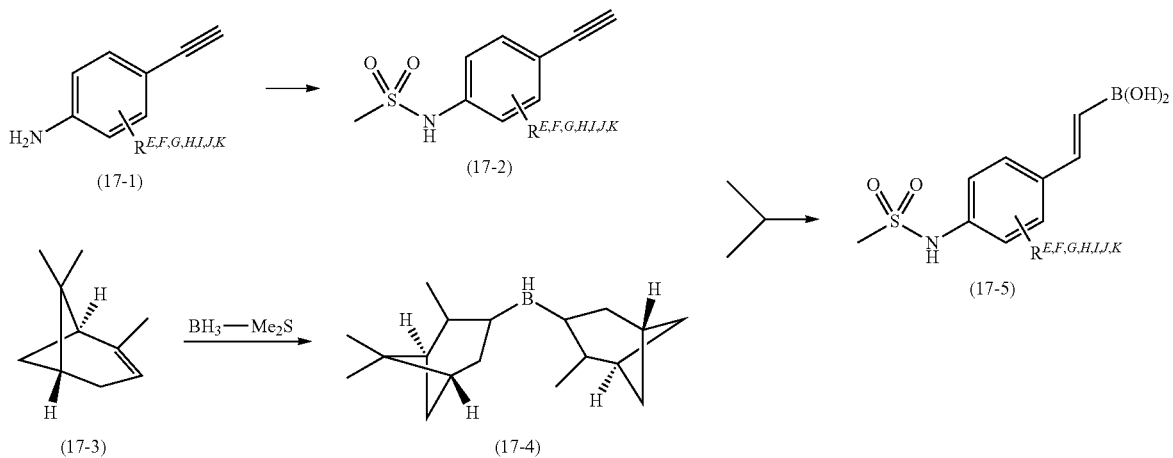

Compound (17-1) can be mesylated to provide compound (17-2) by treatment with methanesulfonyl chloride in the presence of a base such as, for example, pyridine in a solvent such as, for example, dichloromethane. Compound (17-3) can be exposed to borane dimethyl sulfide complex in a solvent such as, for example, tetrahydrofuran at approximately about 0 to about 10° C. to supply compound (17-4). Compounds (17-2) and (17-4) can be combined with acetaldehyde in refluxing tetrahydrofuran. Subsequent treatment with water at room temperature yields compound (17-5).

SCHEME 18

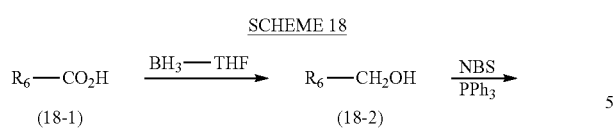

Carboxylic acid (18-1) can be reduced with boron tetrahydrofuran complex with heating to provide alcohol (18-2). Compound (18-2) is converted to the corresponding bromide (18-3) with N-bromosuccinimide and triphenylphosphine in solvents such as, for example, dichloromethane at room temperature in several hours. Treatment of compound (18-3) with triethyl phosphite at about 120° C. for about 1 to about 3 h supplies compound (18-4). Compound (18-4) can be used for example to make compound (9-5) as described in Scheme 9.

SCHEME 19

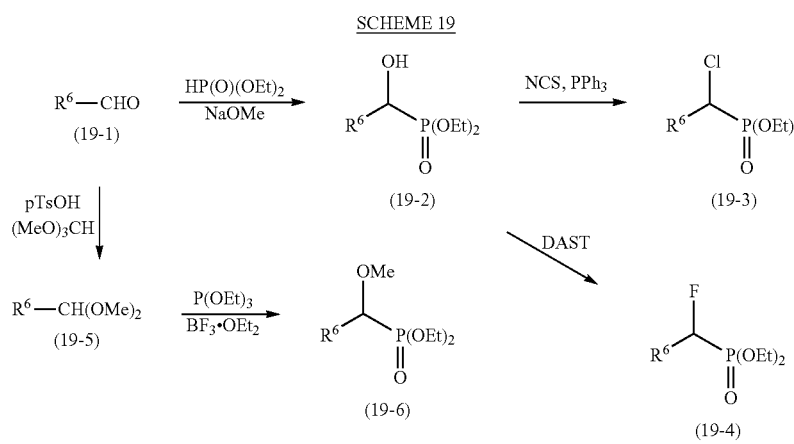

Benzaldehyde (19-1) can be treated with diethyl phosphonate in the presence of a base such as, for example, sodium methoxide in a solvent such as, for example, methanol at room temperature to provide compound (19-2). Compound (19-2) can be treated with N-chlorosuccinimide and triphenylphosphine in dichloromethane at room temperature to yield compound (19-3). Compound (19-2) can also be reacted with (diethylamino)sulfur trifluoride (DAST) to supply compound (19-4).

Compound (19-1) can also be treated with p-toluenesulfonic acid and trimethyl orthoformate in methanol at about 50° C. to provide acetal (19-5). Compound (19-5) can be converted to compound (19-6) by exposure to triethyl phosphite and boron trifluoride diethyl etherate at about −20° C. to about ambient temperature.

Compounds (19-3), (19-4), and (19-6) can be used for example to make compound (9-5) as described in Scheme 9.

SCHEME 20

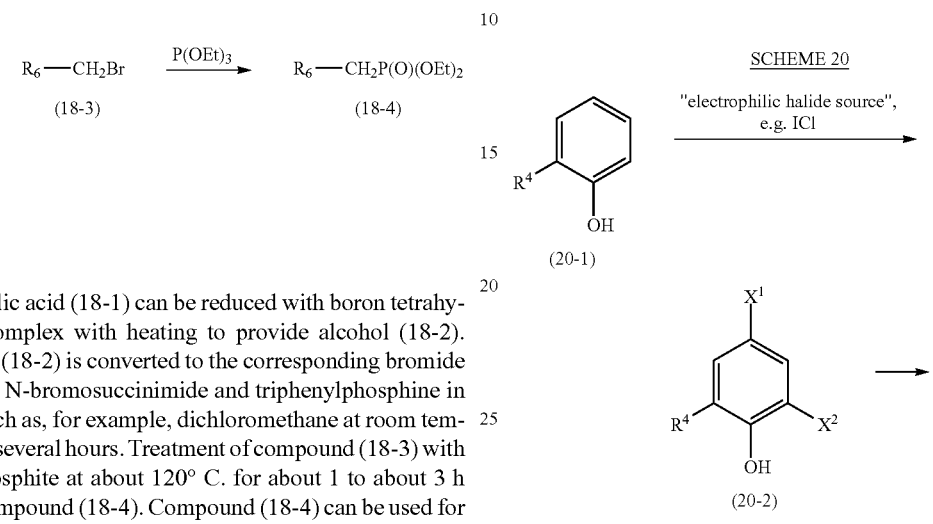

-continued

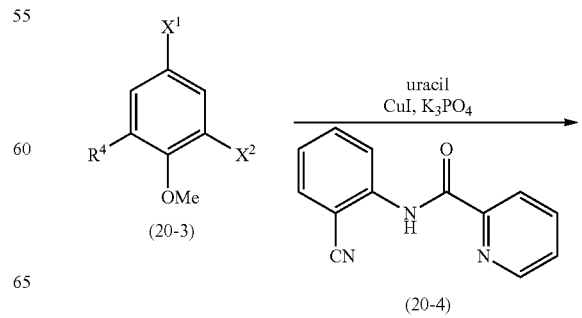

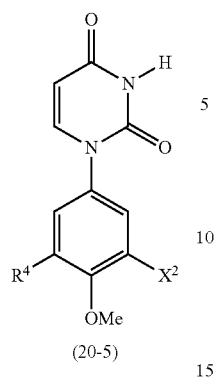

(20-5)

Phenol (20-1), wherein $R^4$ is other than amino, is treated with a source of electrophilic halide, such as, for example, iodine monochloride to provide dihalogenated compound (20-2), wherein $X^1$ and $X^2$ are independently bromine or iodine. Compound (20-2) is transformed to compound (20-3) by reaction of an alkylating agent such as, for example, methyl sulfate with a base such as, for example, potassium carbonate in refluxing acetone. Alternatively, methyl iodide in the presence of a base such as, for example, potassium t-butoxide in a solvent such as, for example, tetrahydrofuran, or dimethylformamide also furnish compound (20-3). In yet another alternative, compound (20-2) can be methylated with (trimethylsilyl)diazomethane in a solvent such as, for example, t-butyl methyl ether. Compound (20-3) can be reacted with uracil, ligand (20-4), copper (I) iodide, and potassium phosphate in dimethyl sulfoxide at about 40° C. to about 100° C. to supply compound (20-5).

For example, when in compound (20-3), $R^4$ is tert-butyl, $X^1$ is iodo, and $X^2$ is iodo or bromo, compound (20-3) can be stirred with uracil and compound (20-4) in the presence of CuI and $K_2PO_4$ in DMSO for about 15 to about 24 h at about 60° C. to supply compound (20-5). Alternatives to ligand (20-4) for making (20-5) are 8-hydroxyquinoline and 2-(2-pyridyl)-benzimidazole.

SCHEME 21

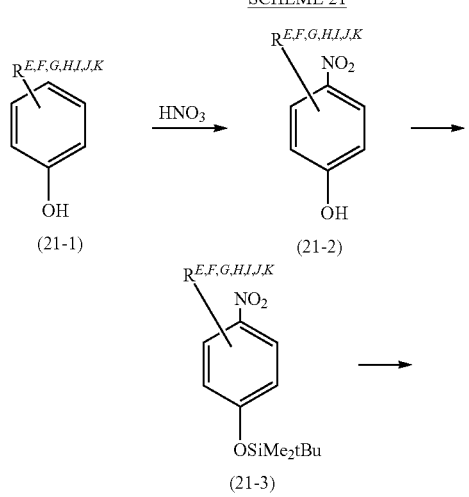

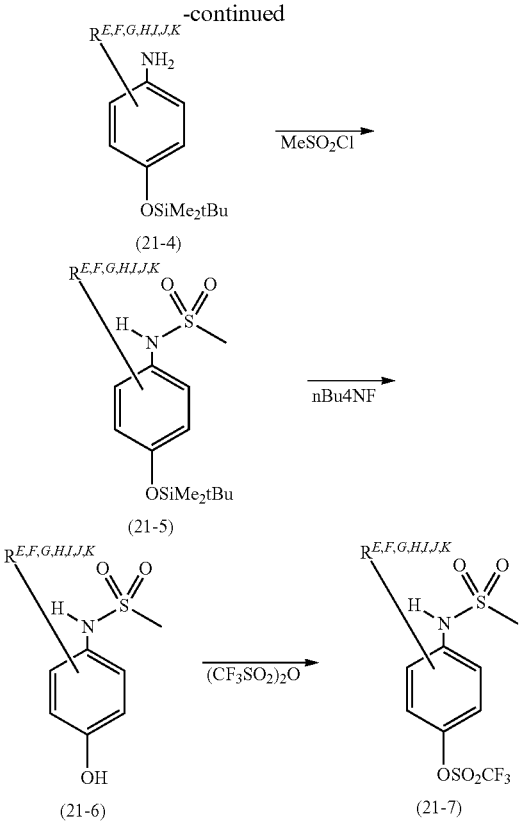

Compound (21-1) can be nitrated with nitric acid in acetic acid in a temperature range of about 10 to about 15° C. to give compound (21-2). The phenol moiety of compound (21-2) can be protected as a silyl ether, e.g. t-butyldimethylsilyl ether, by treatment with a silyl chloride such as, for example, t-butyl dimethylsilyl chloride and imidazole in a solvent such as, for example, dimethyl formamide at ambient temperature to furnish compound (21-3). Compound (21-3) may then be reduced using conditions known to those skilled in the art to furnish the corresponding aniline (21-4).

Typical conditions for this reduction include using hydrogen at a pressure of about 1 to about 5 atmospheres in the presence of a catalyst such as, for example, palladium or platinum on charcoal in a solvent such as, for example, tetrahydrofuran, ethyl acetate, ethanol, methanol, or hexane at or near ambient temperature over a period of about 1 to about 12 h. Dependent on the functional groups present, an alternative reduction procedure may be more appropriate such as, for example, using iron powder in the presence of a mild acid such as, for example, ammonium chloride or dilute hydrochloric acid at reflux temperatures in a mixture of solvents containing, for example, methanol, water, and tetrahydrofuran over about 1 to about 12 h.

Aniline (21-4) can then by sulfonylated with methanesulfonyl chloride in the presence of pyridine in a solvent such as, for example, dichloromethane. The starting material and reagents are combined at about 0° C. and then allowed to gradually warm to ambient temperature over the course of the reaction to supply compound (21-5). The silyl ether protecting group is removed under conditions familiar to one skilled in the art. For example, tetrabutylammonium fluoride in tetrahydrofuran at room temperature transforms compound (21-5) to compound (21-6). The phenol group of compound (21-6) may be sulfonylated with trifluoromethanesulfonic anhydride in the presence of a base such as, for example, pyridine in a solvent such as, for example, dichloromethane at room temperature to provide compound (21-7). Compound (21-7) can be used as described in Scheme 12 to make compound (12-3).

temperature in solvents such as, for example, chloroform or toluene also furnishes compound (22-2). Treatment of the carboxylic acid with oxalyl chloride in dichloromethane with a catalytic amount of dimethylformamide also furnishes compound (22-2).

Compound (22-2) can be treated with an amine or the corresponding salt in a solvent such as, for example, dioxane, dimethylformamide, dimethylacetamide, or dichloromethane optionally in the presence of a base such as, for example, pyridine, triethylamine or diisopropylethylamine at

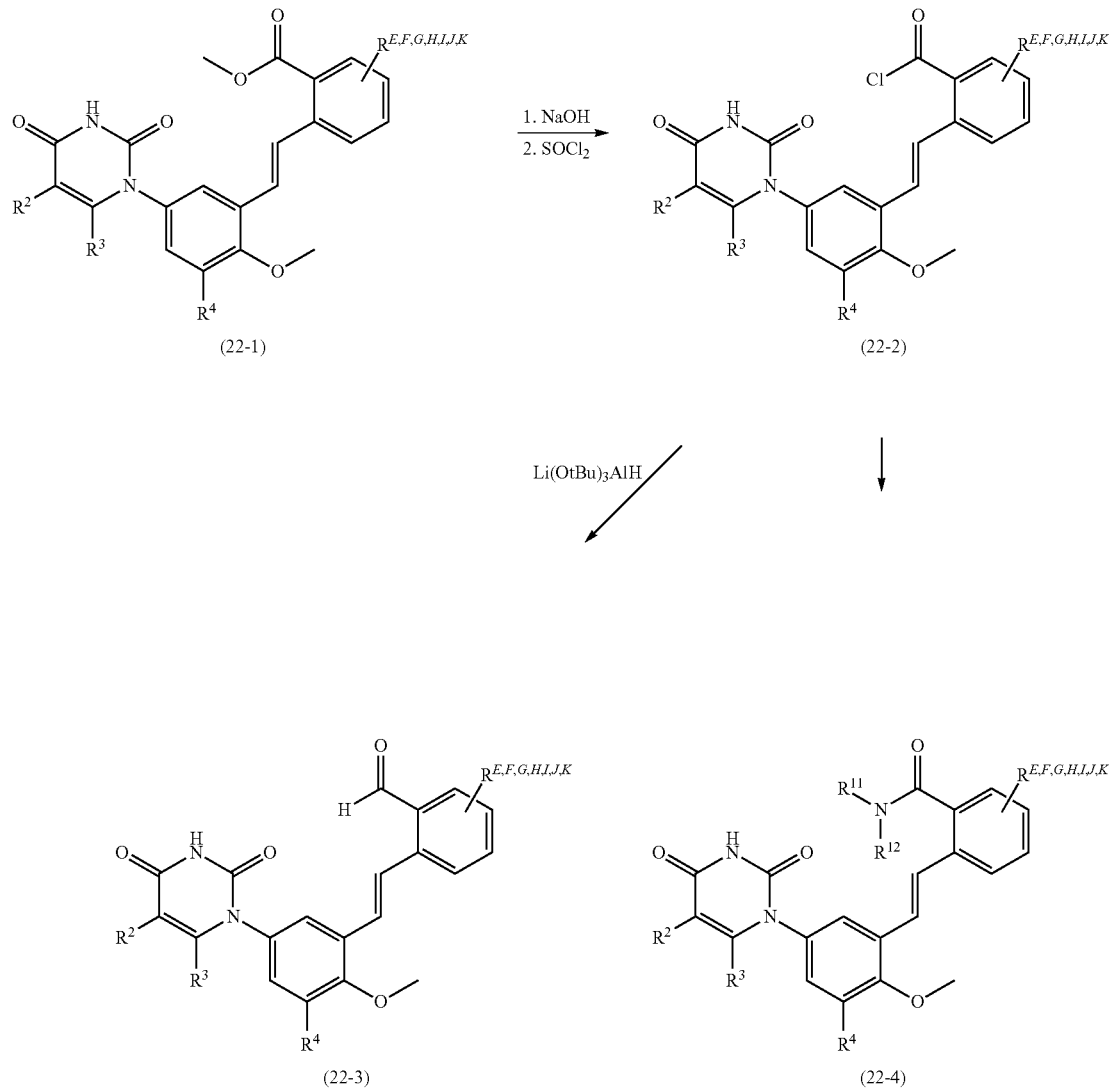

Compound (22-1) is converted to compound (22-2) in a two-step sequence. First, compound (22-1) can be hydrolyzed with a base such as, for example, sodium hydroxide, lithium hydroxide, or potassium hydroxide in a solvent such as, for example, methanol, ethanol, or tetrahydrofuran, or mixtures thereof. The resultant reaction mixture can be stirred for a period of about 6 to about 48 h at ambient temperature. Second, the intermediate carboxylic acid is treated in refluxing thionyl chloride with or without a catalytic amount of dimethylformamide for about 1 to about 4 h to deliver acid chloride (22-2). Treatment with thionyl chloride at reflux temperatures ranging from at or near ambient to about 100° C. for between about 1 and about 24 h to provide compound (22-4) wherein $R^{11}$ and $R^{12}$ are independently hydrogen or $R^F$, or taken together with the nitrogen to which they are attached form a 5-6-membered heterocyclyl or a fused 2-ring heterocyclyl.

Compound (22-2) is converted to the corresponding aldehyde (22-3) by reduction with lithium tri-t-butoxyaluminum hydride in a solvent such as, for example, tetrahydrofuran at about −60° C. to about −78° C.

SCHEME 23

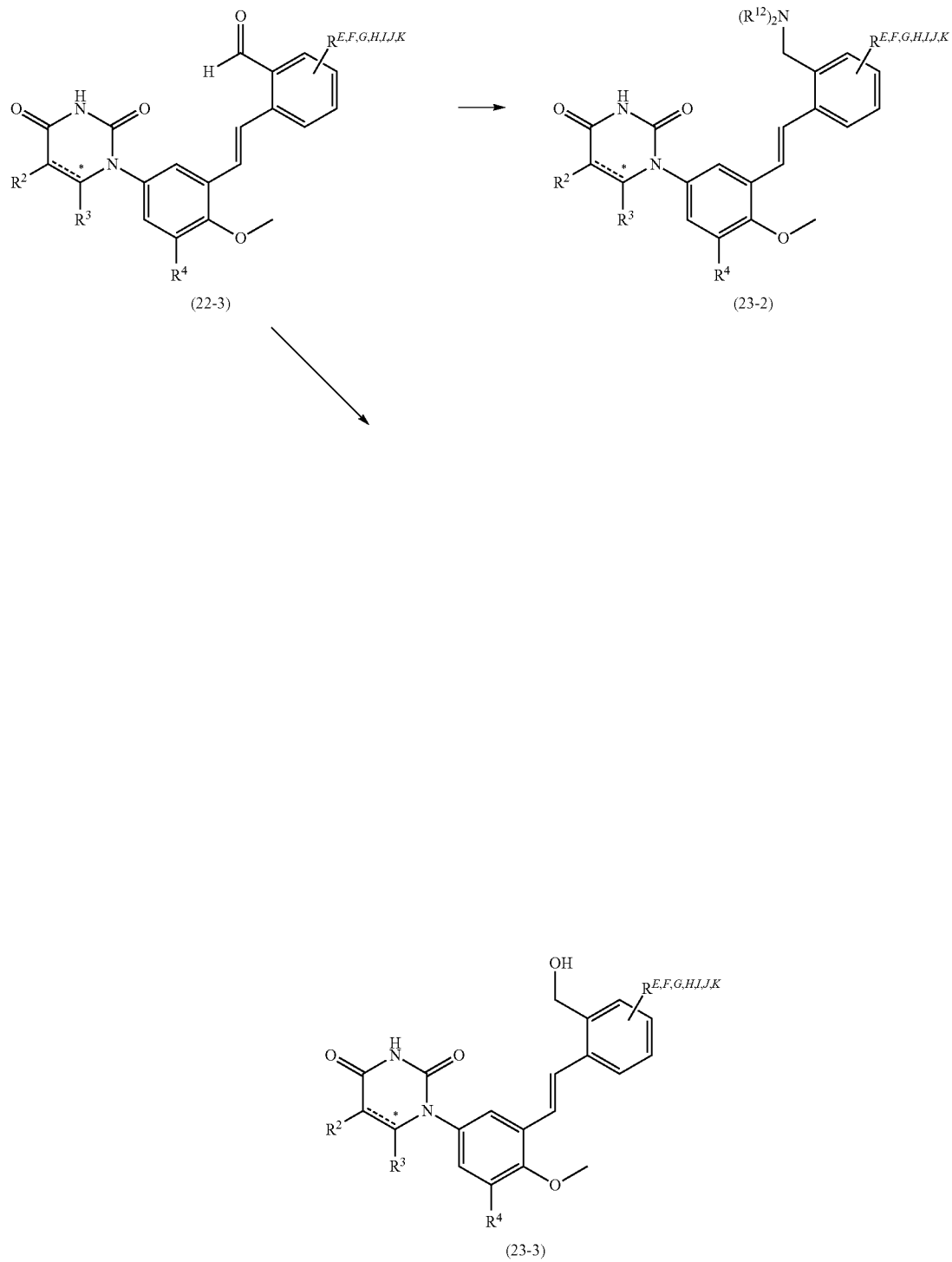

Compound (22-3) can be converted to compound (23-2) wherein $R^{11}$ and $R^{12}$ are independently hydrogen or $R^F$, or taken together with the nitrogen to which they are attached form a 5-6-membered heterocyclyl or a fused 2-ring heterocyclyl by treatment with an amine, $N(R^{11})(R^{12})$, in the presence of a reductant such as, for example, sodium triacetoxyborohydride or sodium cyanoborohydride in a solvent such as, for example, methanol, ethanol, dichloromethane, dimethylacetamide, or dimethylformamide over a period of about 1 to about 24 h. The reaction often proceeds best at an acidic pH that can be maintained by the addition of acetic acid or hydrochloric acid.

Compound (22-3) can also be converted to compound (23-3) by reduction with lithium tri-t-butoxyaluminum hydride in a solvent such as tetrahydrofuran at room temperature.

SCHEME 24

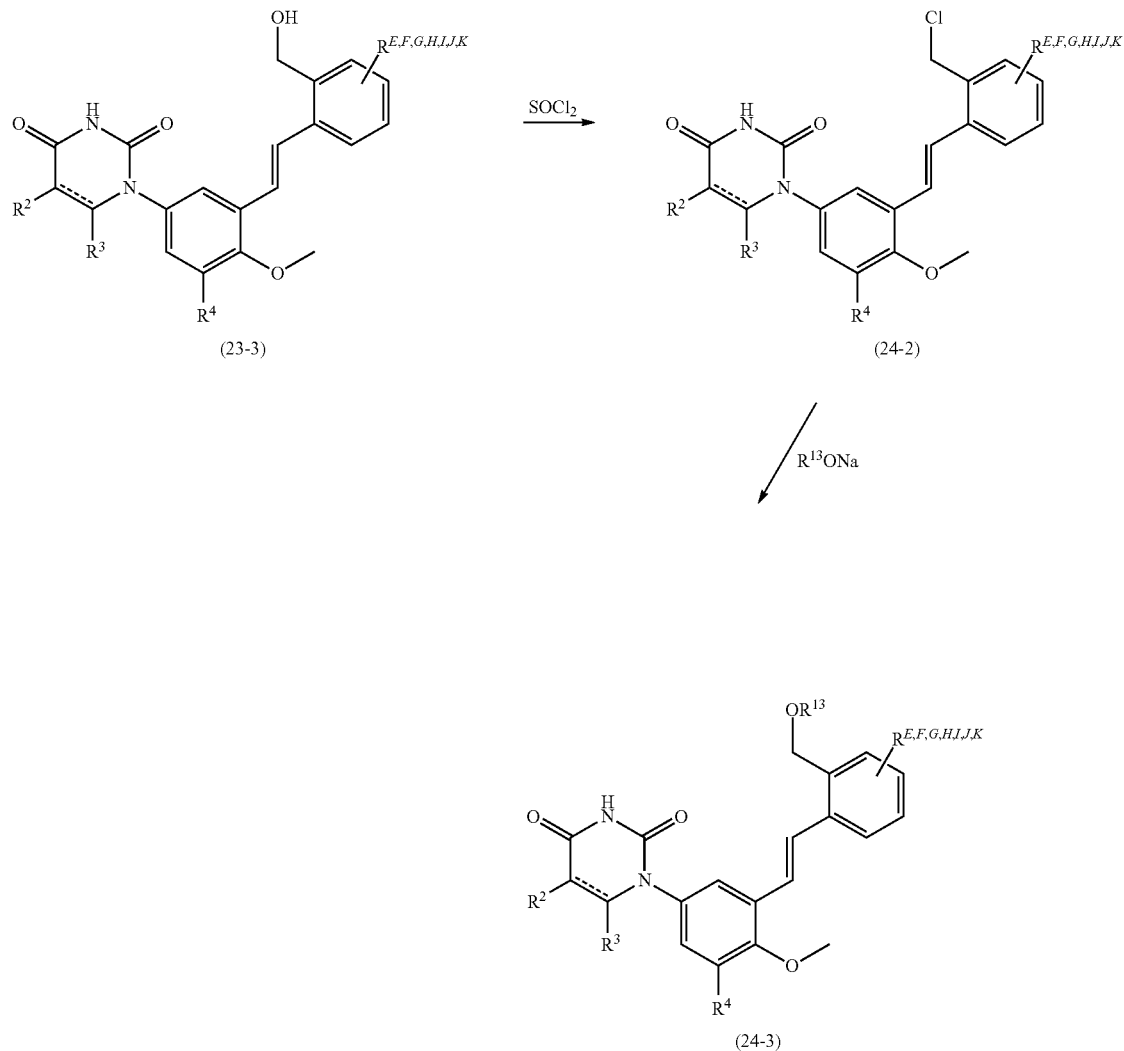

Compound (23-3) can be converted to compound of formula (24-2) by treatment with thionyl chloride in dichloromethane at room temperature. Compound (24-2) can be treated with a sodium alkoxide, $R^{13}ONa$, in a heated solution of the corresponding alcohol to provide compound (24-3), wherein $R^{13}$ is hydrogen or $R^F$.

SCHEME 25

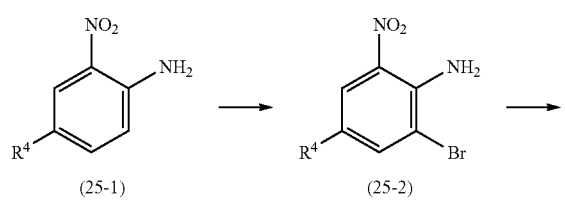

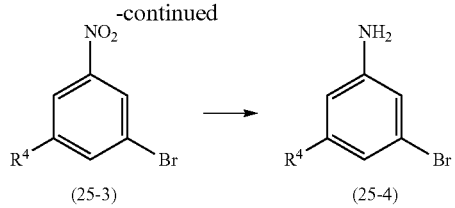

Compound (25-1) can be brominated by treatment with, for example, pyridinium hydrobromide perbromide in a solvent such as, for example, acetic acid at or near ambient temperature over a period of about 1 to about 8 h to give compound (25-2). The amino group of compound (25-2) can be removed by exposure to t-butyl nitrite in a solvent such as, for example, dimethylformamide at a temperature initially at ambient temperature and then increased to the range of about 50 to about 65° C. to give compound (25-3). Additional aliquots of t-butyl nitrite can be added at ambient temperature followed by heating until the transformation is complete. Compound (25-3) can be reduced to compound (25-4) by, for example, treatment with iron and ammonium chloride.

SCHEME 26

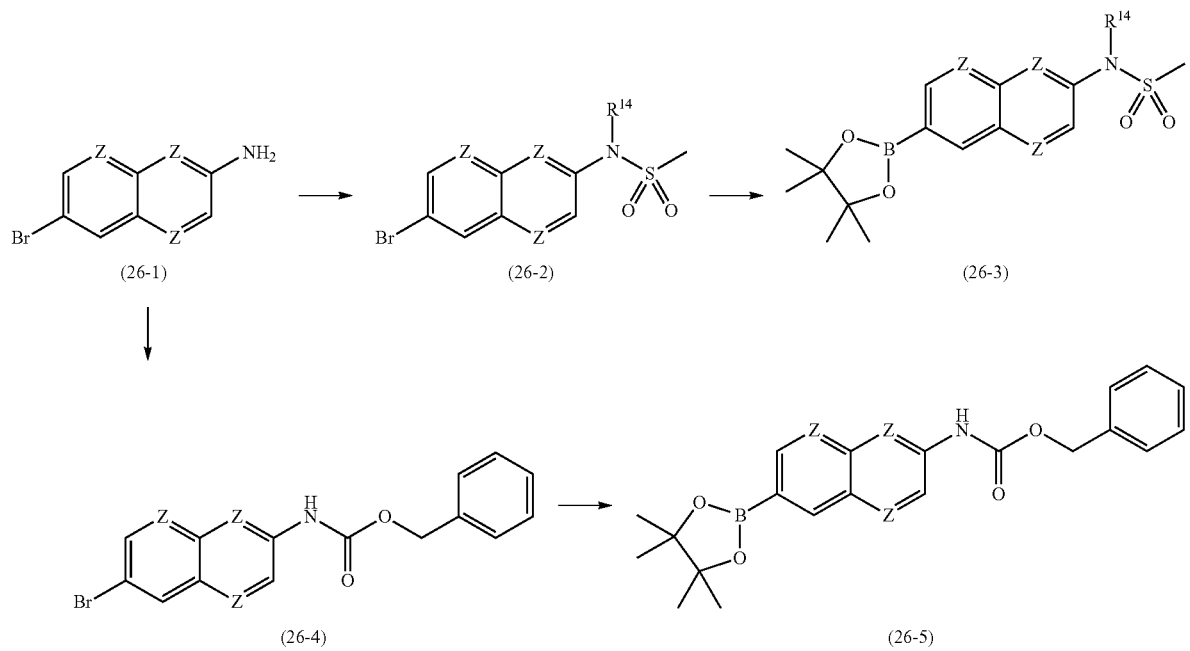

Compound (26-1), wherein each Z is independently N or CH can be converted to a boronic acid ester for use in Suzuki reactions. For example, compound of formula (26-1) can be converted to compound (26-2), wherein $R^{14}$ is hydrogen or methanesulfonyl (when excess methanesulfonyl chloride is used) by treatment with methanesulfonyl chloride in pyridine at approximately ambient temperature in about 1 to about 8 h.

Compound (26-2) can be transformed to compound of (26-3) by treatment with pinacol-borane in the presence of a catalyst such as, for example, tris(dibenzylidineacetone)dipalladium (0), ligand such as, for example, tri-t-butylphosphine, and a base such as triethylamine in solvents such as, for example, tetrahydrofuran, dioxane, or toluene at temperatures ranging from ambient to about 130° C.

Alternatively, compound (26-2) can be reacted with bis(pinacolato)diboron in the presence of a catalyst such as, for example, Combiphos® Pd6, dichloro[1,1'-bis(diphenylphosphino)ferrocene]palladium (II) dichloromethane adduct, or palladium acetate in the presence of a ligand such as, for example, 2-dicyclohexylphosphino-2',4',6'-triisopropylbiphenyl (XPhos), and a base such as, for example, potassium acetate in solvents such as, for example, toluene, dioxane, tetrahydrofuran, dimethylformamide or dimethyl sulfoxide in temperatures from about 60 to about 130° C. to give compound (26-3).

Compound (26-3) can be converted to protected compound (26-4) by treatment with benzyl chloroformate initially at about 0° C. in the presence of saturated aqueous sodium bicarbonate in a mixture of acetone and water. This can be warmed to ambient temperature and maintained at that temperature for about 12 to about 24 h. Subsequently, compound (26-4) can be converted to the boronic acid pinacol ester (26-5) using the reaction conditions described above.

SCHEME 27

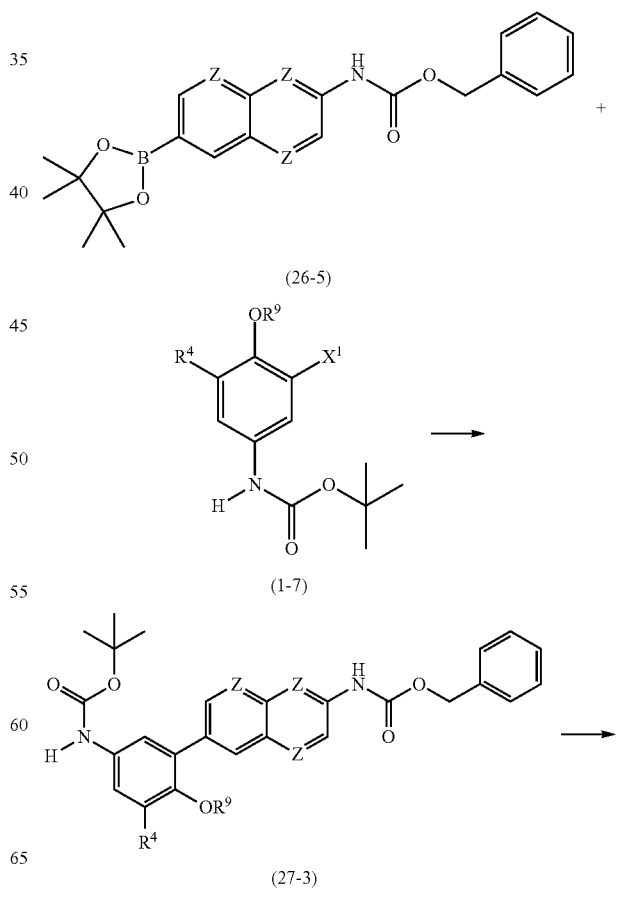

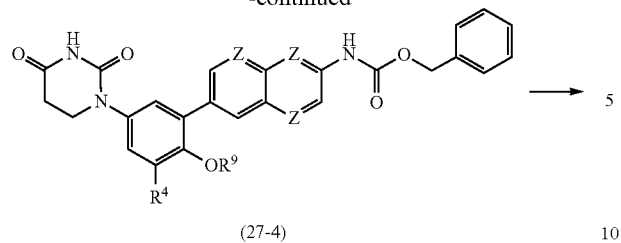

(27-4)

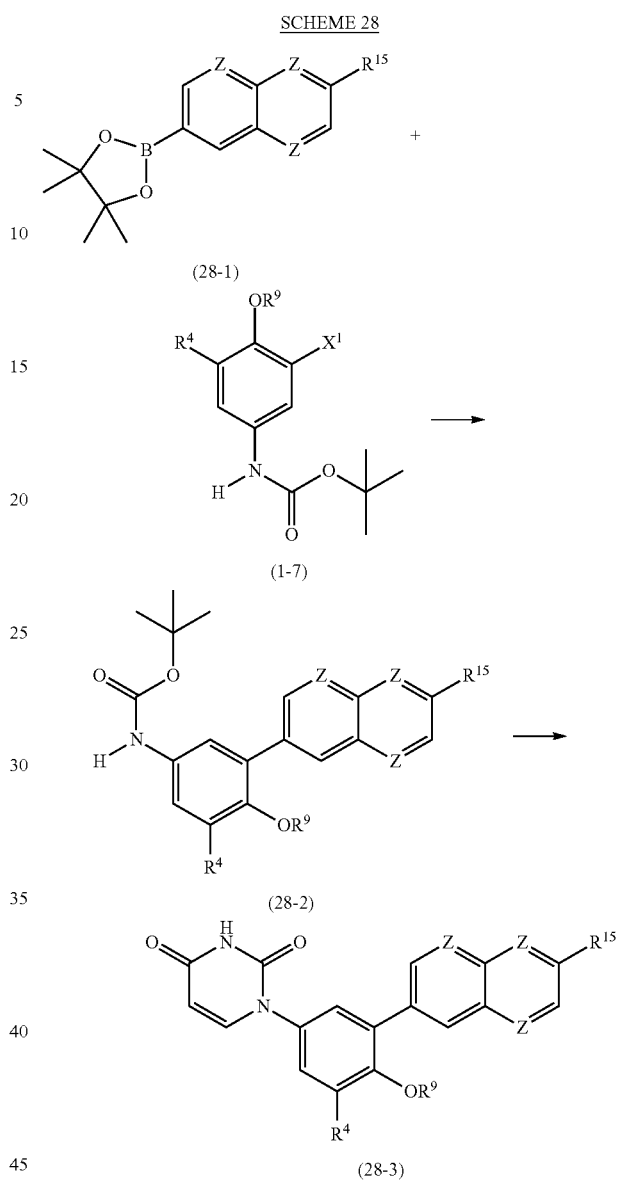

Compound (26-5), wherein each Z is independently N or CH, can be coupled with compound (1-7) under Suzuki reaction conditions to provide compound (27-3). Such conditions include, for example, use of a palladium catalyst such as, for example, tris(dibenzylidineacetone)palladium (0), palladium acetate, bis(triphenylphosphine)palladium (II) chloride, tetrakis(triphenylphosphine)palladium, or dichloro[1,1'-bis(diphenylphosphino)ferrocene]palladium (II) dichloromethane adduct; base such as, for example, potassium carbonate, potassium phosphate, potassium t-butoxide, sodium carbonate, cesium carbonate, or cesium fluoride; and solvent such as, for example, toluene, ethanol, water, or tetrahydrofuran, or mixtures thereof heated in the temperature range from about 40 to about 130° C.

Compound (27-3) can be transformed to compound (27-4) in a three-step process. The initial step involves removal of the t-butoxycarbonyl protecting group with an acid such as, for example, trifluoroacetic acid in solvent such as, for example, dichloromethane or hydrochloric acid in dioxane at room temperature over about 1 to about 24 h. Subsequently, the dihydropyrimidinedione can be introduced as described in Scheme 3.

Compound (27-5) can be obtained from compound (27-4) in a two-step sequence. First, the protecting group is removed from the naphthyl amine under reductive conditions. Typically, hydrogenation (~1 atmosphere pressure) in the presence of a catalyst such as, for example, 10% palladium on charcoal in a solvent such as, for example, ethyl acetate at or near ambient temperature over a period of about 8 to about 24 h. Second, the naphthyl amine can now be sulfonylated by treatment with methanesulfonyl chloride in the presence of a base such as triethylamine in a solvent (e.g., dichloromethane) at room temperature over about 20 min to about 4 h.

Compound (28-1), wherein each Z is independently N or CH, and $R^{15}$ is, for example, hydrogen, —NHSO$_2$Me, —N(SO$_2$Me)$_2$, or methoxy can be coupled with compound (1-7) under Suzuki reaction conditions to provide compound (28-2). Such conditions include, for example, use of palladium catalyst such as, for example, tris(dibenzylidineacetone) palladium (0), palladium acetate, bis(triphenylphosphine)palladium (II) chloride, tetrakis(triphenylphosphine) palladium, or dichloro[1,1'-bis(diphenylphosphino) ferrocene]palladium (II) dichloromethane adduct; a base such as potassium carbonate, potassium phosphate, potassium t-butoxide, sodium carbonate, cesium carbonate, or cesium fluoride; and solvent such as, for example, toluene, ethanol, water or tetrahydrofuran, or mixtures thereof heated in the temperature range from about 40 to about 130° C. The reaction is typically deoxygenated with an inert gas such as nitrogen prior to heating. The heating may occur in conventional glassware, a sealed tube, or in a microwave reactor over about 1 to about 24 h.

Compound (28-2) can be transformed to compound (28-3) in a three-step process. The initial step involves removal of the t-butoxycarbonyl protecting group with an acid such as, for example, trifluoroacetic acid in solvent such as, for example, dichloromethane or hydrochloric acid in dioxane at room temperature over about 1 to about 24 h. Subsequently, the uracil can be introduced as described in Scheme 4.

SCHEME 29

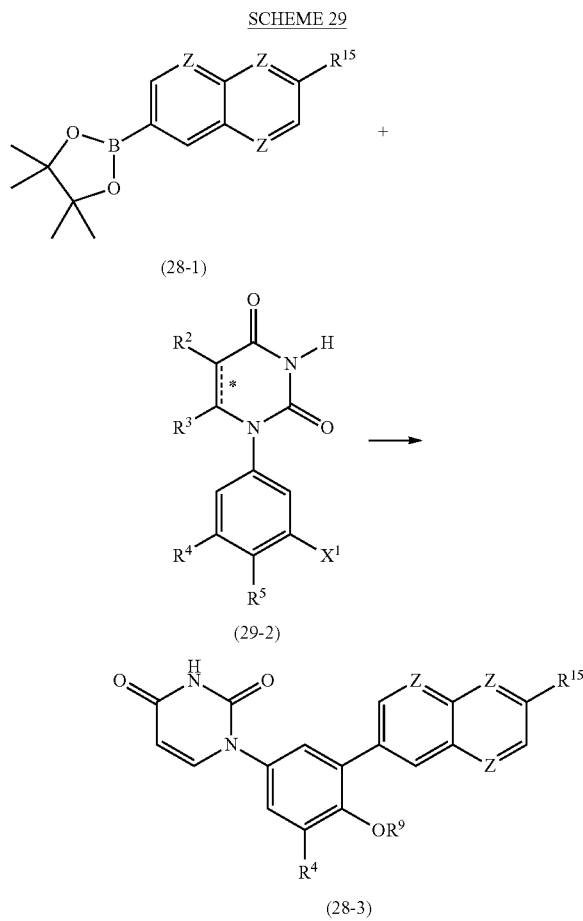

SCHEME 30

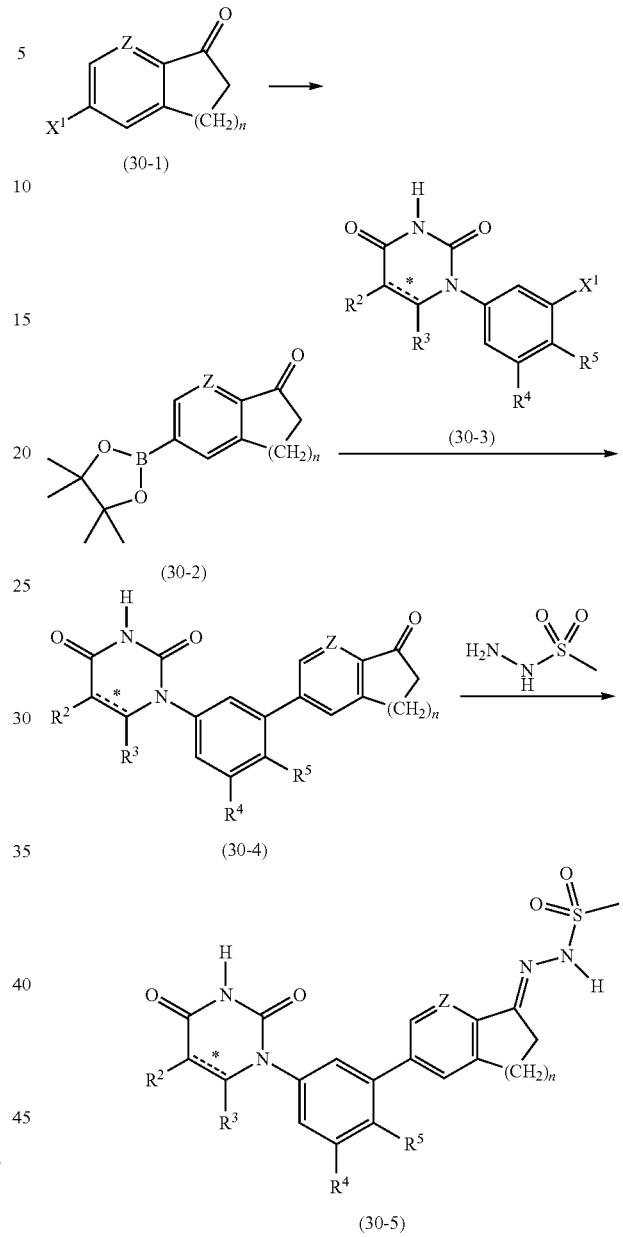

Compound (28-1), wherein each Z is independently N or CH, and $R^{15}$ is, for example, hydrogen, —NHSO$_2$Me, —N(SO$_2$Me)$_2$, or methoxy can be coupled with compound of formula (29-2), wherein $X^1$ is, for example, bromine or iodine, under Suzuki reaction conditions to provide compound of formula (28-3). Such conditions include, for example, use of palladium catalyst such as, for example, tris(dibenzylidineacetone)palladium (0), palladium acetate, bis(triphenylphosphine)palladium (II) chloride, tetrakis (triphenylphosphine) palladium, dichloro[1,1'-bis(diphenylphosphino)ferrocene]palladium (II) dichloromethane adduct, or bis(diphenylphosphino)ferrocene]palladium (II) dichloromethane; base such as, for example, potassium carbonate, potassium phosphate, potassium t-butoxide, sodium carbonate, cesium carbonate, or cesium fluoride; and solvent such as, for example, toluene, ethanol, water, or tetrahydrofuran, or mixtures thereof heated in the temperature range from about 40 to about 130° C. The reaction is typically deoxygenated with an inert gas such as nitrogen prior to heating. The heating may occur in conventional glassware, a sealed tube, or in a microwave reactor over about 1 to about 24 h.

Compound (30-1), wherein $X^1$ is bromine or iodine, n is 1 or 2, and Z is CH or N, can be reacted with bis(pinacolato) diboron in the presence of a catalyst such as, for example, Combiphos® Pd6, dichloro[1,1'-bis(diphenylphosphino)ferrocene]palladium (II) dichloromethane adduct, or palladium acetate in the presence of a ligand such as 2-dicyclohexylphosphino-2',4',6'-triisopropylbiphenyl (XPhos), and a base such as potassium acetate in solvents such as, for example, toluene, dioxane, tetrahydrofuran, dimethylformamide or dimethyl sulfoxide in temperatures from 60-130° C. to give compound (30-2). The reaction is typically deoxygenated with an inert gas such as nitrogen prior to heating. The heating may occur in conventional glassware, a sealed tube, or in a microwave reactor over 1 to 24 h. Compound (30-3) can be reacted with compound (30-2) to give compound (30-4) employing the conditions described in Scheme 29.

Treatment of compound (30-4) with methanesulfonylhydrazide in solvent such as, for example, tetrahydrofuran, methanol, or ethanol, or a mixture thereof at ambient temperature to about 100° C. over a period of 8 to 48 h provides compound (30-5).

SCHEME 31

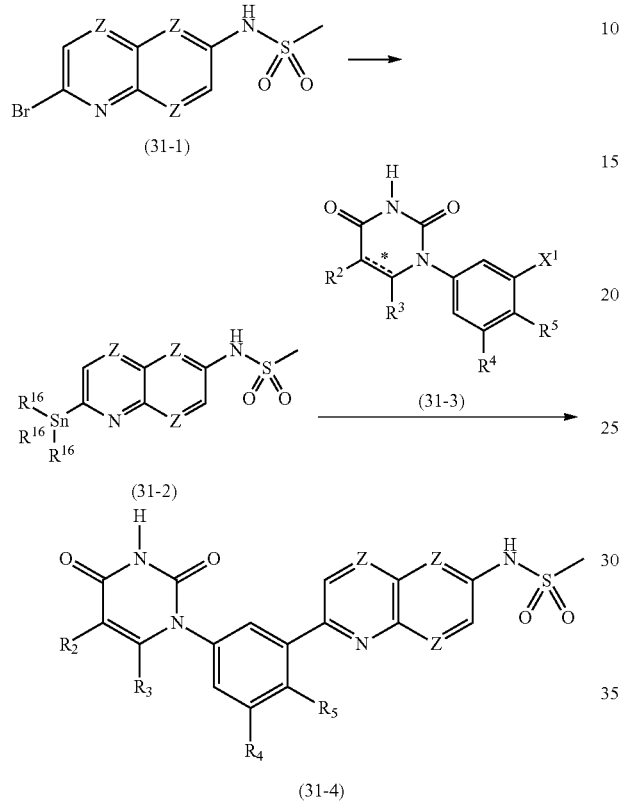

Compound (31-1) can be treated with hexamethylditin or hexabutylditin in the presence of a catalyst such as, for example, bis(triphenylphosphine)palladium (II) chloride in a solvent such as, for example, toluene or dioxane heated to about 50 to about 130° C. to supply compound (31-2). Compound (31-2) can be treated with compound (31-3) in presence of catalyst such as, for example, tris(dibenzylidineacetone)palladium (0) and ligand such as tri(2-furyl)phosphine in solvent such as, for example, toluene, dioxane, or tetrahydrofuran heated to about 40 to about 130° C. to give compound (31-4).

SCHEME 32

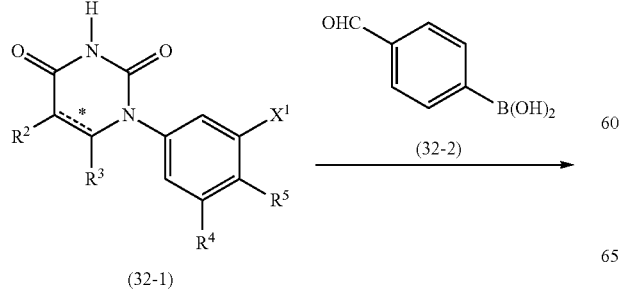

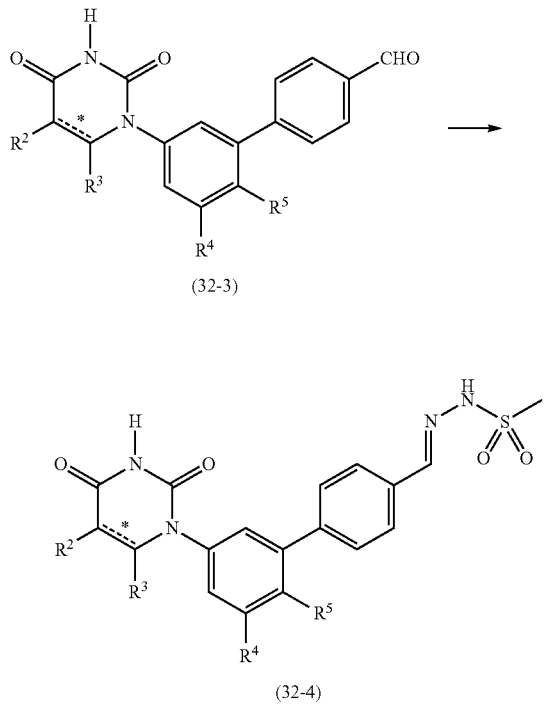

Compound (32-1) can be reacted with compound (32-2) under the Suzuki reaction conditions to give compound (32-3). Treatment with methanesulfonylhydrazide as described in Scheme 30 provides compound (32-4).

SCHEME 33

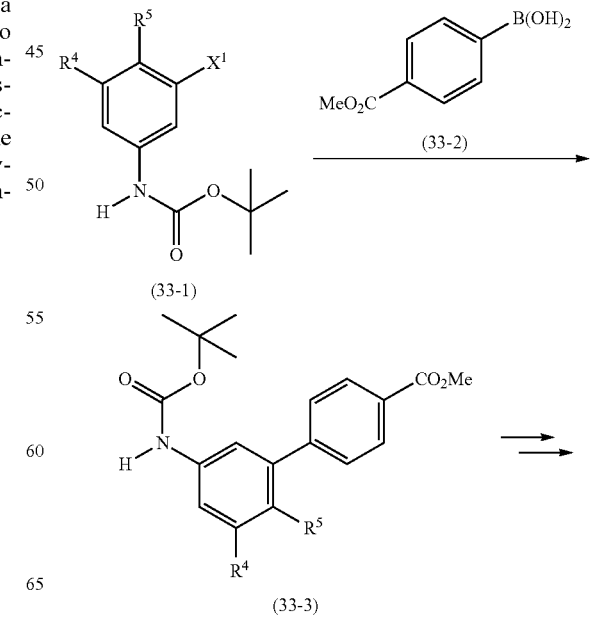

163

-continued

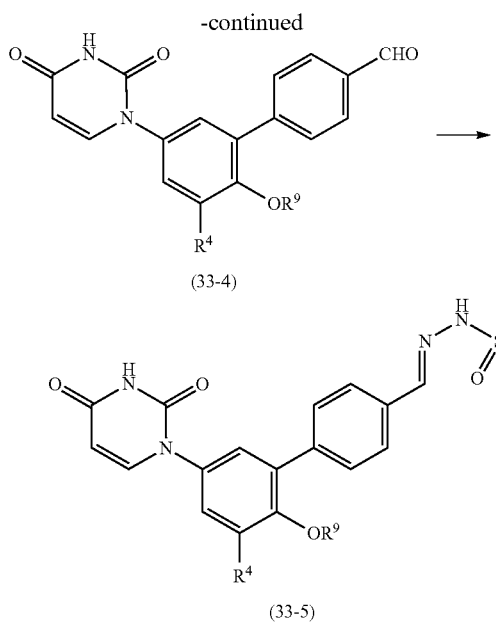

Compound (33-1) can be reacted with compound (33-2) under Suzuki reaction conditions to give compound (33-3). Compound (33-3) can be converted to compound (33-4) by first constructing the uracil ring. Then, the methyl carboxylate can be converted into the corresponding aldehyde. Compound (33-4) can be treated with methanesulfonylhydrazide to provide compound (33-5).

SCHEME 34

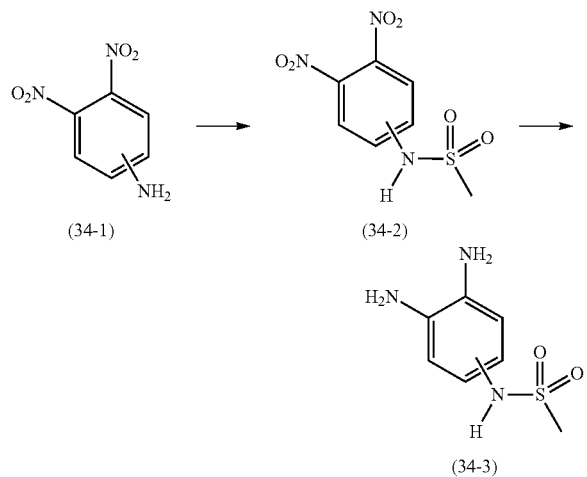

Dinitroaniline (34-1) can be sulfonylated with methanesulfonyl chloride in the presence of a base like, for example, pyridine in a solvent such as, for example, dichloromethane at room temperature over a period of about 8 to about 36 h to give compound (34-2). Compound (34-2) can be converted to compound (34-3) using iron powder in the presence of a mild acid such as, for example, ammonium chloride or dilute hydrochloric acid at reflux temperatures in a mixture of solvents, such as, for example, methanol, water, and tetrahydrofuran over about 1 to about 12 h.

SCHEME 35

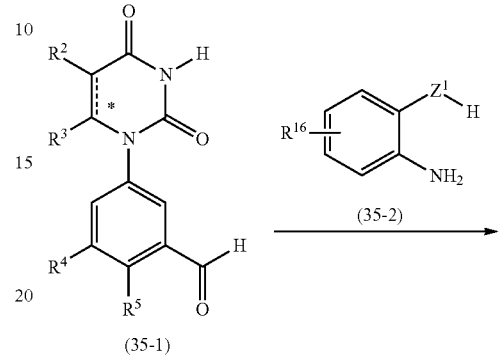

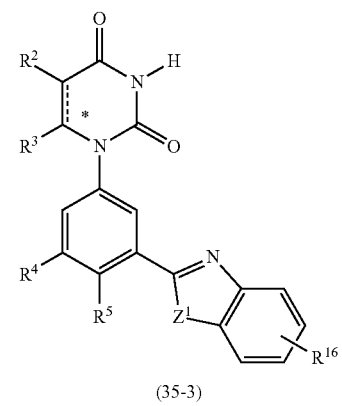

Compound (35-1) can be reacted with compound (35-2), wherein $Z^1$ is O, S, or NH and $R^{16}$ is hydrogen, —NHSO$_2$Me, or NO$_2$, in the presence of charcoal exposed to air in solvent such as, for example, toluene heated from about 90 to about 110° C. for about 24 to about 72 h to give compound (35-3).

SCHEME 36

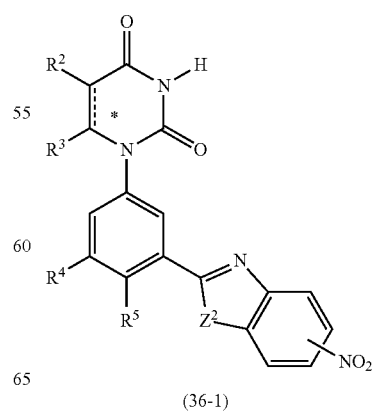

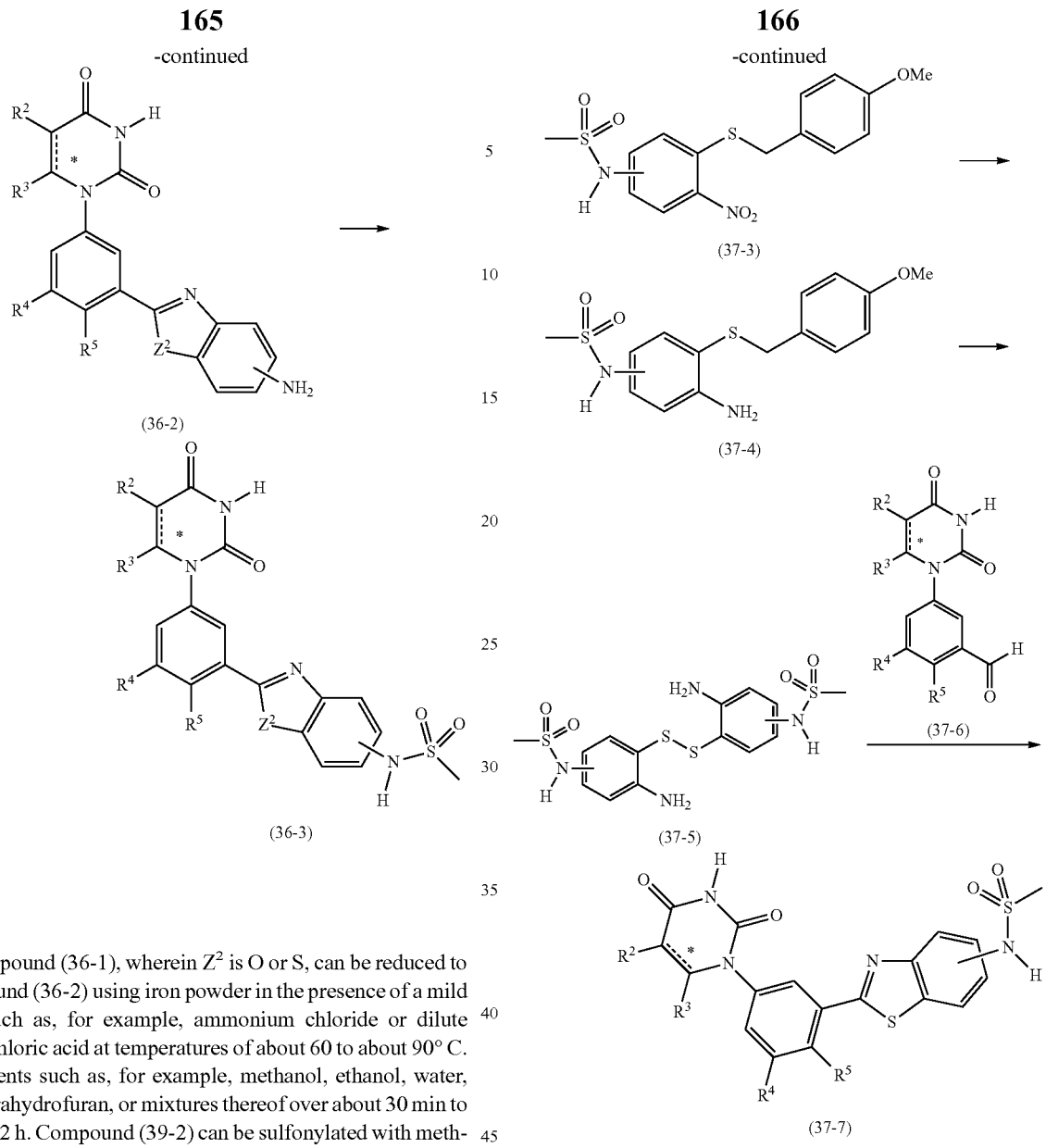

Compound (36-1), wherein $Z^2$ is O or S, can be reduced to compound (36-2) using iron powder in the presence of a mild acid such as, for example, ammonium chloride or dilute hydrochloric acid at temperatures of about 60 to about 90° C. in solvents such as, for example, methanol, ethanol, water, and tetrahydrofuran, or mixtures thereof over about 30 min to about 12 h. Compound (39-2) can be sulfonylated with methanesulfonyl chloride in the presence of a base like, for example, pyridine in a solvent such as, for example, dichloromethane at room temperature over a period of about 8 to about 36 h.

SCHEME 37

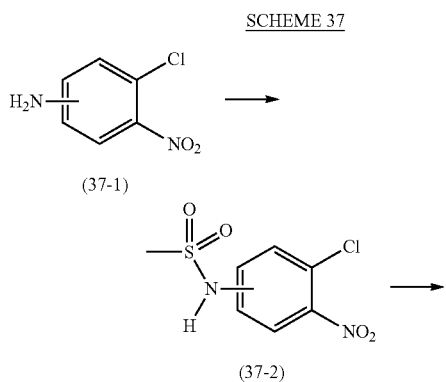

Compound (37-1) can be sulfonylated with methanesulfonyl chloride in the presence of a base like, for example, pyridine in a solvent such as, for example, dichloromethane at room temperature over a period of about 8 to about 36 h to give compound (37-2). Compound (37-2) can be reacted with (4-methoxyphenyl)methanethiol in the presence of a base such as, for example, potassium carbonate in a solvent such as, for example, dimethylformamide heated to about 90 to about 110° C. for about 8 to about 24 h to give compound (37-3). Compound (37-3) can be reduced to compound (37-4) using iron powder in the presence of a mild acid such as, for example, ammonium chloride or dilute hydrochloric acid at temperatures of about 60 to about 90° C. in solvent such as, for example, methanol, ethanol, water, and tetrahydrofuran, or mixtures thereof over about 30 min to about 12 h. Compound (37-4) can be transformed to compound (37-5) in the presence of mercury(II) acetate, anisole, and trifluoroacetic acid at about 0° C. for about 30 to about 90 min and subsequently bubbling hydrogen sulfide through the mixture. Compound (37-5) can be treated with compound (37-6) in the presence of p-toluenesulfonic acid and triphenylphosphine in a solvent such as, for example, toluene heated to reflux for about 2 to about 16 h to supply compound (37-7).

SCHEME 38

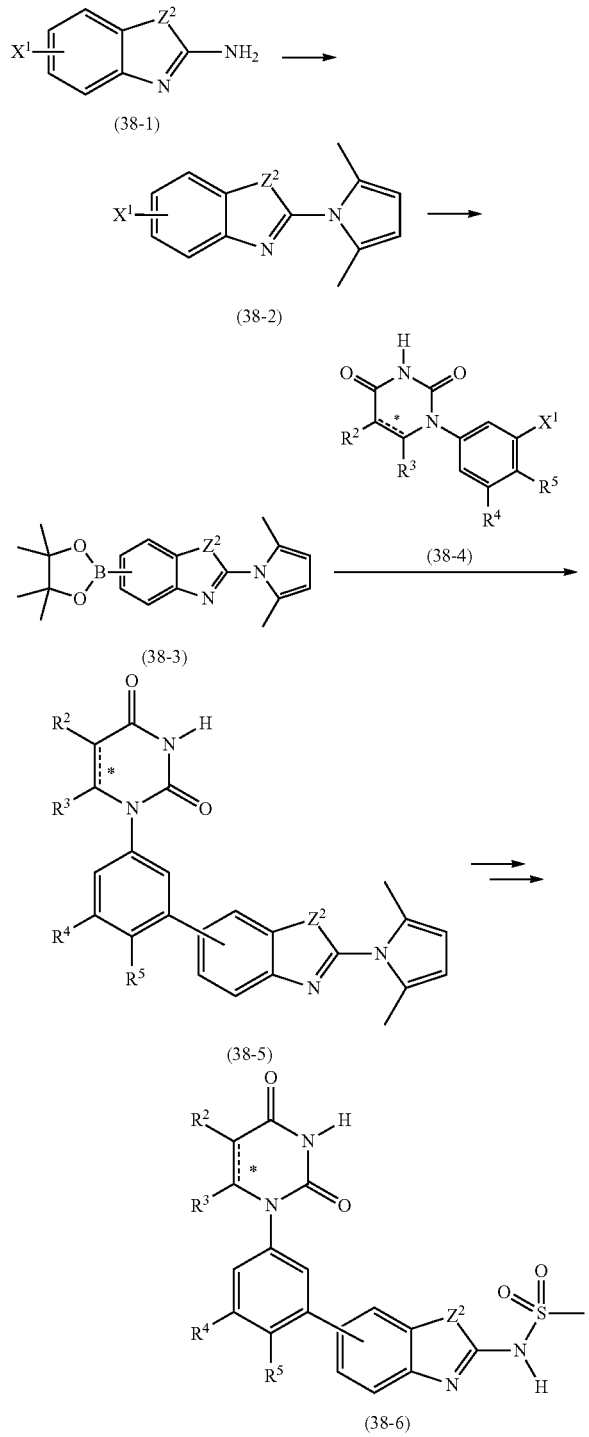

Compound (38-1), wherein $X^1$ is bromine or iodine and $Z^2$ is O or S, can be reacted with 2,5-hexanedione in the presence of a p-toluenesulfonic acid and pyridine heated in benzene to give compound of formula (38-2). Compound (38-2) can be reacted with bis(pinacolato)diboron in the presence of a catalyst such as, for example, Combiphos® Pd6, dichloro[1,1'-bis(diphenylphosphino)ferrocene]palladium (II) dichloromethane adduct, or palladium acetate in the presence of a ligand such as, for example, 2-dicyclohexylphosphino-2',4',6'-triisopropylbiphenyl (XPhos), and a base such as, for example, potassium acetate in a solvent such as, for example, toluene, dioxane, tetrahydrofuran, dimethylformamide or dimethyl sulfoxide at a temperature from about 60 to about 130° C. to give compound (38-3). Compound (38-3) can be reacted with compound (38-4) to give compound (38-5) under Suzuki reaction conditions. Such conditions include, for example, use of a palladium catalyst such as, for example, dihydrogen dichlorobis(di-t-butylphosphinito-KP)palladate (2-), tris(dibenzylidineacetone) palladium (0), palladium acetate, bis(triphenylphosphine)palladium (II) chloride, tetrakis(triphenylphosphine)palladium, or dichloro[1,1'-bis(diphenylphosphino)ferrocene]palladium (II) dichloromethane adduct; a base such as, for example, potassium acetate, potassium carbonate, potassium phosphate, potassium t-butoxide, sodium carbonate, cesium carbonate, or cesium fluoride; and solvent such as, for example, toluene, ethanol, water or tetrahydrofuran, or mixtures thereof heated in the temperature range from about 40 to about 130° C.

Compound (38-5) can be treated with hydroxylamine hydrochloride in heated ethanol to remove the pyrrole-protecting group. Then treatment with methanesulfonyl chloride in the presence of a base such as, for example, pyridine in a solvent such as, for example, dichloromethane at or near ambient temperature supplies compound (38-6).

EXAMPLES

The following examples are merely illustrative, and not limiting to this disclosure in any way.

Example A

Preparation of (E)-N-(3-tert-butyl-5-iodo-4-methoxyphenylcarbamoyl)-3-methoxy acrylamide

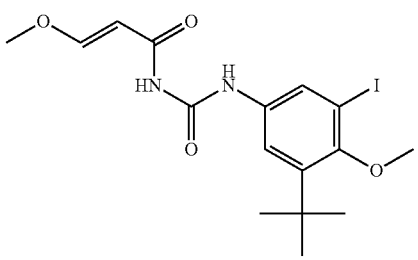

Part A. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part B. Preparation of 2-tert-butyl-6-iodo-4-nitrophenol

To the product from Part A (4.5 g, 23.05 mmol) dissolved in MeOH (120 ml) and water (30 mL) was added iodine monochloride (1.155 ml, 23.05 mmol) drop wise over a period of 10 min. The mixture was stirred for 2 h and diluted into 1 L of water and allowed to stand overnight. The solid material was collected by filtration and washed 3×50 mL with water and dried under vacuum overnight to give a tan solid (7.14 g, 96%).

Part C. Preparation of 1-tert-butyl-3-iodo-2-methoxy-5-nitrobenzene

To an ice bath cooled solution of the product from Part B (5.5 g, 17.13 mmol) in MTBE (15 ml) in a 50 mL pressure vessel was added 2.0M TMS diazomethane (12.85 ml, 25.7 mmol) followed by drop-wise addition of methanol (1.0 mL) resulting in calm bubbling. The vessel was sealed and stirred at room temperature for 16 h, cooled and the pressure was released. The solution was partitioned between EtOAc and water. The organic layer was washed with 1.0M HCl, saturated potassium carbonate solution, and saturated NaCl. The organic layer was dried over sodium sulfate, filtered and concentrated to give a red oil that was used without purification (5.4 g, 84%).

Part D. Preparation of 3-tert-butyl-5-iodo-4-methoxyaniline

A mixture of the product from Part C (5.80 g, 17.31 mmol), ammonium chloride (1.389 g, 26.0 mmol), and iron (4.83 g, 87 mmol) in THF/MeOH/water (200 mL total, 2/2/1) was refluxed for 2 h, cooled and filtered through Celite. The filtrate was evaporated and the residue was partitioned between water and EtOAc. The organic layer was washed with saturated brine, dried with sodium sulfate, filtered and evaporated to give a brown oil (5.28 g, 100% yield).

Part E. Preparation of (E)-N-(3-tert-butyl-5-iodo-4-methoxyphenylcarbamoyl)-3-methoxy acrylamide To a solution of the product from Part E (3.05 g, 10 mmol) in DMF (50 ml) at −20° C. under $N_2$ was added at a fast drip a 0.4M solution in benzene of (E)-3-methoxyacryloyl isocyanate (50.0 ml, 20.00 mmol, prepared by the method of Santana et al., J. Heterocyclic Chem. 36:293 (1999). The solution was stirred for 15 min at −20° C., warmed to room temperature for 45 min and diluted into EtOAc. The EtOAc layer was washed 4×300 mL with water, 2×100 mL with brine, dried ($Na_2SO_4$) and concentrated to a brown solid. The residue was triturated in $Et_2O$/hexane to give a fine powder that was collected by filtration and dried to give a tan powder (2.46 g, 57%).

Example B

Preparation of 1-(3-tert-butyl-5-iodo-4-methoxyphenyl)dihydropyrimidine-2,4(1H,3H)-dione

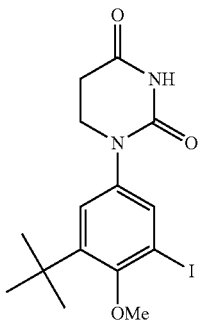 [SMILES: COc1c(I)cc(N2CCC(=O)NC2=O)cc1C(C)(C)C]

To a suspension of the product from Example A (2.46 g, 5.69 mmol) in ethanol (50 ml) was added a solution of 5.5 mL of $H_2SO_4$ in 50 mL water and the mixture was heated at 110° C. for 2.5 h to give a clear solution. The solution was cooled and diluted with 50 mL of water while stirring to give an off-white solid that was collected by filtration, washed with water and dried (2.06 g, 90%).

Example C

Preparation of 1-(3-tert-butyl-5-iodo-4-methoxyphenyl)pyrimidine-2,4(1H,3H)-dione

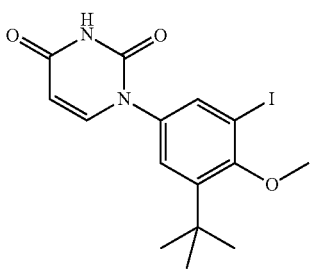 [SMILES: COc1c(I)cc(-n2ccc(=O)[nH]c2=O)cc1C(C)(C)C]

Part A. Preparation of 2-tert-butyl-4,6-diiodophenol

A solution of 2-tert-butylphenol (20.0 g, 133 mmol) in methanol (266 mL) was treated with sodium hydroxide pellets (6.39 g, 160 mmol). The mixture was stirred until all the sodium hydroxide had dissolved and was then cooled in an ice-salt bath to −2° C. Sodium iodide (15.0 g, 100 mmol) was added and then 10% sodium hypochlorite solution (45 mL, 73.3 mmol) was added drop wise at a rate such that the solution temperature rose no higher than 1.3° C. This sequence of events was repeated (3×) until a total of 60 g (400 mmol) of sodium iodide had been added and the sodium hypochlorite solution was added until the solution color changed from a light green-yellow color to the color of weak iced tea. This required all but 16 mL of the 180 mL total sodium hypochlorite solution measured out. With continued cooling at ca. 2° C., a solution of sodium thiosulfate pentahydrate (20 g) in water (100 mL) was added drop wise over 20 min. After addition, the solution was acidified to pH 3 by drop wise addition of concentrated hydrochloric acid (ca. 35 mL required of 40 mL placed in the addition funnel). The precipitate was collected by filtration and washed with >1 liter of water. The salmon-colored solid was sucked as dry as possible, and dried in a vacuum oven at 50° C. for 18 h. These procedures afforded the product (49.61 g, 93%) as a tan solid.

Part B. Preparation of 1-tert-butyl-3,5-diiodo-2-methoxybenzene

A solution of the product from Part A (20.0 g, 49.7 mmol) in acetone (140 mL) was treated with methyl iodide (3.9 mL, 8.83 g, 62.2 mmol) and 50% (w/w) sodium hydroxide solution (3.02 mL, 4.58 g, 57.2 mmol) followed by stirring at ambient temperature for 48 h. The mixture was concentrated in vacuo to a volume of ca. 50-60 mL, followed by dilution with heptane (80 mL) and water (50 mL). The layers were separated and the organic layer was extracted with saturated sodium chloride solution. Drying (Na$_2$SO$_4$) and concentration in vacuo afforded the product (20.59 g, 99%) as a light yellow oil.

Part C

Preparation of 1-(3-tert-butyl-5-iodo-4-methoxyphenyl)pyrimidine-2,4(1H,3H)-dione A suspension of the product from Part B (12.04 g, 28.9 mmol), uracil (3.89 g, 34.7 mmol), N-(2-cyanophenyl)picolinamide (1.29 g, 5.79 mmol) and tribasic potassium phosphate (12.9 g, 60.8 mmol) in DMSO (181 mL) was degassed by nitrogen sparge for 1 h. The mixture was then treated with copper (I) iodide (551 mg, 2.89 mmol) and degassing was continued for another 10 min. The mixture was then warmed at 60° C. for 18 h. The mixture was then poured into water (600 mL) and acidified to pH 3 by addition of 4N hydrochloric acid solution. The mixture was diluted with ethyl acetate, and the organic layer was extracted with water (3×), saturated ammonium chloride solution (1×) and saturated sodium chloride solution. The solution was dried and treated with (3-mercaptopropyl) silica gel, followed by stirring for 2 h. The mixture was filtered and concentrated in vacuo. The solid obtained was triturated with ether-ethyl acetate (>10:1) and collected by filtration and washed with ether. After drying in a vacuum oven at 50° C. for 2 h, these procedures afforded the product (2.75 g) as a white solid. The mother liquors were concentrated in vacuo to afford an amber solid. This material was chromatographed over a Flash 65 silica gel cartridge, eluting with 20-100% ethyl acetate in hexanes. These procedures afforded a nearly white solid, which was triturated with ether-hexanes and collected by filtration. After drying in a vacuum oven for 3 h, these procedures afforded another 4.31 g of the product as a white solid. Total yield: 7.06 g (61%).

Example D

Preparation of 1-(3-tert-Butyl-5-iodo-4-methoxyphenyl)pyrimidine-2,4(1H,3H)-dione

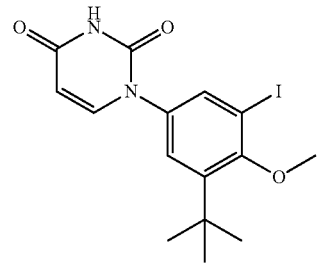 [SMILES: COc1c(I)cc(-n2ccc(=O)[nH]c2=O)cc1C(C)(C)C]

Part A. Preparation of 2-tert-butyl-4,6-diiodophenol 2-tert-Butylphenol (99.95 g, 665.36 mmol) was dissolved in 1250 mL methanol and converted to the corresponding phenoxide with 31.96 g (799.0 mmol, 1.2 equiv.) of sodium hydroxide by stirring the sodium hydroxide pellets at room temperature, and then cooling the reaction mixture in an ice/salt bath. Sodium iodide (299.34 g, 1997.07 mmol, 3.0 equiv.) and 8.3% bleach (1265.83 g, 1411.39 mmol, 2.1 equiv.) were added to the cold reaction solution in four equal portions, the bleach being added while keeping the reaction mixture at <0° C. 500 mL of 20% (w/w) sodium thiosulfate solution was added over an 18-minute period, with the temperature rising from −0.6° C. to 2.5° C. The pH of the reaction mixture was adjusted to approximately 3 by adding 197.5 mL of conc. HCl over a period of 97 min with the reaction temperature going from 1.2° C. to 4.1° C. The resulting slurry was filtered, and the wet cake washed with ~2 L of water. The wet cake was left on the Buchner funnel under vacuum overnight (approximately 15 h) to yield 289.33 g (potency adjusted yield=254.61 g) of the title product.

Part B. Preparation of 1-tert-butyl-3,5-diiodo-2-methoxybenzene

The product from Part A (93% assay, 21.6 g, 50 mmol) was dissolved in 140 mL of acetone. Methyl iodide (4.2 mL, 67.5 mmol, 1.35 equiv.) was added, followed by 50% aqueous sodium hydroxide (5.0 g, 62.5 mmol, 1.25 equiv.). The reaction was stirred overnight, then concentrated to approximately 50-60 mL. 80 mL of heptanes was added followed by 50 mL of water, and the layers were shaken and separated, and the aqueous layer was back extracted with 20 mL of heptanes. The organic layers were combined and washed twice with 50 mL each of 10% aqueous NaCl to afford 91.1 grams of a heptane solution, which assayed to 19.1 g of the title compound.

Part C. Preparation of 1-(3-tert-Butyl-5-iodo-4-methoxyphenyl)pyrimidine-2,4(1H,3H)-dione Uracil (33.3 g, 297 mmol, 1.2 equiv.), K$_3$PO$_4$ (106 g, 500 mmol, 2.1 equiv.), CuI (4.6 g, 24.2 mmol, 0.1 equiv.), and N-(2-cyanophenyl)picolinamide (6.4 g, 28.7 mmol, 0.12 equiv.) were charged to a flask and inerted with argon. The 1-tert-butyl-3,5-diiodo-2-methoxybenzene was solvent switched into MeCN, dissolved in 1 L DMSO and sparged with argon and added to the solids. The reaction was heated to 60° C. for 16 h. After cooling, the reaction was diluted with 2 L EtOAc and washed with 2.6 L water (back extracted with 3×1 L EtOAc). The combined organic layers were washed with 2×1 L of 0.25M (CuOAc)$_2$ then 2×830 mL 15% NH$_4$Cl then 800 mL brine. The organic layer was then concentrated and chased with 1 L heptane, then triturated with refluxing 85:15 (v/v) heptane:iPrOAc for 4 h. After cooling, the product was collected by filtration and washed with an additional 330 mL of 85:15 v/v heptanes:EtOAc to yield after drying 66.9 g (70% yield) of the product as a white solid.

Example E

Preparation of N-(6-(3-tert-Butyl-5-(2,4-dioxo-3,4-dihydropyrimidin-1(2H)-yl)-2-methoxyphenyl)naphthalen-2-yl)methanesulfonamide

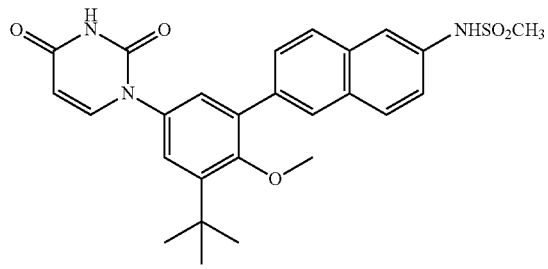

A solution of 100 mL of water and 300 mL of THF was sparged with nitrogen and then transferred via canula and nitrogen pressure to a flask containing 19.9965 g (49.96 mmol) of the product from Example D, 20.8234 g (59.97 mmol, 1.20 equivalents) of N-(6-(4,4,5,5-tetramethyl-1,3,2-dioxaborolan-2-yl)naphthalen-2-yl)methanesulfonamide, and 21.8711 g (103.03 mmol, 2.06 equivalents) of potassium phosphate which had been purged with nitrogen. The resulting solution was again sparged with nitrogen.

THF (100 mL) was sparged with nitrogen and then transferred via canula and nitrogen pressure to a flask containing 462.8 mg (0.51 mmol, 0.01 equivalents) of Pd$_2$ dba$_3$ and 735.8 mg (2.52 mmol, 0.05 equivalents) of 1,3,5,7-tetramethyl-6-phenyl-2,4,8-trioxa-6-phosphaadamantane, which had been purged with nitrogen. The resulting solution was again sparged with nitrogen.

The initial THF/water solution was transferred via canula and nitrogen pressure to the flask containing the catalyst and ligand in THF. The reaction was warmed to 50° C. and stirred overnight under positive nitrogen pressure. A sample of the reaction was taken the following morning. HPLC of the sample showed 0.28 PA % iodouracil starting material, 76.8 PA % product, and 5.2 PA % boronate.

The reaction was cooled to room temperature and washed, in three portions, with a solution of 5.84 g of L-cysteine and 81.4 g of sodium chloride in 550 mL of water which had been sparged with nitrogen. The THF solution was filtered through a celite pad. The pad was rinsed with 100 mL of THF, which was combined with the original THF solution. The THF solution was concentrated on the rotary evaporator to 136 g. To the white slurry was added 405 mL of ethyl acetate with good agitation. The slurry was filtered after stirring overnight. The wet cake was washed with 2×50 mL of ethyl acetate. The solid, an ethyl acetate solvate, was dried in the vacuum oven at 50° C. It weighed 25.49 g.

The solid and 8.7 g of 3-mercaptopropyl derivatized silica gel was stirred in 500 mL of THF then filtered through a celite pad. The filtrate was concentrated on the rotary evaporator to give 13.08 g of white solid. The solid that had been filtered off on the celite pad was extracted with 500 mL of THF at 60° C. The THF solution was concentrated to 66 g and treated with 206 mL of ethyl acetate. The solid which precipitated was filtered and dried, yielding 9.13 g of product. This solid was combined with the original solid and slurried in 100 mL of 200 proof 3 A ethanol. It was filtered and dried in the vacuum oven at 50° C. to give 20.74 g of product.

Example F

Preparation of (E)-N-(4-(3-tert-butyl-5-(2,4-dioxo-3,4-dihydropyrimidin-1(2H)-yl)-2-methoxystyryl)phenyl)methanesulfonamide

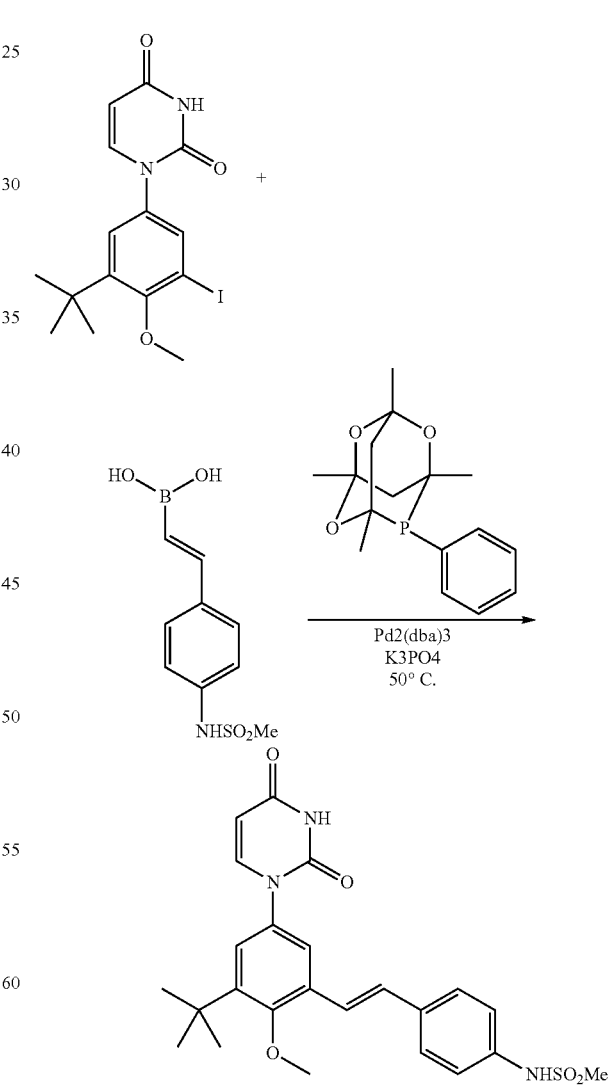

The boronic acid (96% potency) (3.75 g, 15.6 mmol, 1.2 eq), product from Example D (5.0 g, 12.5 mmol), Cytec ligand (175 mg, 5 mol %), Pd2(dba)3 (46 mg, 0.4 mol %) and potassium phosphate (5.25 g, 25.0 mmol, 2 eq.) were charged to a 3 neck RB flask. The solids were purged with nitrogen for 10 min. 75 mL 4:1 THF:water was sparged 10 min and charged to the flask. The mixture was stirred to dissolve the solids followed by heating the mixture at 50° C. in darkness overnight. HPLC showed the reaction was not complete after stirring overnight (~2% iodouracil remained). The reaction mixture was diluted with 375 mL DCM and 250 ml 10% citric acid. The mixture was shaken in a sep funnel and the layers were separated. The DCM layer was washed with a solution of 0.6 g L-cysteine in 250 ml 5% NaHCO3 for 30 min which changed the DCM layer color from orange to yellow. Repeated the 0.6 g L-cysteine in 250 ml 5% NaHCO3 for 30 min treatment followed by a 250 ml 5% NaHCO3 wash, and a 250 ml 10% NaCl wash. The DCM layer was treated with 2 gm thiourea silica for 30 min. Added 1 gm carbon to decolorize mixed 5 min and filtered through hy-flo. The wet cake was washed with DCM. The DCM solution was then stripped to give 6.74 g of a light yellow solid. The solids were ~92% pure. The solids were heated in a mixture of 192 ml DCM and 9 mlL MeOH. They never completely dissolved. Cooled to room temp with mixing. 80 ml heptane was added and more product began to crystallize. The slurry stirred over the weekend. Added 50 ml heptane in portions until a total of 230 ml heptane was added. The product was filtered. Filtrate was measured at 1.21 mg/mL at 210 nm and 1.35 at 220 nm, which equals a 522-582 mg loss in the liquors or 9-10% loss vs. theoretical. The wet cake was washed with 50 ml of a 27 ml Heptane:22 ml DCM: 1 ml MeOH mixture. The wash contained 0.5 mg/mL product or 25 mg (0.4% vs. theoretical). Product yield 5.22 gm (88.9%), purity 99.2% PA. Iodouracil was removed in the crystallization. Samples were submitted to solid state for analysis and analytical for Pd determination. NMR did not show any residual solvent.

Example 1

Preparation of (E)-N'-((3'-tert-butyl-5'-(2,4-dioxo-3,4-dihydropyrimidin-1(2H)-yl)-2'-methoxybiphenyl-4-yl)methylene)methanesulfonohydrazide (compound IB-L0-1.1)

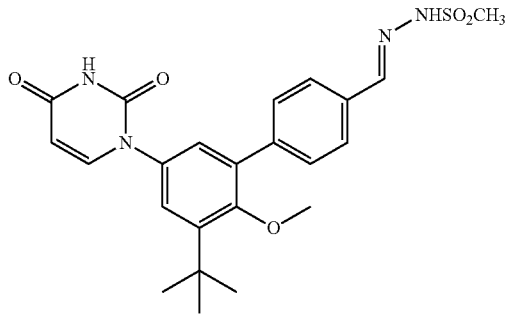

Part A. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part B. Preparation of 2-bromo-6-tert-butyl-4-nitrophenol

A solution of the product from Part A (1.0 g, 5.12 mmol) in glacial acetic acid (10.25 mL) was treated portion wise with pyridine hydrobromide perbromide (1.80 g, 5.63 mmol) followed by stirring at room temperature for 2 h. Additional pyridinium hydrobromide perbromide (3.80 g) was added in two portions and after another 3 h of stirring, the reaction was complete. The mixture was poured into ice water, and the mixture treated with a small amount of sodium sulfite. The resulting solid was filtered and dried under vacuum to give the title compound as a brown solid (1.40 g, 100%).

Part C. Preparation of 1-bromo-3-tert-butyl-2-methoxy-5-nitrobenzene

A solution of the product from Part B (1.40 g, 5.11 mmol) in 10:1 t-butylmethylether-methanol (25.5 mL) was treated with 2.0M trimethylsilyldiazomethane in ether (5.1 mL, 10.21 mmol), followed by stirring at room temperature for 18 h. The mixture was concentrated under vacuum to afford a yellow oil, which was purified by silica gel column chromatography eluting with EtOAc/hexanes to give the title compound as a yellow oil (1.36 g, 92%).

Part D. Preparation of tert-butyl 3-bromo-5-tert-butyl-4-methoxyphenylcarbamate

A solution of the product from Part C (960 mg, 3.33 mmol) in methanol (17 mL) was treated with 5% platinum on sulfided carbon (100 mg), followed by hydrogenation under balloon pressure for 3 h, and then filtered through celite and concentrated under vacuum to afford the 3-bromo-5-tert-butyl-4-methoxyaniline as a yellow oil (860 mg, 3.33 mmol, 100%). A solution of this material in THF (17 mL) was treated with di-tert-butyl dicarbonate (800 mg, 3.66 mmol) followed by warming at reflux for 2 h. Concentration under vacuum afforded a beige solid, which was purified by silica gel column chromatography eluting with EtOAc/hexanes. Solid was triturated with hexanes, collected by filtration, and dried under vacuum to give the title compound as a nearly white solid (890 mg, 75%).

Part E. Preparation of methyl 5'-(tert-butoxycarbonylamino)-3'-tert-butyl-2'-methoxy biphenyl-4-carboxylate Toluene (2 ml) and ethanol (2 ml) were combined with the product from Part E (281 mg, 0.78 mmol), methyl 4-(4,4,5,5-tetramethyl-1,3,2-dioxaborolan-2-yl)benzoate (411 mg, 1.57 mmol) and 1M sodium carbonate (0.78 ml, 0.78 mmol) and de-gassed for 20 min with $N_2$. Tetrakis(triphenyl-phosphine)palladium(0) (18 mg, 0.016 mmol) was added and de-gassing continued for 5-10 min. Heated at 100° C. in a sealed tube for 18 h, cooled and concentrated under vacuum. Purification by silica gel column chromatography eluting with EtOAc/hexanes gave the title compound (182 mg, 56%).

Part F. Preparation of methyl 5'-amino-3'-tert-butyl-2'-methoxybiphenyl-4-carboxylate To a solution of the product from Part E (180 mg, 0.43 mmol) in $CH_2Cl_2$ (4 ml) was added trifluoroacetic acid (2 ml).

Stirred for 30 min and concentrated under vacuum. Dissolved in EtOAc and washed with 10% NaHCO₃ and brine. Dried over Na₂SO₄, filtered and concentrated under vacuum to give title compound (136 mg, 100%).

Part G. Preparation of 3'-tert-butyl-5'-(2,4-dioxo-3,4-dihydropyrimidin-1(2H)-yl)-2'-methoxy biphenyl-4-carboxylate To a solution of the product from Part F (120 mg, 0.38 mmol) in DMF (2.5 ml) at −25° C. was added drop wise, (E)-3-methoxyacryloyl isocyanate (1.34 ml, 0.76 mmol) keeping the temperature below −10° C. until completion. The mixture was warmed to room temperature, stirred for 4 h and poured into ether. Washed with water and brine. Dried over Na₂SO₄, filtered and concentrated under vacuum. Purification by silica gel column chromatography eluting with EtOAc/hexanes gave (E)-methyl-3'-tert-butyl-2'-methoxy-5'-(3-(3-methoxyacryloyeureido)biphenyl-4-carboxylate (105 mg, 62%). Added ethanol (3 ml), H₂O (3 ml) and conc. H₂SO₄ (0.3 ml) and heated at 100° C. for 1 h. Cooled, poured into H₂O and extracted with EtOAc. Dried over Na₂SO₄, filtered and concentrated under vacuum. Purification by silica gel column chromatography eluting with 2% CH₃OH/CHCl₃ gave the title compound (73 mg, 79%).

Part H. Preparation of 3'-tert-butyl-5'-(2,4-dioxo-3,4-dihydropyrimidin-1(2H)-yl)-2'-methoxy biphenyl-4-carbaldehyde A solution of the product from Part G (73 mg, 0.18 mmol) in dioxane (1 ml) was treated with 0.5M LiOH (1 ml, 0.36 mmol) at room temperature for 1 h, poured into 1N HCl and extracted with EtOAc. Dried over Na₂SO₄, filtered and concentrated under vacuum to give 3'-tert-butyl-5'-(2,4-dioxo-3,4-dihydropyrimidin-1(2H)-yl)-2'-methoxybiphenyl-4-carboxylic acid (69 mg, 98%). Dissolved in thionyl chloride (2 ml) and refluxed for 3 h, cooled and concentrated under vacuum. Azeotroped twice with toluene to give 3'-tert-butyl-5'-(2,4-dioxo-3,4-dihydropyrimidin-1(2H)-yl)-2'-methoxy-biphenyl-4-carbonyl chloride (72 mg, 100%) which was dissolved in THF (1.7 ml) and cooled to −78° C. 1M lithium tri-tert-butoxyaluminum hydride (THF) (0.19 ml, 0.19 mmol) was added drop wise and stirring was continued at −78° C. for 2 h. Quenched with 1N HCl (1 ml) and warmed to room temperature. Added water and extracted with EtOAc. Washed with 10% NaHCO₃, dried over Na₂SO₄, filtered and concentrated under vacuum. Purification by silica gel column chromatography eluting with 1:1 EtOAc/hexanes gave the title compound (23 mg, 35%).

Part I. Preparation of (E)-N'-((3'-tert-butyl-5'-(2,4-dioxo-3,4-dihydropyrimidin-1(2H)-yl)-2'-methoxy-biphenyl-4-yl)methylene)methanesulfonohydrazide A solution of the product from Part H (23 mg, 0.061 mmol) in CH₃OH (0.8 ml) was treated with methanesulfonohydrazide (7.7 mg, 0.07 mmol) at room temperature for 1 h, warmed to 35° C. for 2 h, cooled and concentrated under vacuum. Purification by silica gel column chromatography eluting with 5% CH₃OH/CHCl₃ gave title compound (14.8 mg, 52%). ¹H NMR (300 MHz CDCl₃) ppm 1.44 (s, 9H) 3.21 (s, 3H) 3.32 (s, 3H) 5.82 (d, J=8.09 Hz, 1H) 7.14-7.24 (m, 1H) 7.35 (d, J=8.09 Hz, 1H) 7.61 (d, J=8.46 Hz, 2H) 7.75 (d, J=8.46 Hz, 2H) 7.79 (s, 1H) 7.87 (s, 1H) 8.21 (br s, 1H). MS (ESI+) m/z 471 (M+H)+.

Example 2

Preparation of (E)-N'-((3'-tert-butyl-5'-(2,4-dioxotetrahydropyrimidin-1(2H)-yl)-2'-methoxybiphenyl-4-yl)methylene)methanesulfonohydrazide (compound IA-L0-1.1)

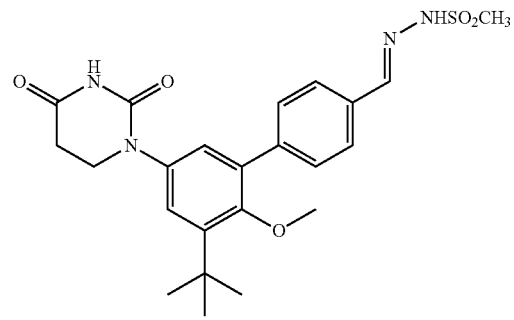

Part A. Preparation of 2-tert-butyl-6-iodo-4-nitrophenol

To the product from Example 1, Part A (4.5 g, 23.05 mmol) dissolved in MeOH (120 ml) and water (30 mL) was added iodine monochloride (1.155 ml, 23.05 mmol) drop wise over a period of 10 min. The mixture was stirred for 2 h and diluted into 1 L of water and allowed to stand overnight. The solid material was collected by filtration and washed 3×50 mL with water and dried under vacuum overnight to give a tan solid (7.14 g, 96%).

Part B. Preparation of 1-tert-butyl-3-iodo-2-methoxy-5-nitrobenzene

To an ice bath cooled solution of the product from Part A (5.5 g, 17.13 mmol) in MTBE (15 ml) in a 50 mL pressure vessel was added 2.0M TMS diazomethane (12.85 ml, 25.7 mmol) followed by drop-wise addition of methanol (1.0 mL) resulting in calm bubbling. The vessel was sealed and stirred at room temperature for 16 h, cooled and the pressure was released. The solution was partitioned between EtOAc and water. The organic layer was washed with 1.0M HCl, saturated potassium carbonate solution, and saturated NaCl. The organic layer was dried over sodium sulfate, filtered and concentrated to give a red oil that was used without purification (5.4 g, 84%).

Part C. Preparation of 3-tert-butyl-5-iodo-4-methoxyaniline

A mixture of the product from Part B (5.80 g, 17.31 mmol), ammonium chloride (1.389 g, 26.0 mmol), and iron (4.83 g, 87 mmol) in THF/MeOH/water (200 mL total, 2/2/1) was refluxed for 2 h, cooled and filtered through Celite. The filtrate was evaporated and the residue was partitioned between water and EtOAc. The organic layer was washed with saturated brine, dried with sodium sulfate, filtered and evaporated to give a brown oil (5.28 g, 100% yield).

Part D. Preparation of 1-(3-tert-butyl-5-iodo-4-methoxyphenyl)dihydropyrimidine-2,4(1H,3H)-dione The product from Part C (8.2 g, 26.9 mmol) was treated with acrylic acid (5.53 ml, 81 mmol) and stirred overnight to give an extremely viscous mixture. The mixture was treated with acetic acid (60 mL) and urea (7.3 g 120 mmol), heated at 120° C. for 24 h, cooled and concentrated. The residue was azeotroped 3×100 mL with toluene to give a brown/tan solid. The solid was suspended in a mixture of 50 mL EtOAc and 100 mL of saturated NaHCO₃ and stirred for thirty min to neutralize any remaining acetic acid. The solid was collected by filtration and washed repeatedly with 50 mL portions of water and finally with 3:1 hexane/EtOAc (50 mL) to give an off-white solid that was dried to constant mass (7.1 g, 66%).

Part E. Preparation of 3'-tert-butyl-5'-(2,4-dioxotetrahydropyrimidin-1(2H)-yl)-2'-methoxy biphenyl-4-carbaldehyde A mixture of the product from Part D (101 mg, 0.25 mmol), 4-formylphenylboronic acid (56.2 mg, 0.38 mmol), 1M sodium carbonate (0.25 mL, 0.25 mmol) and 1,1'-bis(diphenylphosphino) ferrocene-palladium(II)dichloride dichloromethane complex (10.2 mg, 0.013 mmol) in toluene/ethanol (2 mL, 1/1) was purged with bubbling N₂ for 5 min and microwaved at 100° C. for 15 min. Extracted with EtOAc and washed with brine. Dried over Na₂SO₄, filtered and concentrated under vacuum. Purification by silica gel column chromatography eluting with MeOH/CH₂Cl₂ (1% to 5%) gave the title compound (92 mg, 97%).

Part F. Preparation of (E)-N'-((3'-tert-butyl-5'-(2,4-dioxotetrahydropyrimidin-1(2H)-yl)-2'-methoxybiphenyl-4-yl)methylene)methanesulfonohydrazide A mixture of the product from Part E (90 mg, 0 24 mmol) and methanesulfonohydrazide (29 mg, 0.26 mmol) in methanol (4 mL) was heated at 40° C. for 2 h. Evaporated and purified by silica gel column chromatography eluting with MeOH/CH₂Cl₂ (1% to 4%) to give the title compound (80 mg, 72%). m.p. 209-211° C. ¹H NMR (300 MHz, DMSO-D6) δ 1.39 (s, 9H) 2.70 (t, J=6.62 Hz, 2H) 3.08 (s, 3H) 3.24 (s, 3H) 3.80 (t, J=6.62 Hz, 2H) 7.17 (d, J=2.57 Hz, 1H) 7.24 (d, J=2.94 Hz, 1H) 7.59 (d, J=8.46 Hz, 2H) 7.77 (d, J=8.46 Hz, 2H) 8.04 (s, 1H) 10.33 (s, 1H) 11.10 (s, 1H).

Example 3

Preparation of N-(6-(3-tert-butyl-5-(2,4-dioxotetrahydropyrimidin-1(2H)-yl)-2-methoxyphenyl)naphthalen-2-yl)methanesulfonamide (compound IA-L0-2.9)

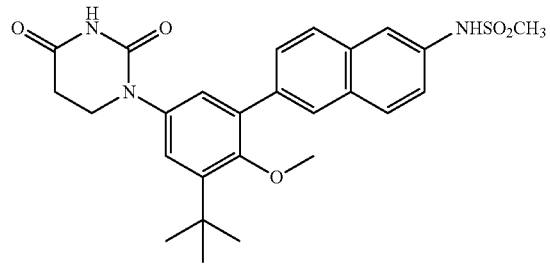

Part A. Preparation of 6-bromo-2-naphthoic acid

A solution of methyl 6-bromo-2-naphthoate (7.70 g, 29.0 mmol) in 2:1 THF:water (150 mL) was treated with lithium hydroxide hydrate (2.44 g, 58.1 mmol) followed by stirring at room temperature for 48 h. Concentrated under vacuum, diluted with water and cooled to 0° C. Acidified to pH3 with 4N HCl. Solids were collected by filtration, dissolved in toluene-EtOAc (ca. 2 L) and washed with brine. Dried over Na₂SO₄, filtered and concentrated under vacuum. Brown solid was triturated with ether, collected by filtration, and dried under vacuum to give the title compound as a nearly white solid (5.07 g, 70%).

Part B. Preparation of 6-bromonaphthalen-2-amine

A solution of the product Part A (5.07 g, 20.19 mmol) and triethylamine (4.22 mL, 3.07 g, 30.3 mmol) in dry DMF (155 mL) was treated with the diphenylphosphoroyl azide (6.55 mL, 8.34 g, 30.3 mmol) followed by stirring at room temperature for 3 h. The solution was then treated with water (20 mL) followed by warming at 100° C. for 1 h. The solution was cooled and the flask fitted with a short-path distillation head and the DMF removed by distillation under high vacuum. The solid residue was dissolved in EtOAc and washed with saturated sodium bicarbonate solution. Filtered through celite and the filtrate was washed with water (3×) and then with brine. Dried over Na₂SO₄, filtered and concentrated under vacuum to give the title compound as a beige solid (4.48 g, 100%).

Part C. Preparation of benzyl 6-bromonaphthalen-2-ylcarbamate

A mixture of the product from Part B (1.79 g, 8.06 mmol) and saturated sodium bicarbonate solution (18 mL) in acetone (40 mL) at 0° C. was treated drop wise with benzyl chloroformate. The mixture was stirred at 0° C. for 1 h, and then allowed to gradually warm to room temperature over 18 h. The mixture was diluted with EtOAc and water and the layers separated. The organic layer was extracted with water and washed with brine. Dried over Na₂SO₄, filtered and concentrated under vacuum. Purification by silica gel column chromatography eluting with EtOAc/hexanes gave the title compound as a pink solid (1.5 g, 52%).

Part D. Preparation of benzyl 6-(4,4,5,5-tetramethyl-1,3,2-dioxaborolan-2-yl)naphthalen-2-yl carbamate A resealable Schlenk tube containing a solution of the product from Part C (1.42 g, 3.99 mmol), bis(pinacolato)diboron (1.11 g, 4.39 mmol), and potassium acetate (1.17 g, 11.96 mmol) in DMF (28 mL) was degassed by three freeze-thaw cycles. The solution was treated with 1,1'-bis(diphenyl phosphino)ferrocene palladium (II) chloride dichloromethane complex (98 mg, 0.12 mmol), followed by degassing by two additional freeze-thaw cycles. The Schlenk tube was then sealed and the mixture warmed at 80° C. for 18 h. Cooled and diluted with ethyl acetate and water. The mixture was treated with Darco G-60 and then filtered through celite. The filtrate was extracted with water (4×) and saturated sodium chloride solution. Dried over $Na_2SO_4$, filtered and concentrated under vacuum afforded a light brown oil. Purification by silica gel column chromatography eluting with EtOAc/hexane gave the title compound as a colorless oil (910 mg, 57%).

Part E. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part F. Preparation of 2-bromo-6-tert-butyl-4-nitrophenol

A solution of the product from Part E (1.0 g, 5.12 mmol) in glacial acetic acid (10.25 mL) was treated portion wise with pyridine hydrobromide perbromide (1.80 g, 5.63 mmol) followed by stirring at room temperature for 2 h. Additional pyridinium hydrobromide perbromide (3.6 g) was added in two portions and after another 3 h of stirring, the reaction was complete. The mixture was poured into ice water, and the mixture treated with a small amount of sodium sulfite. The resulting solid was filtered and dried under vacuum to give the title compound as a brown solid (1.40 g, 100%).

Part G. Preparation of 1-bromo-3-tert-butyl-2-methoxy-5-nitrobenzene

A solution of the product from Part F (1.40 g, 5.11 mmol) in 10:1 t-butylmethylether-methanol (25.5 mL) was treated with 2.0M trimethylsilyldiazomethane in ether (5.1 mL, 10.21 mmol), followed by stirring at room temperature for 18 h. The mixture was concentrated under vacuum to afford a yellow oil, which was purified by silica gel column chromatography eluting with EtOAc/hexanes to give the title compound as a yellow oil (1.36 g, 92%).

Part H. Preparation of tert-butyl 3-bromo-5-tert-butyl-4-methoxyphenylcarbamate

A solution of the product from Part G (960 mg, 3.33 mmol) in methanol (17 mL) was treated with 5% platinum on sulfided carbon (100 mg), followed by hydrogenation under balloon pressure for 3 h, and then filtered through celite and concentrated under vacuum to afford the 3-bromo-5-tert-butyl-4-methoxyaniline as a yellow oil (860 mg, 3.33 mmol, 100%). A solution of this material in THF (17 mL) was treated with di-tert-butyl dicarbonate (800 mg, 3.66 mmol) followed by warming at reflux for 2 h. Concentration under vacuum afforded a beige solid, which was purified by silica gel column chromatography eluting with EtOAc/hexanes. Solid was triturated with hexanes, collected by filtration, and dried under vacuum to give the title compound as a nearly white solid (890 mg, 75%).

Part I. Preparation of benzyl 6-(3-tert-butyl-5-(tert-butylcarbamoyl)-2-methoxyphenyl)naphthalen-2-yl carbamate Toluene (928 ul) and EtOH (928 ul) were combined with the product from Part H (133 mg, 0.37 mmol), the product from Part D (299 mg, 0.74 mmol) and 1M sodium carbonate (371 ul, 0.37 mmol) and de-gassed for 20 min with nitrogen. Tetrakis(triphenylphosphine)palladium(0) (8.6 mg, 7.4 umol) was added and de-gassing continued 5-10 min. Heated at 85-90° C. for 18 h, cooled and concentrated under vacuum. Purification by silica gel column chromatography eluting with EtOAc/hexanes gave the title compound (102 mg, 49%).

Part J. Preparation of benzyl 6-(3-tert-butyl-5-(2,4-dioxotetrahydropyrimidin-1(2H)-yl)-2-methoxyphenyl)naphthalen-2-ylcarbamate A solution of the product from Part I (100 mg, 0.18 mmol) in $CH_2Cl_2$ (1.0 ml) was treated with trifluoroacetic acid (0.5 ml, 6.5 mmol) at room temperature for 1 h. Concentrated under vacuum. Dissolved in ethyl acetate, washed with 10% $NaHCO_3$, brine. Dried over $Na_2SO_4$, filtered and concentrated under vacuum. Dissolved in toluene (1.0 ml) and added $Et_3N$ (25 ul, 0.18 mmol) and acrylic acid (13 ul, 0.19 mmol) and the mixture was refluxed for 16 h. Concentrated under vacuum. Dissolved in acetic acid (1.0 ml, 17.5 mmol) and added urea (11.9 mg, 0.20 mmol) and refluxed for 72 h. Cooled and poured into ice water, extracted three times with $CHCl_3$, combined extracts, dried over $Na_2SO_4$, filtered and concentrated under vacuum. Purification by silica gel column chromatography eluting with EtOAc/hexanes gave title compound (57.5 mg, 58%).

Part K. Preparation of N-(6-(3-tert-butyl-5-(2,4-dioxotetrahydropyrimidin-1(2H)-yl)-2-methoxyphenyl)naphthalen-2-yl)methanesulfonamide Combined the product from Part J (56 mg, 0.10 mmol) and EtOAc (1.0 ml) and added 10% palladium on carbon (10 mg). Stirred under a balloon of $H_2$ gas for 16 h. Filtered through Celite and concentrated under vacuum. Dissolved in $CH_2Cl_2$ (1.0 ml), added $Et_3N$ (16 ul, 0.115 mmol) and methanesulfonyl chloride (8.7 ul, 0.112 mmol) and stirred at room temperature for 30 min. Concentrated under vacuum and purification by silica gel column chromatography eluting with EtOAc/hexanes gave the title compound (10 mg, 20%). $^1H$ NMR (300 MHz, DMSO-d6) δ 1.34-1.48 (m, 9H) 2.71 (t, J=6.62 Hz, 2H) 3.08 (s, 3H) 3.21 (s, 3H) 3.82 (t, J=6.62 Hz, 2H) 7.26 (s, 2H) 7.41 (dd, J=8.82, 1.84 Hz, 1H) 7.59-7.76 (m, 2H) 7.89-8.04 (m, 3H) 10.03 (s, 1H) 10.34 (s, 1H); MS (ESI+) m/z 496 (M+H)+; (ESI−) m/z 494 (M−H)−.

Example 4A

Preparation of N-(6-(3-tert-butyl-5-(2,4-dioxo-3,4-dihydropyrimidin-1(2H)-yl)-2-methoxyphenyl)naphthalen-2-yl)methanesulfonamide (compound IB-L0-2.3)

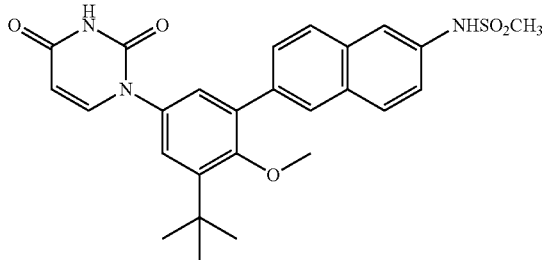

Part A. Preparation of N-(6-bromonaphthalen-2-yl)methanesulfonamide

A solution of the product from Example 3, Part B (4.48 g, 20.17 mmol) in pyridine (100 mL) was treated drop wise with methanesulfonyl chloride (1.97 mL, 2.89 g, 25.2 mmol) followed by stirring at room temperature for 1 h. Diluted with toluene and concentrated under vacuum twice. The residue was extracted with EtOAc and washed with water, 1M citric acid and brine. Treated with Darco G-60, dried over $Na_2SO_4$, filtered through celite and concentrated under vacuum. Solid was triturated with ether-hexane, collected by filtration and dried under vacuum to give the title compound as a faint pink solid (3.32 g, 55%).

Part B. Preparation of N-(6-(4,4,5,5-tetramethyl-1,3,2-dioxaborolan-2-yl)naphthalen-2-yl)methanesulfonamide A mixture of the product from Part A (1.00 g, 3.33 mmol), bis(pincolato)diboron (1.27 g, 5.00 mmol), potassium acetate (0.98 g, 9.99 mmol) and Combiphos Pd6 (84 mg, 0.17 mmol) in toluene (22 mL) was heated at reflux for 3 h. Cooled and diluted with ethyl acetate and water. The mixture was treated with Darco G-60 and filtered through celite. The filtrate was washed with water and brine. Dried over $Na_2SO_4$, filtered and concentrated under vacuum. Oil was dissolved in ether and precipitated by addition of hexanes. The product was collected by filtration and washed with hexanes. Evaporation of the filtrate and purification by silica gel column chromatography eluting with EtOAc/hexanes. The title compound from crystallization and chromatography was obtained as a white solid (927 mg, 80%).

Part C. Preparation of tert-butyl 3-tert-butyl-4-methoxy-5-(6-(methylsulfonamido) naphthalen-2-yl)phenylcarbamate Combined the product from Example 3, Part H (87 mg, 0.243 mmol), the product from Part B (169 mg, 0.486 mmol), toluene (1.0 ml), ethanol (1.0 ml) and sodium carbonate (0.243 ml, 0.243 mmol) in a sealed tube and de-gassed with $N_2$ gas for 20 min. Tetrakis(triphenylphosphine)palladium(0) (5.61 mg, 4.86 mmol) was added and de-gassing was continued another 5-10 min. Heated at 90-95° C. for 16 h. Cooled and concentrated under vacuum. Purification by silica gel column chromatography eluting with EtOAc/hexanes gave the title compound (92.2 mg, 76%).

Part D. Preparation of N-(6-(3-tert-butyl-5-(2,4-dioxo-3,4-dihydropyrimidin-1(2H)-yl)-2-methoxyphenyl)naphthalen-2-yl)methanesulfonamide A solution of the product from Part C (90 mg, 0.180 mmol) in $CH_2Cl_2$ (2.0 ml) was treated with trifluoroacetic acid (1.0 ml, 12.98 mmol) at room temperature for 1 h. Concentrated under vacuum, dissolved residue in EtOAc, washed with 10% $NaHCO_3$, and brine. Dried over $Na_2SO_4$, filtered and concentrated under vacuum. Dissolved in DMF (1.4 ml) and cooled to −25° C. and added (E)-3-methoxy-acryloyl isocyanate (0.633 ml, 0.361 mmol) drop wise while maintaining the temperature below −10° C. Warmed to room temperature and stirred for 2 h. Poured into ether, washed with water, and brine. Dried over $Na_2SO_4$, filtered and concentrated under vacuum. Added a mixture of $H_2SO_4$ (0.1 ml, 1.876 mmol), water (1.0 ml) and EtOH (1.0 ml) and stirred at 100° C. 16 h. Cooled and concentrated under vacuum. Poured into water, extracted with EtOAc, combined extracts and washed with brine. Dried over $Na_2SO_4$, filtered and concentrated under vacuum. Purification by silica gel column chromatography eluting with MeOH/$CHCl_3$ gave the title compound (53 mg, 59%). $^1$H NMR (300 MHz DMSO-d6) δ 1.42 (s, 9H) 3.08 (s, 3H) 3.25 (s, 3H) 5.65 (d, J=7.72 Hz, 1H) 7.34 (dd, J=15.81, 2.57 Hz, 2H) 7.42 (dd, J=8.82, 1.84 Hz, 1H) 7.65-7.76 (m, 2H) 7.80 (d, J=8.09 Hz, 1H) 7.96 (t, J=8.27 Hz, 2H) 8.02 (s, 1H) 10.04 (s, 1H) 11.41 (s, 1H); MS (ESI+) m/z 494 (M+H)+; (ESI−) m/z 492 (M−H)−.

Example 4B

Preparation of N-(6-(3-tert-butyl-5-(2,4-dioxo-3,4-dihydropyrimidin-1(2H)-yl)-2-methoxyphenyl)naphthalen-2-yl)methanesulfonamide (compound IB-L0-2.3)

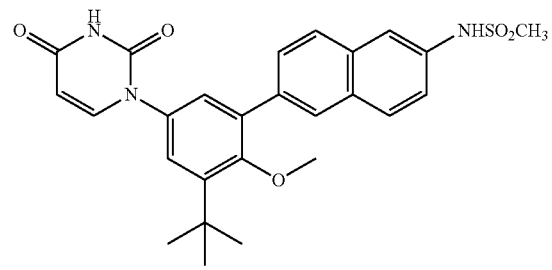

Part A. Preparation of 2-tert-butyl-6-iodo-4-nitrophenol

To the product from Example 3, Part E (4.5 g, 23.05 mmol) dissolved in MeOH (120 ml) and water (30 mL) was added iodine monochloride (1.155 ml, 23.05 mmol) drop wise over a period of 10 min. The mixture was stirred for 2 h and diluted into 1 L of water and allowed to stand overnight. The solid material was collected by filtration and washed 3×50 mL with water and dried under vacuum overnight to give a tan solid (7.14 g, 96%).

Part B. Preparation of
1-tert-butyl-3-iodo-2-methoxy-5-nitrobenzene

To an ice bath cooled solution of the product from Part A (5.5 g, 17.13 mmol) in MTBE (15 ml) in a 50 mL pressure vessel was added 2.0M trimethylsilyl diazomethane (12.85 ml, 25.7 mmol) followed by drop-wise addition of methanol (1.0 mL) resulting in calm bubbling. The vessel was sealed and stirred at room temperature for 16 h, cooled and the pressure was released. The solution was partitioned between EtOAc and water. The organic layer was washed with 1.0M HCl, saturated potassium carbonate solution, and saturated NaCl. The organic layer was dried over sodium sulfate, filtered and concentrated to give a red oil that was used without purification (5.4 g, 84%).

Part C. Preparation of
3-tert-butyl-5-iodo-4-methoxyaniline

A mixture of the product from Part B (5.80 g, 17.31 mmol), ammonium chloride (1.389 g, 26.0 mmol), and iron (4.83 g, 87 mmol) in THF/MeOH/water (200 mL total, 2/2/1) was refluxed for 2 h, cooled and filtered through Celite. The filtrate was evaporated and the residue was partitioned between water and EtOAc. The organic layer was washed with saturated brine, dried with sodium sulfate, filtered and evaporated to give a brown oil (5.28 g, 100% yield).

Part D. Preparation of (E)-N-(3-tert-butyl-5-iodo-4-methoxyphenylcarbamoyl)-3-methoxy acrylamide To a solution of the product from Part C (3.05 g, 10 mmol) in DMF (50 ml) at −20° C. under $N_2$ was added at a fast drip a 0.4M solution in benzene of (E)-3-methoxyacryloyl isocyanate (50.0 ml, 20.00 mmol, prepared by the method of Santana et al., J. Heterocyclic. Chem. 36:293 (1999). The solution was stirred for 15 min at −20° C., warmed to room temperature for 45 min and diluted with EtOAc. The organic was washed with water and brine. Dried over $Na_2SO_4$, filtered and concentrated to a brown solid. The residue was triturated in $Et_2O$/hexane to give a fine powder that was collected by filtration and dried under vacuum to give the title compound as a tan powder (2.46 g, 57%).

Part E. Preparation of 1-(3-tert-butyl-5-iodo-4-methoxyphenyl)dihydropyrimidine-2,4(1H,3H)-dione To a suspension of the product from Part D (2.46 g, 5.69 mmol) in ethanol (50 ml) was added a solution of 5.5 mL of $H_2SO_4$ in 50 mL water and the mixture was heated at 110° C. for 2.5 h to give a clear solution. Cooled and diluted with 50 mL of water while stirring to give an off-white solid that was collected by filtration, washed with water and dried under vacuum to give the title compound (2.06 g, 90%).

Part F. Preparation of N-(6-(3-tert-butyl-5-(2,4-dioxo-3,4-dihydropyrimidin-1(2H)-yl)-2-methoxyphenyl)naphthalen-2-yl)methanesulfonamide In a microwave tube, the product from Part E (104 mg, 0.26 mmol), the product from Example 4A, Part B (108 mg, 0.31 mmol), and 1.0M sodium carbonate solution (312 μL, 0.31 mmol) in 1:1 ethanol-toluene (1.7 mL) was degassed by nitrogen sparge for 15 min. 1,1'-Bis(diphenylphosphino) ferrocene palladium (II) chloride dichloromethane complex (9 mg, 0.011 mmol) was added, and degassing was continued for another 5 min. The tube was sealed and heated in the microwave at 100° C. for 1 h. Diluted with dichloromethane and washed with 1M citric acid solution and brine. The organic layer was then stirred with (3-mercaptopropyl) silica gel for 1 h. Filtered through celite and concentrated under vacuum. Triturated with ether, methanol, and then again with ether to give the title compound as a nearly white solid (32 mg, 25%). $^1$H NMR (300 MHz, DMSO-$d_6$): δ 11.41 (d, J=1.84 Hz, 1H) 10.04 (s, 1H) 8.03 (s, 1H) 7.96 (t, J=8.09 Hz, 2H) 7.80 (d, J=8.09 Hz, 1H) 7.63-7.79 (m, 2H) 7.35-7.45 (m, 1H) 7.37 (d, J=2.57 Hz, 1H) 7.32 (d, J=2.57 Hz, 1H) 5.65 (dd, J=8.09, 2.21 Hz, 1H) 3.25 (s, 3H) 3.09 (s, 3H) 1.43 (s, 9H). MS (+ESI) m/z (rel abundance): 494 (100, M+H), 511 (90, M+NH4), 987 (20, 2M+H), 1009 (8, 2M+Na).

Example 5

Preparation of N-(6-(3-tert-butyl-5-(2,4-dioxo-3,4-dihydropyrimidin-1(2H)-yl)-2-methoxyphenyl)quinolin-2-yl)methanesulfonamide (compound IB-L0-2.5)

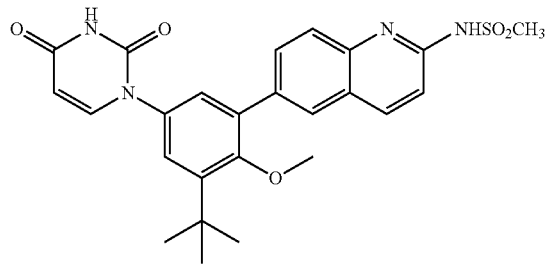

Part A. Preparation of
(E)-N-(4-bromophenyl)-3-methoxyacrylamide

Combined 4-bromoaniline (285 mg, 1.659 mmol), $CH_2Cl_2$ (2.0 ml) and pyridine (0.25 ml, 3.09 mmol) and slowly added (E)-3-methoxyacryloyl chloride (200 mg, 1.659 mmol) sand stirred at room temperature for 2 h. The resulting yellow solid was filtered off and washed with water. The solid was dried under vacuum to give the title compound (406 mg, 96%).

Part B. Preparation of 6-Bromoquinolin-2(1H)-one

The product from Part A (395 mg, 1.542 mmol) was added in portions to $H_2SO_4$ (4.5 ml). Stirred for 3 h at room temperature, poured onto crushed ice. Solid filtered, washed with water and dried under vacuum to give the title compound (203 mg, 59%).

Part C. Preparation of 6-bromo-2-chloroquinoline

To phosphorus oxychloride (2.5 ml, 26.8 mmol) was added, in portions, the product from Part B (200 mg, 0.893 mmol). Refluxed for 1 h, cooled to room temperature and poured onto crushed ice. Extracted with $CHCl_3$, extracts combined, dried over $mgSO_4$, filtered and concentrated under vacuum to give the title compound (173 mg, 80%).

Part D. Preparation of 6-bromo-2-aminoquinoline

The product from Part C (173 mg, 0.713 mmol), acetamide (843 mg, 14.27 mmol) and potassium carbonate (493 mg, 3.57 mmol) were combined and heated at 200° C. for 2 h.

Cooled to room temperature, whereupon it solidified. Dissolved in a mixture of CHCl₃ and water. Aqueous layer was extracted twice more with CHCl₃, extracts were combined, washed with brine, dried over Na₂SO₄, filtered and concentrated under vacuum. Purification by silica gel column chromatography eluting with MeOH/CHCl₃ gave title compound (92 mg, 58%).

Part E. Preparation of N-(6-bromoquinolin-2-yl)-N-(methylsulfonyl)methanesulfonamide Combined the product from Part D (90 mg, 0.403 mmol) and CH₂Cl₂ (2.0 ml) and added triethylamine (0.062 ml, 0.444 mmol) and methanesulfonyl chloride (0.035 ml, 0.444 mmol). Stirred at room temperature 16 h. Added triethylamine (0.062 ml, 0.444 mmol) and methanesulfonyl chloride (0.035 ml, 0.444 mmol) and stirred at room temperature for 1 h. Diluted with EtOAc, washed with 10% citric acid, 10% NaHCO₃ and brine. Dried over Na₂SO₄, filtered and concentrated under vacuum. Dissolved in EtOAc and poured into excess hexane. Solid collected by filtration to give the title compound (94 mg, 61%).

Part F. Preparation of N-(methylsulfonyl)-N-(6-(4,4,5,5-tetramethyl-1,3,2-dioxaborolan-2-yl)quinolin-2-yl)methanesulfonamide Combined the product from Part E (94 mg, 0.248 mmol), bis(pinacolato)diboron (94 mg, 0.372 mmol), potassium acetate (73.0 mg, 0.744 mmol), Combi-Phos® PD6 (6.22 mg, 0.012 mmol) and toluene (1.5 ml) and refluxed 18 h. Cooled to room temperature, diluted with EtOAc and water, filtered through Celite, separated the phases, washed the organic phase with brine. Dried over Na₂SO₄, filtered and concentrated under vacuum. Purification by silica gel column chromatography eluting with EtOAc/hexanes gave title compound (67 mg, 63%).

Part G. Preparation of N-(6-(3-tert-butyl-5-(2,4-dioxo-3,4-dihydropyrimidin-1(2H)-yl)-2-methoxyphenyl)quinolin-2-yl)methanesulfonamide Combined in a microwave tube the product from Example 4B, Part E (27 mg, 0.067 mmol), the product from Part F (37.4 mg, 0.088 mmol), ethanol (1.0 ml), toluene (1.0 ml) and 1M sodium carbonate (0.067 ml, 0.067 mmol) and the solution was degassed using N₂ gas for 20 min. Tetrakis-(triphenylphosphine)palladium(0) (1.559 mg, 1.349 mmol) was added and the solution was degassed an additional 5 min. The tube was sealed and heated in the microwave at 100° C. for 45 min. Cooled solution diluted with 1:1 EtOAc:water and filtered through Celite. Aqueous layer was extracted twice more with EtOAc, combined organic extracts and washed with brine. Dried over Na₂SO₄, filtered and concentrated under vacuum. Purification by silica gel column chromatography eluting with MeOH/CHCl₃ gave title compound (13.7 mg, 41%). ¹H NMR (300 MHz, CDCl₃) δ 1.45 (s, 9H) 3.18 (s, 3H) 3.30 (s, 3H) 5.83 (dd, J=7.91, 2.02 Hz, 1H) 6.99 (d, J=8.82 Hz, 1H) 7.21 (d, J=2.57 Hz, 1H) 7.36 (d, J=7.72 Hz, 1H) 7.52 (d, J=8.46 Hz, 1H) 7.82-7.91 (m, 2H) 7.98 (d, J=9.19 Hz, 1H) 8.29 (s, 1H); MS (ESI+) m/z 495 (M+H)⁺; (ESI−) m/z 493 (M−H)⁻.

Example 6

Preparation of (E)-N'-(5-(3-tert-butyl-5-(2,4-dioxo-3,4-dihydropyrimidin-1(2H)-yl)-2-methoxyphenyl)-2,3-dihydro-1H-inden-1-ylidene)methanesulfonohydrazide (compound IB-L0-2.4)

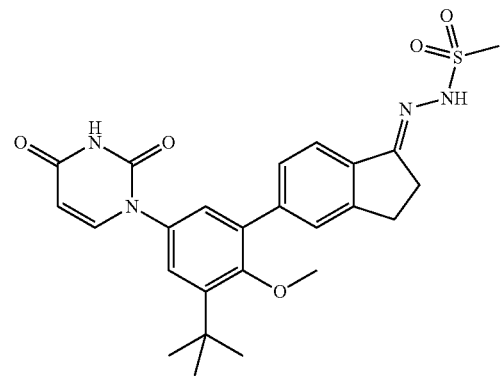 [SMILES: COc1c(-c2ccc3c(c2)CC/C3=N\NS(C)(=O)=O)cc(-n2ccc(=O)[nH]c2=O)cc1C(C)(C)C]

Part A. Preparation of 5-(4,4,5,5-tetramethyl-1,3,2-dioxaborolan-2-yl)-2,3-dihydro-1H-inden-1-one A mixture of 5-bromo-2,3-dihydro-1H-inden-1-one (2.50 g, 11.85 mmol), bis(pinacolato) diboron (3.61 g, 14.21 mmol), potassium acetate (3.49 g, 35.5 mmol) and Combiphos Pd6 (178 mg, 0.36 mmol) in toluene (60 mL) was heated at reflux for 8 h. Cooled, diluted with EtOAc and extracted with water (2×) and washed with brine. Dried over Na₂SO₄ and stirred for 1 h with (3-mercaptopropyl) silica gel. Filtered and concentrated under vacuum to afford a yellow solid. Purification by silica gel column chromatography eluting with EtOAc/hexanes gave a yellow solid. Triturated with cold hexanes, filtered and dried under vacuum to give the title compound as a fine nearly white solid (1.99 g, 65%). A second crop of crystals (140 mg) was obtained from the mother liquors, bringing the yield to 70%.

Part B. Preparation of 1-(3-tert-butyl-4-methoxy-5-(1-oxo-2,3-dihydro-1H-inden-5-yl)phenyl)pyrimidine-2,4(1H,3H)-dione In a microwave tube, a suspension of the product from Example 4B, Part E (130 mg, 0.33 mmol), the product from Part A (101 mg, 0.39 mmol), and 1.0M sodium carbonate solution (390 μL, 0.39 mmol) in 1:1 ethanol-toluene (1.20 mL) was degassed by nitrogen sparge for 15 min. The mixture was treated with 1,1'-bis(diphenylphosphino)ferrocene palladium (II) chloride dichloromethane complex (13 mg, 0.016 mmol) and degassing was continued for another 5 min and heated at 100° C. in the microwave for 1 h. Cooled, diluted with EtOAc and extracted with 1M citric acid solution and brine. The organic layer was then stirred with (3-mercaptopropyl) silica gel for 1 h. Filtered and concentrated under vacuum. Purification by silica gel column chromatography eluting with EtOAc/hexanes gave the title compound as a white solid (80 mg, 61%).

Part C. Preparation of (E)-N'-(5-(3-tert-butyl-5-(2,4-dioxo-3,4-dihydropyrimidin-1(2H)-yl)-2-methoxyphenyl)-2,3-dihydro-1H-inden-1-ylidene)methanesulfonohydrazide A suspension of the product from Part B (77 mg, 0.19 mmol) and methanesulfonylhydrazide (22 mg, 0.20 mmol) in 3:1 THF:MeOH (1.9 mL) was warmed at 60° C. for 24 h. The mixture was concentrated under vacuum and the residue was purified by silica gel column chromatography eluting with EtOAc/hexanes to give the title compound as a white solid (62 mg, 66%). $^1$H NMR (300 MHz, DMSO-$d_6$): δ 11.40 (d, J=1.84 Hz, 1H) 9.94 (s, 1H) 7.76 (dd, J=13.97, 8.09 Hz, 2H) 7.52-7.59 (m, 1H) 7.51 (d, J=8.46 Hz, 1H) 7.11-7.40 (m, 2H) 3.28 (s, 3H) 2.96-3.19 (m, 5H), 2.85 (m, 2H), 1.40 (s, 9H). MS (+ESI) m/z (rel abundance): 497 (100, M+H), 1015 (5, 2M+Na).

Example 7

Preparation of N-(2-(3-tert-butyl-5-(2,4-dioxo-3,4-dihydropyrimidin-1(2H)-yl)-2-methoxyphenyl)benzo[d]oxazol-5-yl)methanesulfonamide (compound IB-L0-2.6)

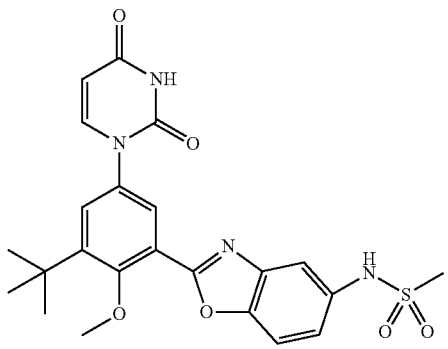 [SMILES: COc1c(-c2nc3cc(NS(C)(=O)=O)ccc3o2)cc(-n2ccc(=O)[nH]c2=O)cc1C(C)(C)C]

Part A. Preparation of methyl 3-tert-butyl-2-hydroxy-5-nitrobenzoate

Methyl 3,5-di-tert-butyl-2-hydroxybenzoate (28.66 g, 108.4 mmol) was dissolved with stirring in 430 mL glacial acetic acid and the resulting mixture was treated drop wise with fuming nitric acid (90%, 179.26 mL). When the addition was complete, the resulting mixture was stirred for 2.5 h. The reaction mixture was poured into a 2.0 L of crushed ice and allowed to stand 30 min. Afterwards, 1.0 L of water was added and the ice water mixture was allowed to melt. The mixture was then filtered, washed with water and dried to provide the title compound (24.57 g, 89%).

Part B. Preparation of methyl 3-tert-butyl-2-methoxy-5-nitrobenzoate

Methyl 3-tert-butyl-2-hydroxy-5-nitrobenzoate (11.41 g, 45.0 mmol), potassium carbonate (9.34 g, 67.6 mmol), acetone (200 mL), and dimethyl sulfate (6.46 g, 67.6 mmol) were added together. The resultant mixture was then heated to reflux for 16 h. The mixture was then filtered and the solid was washed with ethyl acetate. The resulting organic liquid was then concentrated under vacuum to an oil and redissolved in ethyl acetate (600 mL). The organic solution was then washed with water, dried, filtered and concentrated under vacuum to an oil that was then subjected to purification via column chromatography (gradient of 5% to 40% EtOAc/Hexanes) to yield the title compound as an oil (10.42, 87%).

Part C. Preparation of methyl 5-amino-3-tert-butyl-2-methoxybenzoate

Methyl 3-tert-butyl-2-methoxy-5-nitrobenzoate (10.42 g, 39.0 mmol), iron powder (325 mesh, 10.89 g, 195 mmol), ammonium chloride (3.13 g, 58.5 mmol), water (30 mL), and methanol (150 mL) were added together. The resultant mixture was then refluxed for 1 h. The mixture was then cooled to room temperature, filtered through celite, and the celite washed with methanol. The filtrate was then concentrated under vacuum and dissolved in ethyl acetate (600 mL). The resultant solution was then washed with water and brine. The organic extract was then dried, filtered and concentrated under vacuum to yield the title compound as an oil (9.25 g, 100%).

Part D. Preparation of (E)-methyl 3-tert-butyl-2-methoxy-5-(3-(3-methoxyacryloyeureido)benzoate The product obtained as described in Part C (2.0 g, 8.43 mmol) was dissolved in 30 mL of N,N-dimethylacetamide and cooled to −25° C. A 0.5 Molar solution of E-3-methoxyacryloyl isocyanate in benzene (21.9 mL, 10.96 mmol) was added drop wise and the resulting solution was stirred at ambient temperature for 4 h, and then poured into water. The product was extracted into dichloromethane, washed with brine, dried over sodium sulfate, filtered and evaporated under vacuum to give 100% yield.

Part E. Preparation of methyl 3-tert-butyl-5-(2,4-dioxo-3,4-dihydropyrimidin-1(2H)-yl)-2-methoxybenzoate The product from Part D (3.1 g, 8.51 mmol) was dissolved in ethanol (60 mL). Sulfuric acid (6 mL) was added to water (60 mL) then this solution was added in one portion to the ethanol. The heterogeneous mixture was heated at 100° C. for 3 h. The ethanol was removed under vacuum, and then the aqueous solution was extracted with dichloromethane and evaporated to dryness. This residue was purified by flash chromatography, eluting with 1% methanol/dichloromethane to yield 1.23 g (44%).

Part F. Preparation of 3-tert-butyl-5-(2,4-dioxo-3,4-dihydropyrimidin-1(2H)-yl)-2-methoxybenzoic acid The product from Part E (1.23 g, 3.7 mmol) was taken up in ethanol (5 mL) and 1 Molar sodium hydroxide solution (10 mL) and stirred at ambient temperature for 18 h. The solution was diluted with 1M HCl and the resulting solid was filtered and dried to give 0.945 g (80%).

Part G. Preparation of 3-tert-butyl-5-(2,4-dioxo-3,4-dihydropyrimidin-1(2H)-yl)-2-methoxy benzaldehyde The product from Part F (0.945 g, 2.97 mmol) was taken up in thionyl chloride (4.5 mL) and the mixture was heated at 80° C. for 40 min. After evaporation to dryness, the acid chloride was dissolved in dry THF (8 mL) and cooled to −78° C. A 1 Molar solution of lithium tri-tert-butoxyaluminum hydride in THF (3.0 mL, 3.0 mmol) was added drop wise. After 45 min the cold reaction was quenched with 1M HCl (5 mL), extracted into ethyl acetate, and purified by flash column, eluting with dichloromethane followed by 1% methanol/dichloromethane to give 0.635 g (71%).

Part H. Preparation of 1-(3-tert-butyl-4-methoxy-5-(5-nitrobenzo[d]oxazol-2-yl)phenyl)pyrimidine-2,4(1H,3H)-dione The product from Part G (400 mg, 1.323 mmol), 2-amino-4-nitrophenol (204 mg, 1.323 mmol), Charcoal (Darco KB, 191 mg, 15.88 mmol) and toluene (50 mL) were added to a flask and the mixture was heated to 120° C., and stirred open to the air for 48 h. Filtered through Celite and concentrated under vacuum. Purification by silica gel column chromatography eluting with CH$_2$Cl$_2$/MeOH gave the title compound (300 mg, 52%).

Part I. Preparation of N-(2-(3-tert-butyl-5-(2,4-dioxo-3,4-dihydropyrimidin-1(2H)-yl)-2-methoxyphenyl)benzo[d]oxazol-5-yl)methanesulfonamide To the product from Part H (300 mg, 0.687 mmol), iron (192 mg, 3.44 mmol), and ammonium chloride (55 mg, 1.031 mmol) was added to a mixture of THF (15 mL), EtOH (15 mL) and water (4.5 mL). The resultant solution was heated to 90° C. for 45 min, and cooled. Filtered through Celit, washed with ethanol, and concentrated under vacuum. The solid was dissolved in ethyl acetate, and washed with water. Dried over Na$_2$SO$_4$, filtered and concentrated under vacuum. Purification by silica gel column chromatography eluting with CH$_2$Cl$_2$/MeOH provided the aniline. The solid (75 mg, 0.185 mmol) was dissolved in CH$_2$Cl$_2$ (5 mL), and pyridine (0.045 mL, 0.554 mmol) and methanesulfonyl chloride (0.025 mL, 0.323 mmol) were added and stirred at room temperature for 16 h. CH$_2$Cl$_2$ was added followed by washing with a 1N HCl. Dried over Na$_2$SO$_4$, filtered and concentrated under vacuum. Purification by silica gel column chromatography eluting with CH$_2$Cl$_2$/MeOH provided the title compound as a solid (9.8 mg, 3%, two steps). $^1$H NMR (300 MHz, DMSO-d6): δ 11.46 (s, 1H), 9.85 (s, 1H), 7.91 (d, J=2.2 Hz, 1H), 7.81 (dd, J=9.9, 8.8 Hz, 2H), 7.68 (d, J=2.2 Hz, 1H), 7.56 (d, J=2.6 Hz, 1H), 7.33 (dd, J=8.8, 1.8 Hz, 1H), 5.68 (d, J=7.7 Hz, 1H), 3.64 (s, 3H), 3.00 (s, 3H), 1.42 (s, 9H). MS: m/z 485 (M+H)+.

Example 8

Preparation of 1-(3-tert-butyl-4-methoxy-5-(6-nitrobenzo[d]oxazol-2-yl)phenyl) dihydropyrimidine-2,4(1H,3H)-dione (compound IA-L0-2.6)

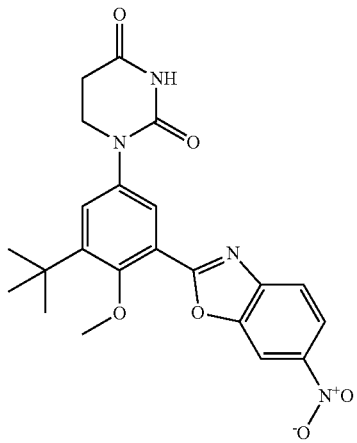

Part A. Preparation of 3-(3-tert-butyl-4-methoxy-5-(methoxycarbonyl)phenylamino)propanoic acid The product from Example 7, Part C (16.44 g, 69.3 mmol) was dissolved in toluene (200 mL). This mixture was heated to reflux and acrylic acid added over time (1 mL of acrylic acid added every 3 h, 5.23 mL total, 76.2 mmol). The mixture was then refluxed for 24 h. The mixture was then cooled and concentrated under vacuum to dryness to yield an oil as the crude title compound that was used directly in the next reaction.

Part B. Preparation of methyl 3-tert-butyl-5-(2,4-dioxotetrahydropyrimidin-1(2H)-yl)-2-methoxybenzoate The product from Part A (21.43 g, 69.3 mmol), urea (10.4 g, 173 mmol) and acetic acid (glacial, 200 mL) were added together. The mixture was then heated to 120° C. for 18.5 h followed by concentration under vacuum to dryness to an oil. To this oil was added methanol (13 mL), and ethyl acetate (350 mL). The resultant mixture was allowed to stand for 24-48 h whereby a precipitate formed. The resulting solid was filtered off and washed with a small amount of methanol (10 mL) and then air dried to yield the title compound as a solid (15.26 g, 66%).

Part C. Preparation of 3-tert-butyl-5-(2,4-dioxotetrahydropyrimidin-1(2H)-yl)-2-methoxy benzoic acid The product from Part B (4.52 g, 13.52 mmol), methanol (70 mL), and tetrahydrofuran (70 mL) were added together. The mixture was then stirred vigorously until a homogenous solution resulted. Once homogenous, a solution of aqueous sodium hydroxide (1.0M, 68 mL) was added. The mixture was then stirred for 12 h, the mixture was then concentrated under vacuum to remove the organic solvent, followed by the addition of aqueous hydrochloric acid (1.0M, 80 mL) that resulted in solid formation. The mixture was then concentrated under vacuum. To this material was added hydrochloric acid (12M, 100 mL) and the resultant material heated to 100° C. for 1.5 h. The reaction was then cooled and water added.

The resulting solid was filtered, washed with water, and dried to yield the title compound as a solid (3.55 g, 82%).

Part D. Preparation of 3-tert-butyl-5-(2,4-dioxotetrahydropyrimidin-1(2H)-yl)-2-methoxy benzaldehyde The product obtained in Part C (4.07 g, 12.71 mmol) and thionyl chloride (40.82 mL, 559 mmol) were combined and the mixture was refluxed for 2 h, followed by concentration under vacuum to provide a light yellow colored solid product. The solid was dissolved in tetrahydrofuran (125 mL), the solution cooled to −78° C. and LiAl(OtBu)$_3$ (1M, 14 mL) was added slowly over 10 min while maintaining the temperature at −78° C. The mixture was stirred at 78° C. for 2 h. The reaction was quenched with hydrochloric acid (aq., 1M, 25 mL) at −78° C. The mixture was warmed to room temperature and ethyl acetate was added. The layers were separated and the aqueous layer was washed with ethyl acetate. The organic extracts were combined and washed with half saturated sodium bicarbonate solution. The organic layer was dried, filtered and concentrated under vacuum to yield a solid as the title compound (3.73 g, 96%).

Part E. Preparation of 1-(3-tert-butyl-4-methoxy-5-(6-nitrobenzo[d]oxazol-2-yl)phenyl)dihydro pyrimidine-2,4(1H,3H)-dione A mixture of the product from Part D (75 mg, 0.246 mmol), 2-amino-5-nitrophenol (38 mg, 0.0246 mmol) and Darco KB charcoal (excess) was refluxed in toluene (10 mL) for 24 h under exposure to atmospheric of oxygen. Cooled, filtered and purified by reverse phase HPLC chromatography eluting with a 40-100% gradient of acetonitrile in water (0.1% TFA) to provide the title compound as a solid (96 mg, 64%). $^1$H NMR (300 MHz, DMSO-d$_6$): δ 1.42 (s, 9H) 2.74 (t, J=6.80 Hz, 2H) 3.66 (s, 3H) 3.82-3.88 (m, 2H) 7.56 (d, J=2.57 Hz, 1H) 7.91 (d, J=2.57 Hz, 1H) 8.09 (d, J=8.82 Hz, 1H) 8.37 (dd, J=8.82, 2.21 Hz, 1H) 8.84 (d, J=2.21 Hz, 1H) 10.44 (s, 1H). MS ESI+ (439) (M+H)+.

Example 9

Preparation of N-(2-(3-tert-butyl-5-(2,4-dioxotetrahydropyrimidin-1(2H)-yl)-2-methoxyphenyl)benzo[d]oxazol-6-yl)methanesulfonamide (compound IA-L0-2.5)

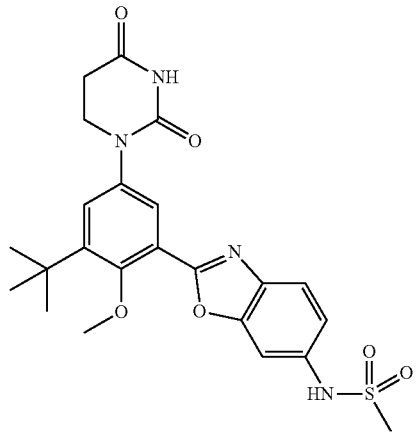 [SMILES: COc1c(-c2nc3ccc(NS(C)(=O)=O)cc3o2)cc(N2CCC(=O)NC2=O)cc1C(C)(C)C]

The product from Example 8 (96 mg. 0.219 mmol) was reacted a iron (0.614 g, 1.10 mmol), and ammonium chloride (0.176 g, 0.329 mmol) in the presence of a mixture of tetrahydrofuran (5 mL), ethanol (5 mL) and water (3 mL). The slurry was heated to 90° C. for 45 min, cooled to ambient temperature. Filtered through a pad of celite (10 g), washed with ethanol (20 mL), and the filtrate was concentrated under vacuum to a solid. The resulting solid was dissolved in ethyl acetate and washed with water. Dried over Na$_2$SO$_4$, filtered and concentrated under vacuum to a yellow solid, providing the corresponding aniline. The solid was dissolved in dichloromethane (10 mL), pyridine (0.670 mL, 0.657 mmol) and methanesulfonyl chloride (0.221 mL, 0.329 mmol) were added and the solution stirred at room temperature 16 h. CH$_2$Cl$_2$ was added followed by washing with a 1N aq. HCl solution. Dried over Na$_2$SO$_4$, filtered and concentrated under vacuum. Purification by silica gel column chromatography eluting with 98:2 CH$_2$Cl$_2$:MeOH gave the title compound as a solid (25 mg, 21%, two steps). $^1$H NMR (300 MHz, DMSO-d$_6$): δ 1.41 (s, 9H) 2.73 (t, J=6.62 Hz, 2H) 3.06 (s, 3H) 3.61 (s, 3H) 3.83 (t, J=6.62 Hz, 2H) 7.28 (dd, J=8.46, 1.84 Hz, 1H) 7.48 (d, J=2.57 Hz, 1H) 7.65 (d, J=1.84 Hz, 1H) 7.80 (d, J=1.47 Hz, 1H) 7.82 (d, J=4.04 Hz, 1H) 10.03 (s, 1H) 10.41 (s, 1H). MS ESI+ (487) (M+H)+.

Example 10

Preparation of 1-(3-tert-butyl-4-methoxy-5-(5-nitrobenzo[d]oxazol-2-yl)phenyl) dihydropyrimidine-2,4(1H,3H)-dione (compound IA-L0-2.7)

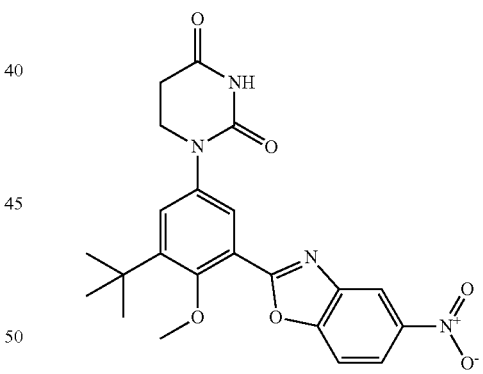

The product from Example 8, Part D (150 mg, 0.493 mmol) was reacted with 2-amino-4-nitrophenol (76 mg, 0.493 mmol) according to the procedures from Example 8, Part E to provide the title compound as a solid (70 mg, 32%). $^1$H NMR (300 MHz, DMSO-d$_6$): δ 1.42 (s, 9H) 2.74 (t, J=6.80 Hz, 2H) 3.65 (s, 3H) 3.85 (t, J=6.62 Hz, 2H) 7.55 (d, J=2.57 Hz, 1H) 7.89 (d, J=2.94 Hz, 1H) 8.12 (d, J=8.82 Hz, 1H) 8.40 (dd, J=9.01, 2.39 Hz, 1H) 8.76 (d, J=2.21 Hz, 1H) 10.43 (s, 1H). MS ESI+ (439) (M+H)+.

Example 11

Preparation of N-(2-(3-tert-butyl-5-(2,4-dioxotetrahydropyrimidin-1(2H)-yl)-2-methoxyphenyl)benzo[d]oxazol-5-yl)methanesulfonamide (compound IA-L0-2.8)

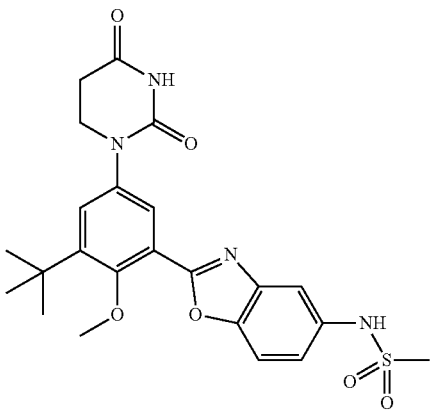 [SMILES: COc1c(-c2nc3cc(NS(C)(=O)=O)ccc3o2)cc(N2CCC(=O)NC2=O)cc1C(C)(C)C]

The product from Example 10 (65 mg, 0.148 mmol) was reacted according to the procedures from Example 9 to provide the title compound as a solid (42 mg, 44%). $^1$H NMR (300 MHz, DMSO-$d_6$): δ 1.41 (s, 9H) 2.73 (t, J=6.43 Hz, 2H) 3.01 (s, 3H) 3.60 (s, 3H) 3.83 (t, J=6.43 Hz, 2H) 7.31 (dd, J=8.64, 2.02 Hz, 1H) 7.49 (d, J=2.94 Hz, 1H) 7.56 (d, J=2.21 Hz, 1H) 7.67 (d, J=2.21 Hz, 1H) 7.81 (s, 1H) 9.82 (s, 1H) 10.41 (s, 1H). MS ESI+ (487) (M+H)+.

Example 12

Preparation of 1-(3-(benzo[d]thiazol-2-yl)-5-tert-butyl-4-methoxyphenyl)dihydropyrimidine-2,4(1H,3H)-dione (compound IA-L0-2.3)

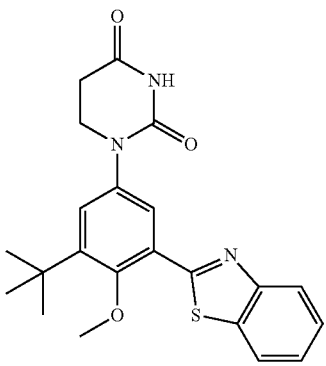 [SMILES: COc1c(-c2nc3ccccc3s2)cc(N2CCC(=O)NC2=O)cc1C(C)(C)C]

The product from Example 8, Part D (75 mg, 0.246 mmol) was reacted with 2-aminobenzene thiol (0.026 mL, 0.246 mmol) according to the procedures from Example 8, Part E to provide the title compound as a solid (25 mg, 25%). $^1$H NMR (300 MHz, DMSO-$d_6$): δ 1.44 (s, 9H) 2.73 (t, J=6.43 Hz, 2H) 3.62 (s, 3H) 3.84 (t, J=6.62 Hz, 2H) 7.46 (d, J=2.57 Hz, 1H) 7.48-7.60 (m, 2H) 7.86 (d, J=2.57 Hz, 1H) 8.13 (dd, J=17.28, 7.72 Hz, 2H) 10.40 (s, 1H). MS ESI+ (410) (M+H)+.

Example 13

Preparation of N-(2-(3-tert-butyl-5-(2,4-dioxotetrahydropyrimidin-1(2H)-yl)-2-methoxyphenyl)-1H-benzo[d]imidazol-5-yl)methanesulfonamide (compound IA-L0-2.1)

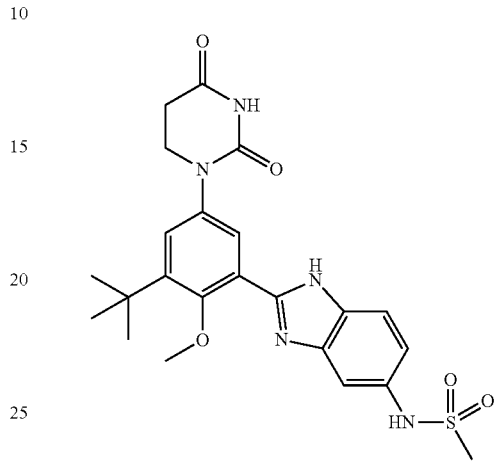

Part A. Preparation of N-(3,4-dinitrophenyl)methanesulfonamide

A mixture of 3,4-dinitroaniline (5.27 g, 28.8 mmol), methanesulfonyl chloride (3.36 mL, 43.1 mmol) and pyridine (5.82 mL, 71.9 mmol) in $CH_2Cl_2$ (100 mL) was stirred for 24 h. Mixture was concentrated under vacuum to provide a crude semi-solid title compound that was used without further purification.

Part B. Preparation of N-(3,4-diaminophenyl)methanesulfonamide

The product from Part A (7.51 g, 28.8 mmol) was reacted with iron (16 g, 288 mmol) and $NH_4Cl$ (3.84 g, 71.9 mmol) in refluxing $CH_3OH$ (100 mL) and water (20 mL) for 2 h. Filtered through celite and concentrated under vacuum. Purification by silica gel column chromatography eluting with MeOH/$CH_2Cl_2$ provided the title compound as a dark semi-solid (0.5 g, 8%).

Part C. Preparation of N-(2-(3-tert-butyl-5-(2,4-dioxotetrahydropyrimidin-1(2H)-yl)-2-methoxy phenyl)-1H-benzo[d]imidazol-5-yl)methanesulfonamide A mixture of the product from Example 8, Part D (200 mg, 0.657 mmol) was reacted with the product from Part B (132 mg, 0.657 mmol) according to the procedures from Example 8, Part E to provide the title compound as a solid (112 mg, 34%). $^1$H NMR (300 MHz, DMSO-$d_6$): δ 1.43 (s, 9H) 2.72 (t, J=6.62 Hz, 2H) 2.93 (s, 3H) 3.44 (s, 3H) 3.82 (t, J=6.43 Hz, 2H) 7.07-7.14 (m, 1H) 7.38 (d, J=2.57 Hz, 1H) 7.48-7.64 (m, 2H) 7.72 (d, J=2.57 Hz, 1H) 9.57 (s, 1H) 10.38 (s, 1H) 12.55 (s, 1H). MS ESI+ (486) (M+H)+.

Example 14

Preparation of N-(2-(3-tert-butyl-5-(2,4-dioxotetrahydropyrimidin-1(2H)-yl)-2-methoxyphenyl)benzo[d]thiazol-6-yl)methanesulfonamide (compound IA-L0-2.2)

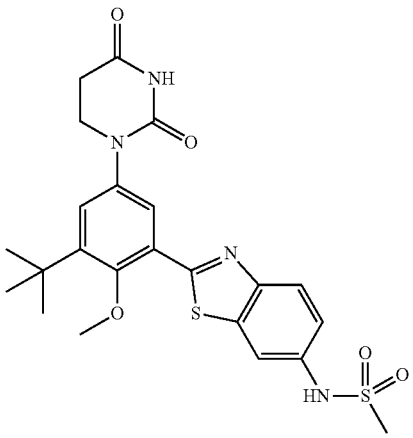

Part A. Preparation of N-(3-chloro-4-nitrophenyl)methanesulfonamide

A mixture of 3-chloro-4-nitroaniline (4.85 g, 28.1 mmol), methanesulfonyl chloride (3.29 mL, 42.2 mmol) and pyridine (6.82 mL, 84 mmol) in THF (100 mL) was stirred for 24 h. Poured in 1M HCl (500 mL). The resulting precipitate was filtered and air-dried to provide the title compound as a solid (7.03 g, 100%).

Part B. Preparation of N-(3-(4-methoxybenzylthio)-4-nitrophenyl)methanesulfonamide A mixture of the product from Part A (7.0 g, 27.9 mmol), (4-methoxyphenyl)methanethiol (3.89 mL, 27.9 mmol) and $K_2CO_3$ (11.58 g, 84 mmol) in DMF was heated at 100° C. for 12 h. Cooled and poured into 1M HCl (800 mL). The resulting precipitate was filtered and air-dried to provide the title compound as a yellow solid (6.98 g, 68%).

Part C. Preparation of N-(4-amino-3-(4-methoxybenzylthio)phenyl)methanesulfonamide The product from Part B (6.98 g, 19.0 mmol) was reacted according to the procedures from Example 13, Part B to provide the title compound as a yellow semi-solid (4.44 g, 69%).

Part D. Preparation of N,N'-(3,3'-disulfanediylbis(4-amino-3,1-phenylene))dimethane-sulfonamide The product from Part C (708 mg, 2.09 mmol) was reacted with mercuric (II) acetate (667 mg, 2.09 mmol), anisole (0.457 mL, 4.18 mmol) and TFA (10 mL) at 0° C. for 45 min. Concentrated under vacuum and dissolved in MeOH. Hydrogen sulfide gas was bubbled into solution for 1 h followed by filtration and concentration under vacuum. Purification by silica gel chromatography eluting with EtOAc/hexane gave the title compound as a yellowish solid (340 mg, 75%).

Part E. Preparation of N-(2-(3-tert-butyl-5-(2,4-dioxotetrahydropyrimidin-1(2H)-yl)-2-methoxyphenyl)benzo[d]thiazol-6-yl)methanesulfonamide The product from Part D (100 mg, 0.23 mmol) was reacted with the product from Example 8, Part D (140 mg, 0.46 mmol), triphenylphosphine (60.4 mg, 0.23 mmol) and 4-methylbenzene-sulfonic acid (0.0054 mL, 0.046 mmol) in refluxing toluene for 3 h. Concentrated under vacuum and purified by reverse phase HPLC chromatography eluting a 40-100% gradient of acetonitrile in water (0.1% TFA) to give the title compound as a solid (99 mg, 43%). $^1$H NMR (300 MHz, DMSO-$d_6$): δ 1.43 (s, 9H) 2.73 (t, J=6.62 Hz, 2H) 3.07 (s, 3H) 3.63 (s, 3H) 3.83 (t, J=6.62 Hz, 2H) 7.39 (dd, J=8.82, 2.21 Hz, 1H) 7.45 (d, J=2.57 Hz, 1H) 7.83 (d, J=2.57 Hz, 1H) 7.95 (d, J=2.21 Hz, 1H) 8.05 (d, J=8.82 Hz, 1H) 10.03 (s, 1H) 10.39 (s, 1H). MS ESI+ (503) (M+H)+.

Example 15

Preparation of N-(2-(3-tert-butyl-5-(2,4-dioxotetrahydropyrimidin-1(2H)-yl)-2-methoxyphenyl)benzo[d]thiazol-5-yl)methanesulfonamide (compound IA-L0-2.4)

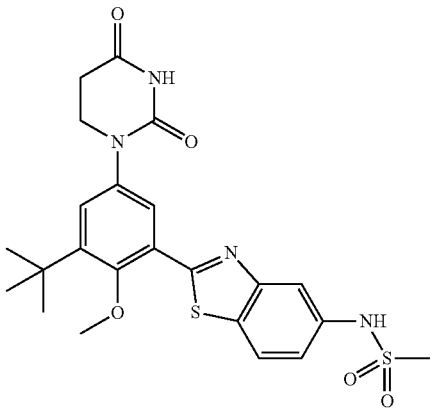

Part A. Preparation of N-(4-chloro-3-nitrophenyl)methanesulfonamide

A mixture of 4-chloro-3-nitroaniline (5.0 g, 29 mmol), methanesulfonyl chloride (2.37 mL, 30.4 mmol) and pyridine (5.9 mL, 72.4 mmol) in THF (100 mL) was stirred for 24 h. Poured in 1M HCl (500 mL). The resulting precipitate was filtered and air-dried to provide the title compound as a solid (6.7 g, 92%).

Part B. Preparation of N-(4-(4-methoxybenzylthio)-3-nitrophenyl)methanesulfonamide A mixture of the product from Part A (3.0 g, 12 mmol), (4-methoxyphenyl)methanethiol (1.67 mL, 12 mmol) and $K_2CO_3$ (4.96 g, 36 mmol) in DMF was heated at 100° C. for 12 h. Cooled and poured into 1M HCl (800 mL). The resulting precipitate was filtered and air-dried to provide the title compound as a yellow solid (1.95 g, 44.2%).

Part C. Preparation of N-(3-amino-4-(4-methoxybenzylthio)phenyl)methanesulfonamide The product from Part B (1.43 g, 3.88 mmol) was reacted according to the procedures from Example 13, Part B to provide the title compound as a white solid (1.31 g, 100%).

Part D. Preparation of N,N'-(4,4'-disulfanediylbis(3-amino-4,1-phenylene))dimethane-sulfonamide The product from Part C (75 mg, 0.222 mmol) was reacted with mercuric (II) acetate (70.6 mg, 0.222 mmol), anisole (0.048 mL, 0.443 mmol) and TFA (10 mL) at 0° C. for 45 min. Concentrated under vacuum and dissolved in MeOH. Hydrogen sulfide gas was bubbled into solution for 1 h followed by filtration and concentration under vacuum. Purification by silica gel column chromatography eluting with EtOAc/Hexane gave the title compound as a yellowish solid (34 mg, 71%).

Part E. Preparation of N-(2-(3-tert-butyl-5-(2,4-dioxotetrahydropyrimidin-1(2H)-yl)-2-methoxy phenyl)benzo[d]thiazol-5-yl)methanesulfonamide The product from Part D (50 mg, 0.115 mmol) was reacted with the product from Example 8, Part D (70 mg, 0.230 mmol), triphenylphosphine (30.2 mg, 0.115 mmol) and 4-methylbenzenesulfonic acid (0.00267 mL, 0.023 mmol) in refluxing toluene for 3 h. Concentrated under vacuum and purified by reverse phase HPLC chromatography eluting with a 40-100% gradient of acetonitrile in water (0.1% TFA) to give the title compound as a solid (40 mg, 33%). $^1$H NMR (300 MHz, DMSO-$d_6$): δ 1.43 (s, 9H) 2.73 (t, J=6.80 Hz, 2H) 3.05 (s, 3H) 3.63 (s, 3H) 3.84 (t, J=6.62 Hz, 2H) 7.35 (dd, J=8.64, 2.02 Hz, 1H) 7.46 (d, J=2.94 Hz, 1H) 7.86 (d, J=2.94 Hz, 1H) 7.92 (d, J=1.84 Hz, 1H) 8.10 (d, J=8.46 Hz, 1H) 9.98 (s, 1H) 10.40 (s, 1H). MS ESI+ (503) (M+H)+.

Example 16

Preparation of 1-(3-tert-butyl-4-methoxy-5-(naphthalen-2-yl)phenyl)pyrimidine-2,4(1H,3H)-dione (compound IB-L0-2.1)

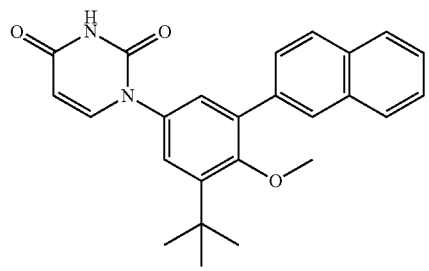 [SMILES: COc1c(-c2ccc3ccccc3c2)cc(-n2ccc(=O)[nH]c2=O)cc1C(C)(C)C]

Part A. Preparation of tert-butyl 3-tert-butyl-4-methoxy-5-(naphthalen-2-yl)phenyl carbamate In a resealable Schlenk tube, a solution of the product from Example 3, Part H (200 mg, 0.56 mmol), naphthalene-2-boronic acid (144 mg, 0.84 mmol), and 1.0M sodium carbonate solution (558 µL, 0.56 mmol) in toluene (2.8 mL) was degassed by nitrogen sparge for 10 min. The mixture was treated with 1,1'-bis(diphenylphosphino)ferrocene palladium (II) chloride dichloromethane complex (14 mg, 0.017 mmol) and degassing was continued for another 5 min. The Schlenk tube was sealed and warmed at 95° C. for 18 h. Cooled and diluted with ethyl acetate and water. Treated with Darco G-60 and filtered through celite. Filtrate was extracted with water (2×) and with brine. Dried over $Na_2SO_4$, filtered and concentrated. Purification by silica gel column chromatography eluting with 10-75% EtOAc in hexanes gave the title compound as an oil (210 mg, 93%).

Part B. Preparation of 3-tert-butyl-4-methoxy-5-(naphthalen-2-yl)aniline

The product from Part A (210 mg, 0.52 mmol) was dissolved in 4N HCl in dioxane (4.0 mL) and stirred at room temperature for 1 h. Concentration under vacuum afforded a solid, which was suspended in ethyl acetate and stirred with saturated sodium bicarbonate solution. The organic layer was dried over $Na_2SO_4$, filtered and concentrated under vacuum to give the title compound, as a brown oil (111 mg, 70%).

Part C. Preparation of (E)-N-(3-tert-butyl-4-methoxy-5-(naphthalen-2-yl)phenylcarbamoyl)-3-methoxyacrylamide A solution of the product from Part B (111 mg, 0.36 mmol) in dry DMF (2.9 mL) at −20° C. was treated with (E)-3-methoxyacryloyl isocyanate solution (0.66 mL, of 0.55M in benzene, 0.36 mmol) followed by gradual warming to room temperature. After stirring for 30 min, the mixture was cooled again to −20° C. and more (E)-3-methoxyacryloyl isocyanate solution (1.0 mL, 0.55 mmol) was added. After warming again to room temperature for 30 min, the reaction was complete. Diluted with EtOAc and extracted with water and brine. Dried over $Na_2SO_4$, filtered and concentrated under vacuum. Purification by silica gel column chromatography eluting with 10-100% EtOAc in hexane gave the title compound as a light yellow oil (144 mg, 92%).

Part D. Preparation of 1-(3-tert-butyl-4-methoxy-5-(naphthalen-2-yl)phenyl)pyrimidine-2,4(1H,3H)-dione A suspension of the product from Part C (144 mg, 0.33 mmol) in 2:2:1 ethanol-water-THF (15 mL) was treated with 1N sulfuric acid solution (3.0 mL) followed by warming at 100° C. for 24 h. Cooled and diluted with EtOAc and extracted with water and brine. Dried over $Na_2SO_4$, filtered and concentrated under vacuum. Purification by silica gel column chromatography eluting with 10-100% EtOAc in hexane gave the title compound as a white solid (62 mg, 47%). $^1$H NMR (300 MHz, DMSO-$d_6$): δ 11.42 (s, 1H), 8.08 (s, 1H), 7.90-8.04 (m, 3H), 7.81 (d, J=7.72 Hz, 1H), 7.72 (d, J=8.46 Hz, 1H), 7.56 (dd, J=6.25, 3.31 Hz, 2H), 7.39 (d, J=2.57 Hz, 1H), 7.33 (d, J=2.57 Hz, 1H), 5.65 (d, J=7.72 Hz, 1H), 3.24 (s, 3H), 1.43 (s, 9H). MS+ESI m/z (rel abundance): 401 (100, M+H), 418 (30, M+NH4).

Example 17

Preparation of 1-(3-tert-butyl-4-methoxy-5-(6-methoxynaphthalen-2-yl)phenyl)pyrimidine-2,4(1H,3H)-dione (compound IB-L0-2.2)

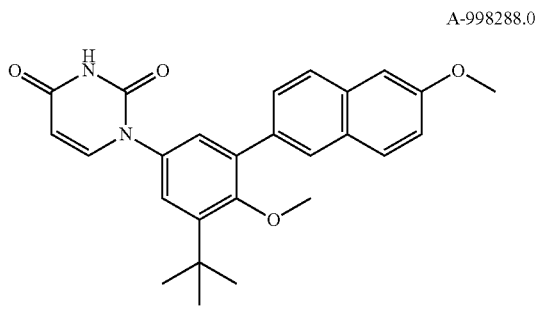 [SMILES: COc1ccc2cc(-c3cc(-n4ccc(=O)[nH]c4=O)cc(C(C)(C)C)c3OC)ccc2c1]

A-998288.0

Part A. Preparation of tert-butyl 3-tert-butyl-4-methoxy-5-(6-methoxynaphthalen-2-yl)phenyl carbamate The product from Example 3, Part H (158 mg, 0.44 mmol) was reacted with 6-methoxy-naphthalen-2-ylboronic acid (107 mg, 0.52 mmol) according to the procedures from Example 16, Part A to provide the title compound as a white solid (92 mg, 47%).

Part B. Preparation of 3-tert-butyl-4-methoxy-5-(6-methoxynaphthalen-2-yl)aniline The product from Part A (92 mg, 0.21 mmol) was reacted according to the procedures from Example 16, Part B to provide the title compound as a pink solid (71 mg, 99%).

Part C. Preparation of (E)-N-(3-tert-butyl-4-methoxy-5-(6-methoxynaphthalen-2-yl)phenyl carbamoyl)-3-methoxyacrylamide The product from Part B (71 mg, 0.21 mmol) was reacted according to the procedures from Example 16, Part C to provide the title compound as a buff-colored solid (58 mg, 59%).

Part D. Preparation of 1-(3-tert-butyl-4-methoxy-5-(6-methoxynaphthalen-2-yl)phenyl)pyrimidine-2,4(1H,3H)-dione A solution of the product from Part C (58 mg, 0.13 mmol) in 2:1:1 ethanol-THF-water (4.0 mL) was treated with 1.0M sulfuric acid solution (3.0 mL) followed by warming at 95° C. for 24 h. Cooled and diluted with EtOAc. Extracted with water and brine. Dried over $Na_2SO_4$, filtered and concentrated under vacuum. Purification by silica gel column chromatography eluting with 10-100% EtOAc in hexanes gave the product as a faint pink solid (28 mg, 52%). $^1$H NMR (300 MHz, DMSO-$d_6$): δ 11.41 (s, 1H), 8.00 (s, 1H), 7.91 (dd, J=8.64, 4.60 Hz, 2H), 7.80 (d, J=7.72 Hz, 1H), 7.67 (d, J=8.82 Hz, 1H), 7.34-7.47 (m, 2H), 7.21-7.32 (m, 1H), 7.20 (dd, J=9.01, 2.39 Hz, 1H), 5.65 (d, J=7.72 Hz, 1H), 3.90 (s, 3H), 3.24 (s, 3H), 1.42 (s, 9H). MS+ESI m/z (rel abundance): 431 (100, M+H), 448 (45, M+NH4).

Example 18

Preparation of N-(6-(3-tert-butyl-5-(2,4-dioxo-3,4-dihydropyrimidin-1(2H)-yl)phenyl)naphthalen-2-yl)methanesulfonamide (compound IB-L0-2.8)

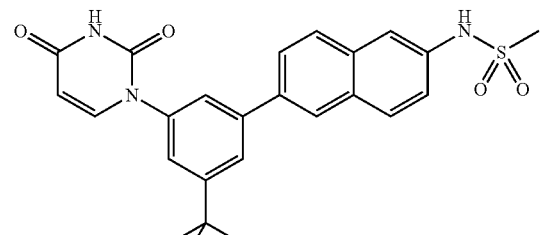

Part A. Preparation of 2-bromo-4-tert-butyl-6-nitroaniline

A suspension of 4-tert-butyl-2-nitroaniline (1.033 g, 5.32 mmol) in glacial acetic acid (7.8 mL) was warmed with a heat gun until all solids had dissolved. The solution was then cooled and treated portion wise with pyridinium hydrobromide perbromide (1.96 g, 6.12 mmol). After addition, the solution was stirred at room temperature for 1 h. The mixture was added to water (50 mL) and treated with a small amount of sodium sulfite. After stirring for 30 min, the precipitate was collected by filtration. The solid obtained was washed with water and dissolved in EtOAc. Washed with water and brine. Dried over $Na_2SO_4$, filtered and concentrated under vacuum to provide the title compound as a yellow-orange solid (1.36 g, 94%).

Part B. Preparation of 1-bromo-3-tert-butyl-5-nitrobenzene

A solution of tert-butyl nitrite (300 μL of 90%, 261 mg, 2.27 mmol) in dry DMF (4 mL) was warmed at 50° C. and was treated with a solution of the product from Part A (414 mg, 1.52 mmol) in DMF (3.5 mL). After a few minutes stirring, the solution began to bubble vigorously. After warming at 50° C. for 1 h, additional (300 μL) tert-butyl nitrite was added followed by warming at 50° C. for 1 h. After 18 h at room temperature, tert-butyl nitrite (1.2 mL) was added and the mixture warmed at 50° C. for 2 h. Cooled and diluted with EtOAc. Washed with water and brine. Dried over $Na_2SO_4$, filtered and concentrated under vacuum. Purification by silica gel column chromatography eluting with 5-40% ethyl acetate in hexanes gave the title compound as a light yellow oil (159 mg, 41%).

Part C. Preparation of 3-bromo-5-tert-butylaniline

A solution of the product from Part B (770 mg, 2.98 mmol) in 3:3:1 methanol-water-THF (14.9 mL) was treated with ammonium chloride (239 mg, 4.47 mmol) and iron powder (833 mg, 14.92 mmol) followed by warming at reflux for 8 h. Diluted with EtOAc and water and filtered through celite. The filtrate was extracted with water and brine. Dried over Na$_2$SO$_4$, filtered and concentrated under vacuum to give the title compound as a yellow oil.

Part D. Preparation of (E)-N-(3-bromo-5-tert-butylphenylcarbamoyl)-3-methoxy acrylamide A solution of the product from Part C (681 mg, 2.99 mmol) in dry DMF (23 mL) at −30° C. was treated drop wise with a 0.4M solution of (E)-3-methoxyacryloyl isocyanate in benzene (14.9 mL, 5.96 mmol). The solution was stirred at −30° C. for 30 min followed by warming gradually to room temperature, and then stirred for 18 h. Diluted with EtOAc and washed with water and brine. Dried over Na$_2$SO$_4$, filtered and concentrated under vacuum to afford a yellow solid, which was triturated with ether-hexanes and collected by filtration. Dried under vacuum to give the title compound as a light brown powder. (95.1 mg, 90%).

Part E. Preparation of 1-(3-bromo-5-tert-butylphenyl)pyrimidine-2,4(1H,3H)-dione A suspension of the product from Part D (951 mg, 2.68 mmol) in ethanol (25 mL) was treated with a solution of concentrated sulfuric acid (2.60 mL, 4.78 g, 18.22 mmol) in water (13.4 mL) followed by warming at 100° C. for 1 h. Cooled and concentrated to remove ethanol. Cooled to 0° C. and the precipitate was collected by filtration and washed with water. Dried under vacuum to give the title compound as an orange solid (619 mg, 72%).

Part F. Preparation of N-(6-(3-tert-butyl-5-(2,4-dioxo-3,4-dihydropyrimidin-1(2H)-yl)phenyl)naphthalen-2-yl)methanesulfonamide In a microwave tube, a suspension of the product from Part E (104 mg, 0.32 mmol), the product from Example 4A, Part B (134 mg, 0.39 mmol), and 1.0M sodium carbonate solution (386 µL, 0.39 mmol) in 1:1 ethanol-toluene (2.1 mL) was degassed by nitrogen sparge for 10 min. The solution was treated with 1,1'-bis(di-tert-butylphosphino)ferrocene-palladium (II) dichloride (20 mg, 0.031 mmol) and degassing was continued for another 5 min. The mixture was heated at 100° C. in the microwave for 30 min. Diluted with EtOAc and washed with water and brine. Dried over Na$_2$SO$_4$ and treated with (3-mercapto propyl) silica gel for 30 min. Filtered and concentrated under vacuum to afford an amber solid, which was triturated with ether-hexanes. Collected the solid by filtration and dried under vacuum to provide the title compound (81 mg, 54%). $^1$H NMR (300 MHz, DMSO-d$_6$): δ 11.46 (s, 1H) 10.05 (s, 1H), 8.25 (s, 1H) 7.98 (dd, J=11.58, 9.01 Hz, 1H) 7.86-7.93 (m, 1H) 7.78-7.85 (m, 2H) 7.72 (s, 1H) 7.67 (s, 1H) 7.31-7.51 (m, 2H) 5.70 (dd, J=7.72, 2.21 Hz, 1H) 3.08 (s, 3H) 1.39 (s, 9H).

Example 19

Preparation of (E)-N-(5-(3-tert-butyl-5-(2,4-dioxo-3,4-dihydropyrimidin-1(2H)-yl)phenyl)-2,3-dihydro-1H-inden-1-ylidene)methanesulfonohydrazide (compound IB-L0-2.7)

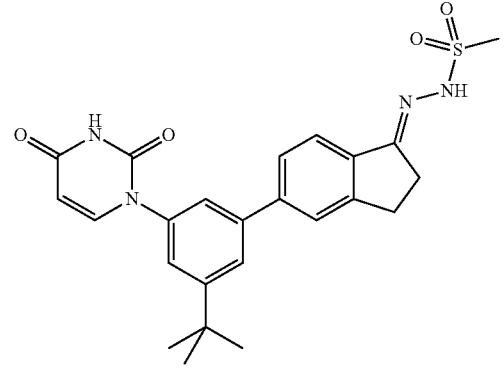 [SMILES: CC(C)(C)c1cc(-c2ccc3c(c2)CC/C3=N\NS(C)(=O)=O)cc(-n2ccc(=O)[nH]c2=O)c1]

Part A. Preparation of 1-(3-tert-butyl-5-(1-oxo-2,3-dihydro-1H-inden-5-yl)phenyl)pyrimidine-2,4(1H,3H)-dione In a microwave tube, a suspension of the product from Example 18, Part E, the product from Example 6, Part A (144 mg, 0.56 mmol), 1.0M sodium carbonate solution (557 µL, 0.56 mmol) in 1:1 ethanol-toluene (3.0 mL) was degassed by nitrogen sparge for 15 min. 1,1'-Bis(di-t-butylphosphino)ferrocene palladium (II) chloride complex (15 mg, 0.023 mmol) was added and degassing was continued for an additional 5 min. The tube was sealed and the mixture was heated at 100° C. in the microwave for 30 min. Diluted with EtOAc and water. Washed with 1M citric acid solution, water, and brine. The organic was stirred with (3-mercaptopropyl) silica gel for 1 h. Dried over Na$_2$SO$_4$, filtered and concentrated under vacuum. Purification by silica gel column chromatography eluting with 10-100% EtOAc in hexanes gave the title compound as an off-white solid (86 mg, 50%).

Part B. Preparation of (E)-N'-(5-(3-tert-butyl-5-(2,4-dioxo-3,4-dihydropyrimidin-1(2H)-yl)phenyl)-2,3-dihydro-1H-inden-1-ylidene)methanesulfonohydrazide The product from Part A (80 mg, 0.21 mmol) was reacted according to the procedures from Example 6, Part C to provide the title compound as a white solid (73 mg, 73%). $^1$H NMR (300 MHz, DMSO-d$_6$): δ 11.44 (s, 1H) 9.92 (s, 1H) 7.64-7.98 (m, 5H) 7.57 (s, 1H) 7.45 (s, 1H) 5.68 (d, J=7.72 Hz, 1H) 3.00-3.20 (m, 5H) 2.85 (d, J=12.50 Hz, 2H) 1.36 (s, 9H). MS+ESI m/z (rel abundance): 467 (100, M+H).

Example 20

Preparation of 3-tert-butyl-5-(2,4-dioxotetrahydropyrimidin-1(2H)-yl)-2-hydroxy-N-(4-(methylsulfonamido)phenyl)benzamide (compound IA-L3-1.6)

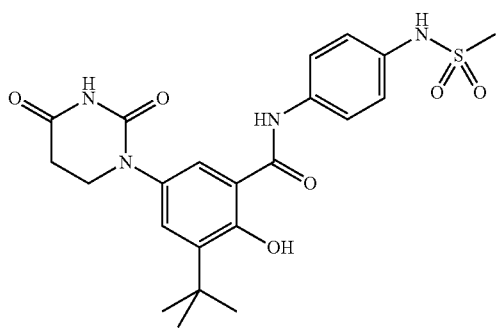 [SMILES: CC(C)(C)c1cc(N2CCC(=O)NC2=O)cc(C(=O)Nc2ccc(NS(C)(=O)=O)cc2)c1O]

Part A. Preparation of methyl 3-tert-butyl-2-hydroxy-5-nitrobenzoate

Methyl 3,5-di-tert-butyl-2-hydroxybenzoate (28.66 g, 108.4 mmol) was dissolved with stirring in 430 mL glacial acetic acid and the resulting mixture was treated drop wise with fuming nitric acid (90%, 179.26 mL). When the addition was complete, the resulting mixture was stirred for 2.5 h. The reaction mixture was poured into a 2.0 L of crushed ice and allowed to stand 30 min. Afterwards, 1.0 L of water was added and the ice water mixture was allowed to melt. The mixture was then filtered, washed with water and dried to provide the title compound (24.57 g, 89%).

Part B. Preparation of methyl 5-amino-3-tert-butyl-2-hydroxybenzoate

The product of Part A (0.43 g, 1.70 mmol) was treated with a catalytic amount of Pd/C in THF (10 mL) under hydrogen balloon for 3 h. The flask was purged with nitrogen and the mixture was filtered, concentrated, and purified by column chromatography on silica gel, eluting with 50% hexane/dichloromethane, followed by dichloromethane to yield 0.37 g (98%).

Part C. Preparation of methyl 5-(3-amino-3-oxopropylamino)-3-tert-butyl-2-hydroxy benzoate The product of Part B (0.37 g, 1.66 mmol) and acrylic acid (0.12 uL, 1.74 mmol) were combined in toluene (10 mL) and heated at reflux for 20 h. The solution was concentrated to dryness.

Part D. Preparation of methyl 3-tert-butyl-5-(2,4-dioxotetrahydropyrimidin-1(2H)-yl)-2-hydroxybenzoate The product of Part C was dissolved in glacial acetic acid (5 mL) and treated with urea (0.24 g, 4.0 mmol) at 120° C. for 3 h. The solution was diluted with cold water, extracted into ethyl acetate, concentrated, and purified by column chromatography on silica gel, eluting with 1%, then 2%, then 4% methanol/dichloro-methane to give both product (0.25 g, 46%) and open dihydrouracil (0.112 g, 20%).

Part E. Preparation of 3-tert-butyl-5-(1-(2-carboxyethyl)ureido)-2-hydroxybenzoic acid The products from Part D were dissolved in methanol (6 mL) and 1M sodium hydroxide solution was added (15 mL). After 20 h, the solution was adjusted to pH2 with concentrated hydrochloric acid and extracted into ethyl acetate, dried over sodium sulfate, and concentrated to give 0.303 g (89%).

Part F. Preparation of 3-tert-butyl-5-(2,4-dioxotetrahydropyrimidin-1(2H)-yl)-2-hydroxy-benzoic acid The product from Part E (0.303 g, 0.93 mmol) was taken up into 7 mL of concentrated hydrochloric acid and heated in an open flask at 120° C. for 1 h, during which time the excess acid evaporated off to leave dry product 0.20 g (70%).

Part G. Preparation of 3-tert-butyl-5-(2,4-dioxotetrahydropyrimidin-1(2H)-yl)-2-hydroxy-N-(4-(methylsulfonamido)phenyl)benzamide The product from Part F (0.13 g, 0.42 mmol) was heated with thionyl chloride (3 mL) at 90° C. for 1.5 h in an open flask leaving dry acid chloride, which was taken up in dioxane (4 mL). N-(4-amino-phenyl)methanesulfonamide.HCl (0.070 mg, 0.3 mmol) was added and the solution was heated at 90° C. for 1 h. The mixture was concentrated and then triturated with dichloromethane, filtered, and dried to give 0.071 mg (48%) of the title compound. $^1$H NMR (300 MHz, DMSO-D6) δ ppm 1.39 (s, 9H), 2.73 (t, J=6.62 Hz, 2H), 2.99 (s, 3H), 3.78 (t, J=6.62 Hz, 2H), 7.24 (d, J=8.82 Hz, 2H), 7.40 (d, J=2.21 Hz, 1H), 7.60 (d, J=9.19 Hz, 2H), 7.89 (d, J=2.21 Hz, 1H), 9.74 (s, 1H), 10.39 (s, 1H), 10.44 (s, 1H),13.30 (s, 1H).

Example 21

Preparation of 3-tert-butyl-5-(2,4-dioxotetrahydropyrimidin-1(2H)-yl)-2-hydroxy-N-(4-(2-methoxyethylsulfonamido)phenyl)benzamide (compound IA-L3-1.8)

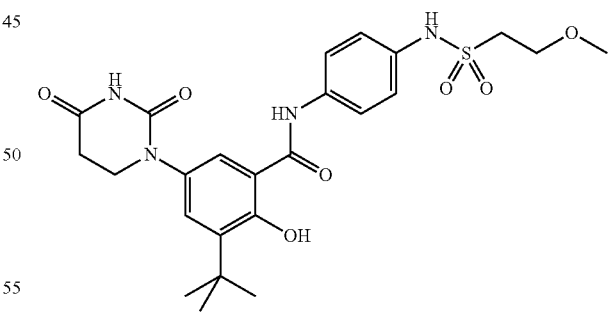

Part A. Preparation of tert-butyl 4-(vinylsulfonamido)phenylcarbamate

A solution of tert-butyl 4-aminophenylcarbamate (2.63 g, 12.63 mmol) and triethylamine (7.04 mL, 50.51 mmol) were combined in dichloromethane (50 mL) and cooled in an ice bath. After drop wise addition of 2-chloroethanesulfonyl chloride (1.45 mL, 13.9 mmol), the solution was stirred at ambient temperature for 4 h then diluted with 0.5M HCl and extracted into dichloromethane. The product was purified by column chromatography on silica gel, eluting with 1% methanol/dichloromethane to give 2.48 g (66%).

Part B. Preparation of tert-butyl 4-(2-methoxyethylsulfonamido)phenylcarbamate The product from Part A (0.70 g, 2.35 mmol) was heated at 60° C. in a sealed tube with 10 mL methanol and 5 mL of 25% weight sodium methoxide in methanol for 16 h. The solution was diluted with water and adjusted to pH 6 with 1M HCl, then extracted into dichloromethane and concentrated to give 0.582 g (75%).

Part C. Preparation of N-(4-aminophenyl)-2-methoxyethanesulfonamide

The product from Part B (0.582 g, 1.76 mmol) was taken up in 15 mL of 4M HCl in dioxane and stirred at ambient temperature for 20 h. The solution was diluted with dichloromethane and the solid product was filtered off and dried to give 0.395 g (84%).

Part D. Preparation of 3-tert-butyl-5-(2,4-dioxotetrahydropyrimidin-1(2H)-yl)-2-hydroxy-N-(4-(2-methoxyethylsulfonamido)phenyl)benzamide The product from Example 20, Part F (0.05 g, 0.163 mmol) was treated with thionyl chloride (0.5 mL) and the product from Part C (0.038 g, 0.163 mmol) as in Example 20, Part G to give 0.038 g (45%) of the title compound. $^1$H NMR (300 MHz, DMSO-D6): δ ppm 1.39 (s, 9H), 2.73 (t, J=6.62 Hz, 2H), 3.20 (s, 3H), 3.33-3.42 (m, 2H), 3.67 (t, J=6.25 Hz, 2H), 3.78 (t, J=6.62 Hz, 2H), 7.23 (d, J=9.19 Hz, 2H), 7.40 (d, J=2.21 Hz, 1H), 7.58 (d, J=9.19 Hz, 2H), 7.89 (d, J=2.21 Hz, 1H), 9.80 (s, 1H), 10.39 (s, 1H), 10.44 (s, 1H), 13.30 (s, 1H).

Example 22

Preparation of 3-tert-butyl-5-(2,4-dioxotetrahydropyrimidin-1(2H)-yl)-2-methoxy-N-(4-methylsulfonamido)phenyl)benzamide (compound IA-L3-1.51)

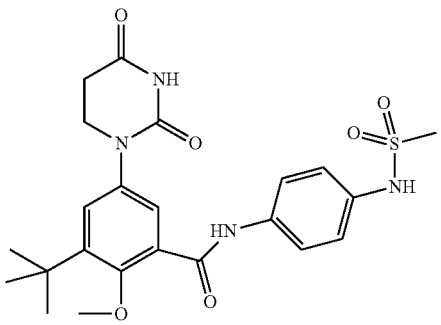 [SMILES: COc1c(C(=O)Nc2ccc(NS(C)(=O)=O)cc2)cc(N2CCC(=O)NC2=O)cc1C(C)(C)C]

Part A. Preparation of methyl 3-tert-butyl-2-hydroxy-5-nitrobenzoate

Methyl 3,5-di-tert-butyl-2-hydroxybenzoate (28.66 g, 108.4 mmol) was dissolved with stirring in 430 mL glacial acetic acid and the resulting mixture was treated drop wise with fuming nitric acid (90%, 179.26 mL). When the addition was complete, the resulting mixture was stirred for 2.5 h. The reaction mixture was poured into a 2.0 L of crushed ice and allowed to stand 30 min. Afterwards, 1.0 L of water was added and the ice water mixture was allowed to melt. The mixture was then filtered, washed with water and dried to provide the title compound (24.57 g, 89%).

Part B. Preparation of methyl 3-tert-butyl-2-methoxy-5-nitrobenzoate

The product from Part A (11.41 g, 45.0 mmol), potassium carbonate (9.34 g, 67.6 mmol), acetone (200 mL), and dimethyl sulfate (6.46 g, 67.6 mmol) were added together. The resultant mixture was then heated to reflux for 16 h. The mixture was then filtered and the solid was washed with ethyl acetate. The resulting organic liquid was then concentrated under vacuum to an oil and redissolved in ethyl acetate (600 mL). The organic solution was then washed with water, dried, filtered and concentrated under vacuum to an oil that was then subjected to purification via column chromatography (gradient of 5% to 40% EtOAc/Hexanes) to yield the title compound as an oil (10.42, 87%).

Part C. Preparation of methyl 5-amino-3-tert-butyl-2-methoxybenzoate

The product from Part B (10.42 g, 39.0 mmol), iron powder (325 mesh, 10.89 g, 195 mmol), ammonium chloride (3.13 g, 58.5 mmol), water (30 mL), and methanol (150 mL) were added together. The resultant mixture was then refluxed for 1 h. The mixture was then cooled to room temperature, filtered through celite, and the celite washed with methanol. The filtrate was then concentrated under vacuum and dissolved in ethyl acetate (600 mL). The resultant solution was then washed with water and brine. The organic extract was then dried, filtered and concentrated under vacuum to yield the title compound as an oil (9.25 g, 100%).

Part D. Preparation of 3-(3-tert-butyl-4-methoxy-5-(methoxycarbonyl)phenylamino)propanoic acid The product from Part C (16.44 g, 69.3 mmol) was dissolved in toluene (200 mL). This mixture was heated to reflux and acrylic acid added over time (1 mL of acrylic acid added every 3 h, 5.23 mL total, 76.2 mmol). The resulting mixture was refluxed for 24 h. The mixture was cooled and concentrated to dryness under vacuum to yield the crude title compound as an oil that was used directly in the next reaction.

Part E. Preparation of methyl 3-tert-butyl-5-(2,4-dioxotetrahydropyrimidin-1(2H)-yl)-2-methoxybenzoate The product from Part D (21.43 g, 69.3 mmol), urea (10.4 g, 173 mmol) and acetic acid (glacial, 200 mL) were added together. The mixture was then heated to 120° C. for 18.5 h followed by concentration under vacuum to dryness to an oil. To this oil was added methanol (13 mL), and ethyl acetate (350 mL). The resultant mixture was allowed to stand for 24-48 h whereby a precipitate formed. The resulting solid was filtered off and washed with a small amount of methanol (10 mL) and then air dried to yield the title compound as a solid (15.26 g, 66%).

Part F. Preparation of 3-tert-butyl-5-(2,4-dioxotetrahydropyrimidin-1(2H)-yl)-2-methoxy benzoic acid The product from Part E (4.52 g, 13.52 mmol), methanol (70 mL), and tetrahydrofuran (70 mL) were added together.

The mixture was then stirred vigorously until a homogenous solution resulted. Once homogenous, a solution of aqueous sodium hydroxide (1.0M, 68 mL) was added. The mixture was then stirred for 12 h, the mixture was then concentrated under vacuum to remove the organic solvent, followed by the addition of aqueous hydrochloric acid (1.0M, 80 mL) that resulted in solid formation. The mixture was then concentrated under vacuum. To this material was added hydrochloric acid (12M, 100 mL) and the resultant material heated to 100° C. for 1.5 h. The reaction was then cooled and water added. The resulting solid was filtered, washed with water, and dried to yield the title compound as a solid (3.55 g, 82%).

Part G. Preparation of 3-tert-butyl-5-(2,4-dioxotetrahydropyrimidin-1(2H)-yl)-2-methoxybenzoyl chloride The product from Part F (2H)-yl)-2-methoxybenzoic acid (4.07 g, 12.71 mmol) and thionyl chloride (40.82 mL, 559 mmol) were added together. The mixture was then refluxed for 2 h, followed by concentration under vacuum to provide the product as a light-yellow solid.

Part H. Preparation of 3-tert-butyl-5-(2,4-dioxotetrahydropyrimidin-1(2H)-yl)-2-methoxy-N-(4-methylsulfonamido)phenyl)benzamide The product prepared in Part G (0.55 g, 1.71 mmole) was dissolved in $CH_2Cl_2$ (35 ml) and added drop wise to a suspension in $CH_2Cl_2$ (40 ml) containing N-(4-aminophenyl)methanesulfonamide hydrochloride salt (0.38 g, 1.71 mmole) and pyridine (0.41 ml, 5.1 mmole). The reaction mixture was stirred 18 h at room temperature. The reaction mixture was filtered and diluted with 400 ml $CH_2Cl_2$. The organic layer was washed with 1N $H_3PO_4$, 10% NaHCO3 and 10% NaCl and dried over anhydrous solid sodium sulfate. The drying agent was filtered and the organic layer was evaporated in vacuo leaving the title compound as a crème-colored solid (474 mg, 57%). $^1$H NMR (300 MHz, DMSO-D6) δ ppm 1.37 (s, 9H) 2.71 (t, J=6.62 Hz, 2H) 2.95 (s, 3H) 3.77 (s, 3H) 3.80 (d, 2H) 7.20 (d, J=9.19 Hz, 2H) 7.28 (d, J=2.57 Hz, 1H) 7.33 (d, J=2.94 Hz, 1H) 7.69 (d, J=9.19 Hz, 2H) 9.59 (s, 1H) 10.35 (s, 1H) 10.38 (s, 1H).

Example 23

Preparation of 4-(3-tert-butyl-5-(2,4-dioxotetrahydropyrimidin-1(2H)-yl)-2-hydroxybenzamido)phenyl methanesulfonate (compound IA-L3-1.19)

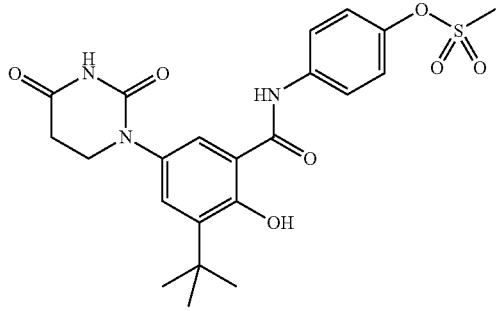 [SMILES: CC(C)(C)c1cc(N2CCC(=O)NC2=O)cc(C(=O)Nc2ccc(OS(C)(=O)=O)cc2)c1O]

Part A. Preparation of 4-(tert-butoxycarbonylamino)phenyl methanesulfonate

Tert-butyl-4-hydroxyphenylcarbamate (1.0 g, 4.78 mmol) and triethylamine (0.80 mL, 5.73 mmol) were combined in dichloromethane (50 mL), cooled in an ice bath and treated with methanesulfonyl chloride (0.41 mL, 5.26 mmol). The solution was stirred at ambient temperature for 2 h, then was washed with 1M HCl, dried over sodium sulfate, filtered, and concentrated to give 1.2 g (87%).

Part B. Preparation of 4-aminophenyl methanesulfonate hydrochloride

The product from Part A (1.2 g, 4.18 mmol) was treated with 4 M HCl in dioxane (10 mL) at ambient temperature and stirred for 18 h. The mixture was concentrated and the solid was triturated with dichloromethane, filtered, and dried to give 0.855 g (92%).

Part C. Preparation of 4-(3-tert-butyl-5-(2,4-dioxotetrahydropyrimidin-1(2H)-yl)-2-hydroxy benzamido)phenyl methanesulfonate The product from Example 20, Part F (0.055 g, 0.18 mmol) was treated with thionyl chloride (0.4 mL, 5.4 mmol) at 80° C. for 35 min then concentrated to dryness. This acid chloride was dissolved in dioxane (2 mL) and treated with the product from Part B (0.060 g, 0.27 mmol) and pyridine (0.037 mL, 0.45 mmol). The resulting mixture was stirred at 80° C. for 1 h, diluted with 1M HCl, extracted into ethyl acetate, concentrated and purified by column chromatography on silica gel, eluting with dichloromethane followed by 2% methanol/dichloromethane to give 0.055 g (64%) of the title compound. $^1$H NMR (300 MHz, DMSO-D6) δ ppm 1.39 (s, 9H), 2.74 (t, J=6.62 Hz, 2H) 3.40 (s, 3H), 3.79 (t, J=6.80 Hz, 2H), 7.36-7.45 (m, 3H) 7.76 (d, J=9.19 Hz, 2H), 7.90 (d, J=2.21 Hz, 1H), 10.40 (s, 1H), 10.58 (s, 1H) 13.13 (s, 1H).

Example 24

Preparation of 3-tert-butyl-5-(2,4-dioxotetrahydropyrimidin-1(2H)-yl)-2-methoxy-N-methyl-N-(4-(methylsulfonamido)phenyl)benzamide (compound IA-L3-1.27)

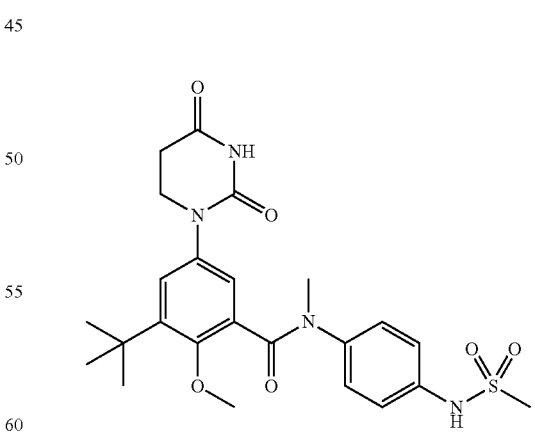

Part A. Preparation of tert-butyl 4-aminophenyl(methyl)carbamate

A mixture of N-methyl-4-nitroaniline (1.00 g, 6.57 mmol), di-tert-butyl dicarbonate (2.51 g, 11.50 mmol), and DMAP (40 mg, 0.33 mmol) in dichloromethane (35 mL) was stirred at reflux for 2 h. The reaction mixture was washed with water (20 mL), dried over Na$_2$SO$_4$, filtered and concentrated under vacuum. The residue was dissolved in a mixture of THF (12 mL) and methanol (12 mL). To the resulting solution was added iron powder (1.50 g, 27.0 mmol) and a solution of ammonium chloride (0.54 g, 10.11 mmol) in water (5 mL). The mixture was stirred at 70° C. for 3 h, cooled to room temperature and filtered through celite, and concentrated under vacuum. The residue was azeotropically dried using toluene (3×) and then triturated with ether to give a solid that was removed by filtration. The filtrate was concentrated under vacuum to give the title compound (1.45 g, 99%).

Part B. Preparation of N-(4-(methylamino)phenyl)methanesulfonamide hydrochloride The product prepared in Part A (1.45 g, 6.52 mmol) was dissolved in anhydrous dichloromethane (25 mL) and treated with pyridine (1.32 mL, 16.31 mmol) and methanesulfonyl chloride (0.57 mL, 7.18 mmol). The resulting solution was stirred at room temperature for 3 h, and then poured into 0.5M aq. HCl (25 mL). The layers were separated and the aqueous phase was washed with dichloromethane (2×25 mL). The combined organic layers were dried over Na$_2$SO$_4$, filtered and concentrated under vacuum. Column chromatography on silica gel using 1% methanol in chloroform as the eluent gave tert-butyl methyl(4-(methylsulfonamido)phenyl)carbamate (1.31 g, 67%), which was dissolved in 4N HCl in 1,4-dioxane (20 mL). The resulting solution was stirred at 40° C. for 1 h and concentrated under vacuum. The residue was triturated with dichloromethane to give the title compound as a solid that was collected by filtration and dried under vacuum (0.99 g, 96%).

Part C. Preparation of 3-tert-butyl-5-(2,4-dioxotetrahydropyrimidin-1(2H)-yl)-2-methoxy-N-methyl-N-(4-(methylsulfonamido)phenyl)benzamide The product prepared in Example 22, Part G (40 mg, 0.13 mmol) and thionyl chloride (0.3 mL, 4 mmol) were refluxed for 30 min, followed by concentration under vacuum. The residue was dissolved in anhydrous N,N-dimethylacetamide (2 mL), and to the resulting solution was added the product from Part B (30 mg, 0.13 mmol) and pyridine (0.025 mL, 0.3 μmol). The mixture was stirred at 80° C. for 30 min, and was partitioned between 1N HCl (5 mL) and ethyl acetate (3×5 mL). The organic extracts were combined, dried over Na$_2$SO$_4$, filtered and concentrated under vacuum to yield a crude product that was purified by column chromatography on silica gel eluting with 19:1 MeOH:CHCl$_3$ to give the title compound as a colorless solid (45 mg, 72%). $^1$H NMR (500 MHz, DMSO-D6) δ ppm 1.07 (s, 9H), 2.69 (t, J=6.1 Hz, 2H), 2.83 (s, 3H) 3.33-3.38 (m, 5H) 3.73 (s, 3H) 6.92 (d, J=8.5 Hz, 2H) 7.01 (d, J=9.2 Hz, 2H) 7.06 (d, J=2.4 Hz, 1H) 7.12 (d, J=2.4 Hz, 1H) 9.52-9.73 (m, 1H) 10.28 (s, 1H).

Example 25

Preparation of (N-(4-(3-tert-butyl-5-(3-(butyryloxymethyl)-2,4-dioxotetrahydro pyrimidin-1(2H)-yl)-2-methoxybenzamido)phenyl)methylsulfonamido)methyl butyrate (compound IA-L3-1.88)

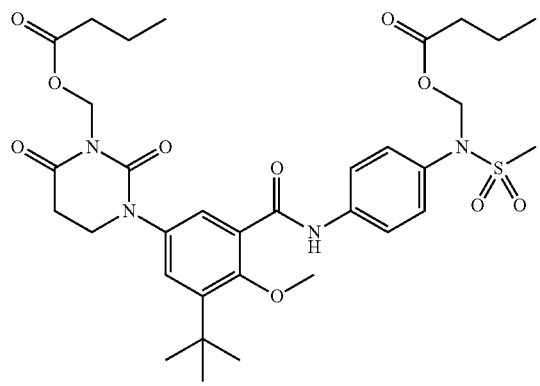 [SMILES: CCCC(=O)OCN1C(=O)CCN(c2cc(C(=O)Nc3ccc(N(COC(=O)CCC)S(C)(=O)=O)cc3)c(OC)c(C(C)(C)C)c2)C1=O]

The product from Example 22, Part G (0.098 g, 0.20 mmole) was dissolved in DMSO (2 ml) and treated with potassium carbonate (0.166 g, 1.20 mmole) and chloromethyl butyrate (0.411 g, 3.0 mmol). The mixture was stirred 20 h at room temperature. The reaction mixture was partitioned with ethyl acetate and water. The organic layer was washed with brine and dried over anhydrous solid sodium sulfate. The drying agent was filtered and the solvent evaporated under vacuum. The residue was purified with silica gel eluting with ethyl acetate/hexane (10% to 80%) to give two major fractions. The first fraction was purified with silica gel eluting with methanol/dichloromethane (1% to 3%) to give the title compound as a foam (0.014, 10%). $^1$H NMR (300 MHz, DMSO-D6) δ ppm 0.88 (m, 6H) 1.38 (s, 9H) 1.55 (m, 4H) 2.26 (t, J=7.17 Hz, 2H) 2.39 (t, J=7.17 Hz, 2H) 2.95 (t, J=6.62 Hz, 2H) 3.14 (s, 3H) 3.77 (s, 3H) 3.81 (t, J=6.62 Hz, 2H) 5.57 (s, 2H) 5.68 (s, 2H) 7.35 (d, J=2.57 Hz, 1H) 7.38 (d, J=2.94 Hz, 1H) 7.42 (d, J=8.82 Hz, 2H) 7.79 (d, J=8.82 Hz, 2H) 10.60 (s, 1H).

Example 26

Preparation of (N-(4-(3-tert-butyl-5-(2,4-dioxotetrahydropyrimidin-1(2H)-yl)-2-methoxybenzamido)phenyl)methylsulfonamido)methyl butyrate (compound IA-L3-1.64)

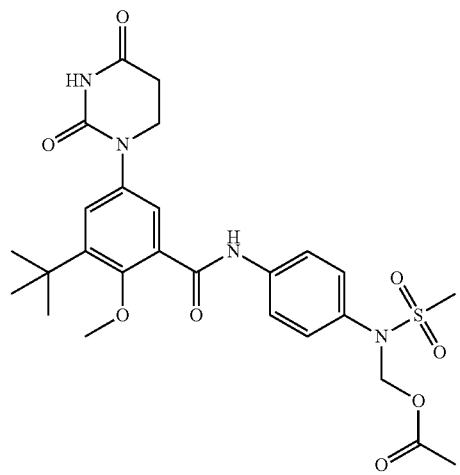 [SMILES: COc1c(C(=O)Nc2ccc(N(COC(C)=O)S(C)(=O)=O)cc2)cc(N2CCC(=O)NC2=O)cc1C(C)(C)C]

The product from Example 22, Part G (0.098 g, 0.20 mmole) was dissolved in DMSO (1 ml) and treated with Cesium carbonate (0.209 g, 0.64 mmole) and bromomethyl acetate (0.123 g, 0.80 mmol). The mixture was stirred 4 h at room temperature. The reaction mixture was partitioned with ethyl acetate and water. The organic layer was washed with brine and dried over anhydrous solid sodium sulfate. The drying agent was filtered and the solvent evaporated under vacuum. The residue was purified by HTP group by preparative HPLC on a Waters Nova-Pak® HR C18 6 um 60 Å Prep-Pak® cartridge column (40 mm×100 mm). A gradient of acetonitrile (A) and 10 mM ammonium acetate in water (B) was used, at a flow rate of 70 mL/min (0-0.5 min 10% A, 0.5-12.0 min linear gradient 10-95% A, 12.0-15.0 min 95% A, 15.0-17.0 min linear gradient 95-10% A) to give the title compound as a white solid (0.034 g, 30%). m.p. 229-230° C. $^1$H NMR (300 MHz, DMSO-D6) δ ppm 1.38 (s, 9H) 2.11 (s, 3H) 2.72 (t, J=6.80 Hz, 2H) 3.15 (s, 3H) 3.78 (m, 5H) 5.55 (s, 2H) 7.30 (d, J=2.57 Hz, 1H) 7.35 (d, J=2.57 Hz, 1H) 7.42 (d, J=9.19 Hz, 2H) 7.79 (d, J=8.82 Hz, 2H) 10.36 (s, 1H) 10.58 (s, 1H).

Example 27

Preparation of N-(3-tert-butyl-5-(2,4-dioxotetrahydropyrimidin-1(2H)-yl)-2-methoxyphenyl)-4-(methylsulfonamido)benzamide (compound IA-L4-1.9)

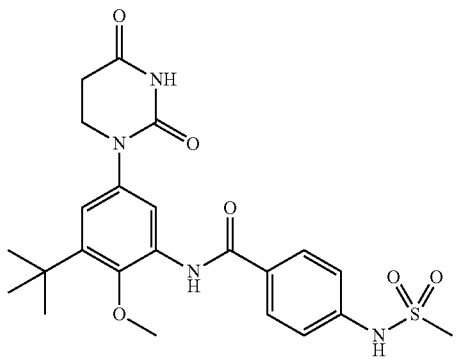 [SMILES: COc1c(NC(=O)c2ccc(NS(C)(=O)=O)cc2)cc(N2CCC(=O)NC2=O)cc1C(C)(C)C]

Part A. Preparation of 2-tert-butyl-1methoxy-4-nitrobenzene

A 1:1 mixture of AcOH and fuming $HNO_3$ (0.6 mL) was slowly added to a solution of 2-tert-butylphenol (1.0 g, 6.6 mmol) in cyclohexane (3 mL) at 0° C. The resulting dark mixture was stirred at 0° C. for 1 h, followed by the addition of hexanes (5 mL). The resulting solid was collected by filtration and washed with hexanes to give a light greenish solid (0.37 g, 29%). The solid was dissolved in acetone (10 ml), and to the resulting solution was added $K_2CO_3$ (0.3 g, 2.2 mmol), followed by the drop wise addition of $Me_2SO_4$ (0.27 mL, 2.8 mmol). The resulting mixture was stirred at room temperature overnight, and then poured into 1N HCl (20 mL). The mixture was extracted with EtOAc (3×20 mL), dried over $Na_2SO_4$, filtered and concentrated to provide the title compound as an oil (0.4 g, quant.).

Part B. Preparation of 1-(3-tert-butyl-4-methoxyphenyl)dihydropyrimidine-2,4(1H,3H)-dione The product described in Part A was dissolved (0.4 g, 1.9 mmol) in EtOAc (10 mL) and treated with 10% Pd on carbon (50 mg). The mixture was stirred at ambient temperature under 1 atm $H_2$ overnight. The mixture was filtered through celite and concentrated under vacuum to give a crude product that was purified on silica gel. The product was eluted using 1:1 EtOAc:hexanes, and isolated as an oil (0.23 g, 68%). Acrylic acid (0.1 mL, 1.46 mmol) and toluene (10 mL) were added to the isolated oil and the resulting mixture was heated at 100° C. overnight, and then concentrated in vacuo to give a dark oil. The oil was treated with AcOH (5 mL) and urea (0.2 g, 3.3 mmol), and the mixture was heated at 120° C. for 6 h. The mixture was cooled to ambient temperature, poured into water (20 mL) and extracted with EtOAc (3×10 mL). The combined organic layers were dried over $Na_2SO_4$, filtered and concentrated under vacuum to give a crude product that was purified by column chromatography on silica gel using 1:1 EtOAc:hexanes. The title compound was obtained as a colorless solid (0.144 g, 41%).

Part C. Preparation of 1-(3-tert-butyl-4-hydroxy-5-nitrophenyl)dihydropyrimidine-2,4(1H,3H)-dione The product prepared in Part B (1.00 g, 3.62 mmol) was dissolved in $CH_2Cl_2$ (25 mL) at 0° C. and treated with a 1M solution of $BBr_3$ in $CH_2Cl_2$ (18 mL, 18 mmol). The mixture was stirred at reflux overnight and poured into water (50 mL). The mixture was extracted with 3:1 $CH_2Cl_2$:2-PrOH (2×50 mL), and the combined extracts were dried over $mgSO_4$, filtered and concentrated under vacuum. The crude product was purified by column chromatography on silica using 2:1 EtOAc:hexanes to elute the product, obtained as a solid (0.60 g, 63%). The solid was suspended in AcOH (20 mL), to which was added fuming $HNO_3$ (0.105 mL). The resulting solution was stirred at room temperature 1 h and poured into ice water (100 mL). The mixture was extracted with 3:1 $CH_2Cl_2$:2-PrOH (2×50 mL), and the combined extracts were dried over $mgSO_4$, filtered and concentrated under vacuum. The residue was triturated with ether to give a solid that was collected by filtration (0.40 g, 57%).

Part D. Preparation of 1-(3-amino-5-tert-butyl-4-methoxyphenyl)dihydropyrimidine-2,4(1H,3H)-dione The product prepared in Part C (0.31 g, 1.0 mmol) was dissolved in 1:1 THF:MeOH (50 mL) and treated with a 2M solution of trimethylsilyldiazomethane in THF (1.5 mL, 3.0 mmol). The resulting solution was stirred at ambient temperature overnight, and concentrated under vacuum. The crude product was purified by column chromatography on silica gel using 1:1 EtOAc:hexanes and a colorless solid (0.235 g, 72%) was obtained. The solid was dissolved in 1:1 $CH_2Cl_2$:MeOH (50 mL), treated with 10% Pd/C (25 mg), and the mixture was stirred at ambient temperature under 1 atm $H_2$ for 2 h. The mixture was filtered through celite and concentrated under vacuum to obtain the title compound (0.215 g, quant.).

Part E. Preparation of N-(3-tert-butyl-5-(2,4-dioxotetrahydropyrimidin-1(2H)-yl)-2-methoxyphenyl)-4-nitrobenzamide The product obtained in Part D (0.215 g, 0.74 mmol) was dissolved in anhydrous $CH_2Cl_2$ (50 mL) and treated with 4-nitrobenzoyl chloride (0.164 g, 0.88 mmol) and pyridine (0.07 mL, 0.88 mmol). The resulting mixture was stirred at ambient temperature overnight, washed with water (50 mL), dried over $Na_2SO_4$, filtered and concentrated under vacuum.

The crude product was purified by column chromatography on silica gel using 1:1 EtOAc:hexanes to give the title compound (0.26 g, 80%).

Part F. Preparation of N-(3-tert-butyl-5-(2,4-dioxotetrahydropyrimidin-1(2H)-yl)-2-methoxyphenyl)-4-(methylsulfonamido)benzamide The product obtained in Part E (0.26 g, 0.59 mmol) was dissolved in a 2:1 mixture of $CH_2Cl_2$:MeOH (6 mL), treated with 10% Pd on carbon (30 mg) and stirred at ambient temperature under 1 atm $H_2$ for 2 h, filtered through celite and concentrated under vacuum. The residue was dissolved in anhydrous $CH_2Cl_2$ (10 mL) treated with methanesulfonyl chloride (0.054 mL, 0.70 mmol) and pyridine (0.056 mL, 0.70 mmol). The resulting mixture was stirred at room temperature overnight, partitioned between water (20 mL) and 3:1 $CH_2Cl_2$:2-PrOH (3×20 mL). The combined organic layers were dried over $Na_2SO_4$, filtered and concentrated under vacuum. The crude product was purified by column chromatography on silica gel using 19:1 $CH_2Cl_2$:MeOH to give the title compound as a solid (0.12 g, 42%). $^1$H NMR (300 MHz, DMSO-D6) δ ppm 1.37 (s, 9H), 2.70 (t, J=6.62 Hz, 2H), 3.10 (s, 3H), 3.71 (s, 3H), 3.76 (t, J=6.62 Hz, 2H), 7.11 (d, J=2.57 Hz, 1H) 7.30 (d, J=8.82 Hz, 2H) 7.37 (d, J=2.57 Hz, 1H), 8.02 (d, J=8.82 Hz, 2H), 9.86 (s, 1H) 10.20 (s, 1H) 10.33 (s, 1H).

Example 28

Preparation of N-(3-tert-butyl-5-(2,4-dioxotetrahydropyrimidin-1(2H)-yl)-2-methoxyphenyl)-4-(methylsulfonylmethyl)benzamide (compound IA-L4-1.10)

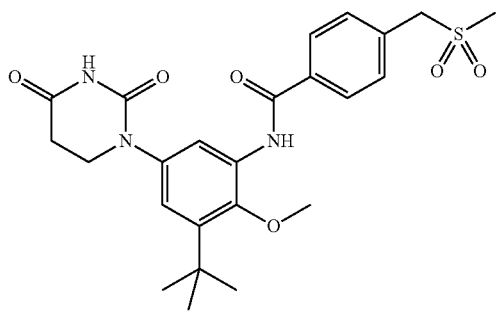 [SMILES: COc1c(NC(=O)c2ccc(CS(C)(=O)=O)cc2)cc(N2CCC(=O)NC2=O)cc1C(C)(C)C]

Thionyl chloride (0.31 mL, 4.2 mmol) and 4-(methylsulfonylmethyl)benzoic acid (0.03 g, 0.14 mmol) were combined and heated at 85° C. for 30 min then concentrated to dryness. This acid chloride was dissolved in N,N-dimethylacetamide (2 mL) with the product from Example 27, Part D (0.041 g, 0.14 mmol) and pyridine (0.025 mL, 2.2 mmol) and heated at 100° C. for 20 min, then cooled to ambient temperature and diluted with 1M HCl. The solid precipitate was isolated by filtration, triturated with methanol and dried to give the title compound) the title compound (0.0175 g, 26%). $^1$H NMR (300 MHz, DMSO-D6) δ ppm 1.37 (s, 9H), 2.71 (t, J=6.62 Hz, 2H), 2.95 (s, 3H), 3.72 (s, 3H), 3.77 (t, J=6.62 Hz, 2H), 4.60 (s, 2H), 7.13 (d, J=2.94 Hz, 1H), 7.38 (d, J=2.57 Hz, 1H), 7.56 (d, J=8.09 Hz, 2H) 8.05 (d, J=8.09 Hz, 2H), 10.03 (s, 1H), 10.33 (s, 1H).

Example 29

Preparation of (E)-N-(4-(3-tert-butyl-5-(2,4-dioxotetrahydropyrimidin-1(2H)-yl)-2-methoxystyryl)phenyl)methanesulfonamide (compound IA-L1-1.9)

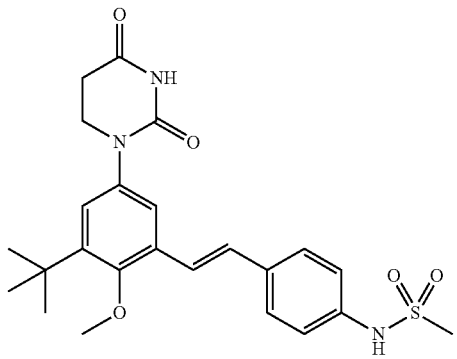 [SMILES: COc1c(/C=C/c2ccc(NS(C)(=O)=O)cc2)cc(N2CCC(=O)NC2=O)cc1C(C)(C)C]

Part A. Preparation of methyl 3-tert-butyl-2-hydroxy-5-nitrobenzoate

Methyl 3,5-di-tert-butyl-2-hydroxybenzoate (28.66 g, 108.4 mmol) was dissolved with stirring in 430 mL glacial acetic acid and the resulting mixture was treated drop wise with fuming nitric acid (90%, 179.26 mL). When the addition was complete, the resulting mixture was stirred for 2.5 h. The reaction mixture was poured into a 2.0 L of crushed ice and allowed to stand 30 min. Afterwards, 1.0 L of water was added and the ice water mixture was allowed to melt. The mixture was then filtered, washed with water and dried to provide the title compound (24.57 g, 89%).

Part B. Preparation of methyl 3-tert-butyl-2-methoxy-5-nitrobenzoate

Methyl 3-tert-butyl-2-hydroxy-5-nitrobenzoate (11.41 g, 45.0 mmol), potassium carbonate (9.34 g, 67.6 mmol), acetone (200 mL), and dimethyl sulfate (6.46 g, 67.6 mmol) were added together. The resultant mixture was then heated to reflux for 16 h. The mixture was then filtered and the solid was washed with ethyl acetate. The resulting organic liquid was then concentrated under vacuum to an oil and redissolved in ethyl acetate (600 mL). The organic solution was then washed with water, dried, filtered and concentrated under vacuum to an oil that was then subjected to purification via column chromatography (gradient of 5% to 40% EtOAc/Hexanes) to yield the title compound as an oil (10.42, 87%).

Part C. Preparation of methyl 5-amino-3-tert-butyl-2-methoxybenzoate

Methyl 3-tert-butyl-2-methoxy-5-nitrobenzoate (10.42 g, 39.0 mmol), iron powder (325 mesh, 10.89 g, 195 mmol), ammonium chloride (3.13 g, 58.5 mmol), water (30 mL), and methanol (150 mL) were added together. The resultant mixture was then refluxed for 1 h. The mixture was then cooled to room temperature, filtered through celite, and the celite washed with methanol. The filtrate was then concentrated under vacuum and dissolved in ethyl acetate (600 mL). The resultant solution was then washed with water and brine. The organic extract was then dried, filtered and concentrated under vacuum to yield the title compound as an oil (9.25 g, 100%).

Part D. Preparation of 3-(3-tert-butyl-4-methoxy-5-(methoxycarbonyl)phenylamino)propanoic acid The product from Part C (16.44 g, 69.3 mmol) was dissolved in toluene (200 mL). This mixture was heated to reflux and acrylic acid added over time (1 mL of acrylic acid added every 3 h, 5.23 mL total, 76.2 mmol). The mixture was then refluxed for 24 h. The mixture was then cooled and concentrated under vacuum to dryness to yield an oil as the crude title compound that was used directly in the next reaction.

Part E. Preparation of methyl 3-tert-butyl-5-(2,4-dioxotetrahydropyrimidin-1(2H)-yl)-2-methoxybenzoate The product from Part D (21.43 g, 69.3 mmol), urea (10.4 g, 173 mmol) and acetic acid (glacial, 200 mL) were added together. The mixture was then heated to 120° C. for 18.5 h followed by concentration under vacuum to give an oil. To this oil was added methanol (13 mL), and ethyl acetate (350 mL). The resultant mixture was allowed to stand for 24-48 h whereby a precipitate formed. The resulting solid was filtered off and washed with a small amount of methanol (10 mL) and then air dried to yield the title compound as a solid (15.26 g, 66%).

Part F. Preparation of 3-tert-butyl-5-(2,4-dioxotetrahydropyrimidin-1(2H)-yl)-2-methoxy benzoic acid The product from Part D (4.52 g, 13.52 mmol), methanol (70 mL), and tetrahydrofuran (70 mL) were added together. The mixture was then stirred vigorously until a homogenous solution resulted. Once homogenous, a solution of aqueous sodium hydroxide (1.0M, 68 mL) was added. The mixture was then stirred for 12 h, the mixture was then concentrated under vacuum to remove the organic solvent, followed by the addition of aqueous hydrochloric acid (1.0M, 80 mL) that resulted in solid formation. The mixture was then concentrated under vacuum. To this material was added hydrochloric acid (12M, 100 mL) and the resultant material heated to 100° C. for 1.5 h. The reaction was then cooled and water added. The resulting solid was filtered, washed with water, and dried to yield the title compound as a solid (3.55 g, 82%).

Part G. Preparation of 3-tert-butyl-5-(2,4-dioxotetrahydropyrimidin-1(2H)-yl)-2-methoxy-benzaldehyde The product obtained in Part F (4.07 g, 12.71 mmol) and thionyl chloride (40.82 mL, 559 mmol) were combined and the mixture was refluxed for 2 h, followed by concentration under vacuum to provide a light yellow colored solid product. The solid was dissolved in tetrahydrofuran (125 mL), the solution cooled to −78° C. and LiAlH(OtBu)$_3$ (1M, 14 mL) was added slowly over 10 min while maintaining the temperature at −78° C. The mixture was stirred at −78° C. for 2 h, and the reaction was quenched with hydrochloric acid (aq., 1M, 25 mL) at −78° C. The mixture was warmed to room temperature and ethyl acetate was added. The layers were separated and the aqueous layer was washed with ethyl acetate. The organic extracts were combined and washed with half saturated sodium bicarbonate solution. The organic layer was dried, filtered and concentrated under vacuum to yield the title compound as a solid (3.73 g, 96%).

Part H. Preparation of 1-(3-tert-butyl-4-methoxy-5-(4-nitrostyryl)phenyl)dihydro-pyrimidine-2,4(1H, 3H)-dione The product prepared in Part G (1.00 g, 3.29 mmol) and diethyl 4-nitrobenzyl-phosphonate (0.853 g, 3.12 mmol) were dissolved in dichloromethane (50 mL). Solid potassium tert-butoxide (0.737 g, 6.57 mmol) was added portion wise at room temperature. The resultant dark red solution was stirred for 1.5 h at room temperature. 1N aqueous HCl (50 mL) solution was added and the mixture was stirred 30 min, and then diluted with dichloromethane (50 mL). The resultant organic layer was separated and dried. The material was purified by column chromatography on silica gel using 99/1 dichloromethane/methanol as eluent to obtain the title compound as a solid (1.12 g, 80%).

Part I. Preparation of Preparation of (E)-N-(4-(3-tert-butyl-5-(2,4-dioxotetrahydro-pyrimidin-1(2H)-yl)-2-methoxystyryl)phenyl)methanesulfonamide The product obtained in Part H (1.1 g, 2.60 mmol), iron (0.725 g, 12.99 mmol), and ammonium chloride (0.208 g, 3.90 mmol) was added to a mixture of tetrahydrofuran (40 mL), ethanol (40 mL) and water (12 mL). The slurry was heated to 90° C. for 45 min, and then cooled to ambient temperature. The solution was filtered through a pad of celite (10 g), washed with ethanol (20 mL), and the filtrate concentrated under vacuum to a solid. The resulting solid was dissolved in ethyl acetate (100 mL), and the solution was washed with water (50 mL) and dried over Na$_2$SO$_4$. The drying agent was filtered off and the solvent removed under vacuum to give the aniline adduct as a yellow solid (830 mg).

The solid (830 mg, 2.109 mmol) was dissolved in dichloromethane (50 mL), and pyridine (0.512 mL, 6.33 mmol) and methanesulfonyl chloride (0.181 mL, 2.32 mmol) were added and the resulting solution was stirred at room temperature 16 h. Dichloromethane (100 mL) was added followed by extraction with a 1N aq. HCl solution (2×50 mL). The organic layer was dried, concentrated under vacuum and purified by column chromatography on silica gel using 98/2 CH$_2$Cl$_2$/MeOH to provide the title compound as a solid (480 mg, 39%, two steps). m.p.=260-261° C. (trans-isomer) $^1$H NMR (500 MHz, DMSO-d$_6$): δ ppm 1.37 (s, 9H), 2.71 (t, J=6.7 Hz, 2H), 3.01 (s, 3H), 3.75 (s, 3H), 3.79 (t, J=6.6 Hz, 2H), 7.13 (d, J=16.5 Hz, 1H), 7.15 (d, J=2.4 Hz, 2H), 7.23 (d, J=8.5 Hz, 2H), 7.25 (d, J=16.5 Hz, 1H), 7.51 (d, J=2.4 Hz, 1H), 7.61 (d, J=8.6 Hz, 2H), 9.80 (bs, 1H), 10.30 (s, 1H). (trans-isomer).

Example 30

Preparation of (Z)—N-(4-(2-(3-tert-butyl-5-(2,4-dioxotetrahydropyrimidin-1(2H)-yl)-2-methoxyphenyl)-1-chlorovinyl)phenyl)methanesulfonamide (compound IA-L1-1.3)

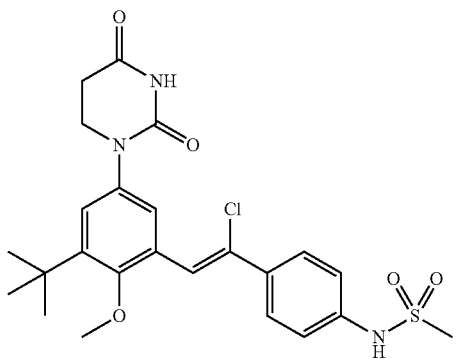 [SMILES: COc1c(/C=C(\Cl)c2ccc(NS(C)(=O)=O)cc2)cc(N2CCC(=O)NC2=O)cc1C(C)(C)C]

Part A. Preparation of diethyl hydroxy(4-nitrophenyl)methylphosphonate

The title compound was prepared as described in Taylor, W P, et. Al, Bioorg. Med. Chem. 4:1515-1520 (1996). 4-Nitrobenzaldehyde (3.0 g, 19.85 mmol) and diethyl phosphonate (2.74 g, 19.85 mmol) were combined and treated with a 0.5N solution of sodium methoxide in methanol (0.993 mL, 0.496 mmol). The resulting red-orange solution was stirred 12 h at room temperature. The reaction mixture was extracted with dichloromethane (20 mL) followed by half saturated ammonium chloride (20 mL). The organic layer was separated, dried and concentrated under vacuum to provide the title compound as a semi-solid (5.1 g, 89%).

Part B. Preparation of diethyl chloro(4-nitrophenyl)methylphosphonate

The product prepared in Part A (500 mg, 1.729 mmol) was dissolved in dichloromethane (10 mL) and treated with triphenylphosphine (998 mg, 3.80 mmol), followed by N-chlorosuccinimide (462 mg, 3.46 mmol). The mixture was stirred at room temperature for 18 h. The solution was concentrated under vacuum and the residue was purified by column chromatography using silica gel eluting with a 1/1 mixture of hexanes/ethyl acetate to provide the title compound as an oil (262 mg, 49%).

Part C. Preparation of (Z)—N-(4-(2-(3-tert-butyl-5-(2,4-dioxotetrahydropyrimidin-1(2H)-yl)-2-methoxyphenyl)-1-chlorovinyl)phenyl)methanesulfonamide The product prepared in Example 29, Part G (100 mg, 0.329 mmole) was treated with the product obtained from Part B using the procedures described in Example 29, Part H and Example 29, Part I to provide 39 mg of the title compound. $^1$H NMR (300 MHz, DMSO-d$_6$): δ ppm 1.36 (s, 9H), 2.71 (t, J=6.8 Hz, 2H), 3.06 (s, 3H), 3.71 (s, 3H), 3.78 (t, J=6.8 Hz, 2H), 7.23 (d, J=2.6 Hz, 1H), 7.27 (s, 1H), 7.28 (d, J=8.6 Hz, 2H), 7.48 (d, J=2.6 Hz, 1H), 7.78 d, J=8.8 Hz, 1H), 10.05 (s, 1H), 10.34 (s, 1H).

Example 31

Preparation of (E)-1-(3-tert-butyl-5-(4-fluorostyryl)-4-methoxyphenyl)dihydropyrimidine-2,4(1H,3H)-dione (compound IA-L1-1.12)

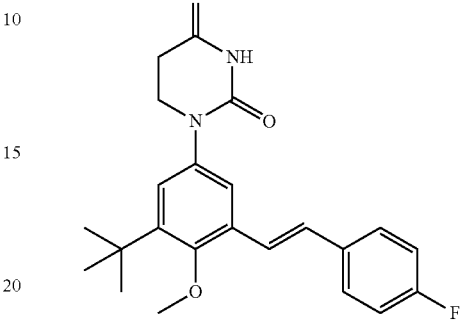

The title compound was prepared according the procedures described in Example 29, Part H and Example 29, Part I using the product obtained in Example 29, Part G (50 mg, 0.164 mmol) and diethyl 4-fluorobenzylphosphonate (40.5 mg, 0.164 mmol). The title compound was obtained as a solid (30 mg, 46%). $^1$H NMR (300 MHz, DMSO-d$_6$): δ ppm 1.37 (s, 9H), 2.72 (t, J=6.6 Hz, 2H), 3.76 (s, 3H), 3.79 (t,=6.6 Hz, 2H), 7.21 (m, 4H), 7.30 (d, J=16.3 Hz, 1H), 7.53 (d, J=2.6 Hz, 1H), 7.73 (m, 2H), 10.35 (s, 1H).

Example 32

Preparation of (Z)—N-(4-(2-(3-tert-butyl-5-(2,4-dioxotetrahydropyrimidin-1(2H)-yl)-2-methoxyphenyl)-1-fluorovinyl)phenyl)methanesulfonamide (compound IA-L1-1.4)

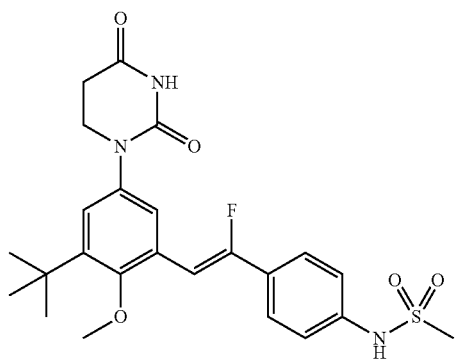 [SMILES: COc1c(/C=C(\F)c2ccc(NS(C)(=O)=O)cc2)cc(N2CCC(=O)NC2=O)cc1C(C)(C)C]

Part A. Preparation of diethyl fluoro(4-nitrophenyl)methylphosphonate

The title compound was prepared as described in Taylor, W P, et. Al, Bioorg. Med. Chem. 4:1515-1520 (1996). The product from Example 30, Part A (500 mg, 1.729 mmol) was dissolved in dichloromethane (10 mL) and treated by drop wise addition of (diethylamino)sulfur trifluoride (DAST) (2.5 mL, 18.9 mmol). The mixture was stirred at room temperature for 18 h. A solution of half saturated sodium phosphate monobasic (20 mL) was added followed by dichloromethane (20 mL) addition and separation of the resulting organic phase. The organic solution was dried and concentrated under vacuum, and then subjected to column chromatography using silica gel eluting with a 1/1 mixture of hexanes/ethyl acetate to provide the title compound as an oil (215 mg, 43%).

Part B. Preparation of (Z)—N-(4-(2-(3-tert-butyl-5-(2,4-dioxotetrahydropyrimidin-1(2H)-yl)-2-methoxyphenyl)-1-fluorovinyl)phenyl)methanesulfonamide The product prepared as described in Part A (100 mg, 0.329 mmole) was treated with the product prepared in Example 29, Part G (96 mg, 0.329 mmole) according to the procedures described in Example 29, Part H and Example 29, Part I to provide 53 mg of the title compound as a 1/1 mixture of cis/trans isomers. Reverse phase HPLC chromatographic separation using a 40-100% gradient of acetonitrile in 0.1% aqueous trifluoroacetic acid provided the title compound as a solid (20 mg). $^1$H NMR (300 MHz, DMSO-d$_6$): δ ppm 1.37 (s, 9H), 2.71 (t, J=6.8 Hz, 2H), 3.06 (s, 3H), 3.77 (s, 3H), 3.78 (m, 2H), 6.62 (d, J=40.4 Hz, 1H), 7.18 (d, J=2.6 Hz, 1H), 7.30 (d, J=8.4 Hz, 2H), 7.55 (d, J=2.6 Hz, 1H), 7.75 (d, J=8.8 Hz, 2H), 10.08 (s, 1H), 10.33 (s, 1H).

Example 33

Preparation of (E)-N-(4-(2-(3-tert-butyl-5-(2,4-dioxotetrahydropyrimidin-1(2H)-yl)-2-methoxyphenyl)-1-fluorovinyl)phenyl)methanesulfonamide (compound IA-L1-1.5)

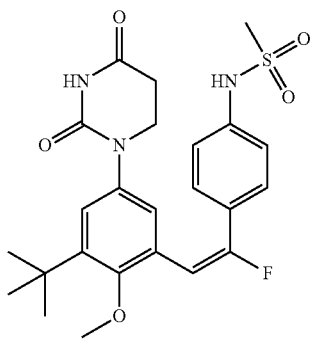 [SMILES: COc1c(/C=C(/F)c2ccc(NS(C)(=O)=O)cc2)cc(N2CCC(=O)NC2=O)cc1C(C)(C)C]

Reverse phase HPLC chromatographic separation of the 1/1 mixture of cis/trans isomeric material (53 mg) from Example 32, Part A using a 40-100% gradient of acetonitrile in 0.1% aqueous trifluoroacetic acid provided the title compound as a solid (16.5 mg). $^1$H NMR (300 MHz, DMSO-d$_6$): δ ppm 1.33 (s, 9H), 2.60 (t, J=6.6 Hz, 2H), 3.01 (s, 3H), 3.57 (t, J=6.6 Hz, 2H) 3.79 (s, 3H), 6.46 (d, J=21.3 Hz, 1H), 6.87 (d, J=2.2 Hz, 1H), 7.14 (m, 3H), 7.36 (d, J=8.8 Hz, 2H), 10.02 (s, 1H), 10.24 (s, 1H).

Example 34

Preparation of (E)-N-(4-(3-tert-butyl-5-(2,4-dioxotetrahydropyrimidin-1(2H)-yl)-2-methoxystyryl)-2-fluorophenyl)methanesulfonamide (compound IA-L1-1.26)

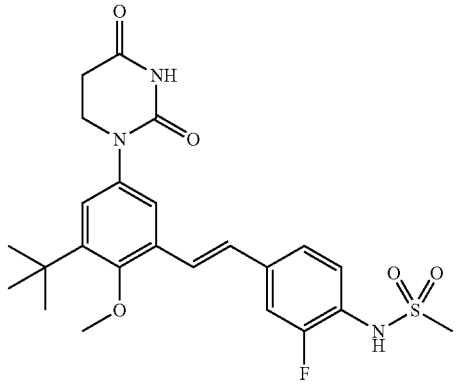 [SMILES: COc1c(/C=C/c2ccc(NS(C)(=O)=O)c(F)c2)cc(N2CCC(=O)NC2=O)cc1C(C)(C)C]

Part A. Preparation of 4-(bromomethyl)-2-fluoro-1-nitrobenzene (3-Fluoro-4-nitrophenol)methanol (1.24 g, 7.25 mmol) was dissolved in dichloromethane (25 mL) and treated with triphenylphosphine (2.281 g, 8.70 mmol) followed by N-bromosuccinimide (1.548 g, 8.70 mmol). The mixture was stirred at room temperature for 2 h. Water (50 mL) and dichloromethane (40 mL) were added, and the organic layer was separated and dried. The solution was concentrated under vacuum and purified by column chromatography using silica gel eluting with a 5/1 mixture of hexanes/ethyl acetate to provide the title compound as a solid (1.27 g, 75%).

Part B. Preparation of diethyl 3-fluoro-4-nitrobenzylphosphonate

The product prepared in Part A (1.27 g, 5.43 mmol) was added to triethyl phosphite (8 mL, 54.3 mmol) and the solution heated to 120° C. for 1 hr. After cooling, the excess triethyl phosphite was removed by heating under vacuum and the residue subjected to column chromatography on silica gel using 99/1 dichloromethane/methanol as eluent to obtain the crude title compound as an oil (800 mg).

Part C. Preparation of (E)-N-(4-(3-tert-butyl-5-(2,4-dioxotetrahydropyrimidin-1(2H)-yl)-2-methoxystyryl)-2-fluorophenyl)methanesulfonamide The product described in Example 29, Part G (533 mg, 1.751 mmole) was treated with the product described in Part B (510 mg, 1.751 mmole) according to the procedures described in Example 29, Part H and Example 29, Part I to provide 80 mg of the title compound. $^1$H NMR (300 MHz, DMSO-d$_6$): δ ppm 1.37 (s, 9H), 2.71 (t, J=6.5 Hz, 2H), 3.05 (s, 3H), 3.76 (s, 3H), 3.79 (t, J=6.6 Hz, 2H), 7.18 (m, 2H), 7.36 (d, J=16.5 Hz, 1H), 7.39 (m, 1H), 7.44 (m, 1H), 7.52 (d, J=2.6 Hz, 1H), 7.63 (m, 1H), 9.65 (s, 1H), 10.35 (s, 1H).

Example 35

Preparation of N-(4-(2-(3-tert-butyl-5-(2,4-dioxotetrahydropyrimidin-1(2H)-yl)-2-methoxyphenyl)cyclopropyl)phenyl)methanesulfonamide (compound IA-L8-1.1)

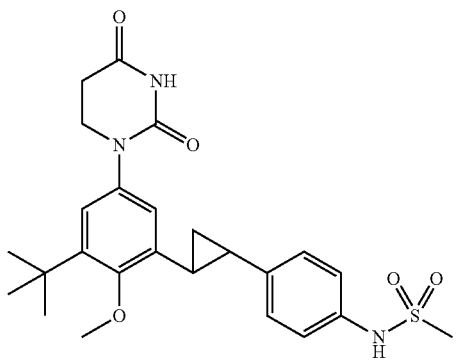 [SMILES: COc1c(C2CC2c2ccc(NS(C)(=O)=O)cc2)cc(N2CCC(=O)NC2=O)cc1C(C)(C)C]

The product obtained as described in Example 29, Part I (30 mg, 0.064 mmol) was dissolved in tetrahydrofuran (2 mL) and treated with 0.95 mL of a 0.67M ether solution of diazomethane (0.636 mmol) followed by palladium acetate (0.7 mg, 0.0031 mmol). The mixture was stirred for 30 min at room temperature followed by removal of the solid by filtration and concentration of the filtrate. The filtrate was purified by column chromatography on silica gel using 98/2 dichloromethane/methanol as eluent to obtain the title compound as a solid (21.6 mg, 70%). m.p. 265-266° C. $^1$H NMR (300 MHz, DMSO-$d_6$): δ ppm 1.33 (s, 9H) 1.50 (m, 2H), 2.13 (m, 1H), 2.27 (m, 1H), 2.69 (t, J=6.6 Hz, 2H), 2.94 (s, 3H), 3.63 (s, 3H), 3.74 (t, J=6.6 Hz, 2H), 6.84 (d, J=2.6 Hz, 1H), 7.04 (d, J=2.6 Hz, 1H), 7.14 (d, J=8.8 Hz, 2H), 7.20 (d, J=8.8 Hz, 2H), 9.60 (s, 1H), 10.29 (s, 1H).

Example 36

Preparation of N-(4-(3-tert-butyl-5-(2,4-dioxotetrahydropyrimidin-1(2H)-yl)-2-methoxyphenethyl)phenyl)methanesulfonamide (compound IA-L5-2-1.1)

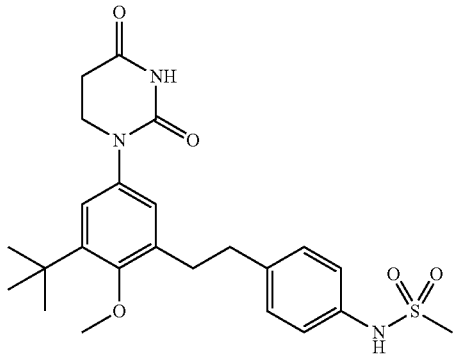 [SMILES: COc1c(CCc2ccc(NS(C)(=O)=O)cc2)cc(N2CCC(=O)NC2=O)cc1C(C)(C)C]

The product obtained as described in Example 29, Part I (415 mg, 0.88 mmol) was dissolved in methanol (30 mL) and treated with 50 mg of 10% palladium on carbon. The slurry was stirred for 48 h at room temperature under 1 atm of hydrogen. The reaction mixture was filtered through celite and concentrated in vacuo to provide the title compound as a solid (230 mg, 55%). m.p. 233-234° C. $^1$H NMR (300 MHz, DMSO-$d_6$): δ ppm 1.34 (s, 9H), 2.68 (t, J=6.8 Hz, 2H), 2.86 (s, 4H), 2.93 (s, 3H), 3.70 (m, 2H), 3.74 (s, 3H), 7.11 (m, 4H), 7.23 (m, 2H), 9.59 (s, 1H), 10.29 (s,).

Example 37

Preparation of (E)-N-(4-(3-tert-butyl-5-(2,4-dioxotetrahydropyrimidin-1(2H)-yl)styryl)phenyl)methanesulfonamide (compound IA-L1-1.16)

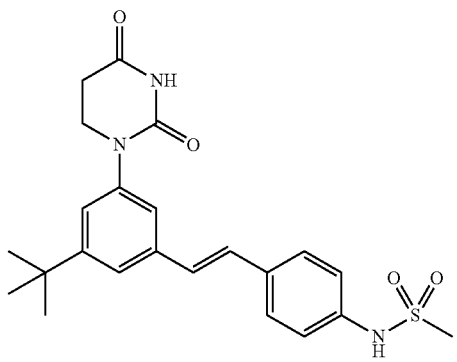 [SMILES: CC(C)(C)c1cc(/C=C/c2ccc(NS(C)(=O)=O)cc2)cc(N2CCC(=O)NC2=O)c1]

Part A. Preparation of methyl 3-tert-butyl-5-(chlorocarbonyl)benzoate

A mixture of 3-tert-butyl-5-(methoxycarbonyl)benzoic acid (9.18 g, 38.9 mmol, prepared by the method of Carter et. al., WO2005021500A1), thionyl chloride (75 mL) and 1 drop of DMF in toluene (200 mL) was heated at reflux for 2 h, cooled and concentrated. The residue was azeotroped with toluene (3×50 mL) and dried under high vacuum to give the title compound as an off-white waxy solid (9.9 g, quantitative yield).

Part B. Preparation of methyl 3-(azidocarbonyl)-5-tert-butylbenzoate

To the product of Part A (9.9 g, 38.9 mmol) in acetone (200 ml) was added at a fast drip a solution of sodium azide (10.12 g, 156 mmol) dissolved in water (20 mL). The mixture was stirred for 2 h and diluted with EtOAc. The organic layer was washed with $H_2O$, saturated brine, dried ($Na_2SO_4$), filtered and concentrated to give the title compound as a white solid (9.9 g, 97%).

Part C. Preparation of methyl 3-amino-5-tert-butylbenzoate

The product from Part B (9.9 g, 37.9 mmol) in toluene (100 mL) was heated at reflux for 1 h and concentrated to give the intermediate isocyanate which was dissolved in DME (60 mL) treated with 8% HCl (150 mL) and stirred for 16 h. The mixture was concentrated and the residue was dissolved in water, neutralized with solid sodium bicarbonate and extracted 3×100 mL with EtOAc. The organics were combined, washed with saturated NaCl, dried ($Na_2SO_4$), filtered and concentrated. The crude product was chromatographed on silica eluting with 2:1 hexane/EtOAc to give the title compound as an oil (2.7 g, 35%).

Part D. Preparation of methyl 3-tert-butyl-5-(2,4-dioxotetrahydropyrimidin-1(2H)-yl)-2-methoxybenzoate A mixture of the product of Part C (2.34 g, 11.29 mmol) and acrylic acid (2.32 ml, 33.9 mmol) in toluene (60 ml) was heated at reflux under nitrogen for 24 h, cooled and concentrated. The resulting residue was then treated with urea (2.03 g, 33.9 mmol) in acetic acid (35 ml) and heated at 120° C. for 24 h, cooled and concentrated. The residue was azeotroped 3×50 mL with toluene and dissolved in 100 mL of EtOAc. The organic layer was washed with dilute aqueous $NaHCO_3$, $H_2O$, saturated brine, dried ($Na_2SO_4$), filtered and concentrated to give the title compound as a white solid (2.1 g, 61%).

Part E. Preparation of 3-tert-butyl-5-(2,4-dioxotetrahydropyrimidin-1(2H)-yl)benzoic acid A mixture of the product from Part D (1.8 g, 5.91 mmol) and 1M NaOH (29.6 ml, 29.6 mmol) in MeOH (15 ml) and THF (15 mL) was stirred for 24 h and concentrated. The residue was treated with 50 mL of 1M HCl and extracted into EtOAc. The EtOAc layer was washed with $H_2O$, saturated brine, dried ($Na_2SO_4$), filtered and concentrated to give a white solid. This intermediate urea was combined with 20 mL of concentrated HCl and heated at 100° C. for 1 h, cooled and diluted with 75 mL of ice water to give a white powder which was collected by filtration and dried to constant mass to give the title compound (1.6 g, 93%).

Part F. Preparation of (E)-N-(4-(3-tert-butyl-5-(2,4-dioxotetrahydropyrimidin-1(2H)-yl) styryl)phenyl) methanesulfonamide The product described in Part E was treated with thionyl chloride and lithium tri-tert-butoxyaluminum hydride according to procedures described in Example 29, Part G to produce 3-tert-butyl-5-(2,4-dioxotetrahydropyrimidin-1 (2H)-yl)benzaldehyde. The aldehyde was treated with diethyl 4-nitrobenzylphosphonate according to the procedures described in Example 29, Part H and Example 29, Part I to provide the title compound (85 mg). $^1$H NMR (300 MHz, DMSO-$d_6$): δ ppm 1.32 (s, 9H) 2.72 (t, J=6.43 Hz, 2H) 3.01 (s, 3H) 3.82 (t, J=6.62 Hz, 2H) 7.18-7.25 (m, 5H) 7.39 (s, 1H) 7.46 (s, 1H) 7.58 (d, J=8.46 Hz, 2H) 9.84 (s, 1H) 10.37 (s, 1H).

Example 38

Preparation of (Z)—N-(4-(2-(3-tert-butyl-5-(2,4-dioxotetrahydropyrimidin-1(2H)-yl)-2-methoxyphenyl)-1-methoxyvinyl)phenyl)methanesulfonamide (compound IA-L1-1.17)

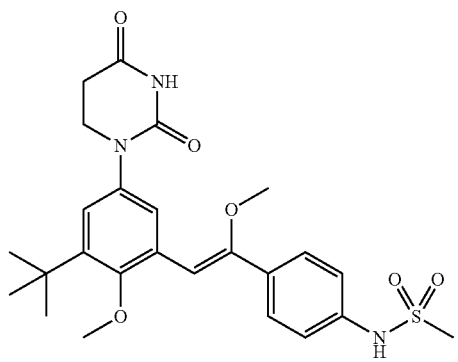

Part A. Preparation of 1-(dimethoxymethyl)-4-nitrobenzene

A flask equipped with a magnetic stir bar and vigreux column was charged with 4-nitro-benzaldehyde (5.0 g, 33.1 mmol), pyridinium p-toluenesulfonate (1.66 g, 6.62 mmol), trimethoxymethane (3.51 g, 33.1 mmol) and methanol (100 mL). The mixture was heated at 50° C. for 12 h and was concentrated in vacuo. The residue was redissolved in EtOAc and washed with aq. NaOH (1M), $H_2O$ and brine. The mixture was dried ($Na_2SO_4$), filtered and concentrated in vacuo to yield the title compound as a clear, light yellow oily product (6.36 g, 97%).

Part B. Preparation of diethyl methoxy(4-nitrophenyl)methylphosphonate

The product from Part A (3.0 g, 15.2 mmol) and triethyl phosphite (2.53 g, 15.2 mmol) were dissolved in dichloromethane (30 mL) under a nitrogen atmosphere, cooled to −20° C. and treated with drop wise addition of boron trifluoride etherate (2.27 g, 16 mmol). The mixture was allowed to slowly warm to room temperature overnight with stirring. Water was added and the resulting mixture was stirred 5 min, separated and the organic layer was dried ($Na_2SO_4$), filtered and concentrated in vacuo to a solid residue. The residue was purified on silica gel (100% EtOAc to 3% $CH_3OH$/EtOAc) to yield the title compound as a light yellow oily product (3.78 g, 82%).

Part C. Preparation of (Z)—N-(4-(2-(3-tert-butyl-5-(2,4-dioxotetrahydropyrimidin-1(2H)-yl)-2-methoxyphenyl)-1-methoxyvinyl)phenyl)methanesulfonamide The product obtained according to the procedure described in Example 29, Part G (400 mg, 1.314 mmole) was treated with the product obtained in Part B (399 mg, 1.314 mmole) according to the procedures described in Example 29, Part H and Example 29, Part I to provide the title compound (17 mg, 6%). $^1$H NMR (300 MHz, DMSO-$d_6$): δ ppm 1.36 (s, 9H) 2.71 (t, J=6.62 Hz, 2H) 3.05 (s, 3H) 3.58 (s, 3H) 3.75 (s, 3H)

3.76-3.81 (m, 2H) 6.25 (s, 1H) 7.11 (d, J=2.57 Hz, 1H) 7.27 (d, J=8.46 Hz, 2H) 7.60 (d, J=8.82 Hz, 2H) 7.67 (d, J=2.57 Hz, 1H) 9.96 (s, 1H) 10.32 (s, 1H).

Example 39

Preparation of (E)-1-(3-tert-butyl-4-methoxy-5-styrylphenyl)dihydro-pyrimidine-2,4(1H,3H)-dione (compound IA-L1-1.18)

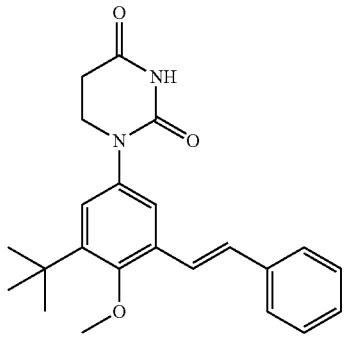 [SMILES: COc1c(/C=C/c2ccccc2)cc(N2CCC(=O)NC2=O)cc1C(C)(C)C]

The product obtained according to procedure described in Example 29, Part G (50 mg, 0.164 mmole) was treated with diethyl benzylphosphonate (0.034 ml, 0.164 mmole) according to the procedure described in Example 29, Part H to provide the title compound (13 mg, 19%). ¹H NMR (300 MHz, DMSO-$d_6$): δ ppm 1.37 (s, 9H) 2.72 (t, J=6.62 Hz, 2H) 3.76 (s, 3H) 3.80 (t, J=6.80 Hz, 2H) 7.16-7.18 (m, 1H) 7.21-7.23 (m, 1H) 7.29-7.33 (m, 2H) 7.36-7.43 (m, 2H) 7.54 (d, J=2.57 Hz, 1H) 7.64 (d, J=7.35 Hz, 2H) 10.35 (s, 1H).

Example 40

Preparation of (E)-1-(3-tert-butyl-4-methoxy-5-(4-methoxystyryl)phenyl)dihydropyrimidine-2,4(1H,3H)-dione (compound IA-L1-1.14)

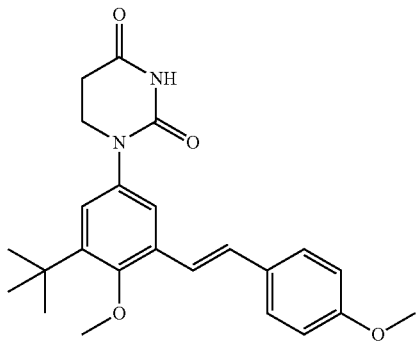 [SMILES: COc1ccc(/C=C/c2cc(N3CCC(=O)NC3=O)cc(C(C)(C)C)c2OC)cc1]

The product obtained according to procedure described in Example 29, Part G (50 mg, 0.164 mmole) was treated with diethyl 4-methoxybenzylphosphonate (0.028 ml, 0.164 mmole) according to the procedure described in Example 29, Part H to provide the title compound (4 mg, 4%). ¹H NMR (300 MHz, DMSO-$d_6$): δ ppm 1.37 (s, 9H) 2.71 (t, J=6.62 Hz, 2H) 3.70-3.81 (m, 8H) 6.96 (d, J=8.82 Hz, 2H) 7.13 (d, J=2.21 Hz, 1H) 7.15 (d, J=2.57 Hz, 2H) 7.50 (d, J=2.57 Hz, 1H) 7.58 (d, J=8.46 Hz, 2H) 10.34 (s, 1H).

Example 41A

Preparation of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1)

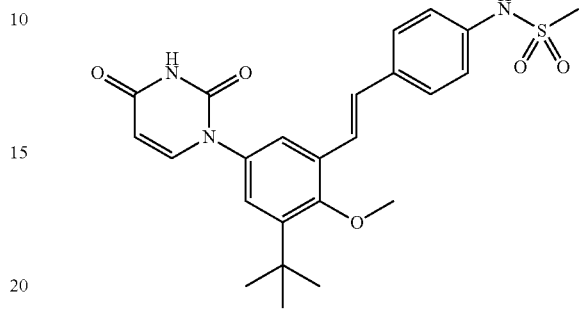

Part A. Preparation of (E)-methyl 3-tert-butyl-2-methoxy-5-(3-(3-methoxyacryloyeureido) benzoate The product obtained as described in Example 29, Part C (2.0 g, 8.43 mmol) was dissolved in 30 mL of N,N-dimethylacetamide and cooled to −25° C. A 0.5 Molar solution of E-3-methoxyacryloyl isocyanate in benzene (21.9 mL, 10.96 mmol) was added drop wise and the resulting solution was stirred at ambient temperature for 4 h, and then poured into water. The product was extracted into dichloromethane, washed with brine, dried over sodium sulfate, filtered and evaporated under vacuum to give the title compound.

Part B. Preparation of methyl 3-tert-butyl-5-(2,4-dioxo-3,4-dihydropyrimidin-1(2H)-yl)-2-methoxybenzoate The product from Part A (3.1 g, 8.51 mmol) was dissolved in ethanol (60 mL). To this solution was added a mixture of concentrated sulfuric acid (6 mL) and water (60 mL). The heterogeneous mixture was heated at 100° C. for 3 h. The ethanol was removed under vacuum, and then the aqueous solution was extracted with dichloromethane and evaporated to dryness. This residue was purified by column chromatography on silica gel, eluting with 1% methanol/dichloromethane to yield the title compound (1.23 g, 44%).

Part C. Preparation of 3-tert-butyl-5-(2,4-dioxo-3,4-dihydropyrimidin-1(2H)-yl)-2-methoxy benzoic acid The product from Part B (1.23 g, 3.7 mmol) was taken up in ethanol (5 mL) and 1M sodium hydroxide solution (10 mL) and stirred at ambient temperature for 18 h. The solution was acidified with 1M HCl and the resulting solid was filtered and dried to give the title compound (0.945 g, 80%).

Part D. Preparation of 3-tert-butyl-5-(2,4-dioxo-3,4-dihydropyrimidin-1(2H)-yl)-2-methoxy benzaldehyde The product from Part C (0.945 g, 2.97 mmol) was taken up in thionyl chloride (4.5 mL) and the mixture was heated at 80°

229

C. for 40 min. After evaporation to dryness, the acid chloride was dissolved in dry THF (8 mL) and cooled to −78° C. A 1 M solution of lithium tri-tert-butoxyaluminum hydride in THF (3.0 mL, 3.0 mmol) was added drop wise. After 45 min the cold reaction was quenched with 1M HCl (5 mL), extracted into ethyl acetate, and purified by column chromatography on silica gel, eluting with dichloromethane followed by 1% methanol/dichloromethane to give the title compound (0.635 g, 71%).

Part E. Preparation of (E)-1-(3-tert-butyl-4-methoxy-5-(4-nitrostyryl)phenyl)pyrimidine-2,4(1H,3H)-dione The product of Part D (0.634 g, 2.1 mmol) and diethyl 4-nitrobenzylphosphonate (0.573 g, 2.1 mmol) were combined in dichloromethane (25 mL) at ambient temperature. Potassium tert-butoxide (0.494 g, 4.4 mmol) was added portion wise and the resulting red/brown heterogeneous mixture was stirred for 1.5 h. This mixture was quenched with 1M HCl (15 mL), poured into water and extracted into ethyl acetate, and the crude product was purified by column chromatography on silica gel, eluting with 1% methanol/dichloromethane to give the title compound (0.735 g, 83%).

Part F. Preparation of (E)-1-(3-(4-aminostyryl)-5-tert-butyl-4-methoxyphenyl)pyrimidine-2,4(1H,3H)-dione The product from Part E (0.735 g, 1.74 mmol), ammonium chloride (0.14 g, 2.62 mmol), and iron (0.487 g, 8.72 mmol) were combined in a solution of ethanol (10 mL), water (5 mL), and THF (10 mL) and heated at 75° C. for 1 h. The mixture was filtered through diatomaceous earth, rinsing well with THF and concentrated to give the title compound.

Part G. Preparation of (E)-N-(4-(3-tert-butyl-5-(2,4-dioxo-3,4-dihydropyrimidin-1(2H)-yl)-2-methoxystyryl)phenyl)methanesulfonamide The product from Part F (0.683 g, 1.75 mmol) and pyridine (0.564 mL, 6.98 mmol) were combined in dichloromethane (15 mL) at ambient temperature. Methane sulfonylchloride (0.163 mL, 2.1 mmol) was added drop wise and the solution was stirred for 18 h. The mixture was poured into 1M HCl and extracted into dichloromethane, concentrated, and purified by column chromatography on silica gel, eluting with 1%, 2% methanol/dichloromethane. Trituration from dichloromethane provided a solid that was filtered and dried to give the title compound as a colorless powder (0.465 g, 57%). $^1$H NMR (300 MHz, DMSO-D6) δ ppm 1.38 (s, 9H), 3.01 (s, 3H), 3.79 (s, 3H) 5.65 (d, J=7.72 Hz, 1H), 7.17-7.28 (m, 5H), 7.58-7.70 (m, 3H), 7.75 (d, J=7.72 Hz, 1H), 9.86 (s, 1H), 11.42 (s, 1H).

Example 41B

Preparation of (E)-N-(4-(3-tert-butyl-5-(2,4-dioxo-3,4-dihydropyrimidin-1(2H)-yl)-2-methoxystyryl)phenyl)methanesulfonamide (compound IB-L1-1.1)

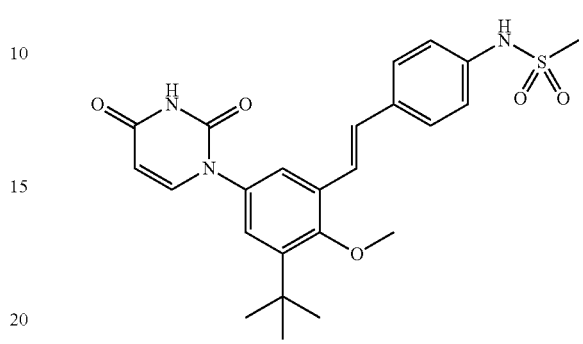

Part A. Preparation of N-(4-ethynylphenyl)methanesulfonamide

In a 2 L, 3-neck round-bottom flask equipped with an overhead stirrer was added 4-ethynylaniline (30 g, 256 mmol) and pyridine (42.5 ml, 525 mmol) in dichloromethane (512 ml) to give an orange solution. The mixture was cooled to 5° C. and methanesulfonyl chloride (19.96 ml, 256 mmol) was added drop wise over 15 min. The reaction solution was stirred at 5° C. for 2 h and washed with 1M aqueous HCl (3×250 mL). The dichloromethane layer was then washed sequentially with saturated aqueous NaHCO$_3$, water, and saturated aqueous NaCl. The dichloromethane layer was dried over sodium sulfate and treated simultaneously with decolorizing charcoal for 30 min, the solution then filtered through Celite and the filtrate was concentrated. The pink/orange solid was dissolved in a minimal amount of hot ethyl acetate (50-75 mL) and slowly diluted with hexanes (500-600 ml) to give orange crystals that were collected by filtration and dried to provide the title compound (40.0 g, 80%).

Part B. Preparation of (E)-4-(methylsulfonamido)styrylboronic acid (Reference: Org. Prep. Proc. Int., 2004, 36, 573-579) To a flask was added borane-methyl sulfide complex (8.03 mL, 85 mmol) followed by tetrahydrofuran (16 mL) and the mixture then cooled to 0° C. (1R)-(+)-alpha-pinene (26.2 mL, 169 mmol) was then added drop wise (over 10 min) to the ice-cooled solution. The mixture was then stirred at 0° C. for 1 h followed by stirring 2 h at room temperature. The resulting thick white slurry was cooled to −40° C. in a dry ice/acetone bath, followed by the addition of the product from Part A (15.0 g, 77 mmol) dissolved in 60 mL of THF, drop wise over 30 min. After the addition was complete, the mixture was stirred for an additional hour at −35° C., then 1 h at room temperature. The light yellow solution was then cooled to 0° C. and acetaldehyde (61.4 mL, 1088 mmol) added, then the mixture refluxed at 50° C. for 18 h. The solvent was then removed under vacuum to provide an orange syrup, to which water (115 mL) was added and the heterogeneous mixture stirred for 3 h at room temperature. The light yellow solid generated was collected and washed with water (250 mL) then dried in a vacuum oven overnight. The resultant material was then dissolved in boiling acetone (190 mL), which provided a homogenous yellow solution, followed by removal of the solution from heating and the addition of hexanes (365 ml) over 5 min time. A white solid formed in the solution and the mixture was stirred until the solution cooled to room temperature, then the white solid was collected and dried in a vacuum oven for 1 hr to provide the title compound (12.1 g, 85%).

Part C. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give a cocoa colored powder that was dried to constant mass (4.65 g, 35.6%).

Part D. Preparation of
2-bromo-6-tert-butyl-4-nitrophenol

A solution of the product from Part C (1.0 g, 5.12 mmol) in glacial acetic acid (10.25 mL) was treated portion wise with pyridine hydrobromide perbromide (1.80 g, 5.63 mmol) followed by stirring at room temperature for 2 h. Additional pyridinium hydrobromide perbromide (3.6 g) was added in two portions and after another 3 h of stirring, the reaction was complete. The mixture was poured into ice water, and the mixture treated with a small amount of sodium sulfite. The resulting solid was filtered and dried under vacuum to give the title compound as a brown solid (1.40 g, 100%).

Part E. Preparation of
1-bromo-3-tert-butyl-2-methoxy-5-nitrobenzene

A solution of the product from Part D (1.40 g, 5.11 mmol) in 10:1 t-butylmethylether-methanol (25.5 mL) was treated with 2.0M trimethylsilyldiazomethane in ether (5.1 mL, 10.21 mmol), followed by stirring at room temperature for 18 h. The mixture was concentrated under vacuum to afford a yellow oil, which was purified by silica gel column chromatography eluting with EtOAc/hexanes to give the title compound as a yellow oil (1.36 g, 92%).

Part F. Preparation of tert-butyl
3-bromo-5-tert-butyl-4-methoxyphenylcarbamate

A solution of the product from Part E (960 mg, 3.33 mmol) in methanol (17 mL) was treated with 5% platinum on sulfided carbon (100 mg), followed by hydrogenation under balloon pressure for 3 h, and then filtered through celite and concentrated under vacuum to afford the 3-bromo-5-tert-butyl-4-methoxyaniline as a yellow oil (860 mg, 3.33 mmol, 100%). A solution of this material in THF (17 mL) was treated with di-tert-butyl dicarbonate (800 mg, 3.66 mmol) followed by warming at reflux for 2 h. Concentration under vacuum afforded a beige solid, which was purified by silica gel column chromatography eluting with EtOAc/hexanes. Solid was triturated with hexanes, collected by filtration, and dried under vacuum to give the title compound as a nearly white solid (890 mg, 75%).

Part G. Preparation of (E)-N-(3-bromo-5-tert-butyl-4-methoxyphenylcarbamoyl)-3-methoxyacrylamide The product from Part F (2.0 g, 5.58 mmol) was dissolved in dichloromethane (10 mL) and trifluoroacetic acid (5 mL) added. The solution was stirred at room temperature for 1 h followed by concentration under vacuum and the addition of 10% aqueous sodium bicarbonate (50 mL), followed by extraction with ethyl acetate (3×50 mL). The combined organic extracts were dried and concentrated to provide a residue that was dissolved in 10 mL of N,N-dimethylacetamide and cooled to −25° C. A 0.5 molar solution of E-3-methoxyacryloyl isocyanate in benzene (20.3 mL, 11.16 mmol) was added drop wise and the resulting solution was stirred at ambient temperature for 4 h, and then poured into water. The product was extracted into dichloromethane, washed with brine, dried over sodium sulfate, filtered and evaporated under vacuum to give the title compound.

Part H. Preparation of 1-(3-bromo-5-tert-butyl-4-methoxyphenyl)pyrimidine-2,4(1H,3H)-dione The product from Part G (2.15 g, 5.58 mmol) was dissolved in ethanol (10 mL). To this solution was added a mixture of concentrated sulfuric acid (1 mL) and water (10 mL). The heterogeneous mixture was heated at 100° C. for 2 h. The ethanol was removed under vacuum, and then the aqueous solution was extracted with dichloromethane and evaporated to dryness. This residue was purified by column chromatography on silica gel, eluting with 1% methanol/dichloromethane to yield the title compound (1.35 g, 69%).

Part I. Preparation of (E)-N-(4-(3-tert-butyl-5-(2,4-dioxo-3,4-dihydropyrimidin-1(2H)-yl)-2-methoxystyryl)phenyl)methanesulfonamide The product from Part H (8.0 g, 22.65 mmol), the product from Part B (5.90 g, 24.46 mmol), 1,1'-bis(di-tert-butylphosphino)ferrocene palladium dichloride (0.738 g, 1.132 mmol), and potassium phosphate (9.62 g, 45.3 mmol) were dissolved in a mixture of tetrahydrofuran (128 mL) and water (32 mL). Nitrogen gas was bubbled through the resultant mixture for 10 min followed by heating the solution at 50° C. for 5 h in darkness. The reaction was allowed to cool to room temperature followed by the addition of saturated aqueous ammonium chloride (50 mL), water (200 mL), and the solution extracted with dichloromethane (600 mL). To the organic extract was added magnesium sulfate, and 3-mercaptopropyl-functionalized silica gel (20 g) and the resultant solution stirred in darkness for 18 h. The solids were then removed by filtration and the filtrate concentrated under vacuum and subjected to silica gel column chromatography using a 99/1 to 99/2 dichloromethane/methanol gradient to provide the title compound (7.4 g, 70%). $^1$H NMR (300 MHz, DMSO-D6) δ ppm 1.38 (s, 9H), 3.01 (s, 3H), 3.79 (s, 3H) 5.65 (d, J=7.72 Hz, 1H), 7.17-7.28 (m, 5H), 7.58-7.70 (m, 3H), 7.75 (d, J=7.72 Hz, 1H), 9.86 (s, 1H), 11.42 (s, 1H).

Example 42

Preparation of (E)-N-(4-(3-tert-butyl-5-(5-fluoro-2,4-dioxo-3,4-dihydro-pyrimidin-1(2H)-yl)-2-methoxy-styryl)phenyl)methanesulfonamide (compound IB-L1-1.2)

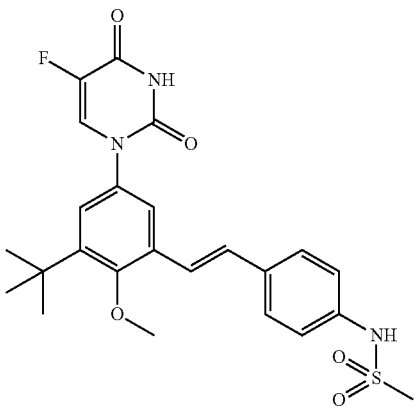 [SMILES: COc1c(/C=C/c2ccc(NS(C)(=O)=O)cc2)cc(-n2cc(F)c(=O)[nH]c2=O)cc1C(C)(C)C]

Part A. Preparation of methyl 3-tert-butyl-5-(5-fluoro-6-methoxy-2,4-dioxotetrahydro-pyrimidin-1(2H)-yl)-2-methoxybenzoate The fluorination procedure was performed as described in Lal, G S, et al. J. Org. Chem., 60:7340-7342 (1995). The product from Example 41A, Part B (0.42 g, 1.26 mmol) and Selectfluor™ (0.672 g, 1.9 mmol) were combined in a mixture of acetonitrile (8 mL) and methanol (1 mL) and heated at 90° C. under $N_2$ for 5 h. The solution was diluted with water, extracted into ethyl acetate, washed with sodium bicarbonate solution, concentrated and purified by column chromatography on silica gel to give the title compound (0.138 g, 29%).

Part B. Preparation of methyl 3-tert-butyl-5-(5-fluoro-2,4-dioxo-3,4-dihydropyrimidin-1(2H)-yl)-2-methoxybenzoate The product from Part A (0.134 g, 0.35 mmol) and triethylamine (1 mL) were combined in methanol (4 mL) and stirred at ambient temperature for 18 h. The solution was quenched with 1M HCl, extracted into dichloromethane and concentrated to give the title compound (0.113 g, 92%).

Part C. Preparation of 3-tert-butyl-5-(5-fluoro-2,4-dioxo-3,4-dihydropyrimidin-1(2H)-yl)-2-methoxybenzoic acid The product from Part B (0.113 g, 0.32 mmol) was treated as described in Example 41A, Part C to give the title compound (0.088 g, 81%).

Part D. Preparation of 3-tert-butyl-5-(5-fluoro-2,4-dioxo-3,4-dihydropyrimidin-1(2H)-yl)-2-methoxybenzaldehyde The product from Part C (0.088 g, 0.26 mmol) was treated as described in Example 41A, Part D to give the title compound (0.075 g, 90%).

Part E. Preparation of (E)-1-(3-tert-butyl-4-methoxy-5-(4-nitrostyryl)phenyl)-5-fluoropyrimidine-2,4(1H,3H)-dione The product of Part D (0.075 g, 0.23 mmol) was treated as described in Example 41A, Part E to give 0.077 g (75%).

Part F. Preparation of (E)-1-(3-(4-aminostyryl)-5-tert-butyl-4-methoxyphenyl)-5-fluoropyrimidine-2,4(1H,3H)-dione The product of Part E (0.077 g, 0.18 mmol) was treated as described in Example 41A, Part F to give the title compound (0.071 g, 94%).

Part G. Preparation of (E)-N-(4-(3-tert-butyl-5-(5-fluoro-2,4-dioxo-3,4-dihydropyrimidin-1(2H)-yl)-2-methoxystyryl)phenyl)methanesulfonamide The product of Part F (0.071 g, 0.17 mmol) was treated as described in Example 41A, Part G to give the title compound (0.048 g, 57%). $^1$H-NMR (300 MHz, DMSO-D6): δ ppm 1.38 (s, 9H), 3.01 (s, 3H), 3.79 (s, 3H) 7.19-7.27 (m, 5H), 7.62 (d, J=8.82 Hz, 2H), 7.66 (d, J=2.57 Hz, 1H), 8.25 (d, J=6.99 Hz, 1H).

Example 43

Preparation of N-(4-((3-tert-butyl-5-(2,4-dioxotetrahydropyrimidin-1(2H)-yl)-2-methoxyphenyl)ethynyl)-3-methylphenyl)methanesulfonamide (compound IA-L2-1.9)

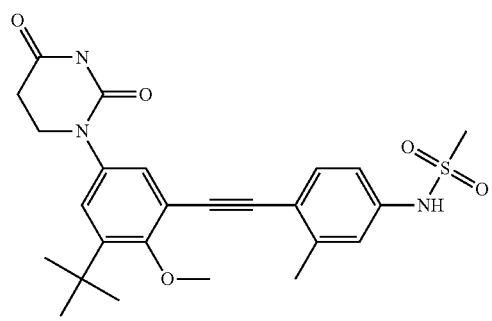 [SMILES: COc1c(C#Cc2ccc(NS(C)(=O)=O)cc2C)cc(N2CCC(=O)NC2=O)cc1C(C)(C)C]

Part A. Preparation of 2-tert-butyl-4-nitrophenol

To a vigorously stirred solution of 2-tert-butylphenol (10 g, 66.6 mmol) in heptane (67 ml) was added at a fast drip a solution of 70% nitric acid (4.25 ml, 66.6 mmol) diluted with water (4.25 ml). The resulting dark red/brown mixture was stirred vigorously for 2 h. The suspended solid was collected by filtration washed with hexane (300 mL), water (200 mL) and once again with hexane (200 mL) to give the title compound as a cocoa colored powder that was dried to constant mass (4.65 g, 35.6%).

Part B. Preparation of 2-tert-butyl-6-iodo-4-nitrophenol

To the product from Part A (4.5 g, 23.05 mmol) dissolved in MeOH (120 ml) and water (30 mL) was added iodine monochloride (1.155 ml, 23.05 mmol) drop wise over a

Part C. Preparation of 1-tert-butyl-3-iodo-2-methoxy-5-nitrobenzene

To an ice bath cooled solution of the product from Part B (5.5 g, 17.13 mmol) in MTBE (15 ml) in a 50 mL pressure vessel was added 2.0M TMS diazomethane (12.85 ml, 25.7 mmol) followed by drop-wise addition of methanol (1.0 mL) resulting in calm bubbling. The vessel was sealed and stirred at room temperature for 16 h, cooled and the pressure was released. The solution was partitioned between EtOAc and water. The organic layer was washed with 1.0M HCl, saturated potassium carbonate solution, and saturated NaCl. The organic layer was dried over sodium sulfate, filtered and concentrated to give the title compound as a red oil that was used without purification (5.4 g, 84%).

Part D. Preparation of 3-tert-butyl-5-iodo-4-methoxyaniline

A mixture of the product from Part C (5.80 g, 17.31 mmol), ammonium chloride (1.389 g, 26.0 mmol), and iron (4.83 g, 87 mmol) in THF/MeOH/water (200 mL total, 2/2/1) was refluxed for 2 h, cooled and filtered through Celite. The filtrate was evaporated and the residue was partitioned between water and EtOAc. The organic layer was washed with saturated brine, dried with sodium sulfate, filtered and evaporated to give the title compound as a brown oil (5.28 g, 100% yield).

Part E. Preparation of 1-(3-tert-butyl-5-iodo-4-methoxyphenyl)dihydropyrimidine-2,4(1H,3H)-dione The product from Part D (8.2 g, 26.9 mmol) was treated with acrylic acid (5.53 ml, 81 mmol) and stirred overnight to give an extremely viscous mixture. The mixture was treated with acetic acid (60 mL) and urea (7.3 g 120 mmol), heated at 120° C. for 24 h, cooled and concentrated. The residue was azeotroped 3×100 mL with toluene to give a brown/tan solid. The solid was suspended in a mixture of 50 mL EtOAc and 100 mL of saturated NaHCO$_3$ and stirred for 30 min to neutralize any remaining acetic acid. The solid was collected by filtration and washed repeatedly with 50 mL portions of water and finally with 3:1 hexane/EtOAc (50 mL) to give the title compound as an off-white solid that was dried to constant mass (7.1 g, 66%).

Part F. Preparation of N-(4-iodo-3-methylphenyl)methanesulfonamide

A solution of 4-iodo-3-methylaniline (4.37 g, 18.75 mmol) in CH$_2$Cl$_2$ (25 ml) was treated with pyridine (6.07 ml, 75 mmol) followed by drop wise addition of methanesulfonyl chloride (1.607 ml, 20.63 mmol) to give a reddish/orange mixture. The mixture was stirred for 2 h, concentrated and diluted with EtOAc. The EtOAc layer was washed with 1M HCl, water, saturated NaCl, dried (Na$_2$SO$_4$) and filtered. The EtOAc filtrate was treated with activated charcoal for 30 min at 50° C. and filtered through a 10 g silica plug and concentrated to give the title compound as a light yellow solid (5.5 g, 94%).

Part G. Preparation of N-(3-methyl-4-((trimethylsilyl)ethynyl)phenyl)methanesulfonamide A mixture of the product from Part F (3.11 g, 10 mmol), copper(I) iodide (0.067 g, 0.35 mmol), dichlorobis(triphenylphosphine)palladium (II) (0.351 g, 0.50 mmol), triethylamine (6.97 ml, 50.0 mmol) and trimethylsilyl acetylene (1.684 ml, 12.0 mmol) in acetonitrile (50 ml) was purged with bubbling N$_2$ for 5 min and heated under N$_2$ at 80° C. for 30 min. The reaction mixture was poured into 200 mL of EtOAc and partitioned with water adding enough 1M HCl to bring the pH to 1. The mixture was stirred vigorously for 15 min and the layers were separated. The EtOAc layer was washed sequentially with 10% aqueous NaHCO$_3$, water, and saturated NaCl, dried over Na$_2$SO$_4$ and filtered. The filtrate was treated with 2.0 g of Silicycle Si-thiol silica gel, stirred for 2 h and filtered though a 1 inch pad of silica gel. The filtrate was concentrated and the residue was flash chromatographed on silica eluting with 9:1 hexane/EtOAc-->3:1 hexane/EtOAc to give the title compound as a beige solid (2.7 g, 96%).

Part H. Preparation of N-(4-ethynyl-3-methylphenyl)methanesulfonamide

The product from Part G (1.13 g, 4.01 mmol) in MeOH (20.07 ml) was treated with 1M NaOH (8.43 ml, 8.43 mmol), stirred for 1 h, partitioned into EtOAc/water and carefully acidified to pH 3 with 1M HCl. The EtOAc layer was washed with brine, dried (Na$_2$SO$_4$) and concentrated to give the title compound as a tan solid (820 mg, 98%).

Part I. Preparation of N-(4-((3-tert-butyl-5-(2,4-dioxotetrahydropyrimidin-1(2H)-yl)-2-methoxyphenyl)ethynyl)-3-methylphenyl)methanesulfonamide A mixture of the products from Part E (1.38 g, 3.43 mmol), Part H (0.79 g, 3.78 mmol), copper(I) iodide (0.023 g, 0.12 mmol) dichlorobis(triphenylphosphine)palladium (II) (0.12 g, 0.172 mmol) and triethylamine (2.392 ml, 17.16 mmol) in acetonitrile (60 ml) was purged with bubbling N$_2$ for 5 min and heated in an oil bath under N$_2$ at 80° C. for 20 min. The reaction mixture was poured into 400 mL of warm EtOAc and partitioned with water adding enough 1M HCl to bring the pH to 1. The mixture was stirred vigorously for 15 min and the layers were separated. The EtOAc layer was washed sequentially with 10% NaHCO$_3$, water, and saturated NaCl. The organic layer was dried (Na$_2$SO$_4$), and filtered. The filtrate was treated with 4.0 g of Silicycle Si-thiol silica gel, heated at gentle reflux for 2 h, cooled and filtered though a 1 inch pad of silica gel. The filtrate was concentrated to a yellow solid that was recrystallized by dissolving in hot EtOAc/MeOH (270 mL/30 mL), reducing the volume to 100 mL and allowing to cool. The resulting precipitate was collected by filtration and recrystallized a second time to give the title compound as a white solid (760 mg, 46%). m.p.>280° C. $^1$H NMR (300 MHz, DMSO-D6) δ ppm 1.35 (s, 9H) 2.46 (s, 3H) 2.70 (t, J=6.62 Hz, 2H) 3.05 (s, 3H) 3.77 (t, J=6.62 Hz, 2H) 4.04 (s, 3H) 7.08 (dd, J=8.46, 1.84 Hz, 1H) 7.14 (s, 1H) 7.25 (d, J=2.57 Hz, 1H) 7.36 (d, J=2.57 Hz, 1H) 7.50 (d, J=8.46 Hz, 1H) 9.99 (s, 1H) 10.36 (s, 1H).

Example 44

Preparation of N-(4-((3-tert-butyl-5-(2,4-dioxotetrahydropyrimidin-1(2H)-yl)phenyl)ethynyl)-3-chlorophenyl)methanesulfonamide (compound IA-L2-1.3)

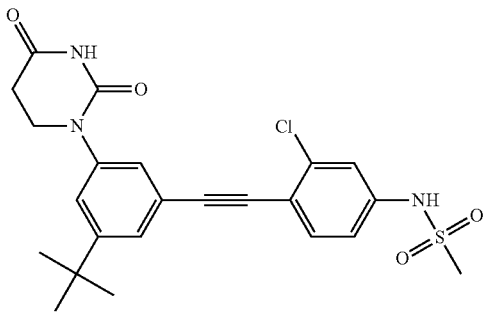 [SMILES: CC(C)(C)c1cc(C#Cc2ccc(NS(C)(=O)=O)cc2Cl)cc(N2CCC(=O)NC2=O)c1]

Part A. Preparation of methyl 3-tert-butyl-5-(chlorocarbonyl)benzoate

A mixture of 3-tert-butyl-5-(methoxycarbonyl)benzoic acid (9.18 g, 38.9 mmol, prepared by the method of Carter et. al., WO2005021500A1), thionyl chloride (75 mL) and 1 drop of DMF in toluene (200 mL) was heated at reflux for 2 h, cooled and concentrated. The residue was azeotroped with toluene (3×50 mL) and dried under high vacuum to give the title compound as an off-white waxy solid (9.9 g, quantitative yield).

Part B. Preparation of methyl 3-(azidocarbonyl)-5-tert-butylbenzoate

To the product of Part A (9.9 g, 38.9 mmol) in acetone (200 ml) was added at a fast drip a solution of sodium azide (10.12 g, 156 mmol) dissolved in water (20 mL). The mixture was stirred for 2 h and diluted with EtOAc. The organic layer was washed with H₂O, saturated brine, dried (Na₂SO₄), filtered and concentrated to give the title compound as a white solid (9.9 g, 97%).

Part C. Preparation of methyl 3-amino-5-tert-butylbenzoate

The product from Part B (9.9 g, 37.9 mmol) in toluene (100 mL) was heated at reflux for 1 h and concentrated to give the intermediate isocyanate which was dissolved in DME (60 mL) treated with 8% HCl (150 mL) and stirred for 16 h. The mixture was concentrated and the residue was dissolved in water, neutralized with solid sodium bicarbonate and extracted 3×100 mL with EtOAc. The organics were combined, washed with saturated NaCl, dried (Na₂SO₄), filtered and concentrated. The crude product was chromatographed on silica eluting with 2:1 hexane/EtOAc to give the title compound as an oil (2.7 g, 35%).

Part D. Preparation of methyl 3-tert-butyl-5-(2,4-dioxotetrahydropyrimidin-1(2H)-yl)-2-methoxybenzoate A mixture of the product of Part C (2.34 g, 11.29 mmol) and acrylic acid (2.32 ml, 33.9 mmol) in toluene (60 ml) was heated at reflux under nitrogen for 24 h, cooled and concentrated. The resulting residue was then treated with urea (2.03 g, 33.9 mmol) in acetic acid (35 ml) and heated at 120° C. for 24 h, cooled and concentrated. The residue was azeotroped 3×50 mL with toluene and dissolved in 100 mL of EtOAc. The organic layer was washed with dilute bicarbonate, H₂O, saturated brine, dried (Na₂SO₄), filtered and concentrated to give the title compound as a white solid (2.1 g, 61%).

Part E. Preparation of 3-tert-butyl-5-(2,4-dioxotetrahydropyrimidin-1(2H)-yl)benzoic acid A mixture of the product from Part D (1.8 g, 5.91 mmol) and 1M NaOH (29.6 ml, 29.6 mmol) in MeOH (15 ml) and THF (15 mL) was stirred for 24 h and concentrated. The residue was treated with 50 mL of 1M HCl and extracted into EtOAc. The EtOAc layer was washed with H₂O, saturated brine, dried (Na₂SO₄), filtered and concentrated to give a white solid. This intermediate urea was combined with 20 mL of concentrated HCl and heated at 100° C. for 1 h, cooled and diluted with 75 mL of ice water to give a solid that was collected by filtration and dried to constant mass to give the title compound as a colorless powder (1.6 g, 93%).

Part F. Preparation of 3-tert-butyl-5-(2,4-dioxotetrahydropyrimidin-1(2H)-yl)benzaldehyde A solution of the product of Part E (0.8 g, 2.76 mmol) in sulfurous dichloride (25 mL) was heated at reflux for 1.5 h, cooled and concentrated. The residue was azeotroped 3×25 mL with toluene to give a white powder. This acid chloride was dissolved in anhydrous THF (25 mL), cooled to −78° C. under nitrogen and treated drop wise with 1M lithium tri-tert-butoxyaluminum hydride (3.03 mL, 3.03 mmol) in THF. The solution was stirred at −78° C. for 3 h and quenched cold with 1M HCl, warmed to ambient temperature and extracted 3×25 mL with EtOAc. The organic extracts were combined, washed with water, 10% bicarbonate, saturated brine and dried with sodium sulfate. The EtOAc was filtered and concentrated to give the title compound as a white solid (0.77 g, quantitative yield).

Part G. Preparation of 1-(3-tert-butyl-5-ethynylphenyl)dihydropyrimidine-2,4(1H,3H)-dione A mixture of the product from Part G (913 mg, 3 mmol), dimethyl 1-diazo-2-oxopropyl phosphonate (749 mg, 3.90 mmol, prepared by the method of Ohira, Syn. Comm. 19 (3&4) 561-564 (1989), and potassium carbonate (829 mg, 6.00 mmol) in MeOH (20 ml) was stirred for 16 h and carefully acidified with 1M HCl. The mixture was extracted 2×50 mL with CH₂Cl₂. The organics were combined, washed with water, saturated NaCl, dried (Na₂SO₄), filtered and concentrated. The crude product was purified via silica gel chromatography eluting with 20:1 (CH₂Cl₂/MeOH) to give the title compound as a white solid (415 mg, 46%).

Part H. Preparation of N-(4-((3-tert-butyl-5-(2,4-dioxotetrahydropyrimidin-1(2H)-yl)phenyl)ethynyl)-3-chlorophenyl)methanesulfonamide A mixture of the product from Part G (40.5 mg, 0.15 mmol), copper(I) iodide (1.4 mg, 7.5 mmol), bis(triphenylphosphine)palladium(II) chloride (5.26 mg, 7.50 mmol), N-(3-chloro-4-iodophenyl)methanesulfonamide (52.2 mg, 0.158 mmol, prepared from 3-chloro-4-iodo aniline by the method of Example 43, Part F) and triethylamine (0.105 ml, 0.750 mmol) in acetonitrile (2 mL) was combined in a sealed microwave 5 mL tube and purged with $N_2$ bubbling for 5 min. The mixture was heated by microwave at 70° C. for 5 min, cooled and concentrated. The crude material was purified on a 4 g silica cartridge eluting with 99.5:0.5 $CH_2Cl_2$/MeOH-->97:3 $CH_2Cl_2$/MeOH. The desired fractions were combined and concentrated. The material was triturated in a minimal amount of EtOAc and the white solid was collected by filtration and dried to give the title compound (28 mg, 39%). m.p. 278-280° C. $^1$H NMR (300 MHz, DMSO-D6) δ ppm 1.31 (s, 9H) 2.72 (t, J=6.62 Hz, 2H) 3.12 (s, 3H) 3.82 (t, J=6.62 Hz, 2H) 7.20 (dd, J=8.46, 2.21 Hz, 1H) 7.35 (s, 2H) 7.38-7.46 (m, 2H) 7.66 (d, J=8.46 Hz, 1H) 10.31 (s, 1H) 10.41 (s, 1H).

Example 45

Preparation of N-(6-((3-tert-butyl-5-(2,4-dioxotetrahydropyrimidin-1(2H)-yl)-2-methoxyphenyl)ethynyl)pyridin-3-yl)methanesulfonamide (compound IA-L2-1.25)

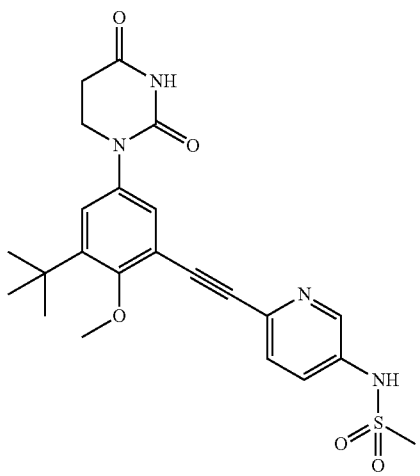 [SMILES: COc1c(C#Cc2ccc(NS(C)(=O)=O)cn2)cc(N2CCC(=O)NC2=O)cc1C(C)(C)C]

Part A. Preparation of N-(6-iodopyridin-3-yl)methanesulfonamide

To a solution of 6-iodopyridin-3-amine (1.077 gm, 4.90 mmole) in dichloromethane (40 ml) and pyridine (1.98 ml, 24.49 mmole) at ice bath temperature was added methanesulfonyl chloride (0.401 ml, 2.444 mmole). The mixture was allowed to warm to room temperature and stir four days. The reaction mixture was treated with 5% acetic acid and allowed to stir 20 min at room temperature. The organic phase was washed with water (2×50 ml), dried (MgSO4) and concentrated in vacuo. The residue was slowly added in portions to rapidly stirred water (100 ml) and the resulting solid collected by filtration, washed with water and dried in vacuo to give the title compound (0.7287 g, 49.9%).

Part B. Preparation of N-(6-((trimethylsilyl)ethynyl)pyridin-3-yl)methanesulfonamide The product from Part A (566 mg, 1.899 mmole) was combined with copper (I) iodide (17 mg, 0.089 mmole) and bis(triphenylphosphine) palladium (II) chloride (73 mg, 0.104 mmole) in a pressure tube. Anhydrous acetonitrile (17 ml) added followed by triethylamine (1.323 ml, 9.49 mmole). Nitrogen was bubbled through the resulting yellow suspension with stirring for 5 min then added trimethylsilyl acetylene (0.526 ml, 3.80 mmole). The vessel was immersed in a pre-heated oil bath at 80° C. The reaction mixture was allowed to stir with heating for 2 h then cooled to room temperature and transferred to a round bottom flask. The volatiles were removed in vacuo and the brown residue fractionated by (flash)silica gel chromatography (ethyl acetate/hexanes) to give the title product (0.4539 g, 89%) as a tan solid.

Part C. Preparation of N-(6-ethynylpyridin-3-yl)methanesulfonamide

The product from Part B (0.533 gm, 1.984 mmole) was dissolved in methanol (17 ml) and a 2N sodium hydroxide (2 ml, 4.17 mmole) solution was added drop wise at room temperature. The mixture was allowed to stir 1 h. The reaction mixture was concentrated in vacuo. The residue was partitioned between ethyl acetate and water and the pH adjusted to neutral with glacial acetic acid. The organic phase was diluted with additional ethyl acetate then washed several times with brine and concentrated in vacuo to give the title compound as a tan solid (0.3266 g, 84%).

Part D. Preparation of N-(6-((3-tert-butyl-5-(2,4-dioxotetrahydropyrimidin-1(2H)-yl)-2-methoxyphenyl)ethynyl)pyridin-3-yl)methanesulfonamide The product from Part C (75 mg, 0.382 mmole) was combined with the product obtained as described in Example 43, Part E (146 mg, 0.363 mmole), copper (I) iodide (7.42 mg, 0.039 mmole) and bis(triphenylphosphine) palladium (II) chloride (18.24 mg, 0.026 mmole) in a heavy wall glass tube and the vessel sealed with a septum crimp cap. Under an atmosphere of nitrogen added anhydrous acetonitrile (10 ml) followed by triethylamine (0.266 ml, 1.911 mmole). Nitrogen was bubbled through the resulting brown suspension for 5 min and then the tube was immersed in a pre-heated 80° C. oil bath. The reaction was monitored by LC/MS. Three additional aliquots of the alkyne (a total of 71 mg, 0.362 mmole) each in THF (1 ml), were added via syringe over the course of 8 h. The reaction mixture was subsequently poured into 150 ml of warm (45° C.) ethyl acetate, partitioned with brine (75 ml) and allowed to stir 15 min. The aqueous phase was extracted with ethyl acetate (2×25 ml) and the combined organic phase dried (MgSO4) and filtered. The filtrate was treated with a gram of Silicycle Sithiol silica gel and heated under nitrogen with stirring for 90 min. The silica gel was removed by filtration and after concentration in vacuo the crude product isolated as a pale orange solid. The title compound (0.1315 gm, 73.1%) was obtained as an off white solid by (flash) silica gel chromatography using a step gradient of ethyl acetate in hexanes followed by methanol in dichloromethane. m.p. 191-192.5° C. (d). $^1$H NMR (300 MHz, DMSO-D6) δ ppm 1.35 (s, 9H) 2.70 (t, J=6.62 Hz, 2H) 3.12 (s, 3H) 3.78 (t, J=6.62 Hz, 2H) 4.07 (s, 3H) 7.30 (d, J=2.94 Hz, 1H) 7.40 (d, J=2.57 Hz, 1H) 7.65 (d, J=1.47 Hz, 2H) 8.44 (s, 1H) 10.29-10.34 (m, 1H) 10.38 (s, 1H).

Example 46

Preparation of N-(4-((3-tert-butyl-5-(2,4-dioxotetrahydropyrimidin-1(2H)-yl)-2-methoxyphenyl)ethynyl)-3-(trifluoromethyl)phenyl)methanesulfonamide (compound IA-L2-1.18)

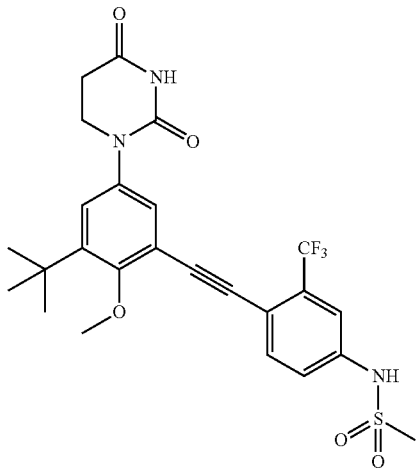 [SMILES: COc1c(C#Cc2ccc(NS(C)(=O)=O)cc2C(F)(F)F)cc(N2CCC(=O)NC2=O)cc1C(C)(C)C]

Part A. Preparation of N-(4-bromo-3-(trifluoromethyl)phenyl)methanesulfonamide The title compound was prepared by the reaction of 4-bromo-3-(trifluoromethyl)aniline with methanesulfonyl chloride as described in Example 45, Part A.

Part B. Preparation of N-(3-(trifluoromethyl)-4-((trimethylsilyl)ethynyl)phenyl)methane sulfonamide The product from Part A (2.00 gm, 6.29 mmole) was combined with triphenylphosphine (0.211 gm, 0.805 mmole) and palladium (II) acetate (0.099 gm, 0.440 mmole) in a 250 ml round bottom flask equipped with a condenser and the reaction was performed as described by W. B Austin et al, J. Org. Chem., 46 (11):2280 (1981). Toluene (40 ml) was added followed by triethylamine (80 ml) and trimethylsilylacetylene (4.41 ml, 31.4 mmole). The resulting yellow solution was purged with nitrogen for 5 min at room temperature. The reaction mixture was heated under nitrogen in an oil bath at 80° C. for 24 h. Cool to room temperature and filter. The filtrate was concentrated in vacuo and the residue chromatographed on silica gel (ethyl acetate-hexanes) to give the title compound as a tan solid (1.4554 gm, 69%).

Part C. Preparation of N-(4-ethynyl-3-(trifluoromethyl)phenyl)methanesulfonamide The product from Part B (0.378 gm, 1.126 mmole) was dissolved in methanol (8 ml) and treated with potassium carbonate (0.322 gm, 2.331 mmole) at room temperature. After 90 min the reaction mixture was partitioned between ethyl acetate and dilute HCl. The organic phase was water washed then dried (MgSO4) and concentrated in vacuo. The residue was purified by silica gel chromatography (ethyl acetate-hexane) to give the title compound as a clear oil, which slowly crystallizes on standing (0.2502 g, 84%).

Part D. Preparation of N-(4-((3-tert-butyl-5-(2,4-dioxotetrahydropyrimidin-1(2H)-yl)-2-methoxyphenyl)ethynyl)-3-(trifluoromethyl)phenyl)methanesulfonamide The product from Part C (0.2502 gm, 0.950 mmole) was treated with the product obtained as described in Example 43, Part E (0.364 gm, 0.905 mmole) as detailed in Example 45, Part D. The title compound (0.3195 g, 65.7%) was obtained as a white solid by trituration of the crude product with ether-dichloromethane. m.p. 257.5-261° C. (d). $^1$H NMR (300 MHz, DMSO-D6) δ ppm 1.35 (s, 9H) 2.71 (t, J=6.62 Hz, 2H) 3.14 (s, 3H) 3.78 (t, J=6.43 Hz, 2H) 4.03 (s, 3H) 7.29 (d, J=2.57 Hz, 1H) 7.34 (d, J=2.57 Hz, 1H) 7.48-7.56 (m, 1H) 7.60 (s, 1H) 7.83 (d, J=8.09 Hz, 1H) 10.37 (s, 1H) 10.45 (s, 1H).

Example 47

Preparation of N-[4-(acetyl-methanesulfonyl-amino)-phenyl]-3-tert-butyl-5-(2,4-dioxo-tetrahydro-pyrimidin-1-yl)-2-methoxy-benzamide (compound IA-L3-1.69)

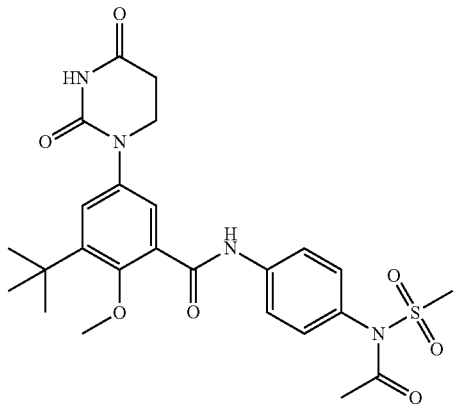 [SMILES: COc1c(C(=O)Nc2ccc(N(C(C)=O)S(C)(=O)=O)cc2)cc(N2CCC(=O)NC2=O)cc1C(C)(C)C]

Part A. Preparation of 3-tert-butyl-5-(2,4-dioxotetrahydropyrimidin-1(2H)-yl)-2-methoxy-benzoyl chloride The product from Example 29, Part F, (2H)-yl)-2-methoxybenzoic acid (4.07 g, 12.71 mmol) and thionyl chloride (40.82 mL, 559 mmol) were added together. The mixture was then refluxed for 2 h, followed by concentration under vacuum to provide the product as a light-yellow solid.

Part B. Preparation of N-[4-(acetyl-methanesulfonyl-amino)-phenyl]-3-tert-butyl-5-(2,4-dioxo-tetrahydro-pyrimidin-1-yl)-2-methoxy-benzamide The product obtained from Part A (0.073 g, 0.15 mmol) was dissolved in pyridine (2 ml) and treated drop wise with acetic anhydride (0.042 mL, 0.45 mmol). The mixture was stirred 3 h at room temperature. The reaction mixture was concentrated in vacuo and the residue was dissolved in ethyl acetate (25 ml). The organic layer was washed with aq. HCl, aq. NaHCO$_3$, brine, and dried over anhydrous solid sodium sulfate. The drying agent was filtered and the solvent evaporated under vacuum giving the title compound as a white solid (55 mg, 68%). mp 228-229° C. $^1$H NMR (300 MHz, DMSO-D6) δ ppm 1.38 (s, 9H) 1.92 (s, 3H) 2.72 (t, J=6.62 Hz, 2H) 3.52 (s, 3H) 3.73-3.82 (m, 5H) 7.32 (d, J=2.57 Hz, 1H) 7.36 (d, J=2.94 Hz, 1H) 7.44 (d, J=8.82 Hz, 2H) 7.83 (d, J=8.82 Hz, 2H) 10.37 (s, 1H) 10.64 (s, 1H).

Example 48

Preparation of N-(6-(3-bromo-5-(2,4-dioxo-3,4-dihydropyrimidin-1(2H)-yl)-2-methoxyphenyl)naphthalen-2-yl)methanesulfonamide (compound IB-L0-2.69)

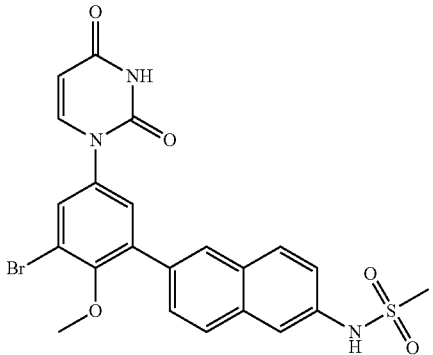 [SMILES: COc1c(Br)cc(-n2ccc(=O)[nH]c2=O)cc1-c1ccc2cc(NS(C)(=O)=O)ccc2c1]

Part A. Preparation of 2-bromo-4,6-diiodophenol

A 1 L round-bottom flask was charged with 2-bromophenol (Aldrich, 8.65 g, 50 mmol) and methanol (100 ml) to give a colorless solution. Sodium hydroxide (2.40 g, 60.0 mmol) was added and stirred until the hydroxide pellets had dissolved. The solution was cooled in an ice water bath and sodium iodide (5.6 g, 37.4 mmol) was added followed by drop-wise addition of sodium hypochlorite (17 mL, 27.5 mmol) to give a transparent brown/red solution and gradual precipitation of a thick, white solid. The addition of sodium iodide and bleach was repeated 3 times to give an orange mixture that was stirred for 2 h, treated with a solution of sodium thiosulfate in water (20 g in 100 mL), stirred for 15 min and treated drop-wise with concentrated HCl to a constant pH of 1. The mixture was stirred for 15 min and filtered to collect a white solid that was washed repeatedly with water and dried to constant mass (14.7 g, 69%).

Part B. Preparation of 1-bromo-3,5-diiodo-2-methoxybenzene

A 500 mL round-bottom flask was charged with the product from Part A (14.7 g, 34.6 mmol), iodomethane (2.70 ml, 43.3 mmol), and sodium hydroxide (2.101 ml, 39.8 mmol) in acetone (96 ml) to give a tan solution. The mixture was stirred for 24 h and concentrated. The residue was dissolved in ethyl acetate, washed with water and saturated sodium chloride, dried over sodium sulfate, filtered and concentrated to give a white solid. The solid was recrystallized from hot hexane to give a white solid that was collected by filtration (12.3 g, 81%).

Part C. Preparation of 1-(3-bromo-5-iodo-4-methoxyphenyl)pyrimidine-2,4(1H,3H)-dione A 250 mL round-bottom flask was charged with the product from Part B (8.09 g, 18.44 mmol), pyrimidine-2,4(1H,3H)-dione (2.273 g, 20.28 mmol), N-(2-cyanophenyl)picolinamide (0.823 g, 3.69 mmol), copper (I) iodide (0.351 g, 1.844 mmol) and potassium phosphate (8.22 g, 38.7 mmol) in DMSO (70 ml). The mixture was sealed, sparged with nitrogen for 15 min and heated at 60° C. for 16 h. The mixture was partitioned with ethyl acetate and water. The organic layer was washed with 1M HCl, water, brine, dried with sodium sulfate, and filtered. The filtrate was treated with 3-mercaptopropyl functionalized silica gel (Aldrich catalog #538086), filtered through celite and evaporated to give an off-white solid (3.92 g, 50%).

Part D. Preparation of N-(6-(3-bromo-5-(2,4-dioxo-3,4-dihydropyrimidin-1(2H)-yl)-2-methoxyphenyl) naphthalen-2-yl)methanesulfonamide To a 5 mL microwave tube was added the product from Part C (212 mg, 0.50 mmol), the product from Example 4A, Part B (174 mg, 0.50 mmol), potassium phosphate (223 mg, 1.05 mmol), PA-Ph (CAS 97739-46-3, 4.38 mg, 0.015 mmol) and tris(dibenzylideneacetone)dipalladium(0) (4.58 mg, 5.00 mmol) in tetrahydrofuran (3.0 ml) and water (1.0 ml). The tube was sealed and the mixture was sparged with nitrogen for 5 min and then stirred for 24 h. The reaction mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel (Aldrich catalog #538086), filtered through celite and evaporated. The residue was triturated with methanol/CH$_2$Cl$_2$ to give the title compound as a white solid (256 mg, 51%). $^1$H NMR (300 MHz, DMSO-D6) δ ppm 3.08 (s, 3H) 3.43 (s, 3H) 5.68 (d, J=8.09 Hz, 1H) 7.43 (dd, J=8.82, 2.21 Hz, 1H) 7.60 (d, J=2.57 Hz, 1H) 7.72 (m, 2H) 7.82 (d, J=3.31 Hz, 1H) 7.84 (d, J=1.84 Hz, 1H) 7.96 (m, 2H) 8.09 (s, 1H) 10.07 (s, 1H) 11.49 (s, 1H). MS (ESI−) m/z 513.9, 515.9 (M−H)$^+$.

Example 49

Preparation of N-(6-(5-(2,4-dioxo-3,4-dihydropyrimidin-1(2H)-yl)-2-methoxy-3-(5-methylfuran-2-yl) phenyl)naphthalen-2-yl)methanesulfonamide (compound IB-L0-2.58)

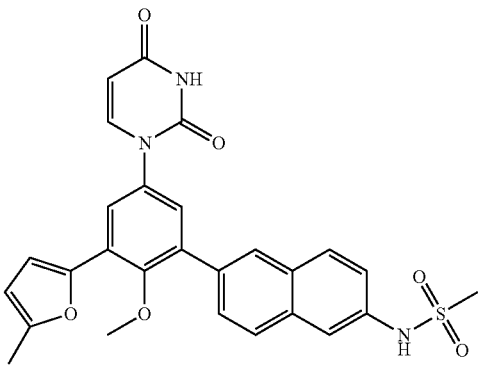 [SMILES: COc1c(-c2ccc3cc(NS(C)(=O)=O)ccc3c2)cc(-n2ccc(=O)[nH]c2=O)cc1-c1ccc(C)o1]

To a 5 mL microwave tube was added the product of Example 48 (52 mg, 0.101 mmol), 4,4,5,5-tetramethyl-2-(5-methylfuran-2-yl)-1,3,2-dioxaborolane (0.025 ml, 0.121 mmol), 1,1'-bis(di-tert-butylphosphino)ferrocene palladium dichloride (3.28 mg, 5.04 mmol) and potassium phosphate (42.8 mg, 0.201 mmol) in THF (3.0 ml) and water (1.0 ml). The tube was sealed and the mixture was sparged with nitrogen for 5 min and then heated at 50° C. for 3 h. The cooled mixture was partitioned with ethyl acetate and 1M HCl. The organic layer was washed with saturated sodium bicarbonate, brine, dried with sodium sulfate, filtered and concentrated. The filtrate was treated with 3-mercaptopropyl functionalized silica gel, filtered and evaporated. The residue was purified by reverse phase chromatography to give the desired product as a white solid (23 mg, 44%, m.p. 174-178° C.) $^1$H NMR (300

MHz, DMSO-D6) δ ppm 2.38 (s, 3H) 3.09 (s, 3H) 3.33 (s, 3H) 5.69 (dd, J=7.72, 2.21 Hz, 1H) 6.30 (d, J=3.31 Hz, 1H) 7.00 (d, J=3.31 Hz, 1H) 7.43 (m, 2H) 7.74 (d, J=2.57 Hz, 2H) 7.78 (dd, J=8.46, 1.84 Hz, 1H) 7.85 (d, J=8.09 Hz, 1H) 7.97 (t, J=8.82 Hz, 2H) 8.12 (s, 1H) 10.05 (s, 1H) 11.46 (d, J=2.21 Hz, 1H). MS (ESI+) m/z 518 (M+H)+.

Example 50

Preparation of N-(6-(5-(2,4-dioxo-3,4-dihydropyrimidin-1(2H)-yl)-2-methoxy-3-(thiophen-3-yl)phenyl)naphthalen-2-yl)methanesulfonamide (compound IB-L0-2.53)

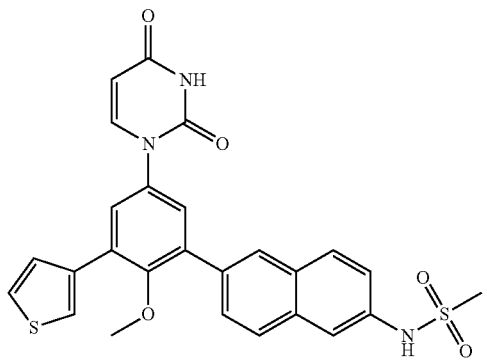

The title compound was prepared according to the procedure of Example 49 substituting thiophen-3-ylboronic acid for 4,4,5,5-tetramethyl-2-(5-methylfuran-2-yl)-1,3,2-dioxaborolane to give a white solid (12 mg, 23%). ¹H NMR (300 MHz, DMSO-D6) δ ppm 3.07 (s, 3H) 3.22 (s, 3H) 5.69 (d, J=7.72 Hz, 1H) 7.41 (dd, J=8.64, 2.02 Hz, 1H) 7.50 (d, J=2.94 Hz, 1H) 7.59 (dd, J=5.13, 1.08 Hz, 1H) 7.69 (m, 3H) 7.76 (dd, J=8.64, 1.65 Hz, 1H) 7.89 (d, J=7.72 Hz, 1H) 7.95 (m, 3H) 8.09 (s, 1H) 10.05 (s, 1H) 11.47 (s, 1H). MS (ESI+) m/z 520 (M+H)+.

Example 51

Preparation of N-(6-(5-(2,4-dioxo-3,4-dihydropyrimidin-1(2H)-yl)-2-methoxy-3-(thiophen-2-yl)phenyl)naphthalen-2-yl)methanesulfonamide (compound IB-L0-2.61)

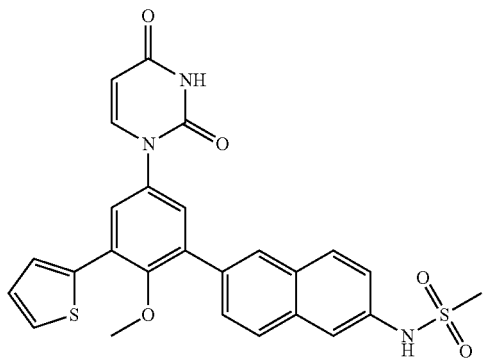 [SMILES: COc1c(-c2ccc3cc(NS(C)(=O)=O)ccc3c2)cc(-n2ccc(=O)[nH]c2=O)cc1-c1cccs1]

The title compound was prepared according to the procedure of Example 49 substituting thiophen-2-ylboronic acid for 4,4,5,5-tetramethyl-2-(5-methylfuran-2-yl)-1,3,2-dioxaborolane to give a white solid (8 mg, 15%). ¹H NMR (300 MHz, DMSO-D6) δ ppm 3.08 (s, 3H) 3.30 (s, 3H) 5.70 (d, J=8.09 Hz, 1H) 7.19 (dd, J=5.33, 3.86 Hz, 1H) 7.42 (dd, J=8.82, 2.21 Hz, 1H) 7.49 (d, J=2.57 Hz, 1H) 7.69 (dd, J=5.15, 1.20 Hz, 1H) 7.80 (m, 3H) 7.88 (d, J=7.72 Hz, 1H) 7.92 (d, J=2.57 Hz, 1H) 7.98 (m, 2H) 8.12 (s, 1H) 10.06 (s, 1H) 11.48 (s, 1H). MS (ESI+) m/z 520 (M+H)+.

Example 52

Preparation of N-(6-(5-(2,4-dioxo-3,4-dihydropyrimidin-1(2H)-yl)-3-(furan-2-yl)-2-methoxyphenyl)naphthalen-2-yl)methanesulfonamide (compound IB-L0-2.59)

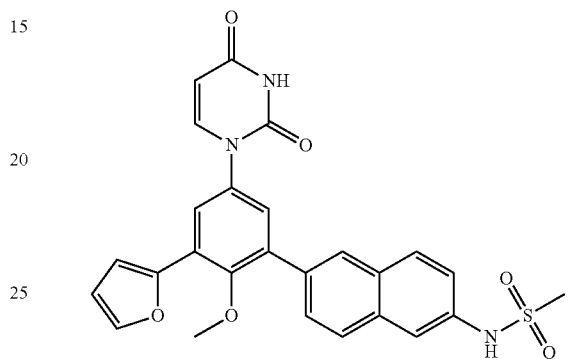

The title compound was prepared according to the procedure of Example 49 substituting furan-2-ylboronic acid for 4,4,5,5-tetramethyl-2-(5-methylfuran-2-yl)-1,3,2-dioxaborolane to give a white solid (16 mg, 32%). ¹H NMR (300 MHz, DMSO-D6) δ ppm 3.09 (s, 3H) 3.35 (s, 3H) 5.69 (d, J=7.72 Hz, 1H) 6.69 (dd, J=3.31, 1.84 Hz, 1H) 7.11 (d, J=3.31 Hz, 1H) 7.43 (dd, J=8.82, 2.21 Hz, 1H) 7.49 (d, J=2.94 Hz, 1H) 7.80 (m, 5H) 7.96 (m, 2H) 8.13 (s, 1H) 10.06 (s, 1H) 11.47 (s, 1H). MS (ESI–) m/z 502.1 (M–H)+.

Example 53

Preparation of N-(6-(5-(2,4-dioxo-3,4-dihydropyrimidin-1(2H)-yl)-3-(furan-3-yl)-2-methoxyphenyl)naphthalen-2-yl)methanesulfonamide (compound IB-L0-2.64)

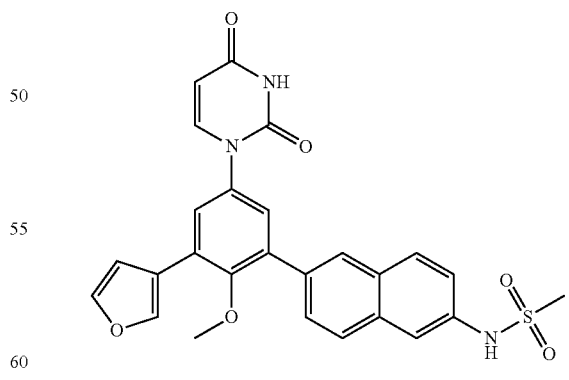

The title compound was prepared according to the procedure of Example 49 substituting furan-3-ylboronic acid for 4,4,5,5-tetramethyl-2-(5-methylfuran-2-yl)-1,3,2-dioxaborolane to give a white solid (6 mg, 12%). ¹H NMR (300 MHz, DMSO-D6) δ ppm 3.09 (s, 3H) 3.30 (s, 3H) 5.69 (dd, J=7.71, 1.83 Hz, 1H) 7.10 (dd, J=1.74, 0.78 Hz, 1H) 7.42 (dd, J=8.82, 2.21 Hz, 1H) 7.46 (d, J=2.57 Hz, 1H) 7.73 (d, J=2.21 Hz, 1H) 7.76 (d, J=2.57 Hz, 1H) 7.78 (d, J=1.84 Hz, 1H) 7.81 (t, J=1.84 Hz, 1H) 7.86 (d, J=7.72 Hz, 1H) 7.96 (t, J=8.82 Hz, 2H) 8.10 (s, 1H) 8.28 (s, 1H) 10.05 (s, 1H) 11.48 (s, 1H). MS (ESI–) m/z 502.1 (M–H)$^+$.

Example 54

Preparation of N-(6-(5-(2,4-dioxo-3,4-dihydropyrimidin-1(2H)-yl)-2-methoxy-biphenyl-3-yl)naphthalen-2-yl)methanesulfonamide (compound IB-L0-2.71)

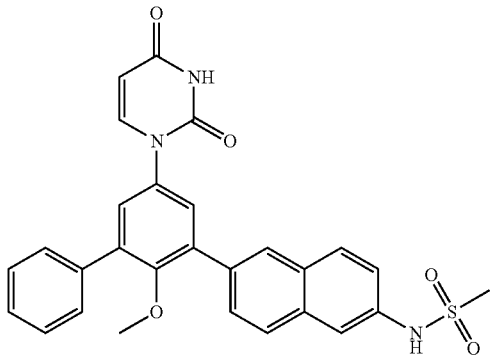 [SMILES: COc1c(-c2ccccc2)cc(-n2ccc(=O)[nH]c2=O)cc1-c1ccc2cc(NS(C)(=O)=O)ccc2c1]

The title compound was prepared according to the procedure of Example 49 substituting phenylboronic acid for 4,4,5,5-tetramethyl-2-(5-methylfuran-2-yl)-1,3,2-dioxaborolane. The crude product was purified by silica gel chromatography eluting with 3% methanol/CH$_2$Cl$_2$ to give a white solid (10 mg, 8%). $^1$H NMR (300 MHz, DMSO-D6) δ ppm 3.08 (s, 3H) 3.12 (s, 3H) 5.69 (dd, J=7.81, 1.47 Hz, 1H) 7.36 (m, 5H) 7.56 (d, J=2.57 Hz, 1H) 7.64 (m, 2H) 7.74 (d, J=2.21 Hz, 1H) 7.78 (dd, J=8.46, 1.84 Hz, 1H) 7.94 (m, 3H) 8.11 (s, 1H) 10.04 (s, 1H) 11.47 (s, 1H). MS (ESI–) m/z 512 (M–H)$^+$.

Example 55

Preparation of N-(6-(3'-chloro-5-(2,4-dioxo-3,4-dihydropyrimidin-1(2H)-yl)-2-methoxybiphenyl-3-yl)naphthalen-2-yl)methanesulfonamide (compound IB-L0-2.74)

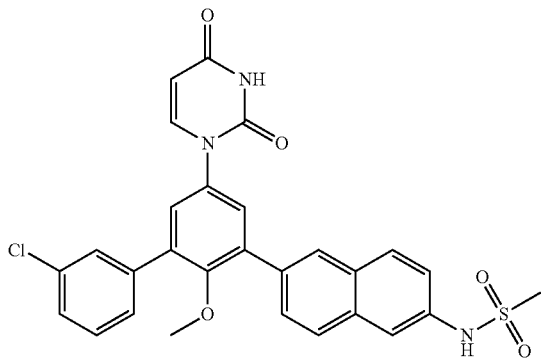 [SMILES: COc1c(-c2cccc(Cl)c2)cc(-n2ccc(=O)[nH]c2=O)cc1-c1ccc2cc(NS(C)(=O)=O)ccc2c1]

The title compound was prepared according to the procedure of Example 49 substituting 3-chlorophenylboronic acid for 4,4,5,5-tetramethyl-2-(5-methylfuran-2-yl)-1,3,2-dioxaborolane to give a white solid (38 mg, 68%). $^1$H NMR (300 MHz, DMSO-D6) δ ppm 3.09 (s, 3H) 3.13 (s, 3H) 5.70 (dd, J=8.09, 2.21 Hz, 1H) 7.43 (dd, J=8.82, 2.21 Hz, 1H) 7.52 (m, 3H) 7.62 (m, 2H) 7.72 (m, 2H) 7.79 (dd, J=8.46, 1.47 Hz, 1H) 7.95 (m, 3H) 8.12 (s, 1H) 10.05 (s, 1H) 11.47 (d, J=2.21 Hz, 1H). MS (ESI–) m/z 546 (M–H)$^+$.

Example 56

Preparation of N-(6-(5-(2,4-dioxo-3,4-dihydropyrimidin-1(2H)-yl)-2-methoxy-3-(5-methylthiophen-2-yl)phenyl)naphthalen-2-yl)methanesulfonamide (compound IB-L0-2.73)

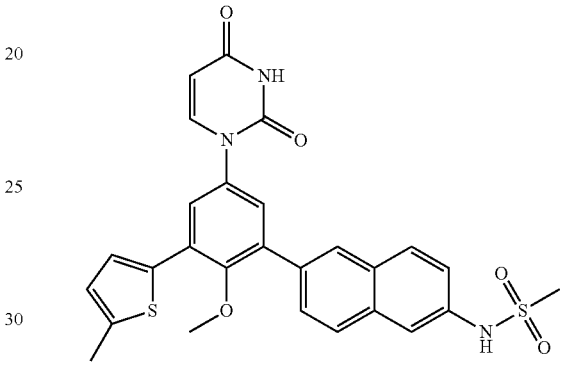

The title compound was prepared according to the procedure of Example 49 substituting 4,4,5,5-tetramethyl-2-(5-methylthiophen-2-yl)-1,3,2-dioxaborolane for 4,4,5,5-tetramethyl-2-(5-methyl-furan-2-yl)-1,3,2-dioxaborolane to give a white solid (22 mg, 41%). $^1$H NMR (300 MHz, DMSO-D6) δ ppm 2.49 (s, 3H) 3.09 (s, 3H) 3.29 (s, 3H) 5.69 (dd, J=8.09, 2.21 Hz, 1H) 6.87 (d, J=2.57 Hz, 1H) 7.43 (m, 2H) 7.54 (d, J=3.68 Hz, 1H) 7.76 (m, 2H) 7.85 (s, 1H) 7.87 (d, J=5.15 Hz, 1H) 7.98 (t, J=9.01 Hz, 2H) 8.11 (s, 1H) 10.06 (s, 1H) 11.47 (d, J=2.21 Hz, 1H). MS (ESI+) m/z 534 (M+H)$^+$.

Example 57

Preparation of N-(6-(5-(2,4-dioxo-3,4-dihydropyrimidin-1(2H)-yl)-3-(1-hydroxy-2-methylpropan-2-yl)-2-methoxyphenyl)naphthalen-2-yl)methanesulfonamide (compound IB-L0-2.54)

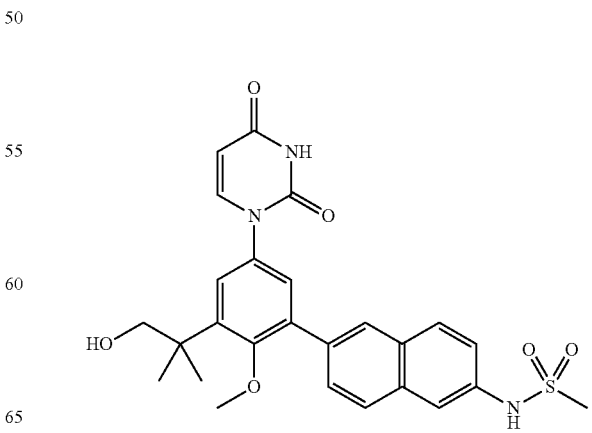

Part A. Preparation of 2-(2-hydroxy-3,5-diiodophenyl)acetic acid

To a 250 mL round bottom flask was added 2-(2-hydroxyphenyl)acetic acid (Aldrich, 3.04 g, 20 mmol) in acetonitrile (50 ml) to give a colorless solution. N-iodosuccimide (9.00 g, 40.0 mmol) was added portionwise over 15 min to give a red/brown transparent solution that was stirred for 16 h. The mixture was concentrated and the resulting solid was triturated in 75 mL of water and filtered to collect an orange solid that was dried under vacuum. The crude solid was recrystallized from toluene to give a light orange powder (6.0 g, 74%).

Part B. Preparation of methyl 2-(3,5-diiodo-2-methoxyphenyl)acetate

To a 250 mL round-bottom flask was added the product from Part A (6 g, 14.85 mmol), potassium carbonate (6.16 g, 44.6 mmol), and dimethyl sulfate (4.12 g, 32.7 mmol) in acetone (49.5 ml) to give a brown suspension. Heated at reflux for 16 h, cooled, concentrated and the residue was partitioned between EtOAc and water. The EtOAc layer was washed with brine, dried ($Na_2SO_4$) and concentrated to a brown oil that was chromatographed on a 40 g silica cartridge eluting with 3:1 hexane/EtOAc to give a yellow oil (6.0 g, 94%).

Part C. Preparation of methyl 2-(3,5-diiodo-2-methoxyphenyl)-2-methylpropanoate To a 100 mL round-bottom flask under nitrogen was added the product from Part B (1.728 g, 4 mmol) in anhydrous THF (20 ml) and HMPA (2 ml) to give a colorless solution. Methyl iodide (1.251 ml, 20.00 mmol) was added and the solution was cooled to −40° C. Potassium t-butoxide (12.00 ml, 12.00 mmol) was added dropwise and the mixture was stirred at −40 to −20° C. for 30 min and quenched with 1M HCl to a pH of 1. The mixture was extracted 3×40 ml with EtOAc. The extracts were combined, washed with brine, dried ($Na_2SO_4$) and concentrated. The crude product was flash chromatographed on a 40 g ISCO silica cartridge eluting with 9:1 hexane/EtOAc to give the bis-methylated product as a yellow oil (1.63 g, 89%).

Part D. Preparation of 2-(3,5-diiodo-2-methoxyphenyl)-2-methylpropanoic acid A suspension of the product from Part C (2.63 g, 5.72 mmol) in MeOH (40 ml) and THF (40 ml) was treated with 4.0M sodium hydroxide (28 ml, 112 mmol) and heated at 80° C. for 48 h. The organic solvent was evaporated and the remaining aqueous solution was acidified with 1M HCl producing a solid that was collected by filtration, washed with water and dried to give the desired carboxylic acid (2.46 g, 96%).

Part E. Preparation of 2-(3,5-diiodo-2-methoxyphenyl)-2-methylpropan-1-ol

A solution of the product from Part D (1.00 g, 2.242 mmol) in THF (40 ml) was treated dropwise with borane THF complex 1.0M (20 ml, 20 mmol) and then heated at 50° C. for 24 h. The mixture was treated with methanol (20 mL), refluxed for 30 min and concentrated. The resulting residue was washed with water, brine, dried with sodium sulfate filtered and evaporated. The residue was chromatographed on silica gel eluting with hexane/EtOAc (4:1) to give the desired product (810 mg, 84%).

Part F. Preparation of tert-butyl(2-(3,5-diiodo-2-methoxyphenyl)-2-methylpropoxy)-dimethylsilane A solution of the product from Part E (432 mg, 1.000 mmol) in DMF (5 ml) was treated with tert-butyldimethylchlorosilane (301 mg, 2.000 mmol), and imidazole (204 mg, 3.00 mmol) and stirred for 2 h. The mixture was partitioned between 1M HCl and ethyl acetate. The organic layer was washed with saturated sodium bicarbonate, brine, dried with sodium sulfate, filtered and evaporated. The residue was chromatographed on silica gel eluting with hexane/EtOAc (9:1) to give the desired product (522 mg, 96%).

Part G. Preparation of 1-(3-(1-(tert-butyldimethylsilyloxy)-2-methylpropan-2-yl)-5-iodo-4-methoxyphenyl)pyrimidine-2,4(1H,3H)-dione To a 50 mL round-bottom flask was added the product from Part F (520 mg, 0.952 mmol), pyrimidine-2,4(1H,3H)-dione (117 mg, 1.047 mmol), N-(2-cyanophenyl)picolinamide (42.5 mg, 0.190 mmol), copper(I) iodide (18.13 mg, 0.095 mmol) and potassium phosphate (424 mg, 1.999 mmol) in DMSO (5 ml). The vessel was sealed, sparged with nitrogen and then heated at 60° C. for 24 h. The mixture was partitioned between 1M HCl and ethyl acetate. The organic layer was washed with saturated sodium bicarbonate, brine, dried with sodium sulfate, and filtered. The filtrate was treated with 3-mercaptopropyl functionalized silica gel, filtered and evaporated. The residue was chromatographed on silica gel eluting with hexane/EtOAc (3:2) to give the product as a solid (285 mg, 65%).

Part H. Preparation of N-(6-(3-(1-(tert-butyldimethylsilyloxy)-2-methylpropan-2-yl)-5-(2,4-dioxo-3,4-dihydropyrimidin-1(2H)-yl)-2-methoxyphenyl)naphthalen-2-yl)methanesulfonamide To a 5 mL microwave tube was added the product from Part G (50 mg, 0.094 mmol), the product from Example 4A, Part B (32.7 mg, 0.094 mmol), potassium phosphate (42.0 mg, 0.198 mmol), PA-Ph (CAS 97739-46-3) (0.827 mg, 2.83 µmol) and tris(dibenzylideneacetone)palladium(0) (0.863 mg, 0.943 µmol) in THF (3.0 ml) and water (1.0 ml). The vessel was sealed and the mixture was sparged with nitrogen for 5 min and then heated at 50° C. for 2 h. The mixture was partitioned between 1M HCl and ethyl acetate. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica gel eluting with hexane/EtOAc (3:7) to give a solid (32 mg, 54%).

Part I. Preparation of N-(6-(5-(2,4-dioxo-3,4-dihydropyrimidin-1(2H)-yl)-3-(1-hydroxy-2-methylpropan-2-yl)-2-methoxyphenyl)naphthalen-2-yl)methanesulfonamide The product from Part H (31 mg, 0.050 mmol) in THF (2.0 ml) was treated with 1M TBAF (0.3 ml, 0.3 mmol) in THF and stirred overnight. The mixture was partitioned with water and ethyl acetate. The organic layer was washed with brine three times, dried with sodium sulfate, filtered and evaporated. The residue was chromatographed on silica gel eluting with 2% to 8% methanol in $CH_2Cl_2$ to give a solid (2.1 mg, 83%). Melting point: 256-257° C. $^1$H NMR (300 MHz, DMSO-D6) δ ppm 1.35 (s, 6H) 3.08 (s, 3H) 3.23 (s, 3H) 3.67 (d, J=4.78 Hz, 2H) 4.72 (t, J=4.78 Hz, 1H) 5.65 (d, J=8.09 Hz, 1H) 7.36 (m, 3H) 7.74 (m, 3H) 7.98 (m, 3H) 10.04 (s, 1H) 11.41 (s, 1H). MS (ESI+) m/z 527 (M+NH4)$^+$.

Example 58

Preparation of N-(6-(5-(2,4-dioxo-3,4-dihydropyrimidin-1(2H)-yl)-2-methoxy-3-(1-methoxy-2-methylpropan-2-yl)phenyl)naphthalen-2-yl)methanesulfonamide (compound IB-L0-2.66)

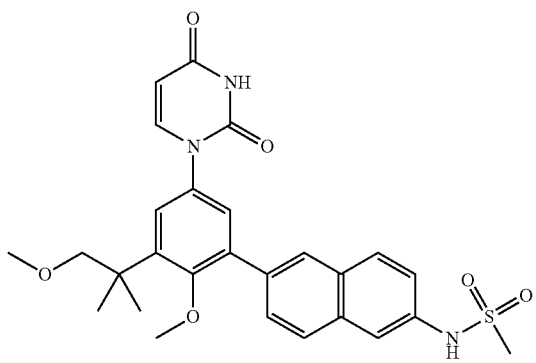 [SMILES: COCC(C)(C)c1cc(-n2ccc(=O)[nH]c2=O)cc(-c2ccc3cc(NS(C)(=O)=O)ccc3c2)c1OC]

Part A. Preparation of 1,5-diiodo-2-methoxy-3-(1-methoxy-2-methylpropan-2-yl)benzene To a 25 mL round-bottom flask was added the product from Example 57, Part E. (259 mg, 0.6 mmol) and sodium hydride (28.8 mg, 1.200 mmol) in THF (5 ml). The mixture was stirred for 30 min and iodomethane (0.0451, 0.720 mmol) was added. The mixture was stirred for 16 h and partitioned between ethyl acetate and 1M HCl. The organic layer was washed with saturated sodium bicarbonate, brine, dried with sodium sulfate, filtered and evaporated to give an oil (235 mg, 88%).

Part B. Preparation of 1-(3-iodo-4-methoxy-5-(1-methoxy-2-methylpropan-2-yl)phenyl)pyrimidine-2,4(1H,3H)-dione In a 25 mL round-bottom flask was added the product from Part A (230 mg, 0.516 mmol), pyrimidine-2,4(1H,3H)-dione (63.6 mg, 0.567 mmol), N-(2-cyanophenyl)picolinamide (23.02 mg, 0.103 mmol), copper(I) iodide (9.82 mg, 0.052 mmol) and potassium phosphate (230 mg, 1.083 mmol) in DMSO (5 ml). The vessel was sealed, sparged with nitrogen and heated at 60° C. for 16 h. The mixture was cooled and partitioned between ethyl acetate and 1M HCl. The organic layer was washed with saturated sodium bicarbonate, brine, dried with sodium sulfate, filtered and evaporated. The residue was chromatographed on silica gel eluting with 2% to 5% methanol in $CH_2Cl_2$ to give a solid (140 mg, 63%).

Part C. Preparation of N-(6-(5-(2,4-dioxo-3,4-dihydropyrimidin-1(2H)-yl)-2-methoxy-3-(1-methoxy-2-methylpropan-2-yl)phenyl)naphthalen-2-yl)methanesulfonamide In a 5 ml microwave tube was added the product from Part B (43 mg, 0.100 mmol), the product from Example 4A, Part B (34.7 mg, 0.100 mmol), potassium phosphate (44.6 mg, 0.210 mmol), PA-Ph (CAS 97739-46-3) (0.876 mg, 3.00 μmol) and tris(dibenzylideneacetone)palladium(0) (0.915 mg, 0.999 μmol) in THF (3.0 ml) and water (1.0 ml). The vessel was sealed, sparged with nitrogen for 5 min and heated at 50° C. for 2 h. The mixture was partitioned with ethyl acetate and 1M HCl. The organic layer was washed with saturated sodium bicarbonate, brine, dried with sodium sulfate, filtered. The filtrate was treated with 3-mercaptopropyl functionalized silica gel, filtered and evaporated. The residue was triturated with methanol/$CH_2Cl_2$ (1:1) to give a solid (28 mg, 54%). $^1$H NMR (300 MHz, DMSO-D6) δ ppm 1.39 (s, 6H) 3.08 (s, 3H) 3.23 (s, 3H) 3.25 (s, 3H) 3.61 (s, 2H) 5.65 (d, J=7.72 Hz, 1H) 7.27 (d, J=2.57 Hz, 1H) 7.37 (d, J=2.57 Hz, 1H) 7.42 (dd, J=8.64, 2.02 Hz, 1H) 7.69 (dd, J=8.46, 1.84 Hz, 1H) 7.73 (d, J=2.21 Hz, 1H) 7.78 (d, J=7.72 Hz, 1H) 7.95 (t, J=8.27 Hz, 2H) 8.02 (s, 1H) 10.04 (s, 1H) 11.41 (s, 1H). MS (ESI+) m/z 541 (M+NH4)$^+$.

Example 59

Preparation of methyl 2-(5-(2,4-dioxo-3,4-dihydropyrimidin-1(2H)-yl)-2-methoxy-3-(6-(methylsulfonamido)naphthalen-2-yl)phenyl)-2-methylpropanoate (compound IB-L0-2.70)

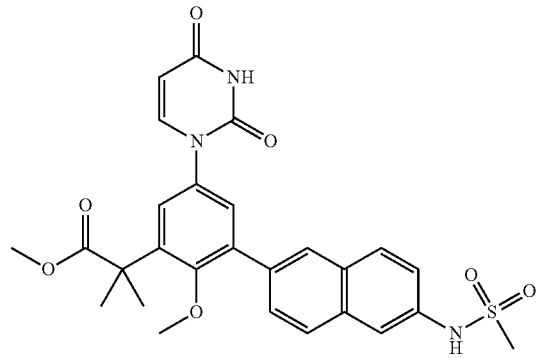 [SMILES: COC(=O)C(C)(C)c1cc(-n2ccc(=O)[nH]c2=O)cc(-c2ccc3cc(NS(C)(=O)=O)ccc3c2)c1OC]

Part A. Preparation of methyl 2-(5-(2,4-dioxo-3,4-dihydropyrimidin-1(2H)-yl)-3-iodo-2-methoxyphenyl)-2-methylpropanoate To a 100 mL round-bottom flask under $N_2$ was added the product from Example 57, Part C (410 mg, 0.891 mmol), 1H-pyrimidine-2,4-dione (120 mg, 1.069 mmol), and potassium phosphate tribasic (397 mg, 1.872 mmol) in DMSO (5 ml) to give a colorless suspension. N-(2-cyanophenyl)picolinamide (39.8 mg, 0.178 mmol) was added and the mix was sparged with $N_2$ for 5 min. Copper(I) iodide (16.97 mg, 0.089 mmol) was added and the mix was sparged once again for 10 min, placed under $N_2$ and heated at 60° C. for 18 h. The mixture was cooled and partitioned between EtOAc and water adjusting the pH to 1 with HCl. The aqueous layer was extracted 2× with EtOAc. The organics were combined, washed with water, saturated $NaHCO_3$, and saturated NaCl. The organic layer was dried ($Na_2SO_4$), treated with 3-mercaptopropyl functionalized silica, filtered and concentrated. The crude product was purified by chromatography on an ISCO 40 g silica cartridge eluting with 3% MeOH in $CH_2Cl_2$ to give a white foam (269 mg, 68%).

Part B. Preparation of methyl 2-(5-(2,4-dioxo-3,4-dihydropyrimidin-1(2H)-yl)-2-methoxy-3-(6-(methylsulfonamido)naphthalen-2-yl)phenyl)-2-methylpropanoate To a 20 mL microwave tube was added the product from Part A (0.444 g, 1.0 mmol), the product from Example 4A, Part B (0.365 g, 1.050 mmol), and potassium phosphate tribasic (0.446 g, 2.100 mmol) in 3:1 tetrahydrofuran-water (12 ml) and degassed by nitrogen sparge for 20 min. The solution was then treated with PA-Ph (CAS 97739-46-3) (8.77 mg, 0.030 mmol) and tris(dibenzylidene-acetone)palladium(0) (9.16 mg, 10.00 μmol) followed by degassing for another 5 min. The microwave tube was then sealed and warmed at 50° C. for 18 h, cooled and partitioned between EtOAc and water adjusting the pH to 1 with 1M HCl. The EtOAc layer was washed with water, saturated NaHCO$_3$, and saturated NaCl. The organic layer was dried over sodium sulfate, stirred for 1 h with 3-mercaptopropyl functionalized silica, filtered and concentrated. The crude product was purified by chromatography on an ISCO 12 g silica cartridge eluting with 1-3% MeOH in CH$_2$Cl$_2$ to give light tan crystals (480 mg, 98%). $^1$H NMR (300 MHz, DMSO-D6) δ ppm 1.52 (s, 6H) 3.08 (s, 3H) 3.14 (s, 3H) 3.64 (s, 3H) 5.67 (dd, J=8.09, 1.84 Hz, 1H) 7.37-7.48 (m, 3H) 7.65 (dd, J=8.46, 1.84 Hz, 1H) 7.73 (d, J=2.21 Hz, 1H) 7.83 (d, J=8.09 Hz, 1H) 7.96 (dd, J=8.64, 5.70 Hz, 2H) 8.01 (s, 1H) 10.05 (s, 1H) 11.45 (s, 1H). MS (ESI−) m/z 536 (M−H)$^+$.

Example 60

Preparation of 2-(5-(2,4-dioxo-3,4-dihydropyrimidin-1(2H)-yl)-2-methoxy-3-(6-(methylsulfonamido)naphthalen-2-yl)phenyl)-2-methylpropanoic acid (compound IB-L0-2.77)

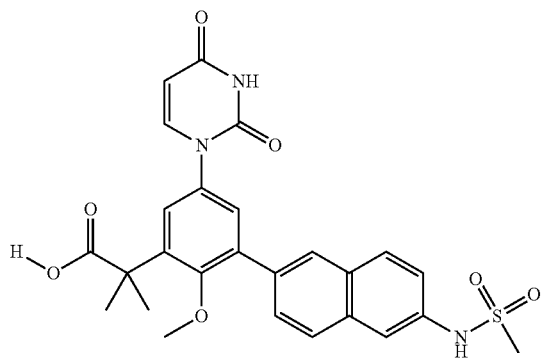 [SMILES: COc1c(-c2ccc3cc(NS(C)(=O)=O)ccc3c2)cc(-n2ccc(=O)[nH]c2=O)cc1C(C)(C)C(=O)O]

A mixture of the product from Example 59 (108 mg, 0.2 mmol) and sodium hydroxide (1 mL, 4.00 mmol) in methanol, THF, water (3:3:1, 10 mL) was heated at 80° C. for 18 h, cooled and carefully acidified to pH 1 with concentrated HCl resulting in the formation of a white precipitate. The solid was collected by filtration, washed with water and dried. The crude material was triturated in 1 mL of 1:1 EtOAc/MeOH, sonicated for 5 min and the solid was collected by filtration as a bright white solid (58 mg, 54% yield), mp>300° C. $^1$H NMR (300 MHz, DMSO-D6) δ ppm 1.50 (s, 6H) 3.08 (s, 3H) 3.18 (s, 3H) 5.66 (d, J=7.72 Hz, 1H) 7.34-7.45 (m, 3H) 7.67 (dd, J=8.64, 1.65 Hz, 1H) 7.73 (d, J=1.84 Hz, 1H) 7.82 (d, J=7.72 Hz, 1H) 7.96 (dd, J=9.01, 4.60 Hz, 2H) 8.02 (s, 1H) 10.04 (s, 1H) 11.43 (s, 1H) 12.15 (s, 1H). MS (ESI−) m/z 522 (M−H)$^+$.

Example 61

Preparation of methyl 5-(2,4-dioxo-3,4-dihydropyrimidin-1(2H)-yl)-2-methoxy-3-(6-(methylsulfonamido)naphthalen-2-yl)benzoate (compound IB-L0-2.72)

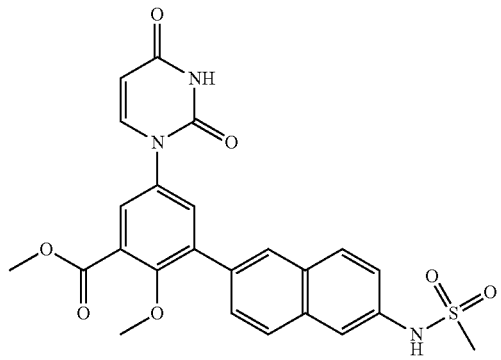 [SMILES: COC(=O)c1cc(-n2ccc(=O)[nH]c2=O)cc(-c2ccc3cc(NS(C)(=O)=O)ccc3c2)c1OC]

Part A. Preparation of methyl 3,5-diiodo-2-methoxybenzoate

A mixture of 2-hydroxy-3,5-diiodobenzoic acid (3.9 g, 10.0 mmol) potassium carbonate (4.15 g, 30.0 mmol) and dimethyl sulfate (2.77 g, 22.0 mmol) in acetone (33 ml) was heated at reflux for 16 h, cooled and concentrated. The residue was dissolved in EtOAc and washed with water, brine, dried (Na$_2$SO$_4$), filtered and concentrated to give an off-white solid (4.2 g, quantitative yield).

Part B. Preparation of methyl 5-(2,4-dioxo-3,4-dihydropyrimidin-1(2H)-yl)-3-iodo-2-methoxybenzoate To a 100 mL round-bottom flask under N$_2$ was added the product from Part A (2.09 g, 5.0 mmol), 1H-pyrimidine-2,4-dione (0.67 g, 6.0 mmol), and potassium phosphate tribasic (2.2 g, 10.5 mmol) in DMSO (20 ml) to give a colorless suspension. N-(2-cyanophenyl)picolinamide (220 mg, 1.0 mmol) was added and the mix was sparged with N$_2$ for 5 min. Copper(I) iodide (95 mg, 0.5 mmol) was added and the mix was sparged once again for 10 min, placed under N$_2$ and heated at 60° C. for 18 h. The mixture was cooled and partitioned between EtOAc and water adjusting the pH to 1 with HCl. The aqueous layer was extracted 2× with EtOAc. The organics were combined, washed with water, saturated NaHCO$_3$, and saturated NaCl. The organic layer was dried (Na$_2$SO$_4$), treated with 3-mercaptopropyl functionalized silica, filtered and concentrated. The crude product was purified by chromatography on an ISCO 40 g silica cartridge eluting with 3% MeOH in CH$_2$Cl$_2$ to give a white foam (1.0 g, 50%).

Part C. Preparation of methyl 5-(2,4-dioxo-3,4-dihydropyrimidin-1(2H)-yl)-2-methoxy-3-(6-(methylsulfonamido)naphthalen-2-yl)benzoate A mixture of the product from Part B (101 mg, 0.25 mmol), the product from Example 4A, Part B (91 mg, 0.263 mmol), and potassium phosphate tribasic (111 mg, 0.525 mmol) in 3:1 tetrahydro-furan-water (12 mL) was degassed by nitrogen sparge for 20 min. The solution was then treated with PA-Ph (CAS 97739-46-3) (2.192 mg, 7.50 µmol) and tris(dibenzylideneacetone)palladium(0) (2.289 mg, 2.500 µmol) followed by degassing for another 5 min. The microwave tube was then sealed, warmed at 50° C. for 18 h, cooled and partitioned between EtOAc and water adjusting the pH to 1 with 1M HCl. The EtOAc layer was washed with water, saturated NaHCO3, and saturated NaCl. The organic layer was dried $Na_2SO_4$, stirred for 1 h with 3-mercaptopropyl functionalized silica, filtered and concentrated. The crude product was purified by chromatography on an ISCO 12 g silica cartridge eluting with 3% MeOH in $CH_2Cl_2$ to give an off-white foam (80 mg, 63%). $^1$H NMR (300 MHz, DMSO-D6) δ ppm 3.09 (s, 3H) 3.45 (s, 3H) 3.89 (s, 3H) 5.69 (d, J=7.72 Hz, 1H) 7.43 (dd, J=8.82, 2.21 Hz, 1H) 7.68-7.79 (m, 4H) 7.84 (d, J=7.72 Hz, 1H) 7.89-8.01 (m, 2H) 8.09 (s, 1H) 10.06 (s, 1H) 11.49 (s, 1H). MS (ESI−) m/z 494 (M−H)$^+$.

Example 62

Preparation of N-(6-(5-(2,4-dioxo-3,4-dihydropyrimidin-1(2H)-yl)-3-iodo-2-methoxyphenyl)naphthalen-2-yl)methanesulfonamide (compound IB-L0-2.57)

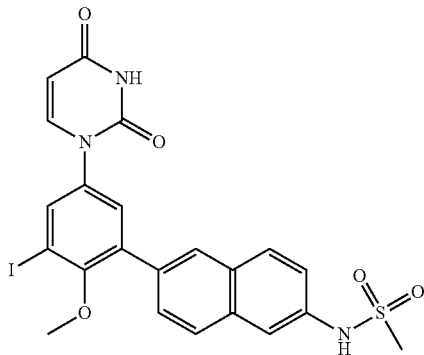 [SMILES: COc1c(I)cc(-n2ccc(=O)[nH]c2=O)cc1-c1ccc2cc(NS(C)(=O)=O)ccc2c1]

Part A. Preparation of 1,3,5-triiodo-2-methoxybenzene

In a 250 mL pressure vessel was added 2,4,6-triiodophenol (5 g, 10.60 mmol) in MTBE (60 ml) to give a yellow solution. The solution was cooled in an ice bath and 2.0M trimethylsilyldiazomethane (7.95 ml, 15.90 mmol) was added at a fast drip followed by dropwise addition of methanol (6 mL) resulting in calm bubbling. The vessel was sealed and stirred at room temperature for 4 h. The reaction solution was partitioned between EtOAc and water and the organic layer was washed with 1M HCl, saturated NaHCO3, and saturated NaCl. The EtOAc was dried (MgSO4), filtered and concentrated to give a tan solid that was used without purification (4.8 g, 94%).

Part B. Preparation of 1-(3,5-diiodo-4-methoxyphenyl)pyrimidine-2,4(1H,3H)-dione To a 100 mL round-bottom flask under N$_2$ was added the product from Part A (3.5 g, 7.2 mmol), 1H-pyrimidine-2,4-dione (0.97 g, 8.64 mmol), and potassium phosphate tribasic (3.2 g, 15.0 mmol) in DMSO (50 ml) to give a colorless suspension. N-(2-cyanophenyl)picolinamide (320 mg, 1.44 mmol) was added and the mix was sparged with N$_2$ for 5 min. Copper(I) iodide (137 mg, 0.72 mmol) was added and the mix was sparged once again for 10 min, placed under N$_2$ and heated at 60° C. for 18 h. The mixture was cooled and partitioned between EtOAc and water adjusting the pH to 1 with HCl. The aqueous layer was extracted 2× with EtOAc. The organics were combined, washed with water, saturated NaHCO$_3$, and saturated NaCl, dried (Na$_2$SO$_4$), treated with 3-mercaptopropyl functionalized silica, filtered and concentrated. The resulting solid was triturated in 2:1 hexane/EtOAc to give an off white powder (2.2 g, 62%).

Part C. Preparation of N-(6-(5-(2,4-dioxo-3,4-dihydropyrimidin-1(2H)-yl)-3-iodo-2-methoxyphenyl)naphthalen-2-yl)methanesulfonamide A mixture of the product from Part B 1-(3,5-diiodo-4-methoxyphenyl)pyrimidine-2,4(1H,3H)-dione (118 mg, 0.25 mmol), the product from Example 4A, Part B (87 mg, 0.25 mmol), 1,1'-bis(diphenylphosphino)ferrocene-palladium(II) dichloride CH$_2$Cl$_2$ complex (10.21 mg, 0.013 mmol) and sodium carbonate (0.250 ml, 0.25 mmol) in toluene (1.0 ml) and ethanol (1.0 ml) was sparged with nitrogen for 5 min and microwaved at 100° C. for 30 min. The mixture was cooled and partitioned with ethyl acetate and 1M HCl. The organic layer was washed with saturated sodium bicarbonate, brine, dried with sodium sulfate, filtered and evaporated. The residue was chromatographed on silica eluting with ethyl acetate/hexane (2:3 to 4:1) to give the title compound (16 mg, 11%). $^1$H NMR (300 MHz, DMSO-D6) δ ppm 3.08 (s, 3H) 3.35 (s, 3H) 5.67 (d, J=8.09 Hz, 1H) 7.42 (dd, J=8.82, 2.21 Hz, 1H) 7.59 (d, J=2.57 Hz, 1H) 7.73 (m, 2H) 7.81 (d, J=8.09 Hz, 1H) 7.95 (m, 3H) 8.09 (s, 1H) 10.06 (s, 1H) 11.47 (s, 1H). MS (ESI−) m/z 562 (M−H)$^+$.

Example 63

Preparation of N-(6-(5-(2,4-dioxo-3,4-dihydropyrimidin-1(2H)-yl)-2-methoxy-3-((trimethylsilyl)ethynyl)phenyl)naphthalen-2-yl)methanesulfonamide (compound IB-L0-2.78)

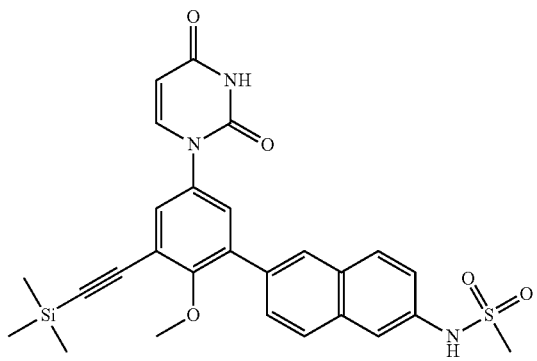 [SMILES: COc1c(C#C[Si](C)(C)C)cc(-n2ccc(=O)[nH]c2=O)cc1-c1ccc2cc(NS(C)(=O)=O)ccc2c1]

In a 5 mL microwave tube were combined ethynyltrimethylsilane (0.044 ml, 0.32 mmol), the product from Example 62 (45.1 mg, 0.08 mmol), copper(I) iodide (0.762 mg, 4.0 µmol), bis(triphenyl-phosphine)palladium(II) chloride (2.81 mg, 4.0 µmol) and triethylamine (0.056 ml, 0.40 mmol) in acetonitrile (2 ml). The mixture was sparged with nitrogen for 5 min, sealed and microwaved at 80° C. for 20 min. The reaction mixture was cooled and partitioned with ethyl acetate and water. The organic layer was washed with brine, dried with sodium sulfate, filtered and evaporated. The residue was chromatographed on silica eluting with 1-4% methanol in CH$_2$Cl$_2$ to give a solid, (18 mg, 42%) m.p. 175-178° C. $^1$H NMR (300 MHz, DMSO-D6) δ ppm 0.25 (s, 9H) 3.07 (s, 3H) 3.65 (s, 3H) 5.66 (dd, J=7.91, 2.02 Hz, 1H) 7.41 (dd, J=8.82, 2.21 Hz, 1H) 7.58 (m, 2H) 7.69 (dd, J=8.46, 1.84 Hz, 1H) 7.72 (d, J=2.21 Hz, 1H) 7.81 (d, J=7.72 Hz, 1H) 7.93 (m, 2H) 8.05 (d, J=1.32 Hz, 1H) 10.04 (s, 1H) 11.45 (d, J=2.21 Hz, 1H). MS (ESI+) m/z 534 (M+H)$^+$.

Example 64

Preparation of N-(6-(5-(2,4-dioxo-3,4-dihydropyrimidin-1(2H)-yl)-2-methoxy-3-(methylsulfonyl)phenyl)naphthalen-2-yl)methanesulfonamide (compound IB-L0-2.68)

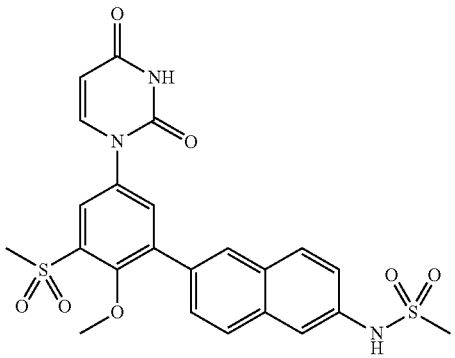

Part A. Preparation of 4-nitrobenzene-2-diazo-1-oxide

To a 250 mL round-bottom flask was added 2-amino-4-nitrophenol (6.165 g, 40.0 mmol) in 48% tetrafluoroboric acid (15 ml). Sodium nitrite (2.76 g, 40.0 mmol) in water (6 ml) was added dropwise at 0° C. and the mixture was stirred at room temperature for 30 min. The solid was collected by filtration, washed with tetrafluoroboric acid and water. The solid was suspended in acetone (50 ml), filtered and dried to give a solid (3.31 g, 50%).

Part B. Preparation of 2-(methylthio)-4-nitrophenol

To a 1 L beaker was added the product from Part A (2.70 g, 16.35 mmol) in ice water (250 g) to give a brown suspension. Copper (0.520 g, 8.18 mmol) was added, followed by addition of sodium thiomethoxide (2.292 g, 32.7 mmol) in water (50 ml) slowly. The mixture was stirred at room temperature for 24 h. The mixture was filtered and the filtrate was acidified with 1M HCl producing a solid that was collected by filtration and dried (2.53 g, 84%).

Part C. Preparation of 2-(methylsulfonyl)-4-nitrophenol

To a 250 mL round-bottom flask was added the product from Part B (1.111 g, 6.00 mmol) in MeOH (20 ml) to give a brown suspension. Oxone (7.746 g, 12.60 mmol) in water (20 ml) was added slowly at 0° C. The mixture was warmed to room temperature, stirred for 1 h and partitioned with ethyl acetate and 1M HCl. The organic layer was washed with brine, dried with sodium sulfate, filtered and evaporated. The residue was chromatographed on silica gel eluting with 1% to 5% methanol in CH$_2$Cl$_2$ to give a solid (0.472 g, 36%).

Part D. Preparation of 2-iodo-6-(methylsulfonyl)-4-nitrophenol

To a 50 mL round-bottom flask was added the product from Part C (470 mg, 2.164 mmol) in MeOH (10 ml) and water (2.5 ml). Iodine monochloride (0.130 ml, 2.60 mmol) in CH$_2$Cl$_2$ (2.0 mL) was added dropwise and the mixture was stirred at room temperature, poured into water (200 mL) and stirred for 10 min. The resulting solid was collected by filtration and dried (636 mg, 86%).

Part E. Preparation of 1-iodo-2-methoxy-3-(methylsulfonyl)-5-nitrobenzene

To a 50 mL pressure vessel was added the product from Part D (630 mg, 1.836 mmol) in MTBE (6 ml) to give a yellow solution. The mixture was cooled in an ice bath and 2M trimethylsilyl-diazomethane (1.377 ml, 2.75 mmol) was added at a fast drip followed by dropwise addition of MeOH (0.4 ml) resulting in calm bubbling. The vessel was sealed and stirred at room temperature for 1 h. The mixture was partitioned with ethyl acetate and 1M HCl. The organic layer was washed with saturated sodium bicarbonate, brine, dried with sodium sulfate, filtered and evaporated to give an off-white solid (655 mg, 100%).

Part F. Preparation of 3-iodo-4-methoxy-5-(methylsulfonyl)aniline

To a 250 mL round-bottom flask was added the product from Part E (0.650 g, 1.820 mmol), ammonium chloride (0.146 g, 2.73 mmol), and iron (0.508 g, 9.10 mmol) in THF/MeOH/water (50 ml, 2/2/1). The mixture was refluxed for 2 h, cooled and filtered. The filtrate was evaporated and the residue was partitioned with ethyl acetate and water. The organic layer was washed with brine, dried with sodium sulfate, filtered and evaporated to give a solid (590 mg, 99%).

Part G. Preparation of (E)-N-(3-iodo-4-methoxy-5-(methylsulfonyl)phenylcarbamoyl)-3-methoxyacrylamide To a 100 mL round-bottom flask was added the product from Part F (500 mg, 1.528 mmol) in DMF (15.0 ml). The solution was cooled under nitrogen to −20° C. and (E)-3-methoxyacryloyl isocyanate (15.28 ml, 6.11 mmol; prepared as described by Santana, L.; et al. J. Heterocyclic Chem. 1999, 36, 293-295) was added dropwise. The mixture was stirred at this temperature for 15 min, then warmed to room temperature and stirred for 45 min. The mixture was diluted with ethyl acetate and washed by water (3×50 ml), brine (3×50 ml), dried with sodium sulfate, filtered and evaporated. The residue was triturated with ethyl acetate/hexane to give a solid (425 mg, 61%).

Part H. Preparation of 1-(3-iodo-4-methoxy-5-(methylsulfonyl)phenyl)pyrimidine-2,4(1H,3H)-dione To a 100 mL round-bottom flask was added the product from Part G (420 mg, 0.925 mmol) in ethanol (10 ml) to give a suspension. Concentrated sulfuric acid (1 mL, 18.76 mmol) in water (10 ml) was added and the mixture was heated at 110° C. for 2 h. The reaction mix was cooled, diluted with water (50 ml) and stirred for 10 min. The solid material was collected by filtration, washed with water and dried to give a white solid (325 mg, 83%).

Part I. Preparation of N-(6-(5-(2,4-dioxo-3,4-dihydropyrimidin-1(2H)-yl)-2-methoxy-3-(methylsulfonyl)phenyl)naphthalen-2-yl)methanesulfonamide To a 5 mL microwave tube was added the product from Part H (63.3 mg, 0.15 mmol), the product from Example 4A, Part B (52.1 mg, 0.150 mmol), 1,1'-bis(diphenylphosphino)ferrocene-palladium(II)dichloride complex (6.12 mg, 7.50 µmol) and 1M sodium carbonate (0.150 ml, 0.150 mmol) in the solvents of toluene (1.0 ml) and ethanol (1.0 ml). The vessel was sealed and the mixture was sparged with nitrogen for 5 min and microwaved at 100° C. for 30 min. The mixture was partitioned with ethyl acetate and 1M HCl. The organic layer was washed with saturated sodium bicarbonate, brine, dried with sodium sulfate, filtered and evaporated. The residue was purified on silica gel eluting with 1% to 8% methanol in $CH_2Cl_2$ to give crude product. A final trituration in 1:1 methanol/ethyl acetate afforded pure solid (26 mg, 34%). $^1$H NMR (300 MHz, DMSO-D6) δ ppm 3.10 (s, 3H) 3.44 (s, 3H) 3.45 (s, 3H) 5.71 (d, J=8.09 Hz, 1H) 7.44 (dd, J=8.82, 2.21 Hz, 1H) 7.75 (d, J=1.84 Hz, 1H) 7.80 (dd, J=8.46, 1.84 Hz, 1H) 7.86 (d, J=8.09 Hz, 1H) 7.91 (d, J=2.57 Hz, 1H) 7.96 (d, J=2.57 Hz, 1H) 8.00 (m, 2H) 8.16 (d, J=1.47 Hz, 1H) 10.10 (s, 1H) 11.51 (s, 1H). MS (ESI+) m/z 533 (M+NH4)$^+$.

Example 65

Preparation of N-(5-(2,4-dioxo-3,4-dihydropyrimidin-1(2H)-yl)-2-methoxy-3-(6-(methylsulfonamido)naphthalen-2-yl)phenyl)methanesulfonamide (compound IB-L0-2.75)

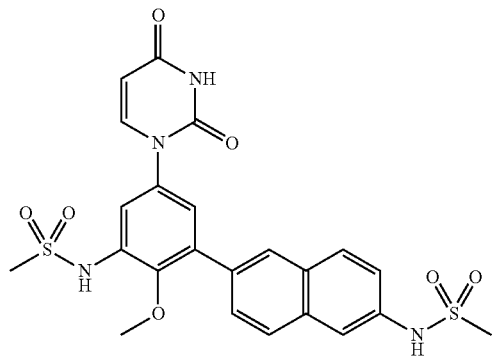

Part A. Preparation of 2,4-diiodo-6-nitrophenol

To a solution of 2-nitrophenol (2.78 g, 20 mmol) in MeOH (120 ml) and water (30 mL) was added dropwise a solution of iodine monochloride (2.105 ml, 42.0 mmol) in 10 mL $CH_2Cl_2$. The mixture was stirred for 2 h, poured into 600 mL water, stirred and sonicated for 30 min. The mixture was filtered to collect a yellow solid that was washed 3× with water (50 mL each wash) and dried to constant mass (7.3 g, 93%). m Part B. Preparation of 1,5-diiodo-2-methoxy-3-nitrobenzene A 50 mL pressure vessel was charged with the product from Part A and MTBE (10 ml) to give a yellow solution. The solution was cooled in an ice bath and 2M trimethylsilyldiazomethane (2.251 ml, 4.50 mmol) was added at a fast drop followed by dropwise addition of MeOH (0.6 ml) resulting in calm bubbling. The vessel was sealed and stirred allowing warm to room temperature over 4 h. The mixture was partitioned with ethyl acetate and 1M HCl. The organic layer was washed with saturated sodium bicarbonate, brine, dried with sodium sulfate, filtered and evaporated to give a yellow solid (1.22 g, 100%).

Part C. Preparation of 3,5-diiodo-2-methoxyaniline

In a 250 round-bottom flask was added the product from Part B (0.98 g, 2.420 mmol), ammonium chloride (0.194 g, 3.63 mmol), and iron (0.676 g, 12.10 mmol) in THF/methanol/water (20 ml/20 ml/10 ml). The mixture was refluxed for 16 ho, cooled and filtered. The filtrate was evaporated and the residue was partitioned with water and ethyl acetate. The organic layer was dried with sodium sulfate, filtered and evaporated to give an oil (780 mg, 86%).

Part D. Preparation of 1-(3-amino-5-iodo-4-methoxyphenyl)pyrimidine-2,4(1H,3H)-dione In a 25 mL round-bottom flask was added the product from Part C (650 mg, 1.734 mmol), pyrimidine-2,4(1H,3H)-dione (214 mg, 1.907 mmol), N-(2-cyanophenyl)picolinamide (77 mg, 0.347 mmol), copper(I) iodide (33.0 mg, 0.173 mmol) and potassium phosphate (773 mg, 3.64 mmol) in DMSO (5 ml). The vessel was sealed and the mixture was sparged with nitrogen for 15 min and heated at 60° C. for 16 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica eluting with 5:95 methanol/D $CH_2Cl_2$CM to give a solid (125 mg, 20%).

Part E. Preparation of N-(5-(2,4-dioxo-3,4-dihydropyrimidin-1(2H)-yl)-3-iodo-2-methoxy-phenyl)methanesulfonamide A solution of the product from Part D (110 mg, 0.306 mmol) in pyridine (2 ml) was treated with methanesulfonyl chloride (0.048 ml, 0.612 mmol) and stirred for 24 h. The solvent was evaporated and the residue was partitioned with ethyl acetate and 1M HCl. The organic layer was washed with brine, dried with sodium sulfate, filtered and evaporated. The residue was purified on silica gel eluting with 2% to 5% methanol in $CH_2Cl_2$ to give a solid (20 mg, 15%).

Part F. Preparation of N-(5-(2,4-dioxo-3,4-dihydropyrimidin-1(2H)-yl)-2-methoxy-3-(6-(methylsulfonamido)naphthalen-2-yl)phenyl)methanesulfonamide To a 5 mL microwave tube was added the product from Part E (18 mg, 0.041 mmol), Example 4A, Part B (14.30 mg, 0.041 mmol), potassium phosphate (18.35 mg, 0.086 mmol), PA-Ph (CAS 97739-46-3) (0.361 mg, 1.235 mmol) and tris(dibenzylideneacetone)dipalladium(0) (0.377 mg, 0.412 mmol) in THF (3.0 ml) and water (1.0 ml). The vessel was sealed and the mixture was sparged with nitrogen for 5 min and heated at 50° C. for 2 h. The mixture was partitioned with ethyl acetate and 1M HCl. The organic layer was washed with saturated sodium bicarbonate, brine, dried with sodium sulfate, filtered and evaporated. The residue was purified on silica gel eluting with 2% to 5% methanol in CH$_2$Cl$_2$ to give a solid. A final trituration in 1:1 methanol/CH$_2$Cl$_2$ gave the desired product (7 mg, 32%). $^1$H NMR (300 MHz, DMSO-D6) δ ppm 3.09 (s, 3H) 3.17 (s, 3H) 3.37 (s, 3H) 5.69 (dd, J=7.91, 2.02 Hz, 1H) 7.34 (d, J=2.57 Hz, 1H) 7.43 (dd, J=8.82, 2.21 Hz, 1H) 7.47 (d, J=2.57 Hz, 1H) 7.73 (m, 2H) 7.81 (d, J=8.09 Hz, 1H) 7.94 (d, J=6.25 Hz, 1H) 7.97 (d, J=6.62 Hz, 1H) 8.07 (s, 1H) 9.45 (s, 1H) 10.05 (s, 1H) 11.45 (d, J=1.84 Hz, 1H). MS (ESI–) m/z 529 (M–H).

Example 66

Preparation of N-(6-(5-(2,4-dioxo-3,4-dihydropyrimidin-1(2H)-yl)-2-methoxy-3-(trifluoromethyl)phenyl)naphthalen-2-yl)methanesulfonamide (compound IB-L0-2.56)

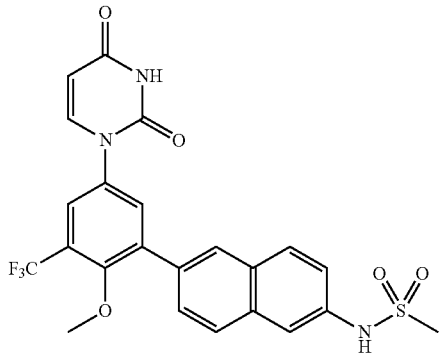 [SMILES: COc1c(-c2ccc3cc(NS(C)(=O)=O)ccc3c2)cc(-n2ccc(=O)[nH]c2=O)cc1C(F)(F)F]

Part A. Preparation of 4-iodo-2-(trifluoromethyl)phenol

To a solution of 2-(trifluoromethyl)phenol (3.24 g, 20 mmol) in MeOH (40 ml) was added sodium hydroxide (0.960 g, 24.0 mmol) and stirred until the hydroxide was dissolved. The mixture was cooled to 0° C. and sodium iodide was added (3.0 g, 20 mmol) followed by dropwise addition of 10% aqueous sodium hypochlorite (9.0 ml, 14.6 mmol). The addition of sodium iodide followed by sodium hypochlorite was repeated twice more. The mixture was stirred at ambient temperature for 2 h and treated dropwise with concentrated HCl to pH 1. The mixture was extracted 3× with EtOAc. The extracts were combined, washed with brine, dried with sodium sulfate, filtered and evaporated. The residue was purified on silica gel eluting with EtOAc/hexane (1:9) to give the mono-iodo product (5.0 g, 87%).

Part B. Preparation of 2-bromo-4-iodo-6-(trifluoromethyl)phenol

In a 250 mL round-bottom flask was added the product from Part A (5.00 g, 17.36 mmol) and 1,3-dibromo-5,-dimethylhydantoin (2.73 g, 9.55 mmol) in CHCl$_3$ (80 ml) to give an orange solution. The mixture was stirred for 2 h, washed with water, brine, dried with sodium sulfate, filtered and evaporated. The crude product was purified on silica gel eluting with ethyl acetate/hexane (5:95) to give a solid (3.5 g, 54%).

Part C. Preparation of 1-bromo-5-iodo-2-methoxy-3-(trifluoromethyl)benzene

A mixture of the product from Part B (3.2 g, 8.72 mmol), iodomethane (1.36 ml, 21.8 mmol), and 50% sodium hydroxide (0.507 ml, 9.59 mmol) in acetone (20 ml) was stirred for 24 h. The solvent was evaporated and the residue was partitioned with ethyl acetate and water. The organic layer was washed with brine, dried with sodium sulfate, filtered and evaporated. The crude material was purified on silica gel eluting with ethyl acetate/hexane (5:95) to give a solid (2.67 g, 80%).

Part D. Preparation of 1-(3-bromo-4-methoxy-5-(trifluoromethyl)phenyl)pyrimidine-2,4(1H,3H)-dione In a 20 mL microwave tube was added the product from Part C (762 mg, 2.0 mmol), pyrimidine-2,4(1H,3H)-dione (247 mg, 2.2 mmol), N-(2-cyanophenyl)picolinamide (89 mg, 0.4 mmol), copper(I) iodide (38.1 mg, 0.2 mmol) and potassium phosphate (892 mg, 4.2 mmol) in DMSO (10 ml). The vessel was sealed and the mixture was sparged with nitrogen for 15 min and heated at 60° C. for 16 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was purified on silica gel eluting with ethyl acetate/hexane (2:3) to give the desired product (63 mg, 9%).

Part E. Preparation of N-(6-(5-(2,4-dioxo-3,4-dihydropyrimidin-1(2H)-yl)-2-methoxy-3-(trifluoromethyl)phenyl)naphthalen-2-yl)methanesulfonamide In a 5 mL microwave tube was added the product from Part D (60 mg, 0.164 mmol), the product from Example 4A, Part B (62.8 mg, 0.181 mmol), 1,1'-bis(di-tert-butylphosphino) ferrocene palladium dichloride (5.36 mg, 8.22 mmol) and potassium phosphate (69.8 mg, 0.329 mmol) in THF/water (3 ml/1 ml). The vessel was sealed and the mixture was sparged with nitrogen for 5 min and heated at 60° C. for 2 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was purified by reverse phase chromatography to give the title compound as a solid (26 mg, 31%). $^1$H NMR (300 MHz, DMSO-D6) δ ppm 3.10 (s, 3H) 3.37 (s, 3H) 5.71 (dd, J=7.72, 2.21 Hz, 1H) 7.44 (dd, J=8.82, 2.21 Hz, 1H) 7.75 (s, 1H) 7.78 (d, J=1.84 Hz, 1H) 7.88 (m, 3H) 7.98 (d, J=3.31 Hz, 1H) 8.01 (d, J=3.68 Hz, 1H) 8.15 (s, 1H) 10.09 (s, 1H) 11.51 (d, J=2.21 Hz, 1H). MS (ESI–) m/z 504.1 (M–H)$^+$.

Example 67

Preparation of N-(6-(5-(2,4-dioxo-3,4-dihydropyrimidin-1(2H)-yl)-2-methoxy-3-(perfluoroethyl)phenyl)naphthalen-2-yl)methanesulfonamide (compound IB-L0-2.60)

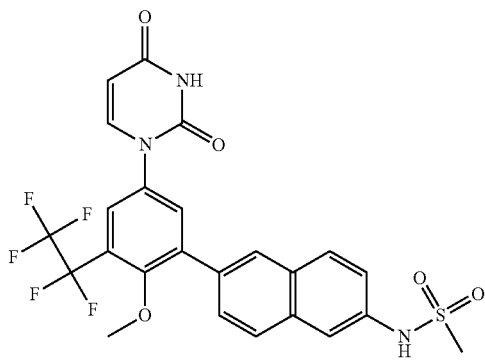 [SMILES: COc1c(-c2ccc3cc(NS(C)(=O)=O)ccc3c2)cc(-n2ccc(=O)[nH]c2=O)cc1C(F)(F)C(F)(F)F]

Part A. Preparation of 1-methoxy-4-nitro-2-(perfluoroethyl)benzene

To a 250 mL round-bottom flask was added 2-bromo-1-methoxy-4-nitrobenzene (3.5 g, 15.08 mmol), copper(I) iodide (5.75 g, 30.2 mmol), and sodium 2,2,3,3,3-pentafluoropropanoate (5.25 g, 28.2 mmol) in DMF (75 ml) and toluene (25 ml) to give a tan suspension. The mixture was heated at 150° C. and toluene was removed by a Dean-Stark trap. The mixture was heated at 155° C. for 6 h under nitrogen, cooled and poured into 100 mL of water and 100 mL of ether, filtered through a 1-inch plug of Celite and the plug was rinsed with ether. The filtrate layers were separated. The organic layer was washed with brine, dried ($Na_2SO_4$) filtered and concentrated. The dark oil was flash chromatographed on an Isco 40 g silica cartridge eluting with 4:1 hexane/EtOAc to give a yellow oil that was a (3:1) mix of desired material and starting material (1.5 g, 37%).

Part B. Preparation of 4-nitro-2-(perfluoroethyl)phenol

In a 100 mL round-bottom flask was added the product from Part A (1.4 g, 5.16 mmol) and pyridine hydrochloride (4 g, 34.6 mmol) neat. The mixture was heated at 210° C. for 20 min, cooled, and partitioned between EtOAc and water. The organic layer was washed with brine, dried ($Na_2SO_4$) and concentrated. The crude product was flash chromatographed on an Isco 12 g silica cartridge eluting with 3:2 hecxane/EtOAc to give a yellow oil (1.3 g, 98%).

Part C. Preparation of 2-iodo-4-nitro-6-(perfluoroethyl)phenol

In a 100 mL round-bottom flask was added the product from Part B (1.3 g, 5.06 mmol) and N-iodosuccinimide (1.251 g, 5.56 mmol) in acetonitrile (16.85 ml) to give a yellow solution. The solution was stirred for 16 h, diluted with 100 mL EtOAc and washed 2×50 ml with 10% sodium thiosulfate, brine, dried ($Na_2SO_4$) and concentrated to an orange semisolid. The semisolid was flash chromatographed on an Isco 40 g silica cartridge eluting with 3:1 hexane EtOAc to give a deep yellow/orange oil (1.3 g, 67%).

Part D. Preparation of 1-iodo-2-methoxy-5-nitro-3-(perfluoroethyl)benzene

In a 100 mL round-bottom flask was added the product from Part C (1.04 g, 2.72 mmol) potassium carbonate (0.563 g, 4.07 mmol) and dimethyl sulfate (0.411 g, 3.26 mmol) in acetone (20 ml) to give a brown suspension. The mixture was heated at gentle reflux for 16 h, cooled, diluted into EtOAc, washed with water and brine. The organic layer was dried Na2SO4, filtered and concentrated to a yellow oil that was purified by flash chromatography on an Isco 40 g silica cartridge eluting with 9:1 hexane/EtOAc (600 mg, 56%).

Part E. Preparation of 3-iodo-4-methoxy-5-(perfluoroethyl)aniline

In a 250 mL round-bottom flask was added the product from Part D (0.6 g, 1.511 mmol), iron (0.422 g, 7.56 mmol), and ammonium chloride (0.121 g, 2.267 mmol) in a solvent mix of EtOH (9 ml), THF (9 ml) and water (3 ml) to give a brown suspension that was heated at 95-100° C. for 2 h. The reaction mix was filtered through a plug of Celite and the Celite was rinsed repeatedly with EtOH. The filtrate was concentrated and the residue was dissolved in EtOAc, washed with water, brine, dried ($Na_2SO_4$), filtered and concentrated to give an oil (560 mg, 99%).

Part F. Preparation of 1,5-diiodo-2-methoxy-3-(perfluoroethyl)benzene

In a 25 mL round-bottom flask under nitrogen was added the product from Part E (0.565 g, 1.539 mmol), tert-butyl nitrite (0.293 ml, 2.463 mmol), copper(I) iodide (0.293 g, 1.539 mmol), sodium iodide (0.231 g, 1.539 mmol) and iodine (0.195 g, 0.770 mmol) in DME (15.39 ml) to give a brown suspension. The mixture was heated at 60° C. for 3 h, cooled and filtered through Celite washing the Celite pad well with EtOAc. The EtOAc filtrate was treated with 10% sodium thiosulfate, brine, dried ($Na_2SO_4$), filtered and concentrated to a dark oil. The crude material was purified by flash chromatography on an Isco 40 g silica cartridge eluting with 95:5 hexane/EtOAc to give a yellow oil (360 mg, 49%).

Part G. Preparation of 1-(3-iodo-4-methoxy-5-(perfluoroethyl)phenyl)pyrimidine-2,4(1H,3H)-dione In a 20 mL microwave tube was added the product from Part F (0.36 g, 0.753 mmol), 1H-pyrimidine-2,4-dione (0.101 g, 0.904 mmol), potassium phosphate tribasic (0.336 g, 1.582 mmol) N-(2-cyanophenyl)picolinamide (0.034 g, 0.151 mmol) and copper(I) iodide (0.014 g, 0.075 mmol in DMSO (7 ml). The vessel was sealed and the mixture was sparged with $N_2$ for 30 min, heated at 60° C. for 24 h, cooled and diluted into EtOAc. The EtOAc layer was washed with 1M HCl, saturated NaHCO3, and saturated NaCl, dried ($Na_2SO_4$), filtered and concentrated. The residue was flash chromatographed on an Isco 40 g silica cartridge eluting with hexane-->1:1 hexane/EtOAc to give a yellow foam (100 mg, 29%).

Part H. Preparation of N-(6-(5-(2,4-dioxo-3,4-dihydropyrimidin-1(2H)-yl)-2-methoxy-3-(perfluoroethyl)phenyl)naphthalen-2-yl)methanesulfonamide In a 5 mL microwave tube were combined the product from Part G (0.10 g, 0.216 mmol), Example 4A, Part B (0.075 g, 0.216 mmol), and potassium phosphate tribasic (0.096 g, 0.454 mmol) in 3:1 tetrahydrofuran-water (5 mL) and degassed by nitrogen sparge for 10 min. The mixture was then treated with PA-Ph (CAS 97739-46-3) (1.898 mg, 6.49 µmol) and tris(dibenzylideneacetone)dipalladium(0) (1.982 mg, 2.164 µmol) followed by degassing for another 5 min. The flask was then sealed and stirred at 50° C. for 16 h and partitioned between EtOAc and water. The EtOAc layer was washed with 0.1M HCl, saturated NaHCO$_3$, and saturated NaCl. The organic was dried Na$_2$SO$_4$, stirred for 0.5 h with 3-mercapto-propyl functionalized silica to remove metals, filtered and concentrated. The crude product was purified by chromatography on an Isco 12 g silica cartridge eluting with CH$_2$Cl$_2$-->3% MeOH in CH$_2$Cl$_2$ to give a light yellow foam (84 mg, 99%) m.p. 162-165° C. $^1$H NMR (300 MHz, DMSO-D6) δ ppm 3.10 (s, 3H) 3.33 (s, 3H) 5.70 (d, J=7.72 Hz, 1H) 7.44 (dd, J=8.82, 2.21 Hz, 1H) 7.70-7.76 (m, 2H) 7.80 (d, J=2.57 Hz, 1H) 7.86 (d, J=8.09 Hz, 1H) 7.91 (d, J=2.57 Hz, 1H) 8.00 (dd, J=8.82, 2.94 Hz, 2H) 8.12 (s, 1H) 10.10 (s, 1H) 11.50 (s, 1H). MS (ESI−) m/z 554 (M−H)$^+$.

Example 68

Preparation of (E)-N'-(6-(5-(2,4-dioxo-3,4-dihydro-pyrimidin-1(2H)-yl)-2-methoxy-3-(thiophen-2-yl) phenyl)-2,3-dihydro-1H-inden-1-ylidene)methane-sulfonohydrazide (compound IB-L0-2.51)

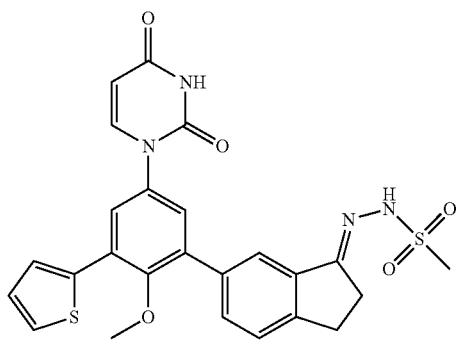 [SMILES: COc1c(-c2ccc3c(c2)/C(=N/NS(C)(=O)=O)CC3)cc(-n2ccc(=O)[nH]c2=O)cc1-c1cccs1]

Part A. Preparation of 1-(3-bromo-4-methoxy-5-(1-oxo-2,3-dihydro-1H-inden-5-yl)phenyl)-pyrimidine-2,4(1H,3H)-dione In a 100 mL round-bottom flask was added the product from Example 48, Part C (846 mg, 2.00 mmol), Example 6, Part A (516 mg, 2.000 mmol), potassium phosphate (892 mg, 4.20 mmol), PA-Ph (CAS 97739-46-3) (17.54 mg, 0.060 mmol) and tris(dibenzylideneacetone)-dipalladium(0) (18.31 mg, 0.020 mmol) in THF (12.0 ml) and water (4.0 ml). The vessel was sealed and the mixture was sparged with nitrogen for 5 min and stirred at ambient temperature for 72 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered through celite and evaporated. The residue was purified with silica gel eluting with 1 to 4% methanol in CH$_2$Cl$_2$ to give a solid (690 mg, 81%).

Part B. Preparation of (E)-N'-(5-(3-bromo-5-(2,4-dioxo-3,4-dihydropyrimidin-1(2H)-yl)-2-methoxyphenyl)-2,3-dihydro-1H-inden-1-ylidene)methanesulfonohydrazide In a 50 mL round-bottom flask was added the product from Part A (685 mg, 1.603 mmol) and methanesulfonohydrazide (194 mg, 1.764 mmol) in MeOH (20 ml). The mixture was warmed to 40° C. and stirred for 24 h. The mixture was cooled, filtered and washed with methanol to give a solid (569 mg, 68%).

Part C. Preparation of (E)-N'-(6-(5-(2,4-dioxo-3,4-dihydropyrimidin-1(2H)-yl)-2-methoxy-3-(thiophen-2-yl)phenyl)-2,3-dihydro-1H-inden-1-ylidene)methanesulfonohydrazide In a 5 mL microwave tube was added the product from Part B (52 mg, 0.100 mmol), thiophen-2-ylboronic acid (12.81 mg, 0.100 mmol), 1,1'-bis(di-tert-butylphosphino)ferrocene palladium dichloride (3.26 mg, 5.01 mmol) and potassium phosphate (42.5 mg, 0.200 mmol) in THF (3.0 ml) and water (1.0 ml). The mixture was sparged by nitrogen for 5 min and heated at 50° C. for 3 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered through celite and evaporated. The residue was purified by reverse phase chromatography AA method to give a white solid (27 mg, 52%). $^1$H NMR (300 MHz, DMSO-D6) δ ppm 2.86 (m, 2H) 3.09 (s, 3H) 3.14 (m, 2H) 3.32 (s, 3H) 5.69 (d, J=7.72 Hz, 1H) 7.18 (dd, J=5.15, 3.68 Hz, 1H) 7.41 (d, J=2.57 Hz, 1H) 7.63 (m, 3H) 7.75 (m, 2H) 7.86 (d, J=8.09 Hz, 1H) 7.91 (d, J=2.94 Hz, 1H) 9.96 (s, 1H) 11.48 (s, 1H). MS (ESI+) m/z 523 (M+H)$^+$.

Example 69

Preparation of (E)-N'-(6-(5-(2,4-dioxo-3,4-dihydro-pyrimidin-1(2H)-yl)-3-(furan-2-yl)-2-methoxyphenyl)-2,3-dihydro-1H-inden-1-ylidene)methane-sulfonohydrazide (compound IB-L0-2.55)

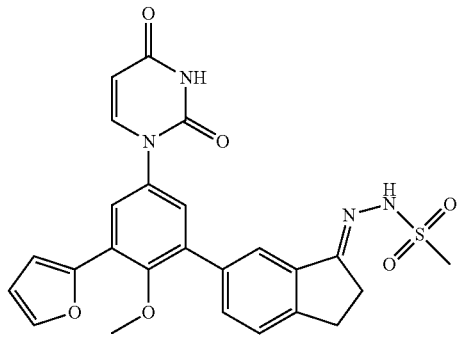 [SMILES: COc1c(-c2ccc3c(c2)/C(=N/NS(C)(=O)=O)CC3)cc(-n2ccc(=O)[nH]c2=O)cc1-c1ccco1]

In a 5 ml microwave tube was added the product from Example 68, Part B (52 mg, 0.100 mmol), furan-2-ylboronic acid (11.20 mg, 0.100 mmol), 1,1'-bis(di-tert-butylphosphino)ferrocene palladium dichloride (3.26 mg, 5.01 mmol) and potassium phosphate (42.5 mg, 0.200 mmol) in THF (3.0 ml) and water (1.0 ml). The mixture was sparged by nitrogen for 5 min and heated at 50° C. for 3 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered through celite and evaporated. The residue was purified by reverse phase chromatography AA method to give a solid (24 mg, 47%). $^1$H NMR (300 MHz, DMSO-D6) δ ppm 2.86 (m, 2H) 3.09 (s, 3H) 3.14 (m, 2H) 3.36 (s, 3H) 5.68 (d, J=8.09 Hz, 1H) 6.69 (dd, J=3.31, 1.84 Hz, 1H) 7.09 (d, J=3.31 Hz, 1H) 7.41 (d, J=2.57 Hz, 1H) 7.62 (m, 2H) 7.75 (d, J=8.09 Hz, 1H) 7.80 (d, J=2.57 Hz, 1H) 7.86 (m, 2H) 9.97 (s, 1H) 11.46 (s, 1H). MS (ESI+) m/z 507 (M+H)$^+$.

Example 70

Preparation of N-(6-(3-tert-butyl-5-(2,4-dioxo-3,4-dihydropyrimidin-1(2H)-yl)-2-ethoxyphenyl)naphthalen-2-yl)methanesulfonamide (compound IB-L0-2.23)

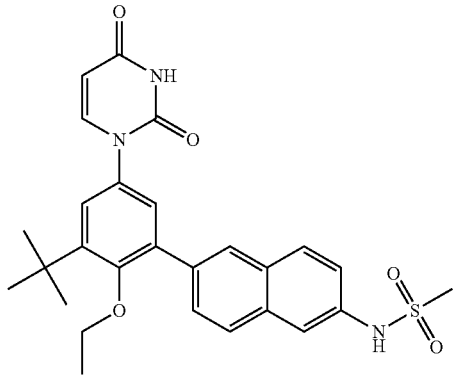 [SMILES: CCOc1c(-c2ccc3cc(NS(C)(=O)=O)ccc3c2)cc(-n2ccc(=O)[nH]c2=O)cc1C(C)(C)C]

Part A. Preparation of 2-tert-butyl-4-iodophenol

To a 250 mL round-bottom flask was added 2-tert-butylphenol (3.76 g, 25 mmol) in MeOH (50.0 ml) to give a colorless solution. Sodium hydroxide (1.200 g, 30.0 mmol) was added and the mix was stirred until the hydroxide was completely dissolved. The solution was cooled to 0° C. and treated with sodium iodide (1.75 g, 11.6 mmol) followed by dropwise addition of 10% sodium hypochlorite solution (7.2 ml, 11.6 mmol). The addition of sodium iodide followed by sodium hypochlorite was repeated twice and the mixture was stirred at 0° C. for 30 min. The mixture was treated with 10% w/w solution of sodium thiosulfate, stirred for 30 min and treated with concentrated HCl dropwise to a constant pH of 1. The mixture was extracted 3× with EtOAc. The extracts were combined, washed with brine, dried (MgSO4), filtered and concentrated. The crude oil was flash chromatographed on an ISCO 80 g silica cartridge eluting with hexane-->4:1 hexane/EtOAc to give a yellow oil (5.2 g, 75%).

Part B. Preparation of 2-bromo-6-tert-butyl-4-iodophenol

To a 250 mL round-bottom flask was added the product from Part A (4.8 g, 17.38 mmol) and 1,3-dibromo-5,5-dimethylhydantoin (2.61 g, 9.13 mmol) in chloroform (87 ml) to give an orange solution. The reaction mixture was stirred for 2 h resulting in a black solution that was washed with water, brine, dried (Na$_2$SO$_4$) and concentrated. The black oil was flash chromatographed on a 120 g Isco silica cartridge eluting with hexane to give a pinkish solid (4.84 g, 78%).

Part C. Preparation of 1-bromo-3-tert-butyl-2-ethoxy-5-iodobenzene

To a 50 mL round-bottom flask was added the product from Part B (888 mg, 2.5 mmol), ethyl iodide (409 mg, 2.63 mmol), and potassium carbonate (415 mg, 3.00 mmol) in acetone (12 ml) to give a green suspension. The mixture was heated at reflux for 16 h, cooled and concentrated. The residue was partitioned between water and EtOAc. The organic layer was washed twice with brine, dried over Na$_2$SO$_4$, filtered and concentrated to a red oil. The oil was flash chromatographed on an Isco 40 g silica cartridge eluting with hexane to give a clear oil (820 mg, 86%).

Part D. Preparation of 1-(3-bromo-5-tert-butyl-4-ethoxyphenyl)pyrimidine-2,4(1H,3H)-dione In a 20 mL microwave tube under nitrogen flush was added the product from Part C (0.4 g, 1.044 mmol), 1H-Pyrimidine-2,4-dione (0.140 g, 1.253 mmol), and potassium phosphate tribasic (0.465 g, 2.193 mmol) in DMSO (5 ml) to give a colorless suspension. N-(2-cyanophenyl)picolinamide (0.047 g, 0.209 mmol) was added and the mix was sparged with nitrogen for 10 min. Copper(I) iodide (0.020 g, 0.104 mmol) was added and the mix was sparged once again for 10 min, placed under nitrogen and heated at 60° C. for 18 h. The mixture was cooled and partitioned between EtOAc and water adjusting the pH to 1 with HCl. The aqueous layer was extracted 2× with EtOAc. The organics were combined, washed with water, saturated NaHCO$_3$, and saturated NaCl. The organic layer was dried (Na$_2$SO$_4$), stirred with 3-mercaptopropyl functionalized silica for 1 h, filtered and concentrated. The crude product was purified by chromatography on an ISCO 12 g silica cartridge eluting with 2% MeOH in CH$_2$Cl$_2$ to give a white powder (266 mg, 69%).

Part E. Preparation of N-(6-(3-tert-butyl-5-(2,4-dioxo-3,4-dihydropyrimidin-1(2H)-yl)-2-ethoxyphenyl)naphthalen-2-yl)methanesulfonamide In a 5 mL microwave tube was added the product from Part D (55.1 mg, 0.15 mmol), the product from Example 4A, Part B (52.1 mg, 0.150 mmol), potassium phosphate tribasic (63.7 mg, 0.300 mmol) and 1,1'-bis(di-tert-butylphosphino)ferrocene palladium dichloride (4.89 mg, 7.50 μmol) in THF (3 ml) water (1 ml). The mixture was sparged for 10 min with nitrogen, heated sealed at 50° C. for 4 h, cooled and diluted into EtOAc. The EtOAc layer was washed with 1M HCl, saturated NaHCO$_3$, saturated NaCl, dried (Na$_2$SO$_4$) and treated simultaneously with mercaptopropyl silica gel, filtered and concentrated. The residue was flash chromatographed on a 12 g Isco silica cartridge eluting with 2% MeOH in CH$_2$Cl$_2$ to give a solid, (16 mg, 21%) m.p. 196-202° C. $^1$H NMR (300 MHz, DMSO-D6) δ ppm 1.00 (t, J=6.99 Hz, 3H) 1.44 (s, 9H) 3.09 (s, 3H) 3.43 (q, J=7.11 Hz, 2H) 5.64 (dd, J=7.91, 1.29 Hz, 1H) 7.32 (d, J=2.94 Hz, 1H) 7.36 (d, J=2.94 Hz, 1H) 7.41 (dd, J=8.82, 2.21 Hz, 1H) 7.72 (s, 1H) 7.74 (d, J=1.47 Hz, 1H) 7.80 (d, J=7.72 Hz, 1H) 7.90-8.00 (m, 2H) 8.05 (s, 1H) 10.04 (s, 1H) 11.41 (s, 1H). MS (ESI−) m/z 506 (M−H)$^+$.

Example 71

Preparation of N-(6-(3-tert-butyl-2-chloro-5-(2,4-dioxo-3,4-dihydropyrimidin-1(2H)-yl)phenyl)naphthalen-2-yl)methanesulfonamide (compound IB-L0-2.14)

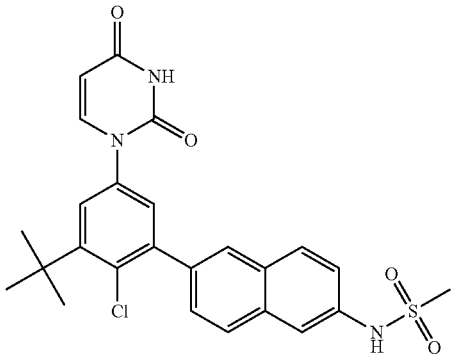 [SMILES: CC(C)(C)c1cc(-n2ccc(=O)[nH]c2=O)cc(-c2ccc3cc(NS(C)(=O)=O)ccc3c2)c1Cl]

Part A. Preparation of 2-bromo-6-tert-butyl-4-iodoaniline

In a 50 mL round-bottom flask was added 2-bromo-6-tert-butylaniline [prepared by the method of Onitsuka, et. al. Organometallics, 25(5), 2006, pp 1270-1278] (1.18 g, 5.17 mmol) and sodium bicarbonate (0.782 g, 9.3 μmol) in water (5 ml). The mixture was cooled in an ice bath and iodine (1.444 g, 5.69 mmol) was added in several portions. The mixture was warmed to ambient temperature and stirred for 16 h. The mixture was treated with aqueous sodium thiosulfate, extracted by ethyl acetate, dried with sodium sulfate, filtered and evaporated. The residue was purified on silica gel eluting with 5% ethyl acetate in hexane to give an oil (1.2 g, 65%).

Part B. Preparation of 1-bromo-3-tert-butyl-2-chloro-5-iodobenzene

To a mixture of tert-butyl nitrite (0.198 ml, 1.5 mmol) and copper(II) chloride (161 mg, 1.2 mmol) in acetonitrile (5 mL) was added the product from Part A (354 mg, 1.0 mmol) as a solution in acetonitrile (5 mL). The mixture was heated at 60° C. for 30 min, cooled, partitioned with ethyl acetate and 1M HCl. The organic layer was washed with brine, dried with sodium sulfate, filtered and evaporated. The residue was purified on silica gel eluting with 5% ethyl acetate in hexane to give the product (300 mg, 81%).

Part C. Preparation of 1-(3-bromo-5-tert-butyl-4-chlorophenyl)pyrimidine-2,4(1H,3H)-dione In a 20 mL microwave tube was added the product from Part B (300 mg, 0.803 mmol), pyrimidine-2,4(1H,3H)-dione (99 mg, 0.884 mmol), N-(2-cyanophenyl)picolinamide (35.9 mg, 0.161 mmol), copper(I) iodide (15.30 mg, 0.080 mmol) and potassium phosphate (358 mg, 1.687 mmol) in DMSO (5 ml). The mixture was sealed, purged with nitrogen and heated at 60° C. for 4 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was purified on silica gel eluting with 10% to 40% ethyl acetate in hexane to give a solid (175 mg, 61%).

Part D. Preparation of N-(6-(3-tert-butyl-2-chloro-5-(2,4-dioxo-3,4-dihydropyrimidin-1(2H)-yl)phenyl)naphthalen-2-yl)methanesulfonamide In a 5 mL microwave tube was added the product from Part C (35.8 mg, 0.10 mmol), the product from Example 4A, Part B (38.2 mg, 0.110 mmol), 1,1'-bis(di-tert-butylphosphino)ferrocene palladium dichloride (3.26 mg, 5.00 μmol) and potassium phosphate (42.5 mg, 0.200 mmol) in THF/Water (3 ml:1 ml). The mixture was purged with nitrogen for 5 min and heated at 60° C. for 2 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was purified on silica gel eluting with 1:1 ethyl acetate/hexane to give a solid that was triturated with 1% methanol in $CH_2Cl_2$ to give a white solid (29 mg, 55%), melting point: >280° C. $^1$H NMR (300 MHz, DMSO-D6) δ ppm 1.53 (s, 9H) 3.08 (s, 3H) 5.69 (d, J=7.72 Hz, 1H) 7.42 (m, 2H) 7.52 (dd, J=8.46, 1.84 Hz, 1H) 7.56 (d, J=2.57 Hz, 1H) 7.74 (d, J=1.84 Hz, 1H) 7.84 (d, J=7.72 Hz, 1H) 7.88 (s, 1H) 7.91 (d, J=8.82 Hz, 1H) 7.95 (d, J=9.19 Hz, 1H) 10.04 (s, 1H) 11.46 (s, 1H). MS (ESI-) m/z 496 (M-H)$^+$.

Example 72

Preparation of N-((6-(3-tert-butyl-5-(2,4-dioxo-3,4-dihydropyrimidin-1(2H)-yl)-2-methoxyphenyl)benzo[d]isoxazol-3-yl)methyl)methanesulfonamide (compound IB-L0-2.45)

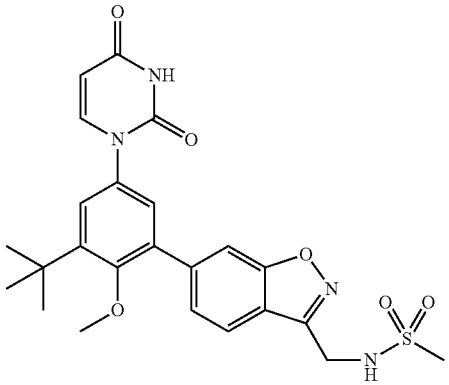 [SMILES: COc1c(-c2ccc3c(CNS(C)(=O)=O)noc3c2)cc(-n2ccc(=O)[nH]c2=O)cc1C(C)(C)C]

Part A. Preparation of N-((6-bromobenzo[d]isoxazol-3-yl)methyl)-N-(4-methoxybenzyl)-methanesulfonamide To a refluxing solution of 6-bromo-3-methylbenzo[d]isoxazole (1.0 g, 4.72 mmol) in $CCl_4$ (25 ml) was added 1-bromopyrrolidine-2,5-dione (0.923 g, 5.19 mmol) and benzoic peroxyanhydride (0.114 g, 0.472 mmol). The mixture was refluxed for 6 h, and then cooled to room temperature, filtered thru celite, and concentrated in vacuo. The crude product was purified by column chromatography on silica gel using $CH_2Cl_2$ as the eluent to give the dibromide as a solid (0.84 g, 43%). To a solution of the dibromide (0.20 g, 0.687 mmol) and N-(4-methoxybenzyl)methanesulfonamide (0.148 g, 0.687 mmol) in EtOH (3 ml) was added 1N aq. NaOH (0.722 ml, 0.722 mmol), and the resulting mixture was stirred at 80° C. for 90 min. The mixture was partitioned between 0.1N aq. HCL (10 mL) and EtOAc (2×10 mL), and the combined organic layers were dried over $Na_2SO_4$, filtered and concentrated in vacuo. The crude product was purified by column chromatography on silica gel using 2:3 EtOAc:hexanes as eluent to give the title compound as an oil (65 mg, 22%).

Part B. Preparation of N-(4-methoxybenzyl)-N-((6-(4,4,5,5-tetramethyl-1,3,2-dioxaborolan-2-yl)benzo[d]isoxazol-3-yl)methyl)methanesulfonamide A solution of the product from Part A (56 mg, 0.132 mmol), bis(pinacolato)diboron (37 mg, 0.145 mmol), and potassium acetate (39 mg, 0.395 mmol) in 1,4-dioxane (1.3 mL) was degassed by bubbling with $N_2$ gas for 15 min. 1,1'-Bis(diphenylphosphino)ferrocene-palladium(II)dichloride dichloromethane complex (3 mg, 0.004 mmol) was added, and the resulting mixture was stirred at 80° C. for 16 h, filtered and concentrated in vacuo. The crude product was purified by column chromatography on silica gel using 1:2 EtOAc:hexanes as the eluent to give the title compound as a colorless oil (49 mg, 79%).

Part C. Preparation of N-((6-(3-tert-butyl-5-(2,4-dioxo-3,4-dihydropyrimidin-1(2H)-yl)-2-methoxyphenyl)benzo[d]isoxazol-3-yl)methyl)-N-(4-methoxybenzyl)methanesulfonamide A mixture of the product from Example C (31.8 mg, 0.079 mmol), the product from Part B (45 mg, 0.095 mmol) in EtOH (0.5 mL), toluene (0.5 mL) 1M aq. $Na_2CO_3$ (0.095 mL, 0.095 mmol) was degassed by bubbling with $N_2$ gas for 10 min. 1,1'-Bis(diphenylphosphino)ferrocene-palladium(II) dichloride dichloromethane complex (2 mg, 2.4 μmol) was added, and degassing with $N_2$ was continued for 5 min. The reaction mixture was sealed and heated at 100° C. in a microwave reactor for 1 h. The mixture was concentrated in vacuo, and the crude product was purified by column chromatography on silica gel using 1:9 MeOH:$CHCl_3$ as the eluent. The title compound was obtained as a light brown solid (41 mg, 83%).

Part D. Preparation of N-((6-(3-tert-butyl-5-(2,4-dioxo-3,4-dihydropyrimidin-1(2H)-yl)-2-methoxyphenyl)benzo[d]isoxazol-3-yl)methyl)methanesulfonamide A solution of the product from Part C (39 mg, 0.063 mmol) in TFA (0.5 mL) was stirred at 40° C. for 6 h. TFA was removed in vacuo and the crude product was purified by column chromatography on silica gel using 4% MeOH in $CHCl_3$ as the eluent to give the title compound (13 mg, 41%). $^1$H NMR (300 MHz, $CDCl_3$) δ 8.39 (s, 1H) 7.74-7.82 (m, 2H) 7.57 (dd, J=8.27, 1.65 Hz, 1H) 7.36 (d, J=7.72 Hz, 1H) 7.25 (d, J=2.57 Hz, 1H) 7.19 (d, J=2.94 Hz, 1H) 5.82 (dd, J=7.72, 2.21 Hz, 1H) 5.25-5.33 (m, 1H) 4.70 (d, J=6.25 Hz, 2H) 3.29 (s, 3H) 3.12 (s, 3H) 1.45 (s, 9H).

Example 73

Preparation of methyl 2-(5-(3-tert-butyl-5-(2,4-dioxo-3,4-dihydropyrimidin-1(2H)-yl)-2-methoxyphenyl)-2,3-dihydro-1H-inden-1-ylidene)hydrazinecarboxylate (compound IB-L0-2.24)

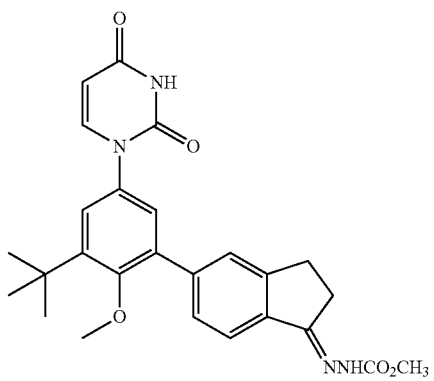

To a solution of the product from Example 6, Part B (0.05 g, 0.124 mmol) in MeOH (1 ml) was added methyl carbazate (17 mg, 0.185 mmol). The mixture was stirred at 60° C. for 16 h, and then concentrated in vacuo. The crude product was purified by column chromatography on silica gel using 5% MeOH in $CH_2Cl_2$ as the eluent to give the title compound (44 mg, 74%). $^1$H NMR (300 MHz, DMSO-$d_6$) δ 11.40 (s, 1H) 10.05 (s, 1H) 7.78 (d, J=8.09 Hz, 1H) 7.69 (d, J=7.72 Hz, 1H) 7.45-7.57 (m, 2H) 7.24-7.33 (m, 2H) 5.64 (d, J=8.09 Hz, 1H) 3.71 (s, 3H) 3.28 (s, 3H) 3.06-3.16 (m, 2H) 2.78-2.88 (m, 2H) 1.40 (s, 9H).

Example 74

Preparation of 1-(3-tert-butyl-4-methoxy-5-(1-oxoisoindolin-5-yl)phenyl)-pyrimidine-2,4(1H,3H)-dione (compound IB-L0-2.30)

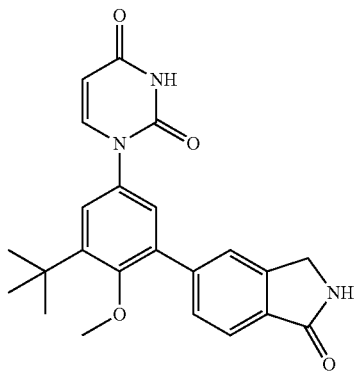 [SMILES: COc1c(-c2ccc3c(c2)CNC3=O)cc(-n2ccc(=O)[nH]c2=O)cc1C(C)(C)C]

Part A. Preparation of 5-bromo-2-(2,4-dimethoxybenzyl)isoindolin-1-one

To a solution of methyl 4-bromo-2-(bromomethyl)benzoate (1.0 g, 3.25 mmol) and (2,4-dimethoxyphenyl)methanamine (0.65 g, 3.90 mmol) in THF (16 mL) was added triethylamine (0.91 mL, 6.5 mmol), and the resulting mixture was stirred at room temperature for 16 h. The resulting solid was filtered off, and the filtrate was concentrated in vacuo. The crude product was purified by column chromatography on silica gel using 1:4 EtOAc:hexanes as the eluent to give the title compound as a colorless solid (0.52 g, 44%).

Part B. Preparation of 2-(2,4-dimethoxybenzyl)-5-(4,4,5,5-tetramethyl-1,3,2-dioxaborolan-2-yl)isoindolin-1-one The product from Part A (100 mg, 0.276 mmol) was subjected to the conditions described for Example 72, Part B to give the title compound as an oil (107 mg, 95%).

Part C. Preparation of 1-(3-tert-butyl-5-(2-(2,4-dimethoxybenzyl)-1-oxoisoindolin-5-yl)-4-methoxyphenyl)pyrimidine-2,4(1H,3H)-dione The product from Part C (44 mg, 0.111 mmol) was subjected to the conditions described for Example 72, Part C to give the title compound (50 mg, 81%).

Part D. Preparation of 1-(3-tert-butyl-4-methoxy-5-(1-oxoisoindolin-5-yl)phenyl)pyrimidine-2,4(1H,3H)-dione A solution of the product from Part C (48 mg, 0.086 mmol) in CH$_2$Cl$_2$ (0.3 ml) and TFA (0.6 ml, 7.79 mmol) was stirred at room temperature for 16 h, and then concentrated in vacuo. The crude product was purified by column chromatography on silica gel using 5% MeOH in CHCl$_3$ as the eluent to give the title compound as a colorless solid (22 mg, 63%). $^1$H NMR (300 MHz, DMSO-d$_6$) δ 11.41 (d, J=1.84 Hz, 1H) 8.61 (s, 1H) 7.72-7.83 (m, 3H) 7.62-7.69 (m, 1H) 7.29-7.36 (m, 2H) 5.65 (dd, J=8.09, 2.21 Hz, 1H) 4.44 (s, 2H) 3.25 (s, 3H) 1.41 (s, 9H).

Example 75

Preparation of N-(2-(6-(3-tert-butyl-5-(2,4-dioxo-3,4-dihydropyrimidin-1(2H)-yl)-2-methoxyphenyl)-1H-inden-3-yl)propan-2-yl)methanesulfonamide (compound IB-L0-2.41)

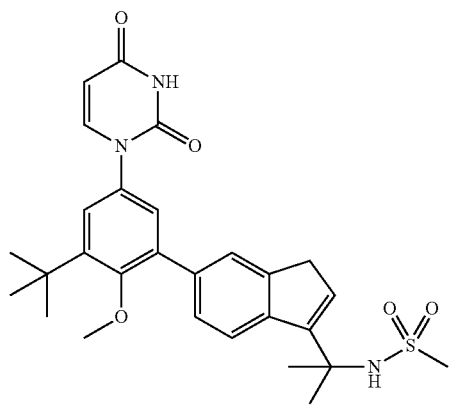 [SMILES: COc1c(-c2ccc3c(c2)CC=C3C(C)(C)NS(C)(=O)=O)cc(-n2ccc(=O)[nH]c2=O)cc1C(C)(C)C]

Part A. Preparation of 6-bromo-1H-indene-3-carbonitrile

To a solution of 5-bromo-2,3-dihydro-1H-inden-1-one (1 g, 4.74 mmol) in anhydrous THF (15 ml) at −10° C. was added 2M lithium diisopropylamide in THF (0.242 ml, 0.483 mmol) dropwise. The resulting mixture was stirred at −10° C. for 15 min before diethylcyanophosphonate (0.791 ml, 5.21 mmol) was added dropwise. Following the addition, the mixture was allowed to warm to room temperature, and was stirred at room temperature for 3 h. The mixture was cooled to −78° C. and borontrifluoride diethyl etherate (1.196 ml, 9.52 mmol) was added dropwise. Following the addition, the mixture was stirred at −78° C. for 1 h and was then allowed to warm to room temperature and was stirred at room temperature for 16 h. The mixture was concentrated in vacuo, and the residue was partitioned between EtOAc (50 mL) and H$_2$O (2×50 mL). The organic layer was dried over Na$_2$SO$_4$, filtered and concentrated in vacuo, and the crude product was purified by column chromatography on silica gel using 9:1 EtOAc:hexanes as the eluent. The title compound was obtained as an tan solid (0.72 g, 69%).

Part B. Preparation of N-(2-(6-bromo-1H-inden-3-yl)propan-2-yl)methanesulfonamide Anhydrous cerium(III) chloride (0.224 g, 0.909 mmol) was flame dried under vacuum and placed under dry N$_2$. Anhydrous THF (1.5 ml) was added, and the resulting mixture was stirred under N$_2$ at 45° C. for 48 h. The mixture was cooled to room temperature, and the product from Part A (0.1 g, 0.454 mmol) was added. The resulting mixture was cooled to −78° C., and a 1.5M solution of methyl-lithium lithium bromide complex (0.757 ml, 1.136 mmol) in Et$_2$O was added dropwise over 15 min. Following the addition, the mixture was allowed to warm to −20° C. and was stirred for 24 h. Concentrated aq. NH$_4$OH (0.3 mL) was added dropwise, and the mixture was allowed to warm to room temperature, was stirred for 30 min, and was then filtered and washed with THF (2×5 mL). The filtrate was concentrated in vacuo, and the crude product was purified by column chromatography on silica gel using 5% MeOH in CH$_2$Cl$_2$ as the eluent to give a solid (23 mg, 20%). To a solution of this solid (23 mg, 0.091 mmol) in CH$_2$Cl$_2$ (1 mL) was added methanesulfonyl chloride (0.011 mL, 0.137 mmol). The mixture was cooled to 0° C. and diisopropylethylamine (0.024 ml, 0.137 mmol) was added dropwise. The resulting mixture was stirred at room temperature for 90 min, and was then partitioned between 0.1 N aq. HCl (2 mL) and CH$_2$Cl$_2$ (3×2 mL). The combined organic layers were dried over Na$_2$SO$_4$, filtered and concentrated in vacuo, and the crude product was purified by column chromatography on silica gel to give the title compound (17 mg, 56%).

Part C. Preparation of N-(2-(6-(4,4,5,5-tetramethyl-1,3,2-dioxaborolan-2-yl)-1H-inden-3-yl)propan-2-yl)methanesulfonamide The product from Part C (50 mg, 0.151 mmol) was subjected to the conditions described for Example 72, Part B to give the title compound as a colorless solid (37 mg, 65%).

Part D. Preparation of N-(2-(6-(3-tert-butyl-5-(2,4-dioxo-3,4-dihydropyrimidin-1(2H)-yl)-2-methoxyphenyl)-1H-inden-3-yl)propan-2-yl)methanesulfonamide The product from Part C (35 mg, 0.093 mmol) was subjected to the conditions described for Example 72, Part C to give the title compound as a colorless solid (41 mg, 84%). $^1$H NMR (300 MHz, DMSO-d$_6$) δ 11.40 (s, 1H) 7.94 (d, J=8.09 Hz, 1H) 7.78 (d, J=8.09 Hz, 1H) 7.65 (d, J=1.50 Hz, 1H) 7.56

(s, 1H) 7.48 (dd, J=8.09, 1.47 Hz, 1H) 7.27 (s, 2H) 6.48 (s, 1H) 5.63 (d, J=8.09 Hz, 1H) 3.43 (s, 2H) 3.25 (s, 3H) 2.63 (s, 3H) 1.68 (s, 6H) 1.41 (s, 9H).

Example 76

Preparation of N-((6-(3-tert-butyl-5-(2,4-dioxo-3,4-dihydropyrimidin-1(2H)-yl)-2-methoxyphenyl)benzo[b]thiophen-3-yl)methyl)methanesulfonamide (compound IB-L0-2.11)

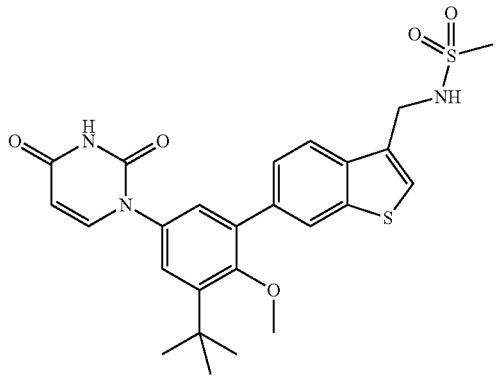 [SMILES: COc1c(-c2ccc3c(CNS(C)(=O)=O)csc3c2)cc(-n2ccc(=O)[nH]c2=O)cc1C(C)(C)C]

Part A. Preparation of ethyl 6-bromobenzo[b]thiophene-2-carboxylate

A solution of ethyl thioglycolate (0.65 g, 5.42 mmol), 4-bromo-2-fluorobenzaldehyde (1.0 g, 4.93 mmol) and triethylamine (1.25 mL, 12.3 mmol) in DMSO (5 mL) was heated at 75° C. for 2 h. The mixture was partitioned between $H_2O$ (50 mL) and $CH_2Cl_2$ (2×50 mL), and the combined organic layers were dried over $Na_2SO_4$. The drying agent was filtered off, and the solvent was removed in vacuo to give the title compound as an oil (1.29 g, 92%).

Part B. Preparation of 6-bromobenzo[b]thiophene-2-carboxylic acid

To a solution of the product from Part A (1.21 g, 4.24 mmol) in THF (10 mL) was added a solution of LiOH (0.305 g, 12.73 mmol) in $H_2O$ (4 mL) and the resulting mixture was stirred at 40° C. for 2 h. The mixture was partitioned between $H_2O$ (50 mL) and $CH_2Cl_2$ (50 mL). The aqueous layer was adjusted to pH=2 using 1N HCl, and extracted with $CH_2Cl_2$ (2×50 mL). The combined organic layers were dried over $Na_2SO_4$, filtered and concentrated in vacuo to give the title compound as an oil (1.04 g, 95%).

Part C. Preparation of 6-bromobenzo[b]thiophene

The product from Part B (0.70 g, 2.73 mmol) and DBU (1.35 mL, 8.94 mmol) were combined in DMA (6 mL) in a sealed tube and heated at 200° C. in a microwave reactor for 70 min. The resulting dark solution was diluted with 1 M HCl (20 mL) and extracted with $CH_2Cl_2$ (2×20 mL). The combined organic layers were dried over $Na_2SO_4$, filtered and concentrated in vacuo, and the crude product was purified by column chromatography on silica gel using $CH_2Cl_2$ as the eluent to give the title compound as an oil (0.484 g 83%).

Part D. Preparation of 6-bromo-3-(chloromethyl)benzo[b]thiophene

To a solution of the product from Part C (0.484 g, 2.27 mmol) in benzene (0.20 mL) was added 37% aq. formaldehyde solution (1 mL) and concentrated HCl (1 mL). The resulting mixture was heated at 70° C. for 1 h. while HCl gas was bubbled through the mixture. The mixture was partitioned between $H_2O$ (20 mL) and $CH_2Cl_2$ (2×20 mL), and the combined organic layers were dried over $Na_2SO_4$, filtered and concentrated in vacuo. The crude product was purified by column chromatography on silica gel using $CH_2Cl_2$ to give the title compound as a waxy solid (0.49 g, 82%).

Part E. Preparation of N-((6-bromobenzo[b]thiophen-3-yl)methyl)-N-(2,4-dimethoxybenzyl)methanesulfonamide To a solution of the product form Part D (275 mg, 1.05 mmol) and N-(2,4-dimethoxybenzyl)-methanesulfonamide (284 mg, 1.15 mmol) in DMA (6 mL) was added $K_2CO_3$ (160 mg, 1.15 mmol), and the mixture was stirred at room temperature for 3 h. The mixture was partitioned between $H_2O$ (20 mL) and $Et_2O$ (2×20 mL), and the combined organic layers were dried over $Na_2SO_4$, filtered and concentrated in vacuo. The crude product was purified by column chromatography on silica gel using 2% EtOAc in $CH_2Cl_2$ as the eluent to give the title compound as a waxy solid (316 mg, 64%).

Part F. Preparation of N-(2,4-dimethoxybenzyl)-N-((6-(4,4,5,5-tetramethyl-1,3,2-dioxaborolan-2-yl)benzo[b]thiophen-3-yl)methyl)methanesulfonamide The product from Part E (300 mg, 0.64 mmol) was subjected to the conditions described for Example 72, Part B to give the title compound as a waxy solid (248 mg, 75%).

Part G. Preparation of N-((6-(3-tert-butyl-5-(2,4-dioxo-3,4-dihydropyrimidin-1(2H)-yl)-2-methoxyphenyl)benzo[b]thiophen-3-yl)methyl)-N-(2,4-dimethoxybenzyl)methanesulfonamide The product from Part F (214 mg, 0.414 mmol) was subjected to the conditions described for Example 72, Part C to give the title compound as a light yellow solid (238 mg, 87%).

Part H. Preparation of N-((6-(3-tert-butyl-5-(2,4-dioxo-3,4-dihydropyrimidin-1(2H)-yl)-2-methoxyphenyl)benzo[b]thiophen-3-yl)methyl)methanesulfonamide To a solution of the product from Part G (230 mg, 0.34 mmol) in $CH_2Cl_2$ (4 mL) was added trifluoroacetic acid (0.5 mL), and the mixture was stirred at room temperature for 30 min. The solution was diluted with $CH_2Cl_2$ (10 mL) and extracted with saturated aq. $NaHCO_3$ (2×10 mL). The organic layer was dried over $Na_2SO_4$, filtered and concentrated in vacuo, and the crude product was purified by column chromatography on silica gel eluting with 3% MeOH in $CH_2Cl_2$ to give the title compound as an off-white solid (149 mg, 84%). $^1$H NMR (300 MHz, DMSO-$d_6$) δ 11.41 (s, 1H) 8.16 (d, J=1.10 Hz, 1H) 8.02 (d, J=8.46 Hz, 1H) 7.79 (d, J=7.72 Hz, 1H) 7.71 (s, 1H) 7.60-7.66 (m, 2H) 7.29-7.38 (m, 2H) 5.65 (d, J=7.72 Hz, 1H) 4.44 (d, J=5.88 Hz, 2H) 3.24 (s, 3H) 2.95 (s, 3H) 1.42 (s, 9H).

Example 77

Preparation of N-(2-(3-tert-butyl-5-(2,4-dioxo-3,4-dihydropyrimidin-1(2H)-yl)-2-methoxyphenyl)-1,2,3,4-tetrahydroisoquinolin-6-yl)methanesulfonamide (compound IB-L0-2.19)

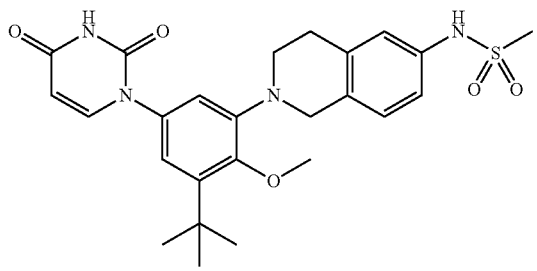 [SMILES: COc1c(N2CCc3cc(NS(C)(=O)=O)ccc3C2)cc(-n2ccc(=O)[nH]c2=O)cc1C(C)(C)C]

Part A. Preparation of 1-(3-amino-5-tert-butyl-4-methoxyphenyl)pyrimidine-2,4(1H,3H)-dione To a solution of the product from Example 7, Part F (170 mg, 0.534 mmol) and triethylamine (223 uL, 1.6 mmol) in THF (5 mL) was added diphenylphosphorylazide (173 uL, 0.80 mmol). The resulting mixture was stirred at room temperature for 1 h, and was then stirred at 45° C. for 1 h. Water (280 uL) was added, and the resulting mixture was stirred at 50° C. for 1 h, and then stirred at room temperature for 16 h. The solution was diluted with $H_2O$ (10 mL), and the resulting solid was filtered off. The solid was suspended in 1M aq. HCl and filtered to give the amine product as the HCl salt. This salt was suspended in aq. $NaHCO_3$ (20 mL) and extracted with EtOAc (2×20 mL). The combined organic layers were dried over $Na_2SO_4$, filtered and concentrated in vacuo to give the title compound as a colorless solid (55 mg, 36%).

Part B. Preparation of 1-(3-tert-butyl-4-methoxy-5-(6-nitro-3,4-dihydroisoquinolin-2(1H)-yl)phenyl)pyrimidine-2,4(1H,3H)-dione A solution of the product from Part A (100 mg, 0.28 mmol) and 2-(2-(methylsulfonyloxy)-ethyl)-4-nitrobenzyl methanesulfonate (196 mg, 0.68 mmol) were in anhydrous DMA (4 mL) was stirred at 80° C. for 18 h. The cooled mixture was partitioned between $H_2O$ (20 mL) and EtOAc (2×20 mL), and the combined organic layers were dried over $Na_2SO_4$, filtered and concentrated in vacuo. The residue was suspended in $CH_2Cl_2$ and filtered to remove unreacted aniline starting material. The filtrate was concentrated in vacuo, and the crude product was purified by column chromatography on silica gel eluting with 1% MeOH in $CH_2Cl_2$ to give the title compound as a light yellow solid (39.3 mg, 31%).

Part C. Preparation of N-(2-(3-tert-butyl-5-(2,4-dioxo-3,4-dihydropyrimidin-1(2H)-yl)-2-methoxyphenyl)-1,2,3,4-tetrahydroisoquinolin-6-yl)methanesulfonamide To a solution of the product from Part B (35 mg, 0.078 mmol) in THF (0.5 mL), MeOH (0.5 mL) and $H_2O$ (0.25 mL) was added Fe powder (17.4 mg, 0.41 mmol) and $NH_4Cl$ (6.2 mg, 0.12 mmol, and the resulting mixture was stirred at 70° C. for 1 h. The hot mixture was filtered through celite and rinsed with THF and MeOH. The filtrate was concentrated and dried in vacuo to give a solid. To a solution of the solid (32 mg, 0.076 mmol) and pyridine (26 uL, 0.32 mmol) in $CH_2Cl_2$ (1.5 mL) was added methanesulfonyl chloride (7.7 uL, 0.099 mmol). The mixture was stirred at room temperature for 1 h then concentrated in vacuo. The crude product was purified by column chromatography on silica gel eluting with 5% MeOH in $CH_2Cl_2$ to give the title compound as a light yellow solid (7 mg, 19%). $^1H$ NMR (300 MHz, DMSO-$d_6$) δ 7.71 (d, J=8.09 Hz, 1H) 7.14-7.21 (m, 1H) 7.05-7.12 (m, 3H) 6.98 (d, J=2.57 Hz, 1H) 5.65 (d, J=7.72 Hz, 1H) 4.18 (s, 2H) 3.86 (s, 3H) 3.03 (t, J=4.23 Hz, 2H) 2.99 (s, 3H) 1.38 (s, 9H).

Example 78

Preparation of N-(2-(3-tert-butyl-5-(2,4-dioxo-3,4-dihydropyrimidin-1(2H)-yl)-2-methoxyphenyl)isoindolin-5-yl)methanesulfonamide (compound IB-L0-2.79)

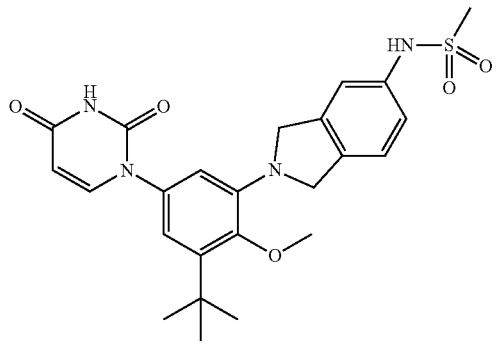 [SMILES: COc1c(N2Cc3ccc(NS(C)(=O)=O)cc3C2)cc(-n2ccc(=O)[nH]c2=O)cc1C(C)(C)C]

Part A. Preparation of (4-nitro-1,2-phenylene)bis(methylene)dimethanesulfonate To a solution of 4-nitrophthalic acid (500 mg, 2.37 mmol) in THF (24 mL) at room temperature was added a 1M solution of $BH_3$.THF complex (9.95 mL, 9.95 mmol) dropwise. This solution was stirred at 65° C. for 1 h, and then allowed to cool to room temperature. To the mixture was added MeOH (1 mL), and the mixture was stirred for 30 min and concentrated in vacuo. The residue was partitioned between 1M aq. HCl (20 mL) and EtOAc (2×20 mL), and the combined organic layers were dried over $Na_2SO_4$, filtered and concentrated in vacuo. The crude product was purified by column chromatography on silica gel eluting with 3% MeOH in $CH_2Cl_2$ to give an oil (253 mg, 58%). To a solution of the oil (250 mg, 2.37 mmol) and triethylamine (438 uL, 3.14 mmol) in anhydrous $CH_2Cl_2$ (30 mL) at 0° C. was added methanesulfonyl chloride (234 uL, 3.0 mmol) dropwise. The solution was stirred at room temperature for 18 h, and was partitioned between 1M aq. HCl (20 mL) and $CH_2Cl_2$ (2×20 mL). The combined organic layers were dried over $Na_2SO_4$, filtered and concentrated in vacuo. The crude product was purified by column chromatography on silica gel eluting with $CH_2Cl_2$ to give the title compound (150 mg, 32%).

Part B. Preparation of 1-(3-tert-butyl-4-methoxy-5-(5-nitroisoindolin-2-yl)phenyl)pyrimidine-2,4(1H,3H)-dione To a solution of the product of Part A (110 mg, 0.324 mmol) and the product of Example 77, Part A (113 mg, 0.389 mmol)

in anhydrous 1,4-dioxane (4 mL) was added sodium bicarbonate (60 mg, 0.71 mmol) and diisopropylethylamine (142 uL, 0.81 mmol) and the resulting mixture was stirred at 95° C. for 16 h. The mixture was partitioned between 0.5M aq. HCl (10 mL) and $CH_2Cl_2$ (2×10 mL), and the combined organic layers were dried over $Na_2SO_4$, filtered and concentrated in vacuo. The crude product was purified by column chromatography on silica gel eluting with 1% MeOH in $CH_2Cl_2$ to give the title compound as a light yellow solid (110 mg, 78%).

Part C. Preparation of N-(2-(3-tert-butyl-5-(2,4-dioxo-3,4-dihydropyrimidin-1(2H)-yl)-2-methoxyphenyl)isoindolin-5-yl)methanesulfonamide The product from Part B (100 mg, 0.25 mmol) was subjected to the conditions described for Example 77, Part C to give the title compound as an off-white solid (53 mg, 45%). $^1H$ NMR (300 MHz, DMSO-$d_6$) δ 11.37 (s, 1H) 9.70 (s, 1H) 7.71 (d, J=7.72 Hz, 1H) 7.34 (d, J=8.09 Hz, 1H) 7.23 (d, J=1.84 Hz, 1H) 7.13 (dd, J=8.09, 1.84 Hz, 1H) 6.98 (d, J=2.57 Hz, 1H) 6.81 (d, J=2.21 Hz, 1H) 5.62 (d, J=7.72 Hz, 1H) 4.52 (s, 2H) 4.50 (s, 2H) 3.63 (s, 3H) 2.98 (s, 3H) 1.38 (s, 9H).

Example 79

Preparation of N-((6-(3-tert-butyl-5-(2,4-dioxo-3,4-dihydropyrimidin-1(2H)-yl)-2-methoxyphenyl)-1H-inden-3-yl)methyl)methanesulfonamide (compound IB-L0-2.13)

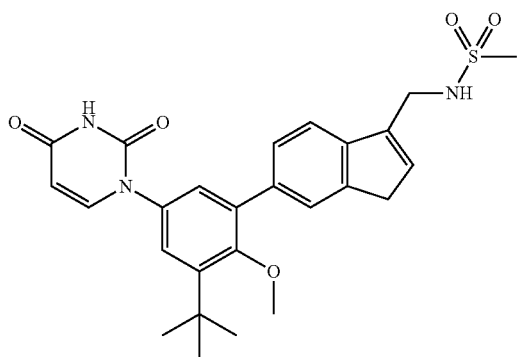 [SMILES: COc1c(-c2ccc3c(c2)CC=C3CNS(C)(=O)=O)cc(-n2ccc(=O)[nH]c2=O)cc1C(C)(C)C]

Part A. Preparation of 5-bromo-1-(trimethylsilyloxy)-2,3-dihydro-1H-indene-1-carbonitrile To a solution of 5-bromo-2,3-dihydro-1H-inden-1-one (10.0 g, 47.4 mmol) and N-methyl-morpholine N-oxide (1.67 g, 14.2 μmol) in $CH_2Cl_2$ (50 ml) was added trimethylsilylcyanide (7.05 g, 71.1 mmol), and the resultant solution was stirred at room temperature for 72 h, and then concentrated in vacuo. The crude product was purified by column chromatography on silica gel using 5% EtOAc in hexanes as the eluent to give the title compound as a colorless liquid (12.65 g, 86%).

Part B. Preparation of 1-(aminomethyl)-5-bromo-2,3-dihydro-1H-inden-1-ol

To a solution of the product from Part A (18.44 g, 59.4 mmol) in anhydrous $Et_2O$ (250 mL) under $N_2$ gas at 0° C. was added a 1M solution of $LiAlH_4$ in $Et_2O$ (62.4 mL, 62.4 mmol) dropwise over 1 h. Following the addition, the mixture was allowed to warm to rt and was stirred at room temperature for 2 h. The mixture was cooled in an ice bath while $H_2O$ (4.3 mL) was added dropwise, followed by the addition of 15% aq. $NH_4OH$ (4.3 mL), and then $H_2O$ (13 mL). The mixture was stirred at room temperature for 15 min, and then filtered through celite and rinsed with EtOAc. The filtrate was concentrated in vacuo, and the residue was suspended in $Et_2O$ (40 mL) to give a precipitate that was filtered and dried to give the title compound as a colorless solid (10.0 g, 70%).

Part C. Preparation of (6-bromo-1H-inden-3-yl)methanamine hydrochloride salt

To a solution of the product from Part B (10.0 g, 41.3 mmol) in MeOH (100 mL) was added 6N aq. HCl (125 mL) and the mixture was stirred at 70° C. for 3 h and then allowed to cool to room temperature. MeOH was removed in vacuo to give a precipitate that was collected by filtration, washed with $H_2O$, and dried in vacuo to provide the title compound as a colorless solid (9.89 g, 92%).

Part D. Preparation of N-((6-bromo-1H-inden-3-yl)methyl)methanesulfonamide

To a suspension of the product from Part C (6.46 g, 24.8 mmol) in anhydrous $CH_2Cl_2$ (260 mL) was added methanesulfonyl chloride (3.86 mL, 49.6 mmol) and diisopropylethylamine (13.0 mL, 74.4 mmol), and the resulting mixture was stirred at room temperature for 10 h. The solution was washed with 1N aq. HCl (2×300 mL), and the organic layer was dried over $Na_2SO_4$, filtered and concentrated in vacuo. The residue was suspended in $Et_2O$ (100 mL) to give a precipitate that was collected by filtration and dried to give the title compound as a colorless solid (6.25 g, 83%).

Part E. Preparation of N-((6-(4,4,5,5-tetramethyl-1,3,2-dioxaborolan-2-yl)-1H-inden-3-yl)methyl)methanesulfonamide A solution of the product from Part D (2.0 g, 6.62 mmol), bis(pinacolato)diboron (1.85 g, 7.28 mmol), potassium acetate (1.95 g, 19.86 mmol) and 1,1'-bis(diphenylphosphino)ferrocene-palladium(II)dichloride dichloromethane complex (0.27 g, 0.33 μmol) in anhydrous 1,4-dioxane (80 mL) under $N_2$ was stirred at 95° C. for 8 h. The cooled mixture was filtered through celite, washed with EtOAc (2×20 mL) and then concentrated in vacuo. The crude product was purified by column chromatography on silica gel using 1:2 EtOAc:hexanes as the eluent to give the title compound as a colorless oil (2.02 g, 87%).

Part F. Preparation of N-((6-(3-tert-butyl-5-(2,4-dioxo-3,4-dihydropyrimidin-1(2H)-yl)-2-methoxyphenyl)-1H-inden-3-yl)methyl)methanesulfonamide A mixture of the product from Part E (3.14 g, 8.99 mmol), the product from Example C (3.78 g, 9.44 mmol), tripotassium phosphate (3.82, 17.98 mmol), 1,3,5,7-tetramethyl-2,4,8-trioxa-6-phospha-6-phenyl-adamantane (Cytec [97739-46-3]) (105 mg, 0.36 mmol), and tris(dibenzylidineacetone)-dipalladium(0) (165 mg, 0.18 mmol) was placed under $N_2$ gas. To the mixture was added, via canula, a mixture of THF (45 mL) and $H_2O$ (15 mL) that had been degassed by bubbling Ar gas for 10 min. The resulting mixture was further degassed by bubbling with Ar for an additional 15 min. The mixture was stirred at 50° C. for 1.5 h while Ar was continuously bubbled through the solution. Additional tris(dibenzylidineacetone)dipalladium(0) (55 mg, 0.6 mmol) in THF (2 mL) was added, and the mixture was stirred at 50° C. for 1 h. The mixture was allowed to cool to rt, and was partitioned between CH$_2$Cl$_2$ (300 ml) and 1N aq. HCl (150 mL). To the orange organic layer was added 3-mercaptopropyl-functionalized silica gel (10 g, Aldrich) and mgSO$_4$, and the mixture was stirred at room temperature for 16 h, filtered and concentrated in vacuo. The crude product was purified by column chromatography on silica gel using 3:1 EtOAc:hexanes as the eluent to give the title compound as a colorless solid (2.7 g, 61%). $^1$H NMR (300 MHz, DMSO-d$_6$) δ 11.40 (s, 1H), 7.78 (d, J=7.4 Hz, 1H), 7.66 (s, 1H), 7.60 (d, J=7.7 Hz, 1H), 7.50 (m, 2H), 7.25 (m, 2H), 6.56 (m, 1H), 5.64 (dd, J=2.2, 7.7 Hz, 1H), 4.18 (d, J=5.1 Hz, 2H), 3.46 (s, 2H), 3.25 (s, 3H), 2.96 (s, 3H), 1.41 (s, 9H).

Example 80

Preparation of N'-(5-(3-tert-butyl-5-(2,4-dioxo-3,4-dihydropyrimidin-1(2H)-yl)-2-methoxyphenyl)-2,3-dihydro-1H-inden-1-yl)methanesulfonohydrazide (compound IB-L0-2.31)

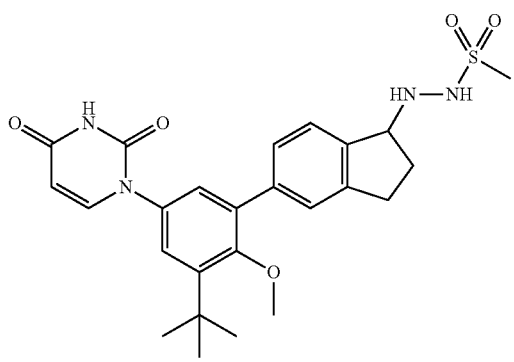 [SMILES: COc1c(-c2ccc3c(c2)CCC3NNS(C)(=O)=O)cc(-n2ccc(=O)[nH]c2=O)cc1C(C)(C)C]

To a solution of the product from Example 6, Part C (100 mg, 0.201 mmol) was in THF (2 mL) and MeOH (2 mL) was added 2 drops of 10% HCl in MeOH, followed by sodium cyanoborohydride (19 mg, 0.302 mmol). The mixture was adjusted to pH 4 with the addition of 10% HCl in MeOH, and was then stirred at room temperature for 1 h. The resulting mixture was partitioned between saturated aq. sodium bicarbonate (5 mL) and CH$_2$Cl$_2$ (20 mL), and the organic layer was dried over Na$_2$SO$_4$, filtered and concentrated. The crude product was purified by column chromatography on silica gel using 3% MeOH in CH$_2$Cl$_2$ as the eluent to provide the title compound as a colorless solid (58 mg, 58%). $^1$H NMR (300 MHz, DMSO-d6) δ 11.39(s, 1H), 8.18 (d, J=3.7 Hz, 1H), 7.77 (d, J=7.7 Hz, 1H), 7.51 (d, J=8.1 Hz, 1H), 7.38 (m, 2H), 7.27 (d, J=2.6 Hz, 1H), 7.21 (d, J=2.9 Hz, 1H), 5.63 (d, J=7.7 Hz, 1H), 5.25 (m, 1H), 4.39 (m, 1H), 3.27 (s, 3H), 2.98 (m, 1H), 2.83 (s, 3H), 2.78 (m, 1H), 2.22 (m, 1H), 2.07 (m, 1H), 1.40 (s, 9H).

Example 81

Preparation of 1-(3-tert-butyl-5-(1-hydroxy-2,3-dihydro-1H-inden-5-yl)-4-methoxyphenyl)pyrimidine-2,4(1H,3H)-dione (compound IB-L0-2.36)

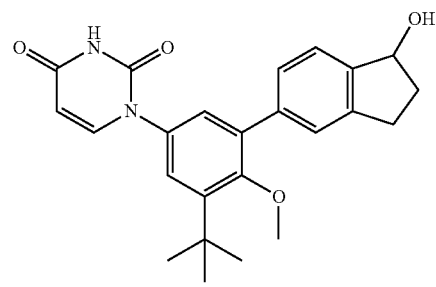 [SMILES: COc1c(-c2ccc3c(c2)CCC3O)cc(-n2ccc(=O)[nH]c2=O)cc1C(C)(C)C]

To a solution of the product from Example 6, Part B (150 mg, 0.371 mmol) in MeOH (3 mL) and CH$_2$Cl$_2$ (3 mL) was added sodium borohydride (28 mg, 0.742 mmol), and the mixture was stirred at room temperature for 1 h. The mixture was partitioned between 1N aq. HCl (10 mL) and CH$_2$Cl$_2$ (20 mL), and the organic layer was dried over Na$_2$SO$_4$, filtered and concentrated in vacuo. The crude product was purified by column chromatography on silica gel using 5% MeOH in CH$_2$Cl$_2$ as the eluent to provide the title compound as a colorless solid (90 mg, 60%). $^1$H NMR (300 MHz, DMSO-d6): δ 11.39(s, 1H), 7.44 (d, J=4.0 Hz, 1H), 7.40 (m, 2H), 7.21 (d, J=2.6 Hz, 1H), 7.26 (d, J=2.6 Hz, 1H), 5.63 (d, J=8.1 Hz, 1H), 5.29 (d, J=5.9 Hz, 1H), 5.09 (m, 1H), 3.26 (s, 3H), 2.97 (m, 1H), 2.79 (m, 1H), 2.38 (m, 1H), 1.83 (m, 1H), 1.40 (s, 9H).

Example 82

Preparation of 1-(3-tert-butyl-5-(2-(2,5-dimethyl-1H-pyrrol-1-yl)benzo[d]thiazol-6-yl)-4-methoxyphenyl)pyrimidine-2,4(1H,3H)-dione (compound IB-L0-2.47)

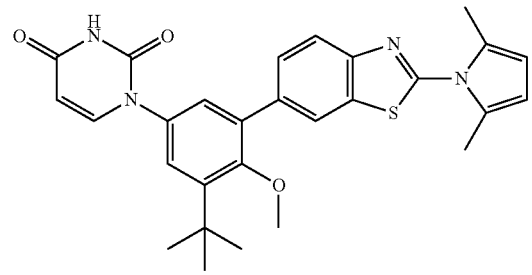 [SMILES: COc1c(-c2ccc3nc(-n4c(C)ccc4C)sc3c2)cc(-n2ccc(=O)[nH]c2=O)cc1C(C)(C)C]

Part A. Preparation of 6-bromo-2-(2,5-dimethyl-1H-pyrrol-1-yl)benzo[d]thiazole

A solution 6-bromobenzo[d]thiazol-2-amine (5.75 g, 25.1 mmol), hexane-2,5-dione (2.95 mL, 25.1 mmol), and PPTS (0.95 g, 3.76 mmol) in benzene (100 ml) was refluxed for 16 h while water was removed with a Dean-Stark trap. The cooled mixture was poured into EtOAc (100 mL) and extracted with saturated aq. NaHCO$_3$ (2×100 mL) and brine.

The organic layer was dried over Na₂SO₄, filtered and concentrated in vacuo. The crude product was purified by column chromatography on silica gel using 9:1 EtOAc:hexanes as the eluent to give the title compound as an orange oil (6.46 g, 84%).

Part B. Preparation of 2-(2,5-dimethyl-1H-pyrrol-1-yl)-6-(4,4,5,5-tetramethyl-1,3,2-dioxaborolan-2-yl)benzo[d]thiazole A mixture of the product from Part A (3.24 g, 10.54 mmol), bis(pinacolato)diboron (4.01 g, 15.81 mmol), bis(di-tert-butyl(hydroxy)phosphino)palladium(II) dichloride (0.264 g, 0.527 mmol), and potassium acetate (3.10 g, 31.6 mmol) in anhydrous toluene (25 mL) was degassed by bubbling with N₂ gas for 15 min, and then heated at reflux under N₂ for 72 h. The cooled mixture was filtered through celite and washed with EtOAc, and the filtrate was concentrated in vacuo. The crude product was purified by column chromatography on silica gel using 9:1 EtOAc:hexanes as the eluent to give the title compound (2.77 g, 74%).

Part C. Preparation of 1-(3-tert-butyl-5-(2-(2,5-dimethyl-1H-pyrrol-1-yl)benzo[d]thiazol-6-yl)-4-methoxyphenyl)pyrimidine-2,4(1H,3H)-dione The product from Part B (405 mg, 1.14 mmol) was subjected to the conditions described for Example 72, Part C to give the title compound (430 mg, 68%). ¹H NMR (300 MHz, DMSO-d₆) δ 11.43 (d, J=2.21 Hz, 1H) 8.32 (d, J=1.47 Hz, 1H) 8.12 (d, J=8.46 Hz, 1H) 7.80 (d, J=7.72 Hz, 1H) 7.76 (dd, J=8.46, 1.84 Hz, 1H) 7.35 (q, J=2.57 Hz, 2H) 5.97 (s, 2H) 5.66 (dd, J=7.72, 2.21 Hz, 1H) 3.30 (s, 3H) 2.30 (s, 6H) 1.43 (s, 9H).

Example 83

Preparation of 1-(3-(2-aminobenzo[d]thiazol-6-yl)-5-tert-butyl-4-methoxy-phenyl)pyrimidine-2,4(1H,3H)-dione (compound IB-L0-2.27)

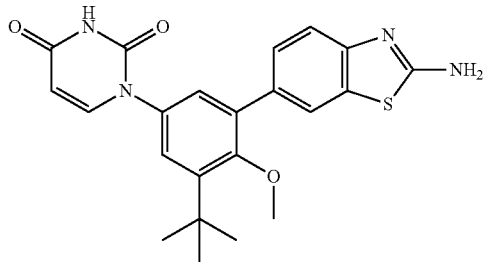 [SMILES: COc1c(-c2ccc3nc(N)sc3c2)cc(-n2ccc(=O)[nH]c2=O)cc1C(C)(C)C]

To a solution of the product from Example 82 (4.0 g, 8.0 mmol) in trifluoroacetic acid (50 mL) was added a few drops of H₂O, and the resulting mixture was stirred at 80° C. for 2.5 h, and then concentrated in vacuo. A solution of the residue in MeOH was neutralized using conc. NH₄OH, concentrated in vacuo, and the crude product was purified by column chromatography on silica gel using 9:1 CH₂Cl₂:MeOH as the eluent to give the title compound (3.3 g, 98%). ¹H NMR (300 MHz, DMSO-d₆) δ 11.40 (s, 1H) 7.81 (s, 1H) 7.77 (d, J=8.09 Hz, 1H) 7.57 (s, 1H) 7.40 (s, 1H) 7.33-7.38 (m, 1H) 7.25 (s, 1H) 5.60-5.69 (m, 1H) 3.26 (s, 3H) 1.40 (s, 9H).

Example 84

Preparation of N-(6-(3-tert-butyl-5-(2,4-dioxo-3,4-dihydropyrimidin-1(2H)-yl)-2-methoxyphenyl)benzo[d]thiazol-2-yl)methanesulfonamide (compound IB-L0-2.28)

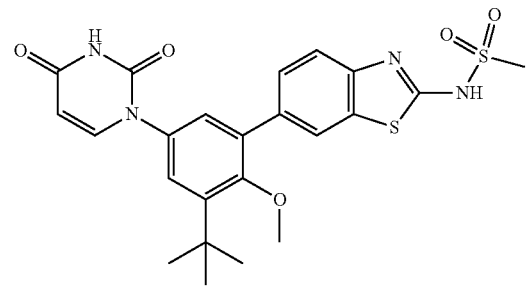 [SMILES: COc1c(-c2ccc3nc(NS(C)(=O)=O)sc3c2)cc(-n2ccc(=O)[nH]c2=O)cc1C(C)(C)C]

To a solution of the product from Example 83 (0.35 g, 0.83 mmol) in anhydrous CH₂Cl₂ (50 mL) was added methanesulfonyl chloride (194 μL, 2.49 mmol) and pyridine (1.34 mL, 16.6 mmol). The resulting mixture was stirred at room temperature for 16 h and concentrated in vacuo. The crude product was purified by C-18 reverse-phase HPLC using an acetonitrile:H₂O (0.1% TFA) gradient to give the title compound (19 mg, 4%). ¹H NMR (300 MHz, DMSO-d₆) δ 13.09 (s, 1H) 11.41 (d, J=1.84 Hz, 1H) 7.96 (d, J=1.47 Hz, 1H) 7.77 (d, J=8.09 Hz, 1H) 7.57 (dd, 1H) 7.42 (d, J=8.09 Hz, 1H) 7.25-7.32 (m, 2H) 5.64 (dd, J=8.09, 2.21 Hz, 1H) 3.25 (s, 3H) 3.02 (s, 3H) 1.40 (s, 9H).

Example 85

Preparation of 1-(3-(benzo[d]thiazol-6-yl)-5-tert-butyl-4-methoxyphenyl)pyrimidine-2,4(1H,3H)-dione (compound IB-L0-2.33)

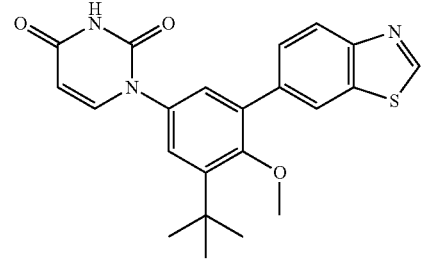 [SMILES: COc1c(-c2ccc3ncsc3c2)cc(-n2ccc(=O)[nH]c2=O)cc1C(C)(C)C]

To a solution of the product from Example 83 (30 mg, 0.071 mmol) in anhydrous 1,4-dioxane (3 mL) under N₂ was added isoamyl nitrite (19 μL, 0.142 mmol). The resulting mixture was stirred at reflux for 1 h, and concentrated in vacuo. The crude product was purified by C-18 reverse-phase HPLC using an acetonitrile:H₂O (0.1% TFA) gradient to give the title compound (14 mg, 48%). ¹H NMR (300 MHz, DMSO-d₆) δ 11.42 (d, J=1.84 Hz, 1H) 9.44 (s, 1H) 8.34 (d, J=1.47 Hz, 1H) 8.19 (d, J=8.46 Hz, 1H) 7.79 (d, J=7.72 Hz, 1H) 7.73 (dd, J=8.46, 1.84 Hz, 1H) 7.32-7.37 (m, 2H) 5.65 (dd, J=7.91, 2.39 Hz, 1H) 3.24 (s, 3H) 1.42 (s, 9H).

Example 86

Preparation of N-(6-(3-tert-butyl-5-(2,4-dioxo-3,4-dihydropyrimidin-1(2H)-yl)-2-methoxyphenyl)benzo[d]thiazol-2-yl)acetamide (compound IB-L0-2.49)

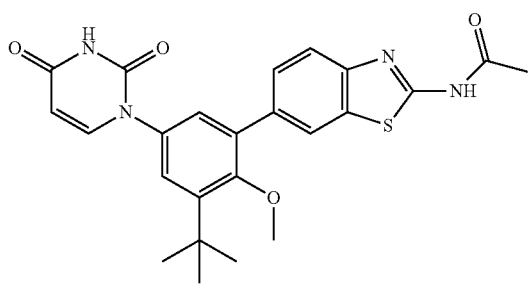 [SMILES: COc1c(-c2ccc3nc(NC(C)=O)sc3c2)cc(-n2ccc(=O)[nH]c2=O)cc1C(C)(C)C]

A mixture of the product from Example 83 (30 mg, 0.071 mmol) and acetic anhydride (3 mL) was stirred at 100° C. for 2 h, and then allowed to cool to room temperature. The resulting solid was collected by filtration, washed with H$_2$O, and dried to give the title compound as an off-white solid (29 mg, 88%). $^1$H NMR (300 MHz, DMSO-d$_6$) δ 12.42 (s, 1H) 11.41 (d, J=2.21 Hz, 1H) 8.12 (d, J=1.47 Hz, 1H) 7.82 (d, J=8.46 Hz, 1H) 7.78 (d, J=8.09 Hz, 1H) 7.61 (dd, J=8.46, 1.84 Hz, 1H) 7.31 (q, J=2.70 Hz, 2H) 5.64 (dd, J=8.09, 2.21 Hz, 1H) 3.24 (s, 3H) 2.22 (s, 3H) 1.41 (s, 9H).

Example 87

Preparation of 1-(3-tert-butyl-4-methoxy-5-(2-(propylamino)benzo[d]thiazol-6-yl)phenyl)pyrimidine-2,4(1H,3H)-dione (compound IB-L0-2.46)

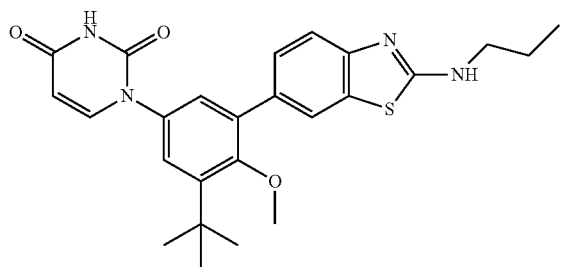 [SMILES: CCCNc1nc2ccc(-c3cc(-n4ccc(=O)[nH]c4=O)cc(C(C)(C)C)c3OC)cc2s1]

Part A. Preparation of 1-(3-tert-butyl-5-(2-chlorobenzo[d]thiazol-6-yl)-4-methoxyphenyl)pyrimidine-2,4(1H,3H)-dione To a mixture of the product from Example 83 (50 mg, 0.118 mmol) and copper(II) chloride (24 mg, 0.178 mmol) in acetonitrile (3 mL) at 0° C. was added tert-butyl nitrite (21 μL, 0.178 mmol). The mixture was stirred at 0° C. for 1 h, and then warmed to 65° C. and stirred for 2 h. The mixture was concentrated in vacuo and purified by column chromatography on silica gel using 5% MeOH in CH$_2$Cl$_2$ to give the title compound as an off-white solid (43 mg, 82%).

Part B. Preparation of 1-(3-tert-butyl-4-methoxy-5-(2-(propylamino)benzo[d]thiazol-6-yl)phenyl)pyrimidine-2,4(1H,3H)-dione A mixture of the product from Part A (50 mg, 0.11 mmol), 1-aminopropane (9 μL, 0.11 mmol), and K$_2$CO$_3$ (15.6 mg, 0.11 mmol) in anhydrous DMF (5 mL) was stirred at 100° C. for 24 h. The mixture was concentrated in vacuo and purified by column chromatography on silica gel using 2% MeOH in EtOAc as the eluent to give the title compound as an off-white solid (2.1 mg, 40%). $^1$H NMR (300 MHz, DMSO-d$_6$) δ 11.39 (d, J=1.84 Hz, 1H) 8.12 (t, J=5.52 Hz, 1H) 7.82 (d, J=1.47 Hz, 1H) 7.77 (d, J=7.72 Hz, 1H) 7.44 (t, J=9.01 Hz, 1H) 7.37-7.41 (m, 1H) 7.25 (s, 2H) 5.63 (dd, J=7.91, 2.02 Hz, 1H) 3.33-3.38 (m, 2H) 3.26 (s, 3H) 1.56-1.69 (m, 2H) 1.40 (s, 9H) 0.94 (t, J=7.35 Hz, 3H).

Example 88

Preparation of 1-(3-tert-butyl-4-methoxy-5-(3-methylbenzofuran-6-yl)phenyl)-pyrimidine-2,4(1H,3H)-dione (compound IB-L0-2.42)

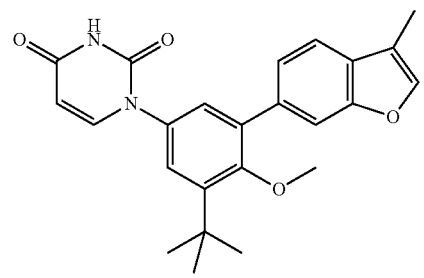 [SMILES: COc1c(-c2ccc3c(C)coc3c2)cc(-n2ccc(=O)[nH]c2=O)cc1C(C)(C)C]

Part A. Preparation of methyl 2-(2-acetyl-5-bromophenoxy)acetate

A solution of 1-(4-bromo-2-hydroxyphenyl)ethanone (1.35 g, 6.28 mmol) in anhydrous DMF (16 mL) was treated in several portions with sodium hydride (377 mg of 60% in oil, 226 mg, 9.42 mmol) followed by stirring at room temperature for 30 min. The mixture was then treated with methyl bromo-acetate (871 μL, 1.45 g, 9.48 mmol) dropwise (solution became warm after addition was complete) followed by stirring at room temperature for 18 h. The mixture was diluted with ethyl acetate and extracted with water (4×) and saturated sodium chloride solution. Drying (Na$_2$SO$_4$) and concentration in vacuo afforded a nearly colorless solid, which was purified by column chromatography on silica gel, eluting with 20-100% ethyl acetate in hexanes. These procedures afforded the title compound as a colorless solid (1.47 g, 82%).

Part B. Preparation of 2-(2-acetyl-5-bromophenoxy)acetic acid

A solution of the product from Part A (1.47 g, 5.12 mmol) in tetrahydrofuran (26 mL) was treated with 1.0N sodium hydroxide solution (6.7 mL, 6.7 mmol) followed by stirring at room temperature for 3 h, at which point the reaction was complete. The mixture was concentrated in vacuo to remove tetrahydrofuran and then was diluted with water and cooled to 0° C. The mixture was acidified to pH 3 by addition of 1N hydrochloric acid solution, and then the product extracted with ethyl acetate. The organic layer was extracted with saturated sodium chloride solution and dried (Na$_2$SO$_4$). Concentration in vacuo afforded the title compound as a colorless solid (1.36 g, 97%).

Part C. Preparation of 6-bromo-3-methylbenzofuran

A solution of the product from Part B (500 mg, 1.83 mmol) in acetic anhydride (9.2 mL) was treated with sodium acetate (300 mg, 3.66 mmol) followed by warming at reflux for 18 h. The mixture was cooled to room temperature and diluted with toluene and concentrated in vacuo to azeotropically remove acetic anhydride. This process was repeated 3×. The mixture was then diluted with ethyl acetate and stirred with saturated sodium bicarbonate solution for 1 h. The layers were separated and the organic layer was extracted with saturated sodium chloride solution. Drying (Na$_2$SO$_4$) and concentration in vacuo afforded amber oil, which was purified by column chromatography on silica gel, eluting with 8-50% ethyl acetate in hexanes. These procedures afforded the title compound as a colorless liquid (316 mg, 82%).

Part D. Preparation of 4,4,5,5-tetramethyl-2-(3-methylbenzofuran-6-yl)-1,3,2-dioxaborolane In a microwave tube, a mixture of the product from Part C (303 mg, 1.44 mmol), bis(pinacolato)diboron (401 mg, 1.58 mmol) and potassium acetate (423 mg, 4.3 μmol) in anhydrous dioxane (5 mL) was degassed by nitrogen sparge for 15 min. The mixture was treated with 1,1'-bis-(diphenylphosphino)ferrocene palladium (II) chloride dichloromethane complex (24 mg, 0.029 mmol) followed by degassing for another 5 min. The microwave tube was sealed and the mixture was warmed at 90° C. for 18 h. The mixture was cooled and diluted with ethyl acetate and extracted with water and saturated sodium chloride solution. The organic layer was dried (Na$_2$SO$_4$) and stirred with (3-mercapto-propyl) silica gel for 1 h. The mixture was filtered and concentrated in vacuo to afford a brown semisolid, which was purified by column chromatography on silica gel, eluting with 8-40% ethyl acetate in hexanes. These procedures afforded the title compound as colorless oil, which slowly solidified upon standing (307 mg, 83%).

Part E. Preparation of 1-(3-tert-butyl-4-methoxy-5-(3-methylbenzofuran-6-yl)phenyl)-pyrimidine-2,4(1H,3H)-dione In a microwave tube, a solution of the product from Part D (307 mg, 1.19 mmol), the product from Example C (414 mg, 1.03 mmol), 1,3,5,7-tetramethyl-2,4,8-trioxa-6-phospha-6-phenyl-adamantane (Cytec [97739-46-3]) (15 mg, 0.052 mmol), and tribasic potassium phosphate (439 mg, 2.07 mmol) in 3:1 tetrahydrofuran-water (8 mL) was degassed by nitrogen sparge for 20 min. The mixture was treated with tris(dibenzylideneacetone)dipalladium (0) (12 mg, 0.012 mmol) followed by degassing for another 10 min. During this period, the solution turned from an initially deep maroon color to a greenish brown color. The microwave tube was sealed and the solution warmed at 50° C. for 56 h. The solution was cooled and diluted with ethyl acetate and acidified with 1M citric acid solution. The organic layer was extracted with saturated sodium chloride solution, dried (Na$_2$SO$_4$), and then stirred with (3-mercaptopropyl) silica gel for 1 h. After filtration and concentration in vacuo, the residue obtained was purified by column chromatography on silica gel, eluting with 4-20% acetone in dichloromethane, followed by a second column chromatography on silica gel, eluting with 20-100% ethyl acetate in hexanes. These procedures afforded the title compound as a colorless solid (355 mg). $^1$H NMR (300 MHz, DMSO-d$_6$): δ 11.40 (d, J=1.84 Hz, 1H) 7.74-7.92 (m, 2H) 7.58-7.76 (m, 2H) 7.46 (dd, J=8.09, 1.47 Hz, 1H) 7.30 (q, J=2.82 Hz, 2H) 5.64 (dd, J=8.09, 2.21 Hz, 1H) 3.22 (s, 3H) 2.25 (s, 3H) 1.41 (s, 9H).

Example 89

Preparation of N-((6-(3-tert-butyl-5-(2,4-dioxo-3,4-dihydropyrimidin-1(2H)-yl)-2-methoxyphenyl)benzofuran-3-yl)methyl)methanesulfonamide (compound IB-L0-2.18)

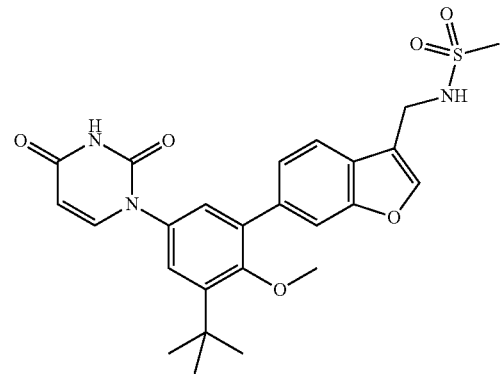 [SMILES: COc1c(-c2ccc3c(CNS(C)(=O)=O)coc3c2)cc(-n2ccc(=O)[nH]c2=O)cc1C(C)(C)C]

Part A. Preparation of 6-bromo-3-(bromomethyl)benzofuran

A solution of the product from Example 88, Part C (1.0 g, 4.74 mmol) and dibenzoyl peroxide (287 mg, 1.19 mmol) in chlorobenzene (24 mL) at reflux was treated in four portions with N-bromosuccinimide (843 mg, 4.74 mmol) over 30 min. The mixture was then stirred at reflux for 2 h. The mixture was cooled, filtered and concentrated and purified by column chromatography on silica gel, eluting with 7-30% chloroform in hexanes. The procedures afforded the title compound as a light yellow oil (438 mg, 32%).

Part B. Preparation of N-((6-bromobenzofuran-3-yl)methyl)-N-(4-methoxybenzyl)methane-sulfonamide A solution of the product from Part A (515 mg, 1.78 mmol), N-(4-methoxybenzyl)methane-sulfonamide (421 mg, 1.95 mmol), and potassium carbonate (260 mg, 1.95 mmol) in anhydrous DMF (8.9 mL) was stirred at 70° C. for 3 h. The mixture was cooled and diluted with ethyl acetate and extracted with water (4×). The organic layer was then extracted with saturated sodium chloride solution and dried (Na$_2$SO$_4$). Concentration in vacuo afforded a beige solid. This material was purified by column chromatography on silica gel, eluting with 20-100% ethyl acetate in hexanes. These procedures afforded the title compound as a colorless solid (224 mg, 35%).

Part C. Preparation of N-(4-methoxybenzyl)-N4-((6-(4,4,5,5-tetramethyl-1,3,2-dioxaborolan-2-yl)benzofuran-3-yl)methyl)methanesulfonamide The product from Part B (186 mg, 0.44 mmol) was subjected to the conditions described for Example 88, Part D to afford the title compound as a colorless solid (177 mg, 86%).

Part D. Preparation of N-((6-(3-tert-butyl-5-(2,4-dioxo-3,4-dihydropyrimidin-1(2H)-yl)-2-methoxyphenyl)benzofuran-3-yl)methyl)-N-(4-methoxybenzyl)methanesulfonamide In a microwave tube, a suspension of the product from Part C (169 mg, 0.36 mmol), the product from Example C (143 mg, 0.36 mmol), and 1.0M sodium carbonate solution (0.5 mL, 0.50 mmol) in 1:1 ethanol-toluene (3 mL) was degassed by nitrogen sparge for 20 min. The solution was treated with 1,1-bis(diphenylphosphino)ferrocene-palladium(II) chloride dichloromethane complex (7 mg, 9 μmol) followed by degassing for another 5 min. The microwave tube was sealed and the mixture heated a 100° C. in the microwave oven for 1 h. The mixture was diluted with ethyl acetate and water, and acidified with 1M citric acid solution. The organic layer was extracted with saturated sodium chloride solution, dried ($Na_2SO_4$), and allowed to stand overnight over (3-mercaptopropyl) silica gel. Filtration and concentration in vacuo afforded an off-white foam which was purified by column chromatography on silica gel, eluting with 5-30% ethyl acetate in dichloromethane. The procedures afforded the title compound as a colorless solid (96 mg, 43%).

Part E. Preparation of N-((6-(3-tert-butyl-5-(2,4-dioxo-3,4-dihydropyrimidin-1(2H)-yl)-2-methoxyphenyl)benzofuran-3-yl)methyl)methanesulfonamide A solution of the product from Part D (88 mg, 0.14 mmo) in dichloromethane (1.4 mL) was treated with trifluoroacetic acid (1.4 mL) followed by stirring at room temperature for 18 h, and then stirring at 40° C. for 2 h. The mixture was concentrated in vacuo to afford a dark, purple-brown foam, which was subjected to column chromatography on silica gel, eluting with 5-50% ethyl acetate in methylene chloride to afford an impure material, which was purified by reverse phase chromatography on a C-18 column, eluting with 1% water-TFA/acetonitrile. The procedures afforded the title compound as a solid (3.9 mg). $^1$H NMR (300 MHz, DMSO-$d_6$): δ 11.31-11.48 (m, 1H) 8.01 (s, 1H) 7.68-7.94 (m, 2H) 7.40-7.65 (m, 2H) 7.10-7.38 (m, 2H) 5.65 (dd, J=7.91, 2.02 Hz, 1H) 4.33 (d, J=5.88 Hz, 2H) 3.23 (s, 3H) 2.95 (s, 3H) 1.41 (s, 9H).

Example 90

Preparation of N-((5-(3-tert-butyl-5-(2,4-dioxo-3,4-dihydropyrimidin-1(2H)-yl)-2-methoxyphenyl)-1-methyl-2,3-dihydro-1H-inden-1-yl)methyl)methanesulfonamide (compound IB-L0-2.25)

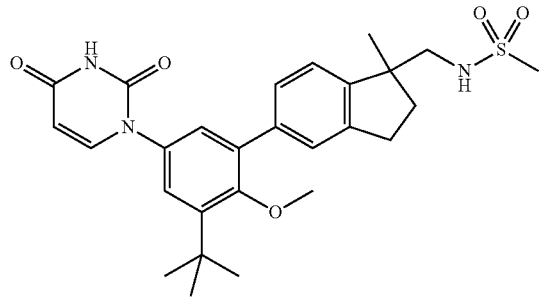 [SMILES: COc1c(-c2ccc3c(c2)CCC3(C)CNS(C)(=O)=O)cc(-n2ccc(=O)[nH]c2=O)cc1C(C)(C)C]

Part A. Preparation of 5-bromo-1-(1,3-dithian-2-yl)-2,3-dihydro-1H-inden-1-ol A solution of 1,3-dithiane (11.96 g, 99 mmol) in anhydrous tetrahydrofuran (100 mL) at −30° C. was treated dropwise over 10 min with n-butyllithium (2.5M in hexanes, 38.4 mL, 96 mmol) followed by stirring at −15° C. for 2 h. The solution was then treated with a solution of 5-bromo-2,3-dihydro-1H-inden-1-one (15 g, 71.1 mmol) in anhydrous tetrahydrofuran (250 mL) over 1 h, maintaining the temperature between −9° C. and 2° C. The mixture was then allowed to set in the refrigerator at 2-8° C. for 18 h. The solution was concentrated in vacuo to afford a maroon oil, which was treated with 1 N hydrochloric acid solution and extracted with ether. The ether layer was extracted with saturated sodium chloride solution, dried ($Na_2SO_4$) and concentrated in vacuo to afford an amber oil (23.55 g).

Part B. Preparation of 2-(5-bromo-2,3-dihydro-1H-inden-1-ylidene)-1,3-dithiane A solution of the product from Part A (23.55 g, 71.1 mmol) in benzene (350 mL) was treated with p-toluenesulfonic acid monohydrate (3.0 g) followed by stirring at reflux for 1 h while removing water by means of a Dean-Stark trap. The mixture was extracted with saturated sodium bicarbonate solution and then with saturated sodium chloride solution. Drying ($Na_2SO_4$) and concentration in vacuo afforded the product as an amber, oil (22.27 g).

Part C. Preparation of 5-bromo-2,3-dihydro-1H-indene-1-carboxylic acid

A solution of the product from Part B (22.27 g, 71.1 mmol) in glatial acetic acid (375 mL) was treated with concentrated hydrochloric acid solution (125 mL) followed by stirring at reflux for 3 h. The mixture was cooled and concentrated in vacuo by azeotroping off the acetic acid and water with toluene (3×). The brown oil obtained was filtered through a plug of 70-230 mesh silica gel in a 2 L sintered glass funnel (volume of silica gel ca. 1800 mL) eluting with dichloromethane to remove non-polar impurities (1,3-propanedithiol, inter alia) and then with ethyl acetate to elute the title compound, which was obtained as a brown solid (9.85 g, 58%).

Part D. Preparation of methyl 5-bromo-2,3-dihydro-1H-indene-1-carboxylate

A suspension of the product from Part C (9.85 g, 40.9 mmol) in methanol (400 mL) was treated with 4 N hydrogen chloride in 1,4-dioxane (125 mL) and the mixture was stirred at reflux for 8 h. The mixture was concentrated in vacuo to afford brown oil, which was purified by column chromatography on silica gel, eluting with 0-30% methyl t-butyl ether in chloroform. These procedures afforded the title compound as an amber oil (7.99 g, 77%).

Part E. Preparation of methyl 5-bromo-1-methyl-2,3-dihydro-1H-indene-1-carboxylate A solution of the product from Part D (2.03 g, 7.96 mmol) in anhydrous tetrahydrofuran (40 mL) at −78° C. under $N_2$ was treated dropwise with lithium bis(trimethylsilyl)amide (1.0M in tetrahydrofuran, 9.55 mL, 9.55 mmol) over 10 min. The solution was stirred at −78° C. for 45 min and then treated with methyl iodide (1.5 mL, previously dried by passage through a plug of basic alumina). The mixture was then gradually allowed to warm to rt and was stirred for 18 h. The mixture was quenched by addition of saturated ammonium chloride solution (2 mL). The mixture was concentrated in vacuo to remove tetrahydrofuran and the residue was diluted with ethyl acetate. The mixture was extracted with saturated ammonium chloride solution and with saturated sodium chloride solution. Drying ($Na_2SO_4$) and concentration in vacuo afforded the title compound as an amber oil (2.06 g, 96%).

Part F. Preparation of 5-bromo-1-methyl-2,3-dihydro-1H-indene-1-carboxylic acid

A solution of the product from Part E (2.06 g, 7.65 mmol) and potassium trimethylsilanoate (5.5 g of 90%, 4.91 g, 38.3 mmol) in tetrahydrofuran (40 mL) was stirred at reflux for 3 h. The mixture was cooled and concentrated in vacuo to remove tetrahydrofuran. The maroon residue was dissolved in water (ca. 175 mL) and extracted with methyl t-butyl ether. The aqueous phase was cooled to 0° C. and acidified to pH 3 by addition of concentrated hydrochloric acid solution. The mixture was extracted with ethyl acetate (2×) and then with saturated sodium chloride solution. The solution was dried ($Na_2SO_4$) and treated with Darco G-60, followed by filtration through celite. The filtrate was concentrated in vacuo to afford the title compound as a light yellow solid (1.93 g, 99%).

Part G. Preparation of 5-bromo-1-methyl-2,3-dihydro-1H-indene-1-carboxamide

A solution of the product from Part F (1.56 g, 6.12 mmol) and DMF (473 µL, 447 mg, 6.12 mmol) in hexanes (100 mL) was treated with oxalyl chloride (1.61 mL, 2.32 g, 18.4 mmol) followed by stirring at room temperature for 1 h. The mixture was treated with celite and then filtered through celite. The filtrate was concentrated in vacuo and dissolved in acetone (75 mL) and cooled to 0° C. The solution was treated with 28% aqueous ammonia solution (75 mL) followed by stirring at 0° C. for 30 min and then warming to room temperature. The mixture was concentrated in vacuo and extracted with ethyl acetate. The organic layer was extracted with saturated sodium chloride solution and dried ($Na_2SO_4$). Concentration in vacuo afforded the title compound as an oil (1.55 g, 100%).

Part H. Preparation of (5-bromo-1-methyl-2,3-dihydro-1H-inden-1-yl)methanamine hydrochloride In a flask equipped with a vigreaux column and a short path distillation head, a solution of the product from Part G (1.21 g, 4.76 mmol) in anhydrous tetrahydrofuran (8 mL) was warmed to a gentle reflux and treated dropwise with borane-dimethylsulfide complex (904 µL, 723 mg, 9.52 mmol). The resulting mixture was stirred at reflux for 2 h. The solution was cooled to rt and carefully treated with methanol until bubbling ceased, followed by careful treatment with 4N hydrogen chloride in 1,4-dioxane solution (4 mL). The mixture was then concentrated in vacuo. The colorless solid obtained was triturated with ether and collected by filtration. After drying in a vacuum oven at 50° C. for 2 h, the title compound was obtained as a colorless solid (893 mg, 68%).

Part I. Preparation of tert-butyl (5-bromo-1-methyl-2,3-dihydro-1H-inden-1-yl)methyl-carbamate A suspension of the product from Part H (893 mg, 3.23 mmo) in tetrahydrofuran (16 mL) was treated with di-tert-butyl dicarbonate (846 mg, 3.87 mmol) and saturated sodium bicarbonate solution (7.2 mL, ca. 6.46 mmol) followed by stirring at room temperature for 18 h. The mixture was diluted with ethyl acetate and extracted with water and saturated sodium chloride solution. The solution was dried ($Na_2SO_4$) and concentrated in vacuo. The residue was purified by flash chromatography, eluting with 5-40% ethyl acetate in hexanes. These procedures afforded the title compound as a colorless solid (1.03 g, 94%).

Part J. Preparation of tert-butyl (1-methyl-5-(4,4,5,5-tetramethyl-1,3,2-dioxaborolan-2-yl)-2,3-dihydro-1H-inden-1-yl)methylcarbamate The product from Part I (1.03 g, 3.03 mmol) was subjected to the conditions described for Example 88, Part D to afford the title compound as a colorless solid (977 mg, 83%).

Part K. Preparation of tert-butyl (5-(3-tert-butyl-5-(2,4-dioxo-3,4-dihydropyrimidin-1(2H)-yl)-2-methoxyphenyl)-1-methyl-2,3-dihydro-1H-inden-1-yl)methylcarbamate The product from Part J (965 mg, 2.49 mmol) was subjected to the conditions described for Example 89, Part D to afford the title compound as a colorless solid (618 mg, 47%).

Part L. Preparation of N-((5-(3-tert-butyl-5-(2,4-dioxo-3,4-dihydropyrimidin-1(2H)-yl)-2-methoxyphenyl)-1-methyl-2,3-dihydro-1H-inden-1-yl)methyl)methanesulfonamide The product from Part K (446 mg, 0.84 mmol) was dissolved in 4N hydrogen chloride in dioxane solution (12 mL), followed by stirring at room temperature for 18 h. The suspension of colorless solid obtained was then concentrated in vacuo. This material was suspended in dichloromethane (5 mL) and cooled to 0° C., followed by sequential treatment with triethylamine (280 µL, 203 mg, 2.01 mmol) and methanesulfonyl chloride (81 µL, 120 mg, 1.05 mmol). The mixture was stirred at 0° C. for 1 h and then warmed to room temperature and diluted with dichloromethane. The mixture was extracted with 1M citric acid solution and then dried ($Na_2SO_4$) and concentrated in vacuo. The residue was dissolved in 3:1 tetrahydrofuran-water (8 mL) and treated with potassium carbonate (231 mg, 1.68 mmol) followed by stirring at room temperature for 1 h. The mixture was concentrated in vacuo and the residue diluted with water and then acidified to ca. pH 2 by addition of 1M citric acid. The product was extracted with ethyl acetate and the organic layer was extracted with saturated sodium chloride solution. Drying ($Na_2SO_4$) and concentration in vacuo afforded a colorless solid, which was purified by column chromatography on silica gel, eluting with 30-100% ethyl acetate in hexanes. The procedures afforded the title compound as a colorless solid (184 mg, 43%). $^1$H NMR (300 MHz, DMSO-$d_6$): δ 11.39 (s, 1H) 7.77 (d, J=7.72 Hz, 1H) 7.14-7.48 (m, 5H) 7.06 (t, J=6.62 Hz, 1H) 5.63 (d, J=7.72 Hz, 1H) 3.18-3.33 (m, 3H) 2.96-3.15 (m, 2H) 2.85-3.00 (m, 2H) 2.70-2.87 (m, 3H) 2.10-2.34 (m, 1H) 1.63-1.90 (m, 1H) 1.40 (s, 9H) 1.20-1.34 (m, 3H).

Example 91

Preparation of N-((5-(3-tert-butyl-5-(2,4-dioxo-3,4-dihydropyrimidin-1(2H)-yl)-2-methoxyphenyl)-1-fluoro-2,3-dihydro-1H-inden-1-yl)methyl)methanesulfonamide (compound IB-L0-2.12)

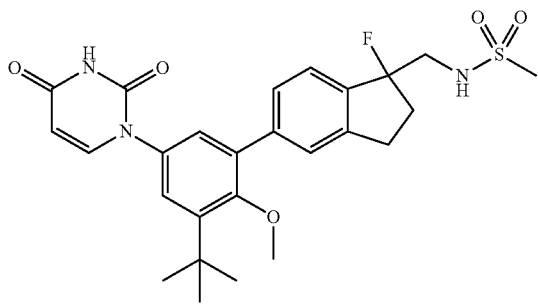 [SMILES: COc1c(-c2ccc3c(c2)CCC3(F)CNS(C)(=O)=O)cc(-n2ccc(=O)[nH]c2=O)cc1C(C)(C)C]

Part A. Preparation of 5-(5-bromo-2,3-dihydro-1H-inden-1-ylidene)-2,2,3,3,7,7,8,8-octamethyl-4,6-dioxa-3,7-disilanonane To a solution of the product from Example 90, Part C (1.2 g, 4.98 mmol) in anhydrous THF (5 mL) was added TBSCl (1.726 g, 11.45 mmol), and the resulting yellow solution was cooled to 0° C. in an ice bath. A 1.0M solution of LiHMDS in THF (11.95 mL, 11.95 mmol) was added dropwise over 5 min, and the resulting dark red solution was stirred at 0° C. for 90 min, and then at room temperature for 6 h. The solvent was removed in vacuo and the oily semi solid residue was treated with pentane (2×35 mL) to precipitate LiCl. The slurry was filtered and the solvent was removed in vacuo to give the title compound as a brown oil (2.3 g).

Part B. Preparation of 5-bromo-1-fluoro-2,3-dihydro-1H-indene-1-carboxylic acid To a mixture of 1-chloromethyl-4-fluoro-1,1-diazoniabicyclo[2.2.2.]octane bis(tetrafluoro-borate) (Selectfluor, 2.26 g, 6.37 mmol in $CH_3CN$ (20 mL) was added the product from Part A (2.3 g, 4.90 mmol) in $CH_3CN$ (6 mL). The resulting yellow-orange solution was stirred at room temperature overnight. The reaction mixture was poured into 50 mL 1N HCl (aqueous), extracted with EtOAc (2×35 mL). The combined organic extracts are washed with 0.5N NaOH (3×30 mL). The combined aqueous extracts are washed with EtOAc (2×25 mL), then adjusted mixture to pH 1 with 5N HCl (10 mL). The resulting cloudy brown solution was extracted with EtOAc (2×50 mL), the combined organic layers were washed with 10% NaCl and then treated with decolorizing carbon and stirred for 1 h. The mixture was dried over anhydrous $Na_2SO_4(s)$, filtered through Celite and the solvent removed in vacuo to give the title compound as leaving a yellow oil (0.84 g).

Part C. Preparation of 5-bromo-1-fluoro-2,3-dihydro-1H-indene-1-carbonyl chloride To a solution of the product from Part B (0.95 g, 3.67 mmol) in $CH_2Cl_2$ was added oxalyl chloride (0.96 mL, 11.00 mmol), followed by DMF (0.28 mL). The resulting bubbling solution was stirred at room temperature for 2 h, filtered through Celite, and the solvent was removed in vacuo to give the title compound as a brown oil (0.99 g).

Part D. Preparation of 5-bromo-1-fluoro-2,3-dihydro-1H-indene-1-carboxamide

To a solution of the product from Part C (0.99 g, 3.57 mmol) in acetone (20 mL) and at 0° C. was added aqueous $NH_4OH$ (28%, 0.28 mL, 3.57 mmol), and the resulting dark brown mixture was stirred at 0° C. for 1 h. The reaction mixture was concentrated in vacuo, and the residue was partitioned between water and EtOAc (2×50 mL). The combined organic extracts were washed with 1N $H_3PO_4$, 10% $NaHCO_3$ (aq), 10% NaCl, and dried over anhydrous $Na_2SO_4(s)$, filtered and concentrated in vacuo. The brown solid was purified by column chromatography on silica gel using a solvent gradient of $CH_2Cl_2$/MeOH (99/1 to 96/4). The title compound was obtained as a brown solid (0.205 g, 22%).

Part E. Preparation of tert-butyl (5-bromo-1-fluoro-2,3-dihydro-1H-inden-1-yl)methyl-carbamate To a solution of the product from Part D (0.234 g, 0.907 mmol) in anhydrous THF (5 mL) at 80° C. was added borane-DMS complex (0.172 mL, 1.813 mmol) dropwise. The reaction flask was equipped with a short-path condenser, and the mixture was stirred at reflux for 2 h, collecting THF and DMS. The mixture was then cooled to room temperature and MeOH (5 mL) was added, followed by 4N HCl in 1,4-dioxane (5 mL). The solvent was removed in vacuo to give a colorless solid (0.25 g, 98%). The solid was dissolved in THF (5 mL), and to the solution was added triethylamine (0.137 mL, 0.980 mmol), followed by di-tert-butyl dicarbonate (0.214 g, 0.980 mmol). The cloudy mixture was stirred at room temperature for 30 min, and 10% aq. $NaHCO_3$ (1 mL) was added. The resulting mixture was stirred at room temperature for 18 h and then concentrated in vacuo to an oily residue. The residue was dissolved in EtOAc (50 mL), washed with water, 1N $H_3PO_4$, 10% NaCl, and dried over anhydrous $Na_2SO_4(s)$. The drying agent was filtered off, and the solvent was removed in vacuo to give the title compound as an oil (0.27 g, 88%).

Part F. Preparation of tert-butyl (1-fluoro-5-(4,4,5,5-tetramethyl-1,3,2-dioxaborolan-2-yl)-2,3-dihydro-1H-inden-1-yl)methylcarbamate The product from Part E (0.27 g, 0.784 mmol) was subjected to the conditions described for Example 72, Part B to give the title compound as a tan solid (0.159 g, 52%).

Part G. Preparation of tert-butyl (5-(3-tert-butyl-5-(2,4-dioxo-3,4-dihydropyrimidin-1(2H)-yl)-2-methoxyphenyl)-1-fluoro-2,3-dihydro-1H-inden-1-yl)methylcarbamate To a solution of the product from Part F (0.159 g, 0.405 mmol), the product from Example C (0.162 g, 0.405 mol), 1,3,5,7 tetramethyl-2,4,8-trioxa-6-phospha-6-phenyl adamantane (PA-Ph, CAS 97739-46-3) (3.55 g, 0.012 mmol) in THF (3 mL) was added $K_3PO_4$ (0.181 g, 0.85 μmol) and water (1 mL), followed by tris(dibenzylideneacetone)dipalladium (0) catalyst (3.71 mg, 0.00405 mmol). The resulting mixture was degassed by bubbling with $N_2$ for 20 min, and then stirred at room temperature for 12 h. The reaction mixture was diluted with EtOAc (50 mL), washed with 1N $H_3PO_4$, 10% $NaHCO_3$, 10% NaCl, and dried over anhydrous $Na_2SO_4(s)$. The mixture was filtered and solvent was removed in vacuo to give a brown oil, which was purified by column chromatography on silica gel, eluting with 98/2 CH$_2$Cl$_2$/MeOH. The title compound was isolated as a colorless solid (0.118 g, 54%).

Part H. Preparation of N-((5-(3-tert-butyl-5-(2,4-dioxo-3,4-dihydropyrimidin-1(2H)-yl)-2-methoxyphenyl)-1-fluoro-2,3-dihydro-1H-inden-1-yl)methyl)methanesulfonamide The product from Part G (0.118 g, 0.219 mmol) was dissolved in 4N HCl in 1,4-dioxane (2 mL) and stirred at room temperature for 1 h. The solvent was removed in vacuo and the residue was suspended in CH$_2$Cl$_2$ and evaporated (2×4 mL) to give a colorless solid (0.10 g, 96%). This solid was dissolved in CH$_2$Cl$_2$ (1 mL) and the resulting slurry was stirred in an ice bath. Triethylamine (0.059 mL, 0.422 mmol) was added to the slurry resulting in a clear solution and to this was added methanesulfonyl chloride (0.02 mL, 0.253 mmol). The resulting mixture was stirred in the ice bath for 1 h. The reaction mixture was diluted with CH$_2$Cl$_2$ 50 mL, washed with 1N H$_3$PO$_4$, 10% NaHCO$_3$, 10% NaCl, and dried over anhydrous Na$_2$SO$_4$(s). The drying agent was filtered off, and solvent was removed in vacuo leaving a crude product that was purified by column chromatography on silica gel, eluting with a gradient of 1:1 to 3:7 hexane:EtOAc. The title compound was obtained as a colorless solid (64 mg, 62%). $^1$H NMR (300 MHz, DMSO-d$_6$) δ 11.39 (s, 1H) 7.77 (d, J=7.72 Hz, 1H) 7.30-7.48 (m, 3H) 7.12-7.32 (m, 3H) 5.63 (d, J=7.72 Hz, 1H) 3.27 (s, 3H) 2.94-3.08 (m, 4H) 2.91 (s, 3H) 2.17-2.38 (m, 1H) 1.76-1.97 (m, 1H) 1.40 (s, 9H).

Example 92

Preparation of N-(6-(3-tert-butyl-5-(2,4-dioxo-3,4-dihydropyrimidin-1(2H)-yl)-2-methoxyphenyl)-3,4-dihydroisoquinolin-2(1H)-yl)methanesulfonamide (compound IB-L0-2.43)

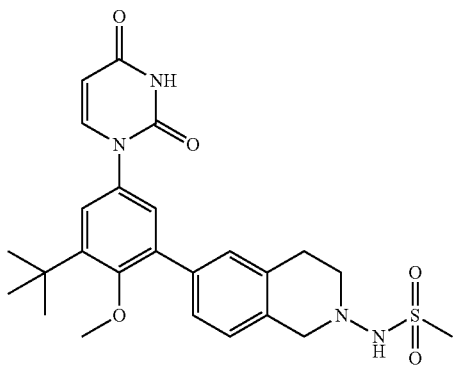 [SMILES: COc1c(-c2ccc3c(c2)CCN(NS(C)(=O)=O)C3)cc(-n2ccc(=O)[nH]c2=O)cc1C(C)(C)C]

Part A. Preparation of N-(3-bromophenethyl)-2,2,2-trifluoroacetamide

To a solution of 2-(3-bromophenyl)ethanamine (10 g, 50.0 mmol) in dichloromethane (200 ml) at 0° C. were added 2,6-lutidine (6.40 ml, 55.0 mmol) and then trifluoroacetic anhydride (7.77 ml, 55.0 mmol) dropwise, and the reaction was stirred at room temperature overnight. Water was added at 0° C. and the reaction was washed with 1M HCl, H$_2$O, and sat NaHCO$_3$. The organic was dried over mgSO$_4$, filtered and concentrated to provide the title compound as a tan solid (14.7 g, 99%).

Part B. Preparation of 1-(6-bromo-3,4-dihydroisoquinolin-2(1H)-yl)-2,2,2-trifluoro-ethanone To the product from Part A (14.70 g, 49.6 mmol) and paraformaldehyde (2.39 g, 80 mmol) was added a mixture of acetic acid (81 ml) and sulfuric acid (53.7 ml) at room temperature. The suspension was stirred for 60 h during which time it became a solution. The reaction was poured into cold water. The reaction was diluted with ethyl acetate and washed with water, sat NaHCO$_3$, and brine. The organic layer was dried over mgSO$_4$, filtered and concentrated to provide the title compound, contaminated with the 8-bromo isomer, as a colorless oil (10.5 g, 67%).

Part C. Preparation of 6-bromo-1,2,3,4-tetrahydroisoquinoline

To a solution of the product from Part B (9.5 g, 30.8 mmol) in methanol (231 ml) and water (77 ml) at room temperature was added potassium carbonate (8.52 g, 61.7 mmol) and the reaction was stirred at room temperature for 30 min. The reaction was diluted with water and 25% isopropanol in chloroform and the pH was adjusted to 9 with 1N HCl. The mixture was extracted twice with 25% isopropanol in chloroform. The combined organic layers were dried over mgSO$_4$, filtered and concentrated to give the title compound, contaminated with the 8-bromo isomer (6.55 g, quantitative).

Part D. Preparation of 6-bromo-2-nitroso-1,2,3,4-tetrahydroisoquinoline

To a solution of the product from Part C (6.55 g, 30.9 mmol) in acetic acid (61.8 ml) and 3N aq. hydrochloric acid (10.29 ml, 30.9 mmol) at 0° C. was added 1.9M sodium nitrite (20.64 ml, 39.2 mmol) dropwise, and the reaction was stirred at room temperature overnight. The solvent was evaporated and the reaction was diluted with 25% isopropanol in chloroform and sat NaHCO$_3$. The aqueous layer was extracted twice with 25% isopropanol in chloroform. The combined organic layers were dried over mgSO$_4$, filtered and concentrated to give the title compound, contaminated with the 8-bromo isomer (6.97 g, 94%).

Part E. Preparation of 6-bromo-3,4-dihydroisoquinolin-2(1H)-amine

To a solution of the product from Part D (0.5 g, 2.074 mmol) in methanol (4.15 ml) was added zinc (0.542 g, 8.30 mmol) and the reaction was cooled to 0° C., followed by dropwise addition of AcOH (4.15 ml). The reaction was warmed to rt and the reaction was stirred for 2.5 h. The reaction was filtered and the solid was washed with methanol. The filtrate was evaporated and the residue was diluted with water and 25% isopropanol in chloroform and saturated NaHCO$_3$ was added. A white solid was removed by filtration, and the aqueous layer was extracted twice with 25% isopropanol in chloroform. The combined organic layers were dried over mgSO$_4$, filtered and concentrated to give the title compound, contaminated with the 8-bromo isomer (0.472 g, quantitative).

Part F. Preparation of tert-butyl 6-bromo-3,4-dihydroisoquinolin-2(1H)-ylcarbamate A solution of the product from Part E (0.472 g, 2.078 mmol) in THF (20.78 ml) was cooled to 0° C. followed by addition of di-tert-butyl dicarbonate (0.531 ml, 2.286 mmol), and the reaction was stirred at room temperature overnight. Solvent was removed in vacuo, and the crude product was purified by column chromatography on silica gel (isolated lower $R_f$ product) using a gradient starting with dichloromethane and ending with 10% ethyl acetate in dichloromethane to give the title compound (49 mg, 73%).

Part G. Preparation of tert-butyl 6-(4,4,5,5-tetramethyl-1,3,2-dioxaborolan-2-yl)-3,4-dihydroisoquinolin-2(1H)-ylcarbamate A solution of the product from Part F (100 mg, 0.306 mmol), bis(pinacolato)diboron (85 mg, 0.336 mmol), and potassium acetate (57.3 ul, 0.917 mmol) in 1,4-dioxane (3.0 mL) was degassed by bubbling with $N_2$ gas for 15 min. 1,1'-Bis(diphenylphosphino)ferrocene-palladium(II)dichloride dichloromethane complex (11.18 mg, 0.015 mmol) was added, and the resulting mixture was stirred at 95° C. for 16 h. The cooled solution was diluted with 25% isopropanol in chloroform and washed with water. The organic layer was dried over mgSO4, filtered and concentrated in vacuo. The product was purified by column chromatography on silica gel eluting with a gradient starting with dichloromethane and ending with 25% ethyl acetate in dichloromethane to give the title compound (70 mg, 61%).

Part H. Preparation of tert-butyl 6-(3-tert-butyl-5-(2,4-dioxo-3,4-dihydropyrimidin-1(2H)-yl)-2-methoxyphenyl)-3,4-dihydroisoquinolin-2(1H)-ylcarbamate A mixture of the product from Example C (74.8 mg, 0.187 mmol), the product from Part G (70 mg, 0.187 mmol) in EtOH (1.0 mL), toluene (1.0 mL) 1M aq. $Na_2CO_3$ (281 ul, 0.281 mmol) was degassed by bubbling with $N_2$ gas for 10 min. 1,1'-Bis(diphenylphosphino)ferrocene-palladium(II) dichloride dichloromethane complex (6.84 mg, 9.35 mmol) was added, and degassing with $N_2$ was continued for 5 min. The reaction mixture was sealed and heated at 78° C. for 16 h. The reaction was cooled and diluted with 25% isopropanol in chloroform and washed with water. The organic was dried over mgSO4, filtered and concentrated. The crude product was purified by column chromatography on silica gel, eluting with a gradient starting with dichloromethane and ending with ethyl acetate to give the title compound (53 mg, 54%).

Part I. Preparation of N-(6-(3-tert-butyl-5-(2,4-dioxo-3,4-dihydropyrimidin-1(2H)-yl)-2-methoxyphenyl)-3,4-dihydroisoquinolin-2(1H)-yl)methanesulfonamide To a solution of the product from Part H (25 mg, 0.048 mmol) in dichloromethane (0.5 mL) at room temperature was added TFA (0.5 mL) and the reaction was stirred for 30 min, and then concentrated in vacuo. The residue was diluted with 25% isopropanol in chloroform and washed with sat $NaHCO_3$. The organic layer was dried over mgSO4, filtered and concentrated to give a solid (17.8 mg, 88%). To a solution of the solid in pyridine (0.5 mL) at 0° C. was added methanesulfonyl chloride (12.6 µl, 0.162 mmol) and the reaction was stirred at room temperature for 90 min. Methanol was added and the reaction was stirred for 10 min. The residue was diluted with 25% isopropanol in chloroform and washed with sat $NaHCO_3$. The organic layer was dried over mgSO4, filtered and concentrated, and the product was purified by column chromatography on silica gel eluting with a gradient starting with dichloromethane and ending with ethyl acetate to give the title compound (11 mg, 52%). $^1$H NMR (300 MHz, DMSO-$d_6$) δ 11.39 (s, 1H) 8.53 (s, 1H) 7.76 (d, J=7.72 Hz, 1H) 7.11-7.42 (m, 5H) 5.63 (d, J=7.72 Hz, 1H) 4.04 (s, 2H) 3.28 (s, 3H) 3.10 (d, J=5.52 Hz, 2H) 2.98 (s, 3H) 2.90-3.05 (m, 2H) 1.40 (s, 9H).

Example 93

Preparation of N-((6-(5-(2,4-dioxo-3,4-dihydropyrimidin-1(2H)-yl)-3-(furan-2-yl)-2-methoxyphenyl)-1H-inden-3-yl)methyl)methanesulfonamide (compound IB-L0-2.65)

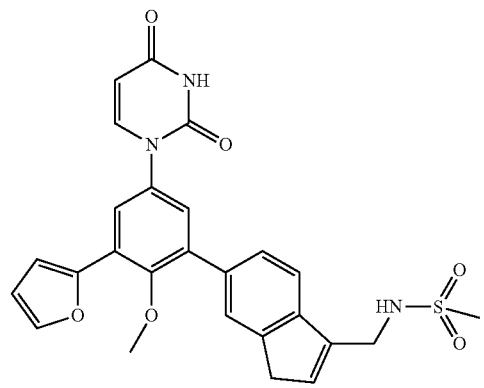 [SMILES: COc1c(-c2ccc3c(c2)CC=C3CNS(C)(=O)=O)cc(-n2ccc(=O)[nH]c2=O)cc1-c1ccco1]

Part A. Preparation of N-((6-(3-bromo-5-(2,4-dioxo-3,4-dihydropyrimidin-1(2H)-yl)-2-methoxyphenyl)-1H-inden-3-yl)methyl)methanesulfonamide The product from Example 48, Part C (0.242 gm, 0.573 mmol) and the product from Example 79, Part E (0.200 gm, 0.57 mmol) was subjected to the conditions described for Example 79, Part F to give the title compound as an off-white solid (0.104 gm, 35%).

Part B. Preparation of N-((6-(5-(2,4-dioxo-3,4-dihydropyrimidin-1(2H)-yl)-3-(furan-2-yl)-2-methoxyphenyl)-1H-inden-3-yl)methyl)methanesulfonamide A solution of the product from Part A (25.2 mg, 0.049 mmol) in 3:1 v/v THF-water (1.3 mL) was combined in a microwave tube at room temperature with furan-2-ylboronic acid (6.91 mg, 0.062 mmol) and potassium phosphate (16.84 mg, 0.097 mmol). To this was added 1,1'-bis(di-tert-butylphosphino)ferrocene palladium dichloride (1.65 mg, 2.53 umole). The tube was sealed and the resulting mixture was purged with nitrogen for 4 min and then heated for 16.5 h in an oil bath at 50° C. The reaction mixture was partitioned between dilute HCl and ethyl acetate, and the organic phase was dried (MgSO4) and concentrated in vacuo. The residue was purified by chromatography on silica gel (ethyl acetate-hexanes) to give the title compound as an off white solid (11.4 mg, 46%). $^1$H NMR (300 MHz, DMSO-$d_6$) δ 11.45 (s, 1H) 7.80-7.89 (m, 2H) 7.73-7.79 (m, 2H) 7.56-7.63 (m, 2H) 7.50 (t, J=6.07 Hz, 1H) 7.38 (d, J=2.94 Hz, 1H) 7.09 (d, J=3.31 Hz, 1H) 6.68 (dd, J=3.68, 1.84 Hz, 1H) 6.58 (s, 1H) 5.68 (d, J=7.72 Hz, 1H) 4.19 (d, J=5.15 Hz, 2H) 3.48 (s, 2H) 3.34 (s, 3H) 2.96 (s, 3H).

Example 94

Preparation of N-((6-(5-(2,4-dioxo-3,4-dihydropyrimidin-1(2H)-yl)-2-methoxy-3-(thiophen-2-yl)phenyl)-1H-inden-3-yl)methyl)methanesulfonamide (compound IB-L0-2.63)

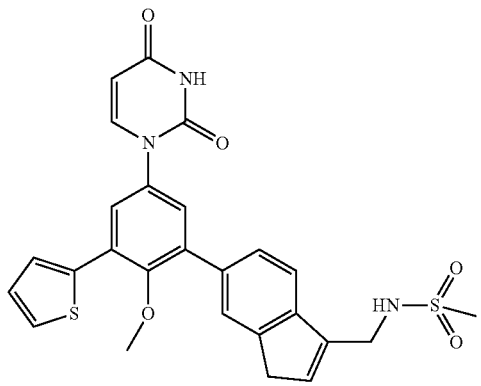 [SMILES: COc1c(-c2ccc3c(c2)CC=C3CNS(C)(=O)=O)cc(-n2ccc(=O)[nH]c2=O)cc1-c1cccs1]

The product from Example 93, Part A (26.5 mg, 0.051 mmol) was reacted with thiophen-2-yl boronic acid (8.3 mg, 0.065 mmol) as described in Example 93, Part B to give the title compound as an off-white solid (8.6 mg, 32%). $^1$H NMR (300 MHz, DMSO-$d_6$) δ 11.47 (s, 1H) 7.86 (d, J=7.72 Hz, 2H) 7.55-7.78 (m, 5H) 7.50 (t, J=6.25 Hz, 1H) 7.38 (d, J=2.57 Hz, 1H) 7.16-7.21 (m, 1H) 6.58 (s, 1H) 5.69 (d, J=7.72 Hz, 1H) 4.19 (d, J=4.78 Hz, 2H) 3.48 (s, 2H) 3.30 (s, 3H) 2.96 (s, 3H).

Example 95

Preparation of N-((6-(5-(2,4-dioxo-3,4-dihydropyrimidin-1(2H)-yl)-2-methoxy-3-(thiophen-3-yl)phenyl)-1H-inden-3-yl)methyl)methanesulfonamide (compound IB-L0-2.62)

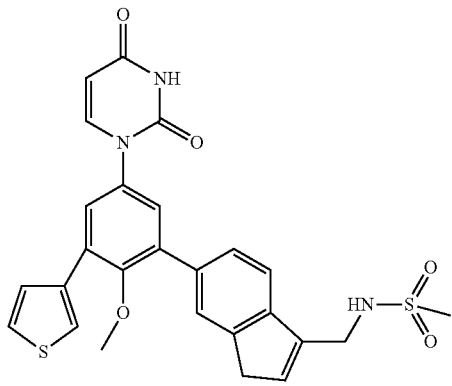 [SMILES: COc1c(-c2ccsc2)cc(-n2ccc(=O)[nH]c2=O)cc1-c1ccc2c(c1)CC=C2CNS(C)(=O)=O]

The product from Example 93, Part A (25.9 mg, 0.050 mmol) was reacted with thiophen-3-yl boronic acid (8.1 mg, 0.063 mmol) as described in Example 93, Part B to give the title compound as an off-solid (8.6 mg, 33%). $^1$H NMR (300 MHz, DMSO-$d_6$) δ 11.45 (d, J=1.84 Hz, 1H) 7.93 (d, J=2.94 Hz, 1H) 7.87 (d, J=7.72 Hz, 1H) 7.53-7.75 (m, 6H) 7.49 (t, J=6.25 Hz, 1H) 7.39 (d, J=2.57 Hz, 1H) 6.57 (s, 1H) 5.68 (dd, J=7.91, 2.02 Hz, 1H) 4.19 (d, J=5.15 Hz, 2H) 3.47 (s, 2H) 3.21 (s, 3H) 2.96 (s, 3H).

Example 96

Preparation of N-((6-(5-(2,4-dioxo-3,4-dihydropyrimidin-1(2H)-yl)-3-(furan-3-yl)-2-methoxyphenyl)-1H-inden-3-yl)methyl)methanesulfonamide (compound IB-L0-2.67)

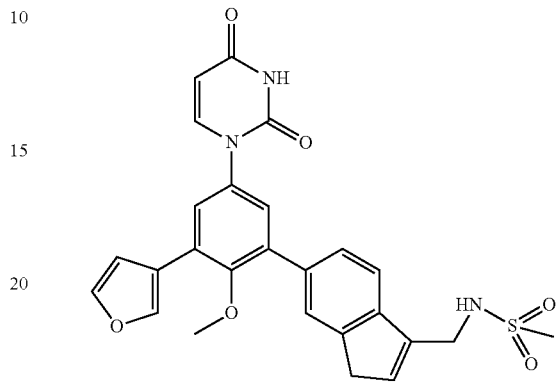

The product from Example 93, Part A (25.9 mg, 0.050 mmol) was reacted with furan-3-yl boronic acid (7.2 mg, 0.064 mmol) as described in Example 93, Part B to give the title compound as an off-white solid (10.6 mg, 45%). $^1$H NMR (300 MHz, DMSO-$d_6$) δ 11.46 (s, 1H) 7.84 (d, J=8.09 Hz, 1H) 7.80 (t, J=1.84 Hz, 1H) 7.68-7.75 (m, 2H) 7.54-7.64 (m, 2H) 7.50 (t, J=6.07 Hz, 1H) 7.35 (d, J=2.57 Hz, 1H) 7.08 (d, J=1.47 Hz, 1H) 6.57 (s, 1H) 5.68 (d, J=8.09 Hz, 1H) 3.47 (s, 2H) 3.30 (s, 3H) 2.96 (s, 3H).

Example 97

Preparation of 1-(3-tert-butyl-4-methoxy-5-(1-(methylsulfonyl)indolin-5-yl)phenyl)pyrimidine-2,4(1H,3H)-dione (compound IB-L0-2.32)

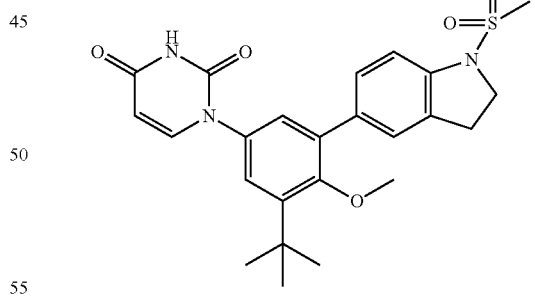

Part A. Preparation of 5-bromo-1-(methylsulfonyl)indoline

To DMF (5.0 ml) was added sodium hydride (53 mg, 1.3 mmol) and the solution stirred at room temperature for 30 min. 5-Bromoindoline (240 mg, 1.2 mmol) was added and the solution was stirred at room temperature for 30 min. Methanesulfonyl chloride (94 ul, 1.2 mmol) was added and the solution stirred at room temperature overnight, then concentrated in vacuo. The crude product was purified by column chromatography on silica gel eluting with 2% CH₃OH/CHCl₃ to give the title compound (202 mg, 60%).

Part B. Preparation of 1-(methylsulfonyl)-5-(4,4,5,5-tetramethyl-1,3,2-dioxaborolan-2-yl) indoline The product from Part A (192 mg, 0.70 mmol) was subjected to the conditions described for Example 72, Part B to give the title compound (114 mg, 51%).

Part C. Preparation of 1-(3-tert-butyl-4-methoxy-5-(1-(methylsulfonyl)indolin-5-yl)phenyl)pyrimidine-2,4(1H,3H)-dione The product from Example C (58 mg, 0.145 mmol) and the product from Part B (56.2 mg, 0.174 mmol) were subjected to the conditions described for Example 72, Part C to give the title compound as a colorless solid (12 mg, 18%). ¹H NMR (300 MHz, DMSO-$d_6$): δ 11.40 (d, J=1.84 Hz, 1H) 7.76 (d, J=7.72 Hz, 1H) 7.53-7.67 (m, 1H) 7.45 (s, 1H) 7.32-7.41 (m, 2H) 7.23 (dd, J=13.60, 2.57 Hz, 2H) 5.63 (dd, J=8.09, 2.21 Hz, 1H) 3.99 (t, J=8.46 Hz, 2H) 3.29 (s, 3H) 3.18 (t, J=8.46 Hz, 2H) 3.04 (s, 3H).

Example 98

Preparation of N-(6-(3-tert-butyl-5-(2,4-dioxo-3,4-dihydropyrimidin-1(2H)-yl)-2-methoxyphenyl)quinoxalin-2-yl)methanesulfonamide (compound IB-L0-2.26)

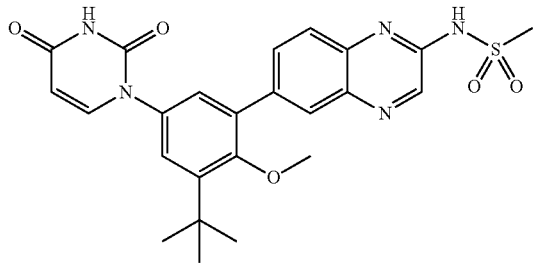 [SMILES: COc1c(-c2ccc3nc(NS(C)(=O)=O)cnc3c2)cc(-n2ccc(=O)[nH]c2=O)cc1C(C)(C)C]

Part A. Preparation of N-(4-bromo-2-nitrophenyl)-3-oxobutanamide

A solution of diketene (0.32 ml, 4.15 mmol) in toluene (2 ml) was added to an 80° C. solution of 4-bromo-2-nitroaniline (900 mg, 4.15 mmol) in toluene (7 ml) and the solution was heated at reflux for 5 h. Triethylamine (0.58 ml, 4.15 mmol) in toluene (2 ml) was added and refluxing was continued for 30 min. The cooled solution was concentrated in vacuo and the crude product purified by column chromatography on silica gel eluting with 2:1 hexane/EtOAc to give the title compound as a yellow solid (920 mg, 74%).

Part B. Preparation of 6-bromoquinoxalin-2(1H)-one

To a solution of sodium hydroxide (337 mg, 8.4 mmol) in H₂O (2.1 ml) was added the product from Part A (423 mg, 1.4 mmol) and stirring was continued at 65° C. for 1 h. The cooled solution was diluted with H₂O (4 ml) and sodium borohydride (31.9 mg, 0.84 mmol) was added and stirring was continued at room temperature for 1.5 h. Ice was added to the solution followed by dropwise addition of 6N HCl until acidic. The resulting solid was collected by filtration, washed with H₂O, and dried in a vacuum oven to give the title compound (273 mg, 86%).

Part C. Preparation of 6-bromo-2-chloroquinoxaline

To a flask containing phosphorus oxychloride (3.4 ml, 36.5 mmol) was added the product from Part B (255 mg, 1.1 mmol) and the solution was heated at 60° C. overnight. The solution was cooled to room temperature, poured over ice and the resulting solid collected by filtration to give the title compound (239 mg, 87%).

Part D. Preparation of 6-bromo-N-(4-methoxybenzyl)quinoxalin-2-amine

To a solution of the product from Part C (2.8 g, 11.5 mmol) in ethanol (58 ml) was added (4-methoxyphenyl)methanamine (7.5 ml, 57.5 mmol) and the solution was stirred at room temperature for 1 h. Solvent was concentrated in vacuo and the crude product was purified by column chromatography on silica gel eluting with 20% EtOAc/hexane to give the title compound (1.97 g, 50%).

Part E. Preparation of N-(4-methoxybenzyl)-6-(4,4,5,5-tetramethyl-1,3,2-dioxaborolan-2-yl)quinoxalin-2-amine The product from Part D (500 mg, 1.45 mmol) was subjected to the conditions described for Example 72, Part B to give the title compound (378 mg, 66%).

Part F. Preparation of 1-(3-tert-butyl-4-methoxy-5-(2-(4-methoxybenzylamino)quinoxalin-6-yl)phenyl)pyrimidine-2,4(1H,3H)-dione The product from Part E (133 mg, 0.34 mmol) was subjected to the conditions described for Example 72, Part C to give the title compound (125 mg, 82%).

Part G. Preparation of N-(6-(3-tert-butyl-5-(2,4-dioxo-3,4-dihydropyrimidin-1(2H)-yl)-2-methoxyphenyl)quinoxalin-2-yl)methanesulfonamide To a solution of the product from Part F (87 mg, 0.16 mmol) in CH₂Cl₂ (1.6 ml) and H₂O (0.07 ml) was added DDQ (40.4 mg, 0.18 mmol) and stirred vigorously at room temperature for 1 h. The solution was filtered through Celite and the dark solid collected on the Celite was dissolved in 5 ml CH₃OH. The methanol solution was filtered, solvent removed in vacuo and the crude intermediate was dissolved in pyridine (0.6 ml). Methanesulfonyl chloride (1.1 ul, 0.14 mmol) was added and the solution was heated at 60° C. overnight. The cooled solution was concentrated in vacuo and the crude product was purified by column chromatography on silica gel eluting with 2% CH₃OH/CHCl₃ to give the title compound (7.7 mg, 12%). ¹H NMR (300 MHz, CDCl₃) δ 8.42 (s, 1H) 8.29 (s, 1H) 8.13 (s, 1H) 7.88 (d, 1H) 7.54 (s, 1H) 7.19-7.43 (m, 4H) 5.83 (dd, J=7.91, 2.39 Hz, 1H) 3.32 (s, 3H) 3.27 (s, 3H) 1.46 (s, 9H).

Example 99

Preparation of N-(5-(3-tert-butyl-5-(2,4-dioxo-3,4-dihydropyrimidin-1(2H)-yl)-2-methoxyphenyl)-2,3-dihydro-1H-inden-1-yl)methanesulfonamide (compound IB-L0-2.44)

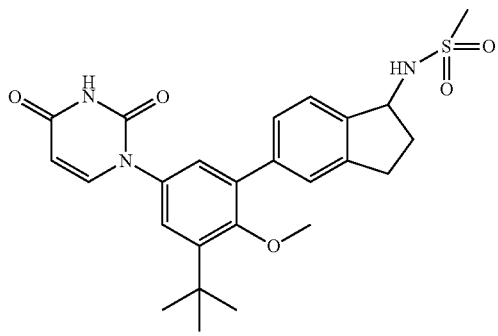 [SMILES: COc1c(-c2ccc3c(c2)CCC3NS(C)(=O)=O)cc(-n2ccc(=O)[nH]c2=O)cc1C(C)(C)C]

Part A. Preparation of 5-bromo-2,3-dihydro-1H-inden-1-ol

A suspension of 5-bromo-2,3-dihydro-1H-inden-1-one (2.07 g, 9.81 mmol) in ethanol (49 mL) was treated with the sodium borohydride (186 mg, 4.90 mmol) all at once. After a few minutes, the solution warmed slightly and all solids dissolved. After stirring at room temperature for 1 h, the mixture was concentrated in vacuo to remove ethanol. The gum obtained was partitioned between ethyl acetate and water. The organic layer was extracted with saturated sodium bicarbonate solution (2×) and saturated sodium chloride solution. Drying ($Na_2SO_4$) and concentration in vacuo afforded the title compound (3.05 g, 98%) as a colorless oil, which crystallized upon pumping under high vacuum overnight.

Part B. Preparation of 1-azido-5-bromo-2,3-dihydro-1H-indene

A solution of the product from Part A (1.01 g, 4.73 mmol) in toluene (8.1 mL) was treated with the diphenyl phosphoroyl azide (1.23 mL, 1.56 g, 5.67 mmol) followed by cooling to 0° C. The solution was treated dropwise with DBU (855 μL, 863 mg, 5.67 mmol) followed by stirring at 0° C. for 2 h, and then warming to room temperature for 48 h. The mixture was diluted with ethyl acetate and extracted with water and 1 M citric acid solution, and then with saturated sodium chloride solution. Drying ($Na_2SO_4$) and concentration in vacuo afforded a brown oil, which was purified by flash chromatography, eluting with 5-50% ethyl acetate in hexanes. These procedures afforded the title compound (889 mg, 79%) as a light yellow oil.

Part C. Preparation of 5-bromo-2,3-dihydro-1H-inden-1-amine

To a −15° C. solution of 1M lithium aluminum hydride in THF (0.84 ml, 0.84 mmol) in THF (0.88 ml) was added dropwise a solution of the product from Part B (200 mg, 0.84 mmol) and the solution was warmed to room temperature and stirred overnight. The solution was cooled to −10° C. and 4:1 THF:$H_2O$ (0.5 ml) was added dropwise. The solution was stirred at room temperature for 4 h, filtered through Celite and the filtrate concentrated in vacuo to give the title compound (151 mg, 85%).

Part D. Preparation of N-(5-bromo-2,3-dihydro-1H-inden-1-yl)methanesulfonamide To a solution of the product from Part C (150 mg, 0.71 mmol) in pyridine (3.5 ml) was added methanesulfonyl chloride (61 ul, 0.78 mmol) and the solution was stirred at room temperature overnight. The solution was concentrated in vacuo and the crude product was purified by column chromatography on silica gel eluting with 20% EtOAc/hexane to give the title compound (111 mg, 54%).

Part E. Preparation of N-(5-(3-tert-butyl-5-(2,4-dioxo-3,4-dihydropyrimidin-1(2H)-yl)-2-methoxyphenyl)-2,3-dihydro-1H-inden-1-yl)methanesulfonamide The product from Part D (109 mg, 0.38 mmol) was subjected to the conditions described for Example 72, Part B and Part C to give the title compound (39 mg, 60%). $^1$H NMR (300 MHz, DMSO-$d_6$) δ 11.39 (d, J=1.84 Hz, 1H) 7.77 (d, J=7.72 Hz, 1H) 7.58 (d, J=8.82 Hz, 1H) 7.39-7.48 (m, 3H) 7.27 (d, J=2.57 Hz, 1H) 7.19-7.23 (m, 1H) 5.63 (dd, J=8.09, 2.21 Hz, 1H) 4.86 (q, J=7.97 Hz, 1H) 3.27 (s, 3H) 3.04 (s, 3H) 2.90-3.01 (m, 1H) 2.71-2.90 (m, 1H) 2.52-2.62 (m, 1H) 1.85-1.98 (m, 1H) 1.40 (s, 9H).

Example 100

Preparation of N-((5-(3-tert-butyl-5-(2,4-dioxo-3,4-dihydropyrimidin-1(2H)-yl)-2-methoxyphenyl)-2,3-dihydro-1H-inden-1-yl)methyl)methanesulfonamide (compound IB-L0-2.17)

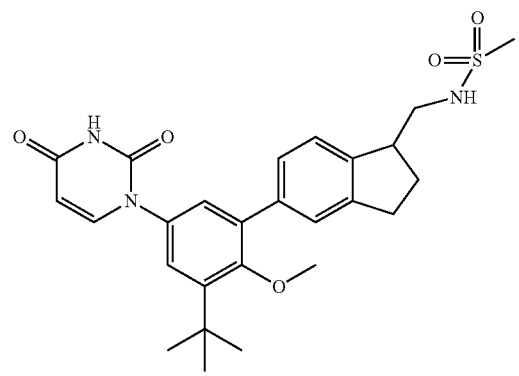 [SMILES: COc1c(-c2ccc3c(c2)CCC3CNS(C)(=O)=O)cc(-n2ccc(=O)[nH]c2=O)cc1C(C)(C)C]

Part A. Preparation of (E)-5-bromo-1-(methoxymethylene)-2,3-dihydro-1H-indene To a suspension of (methoxymethyl)triphenylphosphonium chloride (39.7 g, 116 mmol) in THF (210 ml) at −20° C. was added dropwise 1M potassium t-butoxide (95 ml, 95 mmol) and the solution stirred at −20° C. for 20 min. To this solution was added dropwise a solution of 5-bromo-2,3-dihydro-1H-inden-1-one (10.0 g, 47.4 mmol) in THF (230 ml) and stirring was continued at −20° C. for 30 min then warmed to room temperature and stirred for 2 h. The solution was filtered through Celite and the filtrate was concentrated in vacuo to give crude product which was purified by chromatography on a silica gel cartridge eluting with CH$_2$Cl$_2$/hexane to give the title compound (10.56 g, 93%).

Part B. Preparation of 5-bromo-2,3-dihydro-1H-indene-1-carbaldehyde

To a solution of the product from Part A (1.44 g, 6.0 mmol) in CH$_2$Cl$_2$ (30 ml) at −78° C. was added dropwise 1M boron tribromide in CH$_2$Cl$_2$ (13.8 ml, 13.8 mmol) and stirring was continued at −78° C. for 4 h. The solution was poured into an ice-saturated. sodium bicarbonate mixture and stirred vigorously. The layers were separated and the aqueous layer was extracted with CH$_2$Cl$_2$ (2×), the organic extracts were combined, dried (Na$_2$SO$_4$), and concentrated in vacuo to give crude product which was purified by column chromatography on silica gel eluting with 10% EtOAc/hexane to give the title compound (604 mg, 45%).

Part C. Preparation of 1-(5-bromo-2,3-dihydro-1H-inden-1-yl)-N-(4-methoxybenzyl)-methanamine To a solution of the product from Part B (300 mg, 1.3 mmol) in CH$_3$OH (18.5 ml) was added 4-methoxybenzylamine (0.17 ml, 1.3 mmol) and decaborane (49 mg, 0.4 mmol) and stirring was continued at room temperature for 1 h, solvent was concentrated in vacuo and the crude product was purified by column chromatography on silica gel eluting with 3% CH$_3$OH/CHCl$_3$ to give the title compound (264 mg, 57%).

Part D. Preparation of N-((5-bromo-2,3-dihydro-1H-inden-1-yl)methyl)-N-(4-methoxy-benzyl)methanesulfonamide To a solution of the product from Part C (88 mg, 0.25 mmol) in CH$_2$Cl$_2$ (1.0 ml) was added triethylamine (39 ul, 0.28 mmol) and methanesulfonyl chloride (22 ul, 0.28 mmol) and stirring was continued at room temperature for 1 h, solvent was concentrated in vacuo and the crude product was purified by column chromatography on silica gel eluting with EtOAc/hexane to give the title compound (55 mg, 51%).

Part E. Preparation of N-(4-methoxybenzyl)-N-((5-(4,4,5,5-tetramethyl-1,3,2-dioxaborolan-2-yl)-2,3-dihydro-1H-inden-1-yl)methyl)methanesulfonamide The product from Part D (1.15 g, 2.71 mmol) was subjected to the conditions described for Example 72, Part B to give the title compound (840 mg, 66%).

Part F. Preparation of N-((5-(3-tert-butyl-5-(2,4-dioxo-3,4-dihydropyrimidin-1(2H)-yl)-2-methoxyphenyl)-2,3-dihydro-1H-inden-1-yl)methyl)methanesulfonamide The product from Part E (840 mg, 2.1 mmol) was subjected to the conditions described for Example 72, Part C and the isolated material (1.28 g, 2.07 mmol) was dissolved in CH$_2$Cl$_2$ (10 ml) and trifluoroacetic acid (10 ml) was added slowly. After stirring at room temperature for 1 h, solvent was concentrated in vacuo and the crude product was suspended in 10% NaHCO$_3$, extracted with CH$_2$Cl$_2$ (3×), the organic extracts combined, dried (Na$_2$SO$_4$), and solvent concentrated in vacuo to give crude product which was purified by column chromatography on silica gel eluting with 2% CH$_3$OH/CHCl$_3$ to give title compound (0.84 g, 81%). $^1$H NMR (300 MHz, DMSO-d$_6$) δ 11.39 (s, 1H) 7.77 (d, J=8.09 Hz, 1H) 7.29-7.59 (m, 3H) 7.25 (d, J=2.94 Hz, 1H) 7.10-7.22 (m, 2H) 5.63 (dd, J=7.72, 1.84 Hz, 1H) 3.93 (s, 3H) 3.26 (s, 2H) 3.23-3.40 (m, 1H) 2.89 (s, 3H) 2.71-3.09 (m, 2H) 2.14-2.32 (m, 1H) 1.75-1.95 (m, 1H) 1.40 (s, 9H).

Example 101

Preparation of 5-(3-tert-butyl-5-(2,4-dioxo-3,4-dihydropyrimidin-1(2H)-yl)-2-methoxyphenyl)-N-(methylsulfonyl)-2,3-dihydro-1H-indene-1-carboxamide (compound IB-L0-2.34)

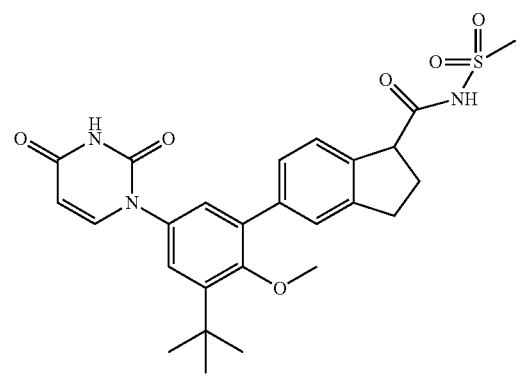 [SMILES: COc1c(-c2ccc3c(c2)CCC3C(=O)NS(C)(=O)=O)cc(-n2ccc(=O)[nH]c2=O)cc1C(C)(C)C]

Part A. Preparation of 5-bromo-2,3-dihydro-1H-indene-1-carboxylic acid

To a solution of the product from Example 100, Part B (300 mg, 1.3 mmol) and 2-methyl-2-pentene (8 ml) in tert-butanol (32 ml) was added a solution of sodium chlorite (1.36 g, 0.12 mmol) in H$_2$O (12 ml) containing sodium dihydrogen phosphate (1.07 g, 8.9 mmol) and the mixture was stirred vigorously for 20 min at room temperature. Solvents were concentrated in vacuo and the residue was diluted with H$_2$O, extracted with EtOAc (3×), extracts combined, dried (Na$_2$SO$_4$), and concentrated in vacuo to give the title compound (180 mg, 56%).

Part B. Preparation of 5-bromo-N-(methylsulfonyl)-2,3-dihydro-1H-indene-1-carboxamide To a solution of the product from Part A (100 mg, 0.42 mmol) in CH$_2$Cl$_2$ (1.7 ml) was added carbonyldiimidazole (67.3 mg, 0.42 mmol) and the reaction was stirred for 2 h at room temperature. Methanesulfonamide (39.5 mg, 0.42 mmol) and DBU (62.5 mg, 0.42 mmol) were added and stirring was continued at room temperature for 2 h. Solution was diluted with CH$_2$Cl$_2$, washed 1N HCl, brine, dried (Na$_2$SO$_4$), concentrated in vacuo and the crude product was purified by column chromatography on silica gel eluting with 20% EtOAc/hexane to give the title compound (121 mg, 92%).

Part C. Preparation of N-(methylsulfonyl)-5-(4,4,5,5-tetramethyl-1,3,2-dioxaborolan-2-yl)-2,3-dihydro-1H-indene-1-carboxamide The product from Part B (159 mg, 0.5 mmol) was subjected to the conditions described for Example 72, Part B to give the title compound (144 mg, 79%).

Part D. Preparation of 5-(3-tert-butyl-5-(2,4-dioxo-3,4-dihydropyrimidin-1(2H)-yl)-2-methoxyphenyl)-N-(methylsulfonyl)-2,3-dihydro-1H-indene-1-carboxamide The product from Part C (134 mg, 0.34 mmol) was subjected to the conditions described for Example 72, Part C to give title compound (14 mg, 8%). $^1$H NMR (300 MHz, CDCl$_3$) δ 8.11 (m, 1H) 7.08-7.57 (m, 7H) 5.80 (dd, J=7.91, 2.39 Hz, 1H) 4.07 (dd, J=9.01, 6.07 Hz, 1H) 3.33 (s, 3H) 3.08 (s, 3H) 2.91-3.22 (m, 1H) 2.35-2.74 (m, 1H) 1.44 (s, 9H) 1.17-1.34 (m, 1H) 0.60-1.00 (m, 1H).

Example 102

Preparation of 1-(3-(2-aminobenzo[d]thiazol-6-yl)-5-tert-butyl-4-methoxy-phenyl)pyrimidine-2,4(1H,3H)-dione (compound IB-L0-2.39)

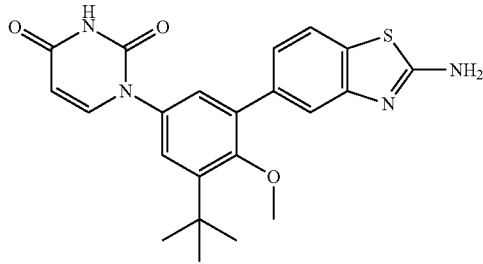 [SMILES: COc1c(-c2ccc3sc(N)nc3c2)cc(-n2ccc(=O)[nH]c2=O)cc1C(C)(C)C]

The title compound was prepared using the procedures described for the preparation of Example 83, substituting 5-bromo[d]thiazol-2-amine for 6-bromobenzo[d]thiazol-2-amine $^1$H NMR (300 MHz, DMSO-d$_6$) δ 11.40 (d, J=1.84 Hz, 1H) 8.40 (s, 2H) 7.84 (d, J=8.09 Hz, 1H) 7.78 (d, J=7.72 Hz, 1H) 7.54 (d, J=1.47 Hz, 1H) 7.27-7.32 (m, 3H) 5.64 (dd, J=8.09, 2.21 Hz, 1H) 3.27 (s, 3H) 1.41 (s, 9H).

Example 103

Preparation of N-(2-(5-(3-tert-butyl-5-(2,4-dioxo-3,4-dihydropyrimidin-1(2H)-yl)-2-methoxyphenyl)-2,3-dihydro-1H-inden-1-yl)propan-2-yl)methanesulfonamide (compound IB-L0-2.29)

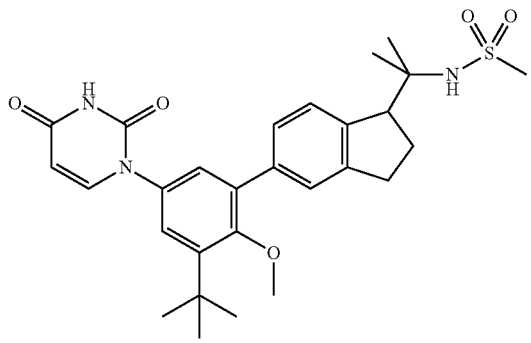 [SMILES: COc1c(-c2ccc3c(c2)CCC3C(C)(C)NS(C)(=O)=O)cc(-n2ccc(=O)[nH]c2=O)cc1C(C)(C)C]

To a solution of the product from Example 75, Part D (20 mg, 0.038 mmol) in 1:1 benzene:MeOH (0.6 ml) was added platinum(IV) oxide (1 mg). The resulting mixture was stirred under 1 atm H$_2$ at room temperature for 1 h, and then filtered thru celite, and concentrated in vacuo. The crude product was purified by column chromatography on silica gel using 3% MeOH in CHCl$_3$ as the eluent to give the title compound as a solid (14 mg, 70%). $^1$H NMR (300 MHz, DMSO-d$_6$) δ 11.39 (s, 1H) 7.77 (d, J=7.72 Hz, 1H) 7.58 (d, J=8.09 Hz, 1H) 7.28-7.38 (m, 2H) 7.21-7.26 (m, 2H) 7.07 (s, 1H) 5.63 (d, J=7.72 Hz, 1H) 3.61 (dd, J=8.64, 5.33 Hz, 1H) 3.25 (s, 3H) 3.00 (s, 3H) 2.75-2.98 (m, 2H) 1.97-2.21 (m, 2H) 1.40 (s, 9H) 1.24 (d, J=8.46 Hz, 6H).

Example 104

Preparation of (S)—N-(2-(5-(3-tert-butyl-5-(2,4-dioxo-3,4-dihydropyrimidin-1(2H)-yl)-2-methoxyphenyl)-2,3-dihydro-1H-inden-1-yl)propan-2-yl)methanesulfonamide (compound IB-L0-2.22)

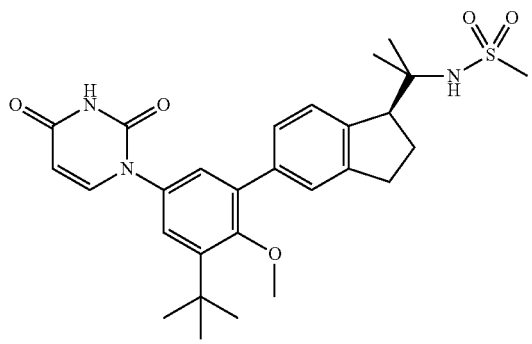 [SMILES: COc1c(-c2ccc3c(c2)CC[C@@H]3C(C)(C)NS(C)(=O)=O)cc(-n2ccc(=O)[nH]c2=O)cc1C(C)(C)C]

The product from Example 103 (10 mg) was subjected to chiral chromatography (Chiralpak AD-H column; eluting with 1:3 2-PrOH:hexanes (0.1% TFA)). Isolation of the earlier eluting component gave the title compound (4.4 mg). $^1$H NMR identical to the product from Example 103.

Example 105

Preparation of (R)—N-(2-(5-(3-tert-butyl-5-(2,4-dioxo-3,4-dihydropyrimidin-1(2H)-yl)-2-methoxyphenyl)-2,3-dihydro-1H-inden-1-yl)propan-2-yl)methanesulfonamide (compound IB-L0-2.37)

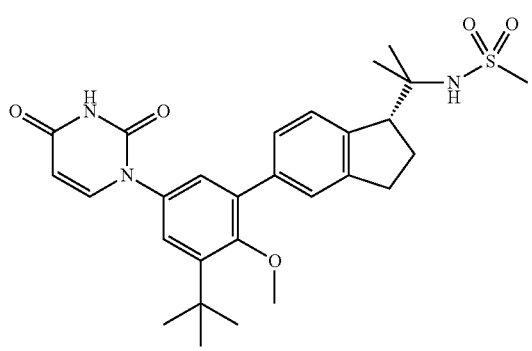 [SMILES: COc1c(-c2ccc3c(c2)CC[C@H]3C(C)(C)NS(C)(=O)=O)cc(-n2ccc(=O)[nH]c2=O)cc1C(C)(C)C]

The product from Example 103 (10 mg) was subjected to chiral chromatography (Chiralpak AD-H column; eluting with 1:3 2-PrOH:hexanes(0.1% TFA)). Isolation of the later

Example 106

Preparation of (S)—N-((5-(3-tert-butyl-5-(2,4-dioxo-3,4-dihydropyrimidin-1(2H)-yl)-2-methoxyphenyl)-2,3-dihydro-1H-inden-1-yl)methyl)methanesulfonamide (compound IB-L0-2.9)

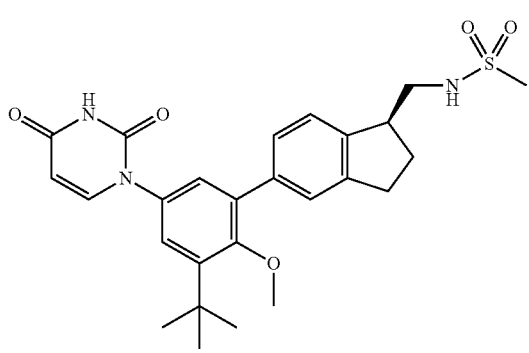 [SMILES: COc1c(-c2ccc3c(c2)CC[C@@H]3CNS(C)(=O)=O)cc(-n2ccc(=O)[nH]c2=O)cc1C(C)(C)C]

The product from Example 100, Part F (20 mg) was subjected to chiral chromatography (Chiralpak AD-H column; eluting with 1:4 2-PrOH:hexanes(0.1% TFA)). Isolation of the earlier eluting component gave the title compound (5.3 mg). $^1$H NMR identical to the product from Example A-100, Part F.

Example 107

Preparation of (R)—N-((5-(3-tert-butyl-5-(2,4-dioxo-3,4-dihydropyrimidin-1(2H)-yl)-2-methoxyphenyl)-2,3-dihydro-1H-inden-1-yl)methyl)methanesulfonamide (compound IB-L0-2.15)

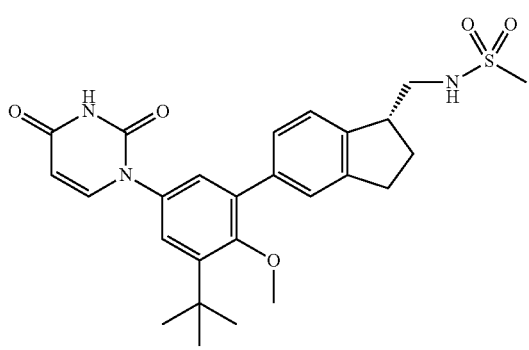 [SMILES: COc1c(-c2ccc3c(c2)CC[C@H]3CNS(C)(=O)=O)cc(-n2ccc(=O)[nH]c2=O)cc1C(C)(C)C]

The product from Example 100, Part F (20 mg) was subjected to chiral chromatography (Chiralpak AD-H column; eluting with 1:4 2-PrOH:hexanes(0.1% TFA)). Isolation of the later eluting component gave the title compound (5.7 mg). $^1$H NMR identical to product from Example 100, Part F.

Example 108

Preparation of (S)—N-((5-(3-tert-butyl-5-(2,4-dioxo-3,4-dihydropyrimidin-1(2H)-yl)-2-methoxyphenyl)-1-fluoro-2,3-dihydro-1H-inden-1-yl)methyl)methanesulfonamide (compound IB-L0-2.20)

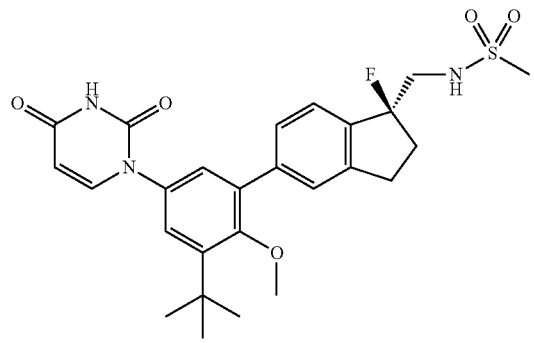 [SMILES: COc1c(-c2ccc3c(c2)CC[C@@]3(F)CNS(C)(=O)=O)cc(-n2ccc(=O)[nH]c2=O)cc1C(C)(C)C]

The product from Example 91, Part H was subjected to the conditions described in Example 104 to give the title compound. $^1$H NMR identical to the product from Example 91, Part H.

Example 109

Preparation of (R)—N-((5-(3-tert-butyl-5-(2,4-dioxo-3,4-dihydropyrimidin-1(2H)-yl)-2-methoxyphenyl)-1-fluoro-2,3-dihydro-1H-inden-1-yl)methyl)methanesulfonamide (compound IB-L0-2.10)

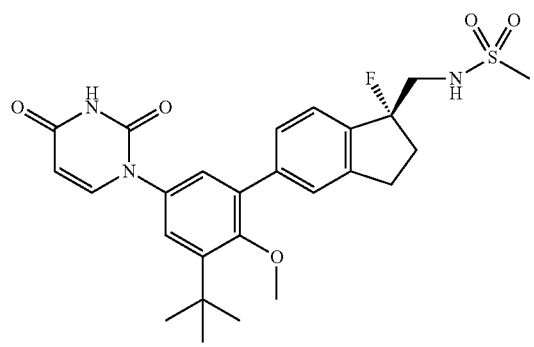 [SMILES: COc1c(-c2ccc3c(c2)CC[C@]3(F)CNS(C)(=O)=O)cc(-n2ccc(=O)[nH]c2=O)cc1C(C)(C)C]

The product from Example 91, Part H was subjected to the conditions described in Example 104 to give the title compound. $^1$H NMR identical to the product from Example 91, Part H.

Example 110

Preparation of N-(6-(5-(2,4-dioxo-3,4-dihydropyrimidin-1(2H)-yl)-2-methoxy-3-tert-pentylphenyl)naphthalen-2-yl)methanesulfonamide (compound IB-L0-2.52)

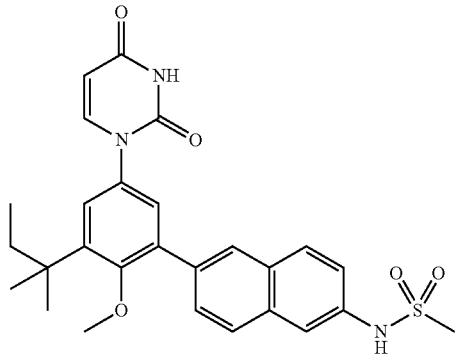 [SMILES: CCC(C)(C)c1cc(-n2ccc(=O)[nH]c2=O)cc(-c2ccc3cc(NS(C)(=O)=O)ccc3c2)c1OC]

Part A. Preparation of 1-(3-tert-butyl-5-iodo-4-methoxyphenyl)pyrimidine-2,4(1H,3H)-dione 2-tert-Amylphenol (5.0 g, 30 mmol) was reacted according to the procedure from Example C, Part A, Part B, and Part C to provide the title product as a colorless solid. (6.7 g, 56% overall yield for 3 steps).

Part B. Preparation of N-(6-(5-(2,4-dioxo-3,4-dihydropyrimidin-1(2H)-yl)-2-methoxy-3-tert-pentylphenyl)naphthalen-2-yl)methanesulfonamide The product from Part A (100 mg, 0.241 mmol), the product from Example 4A, Part B (92 mg, 0.266 mmol), sodium carbonate (38.4 mg, 0.362 mmol) and 1,1'-bis(diphenylphosphino)ferrocene-palladium(II)dichloride dichloromethane complex (9.9 mg, 0.012 mmol) were dissolved in a toluene (4 mL) and ethanol (4 mL) solvent mixture which was sparged with nitrogen for 10 min, then the mixture heated to 85° C. for 18 h. To the solution was then added $CH_2Cl_2$ (20 mL) followed by 1N aqueous HCl (10 mL), the organic layer separated 3-mercaptopropyl silica gel (100 mg) and magnesium sulfate added. The solution was concentrated and purified by column chromatography on silica gel using 3% MeOH in $CH_2Cl_2$ as the eluent to provide the title compound as a colorless solid (7.1 mg, 58%). $^1$H NMR (300 MHz, DMSO-$d_6$): δ 11.41(s, 1H), 10.04 (s, 1H), 8.03 (s, 1H), 7.95 (t, J=8.7 Hz, 2H), 7.79 (d, J=7.7 Hz, 1H), 7.73 (d, J=1.8 Hz, 1H), 7.69 (dd, J=8.8, 1.6 Hz, 1H), 7.42 (dd, J=8.8, 2.2 Hz, 1H), 7.37 (d, J=2.6 Hz, 1H), 7.25 (d, J=2.6 Hz, 1H), 5.65 (dd, J=8.1, 1.6 Hz, 1H), 3.22 (s, 3H), 3.08 (s, 3H), 1.84 (m, 2H), 1.38 (s, 6H), 0.73 (t, J=7.5 Hz, 3H).

Example 111

Preparation of N-((6-(3-tert-butyl-5-(2,4-dioxo-3,4-dihydropyrimidin-1(2H)-yl)-2-methoxyphenyl)-1H-inden-3-yl)methyl)-N-methylmethanesulfonamide (compound IB-L0-2.16)

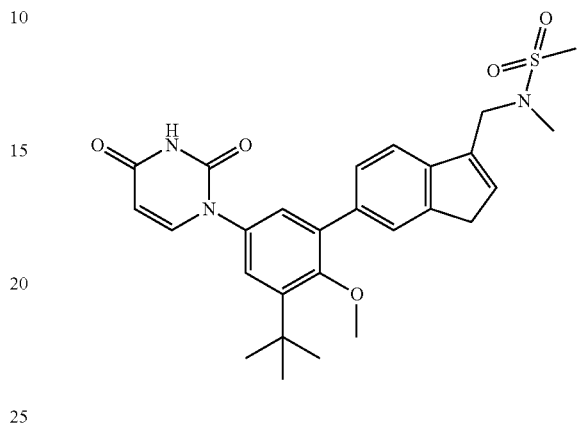

Part A. Preparation of N-methyl-N-((6-(4,4,5,5-tetramethyl-1,3,2-dioxaborolan-2-yl)-1H-inden-3-yl)methyl)methanesulfonamide To a solution of the product from Example 79, Part E (210 mg, 0.60 mmol) in anhydrous THF (5 ml) was added a 1.0M solution of lithium bis(trimethylsilyl)amide in toluene (0.60 ml, 0.60 mmol), and the resulting mixture was stirred at room temperature for 5 min. Iodomethane (0.075 ml, 1.20 mmol) was added and the mixture was stirred at room temperature for 2 h, and was partitioned between ethyl acetate and water. The organic layer was washed with brine, dried with sodium sulfate, filtered and concentrated in vacuo. The residue was purified by column chromatography on silica gel eluting with a gradient of ethyl acetate/in hexane (10% to 25%) to give the title compound as a solid (125 mg, 57%).

Part B. Preparation of N-((6-(3-tert-butyl-5-(2,4-dioxo-3,4-dihydropyrimidin-1(2H)-yl)-2-methoxyphenyl)-1H-inden-3-yl)methyl)-N-methylmethanesulfonamide A mixture of the product from Example C (60.0 mg, 0.15 mmol), the product of Part A (54.5 mg, 0.15 mmol), potassium phosphate (66.9 mg, 0.315 mmol), PA-Ph (CAS 97739-46-3, 1.32 mg, 4.5 mmol) and tris(dibenzylideneacetone)dipalladium(0) (1.37 mg, 1.5 mmol) in tetrahydrofuran (3.0 ml) and water (1.0 ml) was purged with $N_2$ for 30 min. The mixture was stirred at 50° C. for 2 h, and then partitioned between ethyl acetate and 1M HCl. The organic layer was washed with saturated sodium bicarbonate, brine, dried with sodium sulfate, and filtered. The filtrate was treated with 3-mercaptopropyl functionalized silica gel, filtered through celite and concentrated in vacuo. The crude product was purified by column chromatography on C-18 reversed-phase silica gel using a solvent gradient of 10-100% acetonitrile in water (0.1% TFA) to give the title compound as a solid (19 mg, 24%). $^1$H NMR (300 MHz, DMSO-$d_6$) δ 11.40 (d, J=1.84 Hz, 1H) 7.78 (d, J=7.72 Hz, 1H) 7.65 (m, 2H) 7.49 (dd, J=7.72, 1.47 Hz, 1H) 7.26 (m, 2.57 Hz, 2H) 6.63 (s, 1H) 5.64

(dd, J=7.72, 2.21 Hz, 1H) 4.26 (s, 2H) 3.51 (s, 2H) 3.26 (s, 3H) 3.01 (s, 3H) 2.72 (s, 3H) 1.41 (s, 9H).

Example 112

Preparation of N-((6-(3-tert-butyl-5-(2,4-dioxo-3,4-dihydropyrimidin-1(2H)-yl)-2-methoxyphenyl)benzo[b]thiophen-2-yl)methyl)methanesulfonamide (compound IB-L0-2.40)

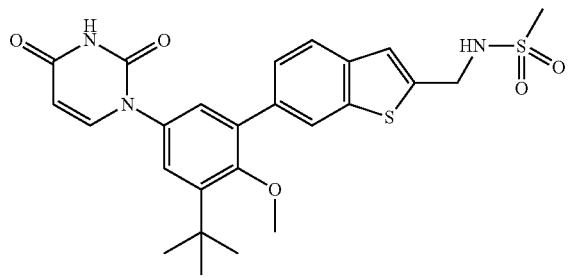 [SMILES: COc1c(-c2ccc3cc(CNS(C)(=O)=O)sc3c2)cc(-n2ccc(=O)[nH]c2=O)cc1C(C)(C)C]

Part A. Preparation of ethyl 6-bromobenzo[b]thiophene-2-carboxylate

To a solution of 4-bromo-2-fluorobenzaldehyde (1.02 g, 4.83 mmol) in DMSO (4 mL), was added ethyl 2-mercaptoacetate (0.58 mL, 5.31 mmol), followed by Et$_3$N (1.35 mL, 9.65 mmol), and the mixture was heated at 80° C. for 3 h. The resulting dark mixture was poured into water (50 mL) and extracted with EtOAc (2×50 mL). The combined organic extracts were washed with 10% NaCl, dried over anhydrous Na$_2$SO$_4$, filtered and concentrated in vacuo to give the title compound as a light yellow waxy solid (1.29 g, 94%).

Part B. Preparation of (6-bromobenzo[b]thiophen-2-yl)methanol

To a solution of the product from Part A (0.82 g, 2.88 mmol) in Et$_2$O (20 mL) at 0° C. was added a 1M solution of lithium aluminum hydride in Et$_2$O (3.16 mL, 3.16 mmol) dropwise, and the resulting slurry was stirred between 5-10° C. for 1 h. The slurry was treated with 0.3 mL H$_2$O, 0.3 mL 15% aq NaOH, 0.7 mL H$_2$O, stirred 30 min, filtered and concentrated in vacuo to give the title compound as a colorless solid (0.58 g, 83%).

Part C. Preparation of 6-bromo-2-(bromomethyl)benzo[b]thiophene

A mixture of the product from Part B (85 mg, 0.35 mmol), N-bromosuccinimide (74 mg, 0.413 mmol) and triphenylphosphine (106 mg, 0.403 mmol) in CH$_2$Cl$_2$ (2 mL) was stirred at room temperature for 2 h. The reaction mixture was diluted with 50 mL CH$_2$Cl$_2$, washed with water, 10% NaHCO$_3$ and 10% NaCl, dried over anhydrous mgSO$_4$, filtered and concentrated in vacuo. The residue was purified by column chromatography on silica gel eluting with 9:1 hexane:EtOAc to yield the title compound as a white solid (96 mg, 89%).

Part D. Preparation of N-(4-methoxybenzyl)methanesulfonamide

To a solution of (4-methoxyphenyl)methanamine (1.317 g, 9.60 mmol) in CH$_2$Cl$_2$ (10 mL) was added methanesulfonyl chloride (0.34 mL, 4.36 mmol) dropwise. The mixture was stirred at room temperature for 2 h. The reaction mixture was diluted with 50 mL CH$_2$Cl$_2$ washed with 1N H$_3$PO$_4$, 10% NaCl, dried over anhydrous mgSO$_4$, filtered and concentrated in vacuo to give the title compound as a white solid (0.84 g, 89%).

Part E. Preparation of N-((6-bromobenzo[b]thiophen-2-yl)methyl)-N-(4-methoxybenzyl)-methanesulfonamide A solution of the product from Part D (0.223 g, 1.037 mmol) in EtOH (2 mL) and 1.0M NaOH (1.1 mL, 1.1 mmol) was added to a slurry containing the product from Part C (0.317 g, 1.037 mmol) in EtOH (4 mL). The resulting slurry was heated at reflux for 1 h, and then concentrated in vacuo to give a pasty solid. The residue was partitioned between 40 mL water and 40 mL EtOAc. The organic layer was washed with 1N H$_3$PO$_4$, 10% NaHCO$_3$, 10% NaCl, dried over anhydrous Na$_2$SO$_4$, filtered and concentrated in vacuo leaving a yellow oil. The crude product was purified by column chromatography on silica gel eluting with CH$_2$Cl$_2$ to give the title compound as a colorless solid (0.15 g, 33%).

Part F. Preparation of N-(4-methoxybenzyl)-N-((6-(4,4,5,5-tetramethyl-1,3,2-dioxaborolan-2-yl)benzo[b]thiophen-2-yl)methyl)methanesulfonamide The product from Part E (0.15 g, 0.34 mmol) was subjected to the conditions described for the preparation of Example 72, Part B to give the title compound as a colorless solid (0.121 g, 73%).

Part G. Preparation of N-((6-(3-tert-butyl-5-(2,4-dioxo-3,4-dihydropyrimidin-1(2H)-yl)-2-methoxyphenyl)benzo[b]thiophen-2-yl)methyl)-N-(4-methoxybenzyl)methanesulfonamide The product from Part F (24 mg, 0.049 mmol) was subjected to the conditions described for the preparation of Example 72, Part C to give the title compound as a colorless solid (20 mg, 65%).

Part H. Preparation of N-((6-(3-tert-butyl-5-(2,4-dioxo-3,4-dihydropyrimidin-1(2H)-yl)-2-methoxyphenyl)benzo[b]thiophen-2-yl)methyl)methanesulfonamide A solution of the product from Part G (14 mg, 0.022 mmol) in CH$_2$Cl$_2$ (0.3 mL) and TFA (0.3 mL) was stirred at room temperature for 4 h and then concentrated in vacuo. The residue was partitioned between 10 mL CH$_2$Cl$_2$ and 2 mL 10% aq. NaHCO$_3$ and the organic layer was concentrated in vacuo. The crude product was purified by column chromatography on silica gel eluting with 99:1 CH$_2$Cl$_2$:MeOH to give the title compound as a colorless solid (5 mg, 44%). $^1$H NMR (300 MHz, DMSO-d$_6$) δ 11.40 (s, 1H) 8.09 (s, 1H) 7.82-7.97 (m, 3H) 7.79 (d, J=7.72 Hz, 1H) 7.47-7.63 (m, 1H) 7.40 (s, 1H) 7.26-7.34 (m, 1H) 5.64 (d, J=7.72 Hz, 1H) 4.48 (d, J=5.88 Hz, 2H) 3.23 (s, 3H) 2.95 (s, 3H) 1.41 (s, 9H).

Example 113

Preparation of N-((6-(3-tert-butyl-5-(2,4-dioxo-3,4-dihydropyrimidin-1(2H)-yl)-2-methoxyphenyl)benzo[b]thiophen-3-yl)methyl)-N-methylmethanesulfonamide (compound IB-L0-2.21)

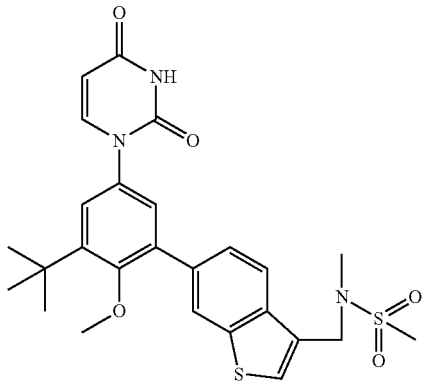 [SMILES: COc1c(-c2ccc3c(CN(C)S(C)(=O)=O)csc3c2)cc(-n2ccc(=O)[nH]c2=O)cc1C(C)(C)C]

Part A. Preparation of N-((6-bromobenzo[b]thiophen-3-yl)methyl)-N-methylmethanesulfonamide A mixture of the product from Example 76, Part D (0.100 g, 0.382 mmol), N-methylmethane-sulfonamide (45.9 mg, 0.421 mmol) and potassium carbonate (0.127 g, 0.918 mmol) in N,N-dimethylacetamide (5 mL). The mixture was stirred at 80° C. for 11 h, cooled to room temperature and partitioned between diethylether and water (3×), dried over mgSO$_4$, filtered and concentrated in vacuo to give the title compound as a colorless waxy solid (0.128 g, quant.).

Part B. Preparation of N-methyl-N-((6-(4,4,5,5-tetramethyl-1,3,2-dioxaborolan-2-yl)benzo[b]thiophen-3-yl)methyl)methanesulfonamide The product from Part A (0.128 g, 0.382 mmol) was subjected to the conditions described for the preparation of Example 72, Part B to give the title compound as a colorless, crystalline solid (0.120 g, 82%).

Part C. Preparation of N-((6-(3-tert-butyl-5-(2,4-dioxo-3,4-dihydropyrimidin-1(2H)-yl)-2-methoxyphenyl)benzo[b]thiophen-3-yl)methyl)-N-methylmethanesulfonamide The product from Part B (50.6 mg, 0.133 mmol) was subjected to the conditions described for the preparation of Example 79, Part F to give the title compound as a colorless solid (61.5 mg, 88%). $^1$H NMR (300 MHz, DMSO-d$_6$) δ 11.41 (s, 1H) 8.17 (d, J=1.47 Hz, 1H) 8.09 (d, J=8.09 Hz, 1H) 7.74-7.85 (m, 2H) 7.63 (dd, J=8.46, 1.47 Hz, 1H) 7.29-7.36 (m, 2H) 5.65 (d, J=7.72 Hz, 1H) 4.52 (s, 2H) 3.24 (s, 3H) 3.03 (s, 3H) 2.70 (s, 3H) 1.42 (s, 9H).

Example 114

Preparation of (E)-N-(4-(3-bromo-5-(2,4-dioxo-3,4-dihydropyrimidin-1(2H)-yl)-2-methoxystyryl)phenyl)methanesulfonamide (compound IB-L1-1.52)

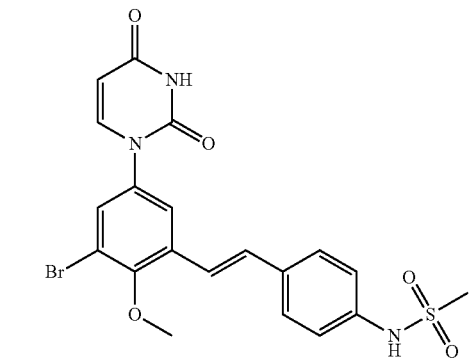 [SMILES: COc1c(Br)cc(-n2ccc(=O)[nH]c2=O)cc1/C=C/c1ccc(NS(C)(=O)=O)cc1]

Part A. Preparation of 2-bromo-4,6-diiodophenol

A 1 L round-bottom flask was charged with 2-bromophenol (8.65 g, 50 mmol) and methanol (100 ml) to give a colorless solution. Sodium hydroxide (2.40 g, 60.0 mmol) was added and stirred until the hydroxide pellets had dissolved. The solution was cooled in an ice water bath and sodium iodide (5.6 g, 37.4 mmol) was added followed by drop-wise addition of sodium hypochlorite (17 mL, 27.5 mmol) to give a transparent brown/red solution and gradual precipitation of a thick, white solid. The addition of sodium iodide and bleach was repeated 3 times to give an orange mixture that was stirred for 2 h, treated with a solution of sodium thiosulfate in water (20 g in 100 mL), stirred for 15 min and treated drop-wise with concentrated HCl to a constant pH of 1. The mixture was stirred for 15 min and filtered to collect a white solid that was washed repeatedly with water and dried to constant mass (14.7 g, 69%).

Part B. Preparation of 1-bromo-3,5-diiodo-2-methoxybenzene

A 500 mL round-bottom flask was charged with the product from Part A (14.7 g, 34.6 mmol), iodomethane (2.70 ml, 43.3 mmol), and sodium hydroxide (2.101 ml, 39.8 mmol) in acetone (96 ml) to give a tan solution. The mixture was stirred for 24 h and concentrated. The residue was dissolved in ethyl acetate, washed with water and saturated sodium chloride, dried over sodium sulfate, filtered and concentrated to give a white solid. The solid was recrystallized from hot hexane to give a white solid that was collected by filtration (12.3 g, 81%).

Part C. Preparation of 1-(3-bromo-5-iodo-4-methoxyphenyl)pyrimidine-2,4(1H,3H)-dione A 250 mL round-bottom flask was charged with the product from Part B (8.09 g, 18.44 mmol), pyrimidine-2,4(1H,3H)-dione (2.273 g, 20.28 mmol), N-(2-cyanophenyl)picolinamide (0.823 g, 3.69 mmol), copper (I) iodide (0.351 g, 1.844 mmol) and potassium phosphate (8.22 g, 38.7 mmol) in DMSO (70 ml). The mixture was sealed, sparged with nitrogen for 15 min and heated at 60° C. for 16 h. The mixture was partitioned with ethyl acetate and water. The organic layer was washed with 1M HCl, water, brine, dried with sodium sulfate, and filtered. The filtrate was treated with 3-mercaptopropyl functionalized silica gel (Aldrich catalog #538086), filtered through celite and evaporated to give an off-white solid (3.92 g, 50%).

Part D. Preparation of (E)-N-(4-(3-bromo-5-(2,4-dioxo-3,4-dihydropyrimidin-1(2H)-yl)-2-methoxystyryl)phenyl)methanesulfonamide To a 100 ml round-bottom flask was added the product from Part C (846 mg, 2.0 mmol), the product from Example 41B, Part B (482 mg, 2.000 mmol), potassium phosphate (892 mg, 4.20 mmol), 1,3,5,7-tetramethyl-6-phenyl-2,4,8-trioxa-6-phosphaadamante (PA-Ph) (CAS 97739-46-3) (17.54 mg, 0.060 mmol) and tris(dibenzylideneacetone)dipalladium(0) (18.31 mg, 0.020 mmol) in THF (12.0 ml) and water (4.0 ml). The flask was sealed and the mixture was sparged with nitrogen for 5 min and stirred at ambient temperature for 72 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was triturated with a minimal amount of methanol/CH$_2$Cl$_2$ to give the title compound as a white solid (595 mg, 60%). $^1$H NMR (300 MHz, DMSO-d$_6$) δ ppm 3.03 (s, 3H) 3.82 (s, 3H) 5.69 (dd, J=7.72, 1.50 Hz, 1H) 7.24 (d, J=8.46 Hz, 2H) 7.35 (m, 2H) 7.61 (d, J=8.46 Hz, 2H) 7.69 (d, J=2.21 Hz, 1H) 7.78 (d, J=8.09 Hz, 1H) 7.87 (d, J=2.21 Hz, 1H) 9.90 (s, 1H) 11.50 (s, 1H). MS (ESI−) m/z 490,492 (M−H)$^+$.

Example 115

Preparation of (E)-N-(4-(5-(2,4-dioxo-3,4-dihydropyrimidin-1(2H)-yl)-2-methoxy-3-(thiophen-2-yl)styryl)phenyl)methanesulfonamide (compound IB-L1-1.48)

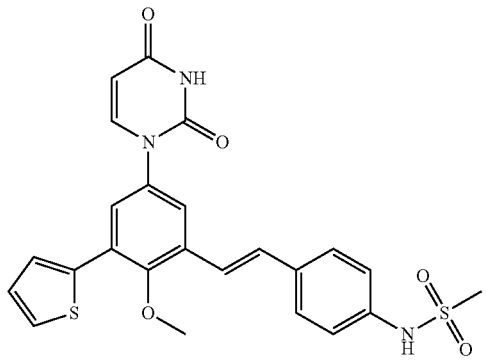 [SMILES: COc1c(/C=C/c2ccc(NS(C)(=O)=O)cc2)cc(-n2ccc(=O)[nH]c2=O)cc1-c1cccs1]

To a 5 ml microwave tube was added the product from Example 114, Part D (40 mg, 0.081 mmol), thiophen-2-ylboronic acid (10.40 mg, 0.081 mmol), 1,1'-bis(di-tert-butylphosphino)ferrocene palladium dichloride (2.65 mg, 4.06 mmol) and potassium phosphate (34.5 mg, 0.162 mmol) in THF (3.0 ml) and water (1.0 ml). The vessel was sealed and the mixture was sparged by nitrogen for 5 min and heated at 50° C. for 3 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered through celite and evaporated. The residue was purified by reverse phase chromatography to give the title compound as a white solid (20 mg, 50%). $^1$H NMR (300 MHz, DMSO-d$_6$) δ ppm 3.03 (s, 3H) 3.70 (s, 3H) 5.70 (dd, J=7.72, 2.21 Hz, 1H) 7.18 (dd, J=5.43, 4.05 Hz, 1H) 7.25 (d, J=8.82 Hz, 2H) 7.35 (s, 2H) 7.63 (d, J=8.82 Hz, 2H) 7.68 (m, 2H) 7.77 (m, 2H) 7.83 (d, J=7.72 Hz, 1H) 9.89 (s, 1H) 11.49 (d, J=2.21 Hz, 1H). MS (ESI+) m/z 496 (M+H)$^+$.

Example 116

Preparation of (E)-N-(4-(5-(2,4-dioxo-3,4-dihydropyrimidin-1(2H)-yl)-3-(furan-2-yl)-2-methoxystyryl)phenyl)methanesulfonamide (compound IB-L1-1.46)

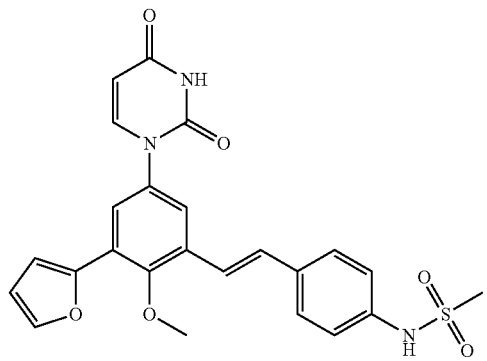 [SMILES: COc1c(/C=C/c2ccc(NS(C)(=O)=O)cc2)cc(-n2ccc(=O)[nH]c2=O)cc1-c1ccco1]

The title compound was prepared according to the procedure of Example 115 substituting furan-2-ylboronic acid for thiophen-2-ylboronic acid to give a white solid (22 mg, 56%). $^1$H NMR (300 MHz, DMSO-d$_6$) δ ppm 3.03 (s, 3H) 3.76 (s, 3H) 5.69 (d, J=7.72 Hz, 1H) 6.69 (dd, J=3.31, 1.84 Hz, 1H) 7.08 (d, J=2.57 Hz, 1H) 7.25 (d, J=8.46 Hz, 2H) 7.36 (m, 2H) 7.63 (d, J=8.82 Hz, 2H) 7.67 (d, J=2.57 Hz, 1H) 7.77 (d, J=2.57 Hz, 1H) 7.82 (m, J=7.72 Hz, 2H) 9.88 (s, 1H) 11.48 (s, 1H). MS (ESI+) m/z 497 (M+NH4)+.

Example 117

Preparation of (E)-N-(4-(5-(2,4-dioxo-3,4-dihydropyrimidin-1(2H)-yl)-2-methoxy-3-(pyridin-4-yl)styryl)phenyl)methanesulfonamide (compound IB-L1-1.55)

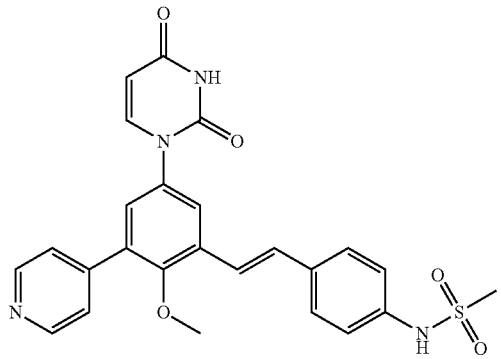 [SMILES: COc1c(/C=C/c2ccc(NS(C)(=O)=O)cc2)cc(-n2ccc(=O)[nH]c2=O)cc1-c1ccncc1]

The title compound was prepared according to the procedure of Example 115 substituting 4-(4,4,5,5-tetramethyl-1,3,2-dioxaborolan-2-yl)pyridine for thiophen-2-ylboronic acid to give a white solid (15 mg, 38%). ¹H NMR (300 MHz, DMSO-$d_6$) δ ppm 3.03 (s, 3H) 3.49 (s, 3H) 5.72 (dd, J=7.72, 2.21 Hz, 1H) 7.25 (d, J=8.46 Hz, 2H) 7.38 (d, J=4.41 Hz, 2H) 7.51 (d, J=2.57 Hz, 1H) 7.63 (d, J=8.82 Hz, 2H) 7.80 (d, J=5.88 Hz, 2H) 7.85 (d, J=7.72 Hz, 1H) 7.97 (d, J=2.57 Hz, 1H) 8.77 (d, J=6.25 Hz, 2H) 9.90 (s, 1H) 11.51 (d, J=2.21 Hz, 1H). MS (ESI+) m/z 491 (M+H)+.

Example 118

Preparation of (E)-N-(4-(5-(2,4-dioxo-3,4-dihydropyrimidin-1(2H)-yl)-2-methoxy-3-(pyridin-3-yl)styryl)phenyl)methanesulfonamide (compound IB-L1-1.53)

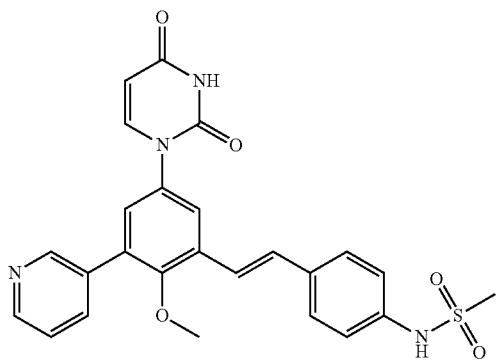 [SMILES: COc1c(/C=C/c2ccc(NS(C)(=O)=O)cc2)cc(-n2ccc(=O)[nH]c2=O)cc1-c1cccnc1]

The title compound was prepared according to the procedure of Example 115 substituting 3-(4,4,5,5-tetramethyl-1,3,2-dioxaborolan-2-yl)pyridine for thiophen-2-ylboronic acid to give a white solid (19 mg, 48%). ¹H NMR (300 MHz, DMSO-$d_6$) δ ppm 3.02 (s, 3H) 3.45 (s, 3H) 5.71 (dd, J=8.09, 2.21 Hz, 1H) 7.24 (d, J=8.46 Hz, 2H) 7.37 (d, J=2.94 Hz, 2H) 7.47 (d, J=2.57 Hz, 1H) 7.63 (m, 3H) 7.85 (d, J=7.72 Hz, 1H) 7.93 (d, J=2.57 Hz, 1H) 8.15 (m, 1H) 8.68 (dd, J=4.80 Hz, 1.47 Hz, 1H) 8.86 (d, J=1.84 Hz, 1H) 9.89 (s, 1H) 11.50 (d, J=2.21 Hz, 1H). MS (ESI+) m/z 491 (M+H)+.

Example 119

Preparation of (E)-N-(4-(5-(2,4-dioxo-3,4-dihydropyrimidin-1(2H)-yl)-2-methoxy-3-(thiophen-3-yl)styryl)phenyl)methanesulfonamide (compound IB-L1-1.47)

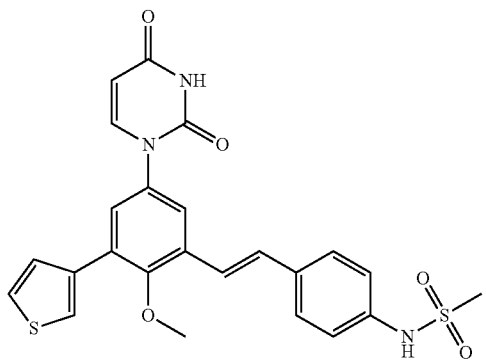 [SMILES: COc1c(/C=C/c2ccc(NS(C)(=O)=O)cc2)cc(-n2ccc(=O)[nH]c2=O)cc1-c1ccsc1]

The title compound was prepared according to the procedure of Example 115 substituting thiophen-3-ylboronic acid for thiophen-2-ylboronic acid to give a white solid (19 mg, 38%). ¹H NMR (300 MHz, DMSO-$d_6$) δ ppm 3.02 (s, 3H) 3.55 (s, 3H) 5.69 (d, J=8.09 Hz, 1H) 7.24 (d, J=8.46 Hz, 2H) 7.36 (s, 2H) 7.55 (m, 2H) 7.61 (d, J=8.46 Hz, 2H) 7.67 (dd, J=5.15, 2.94 Hz, 1H) 7.78 (d, J=2.57 Hz, 1H) 7.83 (d, J=7.72 Hz, 1H) 7.93 (dd, J=2.57, 0.96 Hz, 1H) 9.88 (s, 1H) 11.48 (s, 1H). MS (ESI−) m/z 494 (M−H)+.

Example 120

Preparation of (E)-N-(4-(5-(2,4-dioxo-3,4-dihydropyrimidin-1(2H)-yl)-3-(furan-3-yl)-2-methoxystyryl)phenyl)methanesulfonamide (compound IB-L1-1.50)

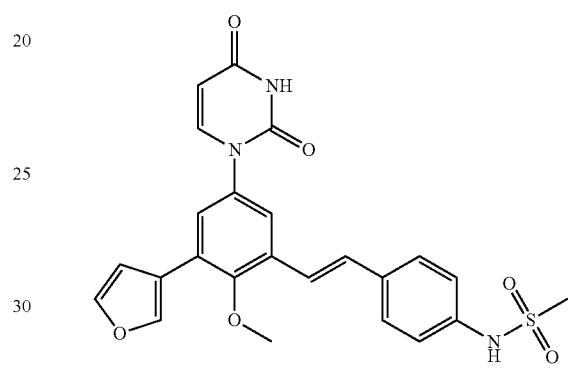

The title compound was prepared according to the procedure of Example 115 substituting furan-3-ylboronic acid acid for thiophen-2-ylboronic acid to give a white solid (14 mg, 29%). ¹H NMR (300 MHz, DMSO-$d_6$) δ ppm 3.02 (s, 3H) 3.69 (s, 3H) 5.69 (d, J=8.09 Hz, 1H) 7.05 (dd, J=2.57, 0.90 Hz, 1H) 7.24 (d, J=8.82 Hz, 2H) 7.34 (s, 2H) 7.61 (m, 3H) 7.74 (d, J=2.57 Hz, 1H) 7.80 (m, 2H) 8.25 (s, 1H) 9.88 (s, 1H) 11.49 (s, 1H). MS (ESI−) m/z 478 (M−H)+.

Example 121

Preparation of (E)-N-(4-(5-(2,4-dioxo-3,4-dihydropyrimidin-1(2H)-yl)-3-(1-hydroxy-2-methylpropan-2-yl)-2-methoxystyryl)phenyl)methanesulfonamide (compound IB-L1-1.45)

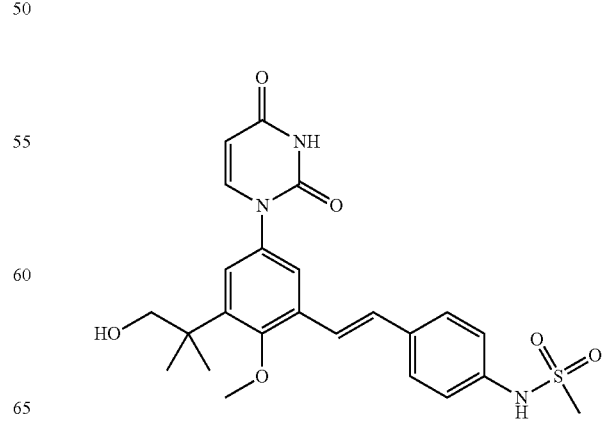

Part A. Preparation of 2-(2-hydroxy-3,5-diiodophenyl)acetic acid

To a 250 mL round-bottom flask was added 2-(2-hydroxyphenyl)acetic acid (Aldrich, 3.04 g, 20 mmol) in acetonitrile (50 ml) to give a colorless solution. N-iodosuccimide (9.00 g, 40.0 mmol) was added portionwise over 15 min to give a red/brown transparent solution that was stirred for 16 h. The mixture was concentrated and the resulting solid was triturated in 75 mL of water and filtered to collect an orange solid that was dried under vacuum. The crude solid was recrystallized from toluene to give a light orange powder (6.0 g, 74%).

Part B. Preparation of methyl 2-(3,5-diiodo-2-methoxyphenyl)acetate

To a 250 mL round-bottom flask was added the product from Part A (6 g, 14.85 mmol), potassium carbonate (6.16 g, 44.6 mmol), and dimethyl sulfate (4.12 g, 32.7 mmol) in acetone (49.5 ml) to give a brown suspension. The suspension was heated at reflux for 16 h, cooled, concentrated and the residue was partitioned between EtOAc and water. The EtOAc layer was washed with brine, dried ($Na_2SO_4$) and concentrated to a brown oil that was chromatographed on a 40 g silica cartridge eluting with 3:1 hexane/EtOAc to give a yellow oil (6.0 g, 94%).

Part C. Preparation of methyl 2-(3,5-diiodo-2-methoxyphenyl)-2-methylpropanoate To a 100 mL round-bottom flask under nitrogen was added the product from Part B (1.728 g, 4 mmol) in anhydrous THF (20 ml) and HMPA (2 ml) to give a colorless solution. Methyl iodide (1.251 ml, 20.00 mmol) was added and the solution was cooled to −40° C. Potassium t-butoxide (12.00 ml, 12.00 mmol) was added drop-wise and the mixture was stirred at −40 to −20° C. for 30 min and quenched with 1M HCl to a pH of 1. The mixture was extracted 3×40 ml with EtOAc. The extracts were combined, washed with brine, dried ($Na_2SO_4$) and concentrated. The crude product was flash chromatographed on a 40 g ISCO silica cartridge eluting with 9:1 hexane/EtOAc to give the bis-methylated product as a yellow oil (1.63 g, 89%).

Part D. Preparation of 2-(3,5-diiodo-2-methoxyphenyl)-2-methylpropanoic acid A suspension of the product from Part C (2.63 g, 5.72 mmol) in MeOH (40 ml) and THF (40 ml) was treated with 4.0M sodium hydroxide (28 ml, 112 mmol) and heated at 80° C. for 48 h. The organic solvent was evaporated and the remaining aqueous solution was acidified with 1M HCl producing a solid that was collected by filtration, washed with water and dried to give the desired carboxylic acid (2.46 g, 96%).

Part E. Preparation of 2-(3,5-diiodo-2-methoxyphenyl)-2-methylpropan-1-ol

A solution of the product from Part D (1.00 g, 2.242 mmol) in THF (40 ml) was treated drop-wise with borane THF complex 1.0M (20 ml, 20 mmol) and then heated at 50° C. for 24 h. The mixture was treated with methanol (20 mL), refluxed for 30 min and concentrated. The resulting residue was washed with water, brine, dried with sodium sulfate, filtered and evaporated. The residue was chromatographed on silica gel eluting with hexane/EtOAc (4:1) to give the desired product (810 mg, 84%).

Part F. Preparation of tert-butyl(2-(3,5-diiodo-2-methoxyphenyl)-2-methylpropoxy)-dimethylsilane A solution of the product from Part E (432 mg, 1.000 mmol) in DMF (5 ml) was treated with tert-butyldimethylchlorosilane (301 mg, 2.000 mmol), and imidazole (204 mg, 3.00 mmol) and stirred for 2 h. The mixture was partitioned between 1M HCl and ethyl acetate. The organic layer was washed with saturated sodium bicarbonate, brine, dried with sodium sulfate, filtered and evaporated. The residue was chromatographed on silica gel eluting with hexane/EtOAc (9:1) to give the desired product (522 mg, 96%).

Part G. Preparation of 1-(3-(1-(tert-butyldimethylsilyloxy)-2-methylpropan-2-yl)-5-iodo-4-methoxyphenyl)pyrimidine-2,4(1H,3H)-dione To a 50 mL round-bottom flask was added the product from Part F (520 mg, 0.952 mmol), pyrimidine-2,4(1H,3H)-dione (117 mg, 1.047 mmol), N-(2-cyanophenyl)picolinamide (42.5 mg, 0.190 mmol), copper(I) iodide (18.13 mg, 0.095 mmol) and potassium phosphate (424 mg, 1.999 mmol) in DMSO (5 ml). The vessel was sealed, sparged with nitrogen and then heated at 60° C. for 24 h. The mixture was partitioned between 1M HCl and ethyl acetate. The organic layer was washed with saturated sodium bicarbonate, brine, dried with sodium sulfate, and filtered. The filtrate was treated with 3-mercaptopropyl functionalized silica gel, filtered and evaporated. The residue was chromatographed on silica gel eluting with hexane/EtOAc (3:2) to give the product as a solid (285 mg, 65%).

Part H. Preparation of (E)-N-(4-(3-(1-(tert-butyldimethylsilyloxy)-2-methylpropan-2-yl)-5-(2,4-dioxo-3,4-dihydropyrimidin-1(2H)-yl)-2-methoxystyryl)phenyl)methanesulfonamide To a 5 ml microwave tube was added the product from Part G (53 mg, 0.1 mmol), the product from Example 41B, Part B (24 mg, 0.1 mmol), potassium phosphate (44.0 mg, 0.2 mmol), PA-Ph (CAS 97739-46-3) (0.87 mg, 3.0 mmol) and tris(dibenzylideneacetone)palladium(0) (0.9 mg, 1 umol) in THF (3.0 ml) and water (1.0 ml). The vessel was sealed and the mixture was sparged with nitrogen for 5 min and then heated at 50° C. for 2 h. The mixture was partitioned between 1M HCl and ethyl acetate. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica gel eluting with hexane/EtOAc (1:1) to give a solid (50 mg, 83%).

Part I. Preparation of (E)-N-(4-(5-(2,4-dioxo-3,4-dihydropyrimidin-1(2H)-yl)-3-(1-hydroxy-2-methylpropan-2-yl)-2-methoxystyryl)phenyl)methanesulfonamide A solution of the product from Part H (120 mg, 0.20 mmol) in THF (5.0 ml) was treated with 1 M TBAF (0.800 ml, 0.800 mmol) in THF and stirred for 16 h. The mixture was partitioned with water and ethyl acetate. The organic layer was washed (3× brine), dried with sodium sulfate, filtered and evaporated. The residue was chromatographed on silica gel eluting with 4% methanol in $CH_2Cl_2$ to give a solid (85 mg, 88%). $^1$H NMR (300 MHz, DMSO-$d_6$) δ ppm 1.30 (s, 6H) 3.01 (s, 3H) 3.62 (d, J=5.52 Hz, 2H) 3.77 (s, 3H) 4.67 (t, J=5.33 Hz, 1H) 5.66 (d, J=8.09 Hz, 1H) 7.21 (m, 5H) 7.62 (m, 3H) 7.72 (d, J=8.09 Hz, 1H) 9.85 (s, 1H) 11.42 (s, 1H). MS (ESI+) m/z 503 (M+NH4)+.

Example 122

Preparation of (E)-N-(4-(5-(2,4-dioxo-3,4-dihydropyrimidin-1(2H)-yl)-3-iodo-2-methoxystyryl)phenyl)methanesulfonamide (compound IB-L1-1.51)

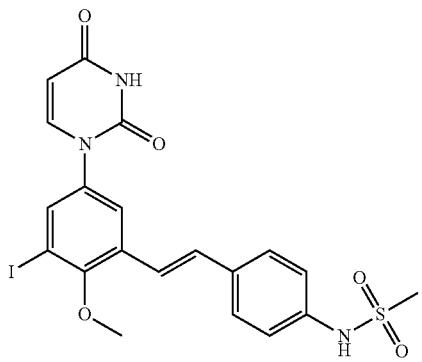 [SMILES: COc1c(I)cc(-n2ccc(=O)[nH]c2=O)cc1/C=C/c1ccc(NS(C)(=O)=O)cc1]

Part A. Preparation of 1,3,5-triiodo-2-methoxybenzene

In a 250 mL pressure vessel was added 2,4,6-triiodophenol (5 g, 10.60 mmol) in MTBE (60 ml) to give a yellow solution. The solution was cooled in an ice bath and 2.0M trimethylsilyldiazomethane (7.95 ml, 15.90 mmol) was added at a fast drip followed by dropwise addition of methanol (6 mL) resulting in calm bubbling. The vessel was sealed and stirred at room temperature for 4 h. The reaction solution was partitioned between EtOAc and water and the organic layer was washed with 1M HCl, saturated NaHCO$_3$, and saturated NaCl. The EtOAc was dried (MgSO$_4$), filtered and concentrated to give a tan solid that was used without purification (4.8 g, 94%).

Part B. Preparation of 1-(3,5-diiodo-4-methoxyphenyl)pyrimidine-2,4(1H,3H)-dione To a 100 mL round-bottom flask under N$_2$ was added the product from Part A (3.5 g, 7.2 mmol), 1H-pyrimidine-2,4-dione (0.97 g, 8.64 mmol), and potassium phosphate tribasic (3.2 g, 15.0 mmol) in DMSO (50 ml) to give a colorless suspension. N-(2-cyanophenyl)picolinamide (320 mg, 1.44 mmol) was added and the mix was sparged with N$_2$ for 5 min. Copper(I) iodide (137 mg, 0.72 mmol) was added and the mix was sparged once again for 10 min, placed under N$_2$ and heated at 60° C. for 18 h. The mixture was cooled and partitioned between EtOAc and water adjusting the pH to 1 with HCl. The aqueous layer was extracted 2× with EtOAc. The organics were combined, washed with water, saturated NaHCO$_3$, and saturated NaCl, dried (Na$_2$SO$_4$), treated with 3-mercaptopropyl functionalized silica, filtered and concentrated. The resulting solid was triturated in 2:1 hexane/EtOAc to give an off white powder (2.2 g, 62%).

Part C. Preparation of (E)-N-(4-(5-(2,4-dioxo-3,4-dihydropyrimidin-1(2H)-yl)-3-iodo-2-methoxystyryl)phenyl)methanesulfonamide In a 5 ml microwave tube was mixed the product from Part B (141 mg, 0.30 mmol), the product from Example 41B, Part B (72.3 mg, 0.300 mmol), 1,1'-bis(diphenylphosphino)ferrocene-palladium(II)dichloride $CH_2Cl_2$ complex (12.25 mg, 0.015 mmol) and potassium phosphate (70.0 mg, 0.330 mmol) in THF (3.0 ml) and water (1.0 ml). The mixture was sparged with nitrogen for 5 min and heated at 50° C. for 2 h. The mixture was partitioned with ethyl acetate and 1M HCl. The organic layer was washed with saturated sodium bicarbonate, brine, dried with sodium sulfate and filtered. The filtrate was treated with 3-mercaptopropyl functionalized silica gel, filtered and evaporated. The residue was chromatographed on silica eluting with 5% methanol in $CH_2Cl_2$ to give a solid (47 mg, 29%). $^1$H NMR (300 MHz, DMSO-$d_6$) δ ppm 3.02 (s, 3H) 3.77 (s, 3H) 5.67 (d, J=7.72 Hz, 1H) 7.28 (m, 4H) 7.60 (d, J=8.82 Hz, 2H) 7.76 (d, J=8.09 Hz, 1H) 7.81 (d, J=2.57 Hz, 1H) 7.86 (d, J=2.21 Hz, 1H) 9.90 (s, 1H) 11.48 (s, 1H). MS (ESI−) m/z 538 (M−H)+.

Example 123

Preparation of (E)-N-(4-(5-(2,4-dioxo-3,4-dihydropyrimidin-1(2H)-yl)-2-methoxy-3-(methylsulfonyl)styryl)phenyl)methanesulfonamide (compound IB-L1-1.49)

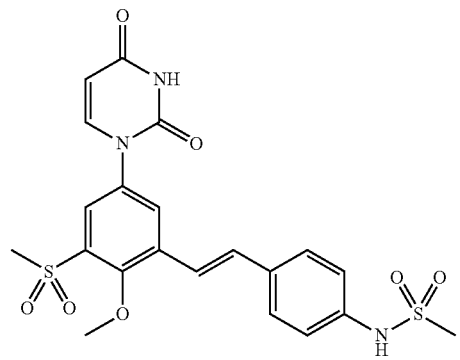

Part A. Preparation of 4-nitrobenzene-2-diazo-1-oxide

To a 250 mL round-bottom flask was added 2-amino-4-nitrophenol (6.165 g, 40.0 mmol) in 48% tetrafluoroboric acid (15 ml). Sodium nitrite (2.76 g, 40.0 mmol) in water (6 ml) was added dropwise at 0° C. and the mixture was stirred at room temperature for 30 min. The solid was collected by filtration, washed with tetrafluoroboric acid and water. The solid was suspended in acetone (50 ml), filtered and dried to give a solid (3.31 g, 50%).

Part B. Preparation of 2-(methylthio)-4-nitrophenol

To a 1 L beaker was added the product from Part A (2.70 g, 16.35 mmol) in ice water (250 g) to give a brown suspension. Copper (0.520 g, 8.18 mmol) was added, followed by addition of sodium thiomethoxide (2.292 g, 32.7 mmol) in water (50 ml) slowly. The mixture was stirred at room temperature for 24 h. The mixture was filtered and the filtrate was acidified with 1M HCl producing a solid that was collected by filtration and dried (2.53 g, 84%).

Part C. Preparation of 2-(methylsulfonyl)-4-nitrophenol

To a 250 mL round-bottom flask was added the product from Part B (1.111 g, 6.00 mmol) in MeOH (20 ml) to give a brown suspension. Oxone (7.746 g, 12.60 mmol) in water (20 ml) was added slowly at 0° C. The mixture was warmed to room temperature, stirred for 1 h and partitioned with ethyl acetate and 1M HCl. The organic layer was washed with brine, dried with sodium sulfate, filtered and evaporated. The residue was chromatographed on silica gel eluting with 1% to 5% methanol in $CH_2Cl_2$ to give a solid (0.472 g, 36%).

Part D. Preparation of 2-iodo-6-(methylsulfonyl)-4-nitrophenol

To a 50 mL round-bottom flask was added the product from Part C (470 mg, 2.164 mmol) in MeOH (10 ml) and water (2.5 ml). Iodine monochloride (0.130 ml, 2.60 mmol) in $CH_2Cl_2$ (2.0 mL) was added drop-wise and the mixture was stirred at room temperature, poured into water (200 mL) and stirred for 10 min. The resulting solid was collected by filtration and dried (636 mg, 86%).

Part E. Preparation of 1-iodo-2-methoxy-3-(methylsulfonyl)-5-nitrobenzene

To a 50 mL pressure vessel was added the product from Part D (630 mg, 1.836 mmol) in MTBE (6 ml) to give a yellow solution. The mixture was cooled in an ice bath and 2M trimethylsilyl-diazomethane (1.377 ml, 2.75 mmol) was added at a fast drip followed by drop-wise addition of MeOH (0.4 ml) resulting in calm bubbling. The vessel was sealed and stirred at room temperature for 1 h. The mixture was partitioned with ethyl acetate and 1M HCl. The organic layer was washed with saturated sodium bicarbonate, brine, dried with sodium sulfate, filtered and evaporated to give an off-white solid (655 mg, 100%).

Part F. Preparation of 3-iodo-4-methoxy-5-(methylsulfonyl)aniline

To a 250 mL round-bottom flask was added the product from Part E (0.650 g, 1.820 mmol), ammonium chloride (0.146 g, 2.73 mmol), and iron (0.508 g, 9.10 mmol) in THF/MeOH/water (50 ml, 2/2/1). The mixture was refluxed for 2 h, cooled and filtered. The filtrate was evaporated and the residue was partitioned with ethyl acetate and water. The organic layer was washed with brine, dried with sodium sulfate, filtered and evaporated to give a solid (590 mg, 99%).

Part G. Preparation of (E)-N-(3-iodo-4-methoxy-5-(methylsulfonyl)phenylcarbamoyl)-3-methoxyacrylamide To a 100 mL round-bottom flask was added the product from Part F (500 mg, 1.528 mmol) in DMF (15.0 ml). The solution was cooled under nitrogen to −20° C. and (E)-3-methoxyacryloyl isocyanate (15.28 ml, 6.11 mmol; prepared as described by Santana, L.; et al. J. Heterocyclic Chem. 1999, 36, 293-295) was added dropwise. The mixture was stirred at this temperature for 15 min, then warmed to room temperature and stirred for 45 min. The mixture was diluted with ethyl acetate and washed by water (3×50 ml), brine (3×50 ml), dried with sodium sulfate, filtered and evaporated. The residue was triturated with ethyl acetate/hexane to give a solid (425 mg, 61%).

Part H. Preparation of 1-(3-iodo-4-methoxy-5-(methylsulfonyl)phenyl)pyrimidine-2,4(1H,3H)-dione To a 100 mL round-bottom flask was added the product from Part G (420 mg, 0.925 mmol) in ethanol (10 ml) to give a suspension. Concentrated sulfuric acid (1 mL, 18.76 mmol) in water (10 ml) was added and the mixture was heated at 110° C. for 2 h. The reaction mix was cooled, diluted with water (50 ml) and stirred for 10 min. The solid material was collected by filtration, washed with water and dried to give a white solid (325 mg, 83%).

Part I. Preparation of (E)-N-(4-(5-(2,4-dioxo-3,4-dihydropyrimidin-1(2H)-yl)-2-methoxy-3-(methylsulfonyl)styryl)phenyl)methanesulfonamide In a 5 ml microwave tube was added the product from Part H (63.3 mg, 0.15 mmol), the product from Example 41B, Part B (36.2 mg, 0.150 mmol), potassium phosphate (66.9 mg, 0.315 mmol), PA-Ph (CAS 97739-46-3) (1.315 mg, 4.50 µmol) and tris(dibenzylideneacetone)dipalladium(0) (1.374 mg, 1.500 µmol) in THF (3.0 ml) and water (1.0 ml). The vessel was sealed and the mixture was sparged with nitrogen for 5 min and heated at 50° C. for 2 h. The mixture was partitioned with ethyl acetate and 1M HCl. The organic layer was washed with saturated sodium bicarbonate, brine, dried with sodium sulfate and filtered. The filtrate was treated with 3-mercaprpropyl functionalized silica gel, filtered and evaporated. The residue was triturated with methanol/$CH_2Cl_2$ to give a solid (62 mg, 84%). $^1H$ NMR (300 MHz, DMSO-$d_6$) δ ppm 3.03 (s, 3H) 3.37 (s, 3H) 3.94 (s, 3H) 5.72 (d, J=7.72 Hz, 1H) 7.26 (m, 3H) 7.45 (m, 1H) 7.65 (d, J=8.46 Hz, 2H) 7.77 (d, J=2.57 Hz, 1H) 7.81 (d, J=8.09 Hz, 1H) 8.21 (d, J=2.57 Hz, 1H) 9.93 (s, 1H) 11.52 (s, 1H). MS (ESI+) m/z 509 (M+NH4)+.

Example 124

Preparation of (E)-methyl 2-(3-tert-butyl-5-(2,4-dioxo-3,4-dihydropyrimidin-1(2H)-yl)-2-methoxystyryl)-5-(methylsulfonamido)benzoate (compound IB-L1-1.7)

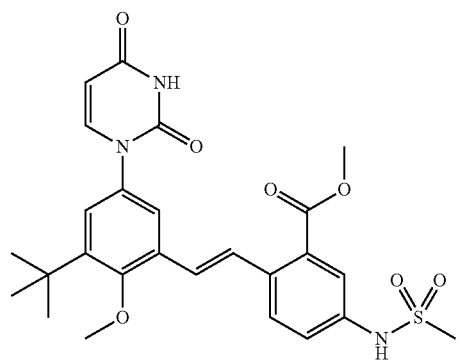 [SMILES: COC(=O)c1cc(NS(C)(=O)=O)ccc1/C=C/c1cc(-n2ccc(=O)[nH]c2=O)cc(C(C)(C)C)c1OC]

327

Part A. Preparation of methyl 2-((diethoxyphosphoryl)methyl)-5-nitrobenzoate To a solution of methyl 2-methyl-5-nitrobenzoate (0.40 g, 2.05 mmol) in CCl$_4$ (20 ml) was added N-bromosuccinimide (365 mg, 2.05 mmol) and 2,2'-azobisisobutyronitrile (34 mg, 0.21 mmol). The resulting mixture was stirred at reflux for 18 h, cooled to room temperature and partitioned between EtOAc (50 ml) and H$_2$O (50 ml). The organic layer was dried over Na$_2$SO$_4$, filtered and concentrated in vacuo. The crude product was purified by column chromatography on silica gel using 1:3 EtOAc:hexanes as the eluent to give the bromide as an oil (345 mg, 61%). The oil was placed in triethylphosphite (5 ml) and heated with stirring at 120° C. for 3 h. The mixture was allowed to cool to room temperature, and the crude product was purified by column chromatography on silica gel using 5% MeOH in CH$_2$Cl$_2$ as the eluent. The title compound was obtained as an oil (313 mg, 75%).

Part B. Preparation of (E)-methyl 2-(3-tert-butyl-5-(2,4-dioxo-3,4-dihydropyrimidin-1(2H)-yl)-2-methoxystyryl)-5-nitrobenzoate To a solution of the product from Part A (360 mg, 1.09 mmol) and the product from Example 41A, Part D (329 mg, 1.09 mmol) in anhydrous CH$_2$Cl$_2$ (10 ml) was added potassium tert-butoxide (305 mg, 2.72 mmol). The resulting dark red solution was stirred at room temperature for 1 h, and then poured into 1 N aq. HCl (10 ml). The resulting mixture was extracted with CH$_2$Cl$_2$ (10 ml), dried over Na$_2$SO$_4$, filtered and concentrated in vacuo to give a solid. A solution of the solid in thionyl chloride (2.3 ml) was heated at 85° C. for 30 min, and the thionyl chloride was removed in vacuo. The residue was stirred in a 2:1 mixture of CH$_2$Cl$_2$ and MeOH (3 ml) for 30 min, and evaporated to dryness in vacuo. The crude product was purified by column chromatography on silica gel using 3% MeOH in CH$_2$Cl$_2$ as the eluent to give the title compound (350 mg, 69%).

Part C. Preparation of (E)-methyl 2-(3-tert-butyl-5-(2,4-dioxo-3,4-dihydropyrimidin-1(2H)-yl)-2-methoxystyryl)-5-(methylsulfonamido)benzoate To a solution of the product from Part B (465 mg, 0.97 mmol) in a 2:2:1 mixture of THF:MeOH:H$_2$O (10 ml) was added iron powder (271 mg, 4.85 mmol), and ammonium chloride (78 mg, 1.46 mmol). The mixture was heated at 80° C. for 45 min, filtered through celite, and concentrated to dryness in vacuo. The residue was combined with methanesulfonyl chloride (0.16 ml, 2.0 mmol) and triethylamine (0.392 ml, 4.85 mmol) in anhydrous CH$_2$Cl$_2$ (10 ml) and the resulting mixture was stirred at room temperature for 3 h. The mixture was partitioned between 1 N HCl (20 ml) and CH$_2$Cl$_2$ (20 ml), and the organic layer was dried over Na$_2$SO$_4$, filtered and concentrated in vacuo. The crude product was purified by column chromatography on silica gel using 3% MeOH in CH$_2$Cl$_2$ as the eluent to give the title compound (270 mg, 53%). $^1$H NMR (300 MHz, DMSO-d$_6$) δ 11.42 (s, 1H) 10.07 (s, 1H) 7.90 (d, J=8.82 Hz, 1H) 7.66-7.79 (m, 3H) 7.52 (d, J=2.57 Hz, 1H) 7.44 (dd, J=8.64, 2.39 Hz, 1H) 7.14-7.26 (m, 2H) 5.65 (dd, J=7.72, 1.84 Hz, 1H) 3.86 (s, 3H) 3.79 (s, 3H) 3.04 (s, 3H) 1.38 (s, 9H).

328

Example 125

Preparation of (E)-2-(3-tert-butyl-5-(2,4-dioxo-3,4-dihydropyrimidin-1(2H)-yl)-2-methoxystyryl)-5-(methylsulfonamido)benzoic acid (compound IB-L1-1.4)

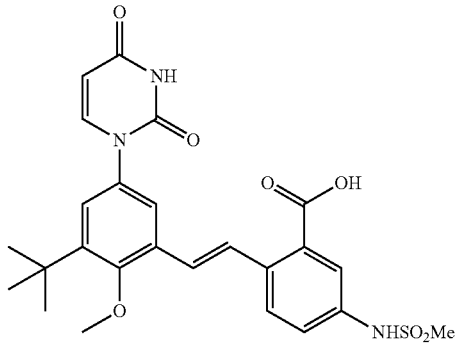

A solution of the product from Example 124 (55 mg, 0.104 mmol) in THF (1 ml) and 1N aq. NaOH (1 ml) was stirred in the dark at room temperature for 1.5 h. 1N aqueous HCl was added until pH 3, and the resulting mixture was extracted with EtOAc (2×2 ml). The combined organic layers were dried over Na$_2$SO$_4$, filtered and concentrated to give the title compound (53 mg, 99%). $^1$H NMR (300 MHz, DMSO-d$_6$) δ 13.22 (br s, 1H) 11.40 (d, J=2.21 Hz, 1H) 10.02 (s, 1H) 7.72-7.91 (m, 3H) 7.68 (d, J=2.57 Hz, 1H) 7.49 (d, J=2.57 Hz, 1H) 7.42 (dd, J=8.64, 2.39 Hz, 1H) 7.21 (d, J=2.57 Hz, 1H) 7.16 (d, J=16.18 Hz, 1H) 5.64 (dd, J=7.72, 2.21 Hz, 1H) 3.79 (s, 3H) 3.04 (s, 3H) 1.38 (s, 9H).

Example 126

Preparation of (E)-N-(4-(3-tert-butyl-5-(2,4-dioxo-3,4-dihydropyrimidin-1(2H)-yl)-2-methoxystyryl)-3-(morpholine-4-carbonyl)phenyl)methanesulfonamide (compound IB-L1-1.23)

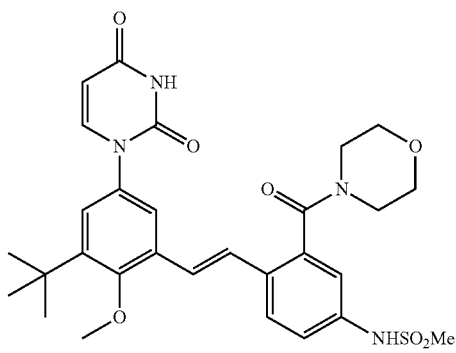

Part A. Preparation of (E)-2-(3-tert-butyl-5-(2,4-dioxo-3,4-dihydropyrimidin-1(2H)-yl)-2-methoxystyryl)-5-(methylsulfonamido)benzoyl chloride A solution of the product from Example 125 (257 mg, 0.50 mmol) in thionyl chloride (1.5 ml) was heated at 85° C. for 40 min and then concentrated and dried in vacuo to give the title compound as a solid (0.27 g).

Part B. Preparation of (E)-N-(4-(3-tert-butyl-5-(2,4-dioxo-3,4-dihydropyrimidin-1(2H)-yl)-2-methoxystyryl)-3-(morpholine-4-carbonyl)phenyl)methanesulfonamide To a solution of the product from Part A (24 mg, 0.045 mmol) in anhydrous $CH_2Cl_2$ (1 ml) was added morpholine (0.02 ml, 0.226 mmol). The mixture was stirred at room temperature for 2 h, and then partitioned between 1 N aq. HCl (5 ml) and EtOAc (2×5 ml). The combined organic layers were dried over $Na_2SO_4$, filtered and concentrated in vacuo. The crude product was purified by column chromatography on silica gel using 4% MeOH in $CH_2Cl_2$ as the eluent to give the title compound (19 mg, 71%). $^1$H NMR (300 MHz, DMSO-$d_6$) δ ppm 11.41 (d, J=1.84 Hz, 1H) 10.04 (s, 1H) 7.85 (d, J=8.46 Hz, 1H) 7.75 (d, J=8.09 Hz, 1H) 7.52 (d, J=2.57 Hz, 1H) 6.99-7.34 (m, 5H) 5.65 (dd, J=7.72, 1.84 Hz, 1H) 3.76 (s, 3H) 3.56-3.71 (m, 4H) 3.40-3.51 (m, 2H) 3.11-3.22 (m, 2H) 3.06 (s, 3H) 1.38 (s, 9H).

Example 127

Preparation of (E)-N-(4-(3-tert-butyl-5-(2,4-dioxo-3,4-dihydropyrimidin-1(2H)-yl)-2-methoxystyryl)-3-(hydroxymethyl)phenyl)methanesulfonamide (compound IB-L1-1.10)

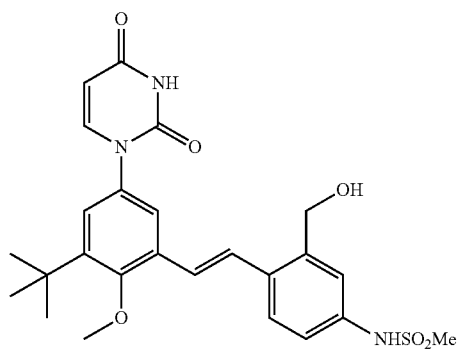

To a solution of the product from Example 126, Part A (375 mg, 0.705 mmol) in anhydrous THF (5 ml) at 0° C. under $N_2$ gas was added a 1.0 M solution of lithium tert-butoxyaluminumhydride (1.8 ml, 1.8 mmol) dropwise. The resulting mixture was stirred at 0° C. for 30 min, and then allowed to warm to room temperature and was stirred for 1 h. The mixture was partitioned between 1 N aq. HCl (10 ml) and EtOAc (2×10 ml). The combined organic layers were dried over $Na_2SO_4$, filtered and concentrated in vacuo. The crude product was purified by column chromatography on silica gel using 3% MeOH in $CH_2Cl_2$ as the eluent to give the title compound (220 mg, 63%). $^1$H NMR (300 MHz, DMSO-$d_6$) δ ppm 11.41 (s, 1H) 9.82 (s, 1H) 7.73 (t, J=8.27 Hz, 2H) 7.66 (d, J=2.57 Hz, 1H) 7.31-7.39 (m, 2H) 7.20 (d, J=2.57 Hz, 1H) 7.12-7.19 (m, 2H) 5.65 (d, J=8.09 Hz, 1H) 5.28 (t, J=5.52 Hz, 1H) 4.65 (d, J=5.52 Hz, 2H) 3.79 (s, 3H) 3.00 (s, 3H) 1.38 (s, 9H).

Example 128

Preparation of (E)-N-(4-(3-tert-butyl-5-(2,4-dioxo-3,4-dihydropyrimidin-1(2H)-yl)-2-methoxystyryl)-3-(methoxymethyl)phenyl)methanesulfonamide (compound IB-L1-1.13)

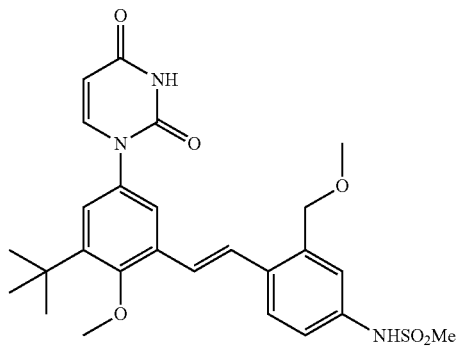

To a solution of the product from Example 127 (32 mg, 0.064 mmol) in anhydrous $CH_2Cl_2$ (1 ml) was added thionyl chloride (23 µL, 0.32 mmol), and the resulting mixture was stirred at room temperature for 30 min. The mixture was partitioned between saturated aq. $NaHCO_3$ (5 ml) and $CH_2Cl_2$ (5 ml) and the organic layer was dried over $Na_2SO_4$, filtered and concentrated. The residue was dissolved in MeOH (1 ml), and a solution of 25% NaOMe in MeOH (58 µL, 0.254 mmol) was added. The resulting mixture was stirred at 50° C. for 2 h. The mixture was partitioned between 1 N aq. HCl (10 ml) and EtOAc (2×10 ml). The combined organic layers were dried over $Na_2SO_4$, filtered and concentrated in vacuo. The crude product was purified by column chromatography on silica gel using 3% MeOH in $CH_2Cl_2$ as the eluent to give the title compound (15 mg, 46%). $^1$H NMR (300 MHz, DMSO-$d_6$) δ 11.43 (s, 1H) 9.86 (s, 1H) 7.62-7.87 (m, 3H) 7.12-7.39 (m, 5H) 5.66 (d, J=7.72 Hz, 1H) 4.58 (s, 2H) 3.78 (s, 3H) 3.35 (s, 3H) 3.00 (s, 3H) 1.38 (s, 9H).

Example 129

Preparation of (E)-N-(4-(3-tert-butyl-5-(2,4-dioxo-3,4-dihydropyrimidin-1(2H)-yl)-2-methoxystyryl)-3-((isopentylamino)methyl)phenyl)methanesulfonamide (compound IB-L1-1.31)

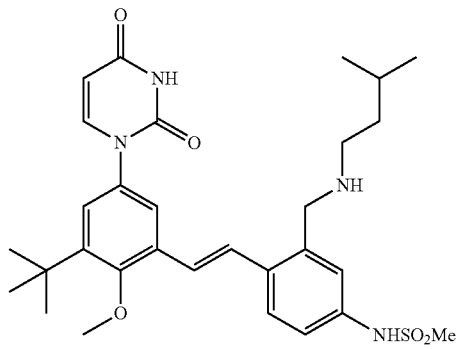

331

Part A. Preparation of (E)-N-(4-(3-tert-butyl-5-(2,4-dioxo-3,4-dihydropyrimidin-1(2H)-yl)-2-methoxy-styryl)-3-formylphenyl)methanesulfonamide To a solution of the product from Example 127 (0.60 g, 1.20 mmol) in anhydrous DMA (15 ml) was added 2-iodoxybenzoic acid (336 mg, 1.20 mmol). The mixture was stirred at room temperature for 1 h, and then partitioned between EtOAc (20 ml) and H$_2$O (2×20 ml). The organic layer was dried over Na$_2$SO$_4$, filtered and concentrated in vacuo. The crude product was purified by column chromatography on silica gel using 2% MeOH in CH$_2$Cl$_2$ as the eluent to give the title compound as a colorless solid (395 mg, 66%). $^1$H NMR (300 MHz, DMSO-d$_6$) δ ppm 11.43 (d, J=2.21 Hz, 1H) 10.45 (s, 1H) 10.15 (s, 1H) 8.06 (d, J=16.18 Hz, 1H) 7.97 (d, J=8.82 Hz, 1H) 7.73-7.78 (m, 2H) 7.69 (d, J=2.57 Hz, 1H) 7.51 (dd, J=8.64, 2.39 Hz, 1H) 7.30 (d, J=16.18 Hz, 1H) 7.26 (d, J=2.57 Hz, 1H) 5.66 (dd, J=7.72, 2.21 Hz, 1H) 3.81 (s, 3H) 3.07 (s, 3H) 1.39 (s, 9H).

Part B. Preparation of (E)-N-(4-(3-tert-butyl-5-(2,4-dioxo-3,4-dihydropyrimidin-1(2H)-yl)-2-methoxy-styryl)-3-((isopentylamino)methyl)phenyl)methane-sulfonamide To a solution of the product from Part A (50 mg, 0.10 mmol) and 3-methylbutan-1-amine (12 μL, 0.10 mmol) in anhydrous THF (3 ml) was added sodium triacetoxyborohydride (32 mg, 0.15 mmol) and AcOH (9 μL, 0.15 mmol). The resulting mixture was stirred at room temperature for 4 h, and then partitioned between H$_2$O (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (37 mg, 65%). $^1$H NMR (300 MHz, DMSO-d$_6$) δ 11.45 (d, J=1.84 Hz, 1H) 10.04 (s, 1H) 8.80-8.87 (m, 1H) 7.88 (d, J=8.46 Hz, 1H) 7.71-7.77 (m, 2H) 7.41-7.48 (m, 1H) 7.37 (d, J=2.21 Hz, 1H) 7.21-7.29 (m, 3H) 5.67 (dd, J=7.91, 2.02 Hz, 1H) 4.30-4.38 (m, 2H) 3.80 (s, 3H) 3.10 (s, 3H) 2.95-3.04 (m, 2H) 1.49-1.67 (m, 3H) 1.38 (s, 9H) 0.86 (d, J=6.25 Hz, 6H).

Example 130

Preparation of N-(4-(3-tert-butyl-5-(2,4-dioxo-3,4-dihydropyrimidin-1(2H)-yl)-2-methoxystyryl)-3-(E)-(methoxyimino)methyl)phenyl)methanesulfonamide (compound IB-L1-1.19)

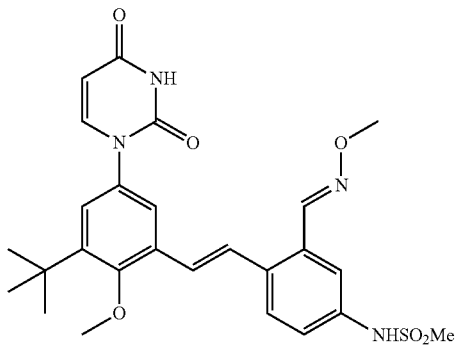

To a solution of the product from Example 129, Part A (35 mg, 0.070 mmol) in EtOH (2 ml) was added O-methoxy-lamine hydrochloride (29 mg, 0.35 mmol) and sodium bicarbonate (30 mg, 0.35 mmol). The resulting mixture was stirred at 70° C. for 2 h. To the mixture was added 1 N aq. HCl (1 ml) to give a colorless precipitate that was filtered and dried to give the title compound as a colorless solid (24 mg, 64%). $^1$H NMR (300 MHz, DMSO-d$_6$) δ ppm 11.43 (d, J=2.21 Hz, 1H) 9.94 (s, 1H) 8.74 (s, 1H) 7.79-7.85 (m, 2H) 7.76 (d, J=7.72 Hz, 1H) 7.57-7.65 (m, 2H) 7.32 (dd, J=8.64, 2.39 Hz, 1H) 7.23 (d, J=2.57 Hz, 1H) 7.18 (d, J=16.18 Hz, 1H) 5.66 (dd, J=7.72, 2.21 Hz, 1H) 3.93 (s, 3H) 3.79 (s, 3H) 3.03 (s, 3H) 1.38 (s, 9H).

Example 131

Preparation of (E)-N-(4-(3-tert-butyl-5-(2,4-dioxo-3,4-dihydropyrimidin-1(2H)-yl)-2-methoxystyryl)-3-(oxazol-2-yl)phenyl)methanesulfonamide (compound IB-L1-1.26)

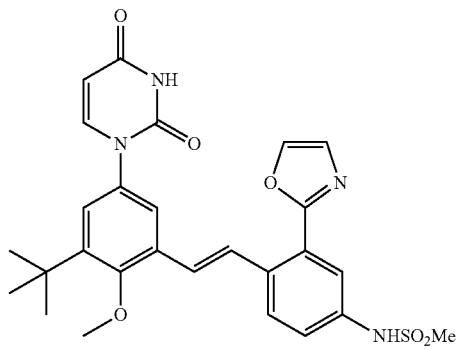

To a solution of the product from Example 126, Part A (80 mg, 0.15 mmol) in tetramethylene sulfone (1.5 ml) was added 1H-1,2,3-triazole (10 μL, 0.17 mmol) and potassium carbonate (73 mg, 0.53 mmol). The mixture was heated for 35 min at 130° C. in a microwave reactor. After cooling to room temperature, the mixture was partitioned between 1 N aqueous HCl (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (37 mg, 46%). $^1$H NMR (300 MHz, DMSO-d$_6$) δ 11.41 (d, J=1.84 Hz, 1H) 10.10 (s, 1H) 8.29 (d, J=1.10 Hz, 1H) 8.05 (d, J=16.18 Hz, 1H) 7.95 (d, J=8.82 Hz, 1H) 7.82 (d, J=2.21 Hz, 1H) 7.74 (d, J=8.09 Hz, 1H) 7.51 (d, J=2.57 Hz, 1H) 7.46 (d, J=0.74 Hz, 1H) 7.39 (dd, J=8.64, 2.39 Hz, 1H) 7.20-7.30 (m, 2H) 5.65 (dd, J=7.91, 2.02 Hz, 1H) 3.80 (s, 3H) 3.07 (s, 3H) 1.38 (s, 9H).

Example 132

Preparation of (E)-N-(4-(3-tert-butyl-5-(2,4-dioxo-3,4-dihydropyrimidin-1(2H)-yl)-2-methoxystyryl)-3-(1H-imidazol-2-yl)phenyl)methanesulfonamide (compound IB-L1-1.16)

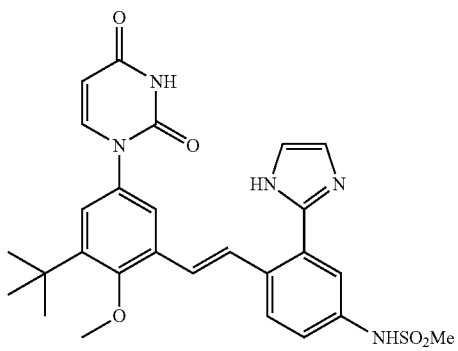

To a solution of the product from Example 129, Part A (50 mg, 0.10 mmol) in EtOH (2 ml) was added glyoxal (57 uL, 0.50 mmol) and concentrated aqueous NH$_4$OH (70 uL, 0.50 mmol). The resulting mixture was stirred at room temperature for 16 h. To the mixture was added 1 N aq. HCl until pH=7, and the mixture was partitioned between H$_2$O (10 ml) and EtOAc (2×10 ml). The combined organic layers were dried over Na$_2$SO$_4$, filtered and concentrated in vacuo. The crude product was purified by column chromatography on silica gel using 5% MeOH in CH$_2$Cl$_2$ as the eluent to give the title compound (27 mg, 50%). $^1$H NMR (300 MHz, DMSO-d$_6$) δ 12.39 (s, 1H) 11.40 (d, J=1.84 Hz, 1H) 9.98 (s, 1H) 7.89 (d, J=8.82 Hz, 1H) 7.66-7.76 (m, 2H) 7.38 (t, J=2.21 Hz, 2H) 7.23-7.31 (m, 2H) 7.06-7.21 (m, 3H) 5.63 (dd, J=8.09, 1.84 Hz, 1H) 3.78 (s, 3H) 3.07 (s, 3H) 1.37 (s, 9H).

Example 133

Preparation of (E)-tert-butyl 2-(3-tert-butyl-5-(2,4-dioxo-3,4-dihydropyrimidin-1(2H)-yl)-2-methoxystyryl)-5-(methylsulfonamido)phenylcarbamate (compound IB-L1-1.32)

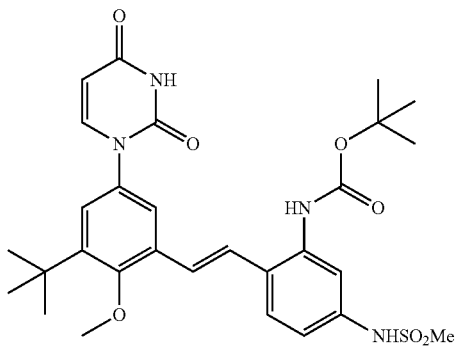

To a solution of the product from Example 125 (75 mg, 0.146 mmol) in tert-butanol (4 ml) was added diphenylphosphoryl azide (47 μL 0.219 mmol) and triethylamine (31 μL, 0.219 mmol). The resulting mixture was stirred at 80° C. for 18 h. The cooled mixture was partitioned between H$_2$O (10 ml) and EtOAc (2×10 ml). The combined organic layers were dried over Na$_2$SO$_4$, filtered and concentrated in vacuo. The crude product was purified by column chromatography on silica gel using 3% MeOH in CH$_2$Cl$_2$ as the eluent to give the title compound (16 mg, 19%). $^1$H NMR (300 MHz, DMSO-d$_6$) δ 11.45 (d, J=1.84 Hz, 1H) 9.86 (s, 1H) 9.03 (s, 1H) 7.75 (d, J=7.72 Hz, 2H) 7.55 (d, J=2.57 Hz, 1H) 7.10-7.33 (m, 4H) 7.04 (dd, J=8.64, 2.39 Hz, 1H) 5.66 (dd, J=7.91, 2.02 Hz, 1H) 3.78 (s, 3H) 3.02 (s, 3H) 1.45 (s, 9H) 1.38 (s, 9H).

Example 134

Preparation of (E)-N-(3-amino-4-(3-tert-butyl-5-(2,4-dioxo-3,4-dihydropyrimidin-1(2H)-yl)-2-methoxystyryl)phenyl)methanesulfonamide (compound IB-L1-1.28)

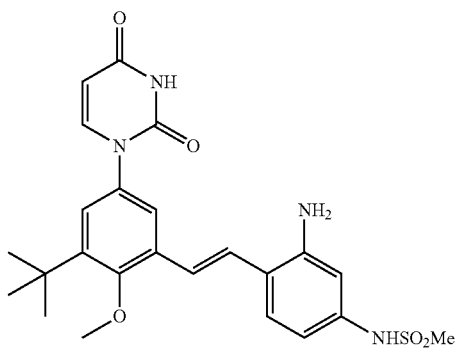

The procedure described for the preparation of Example 133 provided the title compound, which was purified by column chromatography on silica gel using 5% methanol in CH$_2$Cl$_2$ as the eluent (6 mg, 9%). $^1$H NMR (300 MHz, DMSO-d$_6$) δ 11.44 (d, J=2.21 Hz, 1H) 9.55 (s, 1H) 7.77 (d, J=2.57 Hz, 1H) 7.75 (d, J=8.09 Hz, 1H) 7.45 (d, J=8.46 Hz, 1H) 7.33 (d, J=15.81 Hz, 1H) 7.15 (d, J=2.57 Hz, 1H) 7.00 (d, J=16.18 Hz, 1H) 6.56 (d, J=2.21 Hz, 1H) 6.44 (dd, J=8.46, 2.21 Hz, 1H) 5.66 (dd, J=7.91, 2.02 Hz, 1H) 5.56 (s, 2H) 3.78 (s, 3H) 2.97 (s, 3H) 1.37 (s, 9H).

Example 135

Preparation of (E)-N-(4-(3-tert-butyl-5-(2,4-dioxo-3,4-dihydropyrimidin-1(2H)-yl)-2-methoxystyryl)-2-fluorophenyl)methanesulfonamide (compound IB-L1-1.5)

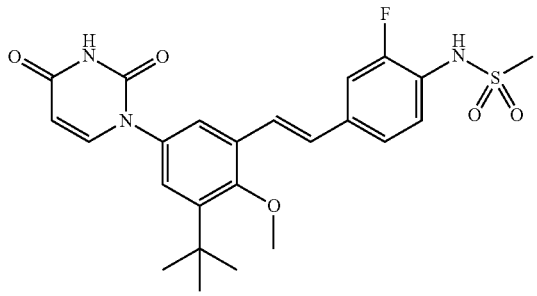 [SMILES: COc1c(/C=C/c2ccc(NS(C)(=O)=O)c(F)c2)cc(-n2ccc(=O)[nH]c2=O)cc1C(C)(C)C]

Part A. Preparation of (3-fluoro-4-nitrophenyl)methanol

To a solution of 3-fluoro-4-nitrobenzoic acid (2.0 g, 10.8 mmol) in THF (50 ml) at 0° C. was added BH$_3$.Me$_2$S complex (2.215 ml, 22.15 mmol) drop-wise. The mixture was stirred at 0° C. for 3 h, and was then stirred at 65° C. for 18 h. To the cooled mixture was added ice (50 g), followed by 1 N aq. HCl (100 ml), and the resulting mixture was extracted with EtOAc (200 ml). The organic layer was dried over Na$_2$SO$_4$, filtered and concentrated in vacuo to provide the title compound as a white solid (1.79 g, 97%).

Part B. Preparation of 4-(bromomethyl)-2-fluoro-1-nitrobenzene

A solution of the product from Part A (1.79 g, 10.46 mmol), N-bromosuccinimide (2.234 g, 12.55 mmol) and triphenylphosphine (3.29 g, 12.55 mmol) in CH$_2$Cl$_2$ (100 ml) and THF (50 ml) was stirred at room temperature for 3 h. The mixture was partitioned between H$_2$O (200 ml) and EtOAc (400 ml), and the organic layer was dried over Na$_2$SO$_4$, filtered and concentrated in vacuo. The crude product was purified by column chromatography on silica gel using 1:1 EtOAc:hexanes as the eluent to give the title compound (1.14 g, 47%).

Part C. Preparation of diethyl 3-fluoro-4-nitrobenzylphosphonate

The product from Part B (1.25 g, 5.34 mmol) was subjected to the conditions described for Example 34, Part B to provide the title product (0.75 g, 48%).

Part D. Preparation of (E)-N-(4-(3-tert-butyl-5-(2,4-dioxo-3,4-dihydropyrimidin-1(2H)-yl)-2-methoxystyryl)-2-fluorophenyl)methanesulfonamide The product from Part C (0.193 g, 0.662 mmol) was subjected to the conditions described for Example 41A, Part E, Part F, and Part G to provide the title product as a colorless solid (15 mg, 5%). $^1$H NMR (300 MHz, DMSO-d$_6$) δ 11.43 (s, 1H), 9.67 (s, 1H), 7.76 (d, J=8.1 Hz, 1H), 7.62 (m, 2H), 7.41 (m, 2H), 7.38 (m, 1H), 7.23 (m, 2H), 5.66 (dd, J=8.0, 2.0 Hz, 1H), 3.80 (s, 3H), 3.05 (s, 3H), 1.38 (s, 9H).

Example 136

Preparation of (E)-N-(4-(3-tert-butyl-5-(2,4-dioxo-3,4-dihydropyrimidin-1(2H)-yl)-2-methoxystyryl)-2-fluoro-5-methylphenyl)methanesulfonamide (compound IB-L1-1.15)

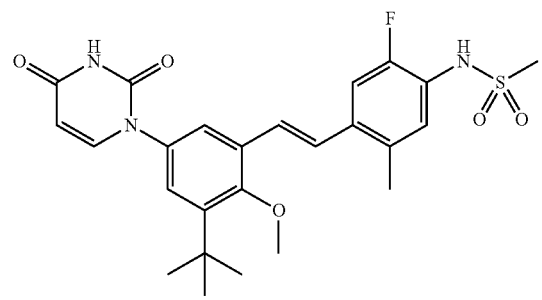 [SMILES: COc1c(/C=C/c2cc(F)c(NS(C)(=O)=O)cc2C)cc(-n2ccc(=O)[nH]c2=O)cc1C(C)(C)C]

Part A. Preparation of N-(4-bromo-2-fluoro-5-methylphenyl)methanesulfonamide To a solution of 4-bromo-2-fluoro-5-methylaniline (2.04 g, 10.0 mmol) in anhydrous CH$_2$Cl$_2$ (20 ml) and pyridine (3.23 ml, 40.0 mmol) was added methanesulfonyl chloride (0.86 ml, 11.0 mmol) and the resulting mixture was stirred at room temperature for 2 h. Solvent was removed in vacuo, and the residue was partitioned between EtOAc and 1M aq. HCl. The organic layer was washed with saturated aqueous NaHCO$_3$, brine and then dried over Na$_2$SO$_4$. The drying agent was filtered off, and the filtrate was concentrated to give the title compound as a solid (2.80 g, 99%).

Part B. Preparation of N-(4-ethynyl-2-fluoro-5-methylphenyl)methanesulfonamide A mixture of the product from Part A (3.0 g, 10.63 mmol), triphenylphosphine (0.279 g, 1.06 mmol), trimethylsilylacetate (6.0 ml, 42.5 mmol) and palladium(II) acetate (0.12 g, 0.53 mmol) in triethylamine (30 ml) and toluene (15 ml) under N$_2$ was heated at 80° C. for 5 h. The mixture was allowed to cool to room temperature, and was partitioned between EtOAc and 1M aq. HCl. The organic layer was washed with saturated NaHCO$_3$ and brine, dried over Na$_2$SO$_4$, filtered and concentrated in vacuo. The crude product was purified by column chromatography on silica gel using a solvent gradient of 10% to 35% EtOAc in hexanes to give an oil (3.0 g, 94%). To a solution of the oil (3.0 g, 10.0 mmol) in MeOH (50 ml) was added 1M aq. NaOH (21 ml, 21.0 mmol), and the resulting mixture was stirred at room temperature for 45 min. The mixture was partitioned between EtOAc and 1M aq. HCl, and the organic layer was washed with brine and dried over Na$_2$SO$_4$. The drying agent was filtered off, and the filtrate was concentrated in vacuo to give the title compound as a solid (2.3 g, quant.).

Part C. Preparation of (E)-5-fluoro-2-methyl-4-(methylsulfonamido)styrylboronic acid The product from Part B (0.20 g, 0.88 mmol) was subjected to the conditions described for the preparation of Example 41B, Part B to give the title compound (42 mg, 17%).

Part D. Preparation of (E)-N-(4-(3-tert-butyl-5-(2,4-dioxo-3,4-dihydropyrimidin-1(2H)-yl)-2-methoxystyryl)-2-fluoro-5-methylphenyl)methanesulfonamide The product from Part C (40 mg, 0.15 mmol) was subjected to the conditions described for the preparation of Example 41B, Part I to give the title compound (51 mg, 83%). $^1$H NMR (300 MHz, DMSO-$d_6$) δ 11.42 (d, J=2.21 Hz, 1H) 9.59 (s, 1H) 7.70-7.78 (m, 2H) 7.66 (d, J=11.77 Hz, 1H) 7.20-7.32 (m, 3H) 5.65 (dd, J=7.72, 2.21 Hz, 1H) 3.79 (s, 3H) 3.05 (s, 3H) 2.38 (s, 3H) 1.38 (s, 9H).

Example 137

Preparation of methyl 2-(3-tert-butyl-5-(2,4-dioxo-3,4-dihydropyrimidin-1(2H)-yl)-2-methoxyphenethyl)-5-(methylsulfonamido)benzoate (compound IB-L5-2-1.1)

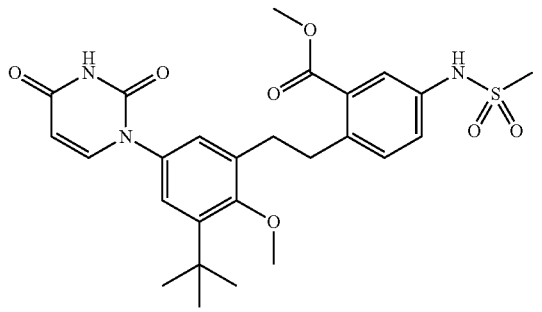 [SMILES: COC(=O)c1cc(NS(C)(=O)=O)ccc1CCc1cc(-n2ccc(=O)[nH]c2=O)cc(C(C)(C)C)c1OC]

To a solution of the product from Example 124 (40 mg, 0.076 mmol) in MeOH (2 ml) and THF (2 ml) was added 10% Pd/C (20 mg) and the resulting mixture was stirred at room temperature under 1 atm H$_2$ for 16 h. The mixture was filtered through celite and concentrated in vacuo to give a solid (27.5 mg, 68%). $^1$H NMR (300 MHz, DMSO-$d_6$) δ 11.39 (s, 1H) 9.88 (s, 1H) 7.61-7.71 (m, 2H) 7.28-7.36 (m, 2H) 7.20 (d, J=2.57 Hz, 1H) 7.13 (d, J=2.94 Hz, 1H) 5.64 (d, J=7.72 Hz, 1H) 3.83 (s, 3H) 3.75 (s, 3H) 3.14 (dd, J=10.30, 5.88 Hz, 2H) 2.96 (s, 3H) 2.83-2.92 (m, 2H) 1.34 (s, 9H).

Example 138

Preparation of N-(4-(3-tert-butyl-5-(2,4-dioxo-3,4-dihydropyrimidin-1(2H)-yl)-2-methoxyphenethyl)phenyl)methanesulfonamide (compound IB-L5-2-1.2)

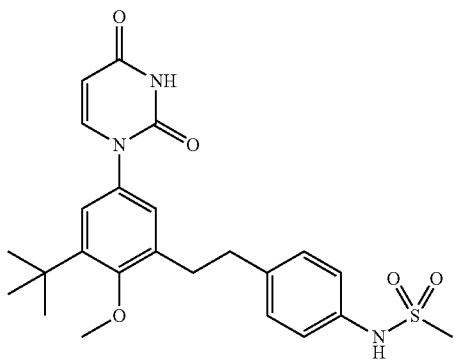 [SMILES: COc1c(CCc2ccc(NS(C)(=O)=O)cc2)cc(-n2ccc(=O)[nH]c2=O)cc1C(C)(C)C]

The product from Example 41B, Part M (200 mg, 0.426 mmol) was dissolved in MeOH (10 ml) followed by the addition of 10% Palladium on activated Carbon (50 mg). The resultant mixture was evacuated and a hydrogen balloon attached then stirred at room temperature for 48 h. The mixture was then filtered through celite and the filtrate concentrated under vacuum to an oil which was dissolved in ethanol (4 ml) then a 1N solution of aqueous sodium hydroxide (3.8 ml, 3.8 mmol) was added and the solution stirred at room temperature for 18 h. The ethanol was then removed under vacuum and a 1N solution of aqueous hydrochloric acid (4 ml) was added to acidify the mixture followed by extraction with EtOAc (2×10 mL). The organic extracts were combined, dried and purified by column chromatography on silica gel using 5% MeOH in CH$_2$Cl$_2$ as the eluent to provide the title compound as a colorless solid (82 mg, 41%). $^1$H NMR (300 MHz, DMSO-$d_6$) δ 11.39 (s, 1H), 9.60 (s, 1H), 7.65 (d, J=8.1 Hz, 1H), 7.23 (m, 3H), 7.17 (m, 3H), 5.64 (d, J=7.7 Hz, 1H), 3.77 (s, 3H), 2.93 (s, 3H), 2.88 (br s, 4H), 1.35 (s, 9H).

Example 139

Preparation of (E)-N-(4-(3-tert-butyl-5-(2,4-dioxo-3,4-dihydropyrimidin-1(2H)-yl)-2-ethoxystyryl)phenyl)methanesulfonamide (compound IB-L1-1.30)

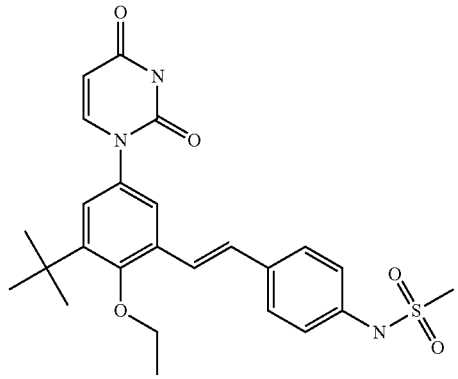 [SMILES: CCOc1c(/C=C/c2ccc(NS(C)(=O)=O)cc2)cc(-n2ccc(=O)[nH]c2=O)cc1C(C)(C)C]

Part A. Preparation of 2-tert-butyl-4-iodophenol

To a 250 mL round-bottom flask was added 2-tert-butylphenol (3.76 g, 25 mmol) in MeOH (50.0 ml) to give a colorless solution. Sodium hydroxide (1.200 g, 30.0 mmol) was added and the mix was stirred until the hydroxide was completely dissolved. The solution was cooled to 0° C. and treated with sodium iodide (1.75 g, 11.6 mmol) followed by drop-wise addition of 10% sodium hypochlorite solution (7.2 ml, 11.6 mmol). The addition of sodium iodide followed by sodium hypochlorite was repeated twice and the mixture was stirred at 0° C. for 30 min. The mixture was treated with 10% w/w solution of sodium thiosulfate, stirred for 30 min and treated with concentrated HCl dropwise to a constant pH of 1. The mixture was extracted 3× with EtOAc. The extracts were combined, washed with brine, dried (MgSO4), filtered and concentrated. The crude oil was flash chromatographed on an Isco 80 g silica cartridge eluting with hexane to >4:1 hexane/EtOAc to give a yellow oil (5.2 g, 75%).

Part B. Preparation of 2-bromo-6-tert-butyl-4-iodophenol

To a 250 mL round-bottom flask was added the product from Part A (4.8 g, 17.38 mmol) and 1,3-dibromo-5,5-dimethylhydantoin (2.61 g, 9.13 mmol) in chloroform (87 ml) to give an orange solution. The reaction mixture was stirred for 2 h resulting in a black solution that was washed with water, brine, dried ($Na_2SO_4$) and concentrated. The black oil was flash chromatographed on a 120 g Isco silica cartridge eluting with hexane to give a pinkish solid (4.84 g, 78%).

Part C. Preparation of 1-bromo-3-tert-butyl-2-ethoxy-5-iodobenzene

To a 50 mL round-bottom flask was added the product from Part B (888 mg, 2.5 mmol), ethyl iodide (409 mg, 2.63 mmol), and potassium carbonate (415 mg, 3.00 mmol) in acetone (12 ml) to give a green suspension. The mixture was heated at reflux for 16 h, cooled and concentrated. The residue was partitioned between water and EtOAc. The organic layer was washed twice with brine, dried over $Na_2SO_4$, filtered and concentrated to a red oil. The oil was flash chromatographed on an Isco 40 g silica cartridge eluting with hexane to give a clear oil (820 mg, 86%).

Part D. Preparation of 1-(3-bromo-5-tert-butyl-4-ethoxyphenyl)pyrimidine-2,4(1H,3H)-dione In a 20 mL microwave tube under nitrogen flush was added the product from Part C (0.4 g, 1.044 mmol), 1H-Pyrimidine-2,4-dione (0.140 g, 1.253 mmol), and potassium phosphate tribasic (0.465 g, 2.193 mmol) in DMSO (5 ml) to give a colorless suspension. N-(2-cyanophenyl)picolinamide (0.047 g, 0.209 mmol) was added and the mix was sparged with nitrogen for 10 min. Copper(I) iodide (0.020 g, 0.104 mmol) was added and the mix was sparged once again for 10 min, placed under nitrogen and heated at 60° C. for 18 h. The mixture was cooled and partitioned between EtOAc and water adjusting the pH to 1 with HCl. The aqueous layer was extracted 2× with EtOAc. The organics were combined, washed with water, saturated $NaHCO_3$, and saturated NaCl. The organic layer was dried ($Na_2SO_4$), stirred with 3-mercaptopropyl functionalized silica for 1 h, filtered and concentrated. The crude product was purified by chromatography on an Isco 12 g silica cartridge eluting with 2% MeOH in $CH_2Cl_2$ to give a white powder (266 mg, 69%).

Part E. Preparation of (E)-N-(4-(3-tert-butyl-5-(2,4-dioxo-3,4-dihydropyrimidin-1(2H)-yl)-2-ethoxystyryl)phenyl)methanesulfonamide A mixture of the product from Part D (55.1 mg, 0.15 mmol), the product from Example 41B, Part B (36.2 mg, 0.150 mmol), potassium phosphate tribasic (63.7 mg, 0.300 mmol) and 1,1'-bis(di-tert-butylphosphino)ferrocene palladium dichloride (4.89 mg, 7.50 mmol) in THF (3 ml) water (1 ml) was sparged for 10 min with nitrogen, and then sealed and heated at 50° C. for 4 h. The mixture was cooled to room temperature and diluted into EtOAc. The EtOAc layer was washed with 1M HCl, saturated NaHCO3, saturated NaCl, dried ($Na_2SO_4$) and treated simultaneously with mercaptopropyl silica gel, filtered and concentrated. The crude product was purified by column chromatography on silica gel using 2% MeOH in $CH_2Cl_2$ as the eluent to give the title compound as a solid (40 mg, 55%) m.p. 265-266° C. $^1$H NMR (300 MHz, DMSO-$d_6$) δ 11.42 (s, 1H) 9.87 (s, 1H) 7.76 (d, J=8.09 Hz, 1H) 7.55-7.66 (m, 3H) 7.17-7.27 (m, 5H) 5.65 (dd, J=7.72, 1.47 Hz, 1H) 3.89 (q, J=6.74 Hz, 2H) 3.02 (s, 3H) 1.45 (t, J=6.99 Hz, 3H) 1.39 (s, 9H).

Example 140

Preparation of N-(4-((3-cyclopropyl-5-(2,4-dioxotetrahydropyrimidin-1(2H)-yl)-2-methoxyphenyl)ethynyl)phenyl)methanesulfonamide (compound IA-L2-1.23)

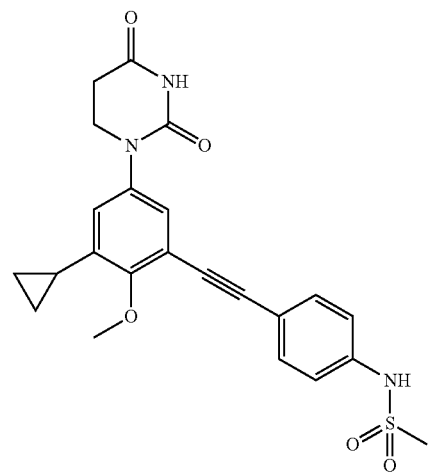 [SMILES: COc1c(C#Cc2ccc(NS(C)(=O)=O)cc2)cc(N2CCC(=O)NC2=O)cc1C1CC1]

Part A. Preparation of 3-bromo-2-methoxy-5-nitrobenzaldehyde

Into an appropriately sized pressure bottle was placed commercially available 3-bromo-2-hydroxy-5-nitrobenzaldehyde (2.46 gm, 10.00 mmol), iodomethane (6.23 mL, 100 mmol), silver oxide (2.317 g, 10.00 mmol) and acetonitrile (50 mL). The bottle was sealed and heated with stirring at 50° C. for 2 h. The reaction mixture was filtered through celite and the filtrate concentrated to give a solid residue that was triturated with hexane, collected by filtration and dried. The resulting solid was purified by silica gel chromatography (hexane-ethylacetate) to give the title compound (1.2 g, 46%).

Part B. Preparation of 3-cyclopropyl-2-methoxy-5-nitrobenzaldehyde

The product from Part A (0.65 gm, 2.50 mmol) was combined with cyclopropyl boronic acid (0.279 g, 3.25 mmol), potassium phosphate (1.85 g, 8.75 mmol), tricyclohexylphosphine teterafluoroborate (0.092 gm, 0.250 mmol), palladium (II) acetate (0.028 gm, 0.125 mmol) and toluene-water, 20:1 v/v (12 mL) in a microwave tube. The reaction mixture was purged with nitrogen for 5 min then heated at 100° C. in a microwave reactor for 20 min. The mixture was subsequently partitioned with ethyl acetate and water. The organic phase was washed with brine and concentrated in vacuo to give a residue that was purified by chromatography on silica gel (hexane-ethylacetate) to afford the title compound as a white solid (0.47 g, 85%).

Part C. Preparation of 1-cyclopropyl-3-ethynyl-2-methoxy-5-nitrobenzene

The product from Part B (0.20 g, 0.904 mmol) was reacted with 1-diazo-2-oxopropyl phosphonate (0.182 g, 0.949 mmol), prepared by the method of Ohira, Syn. Comm. 19 (3&4) 561-564 (1989), as described in Example 44 Part G. The crude product was purified by chromatography on silica gel (ethylacetate-hexanes) to give the title compound as a pale yellow oil which crystallizes in standing (0.155 g, 79%).

Part D. Preparation of N-(4-((3-cyclopropyl-2-methoxy-5-nitrophenyl)ethynyl)phenyl)methanesulfonamide The product from Part C (0.155 g, 0.712 mmol) was combined in a round bottom flask with N-(4-iodophenyl)methanesulfonamide (0.212 gm, 0.712 mmol), prepared as in Example 43, Part F substituting 4-iodoaniline for 4-iodo-3-methylaniline. To this mixture was added copper (I) iodide (10.31 mg, 0.054 mmol), bis(triphenylphosphine)palladium (II)chloride (0.034 g, 0.048 mmol), triethylamine (0.496 mL, 3.56 mmol) and anhydrous acetonitrile (14 mL). A reflux condenser was attached and the mixture was purged with nitrogen for 5 min and then heated under nitrogen in an oil bath at 80° C. for 1 h. The reaction mixture was concentrated in vacuo and the crude product was purified by chromatography on silica gel column eluting with ethylacetate-hexanes to give the title compound as a yellow solid (0.1887 g, 68.6%).

Part E. Preparation of N-(4-((5-amino-3-cyclopropyl-2-methoxyphenyl)ethynyl)phenyl)methanesulfonamide The product from Part D (0.184 gm, 0.475 mmol) was combined with iron (0.133 gm, 2.38 mmol) and ammonium chloride (0.050 gm, 0.932 mmol) in a round bottom flask. To this was added ethanol (1 mL), tetrahydrofuran (THF) (2 mL) and water (2 mL), and the resulting mixture heated with vigorous stirring under nitrogen to 80° C. in an oil bath a total of 4.5 h. On completion of heating the reaction mixture was filtered through a pad of sand and celite. The filter pad was washed with THF and the combined filtrates concentrated in vacuo. The residue was partitioned between water and dichloromethane. The organics were washed with water and then dried (MgSO4) and concentrated. The residue was purified by chromatography on silica gel eluting with ethylacetate-hexanes to give the title compound as an amber oil (0.1098 g, 65%).

Part F. Preparation of N-(4-((3-cyclopropyl-5-(2,4-dioxotetrahydropyrimidin-1(2H)-yl)-2-methoxyphenyl)ethynyl)phenyl)methanesulfonamide The product from Part E (0.1098 g, 0.308 mmol) was reacted with acrylic acid (1.27 mL, 18.48 mmol) as described in Example 43 Part E. The crude product in acrylic acid was treated with urea (0.094 g, 1.558 mmol) and glacial acetic acid (1.3 mL) then heated under nitrogen to 120° C. in an oil bath for eleven hours. The reaction mixture was concentrated in vacuo and diluted with water. The resulting solid was collected by vacuum filtration, washed with water and dried in vacuo to give the title compound as a yellow solid (0.0877 g, 63%). Purification by chromatography on silica gel using ethylacetate-hexane then dichloromethane-methanol gave analytical material. $^1$H NMR (300 MHz, DMSO-$d_6$) δ 10.36 (s, 1H) 10.08 (s, 1H) 7.53 (d, J=8.82 Hz, 2H) 7.26 (dd, J=5.52, 2.94 Hz, 3H) 6.84 (d, J=2.57 Hz, 1H) 3.94 (s, 3H) 3.73 (t, J=6.62 Hz, 2H) 3.06 (s, 3H) 2.68 (t, J=6.62 Hz, 2H) 2.16 (s, 1H) 0.94-1.03 (m, 2H) 0.63-0.74 (m, 2H).

The following compounds were prepared utilizing the above discussion:

(E)-N'-(1-(3'-tert-butyl-5'-(2,4-dioxotetrahydropyrimidin-1(2H)-yl)-2'-methoxybiphenyl-4-yl)ethylidene)methanesulfonohydrazide (compound IA-L0-1.2). $^1$H NMR (300 MHz, DMSO-$d_6$) δ ppm 1.39 (s, 9H) 2.26 (s, 3H) 2.70 (t, J=6.62 Hz, 2H) 3.10 (s, 3H) 3.24 (s, 3H) 3.80 (t, J=6.62 Hz, 2H) 7.17 (d, J=2.57 Hz, 1H) 7.24 (d, J=2.57 Hz, 1H) 7.57 (d, J=8.46 Hz, 2H) 7.87 (d, J=8.46 Hz, 2H) 10.12 (s, 1H) 10.33 (s, 1H).

(E)-N'-((3'-tert-butyl-5'-(2,4-dioxotetrahydropyrimidin-1 (2H)-yl)-3,5-difluoro-2'-methoxy biphenyl-4-yl)methylene)methanesulfonohydrazide (compound IA-L0-1.3). $^1$H NMR (300 MHz, DMSO-$d_6$) δ ppm 1.39 (s, 9H) 2.70 (t, J=6.62 Hz, 2H) 3.08 (s, 3H) 3.30 (s, 3H) 3.80 (t, J=6.43 Hz, 2H) 7.26 (d, J=2.57 Hz, 1H) 7.34 (m, 3H) 8.11 (s, 1H) 10.36 (s, 1H) 11.39 (s, 1H).

(E)-N'-((3'-tert-butyl-5'-(2,4-dioxotetrahydropyrimidin-1 (2H)-yl)-3-fluoro-2'-methoxy biphenyl-4-yl)methylene)methanesulfonohydrazide (compound IA-L0-1.4). $^1$H NMR (300 MHz, DMSO-$d_6$) δ ppm 1.39 (s, 9H) 2.70 (t, J=6.62 Hz, 2H) 3.11 (s, 3H) 3.28 (s, 3H) 3.80 (t, J=6.80 Hz, 2H) 7.22 (d, J=2.57 Hz, 1H) 7.28 (d, J=2.57 Hz, 1H) 7.45 (m, 2H) 7.94 (t, J=8.09 Hz, 1H) 8.20 (s, 1H) 10.35 (s, 1H) 11.32 (s, 1H).

(E)-N'-((3'-tert-butyl-5'-(2,4-dioxotetrahydropyrimidin-1 (2H)-yl)-2',4-dimethoxy-biphenyl-3-yl)methylene)methanesulfonohydrazide (compound IA-L0-1.5). $^1$H NMR (300 MHz, DMSO-$d_6$) δ ppm 1.39 (s, 9H) 2.70 (t, J=6.62 Hz, 2H) 3.03 (s, 3H) 3.24 (s, 3H) 3.78 (t, J=6.80 Hz, 2H) 3.90 (s, 3H) 7.12 (d, J=2.57 Hz, 1H) 7.22 (m, 2H) 7.54 (dd, J=8.46, 2.21 Hz, 1H) 7.86 (d, J=2.21 Hz, 1H) 8.34 (s, 1H) 10.32 (s, 1H) 11.05 (s, 1H).

(E)-N'-((3'-tert-butyl-5'-(2,4-dioxotetrahydropyrimidin-1 (2H)-yl)-2,3-difluoro-2'-methoxy biphenyl-4-yl)methylene) methanesulfonohydrazide (compound IA-L0-1.6). $^1$H NMR (500 MHz, DMSO-$d_6$) δ ppm 1.38 (s, 9H) 2.70 (t, J=6.41 Hz, 2H) 3.11 (s, 3H) 3.28 (s, 3H) 3.79 (t, J=6.71 Hz, 2H) 7.18 (d, J=2.44 Hz, 1H) 7.35 (m, 2H) 7.74 (t, J=7.32 Hz, 1H) 8.19 (s, 1H) 10.32 (s, 1H) 11.44 (s, 1H).

(E)-N'-((3'-tert-butyl-5'-(2,4-dioxotetrahydropyrimidin-1 (2H)-yl)-2'-methoxybiphenyl-3-yl)methylene)methanesulfonohydrazide (compound IA-L0-1.7). $^1$H NMR (300 MHz, DMSO-D6) δ ppm 1.39 (s, 9H) 2.70 (t, J=6.62 Hz, 2H) 3.07 (s, 3H) 3.23 (s, 3H) 3.80 (t, J=6.43 Hz, 2H) 7.17 (d, J=2.57 Hz, 1H) 7.25 (d, J=2.57 Hz, 1H) 7.54 (m, 2H) 7.73 (m, 2H) 8.06 (s, 1H) 10.33 (s, 1H) 11.11 (s, 1H).

(Z)—N'-(1-(3'-tert-butyl-5'-(2,4-dioxotetrahydropyrimidin-1(2H)-yl)-2'-methoxybiphenyl-3-yl)ethylidene)methanesulfonohydrazide (compound IA-L0-1.8). $^1$H NMR (300 MHz, DMSO-$d_6$) δ ppm 1.39 (s, 9H) 2.26 (s, 3H) 2.70 (t, J=6.80 Hz, 2H) 3.07 (s, 3H) 3.22 (s, 3H) 3.80 (t, J=6.62 Hz, 2H) 7.18 (d, J=2.57 Hz, 1H) 7.24 (d, J=2.94 Hz, 1H) 7.46-7.59 (m, 2H) 7.79 (d, J=7.35 Hz, 1H) 7.84 (s, 1H) 10.11 (s, 1H) 10.33 (s, 1H).

N-(3-(2-(3-tert-butyl-5-(2,4-dioxotetrahydropyrimidin-1 (2H)-yl)-2-methoxyphenyl)oxazol-5-yl)phenyl)methanesulfonamide (compound IA-L0-1.9)

1-(3-tert-butyl-4-methoxy-5-(5-(3-nitrophenyl)oxazol-2-yl)phenyl)dihydropyrimidine-2,4(1H,3H)-dione (compound IA-L0-1.10)

1-(3-tert-butyl-4-methoxy-5-(5-(4-nitrophenyl)oxazol-2-yl)phenyl)dihydropyrimidine-2,4(1H,3H)-dione (compound IA-L0-1.11)

N-(3'-tert-butyl-5'-(2,4-dioxo-3,4-dihydropyrimidin-1 (2H)-yl)-2'-methoxybiphenyl-4-yl)methanesulfonamide (compound IB-L0-1.2). $^1$H NMR (300 MHz, CDCl$_3$) δ ppm 1.43 (s, 9H) 3.07 (s, 3H) 3.32 (s, 3H) 5.82 (dd, J=8.09, 2.21

Hz, 1H) 6.79 (s, 1H) 7.14 (d, J=2.94 Hz, 1H) 7.21 (d, J=2.57 Hz, 1H) 7.28 (d, 2H) 7.35 (d, J=8.09 Hz, 1H) 7.54 (d, J=8.46 Hz, 2H) 8.31 (s, 1H).

(E)-N'-((3'-tert-butyl-5'-(2,4-dioxo-3,4-dihydropyrimidin-1(2H)-yl)-3-fluoro-2'-methoxy biphenyl-4-yl)methylene)methanesulfonohydrazide (compound IB-L0-1.3). $^1$H NMR (300 MHz, DMSO-d$_6$) δ ppm 11.42 (s, 1H) 11.33 (s, 1H) 8.21 (s, 1H) 7.95 (s, 1H) 7.78 (d, J=7.72 Hz, 1H) 7.39-7.59 (m, 2H) 7.35 (s, 2H) 5.65 (dd, J=7.91, 2.02 Hz, 1H) 3.20-3.44 (m, 3H) 3.11 (s, 3H) 1.40 (s, 9H).

N-(2-(3'-tert-butyl-5'-(2,4-dioxo-3,4-dihydropyrimidin-1(2H)-yl)-2'-methoxybiphenyl-4-yl)ethyl)methanesulfonamide (compound IB-L0-1.4). $^1$H NMR (300 MHz, CDCl$_3$) δ ppm 1.43 (s, 9H) 2.86-2.99 (m, 2H) 2.91 (s, 3H) 3.31 (s, 3H) 3.38-3.51 (m, 2H) 5.80 (dd, J=8.09, 2.21 Hz, 1H) 7.12 (d, J=2.57 Hz, 1H) 7.21 (d, J=2.57 Hz, 1H) 7.26-7.32 (m, 1H) 7.35 (d, J=8.09 Hz, 1H) 7.52 (d, J=8.09 Hz, 2H) 7.78 (d, J=7.72 Hz, 1H) 8.15 (s, 1H).

(E)-N'-(1-(3'-tert-butyl-5'-(2,4-dioxo-3,4-dihydropyrimidin-1(2H)-yl)-2'-methoxy biphenyl-4-yl)ethylidene)methanesulfonohydrazide (compound IB-L0-1.5). $^1$H NMR (300 MHz, DMSO-d$_6$) δ ppm 11.40 (s, 1H) 10.13 (s, 1H) 7.88 (d, J=8.09 Hz, 2H) 7.78 (d, J=7.72 Hz, 1H) 7.60 (d, J=8.09 Hz, 2H) 7.29 (d, J=4.04 Hz, 2H) 5.64 (dd, J=7.72, 1.84 Hz, 1H) 3.27 (s, 3H) 3.10 (s, 3H) 2.27 (s, 3H) 1.40 (s, 9H).

(E)-N'-((3'-tert-butyl-5'-(2,4-dioxo-3,4-dihydropyrimidin-1(2H)-yl)-2',4-dimethoxy biphenyl-3-yl)methylene)methanesulfonohydrazide (compound IB-L0-1.6). $^1$H NMR (300 MHz, DMSO-d$_6$) δ ppm 11.38 (s, 1H) 11.05 (s, 1H) 8.34 (s, 1H) 7.88 (s, 1H) 7.75 (d, J=8.09 Hz, 2H) 7.41-7.66 (m, 1H) 7.00-7.37 (m, 3H) 5.63 (d, J=7.72 Hz, 1H) 3.91 (s, 3H) 3.27 (s, 3H) 3.03 (s, 3H) 1.40 (s, 9H).

N-(3'-tert-butyl-5'-(2,4-dioxo-3,4-dihydropyrimidin-1(2H)-yl)-2'-methoxybiphenyl-4-ylcarbamoyl)methanesulfonamide (compound IB-L0-1.7). $^1$H NMR (300 MHz, DMSO-d$_6$) δ ppm 1.39 (s, 9H) 2.50 (s, 3H) 3.26 (s, 3H) 5.63 (dd, J=7.91, 2.02 Hz, 1H) 7.23 (d, 2H) 7.38-7.63 (m, 5H) 7.76 (d, J=8.09 Hz, 1H) 8.95 (s, 1H) 10.46 (s, 1H) 11.39 (d, J=2.21 Hz, 1H).

N'-(3'-tert-butyl-5'-(2,4-dioxo-3,4-dihydropyrimidin-1(2H)-yl)-2'-methoxybiphenyl carbonyl)methanesulfonohydrazide (compound IB-L0-1.8). $^1$H NMR (300 MHz, DMSO-d$_6$) δ ppm 1.41 (s, 9H) 3.03 (s, 3H) 3.26 (s, 3H) 5.65 (dd, J=7.72, 1.84 Hz, 1H) 7.27-7.36 (m, 2H) 7.73 (dd, J=28.31, 8.09 Hz, 4H) 8.01 (d, J=8.09 Hz, 2H) 9.65 (s, 1H) 10.82 (s, 1H) 11.41 (s, 1H).

(E)-N'-(1-(3'-tert-butyl-5'-(2,4-dioxo-3,4-dihydropyrimidin-1(2H)-yl)-2'-methoxy biphenyl-3-yl)ethylidene)methanesulfonohydrazide (compound IB-L0-1.9). $^1$H NMR (300 MHz, DMSO-D$_6$) δ ppm 11.40 (s, 1H) 10.12 (s, 1H) 7.82-7.99 (m, 1H) 7.62-7.82 (m, 2H) 7.35-7.71 (m, 2H) 7.30 (s, 2H) 5.64 (dd, J=7.91, 2.02 Hz, 1H) 3.26 (s, 3H) 3.07 (s, 3H) 2.27 (s, 3H) 1.40 (s, 9H).

(E)-N'-(3'-tert-butyl-5'-(2,4-dioxo-3,4-dihydropyrimidin-1(2H)-yl)-2'-methoxy biphenyl-3-yl)methylene)methanesulfonohydrazide (compound IB-L0-1.10). $^1$H NMR (300 MHz, CDCl$_3$) δ ppm 1.44 (s, 9H) 3.19 (s, 3H) 3.31 (s, 3H) 5.44 (s, 1H) 5.82 (d, J=7.72 Hz, 1H) 7.17 (d, J=2.57 Hz, 1H) 7.24 (d, J=2.57 Hz, 1H) 7.36 (d, J=7.72 Hz, 1H) 7.48 (t, J=7.72 Hz, 1H) 7.63 (d, J=7.72 Hz, 1H) 7.70 (d, J=7.72 Hz, 1H) 7.80 (s, 1H) 7.88 (s, 1H) 8.32 (s, 1H).

N-(2-(3-tert-butyl-5-(2,4-dioxotetrahydropyrimidin-1(2H)-yl)-2-methoxyphenyl)-1H-benzo[d]imidazol-5-yl)-N-(methylsulfonyl)methanesulfonamide (compound IA-L1-2.10) $^1$H NMR (300 MHz, DMSO-D6) δ ppm 1.45 (s, 9H) 2.73 (t, J=6.62 Hz, 2H) 3.48 (s, 3H) 3.56 (s, 6H) 3.83 (t, J=6.80 Hz, 2H) 4.05 (t, 2H) 7.38 (dd, J=8.46, 1.84 Hz, 1H) 7.46 (d, J=2.57 Hz, 1H) 7.71 (d, J=8.46 Hz, 1H) 7.76 (d, J=2.57 Hz, 1H) 7.82 (d, J=1.84 Hz, 1H) 10.41 (s, 1H).

N-((6-(3-tert-butyl-2-chloro-5-(2,4-dioxo-3,4-dihydropyrimidin-1(2H)-yl)phenyl)benzo[b]thiophen-3-yl)methyl)methanesulfonamide (compound IB-L0-2.35). $^1$H NMR (300 MHz, DMSO-d$_6$) δ ppm 1.52 (s, 9H) 2.95 (s, 3H) 4.44 (d, J=5.88 Hz, 2H) 5.68 (d, J=8.09 Hz, 1H) 7.40 (d, J=2.57 Hz, 1H) 7.46 (dd, J=8.09, 1.47 Hz, 1H) 7.56 (d, J=2.57 Hz, 1H) 7.62 (t, J=6.07 Hz, 1H) 7.72 (s, 1H) 7.83 (d, J=8.09 Hz, 1H) 8.01 (m, 2H) 11.46 (s, 1H).

1-(3-tert-butyl-5-(2-chlorobenzo[d]thiazol-6-yl)-4-methoxyphenyl)pyrimidine-2,4(1H,3H)-dione (compound IB-L0-2.38). $^1$H NMR (300 MHz, DMSO-D6) δ ppm 1.41 (s, 9H) 3.24 (s, 3H) 5.65 (dd, J=8.09, 2.21 Hz, 1H) 7.34 (s, 2H) 7.73 (dd, J=8.64, 1.65 Hz, 1H) 7.79 (d, J=8.09 Hz, 1H) 8.07 (d, J=8.46 Hz, 1H) 8.30 (d, J=1.84 Hz, 1H) 11.42 (d, J=1.84 Hz, 1H)

N-(2-(3-tert-butyl-5-(2,4-dioxo-3,4-dihydropyrimidin-1(2H)-yl)-2-methoxyphenyl)quinolin-6-yl)methanesulfonamide (compound IB-L0-2.48).

1-(3-tert-butyl-4-methoxy-5-(1-oxo-2,3-dihydro-1H-inden-5-yl)phenyl)pyrimidine-2,4(1H,3H)-dione (compound IB-L0-2.50).

N,N'-(6,6'-(5-(2,4-dioxo-3,4-dihydropyrimidin-1(2H)-yl)-2-methoxy-1,3-phenylene)bis(naphthalene-6,2-diyl))dimethanesulfonamide (compound IB-L0-2.76). $^1$H NMR (300 MHz, DMSO-d$_6$) δ ppm 3.08 (s, 6H) 3.13 (s, 3H) 5.72 (d, J=8.18 Hz, 1H) 7.43 (dd, J=8.46, 1.84 Hz, 2H) 7.59 (s, 2H) 7.79 (m, 4H) 7.96 (m, 5H) 8.14 (s, 2H) 10.05 (s, 2H) 11.48 (s, 1H).

(E)-N-(4-(1-(3-tert-butyl-5-(2,4-dioxotetrahydropyrimidin-1(2H)-yl)-2-methoxyphenyl)prop-1-en-2-yl)phenyl)methanesulfonamide (compound IA-L1-1.6). $^1$H NMR (300 MHz, DMSO-d$_6$) δ 2.14 (s, 3H) 2.70 (t, J=6.62 Hz, 2H) 3.01 (s, 3H) 3.68 (s, 3H) 3.78 (t, J=6.62 Hz, 2H) 6.82 (s, 1H) 7.10-7.17 (m, 2H) 7.23 (d, J=8.46 Hz, 2H) 7.59 (d, J=8.46 Hz, 2H) 9.78 (s, 1H) 10.32 (s, 1H).

(Z)—N-(4-(3-tert-butyl-5-(2,4-dioxotetrahydropyrimidin-1(2H)-yl)-2-methoxystyryl)phenyl)methanesulfonamide (compound IA-L1-1.10). $^1$H NMR (300 MHz, DMSO-d$_6$) δ 10.23 (s, 1H) 9.74 (s, 1H) 7.23 (d, J=8.46 Hz, 2H) 7.13 (d, J=2.57 Hz, 1H) 7.06 (d, J=8.82 Hz, 2H) 6.92 (d, J=2.57 Hz, 1H) 6.54-6.67 (m, 2H) 3.78 (s, 3H) 3.57 (t, J=6.62 Hz, 2H) 2.96 (s, 3H) 2.60 (t, J=6.80 Hz, 2H) 1.34 (s, 9H).

(E)-N-(4-(3-tert-butyl-5-(2,4-dioxotetrahydropyrimidin-1(2H)-yl)-2-methoxystyryl)phenyl)-N-(methylsulfonyl)acetamide (compound IA-L1-1.11). $^1$H NMR (300 MHz, DMSO-d$_6$) δ 10.36 (s, 1H) 7.77 (d, J=8.46 Hz, 2H) 7.56 (d, J=2.21 Hz, 1H) 7.39-7.50 (m, 3H) 7.25 (d, J=16.55 Hz, 1H) 7.19 (d, J=2.57 Hz, 1H) 3.74-3.85 (m, 5H) 3.54 (s, 3H) 2.72 (t, J=6.62 Hz, 2H) 1.94 (s, 3H) 1.38 (s, 9H).

(E)-1-(3-(4-aminostyryl)-5-tert-butyl-4-methoxyphenyl)dihydropyrimidine-2,4(1H,3H)-dione (compound IA-L1-1.13). $^1$H NMR (300 MHz, DMSO-d$_6$) δ 1.36 (s, 9H) 2.70 (t, J=6.62 Hz, 2H) 3.74 (s, 3H) 3.77 (t, J=6.62 Hz, 2H) 5.34 (s, 1H) 6.57 (d, J=8.46 Hz, 2H) 6.98 (s, 1H) 7.07 (d, J=2.21 Hz, 1H) 7.17 (s, 2H) 7.30 (d, J=8.09 Hz, 2H) 7.45 (d, J=2.21 Hz, 1H) 10.32 (s, 1H).

(Z)—N-(4-(3-tert-butyl-5-(2,4-dioxotetrahydropyrimidin-1(2H)-yl)-2-methoxystyryl)phenyl)methanesulfonamide (compound IA-L1-1.20). $^1$H NMR (500 MHz, DMSO-d$_6$): δ ppm 1.37 (s, 9H), 2.71 (t, J=6.7 Hz, 2H), 3.01 (s, 3H), 3.75 (s, 3H), 3.79 (t, J=6.6 Hz, 2H), 7.13 (d, J=16.5 Hz, 1H), 7.15 (d, J=2.4 Hz, 2H), 7.23 (d, J=8.5 Hz, 2H), 7.25 (d, J=16.5 Hz, 1H), 7.51 (d, J=2.4 Hz, 1H), 7.61 (d, J=8.6 Hz, 2H), 9.80 (bs, 1H), 10.30 (s, 1H).

N-(4-(2-(3-tert-butyl-5-(2,4-dioxotetrahydropyrimidin-1 (2H)-yl)-2-methoxyphenyl)-1-fluorovinyl)phenyl)methanesulfonamide (compound IA-L1-1.21). (racemic mixture (1:1) of compounds IA-L1-1.4 and IA-L1-1.5).

(E)-1-(3-tert-butyl-4-methoxy-5-(4-nitrostyryl)phenyl)dihydropyrimidine-2,4(1H,3H)-dione (compound IA-L1-1.22).

1-{3-tert-butyl-5-[(Z)-2-chloro-2-(4-nitro-phenyl)-vinyl]-4-methoxy-phenyl}-dihydro-pyrimidine-2,4-dione (compound IA-L1-1.23).

1-{3-tert-butyl-4-methoxy-5-[(E)-2-(4-nitro-phenyl)-propenyl]-phenyl}-dihydro-pyrimidine-2,4-dione (compound IA-L1-1.24).

1-{3-tert-Butyl-5-[(E)-2-(4-nitro-phenyl)-vinyl]-phenyl}-dihydro-pyrimidine-2,4-dione (compound IA-L1-1.25). $^1$H NMR (300 MHz, DMSO-D6) δ ppm 1.33 (s, 9H) 2.70-2.77 (m, 2H) 3.84 (t, J=6.80 Hz, 2H) 7.33 (s, 1H) 7.49 (d, J=4.04 Hz, 2H) 7.56 (d, J=5.88 Hz, 2H) 7.89 (d, J=8.82 Hz, 2H) 8.25 (d, J=8.82 Hz, 2H) 10.40 (s, 1H)

N-(4-{(E)-2-[3-tert-Butyl-5-(dioxo-tetrahydro-pyrimidin-1-yl)-2-methoxy-phenyl]-vinyl}-3-methoxy-phenyl)-methanesulfonamide (compound IA-L1-1.27). $^1$H NMR (300 MHz, DMSO-D6) δ ppm 10.33 (s, 1H) 9.86 (s, 1H) 7.64 (d, J=8.46 Hz, 1H) 7.45 (d, J=2.21 Hz, 1H) 7.26 (s, 1H) 7.12 (d, J=2.21 Hz, 1H) 6.89 (d, 1H) 6.85 (dd, J=8.46, 1.84 Hz, 1H) 3.84 (s, 3H) 3.78 (t, J=6.80 Hz, 2H) 3.74 (s, 3H) 3.04 (s, 3H) 2.71 (t, J=6.62 Hz, 2H) 1.37 (s, 9H)

N-(4-{(E)-2-[3-tert-Butyl-5-(2,4-dioxo-3,4-dihydro-2H-pyrimidin-1-yl)-2-methoxy-phenyl]-vinyl}-3-formyl-phenyl)-methanesulfonamide (compound IB-L1-1.6). $^1$H NMR (300 MHz, DMSO-D6) δ ppm 1.39 (s, 9H) 3.07 (s, 3H) 3.81 (s, 3H) 5.66 (dd, J=7.72, 2.21 Hz, 1H) 7.26 (d, J=2.57 Hz, 1H) 7.30 (d, J=16.18 Hz, 1H) 7.51 (dd, J=8.64, 2.39 Hz, 1H) 7.69 (d, J=2.57 Hz, 1H) 7.73-7.78 (m, 2H) 7.97 (d, J=8.82 Hz, 1H) 8.06 (d, J=16.18 Hz, 1H) 10.15 (s, 1H) 10.45 (s, 1H) 11.43 (d, J=2.21 Hz, 1H)

N-[4-{(E)-2-[3-tert-Butyl-5-(2,4-dioxo-3,4-dihydro-2H-pyrimidin-1-yl)-2-methoxy-phenyl]-vinyl}-3-(hydroxyimino-methyl)-phenyl]-methanesulfonamide (compound IB-L1-1.8). $^1$H NMR (300 MHz, DMSO-d$_6$) δ 1.38 (s, 9H) 3.03 (s, 3H) 3.79 (s, 3H) 5.66 (dd, J=7.91, 2.02 Hz, 1H) 7.16 (d, J=15.81 Hz, 1H) 7.22 (d, J=2.57 Hz, 1H) 7.26 (dd, J=8.64, 2.39 Hz, 1H) 7.59 (d, J=16.18 Hz, 1H) 7.63 (d, J=2.21 Hz, 1H) 7.73-7.83 (m, 3H) 8.64 (s, 1H) 9.96 (s, 1H) 11.42 (d, J=2.21 Hz, 1H) 11.50 (s, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-N-(2-methoxy-ethyl)-benzamide (compound IB-L1-1.9). $^1$H NMR (300 MHz, DMSO-D6) δ 1.38 (s, 9H) 3.05 (s, 3H) 3.20 (s, 3H) 3.37-3.49 (m, 4H) 3.78 (s, 3H) 5.64 (d, J=7.72 Hz, 1H) 7.15 (d, J=2.57 Hz, 1H) 7.20 (d, J=2.57 Hz, 1H) 7.24 (s, 2H) 7.28 (dd, J=8.46, 2.21 Hz, 1H) 7.42 (d, J=2.57 Hz, 1H) 7.73 (d, J=7.72 Hz, 1H) 7.87 (d, J=8.82 Hz, 1H) 8.49 (t, J=5.15 Hz, 1H) 9.99 (s, 1H) 11.42 (s, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-benzoic acid ethyl ester (compound IB-L1-1.11). $^1$H NMR (300 MHz, DMSO-d$_6$) δ 1.31 (t, J=7.17 Hz, 3H) 1.38 (s, 9H) 3.05 (s, 3H) 3.79 (s, 3H) 4.33 (q, J=7.23 Hz, 2H) 5.65 (dd, J=7.72, 2.21 Hz, 1H) 7.15-7.25 (m, 2H) 7.46 (dd, J=8.64, 2.39 Hz, 1H) 7.52 (d, J=2.57 Hz, 1H) 7.68 (d, J=2.57 Hz, 1H) 7.71-7.81 (m, 2H) 7.90 (d, J=8.46 Hz, 1H) 10.06 (s, 1H) 11.42 (d, J=1.84 Hz, 1H).

N-(4-{(E)-2-[3-tert-Butyl-2-chloro-5-(2,4-dioxo-3,4-dihydro-2H-pyrimidin-1-yl)-phenyl]-vinyl}-phenyl)-methanesulfonamide (compound IB-L1-1.12). $^1$H NMR (300 MHz, DMSO-d$_6$) δ ppm 1.49 (s, 9H) 3.02 (s, 3H) 5.69 (d, J=7.72 Hz, 1H) 7.22 (m, 3H) 7.41 (d, J=2.21 Hz, 1H) 7.51 (d, J=16.18 Hz, 1H) 7.59 (d, J=8.82 Hz, 2H) 7.78 (d, J=2.21 Hz, 1H) 7.80 (d, J=8.09 Hz, 1H) 9.90 (s, 1H) 11.47 (s, 1H).

2-{(E)-2-[3-tert-Butyl-5-(2,4-dioxo-3,4-dihydro-2H-pyrimidin-1-yl)-2-methoxy-phenyl]-vinyl}-5-methanesulfonylamino-N,N-dimethyl-benzamide (compound IB-L1-1.14). $^1$H NMR (300 MHz, DMSO-d$_6$) δ 1.37 (s, 9H) 2.76 (s, 3H) 3.03 (s, 3H) 3.05 (s, 3H) 3.76 (s, 3H) 5.64 (dd, J=7.91, 1.65 Hz, 1H) 6.95 (d, J=16.55 Hz, 1H) 7.02 (d, J=2.21 Hz, 1H) 7.17-7.25 (m, 2H) 7.27 (dd, J=8.64, 2.39 Hz, 1H) 7.48 (d, J=2.57 Hz, 1H) 7.74 (d, J=8.09 Hz, 1H) 7.82 (d, J=8.82 Hz, 1H) 10.03 (s, 1H) 11.39-11.43 (m, 1H).

2-{(E)-2-[3-tert-butyl-5-(2,4-dioxo-3,4-dihydro-2H-pyrimidin-1-yl)-2-methoxy-phenyl]-vinyl}-5-methanesulfonylamino-N-methyl-benzamide (compound IB-L1-1.17). $^1$H NMR (300 MHz, DMSO-d$_6$) δ 1.38 (s, 9H) 2.77 (d, J=4.41 Hz, 3H) 3.06 (s, 3H) 3.77 (s, 3H) 5.64 (dd, J=7.72, 1.84 Hz, 1H) 7.16-7.33 (m, 5H) 7.43 (d, J=2.21 Hz, 1H) 7.73 (d, J=7.72 Hz, 1H) 7.84 (d, J=8.46 Hz, 1H) 8.37 (q, J=4.41 Hz, 1H) 10.00 (s, 1H) 11.40 (d, J=1.84 Hz, 1H).

2-{(E)-2-[3-tert-butyl-5-(2,4-dioxo-3,4-dihydro-2H-pyrimidin-1-yl)-2-methoxy-phenyl]-vinyl}-N-(1,1-dioxo-tetrahydro-1lambda*6*-thiophen-3-yl)-5-methanesulfonylamino-N-methyl-benzamide (compound IB-L1-1.18). $^1$H NMR (300 MHz, DMSO-d$_6$) δ 1.37 (s, 9H) 2.17-2.47 (m, 2H) 2.70 (s, 3H) 3.06 (s, 3H) 3.15-3.31 (m, 2H) 3.36-3.51 (m, 2H) 3.77 (s, 3H) 5.37 (dt, J=17.74, 8.96 Hz, 1H) 5.65 (dd, J=7.91, 2.02 Hz, 1H) 6.93 (d, J=16.18 Hz, 1H) 7.05 (d, J=2.21 Hz, 1H) 7.19-7.35 (m, 3H) 7.50 (d, J=2.57 Hz, 1H) 7.76 (d, J=8.09 Hz, 1H) 7.87 (d, J=8.82 Hz, 1H) 10.04 (s, 1H) 11.38 (d, J=2.21 Hz, 1H).

N-(4-{(E)-2-[3-tert-butyl-5-(5-chloro-2,4-dioxo-3,4-dihydro-2H-pyrimidin-1-yl)-2-methoxy-phenyl]-vinyl}-phenyl)-methanesulfonamide (Compound IB-L1-1.20). $^1$H NMR (300 MHz, DMSO-D6) δ ppm 11.31 (s, 1H) 9.77 (s, 1H) 7.53 (d, J=8.09 Hz, 1H) 7.23 (d, J=8.46 Hz, 2H) 7.17 (d, J=2.57 Hz, 1H) 7.06 (d, J=8.82 Hz, 2H) 7.01 (d, J=2.57 Hz, 1H) 6.53-6.71 (m, 2H) 5.56 (d, J=7.72 Hz, 1H) 3.81 (s, 3H) 2.96 (s, 3H) 1.35 (s, 9H)

2-{(E)-2-[3-tert-butyl-5-(2,4-dioxo-3,4-dihydro-2H-pyrimidin-1-yl)-2-methoxy-phenyl]-vinyl}-5-methanesulfonylamino-benzamide (compound IB-L1-1.21). $^1$H NMR (300 MHz, DMSO-d$_6$) δ 1.38 (s, 9H) 3.07 (s, 3H) 3.78 (s, 3H) 5.64 (d, J=7.72 Hz, 1H) 7.18-7.34 (m, 5H) 7.43 (d, J=2.21 Hz, 1H) 7.54 (s, 1H) 7.73 (d, J=7.72 Hz, 1H) 7.84 (d, J=8.46 Hz, 1H) 7.93 (s, 1H).

N-(3-(azetidine-1-carbonyl)-4-{(E)-2-[3-tert-butyl-5-(2,4-dioxo-3,4-dihydro-2H-pyrimidin-1-yl)-2-methoxy-phenyl]-vinyl}-phenyl)-methanesulfonamide (compound (compound IB-L1-1.22). $^1$H NMR (300 MHz, DMSO-d$_6$) δ 1.38 (s, 9H) 3.07 (s, 3H) 3.78 (s, 3H) 5.64 (d, J=7.72 Hz, 1H) 7.18-7.34 (m, 5H) 7.43 (d, J=2.21 Hz, 1H) 7.54 (s, 1H) 7.73 (d, J=7.72 Hz, 1H) 7.84 (d, J=8.46 Hz, 1H) 7.93 (s, 1H).

2-{(E)-2-[3-tert-butyl-5-(2,4-dioxo-3,4-dihydro-2H-pyrimidin-1-yl)-2-methoxy-phenyl]-vinyl}-5-methanesulfonylamino-N-(2-methoxy-ethyl)-N-methyl-benzamide (compound IB-L1-1.24). $^1$H NMR (300 MHz, DMSO-d$_6$) δ 1.40 (s, 9H) 2.81 (s, 3H) 3.07 (s, 3H) 3.23 (s, 3H) 3.29 (t, J=5.33 Hz, 1H) 3.39 (t, J=4.96 Hz, 1H) 3.62 (t, J=4.78 Hz, 2H) 3.82 (s, 3H) 5.68 (d, J=8.09 Hz, 1H) 6.96-7.07 (m, 1H) 7.09-7.17 (m, 1H) 7.23-7.38 (m, 3H) 7.49 (dd, J=16.55, 2.57 Hz, 1H) 7.71-7.76 (m, 1H) 7.83-7.94 (m, 1H).

N-(4-{(E)-2-[3-tert-butyl-5-(2,4-dioxo-3,4-dihydro-2H-pyrimidin-1-yl)-2-methoxy-phenyl]-vinyl}-3-isopropoxymethyl-phenyl)-methanesulfonamide (compound IB-L1-1.25). $^1$H NMR (300 MHz, DMSO-d$_6$) δ 1.16 (d, J=5.88 Hz, 6H) 1.38 (s, 9H) 3.01 (s, 3H) 3.69 (dt, J=12.13, 6.07 Hz, 1H) 3.79

(s, 3H) 4.59 (s, 2H) 5.65 (dd, J=7.91, 2.02 Hz, 1H) 7.13-7.29 (m, 4H) 7.32-7.40 (m, 1H) 7.59 (d, J=2.57 Hz, 1H) 7.75 (d, J=8.09 Hz, 2H) 9.86 (s, 1H) 11.43 (d, J=1.84 Hz, 1H).

N-[4-{(E)-2-[3-tert-butyl-5-(2,4-dioxo-3,4-dihydro-2H-pyrimidin-1-yl)-2-methoxy-phenyl]-vinyl}-3-(pyrrolidine-1-carbonyl)-phenyl]-methanesulfonamide (compound IB-L1-1.27). $^1$H NMR (300 MHz, DMSO-$d_6$) δ 1.37 (s, 9H) 1.73-1.89 (m, 4H) 3.03-3.12 (m, 5H) 3.51 (t, J=6.80 Hz, 2H) 3.76 (s, 3H) 5.64 (dd, J=7.91, 2.02 Hz, 1H) 6.99-7.06 (m, 1H) 7.08 (d, J=2.21 Hz, 1H) 7.19-7.31 (m, 3H) 7.46 (d, J=2.57 Hz, 1H) 7.75 (d, J=8.09 Hz, 1H) 7.82 (d, J=8.82 Hz, 1H) 10.01 (s, 1H) 11.41 (d, J=2.21 Hz, 1H).

N-[4-{(E)-2-[3-tert-butyl-5-(2,4-dioxo-3,4-dihydro-2H-pyrimidin-1-yl)-2-methoxy-phenyl]-vinyl}-3-(3-hydroxy-azetidin-1-ylmethyl)-phenyl]-methanesulfonamide (compound IB-L1-1.29). $^1$H NMR (300 MHz, DMSO-$d_6$) δ 1.38 (s, 9H) 2.78-2.85 (m, 2H) 2.99 (s, 3H) 3.50-3.58 (m, 2H) 3.71 (s, 2H) 3.79 (s, 3H) 4.19 (td, J=12.41, 6.07 Hz, 1H) 5.29 (d, J=6.25 Hz, 1H) 5.66 (d, J=8.09 Hz, 1H) 7.10-7.18 (m, 2H) 7.20 (t, J=2.21 Hz, 2H) 7.35-7.42 (m, 1H) 7.63 (d, J=2.57 Hz, 1H) 7.69 (d, J=8.46 Hz, 1H) 7.76 (d, J=7.72 Hz, 1H) 9.78 (s, 1H) 11.42 (s, 1H).

N-(4-{(E)-2-[3-tert-Butyl-5-(2,4-dioxo-3,4-dihydro-2H-pyrimidin-1-yl)-2-methoxy-phenyl]-vinyl}-3-pyrrolidin-1-ylmethyl-phenyl)-methanesulfonamide (compound IB-L1-1.33). $^1$H NMR (500 MHz, DMSO-$d_6$) δ 1.40 (s, 9H) 1.72-1.95 (m, 4H) 2.84 (s, 2H) 2.88-2.98 (m, 2H) 3.01 (s, 3H) 3.81 (s, 3H) 3.86-4.23 (m, 2H) 5.63 (d, J=7.81 Hz, 1H) 7.17 (d, J=15.63 Hz, 1H) 7.21-7.28 (m, 2H) 7.32-7.38 (m, 1H) 7.47 (d, J=16.11 Hz, 1H) 7.53-7.59 (m, 1H) 7.61 (d, J=7.81 Hz, 1H) 7.70 (d, J=6.35 Hz, 1H) 9.42 (s, 1H) 10.88 (s, 1H).

N-(4-{(Z)-2-[3-tert-Butyl-5-(2,4-dioxo-3,4-dihydro-2H-pyrimidin-1-yl)-2-methoxy-phenyl]-vinyl}-phenyl)-methanesulfonamide (compound IB-L1-1.34 $^1$H NMR (300 MHz, DMSO-D6) δ ppm 11.31 (s, 1H) 9.77 (s, 1H) 7.53 (d, J=8.09 Hz, 1H) 7.23 (d, J=8.46 Hz, 2H) 7.17 (d, J=2.57 Hz, 1H) 7.06 (d, J=8.82 Hz, 2H) 7.01 (d, J=2.57 Hz, 1H) 6.53-6.71 (m, 2H) 5.56 (d, J=7.72 Hz, 1H) 3.81 (s, 3H) 2.96 (s, 3H) 1.35 (s, 9H)

N-(4-((3-tert-butyl-5-(2,4-dioxotetrahydropyrimidin-1(2H)-yl)phenyl)ethynyl)phenyl)-methanesulfonamide (compound IA-L2-1.1). $^1$H NMR (300 MHz, DMSO-d6) δ ppm 1.30 (s, 9H) 2.72 (t, J=6.43 Hz, 2H) 3.06 (s, 3H) 3.82 (t, J=6.62 Hz, 2H) 7.24 (d, J=8.82 Hz, 2H) 7.33 (s, 1H) 7.39 (d, J=1.47 Hz, 2H) 7.54 (d, J=8.82 Hz, 2H) 10.08 (s, 1H) 10.40 (s, 1H)

N-(4-((3-tert-butyl-5-(2,4-dioxotetrahydropyrimidin-1(2H)-yl)phenyl)ethynyl)-3-methyl-phenyl)methanesulfonamide (compound IA-L2-1.2). $^1$H NMR (300 MHz, DMSO-d6) δ ppm 1.30 (s, 9H) 2.44 (s, 3H) 2.72 (t, J=6.62 Hz, 2H) 3.05 (s, 3H) 3.82 (t, J=6.62 Hz, 2H) 7.07 (dd, J=8.46, 1.47 Hz, 1H) 7.13 (s, 1H) 7.33 (s, 1H) 7.39 (d, J=1.47 Hz, 2H) 7.48 (d, J=8.09 Hz, 1H) 9.98 (s, 1H) 10.40 (s, 1H)

1-(3-tert-butyl-4-methoxy-5-(phenylethynyl)phenyl)dihydropyrimidine-2,4(1H,3H)-dione (compound IA-L2-1.4). $^1$H NMR (300 MHz, DMSO-$d_6$) δ ppm 1.36 (s, 9H) 2.70 (t, J=6.62 Hz, 2H) 3.78 (t, J=6.43 Hz, 2H) 4.07 (s, 3H) 7.27 (d, J=2.57 Hz, 1H) 7.38 (d, J=2.57 Hz, 1H) 7.41-7.49 (m, 3H) 7.55-7.63 (m, 2H) 10.37 (s, 1H).

N-(3-((3-tert-butyl-5-(2,4-dioxotetrahydropyrimidin-1(2H)-yl)-2-methoxyphenyl)ethynyl)phenyl)methanesulfonamide (compound IA-L2-1.7). $^1$H NMR (300 MHz, DMSO-$d_6$) δ ppm 1.36 (s, 9H) 2.70 (t, J=6.62 Hz, 2H) 3.04 (s, 3H) 3.78 (t, J=6.62 Hz, 2H) 4.06 (s, 3H) 7.23-7.35 (m, 3H) 7.35-7.46 (m, 3H) 9.94 (s, 1H) 10.37 (s, 1H).

N-(4-((3-tert-butyl-5-(2,4-dioxotetrahydropyrimidin-1(2H)-yl)-2-methoxyphenyl)ethynyl)-phenyl)methanesulfonamide (compound IA-L2-1.8). $^1$H NMR (300 MHz, DMSO-$d_6$) δ ppm 1.35 (s, 9H) 2.70 (t, J=6.62 Hz, 2H) 3.06 (s, 3H) 3.77 (t, J=6.62 Hz, 2H) 4.05 (s, 3H) 7.25 (dd, J=5.52, 2.94 Hz, 3H) 7.35 (d, J=2.57 Hz, 1H) 7.55 (d, J=8.46 Hz, 2H) 10.09 (s, 1H) 10.37 (s, 1H).

N-(4-((3-tert-butyl-5-(2,4-dioxotetrahydropyrimidin-1(2H)-yl)-2-methoxyphenyl)ethynyl)-2-methylphenyl)methanesulfonamide (compound IA-L2-1.10). $^1$H NMR (300 MHz, DMSO-d6) δ 1.35 (s, 9H) 2.32 (s, 3H) 2.70 (t, J=6.62 Hz, 2H) 3.03 (s, 3H) 3.78 (t, J=6.62 Hz, 2H) 4.06 (s, 3H) 7.26 (d, J=2.57 Hz, 1H) 7.32-7.44 (m, 3H) 7.48 (d, 1H) 9.23 (s, 1H) 10.37 (s, 1H)

N-(4-((3-tert-butyl-5-(2,4-dioxotetrahydropyrimidin-1(2H)-yl)-2-methoxyphenyl)ethynyl)-3-ethylphenyl)methanesulfonamide (compound IA-L2-1.11). $^1$H NMR (300 MHz, DMSO-$d_6$) δ ppm 1.15-1.28 (m, 3H) 1.36 (s, 9H) 2.70 (t, J=6.62 Hz, 2H) 2.81 (q, J=7.72 Hz, 2H) 3.05 (s, 3H) 3.78 (t, J=6.62 Hz, 2H) 4.04 (s, 3H) 7.10 (dd, J=8.27, 2.02 Hz, 1H) 7.14 (s, 1H) 7.25 (d, J=2.57 Hz, 1H) 7.35 (d, J=2.21 Hz, 1H) 7.50 (d, J=8.09 Hz, 1H) 10.01 (s, 1H) 10.36 (s, 1H).

N-(4-((3-tert-butyl-5-(2,4-dioxotetrahydropyrimidin-1(2H)-yl)-2-methoxyphenyl)ethynyl)-3-fluorophenyl)methanesulfonamide (compound IA-L2-1.12). $^1$H NMR (300 MHz, DMSO-$d_6$) δ ppm 1.35 (s, 9H) 2.70 (t, J=6.62 Hz, 2H) 3.13 (s, 3H) 3.78 (t, J=6.62 Hz, 2H) 4.05 (s, 3H) 6.98-7.20 (m, 2H) 7.28 (d, J=2.57 Hz, 1H) 7.36 (d, J=2.57 Hz, 1H) 7.61 (t, J=8.27 Hz, 1H) 10.37 (s, 2H).

N-(4-((3-tert-butyl-5-(2,4-dioxotetrahydropyrimidin-1(2H)-yl)-2-methoxyphenyl)ethynyl)-2-fluorophenyl)methanesulfonamide (compound IA-L2-1.13). $^1$H NMR (300 MHz, DMSO-$d_6$) δ ppm 1.35 (s, 9H) 2.70 (t, J=6.62 Hz, 2H) 3.10 (s, 3H) 3.78 (t, J=6.62 Hz, 2H) 4.05 (s, 3H) 7.28 (d, J=2.57 Hz, 1H) 7.38 (d, J=2.57 Hz, 1H) 7.42-7.61 (m, 3H) 9.89 (s, 1H) 10.38 (s, 1H).

N-(4-((3-tert-butyl-5-(2,4-dioxotetrahydropyrimidin-1(2H)-yl)-2-methoxyphenyl)ethynyl)-3-chlorophenyl)methanesulfonamide (compound IA-L2-1.14). $^1$H NMR (300 MHz, DMSO-$d_6$) δ ppm 1.35 (s, 9H) 2.70 (t, J=6.62 Hz, 2H) 3.12 (s, 3H) 3.78 (t, J=6.80 Hz, 2H) 4.07 (s, 3H) 7.21 (dd, J=8.46, 2.21 Hz, 1H) 7.28 (d, J=2.57 Hz, 1H) 7.36 (dd, J=4.60, 2.39 Hz, 2H) 7.67 (d, J=8.46 Hz, 1H) 10.32 (s, 1H) 10.37 (s, 1H).

N-(4-((3-tert-butyl-5-(2,4-dioxotetrahydropyrimidin-1(2H)-yl)-2-methoxyphenyl)ethynyl)-2-chlorophenyl)methanesulfonamide (compound IA-L2-1.15). $^1$H NMR (300 MHz, DMSO-d6) δ ppm 1.35 (s, 9H) 2.70 (t, J=6.62 Hz, 2H) 3.10 (s, 3H) 3.78 (t, J=6.62 Hz, 2H) 4.06 (s, 3H) 7.29 (d, J=2.94 Hz, 1H) 7.39 (d, J=2.57 Hz, 1H) 7.48-7.59 (m, 2H) 7.75 (s, 1H) 9.65 (s, 1H) 10.38 (s, 1H)

N-(4-((3-tert-butyl-5-(2,4-dioxotetrahydropyrimidin-1(2H)-yl)-2-methoxyphenyl)ethynyl)-3-methoxyphenyl)methanesulfonamide (compound IA-L2-1.16). $^1$H NMR (300 MHz, DMSO-$d_6$) δ ppm 1.35 (s, 9H) 2.63-2.76 (m, 2H) 3.08 (s, 3H) 3.77 (t, J=6.80 Hz, 2H) 3.82 (s, 3H) 4.08 (s, 3H) 6.79-6.89 (m, 1H) 6.91 (d, J=1.84 Hz, 1H) 7.22 (d, J=2.57 Hz, 1H) 7.30 (d, J=2.94 Hz, 1H) 7.45 (d, J=8.46 Hz, 1H) 10.06 (s, 1H) 10.35 (s, 1H).

N-(4-((3-tert-butyl-5-(2,4-dioxotetrahydropyrimidin-1(2H)-yl)-2-methoxyphenyl)ethynyl)-2-(trifluoromethoxy)phenyl)methanesulfonamide (compound IA-L2-1.17). $^1$H NMR (300 MHz, DMSO-$d_6$) δ ppm 1.35 (s, 9H) 2.70 (t, J=6.62 Hz, 2H) 3.13 (s, 3H) 3.78 (t, J=6.62 Hz, 2H) 4.05 (s, 3H) 7.29 (d, J=2.57 Hz, 1H) 7.40 (d, J=2.57 Hz, 1H) 7.52-7.69 (m, 3H) 10.06 (s, 1H) 10.38 (s, 1H).

N-(4-((3-tert-butyl-5-(2,4-dioxotetrahydropyrimidin-1(2H)-yl)-2-methoxyphenyl)ethynyl)-2-(trifluoromethyl)phenyl)methanesulfonamide (compound IA-L2-1.19). $^1$H NMR (300 MHz, DMSO-$d_6$) δ ppm 1.35 (s, 9H) 2.72 (d, J=6.62 Hz, 2H) 3.09 (s, 3H) 3.78 (s, 2H) 4.06 (s, 3H) 7.29 (s, 1H) 7.41 (s, 1H) 7.57-7.73 (m, 1H) 7.80-7.94 (m, 2H) 9.62 (s, 1H) 10.38 (s, 1H).

N-(4-((3-tert-butyl-5-(2,4-dioxotetrahydropyrimidin-1 (2H)-yl)-2-methoxyphenyl)ethynyl)-2-fluoro-5-methylphenyl)methanesulfonamide (compound IA-L2-1.20). $^1$H NMR (300 MHz, DMSO-D6) δ ppm 1.36 (s, 9H) 2.45 (s, 3H) 2.71 (t, J=6.43 Hz, 2H) 3.09 (s, 3H) 3.78 (t, J=6.62 Hz, 2H) 4.05 (s, 3H) 7.28 (d, J=2.57 Hz, 1H) 7.36 (d, J=8.09 Hz, 1H) 7.39 (d, J=2.57 Hz, 1H) 7.47 (d, J=11.03 Hz, 1H) 9.80 (s, 1H) 10.37 (s, 1H)

N-(4-((3-tert-butyl-5-(2,4-dioxotetrahydropyrimidin-1 (2H)-yl)-2-methoxyphenyl)ethynyl)-3-chloro-2-fluorophenyl)methanesulfonamide (compound IA-L2-1.21). $^1$H NMR (300 MHz, DMSO-d$_6$) δ ppm 1.36 (s, 9H) 2.71 (t, J=6.43 Hz, 2H) 3.14 (s, 3H) 3.78 (t, J=6.62 Hz, 2H) 4.08 (s, 3H) 7.31 (d, J=2.94 Hz, 1H) 7.39-7.46 (m, 1H) 7.48 (d, J=7.72 Hz, 1H) 7.51-7.61 (m, 1H) 10.15 (s, 1H) 10.38 (s, 1H).

N-(4-((3-tert-butyl-5-(2,4-dioxotetrahydropyrimidin-1 (2H)-yl)-2-methoxyphenyl)ethynyl)-2-fluoro-5-(trifluoromethyl)phenyl)methanesulfonamide (compound IA-L2-1.22). $^1$H NMR (300 MHz, DMSO-D6) δ ppm 1.35 (s, 9H) 2.71 (t, J=6.62 Hz, 2H) 3.17 (s, 3H) 3.78 (t, J=6.43 Hz, 2H) 4.03 (s, 3H) 7.32 (d, J=2.57 Hz, 1H) 7.37 (d, J=2.21 Hz, 1H) 7.83 (d, J=7.72 Hz, 1H) 7.88 (d, J=10.66 Hz, 1H) 10.27 (s, 1H) 10.38 (s, 1H)

N-(6-((3-tert-butyl-5-(2,4-dioxotetrahydropyrimidin-1 (2H)-yl)-2-methoxyphenyl)ethynyl)-5-methylpyridin-3-yl)methanesulfonamide (compound IA-L2-1.24). $^1$H NMR (300 MHz, DMSO-d$_6$) δ ppm 1.36 (s, 9H) 2.71 (t, J=6.62 Hz, 2H) 3.13 (s, 3H) 3.79 (t, J=6.80 Hz, 2H) 4.07 (s, 3H) 7.30 (d, J=2.57 Hz, 1H) 7.41 (d, J=2.57 Hz, 1H) 7.55 (s, 1H) 8.29 (s, 1H) 10.24 (s, 1H) 10.38 (s, 1H).

N-(5-((3-tert-butyl-5-(2,4-dioxotetrahydropyrimidin-1 (2H)-yl)-2-methoxyphenyl)ethynyl)-pyridin-2-yl)methanesulfonamide 2,2,2-trifluoroacetate (compound IA-L2-1.26). $^1$H NMR (300 MHz, DMSO-d$_6$) δ ppm 1.35 (s, 9H) 2.70 (t, J=6.62 Hz, 2H) 3.78 (t, J=6.80 Hz, 2H) 4.05 (s, 3H) 7.01 (d, J=8.82 Hz, 1H) 7.27 (d, J=2.57 Hz, 1H) 7.37 (d, J=2.57 Hz, 1H) 7.93 (dd, J=8.82, 2.21 Hz, 1H) 8.50 (s, 1H) 10.37 (s, 1H) 10.93 (s, 1H).

N-(4-((3-tert-butyl-5-(2,4-dioxotetrahydropyrimidin-1 (2H)-yl)-2-methoxyphenyl)ethynyl)-naphthalen-1-yl)methanesulfonamide (compound IA-L2-2.1). $^1$H NMR (300 MHz, DMSO-d$_6$) δ ppm 1.39 (s, 9H) 2.73 (t, J=6.62 Hz, 2H) 3.08 (s, 3H) 3.82 (t, J=6.62 Hz, 2H) 4.13 (s, 3H) 7.32 (d, J=2.57 Hz, 1H) 7.55 (d, J=2.57 Hz, 1H) 7.58 (d, J=7.72 Hz, 1H) 7.72 (m, 2H) 7.87 (d, J=7.72 Hz, 1H) 8.35 (d, J=8.82 Hz, 1H) 8.41 (d, J=8.09 Hz, 1H) 9.99 (s, 1H) 10.39 (s, 1H).

N-(4-((3-tert-butyl-5-(2,4-dioxo-3,4-dihydropyrimidin-1 (2H)-yl)-2-methoxyphenyl)ethynyl)-3-methylphenyl)methanesulfonamide (compound IB-L2-1.1). $^1$H NMR (300 MHz, DMSO-D6) δ ppm 1.36 (s, 9H) 2.46 (s, 3H) 3.05 (s, 3H) 4.09 (s, 3H) 5.64 (d, J=7.72 Hz, 1H) 7.09 (dd, J=8.27, 2.02 Hz, 1H) 7.14 (s, 1H) 7.31 (d, J=2.57 Hz, 1H) 7.51 (m, 2H) 7.73 (d, J=7.72 Hz, 1H) 10.00 (s, 1H) 11.42 (s, 1H)

N-(4-((3-tert-butyl-5-(2,4-dioxo-3,4-dihydropyrimidin-1 (2H)-yl)-2-methoxyphenyl)ethynyl)-3-chlorophenyl)methanesulfonamide (compound IB-L2-1.2) $^1$H NMR (300 MHz, DMSO-D6) δ ppm 1.36 (s, 9H) 3.12 (s, 3H) 4.11 (s, 3H) 5.65 (dd, J=7.91, 2.02 Hz, 1H) 7.22 (dd, J=8.46, 2.21 Hz, 1H) 7.34 (d, J=2.57 Hz, 1H) 7.36 (d, J=2.21 Hz, 1H) 7.50 (d, J=2.57 Hz, 1H) 7.68 (d, J=8.82 Hz, 1H) 7.74 (d, J=8.09 Hz, 1H) 10.33 (s, 1H) 11.42 (d, J=1.84 Hz, 1H)

N-(4-((3-tert-butyl-5-(2,4-dioxo-3,4-dihydropyrimidin-1 (2H)-yl)-2-methoxyphenyl)ethynyl)-2-fluoro-5-methylphenyl)methanesulfonamide (compound IB-L2-1.3). $^1$H NMR (300 MHz, DMSO-D6) δ ppm 1.36 (s, 9H) 2.45 (s, 3H) 3.09 (s, 3H) 4.09 (s, 3H) 5.65 (dd, J=7.91, 2.02 Hz, 1H) 7.36 (m, 2H) 7.48 (d, J=10.66 Hz, 1H) 7.53 (d, J=2.57 Hz, 1H) 7.74 (d, J=7.72 Hz, 1H) 9.81 (s, 1H) 11.43 (d, J=1.84 Hz, 1H)

N-(4-((3-tert-butyl-5-(2,4-dioxo-3,4-dihydropyrimidin-1 (2H)-yl)-2-methoxyphenyl)ethynyl)-2,6-difluorophenyl)methanesulfonamide (compound IB-L2-1.4). $^1$H NMR (300 MHz, DMSO-D6) δ ppm 1.36 (s, 9H) 3.10 (s, 3H) 4.10 (s, 3H) 5.66 (dd, J=7.72, 2.21 Hz, 1H) 7.37 (d, J=2.57 Hz, 1H) 7.46-7.58 (m, 3H) 7.74 (d, J=8.09 Hz, 1H) 9.74 (s, 1H) 11.44 (d, J=1.84 Hz, 1H)

N-(4-((3-tert-butyl-5-(2,4-dioxo-3,4-dihydropyrimidin-1 (2H)-yl)-2-methoxyphenyl)ethynyl)-2-fluoro-5-(trifluoromethyl)phenyl)methanesulfonamide (compound IB-L2-1.5). $^1$H NMR (300 MHz, DMSO-D6) δ ppm 1.36 (s, 9H) 3.17 (s, 3H) 4.07 (s, 3H) 5.66 (dd, J=7.91, 2.02 Hz, 1H) 7.38 (d, J=2.57 Hz, 1H) 7.50 (d, J=2.57 Hz, 1H) 7.74 (d, J=8.09 Hz, 1H) 7.83 (d, J=7.72 Hz, 1H) 7.89 (d, J=10.66 Hz, 1H) 10.28 (s, 1H) 11.43 (d, J=1.84 Hz, 1H)

N-(4-((3-tert-butyl-5-(2,4-dioxo-3,4-dihydropyrimidin-1 (2H)-yl)-2-methoxyphenyl)ethynyl)-3-hydroxyphenyl)methanesulfonamide (compound IB-L2-1.6). $^1$H NMR (300 MHz, DMSO-d$_6$) δ ppm 1.36 (s, 9H) 3.04 (s, 3H) 4.12 (s, 3H) 5.64 (dd, J=7.72, 2.21 Hz, 1H) 6.68 (dd, J=8.46, 2.21 Hz, 1H) 6.88 (d, J=1.84 Hz, 1H) 7.26 (d, J=2.57 Hz, 1H) 7.35 (d, J=8.46 Hz, 1H) 7.41 (d, J=2.57 Hz, 1H) 7.73 (d, J=7.72 Hz, 1H) 9.97 (s, 1H) 10.30 (s, 1H) 11.41 (d, J=2.21 Hz, 1H).

methyl 2-((3-tert-butyl-5-(2,4-dioxo-3,4-dihydropyrimidin-1(2H)-yl)-2-methoxyphenyl)-ethynyl)-5-(methylsulfonamido)benzoate (compound IB-L2-1.7). $^1$H NMR (300 MHz, DMSO-d$_6$) δ ppm 1.37 (s, 9H) 3.09 (s, 3H) 3.88 (s, 3H) 4.11 (s, 3H) 5.65 (dd, J=7.72, 2.21 Hz, 1H) 7.32 (d, J=2.57 Hz, 1H) 7.46 (m, 2H) 7.74 (m, 3H) 10.30 (s, 1H) 11.42 (d, J=1.84 Hz, 1H).

N-(6-((3-tert-butyl-5-(2,4-dioxo-3,4-dihydropyrimidin-1 (2H)-yl)-2-methoxyphenyl)ethynyl)-pyridin-3-yl)methanesulfonamide (compound IB-L2-1.8). $^1$H NMR (300 MHz, DMSO-d$_6$) δ ppm 1.36 (s, 9H) 3.13 (s, 3H) 4.11 (s, 3H) 5.65 (dd, J=7.91, 2.02 Hz, 1H) 7.35 (d, J=2.57 Hz, 1H) 7.53 (d, J=2.57 Hz, 1H) 7.66 (d, J=1.47 Hz, 2H) 7.75 (d, J=7.72 Hz, 1H) 8.45 (s, 1H) 10.33 (s, 1H) 11.43 (d, J=1.84 Hz, 1H).

N-(5-((3-tert-butyl-5-(2,4-dioxo-3,4-dihydropyrimidin-1 (2H)-yl)-2-methoxyphenyl)ethynyl)-pyrazin-2-yl)methanesulfonamide (compound IB-L2-1.9). $^1$H NMR (300 MHz, DMSO-d$_6$) δ ppm 1.37 (s, 9H) 3.38 (s, 3H) 4.12 (s, 3H) 5.65 (dd, J=8.09, 2.21 Hz, 1H) 7.38 (d, J=2.94 Hz, 1H) 7.55 (d, J=2.57 Hz, 1H) 7.75 (d, J=7.72 Hz, 1H) 8.32 (s, 1H) 8.62 (d, J=1.47 Hz, 1H) 11.43 (s, 2H).

N-(3-tert-butyl-4-((3-tert-butyl-5-(2,4-dioxo-3,4-dihydropyrimidin-1(2H)-yl)-2-methoxy-phenyl)ethynyl)phenyl)methanesulfonamide (compound IB-L2-1.10). $^1$H NMR (300 MHz, DMSO-d$_6$) δ ppm 1.37 (s, 9H) 1.49 (s, 9H) 3.06 (s, 3H) 4.08 (s, 3H) 5.64 (d, J=7.72 Hz, 1H) 7.13 (dd, J=8.27, 2.02 Hz, 1H) 7.30 (dd, J=6.80, 2.39 Hz, 2H) 7.43 (d, J=2.57 Hz, 1H) 7.56 (d, J=8.09 Hz, 1H) 7.74 (d, J=8.09 Hz, 1H) 10.01 (s, 1H) 11.41 (s, 1H).

N-(4-((3-tert-butyl-5-(2,4-dioxo-3,4-dihydropyrimidin-1 (2H)-yl)-2-methoxyphenyl)ethynyl)-3-(morpholine-4-carbonyl)phenyl)methanesulfonamide (compound IB-L2-1.11). $^1$H NMR (300 MHz, DMSO-d$_6$) δ ppm 1.36 (s, 9H) 3.11 (s, 3H) 3.19 (t, J=4.92 Hz, 2H) 3.50 (t, J=4.95 Hz, 2H) 3.65 (m, 4H) 4.01 (s, 3H) 5.65 (dd, J=7.91, 2.02 Hz, 1H) 7.13 (d, J=1.84 Hz, 1H) 7.29 (m, 2H) 7.42 (d, J=2.57 Hz, 1H) 7.62 (d, J=8.82 Hz, 1H) 7.75 (d, J=8.09 Hz, 1H) 10.28 (s, 1H) 11.43 (d, J=1.56 Hz, 1H).

N-(2-((3-tert-butyl-5-(2,4-dioxo-3,4-dihydropyrimidin-1 (2H)-yl)-2-methoxyphenyl)ethynyl)-5-(methylsulfonamido)

phenyl)acetamide (compound IB-L2-1.12). $^1$H NMR (300 MHz, DMSO-d$_6$) δ ppm 1.36 (s, 9H) 2.10 (s, 3H) 3.07 (s, 3H) 4.08 (s, 3H) 5.66 (dd, J=7.72, 2.21 Hz, 1H) 7.04 (dd, J=8.46, 2.21 Hz, 1H) 7.31 (d, J=2.94 Hz, 1H) 7.53 (m, 2H) 7.67 (s, 1H) 7.73 (d, J=8.09 Hz, 1H) 9.50 (s, 1H) 10.13 (s, 1H) 11.44 (d, J=2.21 Hz, 1H).

N-(4-((5-(2,4-dioxo-3,4-dihydropyrimidin-1(2H)-yl)-3-iodo-2-methoxyphenyl)ethynyl)-3-methylphenyl)methanesulfonamide (compound IB-L2-1.15). $^1$H NMR (300 MHz, DMSO-d$_6$) δ ppm 2.46 (s, 3H) 3.06 (s, 3H) 3.95 (s, 3H) 5.65 (dd, J=8.09, 1.47 Hz, 1H) 7.09 (dd, J=8.46, 2.19 Hz, 1H) 7.15 (d, J=1.84 Hz, 1H) 7.49 (d, J=8.46 Hz, 1H) 7.67 (d, J=2.57 Hz, 1H) 7.73 (d, J=7.72 Hz, 1H) 7.94 (d, J=2.57 Hz, 1H) 10.04 (s, 1H) 11.47 (d, J=1.26 Hz, 1H).

N-(4-((3-tert-butyl-5-(2,4-dioxo-3,4-dihydropyrimidin-1(2H)-yl)-2-methoxyphenyl)ethynyl)-naphthalen-1-yl)methanesulfonamide (compound IB-L2-2.1). $^1$H NMR (300 MHz, DMSO-d$_6$) δ ppm 1.40 (s, 9H) 3.08 (s, 3H) 4.17 (s, 3H) 5.67 (dd, J=7.91, 2.02 Hz, 1H) 7.37 (d, J=2.57 Hz, 1H) 7.58 (d, J=7.72 Hz, 1H) 7.71 (m, 3H) 7.78 (d, J=8.09 Hz, 1H) 7.88 (d, J=7.72 Hz, 1H) 8.35 (d, J=8.46 Hz, 1H) 8.42 (d, J=8.09 Hz, 1H) 10.00 (s, 1H) 11.45 (d, J=1.84 Hz, 1H).

3-tert-butyl-5-(2,4-dioxotetrahydropyrimidin-1(2H)-yl)-2-hydroxy-N-methyl-N-phenyl-benzamide (compound IA-L3-1.1) $^1$H NMR (300 MHz, DMSO-d$_6$) δ 1.27 (s, 9H) 2.53-2.61 (m, 5H) 3.28 (t, J=6.80 Hz, 2H) 6.69 (d, J=2.57 Hz, 1H) 7.06 (d, J=2.57 Hz, 1H) 7.16-7.25 (m, 3H) 7.26-7.34 (m, 2H) 10.22 (s, 1H) 10.32 (s, 1H).

3-tert-butyl-5-(2,4-dioxotetrahydropyrimidin-1(2H)-yl)-2-hydroxy-N-methyl-N-(4-(methyl-sulfonamido)phenyl)benzamide (compound IA-L3-1.2). $^1$H NMR (300 MHz, DMSO-d$_6$) δ 1.28 (s, 9H) 2.57 (t, J=6.62 Hz, 2H) 2.95 (s, 3H) 3.33-3.45 (m, 5H) 6.68 (d, J=1.10 Hz, 1H) 7.08 (d, J=8.82 Hz, 3H) 7.14-7.19 (m, 2H) 9.76 (s, 1H) 10.21 (s, 1H) 10.43 (s, 1H).

3-tert-butyl-5-(2,4-dioxotetrahydropyrimidin-1(2H)-yl)-2-hydroxy-N-phenylbenzamide (compound IA-L3-1.3). $^1$H NMR (300 MHz, DMSO d6) δ 1.39 (s, 9H) 2.74 (t, J=6.80 Hz, 2H) 3.79 (t, J=6.62 Hz, 2H) 7.20 (t, J=7.35 Hz, 1H) 7.35-7.47 (m, 3H) 7.64 (d, J=7.35 Hz, 2H) 7.91 (d, J=2.21 Hz, 1H) 10.39 (s, 1H) 10.45 (s, 1H) 13.27 (s, 1H).

3-tert-butyl-5-(2,4-dioxotetrahydropyrimidin-1(2H)-yl)-2-hydroxy-N-(4-(N-methyl methylsulfonamido)phenyl)benzamide (compound IA-L3-1.4). $^1$H NMR (300 MHz, DMSO-d$_6$) δ ppm 1.39 (s, 9H) 2.74 (t, J=6.62 Hz, 2H) 2.96 (s, 3H) 3.24 (s, 3H) 3.79 (t, J=6.62 Hz, 2H) 7.38-7.49 (m, 3H) 7.69 (d, J=8.82 Hz, 2H) 7.90 (d, J=2.57 Hz, 1H) 10.39 (s, 1H) 10.51 (s, 1H) 13.21 (s, 1H).

3-tert-butyl-5-(2,4-dioxotetrahydropyrimidin-1(2H)-yl)-2-hydroxy-N-(3-(methylsulfonamido)phenyl)benzamide (compound IA-L3-1.5). $^1$H NMR (300 MHz, DMSO-d$_6$) δ 1.39 (s, 9H) 2.74 (t, J=6.62 Hz, 2H) 3.02 (s, 3H) 3.79 (t, J=6.62 Hz, 2H) 7.03 (d, J=7.72 Hz, 1H) 7.30-7.47 (m, 3H) 7.54-7.62 (m, 1H) 7.90 (d, J=2.57 Hz, 1H) 9.86 (s, 1H) 10.39 (s, 1H) 10.49 (s, 1H) 13.20 (s, 1H).

3-tert-butyl-5-(2,4-dioxotetrahydropyrimidin-1(2H)-yl)-2-hydroxy-N-(4-(2-methyl propylsulfonamido)phenyl)benzamide (compound IA-L3-1.7). $^1$H NMR (300 MHz, DMSO-d$_6$) δ 1.00 (d, J=6.62 Hz, 6H) 1.39 (s, 9H) 2.14 (ddd, J=19.76, 13.14, 6.80 Hz, 1H) 2.73 (t, J=6.62 Hz, 2H) 2.98 (d, J=6.25 Hz, 2H) 3.78 (t, J=6.62 Hz, 2H) 7.22 (d, J=8.82 Hz, 2H) 7.40 (d, J=2.21 Hz, 1H) 7.59 (d, J=8.82 Hz, 2H) 7.89 (d, J=2.21 Hz, 1H) 9.80 (s, 1H) 10.39 (s, 1H) 10.43 (s, 1H) 13.30 (s, 1H).

3-tert-butyl-5-(2,4-dioxotetrahydropyrimidin-1(2H)-yl)-2-hydroxy-N-(4-(2,2,2-trifluoro ethylsulfonamido)phenyl) benzamide (compound IA-L3-1.9). $^1$H NMR (300 MHz, DMSO-d$_6$) δ 1.39 (s, 9H) 2.73 (t, J=6.62 Hz, 2H) 3.78 (t, J=6.43 Hz, 2H) 4.52 (q, J=9.44 Hz, 2H) 7.25 (d, J=8.82 Hz, 2H) 7.40 (d, J=1.84 Hz, 1H) 7.62 (d, J=8.82 Hz, 2H) 7.89 (d, J=2.21 Hz, 1H) 10.39 (s, 1H) 10.45 (d, J=2.57 Hz, 2H) 13.28 (s, 1H).

3-tert-butyl-5-(2,4-dioxotetrahydropyrimidin-1(2H)-yl)-2-hydroxy-N-(4-(phenylsulfonamido)phenyl)benzamide (compound IA-L3-1.10). $^1$H NMR (300 MHz, DMSO-d$_6$) δ 1.37 (s, 9H) 2.72 (t, J=6.62 Hz, 2H) 3.76 (t, J=6.62 Hz, 2H) 7.11 (d, J=8.82 Hz, 2H) 7.38 (d, J=2.21 Hz, 1H) 7.48 (d, J=8.82 Hz, 2H) 7.52-7.64 (m, 3H) 7.76 (d, J=6.62 Hz, 2H) 7.83 (d, J=2.21 Hz, 1H) 10.29 (s, 1H) 10.37 (d, J=1.84 Hz, 2H) 13.21 (s, 1H).

3-tert-butyl-5-(2,4-dioxotetrahydropyrimidin-1(2H)-yl)-2-hydroxy-N-(3-(methylsulfonamido)methyl)phenyl)benzamide (compound IA-L3-1.11). $^1$H NMR (300 MHz, DMSO-d$_6$) δ 1.39 (s, 9H) 2.74 (t, J=6.62 Hz, 2H) 2.89 (s, 3H) 3.79 (t, J=6.62 Hz, 2H) 4.18 (d, J=6.62 Hz, 2H) 7.18 (d, J=7.72 Hz, 1H) 7.35-7.43 (m, 2H) 7.57-7.66 (m, 3H) 7.93 (d, J=2.21 Hz, 1H) 10.39 (s, 1H) 10.49 (s, 1H) 13.27 (s, 1H).

3-tert-butyl-5-(2,4-dioxotetrahydropyrimidin-1(2H)-yl)-2-hydroxy-N-(4-(phenylmethyl-sulfonamido)phenyl)benzamide (compound IA-L3-1.12). $^1$H NMR (300 MHz, DMSO-d$_6$) δ 1.39 (s, 9H) 2.74 (t, J=6.80 Hz, 2H) 3.79 (t, J=6.62 Hz, 2H) 4.47 (s, 2H) 7.22 (d, J=8.82 Hz, 2H) 7.26-7.33 (m, 2H) 7.34-7.44 (m, 4H) 7.60 (d, J=8.82 Hz, 2H) 7.90 (d, J=1.10 Hz, 1H) 9.87 (s, 1H) 10.39 (s, 1H) 10.44 (s, 1H) 13.32 (s, 1H).

3-tert-butyl-N-(4-(3,5-dimethylisoxazole-4-sulfonamido) phenyl)-5-(2,4-dioxotetrahydro-pyrimidin-1(2H)-yl)-2-hydroxybenzamide (compound IA-L3-1.13). $^1$H NMR (300 MHz, DMSO-d$_6$) δ 1.38 (s, 9H) 2.22 (s, 3H) 2.44 (s, 3H) 2.73 (t, J=6.62 Hz, 2H) 3.77 (t, J=6.43 Hz, 2H) 7.13 (d, J=8.82 Hz, 2H) 7.40 (d, J=2.21 Hz, 1H) 7.59 (d, J=8.82 Hz, 2H) 7.87 (d, J=1.84 Hz, 1H) 10.38 (s, 1H) 10.40 (s, 1H) 10.45 (s, 1H) 13.19 (s, 1H).

3-tert-butyl-5-(2,4-dioxotetrahydropyrimidin-1(2H)-yl)-2-hydroxy-N-(4-(2-morpholino ethylsulfonamido)phenyl) benzamide (compound IA-L3-1.14). $^1$H NMR (300 MHz, DMSO-d$_6$) δ 1.39 (s, 9H) 2.25-2.37 (m, 4H) 2.63-2.81 (m, 4H) 3.20-3.29 (m, 2H) 3.44-3.53 (m, 4H) 3.78 (t, J=6.80 Hz, 2H) 7.25 (d, J=8.82 Hz, 2H) 7.40 (d, J=2.21 Hz, 1H) 7.59 (d, J=9.19 Hz, 2H) 7.89 (d, J=2.57 Hz, 1H) 9.83 (s, 1H) 10.39 (s, 1H) 10.44 (s, 1H) 13.30 (s, 1H).

3-(4-(3-tert-butyl-5-(2,4-dioxotetrahydropyrimidin-1(2H)-yl)-2-hydroxybenzamido) phenyl)-acetic acid (compound IA-L3-1.15). $^1$H NMR (300 MHz, DMSO-d$_6$) δ 1.39 (s, 9H) 2.73 (t, J=6.62 Hz, 2H) 3.57 (s, 2H) 3.78 (t, J=6.80 Hz, 2H) 7.28 (d, J=8.46 Hz, 2H) 7.39 (d, J=0.74 Hz, 1H) 7.58 (d, J=8.46 Hz, 2H) 7.90 (s, 1H) 10.38 (s, 1H) 10.44 (s, 1H) 12.34 (s, 1H) 13.31 (s, 1H).

3-tert-butyl-5-(2,4-dioxotetrahydropyrimidin-1(2H)-yl)-2-hydroxy-N-(4-(N-methyl sulfamoylmethyl)phenyl)benzamide (compound IA-L3-1.16). $^1$H NMR (300 MHz, DMSO-d$_6$) δ 2.50 (s, 9H) 2.58 (d, J=5.15 Hz, 3H) 2.74 (t, J=6.80 Hz, 2H) 3.79 (t, J=6.62 Hz, 2H) 4.33 (s, 2H) 6.95 (q, J=4.78 Hz, 1H) 7.36-7.44 (m, 3H) 7.66 (d, J=8.82 Hz, 2H) 7.91 (d, J=2.21 Hz, 1H) 10.39 (s, 1H) 10.49 (s, 1H) 13.25 (s, 1H).

3-tert-butyl-N-(4-(cyanomethoxy)phenyl)-5-(2,4-dioxotetrahydropyrimidin-1(2H)-yl)-2-hydroxybenzamide (compound IA-L3-1.17). $^1$H NMR (300 MHz, DMSO-D6) δ ppm 1.39 (s, 9H) 2.73 (t, J=6.62 Hz, 2H) 3.79 (t, J=6.80 Hz, 2H) 5.18 (s, 2H) 7.08 (m, 2H) 7.40 (d, J=2.57 Hz, 1H) 7.60 (m, 2H) 7.89 (d, J=2.21 Hz, 1H) 10.39 (s, 1H) 10.44 (s, 1H) 13.33 (s, 1H).

N-(4-(2-amino-2-oxoethoxy)phenyl)-3-tert-butyl-5-(2,4-dioxotetrahydropyrimidin-1(2H)-yl)-2-hydroxybenzamide (compound IA-L3-1.18). $^1$H NMR (300 MHz, DMSO-D6) δ ppm 1.39 (s, 9H) 2.73 (t, J=6.62 Hz, 2H) 3.78 (t, J=6.80 Hz, 2H) 4.43 (s, 2H) 6.97 (m, 2H) 7.40 (m, 2H) 7.53 (m, 3H) 7.89 (d, J=2.21 Hz, 1H) 10.40 (m, 2H) 13.41 (s, 1H)

3-tert-butyl-5-(2,4-dioxotetrahydropyrimidin-1(2H)-yl)-2-hydroxy-N-(2-(methyl sulfonyl)phenyl)benzamide (compound IA-L3-1.20). $^1$H NMR (300 MHz, DMSO-d$_6$) δ 1.39 (s, 9H) 2.74 (t, J=6.62 Hz, 2H) 3.27 (s, 3H) 3.78 (t, J=6.62 Hz, 2H) 7.45 (d, J=1.47 Hz, 1H) 7.57-7.66 (m, 1H) 7.77 (d, J=1.84 Hz, 1H) 7.81-7.89 (m, 2H) 8.02 (d, J=7.72 Hz, 1H) 10.40 (s, 1H) 10.64 (s, 1H) 12.99 (s, 1H).

3-tert-butyl-5-(2,4-dioxotetrahydropyrimidin-1(2H)-yl)-2-hydroxy-N-(4-(methyl sulfonyl)phenyl)benzamide (compound IA-L3-1.21). $^1$H NMR (300 MHz, DMSO-d$_6$) δ 1.40 (s, 9H) 2.74 (t, J=6.62 Hz, 2H) 3.22 (s, 3H) 3.79 (t, J=6.80 Hz, 2H) 7.44 (d, J=2.21 Hz, 1H) 7.92 (d, J=2.21 Hz, 1H) 7.96 (s, 4H) 10.41 (s, 1H) 10.75 (s, 1H) 12.89 (s, 1H).

3-tert-butyl-5-(2,4-dioxotetrahydropyrimidin-1(2H)-yl)-2-hydroxy-N-(2-sulfamoyl phenyl)benzamide (compound IA-L3-1.22). $^1$H NMR (300 MHz, DMSO-d$_6$) δ 1.40 (s, 9H) 2.74 (t, J=6.62 Hz, 2H) 3.78 (t, J=6.62 Hz, 2H) 7.39-7.49 (m, 2H) 7.61-7.74 (m, 4H) 7.93 (d, J=8.09 Hz, 1H) 8.01 (d, J=8.09 Hz, 1H) 10.39 (s, 1H) 10.42 (s, 1H) 12.93 (s, 1H).

3-tert-butyl-5-(2,4-dioxotetrahydropyrimidin-1(2H)-yl)-2-methoxy-N-phenylbenzamide (compound IA-L3-1.24). $^1$H NMR (300 MHz, DMSO-d$_6$) δ 1.37 (s, 9H) 2.71 (t, J=6.80 Hz, 2H) 3.70-3.86 (m, 5H) 3.78 (t, J=7.35 Hz, 1H) 7.24-7.44 (m, 4H) 7.73 (d, J=7.35 Hz, 2H) 10.36 (s, 1H) 10.39 (s, 1H).

3-tert-butyl-N-[4-(methanesulfonyl-methyl-amino)-phenyl]-2-methoxy-5-(3-methyl-2,4-dioxo-tetrahydro-pyrimidin-1-yl)-benzamide (compound IA-L3-1.25). $^1$H NMR (300 MHz, DMSO-D6) δ ppm 1.37 (s, 9H) 2.84 (t, J=6.80 Hz, 2H) 2.94 (s, 3H) 3.04 (s, 3H) 3.22 (s, 3H) 3.71-3.81 (m, 5H) 7.30 (d, J=2.57 Hz, 1H) 7.35 (d, J=2.57 Hz, 1H) 7.39 (d, J=8.82 Hz, 2H) 7.75 (d, J=8.82 Hz, 2H) 10.51 (s, 1H)

3-tert-butyl-2-methoxy-5-(3-methyl-2,4-dioxotetrahydropyrimidin-1(2H)-yl)-N-(4-(N-methylmethylsulfonamido)phenyl)benzamide (compound IA-L3-1.26). $^1$H NMR (300 MHz, DMSO-d$_6$) δ 1.37 (s, 9H) 2.84 (t, J=6.80 Hz, 2H) 2.94 (s, 3H) 3.04 (s, 3H) 3.22 (s, 3H) 3.71-3.81 (m, 5H) 7.30 (d, J=2.57 Hz, 1H) 7.35 (d, J=2.57 Hz, 1H) 7.39 (d, J=8.82 Hz, 2H) 7.75 (d, J=8.82 Hz, 2H) 10.51 (s, 1H).

2-tert-butyl-5-(2,4-dioxotetrahydropyrimidin-1(2H)-yl)-N-(2-ethylphenyl)-2-methoxy benzamide (compound IA-L3-1.28).

3-(4-(3-tert-butyl-5-(2,4-dioxotetrahydropyrimidin-1(2H)-yl)-2-methoxybenzamido) phenyl)-acetic acid (compound IA-L3-1.30). $^1$H NMR (300 MHz, DMSO-d$_6$) δ 1.37 (s, 9H) 2.71 (t, J=6.62 Hz, 2H) 3.53 (s, 2H) 3.73-3.82 (m, 5H) 7.23 (d, J=8.46 Hz, 2H) 7.28 (d, J=2.57 Hz, 1H) 7.33 (d, 1H) 7.66 (d, J=8.46 Hz, 2H) 10.35 (s, 1H) 10.37 (s, 1H) 12.29 (s, 1H).

3-tert-butyl-5-(2,4-dioxotetrahydropyrimidin-1(2H)-yl)-2-methoxy-N-(4-(N-methyl sulfamoyl methyl)phenyl)benzamide (compound IA-L3-1.31). $^1$H NMR (300 MHz, DMSO-d$_6$) δ 1.37 (s, 9H) 2.58 (d, J=4.78 Hz, 3H) 2.71 (t, J=6.62 Hz, 2H) 3.72-3.84 (m, 5H) 4.29 (s, 2H) 6.89 (q, J=4.78 Hz, 1H) 7.29 (d, J=2.57 Hz, 1H) 7.31-7.40 (m, 3H) 7.72 (d, J=8.46 Hz, 2H) 10.36 (s, 1H) 10.46 (s, 1H).

3-tert-butyl-5-(2,4-dioxo-tetrahydro-pyrimidin-1-yl)-2-methoxy-N-(4-trifluoromethyl-phenyl)-benzamide (compound IA-L3-1.32).

3-tert-butyl-5-(2,4-dioxotetrahydropyrimidin-1(2H)-yl)-N-(4-hydroxyphenyl)-2-methoxybenzamide (compound IA-L3-1.33). $^1$H NMR (300 MHz, DMSO-d$_6$) δ ppm 1.37 (s, 9H) 2.71 (t, J=6.62 Hz, 2H) 3.76 (s, 3H) 3.76-3.82 (m, 2H) 6.73 (d, J=8.82 Hz, 2H) 7.25 (d, J=2.57 Hz, 1H) 7.31 (d, J=2.57 Hz, 1H) 7.50 (d, J=9.19 Hz, 2H) 9.25 (s, 1H) 10.11 (s, 1H) 10.35 (s, 1H).

3-tert-butyl-5-(2,4-dioxo-tetrahydro-pyrimidin-1-yl)-2-methoxy-N-(2-methoxy-phenyl)-benzamide (compound IA-L3-1.34).

3-tert-butyl-5-(2,4-dioxo-tetrahydro-pyrimidin-1-yl)-2-methoxy-N-(3-methoxy-phenyl)-benzamide (compound IA-L3-1.35).

3-tert-butyl-5-(2,4-dioxo-tetrahydro-pyrimidin-1-yl)-2-methoxy-N-(4-methoxy-phenyl)-benzamide (compound IA-L3-1.36).

3-tert-butyl-5-(2,4-dioxo-tetrahydro-pyrimidin-1-yl)-N-(2-ethoxy-phenyl)-2-methoxy-benzamide (compound IA-L3-1.37).

3-tert-butyl-N-(4-(cyanomethoxy)phenyl)-5-(2,4-dioxotetrahydropyrimidin-1(2H)-yl)-2-methoxybenzamide (compound IA-L3-1.38). $^1$H NMR (300 MHz, DMSO-D6) δ ppm 1.37 (s, 9H) 2.71 (t, J=6.62 Hz, 2H) 3.76 (m, 5H) 5.15 (s, 2H) 7.07 (m, 2H) 7.29 (d, J=2.94 Hz, 1H) 7.33 (d, J=2.57 Hz, 1H) 7.69 (m, 2H) 10.35 (m, 2H)

N-(4-(2-amino-2-oxoethoxy)phenyl)-3-tert-butyl-5-(2,4-dioxotetrahydropyrimidin-1(2H)-yl)-2-methoxybenzamide (compound IA-L3-1.39). $^1$H NMR (300 MHz, DMSO-D6) δ ppm 1.37 (s, 9H) 2.71 (t, J=6.80 Hz, 2H) 3.78 (m, 5H) 4.40 (s, 2H) 6.95 (m, 2H) 7.27 (d, J=2.57 Hz, 1H) 7.32 (d, J=2.57 Hz, 1H) 7.39 (s, 1H) 7.51 (s, 1H) 7.64 (m, 2H) 10.26 (s, 1H) 10.35 (s, 1H)

3-tert-butyl-5-(2,4-dioxo-tetrahydro-pyrimidin-1-yl)-2-methoxy-N-(4-trifluoromethoxy-phenyl)-benzamide (compound IA-L3-1.40).

3-(3-tert-butyl-5-(2,4-dioxotetrahydropyrimidin-1(2H)-yl)-2-methoxybenzamido)phenyl methanesulfonate (compound IA-L3-1.41). $^1$H NMR (300 MHz, DMSO-d$_6$) δ 1.37 (s, 9H) 2.72 (t, J=6.62 Hz, 2H) 3.43 (s, 3H) 3.73-3.83 (m, 5H) 7.30 (d, J=2.94 Hz, 1H) 7.33-7.39 (m, 3H) 7.82 (d, J=8.82 Hz, 2H) 10.36 (s, 1H) 10.58 (s, 1H).

N-(4-acetylphenyl)-3-tert-butyl-5-(2,4-dioxotetrahydropyrimidin-1(2H)-yl)-2-methoxy-benzamide (compound IA-L3-1.42). $^1$H NMR (300 MHz, DMSO d6) δ ppm 1.38 (s, 9H) 2.71 (t, J=6.62 Hz, 2H) 3.75 (s, 3H) 3.78 (t, J=6.62 Hz, 2H) 6.02 (s, 1H) 6.55 (d, J=8.82 Hz, 1H) 7.34 (dd, J=11.77, 2.57 Hz, 2H) 7.66 (d, J=8.82 Hz, 1H) 7.83-7.92 (m, 2H) 7.92-8.04 (m, 2H) 10.37 (s, 1H) 10.75 (s, 1H).

ethyl 3-(4-(3-tert-butyl-5-(2,4-dioxotetrahydropyrimidin-1(2H)-yl)-2-methoxybenzamido) phenyl)-3-oxopropanoate (compound IA-L3-1.43). $^1$H NMR (300 MHz, DMSO d6) δ ppm 1.19 (t, J=7.17 Hz, 3H) 1.38 (s, 9H) 2.71 (t, J=6.62 Hz, 2H) 3.61-3.83 (m, 5H) 4.06-4.20 (m, 4H) 7.35 (dd, J=12.13, 2.57 Hz, 2H) 7.84-7.91 (m, 2H) 7.96-8.06 (m, 2H) 10.37 (s, 1H) 10.80 (s, 1H).

3-tert-butyl-N-(3-carbamoyl-phenyl)-5-(2,4-dioxo-tetrahydro-pyrimidin-1-yl)-2-methoxy-benzamide (compound IA-L3-1.44).

3-tert-butyl-5-(2,4-dioxo-tetrahydro-pyrimidin-1-yl)-N-(4-fluoro-phenyl)-2-methoxy-benzamide (compound IA-L3-1.45).

3-tert-butyl-N-(4-chloro-phenyl)-5-(2,4-dioxo-tetrahydro-pyrimidin-1-yl)-2-methoxy-benzamide (compound IA-L3-1.46).

N-(4-acetamidophenyl)-3-tert-butyl-5-(2,4-dioxotetrahydropyrimidin-1(2H)-yl)-2-methoxy-benzamide (compound IA-L3-1.47). $^1$H NMR (300 MHz, DMSO d6) δ 10.35 (s, 1H), 10.31 (s, 1H), 9.91 (s, 1H), 7.59-7.72 (m, 2H), 7.41-7.59 (m, 2H), 7.33 (d, J=2.57 Hz, 1H), 7.28 (d, J=2.94 Hz, 1H), 3.58-3.93 (m, 5H), 2.71 (t, J=6.62 Hz, 2H), 2.03 (s, 3H), 1.37 (s, 9H).

2-(4-(3-tert-butyl-5-(2,4-dioxotetrahydropyrimidin-1(2H)-yl)-2-methoxybenzamido) phenyl-amino)-2-oxoethyl acetate (compound IA-L3-1.48). $^1$H NMR (300 MHz, DMSO d6) δ 10.35 (s, 2H), 10.06 (s, 1H), 7.64-7.76 (m, 2H), 7.54 (d, J=9.19 Hz, 1H), 7.33 (d, J=2.57 Hz, 1H), 7.28 (d, J=2.94 Hz, 1H), 4.63 (s, 2H), 3.60-3.90 (m, 5H), 2.71 (t, J=6.62 Hz, 2H), 2.12 (s, 3H), 1.39 (s, 9H).

Methyl 4-(3-tert-butyl-5-(2,4-dioxotetrahydropyrimidin-1(2H)-yl)-2-methoxybenzamido) phenylcarbamate (compound IA-L3-1.49). $^1$H NMR (300 MHz, DMSO d6) δ 10.35 (s, 1H), 10.28 (s, 1H), 9.59 (s, 1H), 7.62 (d, J=9.19 Hz, 2H), 7.41 (d, J=8.82 Hz, 2H), 7.32 (d, J=2.94 Hz, 1H), 7.27 (d, J=2.57 Hz, 1H), 3.69-3.88 (m, 5H), 3.66 (s, 3H), 2.71 (t, J=6.80 Hz, 2H), 1.37 (s, 9H).

Tert-butyl 4-(3-tert-butyl-5-(2,4-dioxotetrahydropyrimidin-1(2H)-yl)-2-methoxybenzamido)-phenylcarbamate (compound IA-L3-1.50). $^1$H NMR (300 MHz, DMSO d6) δ 1.37 (s, 9H) 1.47 (s, 9H) 2.71 (t, J=6.62 Hz, 2H) 3.71-3.84 (m, 5H) 7.27 (d, J=2.57 Hz, 1H) 7.32 (d, J=2.94 Hz, 1H) 7.40 (d, J=8.82 Hz, 2H) 7.59 (d, J=8.82 Hz, 2H) 9.29 (s, 1H) 10.25 (s, 1H) 10.35 (s, 1H).

3-tert-butyl-5-(2,4-dioxotetrahydropyrimidin-1(2H)-yl)-2-methoxy-N-(4-(2-methylpropyl-sulfonamido)phenyl)benzamide (compound IA-L3-1.52). $^1$H NMR (300 MHz, DMSO d6) δ 0.99 (d, J=6.62 Hz, 6H) 1.37 (s, 9H) 2.03-2.25 (m, 1H) 2.71 (t, J=6.80 Hz, 2H) 2.94 (d, J=6.25 Hz, 2H) 3.69-3.84 (m, 5H) 7.18 (d, J=8.82 Hz, 2H) 7.28 (d, J=2.57 Hz, 1H) 7.33 (d, J=2.57 Hz, 1H) 7.67 (d, J=8.82 Hz, 2H) 9.66 (s, 1H) 10.36 (s, 1H) 10.37 (s, 1H).

3-tert-butyl-5-(2,4-dioxotetrahydropyrimidin-1(2H)-yl)-N-(4-(2-hydroxyethylsulfonamido) phenyl)-2-methoxybenzamide (compound IA-L3-1.53). $^1$H NMR (300 MHz, DMSO-D6) δ 1.37 (s, 9H) 2.71 (t, J=6.80 Hz, 2H) 3.19 (t, J=6.80 Hz, 2H) 3.69-3.86 (m, 7H) 4.93 (t, J=5.70 Hz, 1H) 7.20 (d, J=8.82 Hz, 2H) 7.28 (d, J=2.94 Hz, 1H) 7.33 (d, J=2.57 Hz, 1H) 7.68 (d, J=8.82 Hz, 2H) 9.60 (s, 1H) 10.36 (s, 1H) 10.38 (s, 1H)

3-tert-butyl-5-(2,4-dioxotetrahydropyrimidin-1(2H)-yl)-2-methoxy-N-(4-(2-methoxyethyl sulfonamido)phenyl)benzamide (compound IA-L3-1.54). $^1$H NMR (300 MHz, DMSO d6) δ 1.37 (s, 9H) 2.71 (t, J=6.62 Hz, 2H) 3.21 (s, 3H) 3.25-3.31 (m, 2H) 3.66 (t, J=6.07 Hz, 2H) 3.71-3.83 (m, 5H) 7.19 (d, J=8.82 Hz, 2H) 7.28 (d, J=2.57 Hz, 1H) 7.33 (d, J=2.57 Hz, 1H) 7.67 (d, J=8.82 Hz, 2H) 9.67 (s, 1H) 10.35 (s, 1H) 10.37 (s, 1H).

3-tert-butyl-5-(2,4-dioxotetrahydropyrimidin-1(2H)-yl)-2-methoxy-N-(4-(2,2,2-trifluoro-ethylsulfonamido)phenyl)benzamide (compound IA-L3-1.55). $^1$H NMR (300 MHz, DMSO d6) δ 1.37 (s, 9H) 2.71 (t, J=6.62 Hz, 2H) 3.71-3.85 (m, 5H) 4.46 (q, J=9.93 Hz, 2H) 7.20 (d, J=8.82 Hz, 2H) 7.28 (d, J=2.57 Hz, 1H) 7.33 (d, J=2.57 Hz, 1H) 7.70 (d, J=8.82 Hz, 2H) 10.32 (s, 1H) 10.36 (s, 1H) 10.41 (s, 1H).

N-(4-(2-(bis(2-hydroxyethyl)amino)ethylsulfonamido) phenyl)-3-tert-butyl-5-(2,4-dioxo-tetrahydropyrimidin-1(2H)-yl)-2-methoxybenzamide (compound IA-L3-1.56). $^1$H NMR (300 MHz, DMSO d6) δ 1.37 (s, 9H) 2.44-2.49 (m, 2H) 2.71 (t, J=6.62 Hz, 2H) 2.90-2.96 (m, 2H) 3.18 (dd, J=9.01, 5.70 Hz, 2H) 3.35-3.41 (m, 4H) 3.73-3.81 (m, 5H) 4.41 (s, 2H) 7.20 (d, J=8.82 Hz, 2H) 7.28 (d, J=2.57 Hz, 1H) 7.33 (d, J=2.57 Hz, 1H) 7.68 (d, J=9.19 Hz, 2H) 9.65 (s, 1H) 10.35 (s, 1H) 10.38 (s, 1H).

3-tert-butyl-5-(2,4-dioxotetrahydropyrimidin-1(2H)-yl)-2-methoxy-N-(4-(phenylmethyl-sulfonamido)phenyl)benzamide (compound IA-L3-1.57). $^1$H NMR (300 MHz, DMSO-d$_6$) δ 1.38 (s, 9H) 2.72 (t, J=6.62 Hz, 2H) 3.72-3.84 (m, 5H) 4.43 (s, 2H) 7.18 (d, J=8.82 Hz, 2H) 7.25-7.41 (m, 7H) 7.68 (d, J=8.82 Hz, 2H) 9.75 (s, 1H) 10.36 (s, 1H) 10.38 (s, 1H).

3-tert-butyl-5-(2,4-dioxotetrahydropyrimidin-1(2H)-yl)-2-methoxy-N-(4-(2-morpholinoethyl sulfonamido)phenyl) benzamide (compound IA-L3-1.58). $^1$H NMR (300 MHz, DMSO-d$_6$) δ 1.37 (s, 9H) 2.28-2.35 (m, 4H) 2.63-2.75 (m, 4H) 3.20-3.28 (m, 2H) 3.46-3.54 (m, 4H) 3.72-3.82 (m, 5H) 7.20 (d, J=8.82 Hz, 2H) 7.28 (d, J=2.57 Hz, 1H) 7.33 (d, J=2.57 Hz, 1H) 7.68 (d, J=8.82 Hz, 2H) 9.70 (s, 1H) 10.35 (s, 1H) 10.37 (s, 1H).

3-tert-butyl-N-[4-(3,5-dimethyl-isoxazole-4-sulfonylamino)-phenyl]-5-(2,4-dioxo-tetrahydro-pyrimidin-1-yl)-2-methoxy-benzamide (compound IA-L3-1.59). $^1$H NMR (300 MHz, DMSO-D6) δ ppm 1.38 (s, 9H) 2.22 (s, 3H) 2.44 (s, 3H) 2.73 (t, J=6.62 Hz, 2H) 3.77 (t, J=6.43 Hz, 2H) 7.13 (d, J=8.82 Hz, 2H) 7.40 (d, J=2.21 Hz, 1H) 7.59 (d, J=8.82 Hz, 2H) 7.87 (d, J=1.84 Hz, 1H) 10.38 (s, 1H) 10.40 (s, 1H) 10.45 (s, 1H) 13.19 (s, 1H)

3-tert-butyl-5-(2,4-dioxotetrahydropyrimidin-1(2H)-yl)-2-methoxy-N-(4-(phenylsulfonamido) phenyl)benzamide (compound IA-L3-1.60). $^1$H NMR (300 MHz, DMSO-d$_6$) δ 1.35 (s, 9H) 2.70 (t, J=6.62 Hz, 2H) 3.71 (s, 3H) 3.75 (t, J=6.62 Hz, 2H) 7.05 (d, J=8.82 Hz, 2H) 7.24 (d, J=2.57 Hz, 1H) 7.31 (d, J=2.57 Hz, 1H) 7.51-7.64 (m, 5H) 7.70-7.80 (m, 2H) 10.17 (s, 1H) 10.31 (s, 1H) 10.34 (s, 1H).

3-tert-butyl-5-(2,4-dioxotetrahydropyrimidin-1(2H)-yl)-2-methoxy-N-(4-(N-methylmethyl sulfonamido)phenyl)benzamide (compound IA-L3-1.62). $^1$H NMR (300 MHz, DMSO-d$_6$) δ ppm 1.37 (s, 9H) 2.71 (t, J=6.62 Hz, 2H) 2.94 (s, 3H) 3.22 (s, 3H) 3.73-3.84 (m, 5H) 7.29 (d, J=2.57 Hz, 1H) 7.34 (d, J=2.57 Hz, 1H) 7.40 (d, J=8.82 Hz, 2H) 7.75 (d, J=8.82 Hz, 2H) 10.36 (s, 1H) 10.50 (s, 1H).

3-tert-butyl-5-(2,4-dioxotetrahydropyrimidin-1(2H)-yl)-N-(4-(N-ethylmethylsulfonamido) phenyl)-2-methoxybenzamide (compound IA-L3-1.63). $^1$H NMR (300 MHz, DMSO d6) δ ppm 1.01 (t, J=6.99 Hz, 3H) 1.38 (s, 9H) 2.72 (t, J=6.62 Hz, 2H) 2.97 (s, 3H) 3.64 (d, J=7.35 Hz, 2H) 3.74-3.83 (m, 5H) 7.22-7.48 (m, 4H) 7.77 (d, J=8.82 Hz, 2H) 10.36 (s, 1H) 10.53 (s, 1H).

(N-(4-(3-tert-butyl-5-(2,4-dioxotetrahydropyrimidin-1(2H)-yl)-2-methoxybenzamido)phenyl)methylsulfonamido) methyl pivalate (compound IA-L3-1.65). $^1$H NMR (300 MHz, DMSO-D6) δ ppm 1.19 (s, 9H) 1.38 (s, 9H) 2.71 (t, J=6.62 Hz, 2H) 3.17 (s, 3H) 3.74-3.82 (m, 5H) 5.56 (s, 2H) 7.30 (d, J=2.57 Hz, 1H) 7.35 (d, J=2.57 Hz, 1H) 7.41 (d, J=8.82 Hz, 2H) 7.80 (d, J=8.82 Hz, 2H) 10.36 (s, 1H) 10.58 (s, 1H)

3-tert-butyl-N-(4-(N-(cyclopropylmethyl)methylsulfonamido)phenyl)-5-(2,4-dioxotetrahydro pyrimidin-1(2H)-yl)-2-methoxybenzamide (compound IA-L3-1.66). $^1$H NMR (300 MHz, DMSO-d$_6$) δ ppm 0.09 (d, J=4.78 Hz, 2H) 0.40 (d, J=7.72 Hz, 2H) 0.84 (d, 1H) 1.38 (s, 9H) 2.72 (t, J=6.43 Hz, 2H) 2.97 (s, 3H) 3.47 (d, J=6.62 Hz, 2H) 3.68-3.88 (m, 5H) 7.19-7.54 (m, 4H) 7.77 (d, J=8.82 Hz, 2H) 10.36 (s, 1H) 10.53 (s, 1H).

3-tert-butyl-5-(2,4-dioxotetrahydropyrimidin-1(2H)-yl)-2-methoxy-N-(4-(N-(4-methoxy-benzyl)methylsulfonamido)phenyl)benzamide (compound IA-L3-1.67). $^1$H NMR (300 MHz, DMSO-d$_6$) δ ppm 1.36 (s, 9H) 2.64-2.79 (m, 2H) 3.06 (s, 3H) 3.69 (s, 3H) 3.76 (s, 3H) 3.75-3.83 (m, 2H) 4.75 (s, 2H) 6.83 (d, J=8.46 Hz, 2H) 7.16 (d, J=8.46 Hz, 2H) 7.24-7.39 (m, 4H) 7.65 (d, J=8.82 Hz, 2H) 10.35 (s, 1H) 10.45 (s, 1H).

3-tert-butyl-5-(2,4-dioxotetrahydropyrimidin-1(2H)-yl)-2-methoxy-N-(4-(N-(methylsulfonyl) propionamido)phenyl)benzamide (compound IA-L3-1.70). $^1$H NMR (300 MHz, DMSO-D6) δ ppm 0.93 (t, J=7.35 Hz, 3H) 1.38 (s, 9H) 2.12 (q, J=7.35 Hz, 2H) 2.72 (t, J=6.62 Hz, 2H) 3.52 (s, 3H) 3.78 (m, 5H) 7.31 (d, J=2.57 Hz, 1H) 7.36 (d, J=2.57 Hz, 1H) 7.44 (d, J=8.46 Hz, 2H) 7.83 (d, J=8.82 Hz, 2H) 10.37 (s, 1H) 10.64 (s, 1H)

3-tert-butyl-5-(2,4-dioxotetrahydropyrimidin-1(2H)-yl)-2-methoxy-N-(4-(N-(methylsulfonyl) butyramido)phenyl)benzamide (compound IA-L3-1.71). $^1$H NMR (300 MHz, DMSO-D6) δ ppm 0.79 (t, J=7.35 Hz, 3H) 1.38 (s, 9H) 1.48 (m, 2H) 2.09 (t, J=7.17 Hz, 2H) 2.72 (t, J=6.62 Hz, 2H) 3.52 (s, 3H) 3.78 (m, 5H) 7.32 (d, J=2.57 Hz, 1H) 7.36 (d, J=2.57 Hz, 1H) 7.43 (d, J=8.82 Hz, 2H) 7.83 (d, J=8.82 Hz, 2H) 10.37 (s, 1H) 10.65 (s, 1H)

3-tert-butyl-5-(2,4-dioxotetrahydropyrimidin-1(2H)-yl)-2-methoxy-N-(4-(N-(methylsulfonyl) isobutyramido)phenyl)benzamide (compound IA-L3-1.72). $^1$H NMR (300 MHz, DMSO-D6) δ ppm 0.99 (d, J=6.62 Hz, 6H) 1.38 (s, 9H) 2.29-2.41 (m, 1H) 2.72 (t, J=6.62 Hz, 2H) 3.51 (s, 3H) 3.75-3.83 (m, 5H) 7.32 (d, J=2.57 Hz, 1H) 7.36 (d, J=2.57 Hz, 1H) 7.48 (d, J=8.82 Hz, 2H) 7.84 (d, J=8.82 Hz, 2H) 10.37 (s, 1H) 10.66 (s, 1H)

Methyl 4-(3-tert-butyl-5-(2,4-dioxotetrahydropyrimidin-1(2H)-yl)-2-methoxybenzamido) phenyl(methylsulfonyl)carbamate (compound IA-L3-1.73). $^1$H NMR (300 MHz, DMSO-D6) δ ppm 1.38 (s, 9H) 2.72 (t, J=6.62 Hz, 2H) 3.56 (s, 3H) 3.72 (s, 3H) 3.74-3.84 (m, 5H) 7.31 (d, J=2.57 Hz, 1H) 7.35 (dd, J=5.70, 2.76 Hz, 3H) 7.77 (d, J=8.82 Hz, 2H) 10.37 (s, 1H) 10.58 (s, 1H)

Ethyl 4-(3-tert-butyl-5-(2,4-dioxotetrahydropyrimidin-1(2H)-yl)-2-methoxybenzamido)-phenyl(methylsulfonyl)carbamate (compound IA-L3-1.74). $^1$H NMR (300 MHz, DMSO-D6) δ ppm 1.16 (t, J=7.17 Hz, 3H) 1.38 (s, 9H) 2.71 (t, J=6.62 Hz, 2H) 3.56 (s, 3H) 3.73-3.84 (m, 5H) 4.20 (q, J=6.99 Hz, 2H) 7.26-7.41 (m, 4H) 7.77 (d, J=8.82 Hz, 2H) 10.37 (s, 1H) 10.58 (s, 1H)

Isobutyl 4-(3-tert-butyl-5-(2,4-dioxotetrahydropyrimidin-1(2H)-yl)-2-methoxybenzamido) phenyl(methylsulfonyl)carbamate (compound IA-L3-1.76). $^1$H NMR (300 MHz, DMSO-D6) δ ppm 0.79 (d, J=6.99 Hz, 6H) 1.38 (s, 9H) 1.74-1.92 (m, 1H) 2.71 (t, J=6.62 Hz, 2H) 3.56 (s, 3H) 3.73-3.83 (m, 5H) 3.94 (d, J=6.62 Hz, 2H) 7.29-7.41 (m, 4H) 7.78 (d, J=8.82 Hz, 2H) 10.36 (s, 1H) 10.58 (s, 1H)

2-methoxyethyl 4-(3-tert-butyl-5-(2,4-dioxotetrahydropyrimidin-1(2H)-yl)-2-methoxy benzamido)phenyl(methylsulfonyl)carbamate (compound IA-L3-1.77). $^1$H NMR (300 MHz, DMSO-D6) δ ppm 1.38 (s, 9H) 2.71 (t, J=6.62 Hz, 2H) 3.19 (s, 3H) 3.46-3.52 (m, 2H) 3.57 (s, 3H) 3.72-3.84 (m, 5H) 4.28 (dd, J=5.52, 3.68 Hz, 2H) 7.27-7.42 (m, 4H) 7.78 (d, J=8.82 Hz, 2H) 10.36 (s, 1H) 10.58 (s, 1H)

3-tert-butyl-5-(2,4-dioxotetrahydropyrimidin-1(2H)-yl)-2-methoxy-N-(4-(methylsulfonyl)phenyl)benzamide (compound IA-L3-1.78). $^1$H NMR (300 MHz, DMSO-d$_6$) δ 1.38 (s, 9H) 2.72 (t, J=6.62 Hz, 2H) 3.19 (s, 3H) 3.74 (s, 3H) 3.78 (t, J=6.62 Hz, 2H) 7.35 (dd, 2H) 7.95 (dd, 4H) 10.37 (s, 1H) 10.86 (s, 1H).

3-tert-butyl-5-(2,4-dioxotetrahydropyrimidin-1(2H)-yl)-2-methoxy-N-(2-(methylsulfonyl)phenyl)benzamide (compound IA-L3-1.79). $^1$H NMR (300 MHz, DMSO-d$_6$) δ 1.39 (s, 9H) 2.72 (t, J=6.43 Hz, 2H) 3.29 (s, 3H) 3.77-3.85 (m, 5H) 7.43 (d, J=2.57 Hz, 1H) 7.45-7.49 (m, 1H) 7.50 (d, J=2.57 Hz, 1H) 7.77-7.85 (m, 1H) 7.95 (d, J=8.46 Hz, 1H) 8.45 (d, J=8.46 Hz, 1H) 10.39 (s, 2H).

3-tert-butyl-5-(2,4-dioxotetrahydropyrimidin-1(2H)-yl)-2-methoxy-N-(2-sulfamoylphenyl)benzamide (compound IA-L3-1.80). $^1$H NMR (300 MHz, DMSO-d$_6$) δ 1.38 (s, 9H) 2.72 (t, J=6.62 Hz, 2H) 3.73-3.89 (m, 5H) 7.34 (t, J=7.72 Hz, 1H) 7.42 (d, J=2.94 Hz, 1H) 7.49 (d, J=2.57 Hz, 1H) 7.66 (t, J=7.17 Hz, 1H) 7.72 (s, 2H) 7.91 (d, J=8.09 Hz, 1H) 8.48 (d, J=8.09 Hz, 1H) 10.31 (s, 1H) 10.39 (s, 1H).

3-tert-butyl-5-(2,4-dioxo-tetrahydro-pyrimidin-1-yl)-N-(3-hydroxy-2-methyl-phenyl)-2-methoxy-benzamide (compound IA-L3-1.81).

3-tert-butyl-5-(2,4-dioxo-tetrahydro-pyrimidin-1-yl)-N-(4-fluoro-2-methyl-phenyl)-2-methoxy-benzamide (compound IA-L3-1.82).

3-tert-butyl-5-(2,4-dioxotetrahydropyrimidin-1(2H)-yl)-2-methoxy-N-(2-methyl-4-(methyl sulfonamido)phenyl)benzamide (compound IA-L3-1.83). $^1$H NMR (300 MHz, DMSO-D6) δ ppm 1.38 (s, 9H) 2.26 (s, 3H) 2.72 (t, J=6.62 Hz, 2H) 2.98 (s, 3H) 3.79 (t, J=6.62 Hz, 2H) 3.83 (s, 3H) 7.04 (m, 2H) 7.33 (m, 2H) 7.47 (d, J=8.09 Hz, 1H) 9.65 (s, 1H) 9.78 (s, 1H) 10.36 (s, 1H)

N-(3-tert-butyl-5-(2,4-dioxotetrahydropyrimidin-1(2H)-yl)phenyl)-4-(methylsulfonamido)benzamide (compound IA-L3-1.84). $^1$H NMR (300 MHz, DMSO-D6) δ ppm 1.38 (s, 9H) 2.72 (t, J=6.62 Hz, 2H) 3.09 (s, 3H) 3.79 (t, J=6.62 Hz, 2H) 3.84 (s, 3H) 7.33 (d, J=2.21 Hz, 1H) 7.37 (d, J=2.57 Hz, 1H) 7.55 (m, 2H) 7.67 (d, J=8.82 Hz, 1H) 10.03 (s, 1H) 10.18 (s, 1H) 10.38 (s, 1H)

3-tert-butyl-5-(2,4-dioxotetrahydropyrimidin-1(2H)-yl)-2-methoxy-N-(2-methoxy-4-(methyl sulfonamido)phenyl)benzamide (compound IA-L3-1.85). $^1$H NMR (300 MHz, DMSO-d$_6$) δ 1.39 (s, 9H) 2.68-2.76 (m, 2H) 3.00 (s, 3H) 3.75-3.87 (m, 8H) 6.84 (dd, J=8.46, 2.21 Hz, 1H) 6.94 (d, J=2.21 Hz, 1H) 7.39 (d, J=2.94 Hz, 1H) 7.47 (d, J=2.57 Hz, 1H) 7.93-7.99 (m, 1H) 9.59 (s, 1H) 9.68 (s, 1H) 10.37 (s, 1H).

N-(5-acetylamino-2-methoxy-phenyl)-3-tert-butyl-5-(2,4-dioxo-tetrahydro-pyrimidin-1-yl)-2-methoxy-benzamide (compound IA-L3-1.86).

3-tert-butyl-5-(2,4-dioxotetrahydropyrimidin-1(2H)-yl)-2-methoxy-N-(4-(methylsulfonamido)-3-nitrophenyl)benzamide (compound IA-L3-1.87). $^1$H NMR (300 MHz, DMSO-d$_6$) δ 10.84 (s, 1H) 10.37 (s, 1H) 9.71 (s, 1H) 8.52 (d, J=2.57 Hz, 1H) 7.98 (dd, J=9.01, 2.39 Hz, 1H) 7.62 (d, J=8.82 Hz, 1H) 7.35 (dd, J=12.50, 2.57 Hz, 2H) 3.71-3.83 (m, 5H) 3.11 (s, 3H) 2.71 (t, J=6.62 Hz, 2H) 1.38 (s, 9H).

butyric acid ({4-[3-tert-butyl-5-(3-butyryloxymethyl-2,4-dioxo-tetrahydro-pyrimidin-1-yl)-2-methoxy-benzoylamino]-phenyl}-methanesulfonyl-amino)-methyl ester (compound IA-L3-1.88). $^1$H NMR (300 MHz, DMSO-D6) δ ppm 0.88 (m, 6H) 1.38 (s, 9H) 1.55 (m, 4H) 2.26 (t, J=7.17 Hz, 2H) 2.39 (t, J=7.17 Hz, 2H) 2.95 (t, J=6.62 Hz, 2H) 3.14 (s, 3H) 3.77 (s, 3H) 3.81 (t, J=6.62 Hz, 2H) 5.57 (s, 2H) 5.68 (s, 2H) 7.35 (d, J=2.57 Hz, 1H) 7.38 (d, J=2.94 Hz, 1H) 7.42 (d, J=8.82 Hz, 2H) 7.79 (d, J=8.82 Hz, 2H) 10.60 (s, 1H).

3-tert-butyl-5-(2,4-dioxotetrahydropyrimidin-1(2H)-yl)-2-hydroxy-N-(4-(methylsulfonamido methyl)-3-sulfamoylthiophen-2-yl)benzamide (compound IA-L3-1.89). $^1$H NMR (300 MHz, DMSO-d$_6$) δ 1.40 (s, 9H) 2.70-2.78 (m, 2H) 2.97 (s, 3H) 3.78 (t, J=6.43 Hz, 2H) 4.36 (d, J=6.99 Hz, 2H) 7.14 (s, 1H) 7.42 (d, J=2.21 Hz, 1H) 7.47 (d, J=2.21 Hz, 1H) 7.60 (t, J=6.43 Hz, 1H) 7.82 (s, 2H) 10.42 (s, 1H) 11.43 (s, 1H) 11.93 (s, 1H).

3-tert-butyl-5-(2,4-dioxotetrahydropyrimidin-1(2H)-yl)-2-methoxy-N-(4-(methylsulfonamide methyl)-3-sulfamoylthiophen-2-yl)benzamide (compound IA-L3-1.90). $^1$H NMR (300 MHz, DMSO-d$_6$) δ 1.40 (s, 9H) 2.72 (t, J=6.62 Hz, 2H) 2.97 (s, 3H) 3.73 (s, 3H) 3.80 (t, J=6.80 Hz, 2H) 4.36 (d, J=5.52 Hz, 2H) 7.06 (s, 1H) 7.47 (d, J=2.57 Hz, 1H) 7.57 (t, J=6.43 Hz, 1H) 7.61 (d, J=2.57 Hz, 1H) 7.70 (s, 2H) 10.40 (s, 1H) 11.56 (s, 1H).

3-tert-butyl-5-(2,4-dioxotetrahydropyrimidin-1(2H)-yl)-2-hydroxy-N-(4-(methylsulfonamido methyl)thiophen-2-yl)benzamide (compound IA-L3-1.91). $^1$H NMR (300 MHz, DMSO-d$_6$) δ ppm 1.39 (s, 9H) 2.74 (t, J=6.80 Hz, 2H) 2.86 (s, 3H) 3.79 (t, J=6.62 Hz, 2H) 4.10 (d, J=6.25 Hz, 2H) 6.98 (s, 1H) 7.04 (d, J=1.47 Hz, 1H) 7.42 (d, J=2.57 Hz, 1H) 7.55 (t, J=6.25 Hz, 1H) 7.89 (d, J=2.21 Hz, 1H) 10.41 (s, 1H) 11.68 (s, 1H) 12.95 (s, 1H).

3-tert-butyl-5-(2,4-dioxotetrahydropyrimidin-1(2H)-yl)-2-methoxy-N-(4-(methylsulfonamido methyl)thiophen-2-yl)benzamide (compound IA-L3-1.94). $^1$H NMR (300 MHz, DMSO-d$_6$) δ ppm 1.37 (s, 9H) 2.71 (t, J=6.80 Hz, 2H) 2.85 (s, 3H) 3.67 (s, 3H) 3.78 (t, J=6.62 Hz, 2H) 4.07 (d, J=5.88 Hz, 2H) 6.82 (d, J=1.84 Hz, 1H) 6.87 (s, 1H) 7.28-7.32 (m, 1H) 7.36 (d, J=2.57 Hz, 1H) 7.49 (t, J=6.25 Hz, 1H) 10.37 (s, 1H) 11.59 (s, 1H).

3-tert-butyl-5-(2,4-dioxotetrahydropyrimidin-1(2H)-yl)-2-hydroxy-N-(4-((N-methylmethyl sulfonamido)methyl)thiophen-2-yl)benzamide (compound IA-L3-1.95). $^1$H NMR (300 MHz, DMSO-d$_6$) δ ppm 1.39 (s, 9H) 2.70 (s, 3H) 2.74 (t, J=6.80 Hz, 2H) 2.92 (s, 3H) 3.79 (t, J=6.80 Hz, 2H) 4.18 (s, 2H) 7.01 (m, 2H) 7.42 (d, J=2.21 Hz, 1H) 7.89 (d, J=2.57 Hz, 1H) 10.41 (s, 1H) 11.68 (s, 1H) 12.92 (s, 1H).

tert-butyl (5-(3-tert-butyl-5-(2,4-dioxotetrahydropyrimidin-1(2H)-yl)-2-methoxybenzamido)thiophen-3-yl)methyl (methylsulfonyl)carbamate (compound IA-L3-1.96). $^1$H NMR (300 MHz, DMSO-d$_6$) δ ppm 1.37 (s, 9H) 1.48 (s, 9H) 2.71 (t, J=6.62 Hz, 2H) 3.30 (s, 3H) 3.67 (s, 3H) 3.78 (t, J=6.62 Hz, 2H) 4.66 (s, 2H) 6.77-6.87 (m, 2H) 7.30 (d, J=2.57 Hz, 1H) 7.36 (d, J=2.57 Hz, 1H) 10.37 (s, 1H) 11.63 (s, 1H).

3-tert-butyl-5-(2,4-dioxotetrahydropyrimidin-1(2H)-yl)-2-methoxy-N-(4-((N-methylmethyl sulfonamido)methyl)thiophen-2-yl)benzamide (compound IA-L3-1.97). $^1$H NMR (300 MHz, DMSO-d$_6$) δ ppm 1.37 (s, 9H) 2.70 (m, 5H) 2.91 (s, 3H) 3.68 (s, 3H) 3.78 (t, J=6.62 Hz, 2H) 4.15 (s, 2H) 6.80 (d, J=1.47 Hz, 1H) 6.94 (d, J=1.47 Hz, 1H) 7.31 (d, J=2.57 Hz, 1H) 7.36 (d, J=2.94 Hz, 1H) 10.37 (s, 1H) 11.59 (s, 1H).

tert-butyl (5-(3-tert-butyl-5-(2,4-dioxotetrahydropyrimidin-1(2H)-yl)-2-hydroxybenzamido)thiophen-3-yl)methyl (methylsulfonyl)carbamate (compound IA-L3-1.98). $^1$H NMR (300 MHz, DMSO-d$_6$) δ ppm 1.39 (s, 9H) 1.47 (s, 9H) 2.74 (t, J=6.80 Hz, 2H) 3.35 (s, 3H) 3.78 (t, J=6.62 Hz, 2H) 4.68 (s, 2H) 6.96 (s, 1H) 7.04 (d, J=1.47 Hz, 1H) 7.41 (d, J=2.21 Hz, 1H) 7.88 (d, J=2.21 Hz, 1H) 10.40 (s, 1H) 11.70 (s, 1H) 12.92 (s, 1H).

3-tert-butyl-5-(2,4-dioxotetrahydropyrimidin-1(2H)-yl)-2-methoxy-N-(6-(methylsulfonamido) pyridin-3-yl)benzamide (compound IA-L3-1.99). $^1$H NMR (300 MHz, DMSO-d$_6$) δ ppm 1.37 (s, 9H) 2.71 (t, J=6.62 Hz, 2H) 3.28 (s, 3H) 3.77 (m, 5H) 7.01 (d, J=8.82 Hz, 1H) 7.31 (d, J=2.57 Hz, 1H) 7.35 (d, J=2.57 Hz, 1H) 8.07 (dd, J=8.82, 2.57 Hz, 1H) 8.61 (d, J=2.57 Hz, 1H) 10.36 (s, 1H) 10.49 (s, br, 1H) 10.50 (s, 1H).

N-(6-aminopyridin-3-yl)-3-tert-butyl-5-(2,4-dioxotetrahydropyrimidin-1(2H)-yl)-2-methoxy benzamide (compound IA-L3-1.100). $^1$H NMR (300 MHz, DMSO-d$_6$) δ ppm 1.37 (s, 9H) 2.71 (t, J=6.62 Hz, 2H) 3.74 (s, 3H) 3.78 (t, J=6.62 Hz, 2H) 7.06 (d, J=9.56 Hz, 1H) 7.31 (d, J=2.57 Hz, 1H) 7.37 (d, J=2.57 Hz, 1H) 7.99 (s, 2H) 8.04 (dd, J=9.56, 2.21 Hz, 1H) 8.53 (d, J=1.84 Hz, 1H) 10.38 (s, 1H) 10.67 (s, 1H) 13.64 (s, 1H).

3-tert-butyl-5-(2,4-dioxotetrahydropyrimidin-1(2H)-yl)-2-methoxy-N-(5-(N-(methylsulfonyl)methylsulfonamido)pyridin-2-yl)benzamide (compound IA-L3-1.101). $^1$H NMR (300 MHz, DMSO-d$_6$) δ ppm 1.38 (s, 9H) 2.72 (t, J=6.62 Hz, 2H) 3.58 (s, 6H) 3.75 (s, 3H) 3.80 (t, J=6.62 Hz, 2H) 7.36 (m, 2H) 8.06 (dd, J=8.82, 2.57 Hz, 1H) 8.30 (d, J=8.82 Hz, 1H) 8.51 (d, J=2.21 Hz, 1H) 10.37 (s, 1H) 11.10 (s, 1H).

3-tert-butyl-5-(2,4-dioxotetrahydropyrimidin-1(2H)-yl)-2-methoxy-N-(5-(methylsulfonamido) pyridin-2-yl)benzamide (compound IA-L3-1.102). $^1$H NMR (300 MHz, DMSO-d$_6$) δ ppm 1.37 (s, 9H) 2.71 (t, J=6.62 Hz, 2H) 3.02 (s, 3H) 3.74 (s, 3H) 3.79 (t, J=6.62 Hz, 2H) 7.35 (m, 2H) 7.71 (dd, J=8.82, 2.57 Hz, 1H) 8.18 (m, 2H) 9.81 (s, 1H) 10.36 (s, 1H) 10.74 (s, 1H).

3-tert-butyl-5-(2,4-dioxotetrahydropyrimidin-1(2H)-yl)-2-methoxy-N-((1r,4r)-4-(methylsulfonamido)cyclohexyl)benzamide (compound IA-L3-1.103). $^1$H NMR (300 MHz, DMSO-d$_6$) δ ppm 1.32 (d, 11H) 1.91 (s, 2H) 2.65-2.78 (m, 4H) 2.91 (s, 3H) 3.07 (s, 2H) 3.39 (s, 2H) 3.66-3.80 (m, 5H) 7.03 (d, J=7.35 Hz, 1H) 7.12 (d, J=2.57 Hz, 1H) 7.25 (d, J=2.57 Hz, 1H) 8.19 (d, J=8.09 Hz, 1H) 10.32 (s, 1H).

3-tert-butyl-5-(2,4-dioxotetrahydropyrimidin-1(2H)-yl)-2-hydroxy-N-(thiazol-2-yl)benzamide (compound IA-L3-1.104). $^1$H NMR (300 MHz, DMSO-d$_6$) δ 1.56-1.68 (m, 9H) 2.92 (t, J=6.62 Hz, 2H) 3.90-4.07 (m, 2H) 7.27-7.70 (m, 2H) 7.80 (d, J=4.04 Hz, 1H) 8.03 (s, 1H) 10.51 (s, 1H) 14.06 (d, J=116.92 Hz, 1H).

3-tert-butyl-5-(2,4-dioxotetrahydropyrimidin-1(2H)-yl)-N-(4-(methylsulfonamido)phenyl)benzamide (compound IA-L3-1.105). $^1$H NMR (300 MHz, DMSO-d$_6$) δ ppm 1.34 (s, 9H) 2.74 (t, J=6.62 Hz, 2H) 2.96 (s, 3H) 3.86 (t, J=6.62 Hz, 2H) 7.09-7.90 (m, 7H) 9.62 (s, 1H) 10.24 (s, 1H) 10.43 (s, 1H).

N-(4-aminophenyl)-3-tert-butyl-5-(2,4-dioxotetrahydropyrimidin-1(2H)-yl)-2-methoxy benzamide (compound IA-L3-1.107). $^1$H NMR (300 MHz, DMSO-d$_6$) δ 1.37 (s, 9H) 2.71 (t, J=6.62 Hz, 2H) 3.71-3.83 (m, 5H) 7.26-7.39 (m, 4H) 7.82 (d, J=8.82 Hz, 2H) 9.95 (s, 1H) 10.36 (s, 1H) 10.57 (s, 1H).

N-(4-(N-allylmethylsulfonamido)phenyl)-3-tert-butyl-5-(2,4-dioxotetrahydropyrimidin-1(2H)-yl)-2-methoxybenzamide (compound IA-L3-1.108). $^1$H NMR (300 MHz, DMSO-d$_6$) δ ppm 1.37 (s, 9H) 2.71 (t, J=6.62 Hz, 2H) 3.01 (s, 3H) 3.70-3.83 (m, 5H) 4.25 (d, J=5.88 Hz, 2H) 5.00-5.24 (m, 2H) 5.68-5.84 (m, 1H) 7.29 (d, J=2.57 Hz, 1H) 7.30-7.41 (m, 3H) 7.74 (d, J=8.82 Hz, 2H) 10.36 (s, 1H) 10.51 (s, 1H).

5-(2,4-dioxotetrahydropyrimidin-1(2H)-yl)-3-isopropyl-2-methoxy-N-(4-(methylsulfonamido) phenyl)benzamide (compound IA-L3-1.111). $^1$H NMR (500 MHz, DMSO-d$_6$) δ ppm 1.22 (d, J=6.71 Hz, 6H) 2.72 (t, J=6.71 Hz, 2H) 2.95 (s, 3H) 3.23-3.39 (m, 1H) 3.75 (s, 3H) 3.79 (t, J=6.71 Hz, 2H) 7.19 (d, J=9.16 Hz, 2H) 7.31 (d, J=2.44 Hz, 1H) 7.38 (d, J=2.44 Hz, 1H) 7.69 (d, J=9.16 Hz, 2H) 9.55 (s, 1H) 10.29 (s, 1H) 10.34 (s, 1H).

5-(2,4-dioxotetrahydropyrimidin-1(2H)-yl)-3-ethyl-2-methoxy-N-(4-(methylsulfonamido) phenyl)benzamide (compound IA-L3-1.112). $^1$H NMR (300 MHz, DMSO-d$_6$) δ ppm 1.20 (t, J=7.35 Hz, 3H) 2.60-2.78 (m, 4H) 2.95 (s, 3H) 3.69-3.84 (m, 5H) 7.19 (d, J=9.19 Hz, 2H) 7.27-7.41 (m, 2H) 7.69 (d, J=8.82 Hz, 2H) 9.59 (s, 1H) 10.31 (s, 1H) 10.38 (s, 1H).

5-(2,4-dioxotetrahydropyrimidin-1(2H)-yl)-3-ethyl-2-hydroxy-N-(4-(methylsulfonamido) phenyl)benzamide (compound IA-L3-1.113). $^1$H NMR (300 MHz, DMSO-d$_6$) δ ppm 1.17 (t, J=7.54 Hz, 3H) 2.54-2.66 (m, 2H) 2.73 (t, J=6.62 Hz, 2H) 2.99 (s, 3H) 3.78 (t, J=6.62 Hz, 2H) 7.24 (d, J=8.82 Hz, 2H) 7.37 (d, J=1.84 Hz, 1H) 7.62 (d, J=8.82 Hz, 2H) 7.87 (d, J=2.21 Hz, 1H) 9.72 (s, 1H) 10.40 (s, 1H) 10.43 (s, 1H) 12.70 (s, 1H).

5-(2,4-dioxotetrahydropyrimidin-1(2H)-yl)-2-hydroxy-N-(4-(methylsulfonamido)phenyl)benzamide (compound IA-L3-1.114). $^1$H NMR (300 MHz, DMSO-d$_6$) δ ppm 2.72 (t, J=6.80 Hz, 2H) 2.97 (s, 3H) 3.76 (t, J=6.80 Hz, 2H) 6.99 (d, J=8.82 Hz, 1H) 7.22 (d, J=9.19 Hz, 2H) 7.40 (dd, J=8.82, 2.57 Hz, 1H) 7.65 (d, J=8.82 Hz, 2H) 7.87 (d, J=2.57 Hz, 1H) 9.66 (s, 1H) 10.38 (d, J=1.84 Hz, 2H) 11.83 (s, 1H).

3-tert-butyl-5-(3-(2-(ethylamino)-2-oxoethyl)-2,4-dioxotetrahydropyrimidin-1(2H)-yl)-N-(4-(N-(2-(ethylamino)-2-oxoethyl)methylsulfonamido)phenyl)-2-methoxybenzamide (compound IA-L3-1.115). $^1$H NMR (300 MHz, DMSO-d$_6$) δ ppm 0.92-1.04 (m, 6H) 1.37 (s, 9H) 2.88 (t, J=6.62 Hz, 2H) 3.01-3.08 (m, 4H) 3.09 (s, 3H) 3.75 (s, 3H) 3.81 (t, J=6.62 Hz, 2H) 4.22 (d, J=5.52 Hz, 4H) 7.30 (d, J=2.57 Hz, 1H) 7.31-7.37 (m, 1H) 7.47 (d, J=8.82 Hz, 2H) 7.74 (d, J=8.82 Hz, 2H) 7.88-8.04 (m, 2H) 10.53 (s, 1H).

(3-(3-tert-butyl-4-methoxy-5-(4-(N-(pivaloyloxymethyl) methylsulfonamido)phenylcarbamoyl)phenyl)-2,6-dioxotetrahydropyrimidin-1(2H)-yl)methyl pivalate (compound IA-L3-1.116). $^1$H NMR (300 MHz, DMSO-$d_6$) δ ppm 1.11 (s, 9H) 1.19 (s, 9H) 1.38 (s, 9H) 2.95 (t, J=6.62 Hz, 2H) 3.17 (s, 3H) 3.77 (s, 3H) 3.81 (t, J=6.62 Hz, 2H) 5.56 (s, 2H) 5.67 (s, 2H) 7.35 (d, J=2.57 Hz, 1H) 7.38 (d, J=2.57 Hz, 1H) 7.41 (d, J=9.19 Hz, 2H) 7.80 (d, J=8.82 Hz, 2H) 10.61 (s, 1H).

5-(3-((1,3-dioxolan-2-yl)methyl)-2,4-dioxotetrahydropyrimidin-1(2H)-yl)-3-tort-butyl-2-methoxy-N-(4-(methylsulfonamido)phenyl)benzamide (compound IA-L3-1.117). $^1$H NMR (300 MHz, DMSO-$d_6$) δ ppm 1.37 (s, 9H) 2.87 (t, J=6.62 Hz, 2H) 2.95 (s, 3H) 3.78 (s, 3H) 3.76-3.85 (m, 4H) 3.87-3.96 (m, 4H) 5.07 (t, J=4.96 Hz, 1H) 7.20 (d, J=8.82 Hz, 2H) 7.32 (dd, J=13.97, 2.57 Hz, 2H) 7.69 (d, J=8.82 Hz, 2H) 9.60 (s, 1H) 10.40 (s, 1H).

5-(3-allyl-2,4-dioxotetrahydropyrimidin-1(2H)-yl)-N-(4-(N-allylmethylsulfonamido)phenyl)-3-tert-butyl-2-methoxybenzamide (compound IA-L3-1.118). $^1$H NMR (300 MHz, DMSO-$d_6$) δ ppm 1.37 (s, 9H) 2.78-2.93 (m, 2H) 3.01 (s, 3H) 3.78 (s, 3H) 3.76-3.85 (m, 2H) 4.25 (d, J=5.88 Hz, 4H) 4.94-5.29 (m, 4H) 5.67-5.96 (m, 1H) 7.00-7.21 (m, 1H) 7.31 (d, J=2.57 Hz, 1H) 7.35-7.42 (m, 3H) 7.74 (d, J=8.82 Hz, 2H) 10.52 (s, 1H).

3-tert-butyl-5-(2,4-dioxotetrahydropyrimidin-1(2H)-yl)-2-hydroxy-N-(2-methoxy-4-(methyl sulfonamido)phenyl) benzamide (compound IA-L3-1.119). $^1$H NMR (300 MHz, DMSO-$d_6$) δ 1.38 (s, 9H) 2.73 (t, J=6.62 Hz, 2H) 3.05 (s, 3H) 3.74-3.81 (m, 5H) 6.84 (dd, J=8.46, 2.21 Hz, 1H) 6.95 (d, J=2.21 Hz, 1H) 7.30 (d, J=8.46 Hz, 1H) 7.39 (d, J=2.21 Hz, 1H) 7.89 (d, J=2.57 Hz, 1H) 9.82 (s, 1H) 10.06 (s, 1H) 10.37 (s, 1H) 13.50 (s, 1H).

3-tert-butyl-5-(2,4-dioxotetrahydropyrimidin-1(2H)-yl)-2-methoxy-N-(3-(methylsulfonamido methyl)phenyl)benzamide (compound IA-L3-1.120). $^1$H NMR (300 MHz, DMSO-$d_6$) δ 1.37 (s, 9H) 2.71 (t, J=6.62 Hz, 2H) 2.89 (s, 3H) 3.69-3.88 (m, 5H) 4.15 (d, J=6.25 Hz, 2H) 7.00-7.16 (m, 1H) 7.26-7.40 (m, 3H) 7.59 (t, J=6.43 Hz, 1H) 7.65 (d, J=8.82 Hz, 1H) 7.74 (d, J=8.82 Hz, 2H) 10.36 (s, 1H) 10.44 (s, 1H).

3-tert-butyl-N-(4-(2,5-dimethoxyphenylsulfonamido) phenyl)-5-(2,4-dioxotetrahydro-pyrimidin-1(2H)-yl)-2-methoxybenzamide (compound IA-L3-1.121). $^1$H NMR (300 MHz, DMSO d6) δ 1.35 (s, 9H) 2.69 (t, J=6.80 Hz, 2H) 3.71 (s, 6H) 3.75 (t, J=6.62 Hz, 2H) 3.85 (s, 3H) 7.06 (d, J=8.82 Hz, 2H) 7.13 (s, 2H) 7.22 (dd, J=3.68, 2.21 Hz, 2H) 7.31 (d, J=2.57 Hz, 1H) 7.53 (d, J=8.82 Hz, 2H) 9.87 (s, 1H) 10.28 (s, 1H) 10.34 (s, 1H).

3-tert-butyl-5-(2,4-dioxotetrahydropyrimidin-1(2H)-yl)-N-(4-(2-hydroxyethylsulfonamido) phenyl)-2-methoxybenzamide (compound IA-L3-1.122). $^1$H NMR (300 MHz, DMSO-$d_6$) δ 1.37 (s, 9H) 2.71 (t, J=6.80 Hz, 2H) 3.19 (t, J=6.80 Hz, 2H) 3.69-3.86 (m, 7H) 4.93 (t, J=5.70 Hz, 1H) 7.20 (d, J=8.82 Hz, 2H) 7.28 (d, J=2.94 Hz, 1H) 7.33 (d, J=2.57 Hz, 1H) 7.68 (d, J=8.82 Hz, 2H) 9.60 (s, 1H) 10.36 (s, 1H) 10.38 (s, 1H).

(N-(4-(3-tert-butyl-5-(2,4-dioxotetrahydropyrimidin-1 (2H)-yl)-2-methoxybenzamido)phenyl)methylsulfonamido) methyl butyrate (compound IA-L3-1.123). $^1$H NMR (300 MHz, DMSO-d6) δ 0.90 (t, J=7.54 Hz, 3H) 1.38 (s, 9H) 1.57 (m, 2H) 2.39 (t, J=7.35 Hz, 2H) 2.71 (t, J=6.62 Hz, 2H) 3.14 (s, 3H) 3.77 (m, 5H) 5.57 (s, 2H) 7.30 (d, J=2.57 Hz, 1H) 7.35 (d, J=2.57 Hz, 1H) 7.41 (d, J=8.82 Hz, 2H) 7.79 (d, J=8.82 Hz, 2H) 10.36 (s, 1H) 10.57 (s, 1H)

3-tert-butyl-5-(2,4-dioxotetrahydropyrimidin-1(2H)-yl)-2-hydroxy-N-(quinolin-6-yl)benzamide (compound IA-L3-2.1). $^1$H NMR (300 MHz, DMSO-$d_6$) δ 1.41 (s, 9H) 2.75 (t, J=6.62 Hz, 2H) 3.77-3.86 (m, 2H) 7.45 (d, J=2.21 Hz, 1H) 7.68 (dd, J=8.46, 4.41 Hz, 1H) 7.98 (d, J=2.57 Hz, 1H) 8.11 (s, 2H) 8.44 (s, 1H) 8.58 (d, J=8.46 Hz, 1H) 8.96 (dd, J=4.41, 1.47 Hz, 1H) 10.41 (s, 1H) 10.81 (s, 1H).

3-tert-butyl-5-(2,4-dioxotetrahydropyrimidin-1(2H)-yl)-2-methoxy-N-(2-oxoindolin-5-yl)benzamide (compound IA-L3-2.2). $^1$H NMR (300 MHz, DMSO-$d_6$) δ 1.37 (s, 9H) 2.71 (t, J=6.62 Hz, 2H) 3.50 (s, 2H) 3.75 (s, 3H) 3.77 (t, J=6.62 Hz, 2H) 6.78 (d, J=8.46 Hz, 1H) 7.26 (d, J=2.21 Hz, 1H) 7.32 (d, J=2.57 Hz, 1H) 7.48 (dd, J=8.46, 1.84 Hz, 1H) 7.64 (s, 1H) 10.24 (s, 1H) 10.34 (s, 1H) 10.35 (s, 1H).

3-tert-butyl-N-(2,2-dioxo-1,3-dihydrobenzo[c]thiophen-5-yl)-5-(2,4-dioxotetrahydro pyrimidin-1(2H)-yl)-2-methoxybenzamide (compound IA-L3-2.3). $^1$H NMR (300 MHz, DMSO-$d_6$) δ 1.37 (s, 9H) 2.71 (t, J=6.43 Hz, 2H) 3.70-3.85 (m, 5H) 4.45 (s, 2H) 4.53 (s, 2H) 7.29 (d, J=2.57 Hz, 1H) 7.32-7.40 (m, 2H) 7.62 (dd, J=8.27, 1.65 Hz, 1H) 7.86 (s, 1H) 10.36 (s, 1H) 10.54 (s, 1H).

3-tert-butyl-5-(2,4-dioxotetrahydropyrimidin-1(2H)-yl)-2-methoxy-N-(2-oxo-1,2,3,4-tetra hydroquinolin-6-yl)benzamide (compound IA-L3-2.4). $^1$H NMR (300 MHz, DMSO-$d_6$) δ 1.37 (s, 9H) 2.44 (t, 2H) 2.71 (t, J=6.62 Hz, 2H) 2.86 (t, J=7.35 Hz, 2H) 3.77 (t, 2H) 3.75 (s, 3H) 6.82 (d, J=8.46 Hz, 1H) 7.26 (d, J=2.57 Hz, 1H) 7.32 (d, J=2.57 Hz, 1H) 7.45 (dd, J=8.46, 2.21 Hz, 1H) 7.57 (d, 1H) 10.05 (s, 1H) 10.24 (s, 1H) 10.35 (s, 1H).

3-tert-butyl-N-(2,2-dioxo-1,3-dihydrobenzo[c]thiophen-5-yl)-5-(2,4-dioxotetrahydro pyrimidin-1(2H)-yl)-2-hydroxybenzamide (compound IA-L3-2.5). $^1$H NMR (300 MHz, DMSO-$d_6$) δ 1.39 (s, 9H) 2.74 (t, J=6.80 Hz, 2H) 3.79 (t, J=6.62 Hz, 2H) 4.49 (s, 2H) 4.55 (s, 2H) 7.42 (dd, J=4.96, 2.76 Hz, 2H) 7.59 (dd, J=8.27, 1.65 Hz, 1H) 7.74 (s, 1H) 7.90 (d, J=1.84 Hz, 1H) 10.40 (s, 1H) 10.54 (s, 1H) 13.15 (s, 1H).

3-tert-butyl-5-(2,4-dioxo-3,4-dihydropyrimidin-1(2H)-yl)-2-methoxy-N-(4-(methylsulfonamido)phenyl)benzamide (compound IB-L3-1.1). $^1$H NMR (300 MHz, DMSO-$d_6$) δ ppm 2.50 (s, 9H) 2.94 (s, 3H) 3.79 (s, 3H) 5.66 (d, J=8.09 Hz, 1H) 7.14-7.25 (m, 2H) 7.39 (s, 2H) 7.62-7.75 (m, 3H) 9.60 (s, 1H) 10.44 (s, 1H) 11.42 (s, 1H).

3-tert-butyl-5-(2,4-dioxo-3,4-dihydropyrimidin-1(2H)-yl)-2-hydroxy-N-(4-(methylsulfonamido)phenyl)benzamide (compound IB-L3-1.2). $^1$H NMR (300 MHz, DMSO-d6) δ 1.40 (s, 9H) 2.99 (s, 3H) 5.70 (dd, J=7.72, 2.21 Hz, 1H) 7.24 (d, J=8.82 Hz, 2H) 7.46 (d, J=2.21 Hz, 1H) 7.61 (d, J=8.82 Hz, 2H) 7.76 (d, J=7.72 Hz, 1H) 8.03 (d, J=2.21 Hz, 1H) 9.75 (s, 1H) 10.45 (s, 1H) 11.48 (d, J=2.21 Hz, 1H) 13.52 (s, 1H)

3-tert-butyl-2-methoxy-5-(6-methyl-2,4-dioxo-3,4-dihydropyrimidin-1(2H)-yl)-N-(4-(methyl sulfonamido)phenyl) benzamide (compound IB-L3-1.3). $^1$H NMR (300 MHz, DMSO-$d_6$) δ ppm 1.37 (s, 9H) 1.82 (s, 3H) 2.96 (s, 3H) 3.80 (s, 3H) 5.63 (s, 1H) 7.20 (d, J=8.82 Hz, 2H) 7.34 (s, 2H) 7.69 (d, J=8.82 Hz, 2H) 9.60 (s, 1H) 10.41 (s, 1H) 11.27 (s, 1H).

3-tert-butyl-2-hydroxy-5-(6-methyl-2,4-dioxo-3,4-dihydropyrimidin-1(2H)-yl)-N-(4-(methyl sulfonamido)phenyl) benzamide (compound IB-L3-1.4). $^1$H NMR (300 MHz, DMSO-$d_6$) δ ppm 1.39 (s, 9H) 1.86 (s, 3H) 2.99 (s, 3H) 5.68 (s, 1H) 7.24 (d, J=8.82 Hz, 2H) 7.40 (s, 1H) 7.61 (d, J=8.82 Hz, 2H) 7.95 (s, 1H) 9.74 (s, 1H) 10.39 (s, 1H) 11.35 (s, 1H) 13.57 (s, 1H).

N-(3-tert-butyl-5-(2,4-dioxotetrahydropyrimidin-1(2H)-yl)phenyl)-4-(methylsulfonamido)benzamide (compound IA-L4-1.1). $^1$H NMR (300 MHz, DMSO-d6) δ 1.29 (s, 9H) 2.72 (t, J=6.62 Hz, 2H) 3.09 (s, 3H) 3.79 (t, J=6.62 Hz, 2H)

7.08 (t, J=1.84 Hz, 1H) 7.30 (d, J=8.82 Hz, 2H) 7.67 (dd, J=6.99, 1.84 Hz, 2H) 7.95 (d, J=8.82 Hz, 2H) 10.16 (s, 1H) 10.19 (s, 1H) 10.35 (s, 1H).

N-(3-tert-butyl-5-(2,4-dioxotetrahydropyrimidin-1(2H)-yl)-2-hydroxyphenyl)benzamide (compound IA-L4-1.2). $^1$H NMR (300 MHz, DMSO-$d_6$) δ 10.28 (s, 1H) 10.17 (s, 1H) 8.99 (s, 1H) 8.04 (d, J=6.99 Hz, 2H) 7.49-7.67 (m, 3H) 7.22 (d, J=2.57 Hz, 1H) 7.06 (d, J=2.57 Hz, 1H) 3.73 (t, J=6.80 Hz, 2H) 2.70 (t, J=6.80 Hz, 2H) 1.40 (s, 9H).

N-(3-tert-butyl-5-(2,4-dioxotetrahydropyrimidin-1(2H)-yl)-2-hydroxyphenyl)-4-(methylsulfonamido)benzamide (compound IA-L4-1.3). $^1$H NMR (300 MHz, DMSO-$d_6$) δ 10.29 (s, 1H) 10.25 (br s, 1H) 10.11 (s, 1H) 9.02 (s, 1H) 8.02 (d, J=8.82 Hz, 2H) 7.30 (d, J=8.82 Hz, 2H) 7.19 (d, J=2.21 Hz, 1H) 7.06 (d, J=2.57 Hz, 1H) 3.73 (t, J=6.80 Hz, 2H) 3.10 (s, 3H) 2.71 (t, J=6.62 Hz, 2H) 1.39 (s, 9H).

N-(3-tert-butyl-5-(2,4-dioxotetrahydropyrimidin-1(2H)-yl)-2-hydroxyphenyl)-4-(methyl sulfonylmethyl)benzamide (compound IA-L4-1.4). $^1$H NMR (300 MHz, DMSO-$d_6$) δ 1.40 (s, 9H) 2.70 (t, J=6.62 Hz, 2H) 2.95 (s, 3H) 3.73 (t, J=6.80 Hz, 2H) 4.61 (s, 2H) 7.07 (d, J=2.57 Hz, 1H) 7.21 (d, J=2.57 Hz, 1H) 7.57 (d, J=8.46 Hz, 2H) 8.05 (d, J=8.09 Hz, 2H) 8.95 (s, 1H) 10.16 (s, 1H) 10.29 (s, 1H).

N-(3-tert-butyl-5-(2,4-dioxotetrahydropyrimidin-1(2H)-yl)-2-hydroxyphenyl)-4-nitro benzamide (compound IA-L4-1.5). $^1$H NMR (300 MHz, DMSO-$d_6$) δ 10.28 (s, 1H) 10.26-1H) 8.91 (s, 1H) 8.38 (d, J=8.82 Hz, 2H) 8.26 (d, J=9.20 Hz, 2H) 7.19 (d, J=2.57 Hz, 1H) 7.09 (d, J=2.57 Hz, 1H) 3.73 (t, J=6.62 Hz, 2H) 2.70 (t, J=6.80 Hz, 2H) 1.40 (s, 9H).

4-amino-N-(3-tert-butyl-5-(2,4-dioxotetrahydropyrimidin-1(2H)-yl)-2-hydroxyphenyl)benzamide (compound IA-L4-1.6). $^1$H NMR (300 MHz, DMSO-$d_6$) δ 10.29 (s, 1H) 9.95 (s, 1H) 9.46 (s, 1H) 7.79 (d, J=8.82 Hz, 2H) 7.16 (d, J=2.57 Hz, 1H) 7.03 (d, J=2.21 Hz, 1H) 6.61 (d, J=8.46 Hz, 2H) 5.90 (s, 2H) 3.72 (t, J=6.80 Hz, 2H) 2.70 (t, J=6.62 Hz, 2H) 1.39 (s, 9H).

N-(3-tert-butyl-5-(2,4-dioxotetrahydropyrimidin-1(2H)-yl)-2-methoxyphenyl)-N-methyl-4-(methylsulfonamido)benzamide (compound IA-L4-1.7). $^1$H NMR (300 MHz, DMSO-$d_6$) δ 10.36 (s, 1H) 9.81 (s, 1H) 7.36 (d, J=2.21 Hz, 1H) 7.15 (d, J=8.46 Hz, 2H) 7.05 (d, J=2.21 Hz, 1H) 6.92 (d, J=8.46 Hz, 2H) 3.65-3.90 (m, 2H) 3.41 (s, 3H) 3.17 (d, J=5.52 Hz, 3H) 2.88 (s, 3H) 2.66-2.76 (m, 2H) 1.03 (s, 9H).

N-(3-tert-butyl-5-(2,4-dioxotetrahydropyrimidin-1(2H)-yl)-2-methoxyphenyl)benzamide (compound IA-L4-1.8). $^1$H NMR (300 MHz, DMSO-$d_6$) δ 10.33 (s, 1H) 9.98 (s, 1H) 8.00-8.07 (m, 2H) 7.49-7.64 (m, 3H) 7.38 (d, J=2.57 Hz, 1H) 7.13 (d, J=2.57 Hz, 1H) 3.77 (t, J=6.62 Hz, 2H) 3.72 (s, 3H) 2.71 (t, J=6.62 Hz, 2H) 1.37 (s, 9H).

N-(3-tert-butyl-5-(2,4-dioxotetrahydropyrimidin-1(2H)-yl)-2-methoxyphenyl)-2-methoxy-4-(methylsulfonamido)benzamide (compound IA-L4-1.11). $^1$H NMR (300 MHz, DMSO-$d_6$) δ 10.33 (s, 1H) 10.31 (s, 1H) 10.20 (s, 1H) 8.21 (d, J=2.57 Hz, 1H) 8.02 (d, J=8.82 Hz, 1H) 7.01-7.07 (m, 2H) 6.96 (dd, J=8.46, 1.84 Hz, 1H) 4.03-4.07 (m, 3H) 3.79-3.82 (m, 3H) 3.76 (t, J=6.80 Hz, 2H) 3.14 (s, 3H) 2.71 (t, J=6.62 Hz, 2H) 1.39 (s, 9H).

N-(3-tert-butyl-5-(2,4-dioxotetrahydropyrimidin-1(2H)-yl)-2-methoxyphenyl)-2-chloro-4-(methylsulfonamido)benzamide (compound IA-L4-1.12). $^1$H NMR (300 MHz, DMSO-$d_6$) δ 10.33 (s, 1H) 10.23 (s, 1H) 10.02 (s, 1H) 7.52-7.65 (m, 2H) 7.20-7.33 (m, 2H) 7.09 (d, J=2.57 Hz, 1H) 3.71-3.82 (m, 5H) 3.11 (s, 3H) 2.71 (t, J=6.62 Hz, 2H) 1.35 (s, 9H).

N-(3-tert-butyl-5-(2,4-dioxo-3,4-dihydropyrimidin-1(2H)-yl)-2-methoxyphenyl)-2-methoxy-4-(methylsulfonamido)benzamide (compound IB-L4-1.1). $^1$H NMR (300 MHz, DMSO-$d_6$) δ 1.40 (s, 9H) 3.14 (s, 3H) 3.84 (s, 3H) 4.06 (s, 3H) 5.65 (dd, J=7.72, 2.21 Hz, 1H) 6.96 (dd, J=8.46, 1.84 Hz, 1H) 7.04 (d, J=1.84 Hz, 1H) 7.09 (d, J=2.94 Hz, 1H) 7.71 (d, J=7.72 Hz, 1H) 8.01 (d, J=8.82 Hz, 1H) 8.28 (d, J=2.57 Hz, 1H) 10.27 (s, 1H) 10.32 (s, 1H) 11.41 (d, J=2.21 Hz, 1H).

{1-[3-tert-butyl-5-(2,4-dioxo-tetrahydro-pyrimidin-1-yl)-2-hydroxy-benzyl]-piperidin-4-yl}-carbamic acid tert-butyl ester (compound IA-L5-1-1.1). $^1$H NMR (300 MHz, CDCl$_3$) δ ppm 7.36 (s, 1H) 7.03 (d, J=2.94 Hz, 1H) 6.77 (d, J=2.57 Hz, 1H) 4.43 (s, 1H) 3.79 (t, J=6.62 Hz, 2H) 3.66 (s, 2H) 3.44-3.61 (m, 1H) 2.88-3.01 (m, 1H) 2.81 (t, J=6.62 Hz, 2H) 2.22 (s, 2H) 1.98 (s, 2H) 1.44 (s, 9H) 1.39 (s, 9H) 1.28-1.71 (m, 2H)

N-{1-[3-tert-butyl-5-(2,4-dioxo-tetrahydro-pyrimidin-1-yl)-2-hydroxy-benzyl]-piperidin-3-ylmethyl}-methanesulfonamide (compound IA-L5-1-1.2). $^1$H NMR (300 MHz, CDCl$_3$) δ ppm 7.45 (s, 1H) 7.03 (d, J=2.57 Hz, 1H) 6.78 (d, J=2.21 Hz, 1H) 4.37 (s, 1H) 3.81 (t, J=6.80 Hz, 2H) 3.58-3.73 (m, 2H) 3.07 (s, 2H) 2.92 (s, 3H) 2.81 (t, J=6.62 Hz, 2H) 1.72-1.95 (m, 4H) 1.49-1.72 (m, 4H) 1.39 (s, 9H)

1-[3-tert-butyl-5-(2,4-dioxo-tetrahydro-pyrimidin-1-yl)-2-hydroxy-benzyl]-piperidine-3-carboxylic acid ethyl ester (compound IA-L5-1-1.3). $^1$H NMR (300 MHz, CDCl$_3$) δ ppm 7.39 (s, 1H) 7.03 (d, J=2.57 Hz, 1H) 6.78 (d, J=2.57 Hz, 1H) 4.09-4.22 (m, 2H) 3.79 (t, J=6.62 Hz, 2H) 3.67 (s, 2H) 3.05 (s, 1H) 2.81 (t, J=6.80 Hz, 2H) 2.51-2.69 (m, 1H) 2.38 (s, 1H) 2.15 (s, 1H) 1.88-2.07 (m, 1H) 1.70-1.85 (m, 1H) 1.46-1.69 (m, 3H) 1.39 (s, 9H) 1.21-1.30 (m, 3H)

1-[3-tert-butyl-4-hydroxy-5-(3-methyl-piperidin-1-ylmethyl)-phenyl]-dihydro-pyrimidine-2,4-dione; compound with trifluoroacetic acid (compound IA-L5-1-1.4).

1-[3-tert-butyl-5-(2,4-dioxo-tetrahydro-pyrimidin-1-yl)-2-hydroxy-benzyl]-piperidine-4-carboxylic acid methyl ester (compound IA-L5-1-1.5). $^1$H NMR (300 MHz, CDCl$_3$) δ ppm 7.38 (s, 1H) 7.03 (d, J=2.57 Hz, 1H) 6.77 (d, J=2.57 Hz, 1H) 3.79 (t, J=6.80 Hz, 2H) 3.69 (s, 3H) 3.66 (s, 2H) 2.97 (s, 2H) 2.80 (t, J=6.80 Hz, 2H) 2.30-2.46 (m, 2H) 2.17 (s, 2H) 1.91-2.03 (m, 2H) 1.83 (s, 2H) 1.39 (s, 9H)

1-[3-tert-butyl-4-hydroxy-5-((R)-3-hydroxy-piperidin-1-ylmethyl)-phenyl]-dihydro-pyrimidine-2,4-dione; compound with trifluoroacetic acid (compound IA-L5-1-1.6).

1-[3-tert-butyl-5-(2,4-dioxo-tetrahydro-pyrimidin-1-yl)-2-hydroxy-benzyl]-piperidine-3-carboxylic acid diethylamide, trifluoroacetic acid salt (compound IA-L5-1-1.7).

1-[3-tert-butyl-5-(2,4-dioxo-tetrahydro-pyrimidin-1-yl)-2-hydroxy-benzyl]-piperidine-3-carboxylic acid amide, trifluoroacetic acid salt (compound IA-L5-1-1.8).

1-[3-tert-butyl-5-(2,4-dioxo-tetrahydro-pyrimidin-1-yl)-2-hydroxy-benzyl]-piperazine-1-carboxylic acid tert-butyl ester (compound IA-L5-1-1.10). $^1$H NMR (300 MHz, CDCl$_3$) δ ppm 7.37 (s, 1H) 7.05 (d, J=2.57 Hz, 1H) 6.80 (d, J=2.57 Hz, 1H) 3.79 (t, J=6.62 Hz, 2H) 3.69 (s, 2H) 3.34-3.61 (m, 2H) 2.81 (t, J=6.62 Hz, 2H) 2.52 (s, 2H) 1.56 (s, 4H) 1.46 (s, 9H) 1.39 (s, 9H)

N-{1-[3-tert-butyl-5-(2,4-dioxo-tetrahydro-pyrimidin-1-yl)-2-hydroxy-benzyl]-pyrrolidin-3-yl}-methanesulfonamide (compound IA-L5-1-1.11). $^1$H NMR (300 MHz, CDCl$_3$) δ ppm 7.48 (s, 1H) 7.04 (d, J=2.57 Hz, 1H) 6.81 (d, J=2.21 Hz, 1H) 4.66 (s, 1H) 4.04-4.17 (m, 2H) 3.80 (t, J=6.62 Hz, 2H) 2.96 (s, 3H) 2.85-2.93 (m, 1H) 2.82 (t, J=6.62 Hz, 2H) 2.65-2.76 (m, 1H) 2.50-2.64 (m, 1H) 2.34-2.49 (m, 1H) 1.73-1.89 (m, 1H) 1.39 (s, 9H)

{1-[3-tert-butyl-5-(2,4-dioxo-tetrahydro-pyrimidin-1-yl)-2-hydroxy-benzyl]-pyrrolidin-3-yl}-carbamic acid tert-butyl ester (compound IA-L5-1-1.12). $^1$H NMR (300 MHz, CDCl$_3$) δ ppm 7.38 (s, 1H) 7.01-7.04 (m, 1H) 6.77-6.80 (m, 1H) 4.66-4.75 (m, 1H) 4.16-4.27 (m, 1H) 3.80 (t, 2H) 3.68-3.87 (m, 2H) 2.81 (t, 2H) 2.26-2.96 (m, 5H) 1.49-1.74 (m, 2H) 1.43 (s, 9H) 1.40 (s, 9H)

1-(3-tert-butyl-5-((2,6-dimethylmorpholino)methyl)-4-hydroxyphenyl)dihydro pyrimidine-2,4(1H,3H)-dione 2,2,2-trifluoroacetate (compound IA-L5-1-1.13).

1-(3-tert-butyl-4-hydroxy-5-(morpholinomethyl)phenyl)dihydropyrimidine-2,4(1H,3H)-dione 2,2,2-trifluoroacetate (compound IA-L5-1-1.14).

1-(3-tert-butyl-4-methoxy-5-((1-methyl-1H-indol-3-yl)methyl)phenyl)dihydropyrimidine-2,4(1H,3H)-dione (compound IA-L5-1-2.1). $^1$H NMR (300 MHz, DMSO-d6): δ 10.23 (s, 1H), 7.48 (d, J=8.1 Hz, 1H), 7.38 (d, J=8.1 Hz, 1H), 7.17 (m, 1H), 7.08 (d, J=2.6 Hz, 1H), 7.04 (s, 1H), 6.98 (m, 2H), 4.05 (s, 2H), 3.76 (s, 3H), 3.72 (s, 3H), 3.66 (t, J=6.6 Hz, 1H), 2.62 (t, J=6.6 Hz, 1H), 1.37 (s, 9H)

N-(1-(3-tert-butyl-5-(2,4-dioxotetrahydropyrimidin-1(2H)-yl)-2-hydroxybenzyl)-1,2,3,4-tetrahydroquinolin-6-yl)methanesulfonamide (compound IA-L5-1-2.2). $^1$H NMR (300 MHz, CDCl$_3$) δ 9.38 (s, 1H) 7.46 (s, 1H) 7.09 (d, J=2.21 Hz, 1H) 6.94-7.06 (m, 2H) 6.91 (d, J=2.57 Hz, 1H) 6.23-6.31 (m, 1H) 5.37 (d, J=6.99 Hz, 1H) 3.77-3.89 (m, 3H) 3.04-3.12 (m, 2H) 2.97 (s, 3H) 2.78-2.96 (m, 3H) 1.94-2.04 (m, 2H) 1.39 (s, 9H).

N-(4-(3-tert-butyl-5-(2,4-dioxotetrahydropyrimidin-1(2H)-yl)phenethyl)phenyl)methane sulfonamide (compound IA-L5-2-1.2). $^1$H NMR (300 MHz, DMSO-d$_6$) δ 1.25 (s, 9H) 2.69 (t, J=6.62 Hz, 2H) 2.83 (s, 4H) 2.91 (s, 3H) 3.75 (t, J=6.62 Hz, 2H) 6.99-7.21 (m, 7H) 9.60 (s, 1H) 10.31 (s, 1H).

methyl 2-(3-tert-butyl-5-(2,4-dioxo-3,4-dihydropyrimidin-1(2H)-yl)-2-methoxyphen ethyl)-5-(methylsulfonamido)benzoate (compound IB-L5-2-1.1). $^1$H NMR (300 MHz, DMSO-d6) δ 1.34 (s, 9H) 2.83-2.92 (m, 2H) 2.96 (s, 3H) 3.14 (dd, J=10.30, 5.88 Hz, 2H) 3.75 (s, 3H) 3.83 (s, 3H) 5.64 (d, J=7.72 Hz, 1H) 7.13 (d, J=2.94 Hz, 1H) 7.20 (d, J=2.57 Hz, 1H) 7.28-7.36 (m, 2H) 7.61-7.71 (m, 2H) 9.88 (s, 1H) 11.39 (s, 1H)

N-(4-(3-tert-butyl-5-(2,4-dioxo-3,4-dihydropyrimidin-1(2H)-yl)-2-methoxyphenethyl)phenyl)methanesulfonamide (compound IB-L5-2-1.2). $^1$H NMR (300 MHz, DMSO-d6): δ 11.39 (s, 1H), 9.60 (s, 1H), 7.65 (d, J=8.1 Hz, 1H), 7.23 (m, 3H), 7.17 (m, 3H), 5.64 (d, J=7.7 Hz, 1H), 3.77 (s, 3H), 2.93 (s, 3H), 2.88 (bs, 4H), 1.35 (s, 9H)

N-(4-(3-tert-butyl-5-(2,4-dioxotetrahydropyrimidin-1(2H)-yl)-2-methoxybenzyloxy)phenyl)methanesulfonamide (compound IA-L6-1.1). $^1$H NMR (300 MHz, DMSO-d$_6$) δ ppm 1.36 (s, 9H) 2.69 (t, J=6.62 Hz, 2H) 2.89 (s, 3H) 3.71-3.76 (m, 2H) 3.78 (s, 3H) 5.05 (s, 2H) 6.96-7.12 (m, 2H) 7.10-7.21 (m, 2H) 7.23 (d, J=2.94 Hz, 1H) 7.32 (d, J=2.57 Hz, 1H) 9.39 (s, 1H) 10.32 (s, 1H).

1-(3-tert-butyl-5-((cyclohexyl(ethyl)amino)methyl)-4-hydroxyphenyl)dihydropyrimidine-2,4(1H,3H)-dione 2,2,2-trifluoroacetate (compound IA-L9-1.1).

1-(3-tert-butyl-5-((cyclohexyl(ethyl)amino)methyl)-4-hydroxyphenyl)dihydro pyrimidine-2,4(1H,3H)-dione 2,2,2-trifluoroacetate (compound IA-L9-1.2).

N-(4-(3-tert-butyl-5-(2,4-dioxotetrahydropyrimidin-1(2H)-yl)-2-hydroxybenzylamino)phenyl)methanesulfonamide (compound IA-L9-1.3). $^1$H NMR (300 MHz, DMSO-d$_6$) δ 1.37 (s, 9H) 2.66 (t, J=6.62 Hz, 2H) 2.82 (s, 3H) 3.65 (t, J=6.62 Hz, 2H) 4.24 (d, J=5.15 Hz, 2H) 6.10 (t, J=5.52 Hz, 1H) 6.64 (d, J=8.82 Hz, 2H) 6.98 (d, J=8.82 Hz, 2H) 7.03 (s, 2H) 8.79 (s, 1H) 9.04 (s, 1H) 10.22 (s, 1H).

N-(4-(3-tert-butyl-5-(2,4-dioxotetrahydropyrimidin-1(2H)-yl)-2-methoxybenzylamino)phenyl)methanesulfonamide (compound IA-L9-1.4). $^1$H NMR (500 MHz, DMSO-d$_6$) δ 1.36 (s, 9H), 2.65 (t, J=6.7 Hz, 2H), 2.80 (s, 3H), 3.68 (t, 6.7 Hz, 2H), 3.79 (s, 3H), 4.25 (d, J=5.5 Hz, 2H), 6.10 (m, 1H), 6.55 (d, J=8.5 Hz, 2H), 6.94 (d, J=8.5 Hz, 2H), 7.13 (d, J=2.5 Hz, 1H), 7.19 (d, J=2.4 Hz, 1H), 8.92 (s, 1H), 10.23 (s, 1H).

N-(4-(2-(3-tert-butyl-5-(2,4-dioxotetrahydropyrimidin-1(2H)-yl)-2-methoxyphenyl)-2-oxoethyl)phenyl)methanesulfonamide (compound IA-L11-1.1). $^1$H NMR (300 MHz, DMSO-d$_6$) δ 1.36 (s, 9H) 2.70 (t, J=6.62 Hz, 2H) 2.96 (s, 3H) 3.64 (s, 3H) 3.76 (t, J=6.62 Hz, 2H) 4.27 (s, 2H) 7.10-7.26 (m, 4H) 7.32-7.41 (m, 2H) 9.67 (s, 1H) 10.37 (s, 1H).

N-(4-(2-(3-tert-butyl-5-(2,4-dioxotetrahydropyrimidin-1(2H)-yl)-2-methoxyphenyl)acetyl)phenyl)methanesulfonamide (compound IA-L12-1.1). $^1$H NMR (300 MHz, DMSO-d$_6$) δ 1.33 (s, 9H) 2.68 (t, J=6.62 Hz, 2H) 3.12 (s, 3H) 3.61 (s, 3H) 3.72 (t, J=6.62 Hz, 2H) 4.36 (s, 2H) 7.01 (d, J=2.94 Hz, 1H) 7.15 (d, J=2.57 Hz, 1H) 7.29 (d, J=8.82 Hz, 2H) 8.04 (d, J=8.82 Hz, 2H) 10.29 (s, 1H) 10.35 (s, 1H).

The following compounds can be prepared utilizing the above discussion:

TABLE A

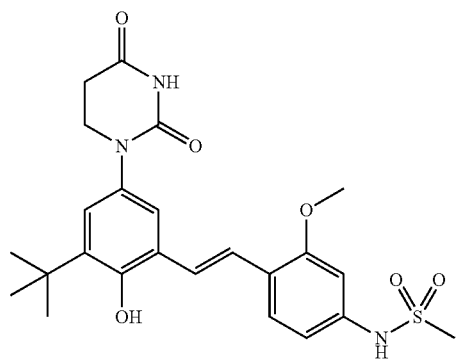 [SMILES: COc1cc(NS(C)(=O)=O)ccc1/C=C/c1cc(N2CCC(=O)NC2=O)cc(C(C)(C)C)c1O]

IA-L1-1.2

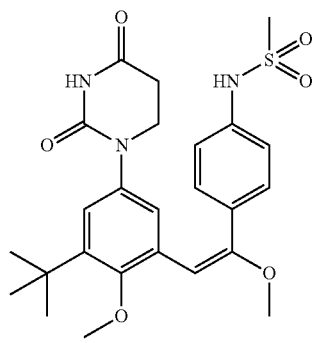 [SMILES: CO/C(=C/c1cc(N2CCC(=O)NC2=O)cc(C(C)(C)C)c1OC)c1ccc(NS(C)(=O)=O)cc1]

IA-L1-1.7

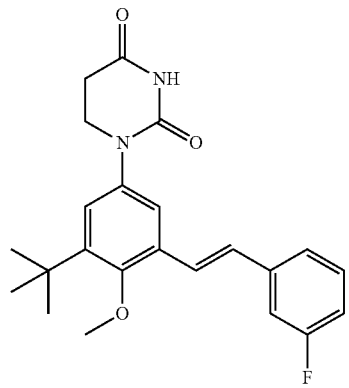 [SMILES: COc1c(/C=C/c2cccc(F)c2)cc(N2CCC(=O)NC2=O)cc1C(C)(C)C]

IA-L1-1.15

TABLE A-continued

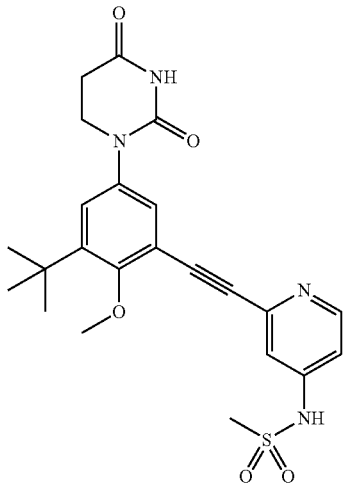 [SMILES: COc1c(C#Cc2cc(NS(C)(=O)=O)ccn2)cc(N2CCC(=O)NC2=O)cc1C(C)(C)C]

IA-L2-1.5

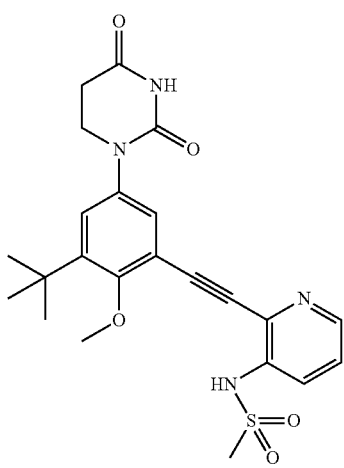 [SMILES: COc1c(C#Cc2ncccc2NS(C)(=O)=O)cc(N2CCC(=O)NC2=O)cc1C(C)(C)C]

IA-L2-1.6

TABLE B

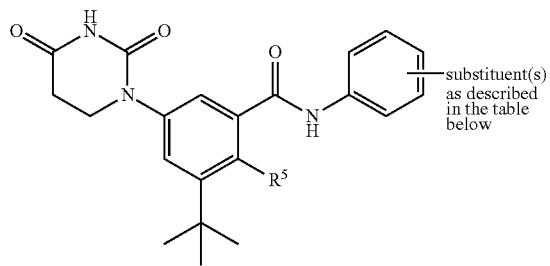

| compound | R[5] | substituent(s) |
|---|---|---|
| IA-L3-1.23 | —OH | -2-OCH$_3$— |
| IA-L3-1.29 | —OCH$_3$ | -4-C(H)$_2$N(H)S(O)$_2$CH$_3$ |
| IA-L3-1.61 | —OCH$_3$ | 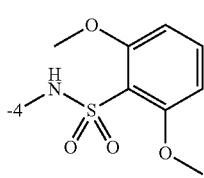 |
| IA-L3-1.68 | —OCH$_3$ | -4-N[C(H)$_2$C(H)=CH$_2$]S(O)$_2$CH$_3$ |
| IA-L3-1.75 | —OCH$_3$ | -4-N[C(O)OC(H)$_2$C(H)$_2$CH$_3$]S(O)$_2$CH$_3$ |

HCV Polymerase Inhibition Assay

Either two-fold serial dilutions (fractional inhibition assay) or a narrower range of dilutions spanning the IC$_{50}$ of the inhibitor (tight binding assay) of the inhibitors were incubated with 20 mM Tris-Cl pH 7.4, 2 mM MnCl$_2$, 1 mM dithiothreitol, 1 mM ethylene diamine tetraacetic acid (EDTA), 60 to 125 µM GTP and 20 to 50 nM Δ21 NS5B (HCV Strain 1B (BK, Genbank accession number M58335, or H77, Genbank accession number AF011751)) for 15 min at room temperature. The reaction was initiated by the addition of 20 µM CTP, 20 µM ATP, 1 µM $^3$H-UTP (10 mCi/umol), 5 nM template RNA and 0.1 U/µl RNase inhibitor (RNasin, Promega), and allowed to proceed for 2 to 4 h at room temperature. Reaction volume was 50 µl. The reaction was terminated by the addition of 1 volume of 4 mM spermine in 10 mM Tris-Cl pH 8.0, 1 mM EDTA. After incubation for at least 15 min at room temperature, the precipitated RNA was captured by filtering through a GF/B filter (Millipore) in a 96 well format. The filter plate was washed three times with 200 µl each of 2 mM spermine, 10 mM Tris-Cl pH 8.0, 1 mM EDTA, and 2 times with ethanol. After air-drying, 30 µl of Microscint 20 scintillation cocktail (Packard) was added to each well, and the retained cpm were determined by scintillation counting. IC$_{50}$ values were calculated by a two-variable nonlinear regression equation using an uninhibited control and a fully inhibited control sample to determine the minimum and maximum for the curve. Tight-binding assays were performed on those compounds exhibiting IC$_{50}$ values less than 0.005 µM in the fractional inhibition assay in order to more precisely measure the IC$_{50}$ values. Retained cpm were plotted vs. inhibitor concentration and fit to equation 1 using nonlinear regression (ref. 1) to obtain the IC$_{50}$ values:

$$\text{Retained } cpm = A [sqrt\{(IC_{50}+I_t-E_t)^2+4*IC_{50}*E_t\}-(IC_{50}-I_t-E_t)] \quad (\text{eqn 1})$$

where A=Vmax[S]/2(Km+[S]); It=total inhibitor concentration and Et=total active concentration of enzyme.

Ref. Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was: 5'-GGGC-GAAUUG GGCCCUCUAG AUGCAUGCUC GAGCGGC-CGC CAGUGUGAUG GAUAUCUGCA GAAUUCGCCC UUGGUGGCUC CAUCUUAGCC CUAGUCACGG CUAGCUGUGA AAGGUCCGUG AGCCGCUUGA CUG-CAGAGAG UGCUGAUACU GGCCUCUCUG CAGAUCAAGUC-3'

When tested by the above method, the compounds of this invention inhibit HCV polymerase 1A and/or 1B. The legend in the table below is as follows: A—IC$_{50}$≤0.01 uM; B—0.1 uM≥IC$_{50}$>0.01 uM; C—1 uM≥IC$_{50}$≥0.1 uM; and D—IC$_{50}$≥1 uM; ND—not determined.

TABLE IC$_{50}$

| compound | 1a | 1b | compound | 1a | 1b |
|---|---|---|---|---|---|
| IA-L0-1.1 | A | B | IA-L0-1.2 | B | B |
| IA-L0-1.3 | C | C | IA-L0-1.4 | B | B |
| IA-L0-1.5 | C | C | IA-L0-1.6 | B | B |
| IA-L0-1.7 | D | C | IA-L0-1.8 | C | C |
| IA-L0-1.9 | B | C | IA-L0-1.10 | D | D |
| IA-L0-1.11 | D | D | IB-L0-1.1 | A | A |
| IB-L0-1.2 | C | C | IB-L0-1.3 | B | B |
| IB-L0-1.4 | B | B | IB-L0-1.5 | B | B |
| IB-L0-1.6 | C | C | IB-L0-1.7 | B | B |
| IB-L0-1.8 | C | C | IB-L0-1.9 | C | C |
| IB-L0-1.10 | C | C | IA-L0-2.1 | C | C |

TABLE IC$_{50}$-continued

| compound | 1a | 1b | compound | 1a | 1b |
|---|---|---|---|---|---|
| IA-L0-2.2 | B | B | IA-L0-2.3 | C | C |
| IA-L0-2.4 | B | B | IA-L0-2.5 | C | C |
| IA-L0-2.6 | C | C | IA-L0-2.7 | C | C |
| IA-L0-2.8 | B | B | IA-L0-2.9 | A | A |
| IA-L0-2.10 | D | D | IB-L0-2.1 | C | C |
| IB-L0-2.2 | C | C | IB-L0-2.3 | A | A |
| IB-L0-2.4 | A | A | IB-L0-2.5 | B | B |
| IB-L0-2.6 | B | B | IB-L0-2.7 | B | B |
| IB-L0-2.8 | B | B | IB-L0-2.9 | A | A |
| IB-L0-2.10 | A | B | IB-L0-2.11 | A | A |
| IB-L0-2.12 | A | B | IB-L0-2.13 | A | B |
| IB-L0-2.14 | A | A | IB-L0-2.15 | A | B |
| IB-L0-2.16 | A | B | IB-L0-2.17 | A | B |
| IB-L0-2.18 | A | B | IB-L0-2.19 | A | B |
| IB-L0-2.20 | A | B | IB-L0-2.21 | B | B |
| IB-L0-2.22 | B | B | IB-L0-2.23 | B | A |
| IB-L0-2.24 | B | B | IB-L0-2.25 | B | B |
| IB-L0-2.26 | B | B | IB-L0-2.27 | B | B |
| IB-L0-2.28 | B | B | IB-L0-2.29 | B | B |
| IB-L0-2.30 | B | B | IB-L0-2.31 | B | B |
| IB-L0-2.32 | B | B | IB-L0-2.33 | B | B |
| IB-L0-2.34 | B | B | IB-L0-2.35 | B | B |
| IB-L0-2.36 | B | C | IB-L0-2.37 | C | C |
| IB-L0-2.38 | C | B | IB-L0-2.39 | C | C |
| IB-L0-2.40 | C | C | IB-L0-2.41 | C | C |
| IB-L0-2.42 | C | C | IB-L0-2.43 | C | C |
| IB-L0-2.44 | C | C | IB-L0-2.45 | C | C |
| IB-L0-2.46 | C | C | IB-L0-2.47 | D | D |
| IB-L0-2.48 | D | D | IB-L0-2.49 | D | D |
| IB-L0-2.50 | B | B | IB-L0-2.51 | A | B |
| IB-L0-2.52 | A | B | IB-L0-2.53 | A | B |
| IB-L0-2.54 | A | B | IB-L0-2.55 | A | B |
| IB-L0-2.56 | A | B | IB-L0-2.57 | A | B |
| IB-L0-2.58 | A | B | IB-L0-2.59 | A | B |
| IB-L0-2.60 | A | B | IB-L0-2.61 | A | B |
| IB-L0-2.62 | B | B | IB-L0-2.63 | B | B |
| IB-L0-2.64 | B | B | IB-L0-2.65 | B | A |
| IB-L0-2.66 | B | B | IB-L0-2.67 | B | B |
| IB-L0-2.68 | B | B | IB-L0-2.69 | B | B |
| IB-L0-2.70 | B | C | IB-L0-2.71 | C | C |
| IB-L0-2.72 | C | C | IB-L0-2.73 | C | C |
| IB-L0-2.74 | C | C | IB-L0-2.75 | C | D |
| IB-L0-2.76 | C | D | IB-L0-2.77 | D | D |
| IB-L0-2.78 | D | D | IB-L0-2.79 | B | B |
| IA-L1-1.3 | A | A | IA-L1-1.4 | A | A |
| IA-L1-1.5 | A | B | IA-L1-1.6 | A | B |
| IA-L1-1.9 | A | B | IA-L1-1.10 | B | B |
| IA-L1-1.11 | B | B | IA-L1-1.12 | C | C |
| IA-L1-1.13 | C | C | IA-L1-1.14 | D | D |
| IA-L1-1.16 | A | A | IA-L1-1.17 | B | B |
| IA-L1-1.18 | C | C | IA-L1-1.20 | A | B |
| IA-L1-1.21 | B | B | IA-L1-1.22 | C | C |
| IA-L1-1.23 | C | C | IA-L1-1.24 | D | D |
| IA-L1-1.25 | D | D | IA-L1-1.26 | B | B |
| IA-L1-1.27 | A | B | IB-L1-1.1 | A | A |
| IB-L1-1.2 | B | B | IB-L1-1.4 | A | A |
| IB-L1-1.5 | A | A | IB-L1-1.6 | A | B |
| IB-L1-1.7 | A | B | IB-L1-1.8 | A | B |
| IB-L1-1.9 | A | B | IB-L1-1.10 | A | B |
| IB-L1-1.11 | A | B | IB-L1-1.12 | A | B |
| IB-L1-1.13 | A | B | IB-L1-1.14 | A | B |
| IB-L1-1.15 | A | B | IB-L1-1.16 | A | B |
| IB-L1-1.17 | A | B | IB-L1-1.18 | A | B |
| IB-L1-1.19 | A | B | IB-L1-1.20 | A | B |
| IB-L1-1.21 | A | B | IB-L1-1.22 | B | B |
| IB-L1-1.23 | B | B | IB-L1-1.24 | B | B |
| IB-L1-1.25 | B | B | IB-L1-1.26 | B | B |
| IB-L1-1.27 | B | B | IB-L1-1.28 | B | B |
| IB-L1-1.29 | B | B | IB-L1-1.30 | B | B |
| IB-L1-1.31 | B | C | IB-L1-1.32 | C | C |
| IB-L1-1.33 | C | C | IB-L1-1.34 | D | D |
| IB-L1-1.45 | A | B | IB-L1-1.46 | B | B |
| IB-L1-1.47 | B | B | IB-L1-1.48 | B | B |
| IB-L1-1.49 | B | C | IB-L1-1.50 | B | B |
| IB-L1-1.51 | B | B | IB-L1-1.52 | C | C |
| IB-L1-1.53 | D | D | IB-L1-1.55 | D | D |
| IA-L2-1.1 | B | A | IA-L2-1.2 | A | A |
| IA-L2-1.3 | A | A | IA-L2-1.4 | C | C |
| IA-L2-1.7 | B | B | IA-L2-1.8 | A | A |
| IA-L2-1.9 | A | A | IA-L2-1.10 | B | B |
| IA-L2-1.11 | A | B | IA-L2-1.12 | A | A |
| IA-L2-1.13 | A | A | IA-L2-1.14 | A | A |
| IA-L2-1.15 | B | B | IA-L2-1.16 | A | B |
| IA-L2-1.17 | B | B | IA-L2-1.18 | A | A |
| IA-L2-1.19 | C | B | IA-L2-1.20 | A | B |
| IA-L2-1.21 | A | B | IA-L2-1.22 | B | B |
| IA-L2-1.23 | C | C | IA-L2-1.24 | A | B |
| IA-L2-1.25 | A | B | IA-L2-1.26 | B | B |
| IB-L2-1.1 | A | B | IB-L2-1.2 | A | B |
| IB-L2-1.3 | A | B | IB-L2-1.4 | B | B |
| IB-L2-1.5 | B | B | IB-L2-1.6 | A | B |
| IB-L2-1.7 | A | B | IB-L2-1.8 | A | B |
| IB-L2-1.9 | C | B | IB-L2-1.10 | A | B |
| IB-L2-1.11 | B | B | IB-L2-1.12 | B | B |
| IB-L2-1.15 | C | C | IA-L2-2.1 | B | B |
| IB-L2-2.1 | B | B | IA-L3-1.1 | D | D |
| IA-L3-1.2 | D | B | IA-L3-1.3 | D | C |
| IA-L3-1.4 | C | B | IA-L3-1.5 | C | B |
| IA-L3-1.6 | B | A | IA-L3-1.7 | C | B |
| IA-L3-1.8 | B | B | IA-L3-1.9 | C | B |
| IA-L3-1.10 | B | B | IA-L3-1.11 | D | C |
| IA-L3-1.12 | C | B | IA-L3-1.13 | C | A |
| IA-L3-1.14 | B | A | IA-L3-1.15 | D | C |
| IA-L3-1.16 | D | B | IA-L3-1.17 | D | ND |
| IA-L3-1.18 | D | ND | IA-L3-1.19 | C | B |
| IA-L3-1.20 | D | D | IA-L3-1.21 | D | C |
| IA-L3-1.22 | C | B | IA-L3-1.24 | C | C |
| IA-L3-1.25 | D | D | IA-L3-1.26 | D | D |
| IA-L3-1.27 | C | C | IA-L3-1.28 | ND | ND |
| IA-L3-1.30 | D | C | IA-L3-1.31 | D | D |
| IA-L3-1.32 | ND | ND | IA-L3-1.33 | D | C |
| IA-L3-1.34 | ND | ND | IA-L3-1.35 | ND | ND |
| IA-L3-1.36 | ND | ND | IA-L3-1.37 | ND | ND |
| IA-L3-1.38 | D | C | IA-L3-1.39 | D | C |
| IA-L3-1.40 | ND | ND | IA-L3-1.41 | C | D |
| IA-L3-1.42 | D | D | IA-L3-1.43 | D | D |
| IA-L3-1.44 | ND | ND | IA-L3-1.45 | ND | ND |
| IA-L3-1.46 | ND | ND | IA-L3-1.47 | D | D |
| IA-L3-1.48 | D | D | IA-L3-1.49 | D | D |
| IA-L3-1.50 | D | D | IA-L3-1.51 | B | B |
| IA-L3-1.52 | C | C | IA-L3-1.53 | ND | ND |
| IA-L3-1.54 | B | C | IA-L3-1.55 | C | C |
| IA-L3-1.56 | C | C | IA-L3-1.57 | B | C |
| IA-L3-1.58 | C | C | IA-L3-1.59 | C | B |
| IA-L3-1.60 | B | B | IA-L3-1.62 | C | C |
| IA-L3-1.63 | D | D | IA-L3-1.64 | C | D |
| IA-L3-1.65 | D | D | IA-L3-1.66 | D | D |
| IA-L3-1.67 | D | D | IA-L3-1.69 | C | C |
| IA-L3-1.70 | D | D | IA-L3-1.71 | C | D |
| IA-L3-1.72 | D | D | IA-L3-1.73 | D | D |
| IA-L3-1.74 | D | D | IA-L3-1.76 | D | D |
| IA-L3-1.77 | D | D | IA-L3-1.78 | D | D |
| IA-L3-1.79 | D | D | IA-L3-1.80 | D | D |
| IA-L3-1.81 | ND | ND | IA-L3-1.82 | ND | ND |
| IA-L3-1.83 | B | C | IA-L3-1.84 | C | C |
| IA-L3-1.85 | C | C | IA-L3-1.86 | ND | ND |
| IA-L3-1.87 | D | C | IA-L3-1.88 | D | D |
| IA-L3-1.89 | B | B | IA-L3-1.90 | B | B |
| IA-L3-1.91 | B | B | IA-L3-1.94 | C | C |
| IA-L3-1.95 | C | B | IA-L3-1.96 | C | D |
| IA-L3-1.97 | D | D | IA-L3-1.98 | D | C |
| IA-L3-1.99 | B | C | IA-L3-1.100 | D | C |
| IA-L3-1.101 | D | D | IA-L3-1.102 | C | C |
| IA-L3-1.103 | C | D | IA-L3-1.104 | C | C |
| IA-L3-1.105 | C | B | IA-L3-1.107 | D | D |
| IA-L3-1.108 | D | D | IA-L3-1.111 | B | C |
| IA-L3-1.112 | C | C | IA-L3-1.113 | D | D |
| IA-L3-1.114 | D | D | IA-L3-1.115 | D | D |
| IA-L3-1.116 | D | D | IA-L3-1.117 | D | D |
| IA-L3-1.118 | D | D | IA-L3-1.119 | B | A |
| IA-L3-1.120 | C | C | IA-L3-1.121 | C | C |
| IA-L3-1.122 | B | B | IA-L3-1.123 | D | D |
| IB-L3-1.1 | B | B | IB-L3-1.2 | B | A |
| IB-L3-1.3 | C | D | IB-L3-1.4 | C | B |
| IA-L3-2.1 | D | C | IA-L3-2.2 | C | C |
| IA-L3-2.3 | D | D | IA-L3-2.4 | D | D |

TABLE IC$_{50}$-continued

| compound | 1a | 1b | compound | 1a | 1b |
|---|---|---|---|---|---|
| IA-L3-2.5 | D | C | IA-L4-1.1 | C | C |
| IA-L4-1.2 | D | D | IA-L4-1.3 | C | C |
| IA-L4-1.4 | D | D | IA-L4-1.5 | D | D |
| IA-L4-1.6 | D | D | IA-L4-1.7 | C | D |
| IA-L4-1.8 | D | C | IA-L4-1.9 | B | B |
| IA-L4-1.10 | D | D | IA-L4-1.11 | A | B |
| IA-L4-1.12 | B | B | IB-L4-1.1 | A | B |
| IA-L5-1-1.1 | D | D | IA-L5-1-1.2 | D | D |
| IA-L5-1-1.3 | D | D | IA-L5-1-1.4 | D | D |
| IA-L5-1-1.5 | D | D | IA-L5-1-1.6 | D | D |
| IA-L5-1-1.7 | D | D | IA-L5-1-1.8 | D | D |
| IA-L5-1-1.10 | D | D | IA-L5-1-1.11 | D | D |
| IA-L5-1-1.12 | D | D | IA-L5-1-1.13 | D | D |
| IA-L5-1-1.14 | D | D | IA-L5-1-2.1 | D | D |
| IA-L5-1-2.2 | D | D | IA-L5-2-1.1 | B | B |
| IA-L5-2-1.2 | B | B | IB-L5-2-1.1 | A | B |
| IB-L5-2-1.2 | B | B | IA-L6-1.1 | B | C |
| IA-L8-1.1 | C | C | IA-L9-1.1 | D | D |
| IA-L9-1.2 | D | D | IA-L9-1.3 | D | D |
| IA-L9-1.4 | B | C | IA-L11-1.1 | B | B |
| IA-L12-1.1 | B | B | | | |

HCV Polymerase Replicon Assay

Two stable subgenomic replicon cell lines were used for compound characterization in cell culture: one derived from genotype 1a-H77 and one derived from genotype 1b-Con1 (obtained from Apath, LLC, St. Louis, Mo.). All replicon constructs were bicistronic subgenomic replicons similar to those described by Bartenschlager and coworkers (Lohmann et al., *Replication of Subgenomic Hepatitis C Virus RNAs in a Hepatoma Cell Line*, SCIENCE 285:110-3 (1999)). The genotype 1a replicon construct contains NS3-NS5B coding region derived from the H77 strain of HCV (1a-H77) (Blight et al., *Efficient Replication of Hepatitis C Virus Genotype 1a RNAs in Cell Culture*, J. VIROL. 77:3181-90 (2003)). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the NS3-NS5B coding region was derived from the 1b-Con1 strain, and the adaptive mutations are E1202G, T12801 and S2204I. Replicon cell lines were maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of compounds on HCV replication were determined by measuring activity of the luciferase reporter gene. Briefly, replicon-containing cells were seeded into 96 well plates at a density of 5000 cells per well in 100 ul DMEM containing 5% FBS. 16-24 h later, the compounds were diluted in dimethyl sulfoxide (DMSO) to generate a 200× stock in a series of eight half-log dilutions. The dilution series was then further diluted 100-fold in the medium containing 5% FBS. Medium with the inhibitor was added to the overnight cell culture plates already containing 100 ul of DMEM with 5% FBS. In assays measuring inhibitory activity in the presence of human plasma, the medium from the overnight cell culture plates was replaced with DMEM containing 40% human plasma and 5% FBS. The cells were incubated for three days in the tissue culture incubators and were then lysed for RNA extraction. For the luciferase assay, 30 ul of Passive Lysis buffer (Promega) was added to each well, and then the plates were incubated for 15 min with rocking to lyse the cells. Luciferin solution (50 to 100 ul, Promega) was added to each well, and luciferase activity was measured with a Victor II luminometer (Perkin-Elmer). The percent inhibition of HCV RNA replication was calculated for each compound concentration and the EC$_{50}$ value was calculated using nonlinear regression curve fitting to the 4-parameter logistic equation and GraphPad Prism 4 software.

When tested by the above method, the compounds of this invention inhibit HCV polymerase 1A and/or 1B. The legend in the table below is as follows: A—EC$_{50}$≤0.01 uM; B—0.1 uM≥EC$_{50}$>0.01 uM; C—1 uM≥EC$_{50}$>0.1 uM; and D—EC$_{50}$>1 uM; ND—not determined.

TABLE EC$_{50}$

| compound | 1a | 1b | compound | 1a | 1b |
|---|---|---|---|---|---|
| IA-L0-1.1 | C | A | IA-L0-1.2 | C | B |
| IA-L0-1.3 | C | C | IA-L0-1.4 | C | B |
| IA-L0-1.5 | D | D | IA-L0-1.6 | C | B |
| IA-L0-1.7 | D | D | IA-L0-1.8 | D | D |
| IA-L0-1.9 | D | C | IA-L0-1.10 | ND | ND |
| IA-L0-1.11 | ND | ND | IB-L0-1.1 | B | B |
| IB-L0-1.2 | D | D | IB-L0-1.3 | C | B |
| IB-L0-1.4 | C | B | IB-L0-1.5 | B | B |
| IB-L0-1.6 | D | C | IB-L0-1.7 | D | C |
| IB-L0-1.8 | D | D | IB-L0-1.9 | D | D |
| IB-L0-1.10 | D | D | IA-L0-2.1 | D | D |
| IA-L0-2.2 | C | B | IA-L0-2.3 | C | C |
| IA-L0-2.4 | D | C | IA-L0-2.5 | D | D |
| IA-L0-2.6 | D | D | IA-L0-2.7 | D | C |
| IA-L0-2.8 | C | B | IA-L0-2.9 | A | A |
| IA-L0-2.10 | ND | ND | IB-L0-2.1 | D | C |
| IB-L0-2.2 | D | D | IB-L0-2.3 | A | A |
| IB-L0-2.4 | ND | A | IB-L0-2.5 | B | A |
| IB-L0-2.6 | C | B | IB-L0-2.7 | C | B |
| IB-L0-2.8 | ND | B | IB-L0-2.9 | A | A |
| IB-L0-2.10 | A | A | IB-L0-2.11 | B | A |
| IB-L0-2.12 | B | A | IB-L0-2.13 | B | A |
| IB-L0-2.14 | C | B | IB-L0-2.15 | C | B |
| IB-L0-2.16 | C | A | IB-L0-2.17 | B | A |
| IB-L0-2.18 | C | B | IB-L0-2.19 | B | B |
| IB-L0-2.20 | C | B | IB-L0-2.21 | C | B |
| IB-L0-2.22 | C | B | IB-L0-2.23 | C | B |
| IB-L0-2.24 | B | B | IB-L0-2.25 | C | B |
| IB-L0-2.26 | D | C | IB-L0-2.27 | C | B |
| IB-L0-2.28 | D | C | IB-L0-2.29 | C | B |
| IB-L0-2.30 | C | B | IB-L0-2.31 | C | B |
| IB-L0-2.32 | C | B | IB-L0-2.33 | C | C |
| IB-L0-2.34 | D | C | IB-L0-2.35 | D | C |
| IB-L0-2.36 | C | B | IB-L0-2.37 | D | C |
| IB-L0-2.38 | D | D | IB-L0-2.39 | D | C |
| IB-L0-2.40 | D | C | IB-L0-2.41 | C | C |
| IB-L0-2.42 | C | C | IB-L0-2.43 | D | C |
| IB-L0-2.44 | D | D | IB-L0-2.45 | D | C |
| IB-L0-2.46 | ND | ND | IB-L0-2.47 | ND | ND |
| IB-L0-2.48 | ND | ND | IB-L0-2.49 | ND | ND |
| IB-L0-2.50 | C | C | IB-L0-2.51 | B | A |
| IB-L0-2.52 | B | A | IB-L0-2.53 | B | B |
| IB-L0-2.54 | B | B | IB-L0-2.55 | B | A |
| IB-L0-2.56 | C | A | IB-L0-2.57 | C | B |
| IB-L0-2.58 | B | A | IB-L0-2.59 | C | B |
| IB-L0-2.60 | C | B | IB-L0-2.61 | C | B |
| IB-L0-2.62 | C | B | IB-L0-2.63 | C | B |
| IB-L0-2.64 | C | A | IB-L0-2.65 | C | B |
| IB-L0-2.66 | C | B | IB-L0-2.67 | C | B |
| IB-L0-2.68 | D | C | IB-L0-2.69 | C | B |
| IB-L0-2.70 | D | C | IB-L0-2.71 | C | B |
| IB-L0-2.72 | D | C | IB-L0-2.73 | C | C |
| IB-L0-2.74 | D | C | IB-L0-2.75 | D | D |
| IB-L0-2.76 | ND | ND | IB-L0-2.77 | ND | ND |
| IB-L0-2.78 | ND | ND | IB-L0-2.79 | C | C |
| IA-L1-1.3 | B | A | IA-L1-1.4 | A | A |
| IA-L1-1.5 | B | A | IA-L1-1.6 | B | B |
| IA-L1-1.9 | B | A | IA-L1-1.10 | B | B |
| IA-L1-1.11 | A | A | IA-L1-1.12 | C | C |
| IA-L1-1.13 | D | C | IA-L1-1.14 | D | D |
| IA-L1-1.16 | B | B | IA-L1-1.17 | B | B |
| IA-L1-1.18 | C | C | IA-L1-1.20 | B | B |

TABLE EC$_{50}$-continued

| compound | 1a | 1b | compound | 1a | 1b |
|---|---|---|---|---|---|
| IA-L1-1.21 | A | A | IA-L1-1.22 | D | C |
| IA-L1-1.23 | D | D | IA-L1-1.24 | D | D |
| IA-L1-1.25 | ND | ND | IA-L1-1.26 | B | B |
| IA-L1-1.27 | B | A | IB-L1-1.1 | A | A |
| IB-L1-1.2 | ND | B | IB-L1-1.4 | B | A |
| IB-L1-1.5 | B | A | IB-L1-1.6 | A | A |
| IB-L1-1.7 | A | A | IB-L1-1.8 | B | A |
| IB-L1-1.9 | B | A | IB-L1-1.10 | A | A |
| IB-L1-1.11 | B | A | IB-L1-1.12 | B | B |
| IB-L1-1.13 | B | A | IB-L1-1.14 | B | A |
| IB-L1-1.15 | A | A | IB-L1-1.16 | C | B |
| IB-L1-1.17 | B | A | IB-L1-1.18 | B | B |
| IB-L1-1.19 | B | A | IB-L1-1.20 | B | A |
| IB-L1-1.21 | B | A | IB-L1-1.22 | B | A |
| IB-L1-1.23 | C | A | IB-L1-1.24 | B | A |
| IB-L1-1.25 | B | A | IB-L1-1.26 | B | A |
| IB-L1-1.27 | B | A | IB-L1-1.28 | A | A |
| IB-L1-1.29 | C | C | IB-L1-1.30 | C | B |
| IB-L1-1.31 | D | D | IB-L1-1.32 | C | B |
| IB-L1-1.33 | C | B | IB-L1-1.34 | B | A |
| IB-L1-1.45 | B | A | IB-L1-1.46 | C | A |
| IB-L1-1.47 | C | B | IB-L1-1.48 | C | A |
| IB-L1-1.49 | D | D | IB-L1-1.50 | C | B |
| IB-L1-1.51 | D | B | IB-L1-1.52 | D | C |
| IB-L1-1.53 | ND | ND | IB-L1-1.55 | ND | ND |
| IA-L2-1.1 | C | B | IA-L2-1.2 | B | B |
| IA-L2-1.3 | B | A | IA-L2-1.4 | C | C |
| IA-L2-1.7 | D | C | IA-L2-1.8 | B | A |
| IA-L2-1.9 | A | A | IA-L2-1.10 | C | B |
| IA-L2-1.11 | A | A | IA-L2-1.12 | B | A |
| IA-L2-1.13 | C | B | IA-L2-1.14 | A | A |
| IA-L2-1.15 | C | C | IA-L2-1.16 | B | A |
| IA-L2-1.17 | C | B | IA-L2-1.18 | B | A |
| IA-L2-1.19 | D | D | IA-L2-1.20 | B | A |
| IA-L2-1.21 | B | A | IA-L2-1.22 | C | B |
| IA-L2-1.23 | D | C | IA-L2-1.24 | C | B |
| IA-L2-1.25 | C | B | IA-L2-1.26 | B | B |
| IB-L2-1.1 | A | A | IB-L2-1.2 | ND | A |
| IB-L2-1.3 | B | A | IB-L2-1.4 | ND | C |
| IB-L2-1.5 | C | B | IB-L2-1.6 | B | A |
| IB-L2-1.7 | ND | A | IB-L2-1.8 | B | A |
| IB-L2-1.9 | D | ND | IB-L2-1.10 | ND | B |
| IB-L2-1.11 | C | B | IB-L2-1.12 | C | B |
| IB-L2-1.15 | D | C | IA-L2-2.1 | C | C |
| IB-L2-2.1 | C | C | IA-L3-1.1 | ND | ND |
| IA-L3-1.2 | D | D | IA-L3-1.3 | D | D |
| IA-L3-1.4 | D | D | IA-L3-1.5 | D | D |
| IA-L3-1.6 | C | B | IA-L3-1.7 | D | D |
| IA-L3-1.8 | D | C | IA-L3-1.9 | D | D |
| IA-L3-1.10 | C | C | IA-L3-1.11 | D | D |
| IA-L3-1.12 | D | D | IA-L3-1.13 | D | D |
| IA-L3-1.14 | ND | C | IA-L3-1.15 | D | D |
| IA-L3-1.16 | D | D | IA-L3-1.17 | D | D |
| IA-L3-1.18 | D | C | IA-L3-1.19 | D | D |
| IA-L3-1.20 | D | D | IA-L3-1.21 | D | D |
| IA-L3-1.22 | D | D | IA-L3-1.24 | D | D |
| IA-L3-1.25 | ND | ND | IA-L3-1.26 | ND | ND |
| IA-L3-1.27 | D | D | IA-L3-1.28 | ND | ND |
| IA-L3-1.30 | D | D | IA-L3-1.31 | D | D |
| IA-L3-1.32 | ND | ND | IA-L3-1.33 | D | D |
| IA-L3-1.34 | ND | ND | IA-L3-1.35 | ND | ND |
| IA-L3-1.36 | ND | ND | IA-L3-1.37 | ND | ND |
| IA-L3-1.38 | D | D | IA-L3-1.39 | D | D |
| IA-L3-1.40 | ND | ND | IA-L3-1.41 | D | C |
| IA-L3-1.42 | ND | ND | IA-L3-1.43 | ND | ND |
| IA-L3-1.44 | ND | ND | IA-L3-1.45 | ND | ND |
| IA-L3-1.46 | ND | ND | IA-L3-1.47 | ND | ND |
| IA-L3-1.48 | ND | ND | IA-L3-1.49 | ND | ND |
| IA-L3-1.50 | ND | ND | IA-L3-1.51 | C | B |
| IA-L3-1.52 | D | C | IA-L3-1.53 | ND | ND |
| IA-L3-1.54 | ND | B | IA-L3-1.55 | D | D |
| IA-L3-1.56 | ND | C | IA-L3-1.57 | C | C |
| IA-L3-1.58 | ND | C | IA-L3-1.59 | D | D |
| IA-L3-1.60 | C | B | IA-L3-1.62 | D | C |
| IA-L3-1.63 | ND | ND | IA-L3-1.64 | ND | ND |
| IA-L3-1.65 | ND | ND | IA-L3-1.66 | ND | ND |
| IA-L3-1.67 | D | C | IA-L3-1.69 | C | B |
| IA-L3-1.70 | C | B | IA-L3-1.71 | C | B |
| IA-L3-1.72 | ND | ND | IA-L3-1.73 | ND | ND |
| IA-L3-1.74 | ND | ND | IA-L3-1.76 | ND | ND |
| IA-L3-1.77 | ND | ND | IA-L3-1.78 | ND | ND |
| IA-L3-1.79 | ND | ND | IA-L3-1.80 | ND | ND |
| IA-L3-1.81 | ND | ND | IA-L3-1.82 | ND | ND |
| IA-L3-1.83 | C | C | IA-L3-1.84 | D | D |
| IA-L3-1.85 | C | C | IA-L3-1.86 | ND | ND |
| IA-L3-1.87 | ND | D | IA-L3-1.88 | ND | ND |
| IA-L3-1.89 | C | B | IA-L3-1.90 | D | C |
| IA-L3-1.91 | C | C | IA-L3-1.94 | D | C |
| IA-L3-1.95 | D | D | IA-L3-1.96 | C | D |
| IA-L3-1.97 | D | D | IA-L3-1.98 | D | C |
| IA-L3-1.99 | ND | C | IA-L3-1.100 | ND | D |
| IA-L3-1.101 | ND | ND | IA-L3-1.102 | ND | C |
| IA-L3-1.103 | D | D | IA-L3-1.104 | D | D |
| IA-L3-1.105 | D | D | IA-L3-1.107 | D | D |
| IA-L3-1.108 | ND | ND | IA-L3-1.111 | ND | C |
| IA-L3-1.112 | D | C | IA-L3-1.113 | D | D |
| IA-L3-1.114 | ND | ND | IA-L3-1.115 | D | D |
| IA-L3-1.116 | ND | ND | IA-L3-1.117 | ND | ND |
| IA-L3-1.118 | ND | ND | IA-L3-1.119 | C | B |
| IA-L3-1.120 | D | D | IA-L3-1.121 | D | C |
| IA-L3-1.122 | ND | B | IA-L3-1.123 | C | B |
| IB-L3-1.1 | C | B | IB-L3-1.2 | C | B |
| IB-L3-1.3 | ND | C | IB-L3-1.4 | D | D |
| IA-L3-2.1 | D | D | IA-L3-2.2 | D | D |
| IA-L3-2.3 | ND | ND | IA-L3-2.4 | D | D |
| IA-L3-2.5 | D | D | IA-L4-1.1 | D | D |
| IA-L4-1.2 |  |  | IA-L4-1.3 | D | D |
| IA-L4-1.4 | D | D | IA-L4-1.5 | ND | ND |
| IA-L4-1.6 | ND | ND | IA-L4-1.7 | D | D |
| IA-L4-1.8 | D | C | IA-L4-1.9 | ND | B |
| IA-L4-1.10 | ND | ND | IA-L4-1.11 | C | B |
| IA-L4-1.12 | C | C | IB-L4-1.1 | C | B |
| IA-L5-1-1.1 | ND | ND | IA-L5-1-1.2 | ND | ND |
| IA-L5-1-1.3 | ND | ND | IA-L5-1-1.4 | ND | ND |
| IA-L5-1-1.5 | ND | ND | IA-L5-1-1.6 | ND | ND |
| IA-L5-1-1.7 | ND | ND | IA-L5-1-1.8 | ND | ND |
| IA-L5-1-1.10 | ND | ND | IA-L5-1-1.11 | ND | ND |
| IA-L5-1-1.12 | ND | ND | IA-L5-1-1.13 | ND | ND |
| IA-L5-1-1.14 | ND | ND | IA-L5-1-2.1 | ND | ND |
| IA-L5-1-2.2 | ND | ND | IA-L5-2-1.1 | C | B |
| IA-L5-2-1.2 | C | C | IB-L5-2-1.1 | B | A |
| IB-L5-2-1.2 | C | B | IA-L6-1.1 | C | B |
| IA-L8-1.1 | C | C | IA-L9-1.1 | ND | ND |
| IA-L9-1.2 | ND | ND | IA-L9-1.3 | ND | ND |
| IA-L9-1.4 | D | C | IA-L11-1.1 | C | B |
| IA-L12-1.1 | C | B |  |  |  |

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

We claim:

1. A compound or salt thereof, wherein the compound corresponds in structure to formula II:

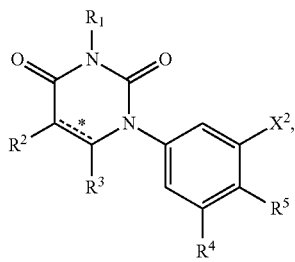

(II)

wherein $=\overset{*}{=}=$ is selected from the group consisting of single carbon-carbon bond and double carbon-carbon bond;

$R^1$ is selected from the group consisting of hydrogen, methyl, and nitrogen-protecting group;

$R^2$ is selected from the group consisting of hydrogen, halo, hydroxy, methyl, cyclopropyl, and cyclobutyl;

$R^3$ is selected from the group consisting of hydrogen, halo, oxo, and methyl;

$R^4$ is selected from the group consisting of alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

(a) the amino, aminocarbonyl, and aminosulfonyl optionally are substituted with:
  (1) one or two substituents independently selected from the group consisting of alkyl, alkenyl, alkynyl, and alkylsulfonyl, or
  (2) two substituents that, together with the amino nitrogen, form a single-ring heterocyclyl, and (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
  the amino optionally is substituted with:
  (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
  (2) two substituents that, together with the amino nitrogen, form a single-ring heterocyclyl, and (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
  the amino optionally is substituted with:
  (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
  (2) two substituents that, together with the amino nitrogen, form a single-ring heterocyclyl;

$R^5$ is selected from the group consisting of hydrogen, hydroxy, alkyl, alkenyl, alkynyl, alkyloxy, alkenyloxy, alkynyloxy, alkylsulfonyloxy, carbocyclylsulfonyloxy, haloalkylsulfonyloxy, and halo; and $X^2$ is halo.

2. The compound or salt of claim 1, wherein $=\overset{*}{=}=$ is a single carbon-carbon bond.

3. The compound or salt of claim 1, wherein $=\overset{*}{=}=$ is a double carbon-carbon bond.

4. The compound or salt of claim 1, wherein $R^1$ is selected from the group consisting of hydrogen and methyl.

5. The compound or salt of claim 1, wherein $R^1$ is hydrogen.

6. The compound or salt of claim 1, wherein $R^2$ is selected from the group consisting of hydrogen, methyl, and halo.

7. The compound or salt of claim 1, wherein $R^2$ is hydrogen.

8. The compound or salt of claim 1, wherein $R^3$ is selected from the group consisting of hydrogen and methyl.

9. The compound or salt of claim 1, wherein $R^3$ is hydrogen.

10. The compound or salt of claim 1, wherein $R^4$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:

the amino optionally is substituted with one or two substituents independently selected from the group consisting of alkyl, alkenyl, alkynyl, and alkylsulfonyl, the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and the $C_3$-$C_6$-carbocyclyl and 5-6-membered heterocyclyl optionally are substituted with up to three substituents independently selected from the group consisting of alkyl, alkenyl, alkynyl, halo, and amino, wherein:

the amino optionally is substituted with one or two substituents independently selected from the group consisting of alkyl, alkenyl, alkynyl, and alkylsulfonyl.

11. The compound or salt of claim 1, wherein:
$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

12. The compound or salt of claim 1, wherein $R^4$ is selected from the group consisting of alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl.

13. The compound or salt of claim 1, wherein $R^4$ is selected from the group consisting of $C_1$-$C_4$-alkyl, $C_3$-$C_6$-carbocyclyl, and 5-6-membered heterocyclyl.

14. The compound or salt of claim 1, wherein $R^4$ is selected from the group consisting of tert-butyl, $C_3$-$C_6$-carbocyclyl, and 5-6-membered heterocyclyl.

15. The compound or salt of claim 1, wherein R is selected from the group consisting of tert-butyl, $C_3$-$C_6$-carbocyclyl, and 5-6-membered heterocyclyl.

16. The compound or salt of claim 1, wherein $R^4$ is alkyl.

17. The compound or salt of claim 1, wherein $R^4$ is tert-butyl.

18. The compound or salt of claim 1, wherein $R^5$ is selected from the group consisting of hydrogen, hydroxy, alkyloxy, and halo.

19. The compound or salt of claim 1, wherein $R^5$ is selected from the group consisting of hydrogen, methoxy, and halo.

20. The compound or salt of claim 1, wherein $R^5$ is methoxy.

21. The compound or salt of claim 1, wherein $X^2$ is selected from the group consisting of chloro, bromo, and iodo.

22. The compound or salt of claim 1, wherein $X^2$ is iodo.

23. The compound or salt of claim 1, wherein $R^1$ is selected from the group consisting of hydrogen, methyl, and nitrogen-protecting group;

$R^2$ is selected from the group consisting of hydrogen and halo;

$R^3$ is selected from the group consisting of hydrogen and halo;

$R^4$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and (b) the $C_3$-$C_6$-carbocyclyl and 5-6-membered heterocyclyl optionally are substituted with one or two substituents independently selected from the group consisting of alkyl, halo, and alkylsulfonylamino;

$R^5$ is selected from the group consisting of hydrogen, hydroxy, alkyloxy, and halo; and $X^2$ is selected from the group consisting of chloro, bromo, and iodo.

24. The compound or salt of claim 1, wherein

--*-- is a double carbon-carbon bond;

$R^1$ is hydrogen;

$R^2$ is selected from the group consisting of hydrogen and halo;

$R^3$ is hydrogen;

$R^4$ is tert-butyl;

$R^5$ is selected from the group consisting of hydrogen, hydroxy, and methoxy; and $X^2$ is selected from the group consisting of bromo and iodo.

25. The compound or salt of claim 1, wherein $R^1$ is selected from the group consisting of hydrogen and methyl;

$R^2$ is selected from the group consisting of hydrogen and methyl;

$R^3$ is selected from the group consisting of hydrogen and methyl;

$R^4$ is tert-butyl;

$R^5$ is selected from the group consisting of hydroxy and methoxy; and $X^2$ is selected from the group consisting of chloro, bromo, and iodo.

26. The compound or salt of claim 1, wherein

--*-- is a double carbon-carbon bond;

$R^1$ is hydrogen;

$R^2$ is hydrogen;

$R^3$ is hydrogen;

$R^4$ is tert-butyl;

$R^5$ is selected from the group consisting of hydroxy and methoxy; and $X^2$ is selected from the group consisting of chloro, bromo, and iodo.

27. The compound or salt of claim 1, wherein the compound is selected from the group consisting of

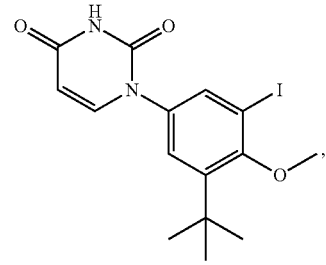

(II-I)

-continued

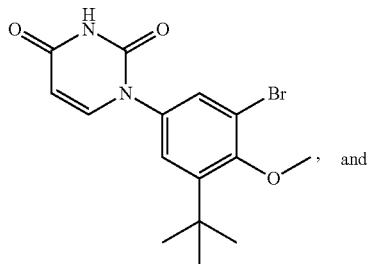

(II-Br)

, and

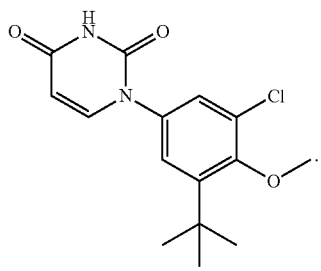

(II-Cl)

28. A process for preparing the compound or salt of claim 1, wherein the process comprises reacting a compound of formula III with a compound of formula IV in the presence of (i) copper (I) salt catalyst and (ii) nitrogenous heteroaryl ligand

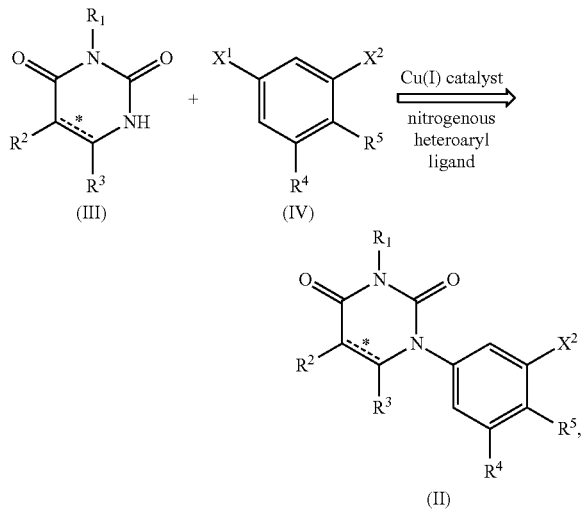

wherein $R^1$, $R^2$, $R^3$, $R^4$, $R^5$ and $X^2$ are as defined in claim 1, and $X^1$ is halo.

29. The process of claim 28, wherein $X^1$ is selected from the group consisting of chloro, bromo, and iodo.

30. The process of claim 28, wherein the process is conducted in the presence of a base.

31. The process of claim 30, wherein the base is selected from the group consisting of potassium salt, sodium salt, and cesium salt.

32. The process of claim 28, wherein the nitrogenous heteroaryl ligand comprises a picolinamide compound corresponding in structure to formula V:

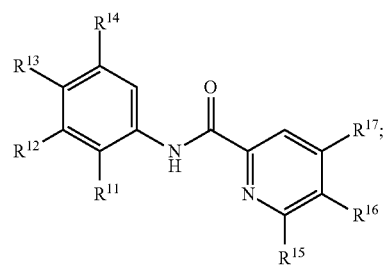

(V)

and $R^{11}$, $R^{12}$, $R^{13}$, $R^{14}$, $R^{15}$, $R^{16}$, and $R^{17}$ are independently selected from the group consisting of hydrogen, $C_{1-4}$-perfluoroalkyl, $C_{1-4}$-alkyloxy, $C_{1-4}$-haloalkyl, chloro, and cyano.

33. The process of claim 28, wherein the nitrogenous heteroaryl ligand is selected from the group consisting of 8-hydroxyquinoline, 2-(2-pyridyl)-benzimidazole, N-(4-cyanophenyl)picolinamide, and N-(2-cyanophenyl)picolinamide.

34. The compound or salt of claim 1, wherein the compound is 1-(3-tert-butyl-5-iodo-4-methoxyphenyl)pyrimidine-2,4(1H,3H)-dione.

35. 1-(3-tert-butyl-5-iodo-4-methoxyphenyl)pyrimidine-2,4(1H,3H)-dione.

* * * * *